(12) United States Patent
Ren et al.

(10) Patent No.: US 11,142,527 B2
(45) Date of Patent: Oct. 12, 2021

(54) DIHYDROPYRIMIDINE COMPOUNDS AND USES THEREOF IN MEDICINE

(71) Applicant: SUNSHINE LAKE PHARMA CO., LTD., Guangdong (CN)

(72) Inventors: Qingyun Ren, Dongguan (CN);
Xinchang Liu, Dongguan (CN);
Jianzhou Huang, Dongguan (CN);
Yingjun Zhang, Dongguan (CN);
Siegfried Goldmann, Dongguan (CN)

(73) Assignee: SUNSHINE LAKE PHARMA CO., LTD., Dongguan (CN)

( * ) Notice: Subject to any disclaimer, the term of this patent is extended or adjusted under 35 U.S.C. 154(b) by 21 days.

(21) Appl. No.: 16/624,466

(22) PCT Filed: Jun. 25, 2018

(86) PCT No.: PCT/CN2018/092699
§ 371 (c)(1),
(2) Date: Dec. 19, 2019

(87) PCT Pub. No.: WO2019/001396
PCT Pub. Date: Jan. 3, 2019

(65) Prior Publication Data
US 2020/0115381 A1    Apr. 16, 2020

(30) Foreign Application Priority Data

Jun. 26, 2017  (CN) .......................... 201710492934.5
Oct. 18, 2017  (CN) .......................... 201710969509.0
Jan. 30, 2018  (CN) .......................... 201810088155.3

(51) Int. Cl.
*A61K 31/495*    (2006.01)
*C07D 401/00*    (2006.01)
(Continued)

(52) U.S. Cl.
CPC ........ *C07D 487/04* (2013.01); *A61K 31/4985* (2013.01); *A61P 31/20* (2018.01); *A61K 45/06* (2013.01)

(58) Field of Classification Search
CPC ... A61K 31/4985; A61K 31/506; A61P 31/12; A61P 31/20
(Continued)

(56) References Cited

U.S. PATENT DOCUMENTS 9,758,530 B2    9/2017  Guo et al.
10,081,627 B2   9/2018  Guo et al.
(Continued)

FOREIGN PATENT DOCUMENTS

CN    108567783 A     9/2018
WO    2017/064156 A1  4/2017
(Continued)

OTHER PUBLICATIONS

Sep. 10, 2018 International Search Report issued in International Patent Application No. PCT/CN2018/092699.
(Continued)

*Primary Examiner* — Shengjun Wang
(74) *Attorney, Agent, or Firm* — Oliff PLC

(57) ABSTRACT

A dihydropyrimidine compound and a pharmaceutical application thereof, especially the application used for treating and preventing HBV diseases. Specifically, a compound having Formula (I) or (Ia), or an enantiomer, a diastereoisomer, a tautomer, a hydrate, a solvate, or a pharmaceutically acceptable salt thereof, wherein the variables of the formulas are as defined in the specification. Also, use of the compound having Formula (I) or (Ia), or an enantiomer, a diastereoisomer, a tautomer, a hydrate, a solvate, or a pharmaceutically acceptable salt thereof as a medicine, especially for treating and preventing HBV diseases.

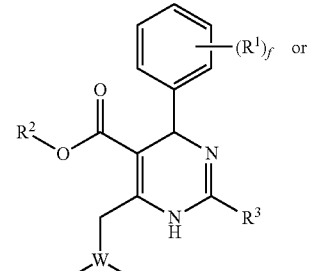

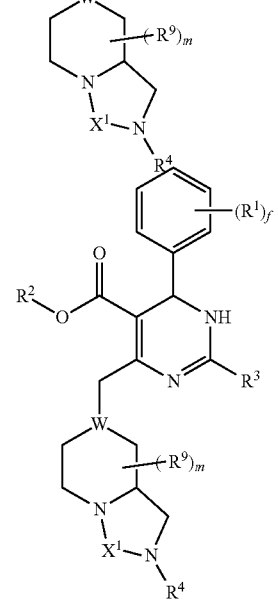

21 Claims, No Drawings

(51) Int. Cl.
  *C07D 487/04* (2006.01)
  *A61P 31/20* (2006.01)
  *A61K 31/4985* (2006.01)
  *A61K 45/06* (2006.01)

(58) Field of Classification Search
  USPC .......................................................... 514/249
  See application file for complete search history.

(56) References Cited

U.S. PATENT DOCUMENTS

| | | |
|---|---|---|
| 10,179,131 B2 | 1/2019 | Qiu et al. |
| 10,428,069 B2 | 10/2019 | Guo et al. |
| 2018/0000824 A1 | 1/2018 | Dai et al. |
| 2019/0010155 A1 | 1/2019 | Chen |

FOREIGN PATENT DOCUMENTS

| | | |
|---|---|---|
| WO | 2017/108630 A1 | 6/2017 |
| WO | 2018/045911 A1 | 3/2018 |
| WO | 2019/076310 A1 | 4/2019 |

OTHER PUBLICATIONS

Sep. 10, 2018 Written Opinion issued in International Patent Application No. PCT/CN2018/092699.

DIHYDROPYRIMIDINE COMPOUNDS AND USES THEREOF IN MEDICINE

CROSS-REFERENCE TO RELATED APPLICATIONS

This application claims priority to Chinese Patent Application Serial Nos 201710492934.5, 201710969509.0 and 201810088155.3, filed with the State Intellectual Property Office of china respectively on Jun. 26, 2017, Oct. 18, 2017 and Jan. 30, 2018, which are hereby incorporated by reference in its entirety.

FIELD OF THE INVENTION

The invention relates to use of a dihydropyrimidine compound as a medicine, especially for treating and preventing HBV diseases. The invention also relates to a composition of the dihydropyrimidine compound and one or more other anti-viral agents, and an application in treating and preventing HBV infection diseases.

BACKGROUND OF THE INVENTION

The hepatitis B virus belongs to the family of hepadnaviridae. It can cause acute and/or persistent or progressive chronic diseases. Many other clinical manifestations in the pathological morphology can be also caused by HBVin—particular chronic hepatitis, cirrhosis and hepatocellular carcinoma. Additionally, coinfection with hepatitis D virus may have adverse effects on the progress of the disease.

The conventional medicaments approved to be used for treating chronic hepatitis are interferon and lamivudine. However, the interferon has just moderate activity but has an adverse side reaction. Although lamivudine has a good activity, its resistance develops rapidly during the treatment and relapse effects often appear after the treatment has stopped. The $IC_{50}$ value of lamivudine (3-TC) is 300 nM (Science, 2003, 299, 893-896).

Deres, et al., have reported heteroaryl-substituted dihydropyrimidine (HAP) compounds including Bay41-4109 and Bay39-5493, and these compounds play a role in blocking HBV replication by preventing the proper formation of viral core particles (nucleocapsids). Bay41-4109 has a good drug metabolism properties in clinical research (Science, 299(2003), 893-896). The study of these compounds' mechanism indicated that through reacting with 113-143 amino acid residues of a core protein, heteroaryl-substituted dihydropyrimidine compounds have changed the angle between dimers which can form nucleocapsids, and thus led to forming unstably expanded nucleocapsids, which accelerate the degradation of the core protein (Biochem. Pharmacol, 2003, 66, 2273-2279).

Novel compounds with effective antiviral effects are still desired at present, especially drugs used for the treatment and/or prevention of hepatitis B.

The novel dihydropyrimidine compounds disclosed herein have advantages like good inhibitory activity to HBV, and good pharmacokinetic properties, good solubility, good stability, no inducing effect on liver enzymes and small toxicity, and so on. It has a good application prospect in the field of anti HBV virus.

SUMMARY OF THE INVENTION

The present invention relates to a novel dihydropyrimidine compound and use thereof in the manufacture of a medicament for treating and preventing an HBV infection. Especially, the present invention relates to a novel dihydropyrimidine compound and a pharmaceutically acceptable composition thereof, the compound has good pharmacokinetic properties, good solubility, good stability, no inducing effect on liver enzymes and small toxicity, and so on, which can inhibit HBV infection effectively and has a good prospect in anti HBV virus.

In one aspect, provided herein is a compound having Formula (I) or Formula (Ia) or a stereoisomer, a tautomer, an N-oxide, a solvate, a metabolite, a pharmaceutically acceptable salt or a prodrug thereof,

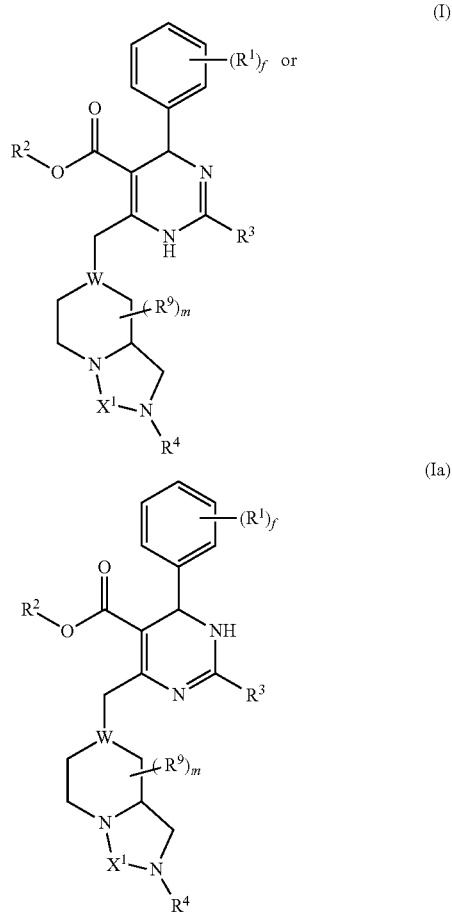

wherein each $R^1$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl;

each $R^2$ is independently $C_{1-6}$ alkyl, $C_{1-6}$ haloalkyl, $C_{3-6}$ cycloalkyl-$C_{1-6}$ alkylene or 5-6 membered heterocyclyl-$C_{1-6}$ alkylene;

each $R^3$ is independently $C_{6-10}$ aryl or 5-6 membered heteroaryl, wherein each of the $C_{6-10}$ aryl or 5-6 membered heteroaryl is independently unsubstituted or substituted with one, two, three, four or five substituents independently selected from deuterium, F, Cl, Br, OH, CN, $C_{1-6}$ alkyl, hydroxy-$C_{1-6}$ alkyl, $C_{1-6}$ alkyl-OC(=O)—, $C_{1-6}$-alkyl-OC(=O)—$C_{1-6}$ alkylene, HOOC—$C_{1-6}$ alkylene, $C_{1-6}$ alkoxy-$C_{1-6}$ alkylene and $C_{1-6}$ alkyl-S(=O)$_2$—;

each W is independently CH or N;

each $X^1$ is independently —C(=O)—, —S(=O)$_2$—, —(O=)P(OH)— or —(CR$^7$R$^8$)$_j$—;

each $R^4$ is independently —(CR$^7$R$^8$)$_j$—R$^5$-L-R$^6$;

$R^5$ is 3-12 membered heterocyclyl, $C_{3-7}$ cycloalkyl, $C_{2-12}$ alkynyl, 5-12 membered heteroaryl or $C_{6-10}$ aryl, wherein each of the 3-12 membered heterocyclyl, $C_{3-7}$ cycloalkyl, $C_{2-12}$ alkynyl, 5-12 membered heteroaryl and $C_{6-10}$ aryl is independently unsubstituted or substituted with one, two, three, four or five substituents independently selected from deuterium, F, Cl, Br, OH, CN, $C_{1-6}$ alkoxy, $C_{1-6}$ alkyl, HOOC—(CR$^7$R$^8$)$_h$— and $C_{1-6}$ alkoxy-C(=O)—;

$R^6$ is 3-12 membered heterocyclyl, $C_{3-7}$ cycloalkyl, $C_{2-12}$ alkynyl, 5-12 membered heteroaryl or $C_{6-10}$ aryl, wherein each of the 3-12 membered heterocyclyl, $C_{3-7}$ cycloalkyl, $C_{2-12}$ alkynyl, 5-12 membered heteroaryl and $C_{6-10}$ aryl is independently unsubstituted or substituted with one, two, three, four or five $R^w$;

L is a single bond, —O—, —S(=O)$_t$—, —C(=O)—, —NH—, —(CR$^7$R$^8$)$_j$— or —O—(CR$^7$R$^8$)$_j$—;

each $R^w$ is independently deuterium, F, Cl, Br, OH, CN, HOOC—(CR$^7$R$^8$)$_h$—, R$^{11}$C(=O)—, R$^c$R$^d$P(=O)—, R$^{10}$—S(=O)$_t$—, R$^{13}$O—, R$^{12}$—(CR$^7$R$^8$)$_j$—, amino, $C_{1-2}$ alkoxy, $C_{3-7}$ cycloalkyl, $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-10 membered heterocyclyl or 5-10 membered heteroaryl, wherein each of the amino, $C_{1-12}$ alkoxy, $C_{3-7}$ cycloalkyl, $C_{1-8}$ alkoxy of $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-10 membered heterocyclyl and 5-10 membered heteroaryl is independently unsubstituted or substituted with one, two, three, four or five $R^x$;

each $R^{10}$ and $R^{11}$ is independently $R^aR^bN$—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five $R^y$;

each $R^{12}$ is independently OH, HOOC—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five $R^z$;

each $R^{13}$ is independently $C_{1-8}$ alkyl, $C_{3-7}$ cycloalkyl, 5-10 membered heteroaryl, $C_{6-10}$ aryl or 5-10 membered heterocyclyl, wherein each of the $C_{1-8}$ alkyl, $C_{3-7}$ cycloalkyl, 5-10 membered heteroaryl, $C_{6-10}$ aryl and 5-10 membered heterocyclyl is independently unsubstituted or substituted with one, two, three, four or five $R^g$;

each $R^x$, $R^y$, $R^z$ and $R^g$ is independently deuterium, F, Cl, Br, OH, CN, HOOC—(CR$^7$R$^8$)$_h$—, R$^{14}$C(=O)—, R$^cR^dP$(=O)—, R$^{15}$—S(=O)$_t$—, R$^{16}$O—, R$^{17}$—(CR$^7$R$^8$)$_j$—, amino, $C_{1-2}$ alkoxy, $C_{3-7}$ cycloalkyl, $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-12 membered heterocyclyl or 5-10 membered heteroaryl, wherein each of the amino, $C_{1-12}$ alkoxy, $C_{3-7}$ cycloalkyl, $C_{1-8}$ alkoxy of $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-12 membered heterocyclyl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, hydroxy-$C_{1-8}$ alkyl, HOOC—(CR$^7$R$^8$)$_h$— and $C_{1-8}$ alkoxy-(CR$^7$R$^8$)$_n$—O—;

each $R^{14}$ and $R^{15}$ is independently $R^aR^bN$—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, HOOC—(CR$^7$R$^8$)$_h$— and $C_{1-8}$ alkoxy-(CR$^7$R$^8$)$_n$—O—;

each $R^{17}$ is independently OH, HOOC—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, HOOC—(CR$^7$R$^8$)$_h$— and $C_{1-8}$ alkoxy-(CR$^7$R$^8$)$_n$—O—;

each $R^{16}$ is independently $C_{1-8}$ alkyl, $C_{3-7}$ cycloalkyl, 5-10 membered heteroaryl, $C_{6-10}$ aryl or 5-10 membered heterocyclyl, wherein each of the $C_{1-8}$ alkyl, $C_{3-7}$ cycloalkyl, 5-10 membered heteroaryl, $C_{6-10}$ aryl and 5-10 membered heterocyclyl is independently unsubstituted or substituted with one, two, three, four or five substituents independently selected from deuterium, F, Cl, Br, OH, $C_{1-8}$ alkoxy, $C_{1-8}$ alkyl, HOOC—(CR$^7$R$^8$)$_h$— and $C_{1-8}$ alkoxy-(CR$^7$R$^8$)$_n$—O—;

each $R^a$, $R^b$, $R^c$ and $R^d$ is independently H, deuterium, $C_{1-8}$ alkyl, $C_{2-8}$ alkynyl, $C_{1-8}$ alkoxy, $C_{3-7}$ cycloalkyl, HOOC—(CR$^7$R$^8$)$_h$—, $C_{6-10}$ aryl-$C_{1-4}$ alkylene or 3-12 membered heterocyclyl, wherein each of the $C_{1-8}$ alkyl, $C_{2-8}$ alkynyl, $C_{1-8}$ alkoxy, $C_{3-7}$ cycloalkyl, $C_{6-10}$ aryl of $C_{6-10}$ aryl $C_{1-4}$-alkylene and 3-12 membered heterocyclyl is independently unsubstituted or substituted with one, two, three, four or five substituents independently selected from deuterium, F, Cl, Br, OH, $C_{1-8}$ alkyl, $(C_{1-6}$ alkyl)$_2$NC(=O)—, $C_{1-8}$ alkoxy, HOOC—(CR$^7$R$^8$)$_h$— and $C_{1-8}$ alkoxy-(CR$^7$R$^8$)$_n$—O—;

each $R^7$, $R^8$ and $R^9$ is independently H, deuterium, F, Cl, Br, $C_{1-6}$ alkyl, $NH_2C$(=O)—, $C_{1-6}$ alkyl-OC(=O)—, carboxy, carboxy-$C_{1-6}$ alkylene, hydroxy-$C_{1-6}$ alkyl or $C_{1-6}$ haloalkyl, or $R^7$ and $R^8$, together with the carbon atom to which they are attached, form $C_{3-6}$ cycloalkyl or carbonyl;

each f m and h is independently 0, 1, 2, 3, or 4;
each n is independently 1, 2, 3 or 4;
each t is independently 0, 1 or 2;
each j is independently 0, 1, 2 or 3.

In some embodiments, provided herein is a compound having Formula (II) or Formula (IIa):

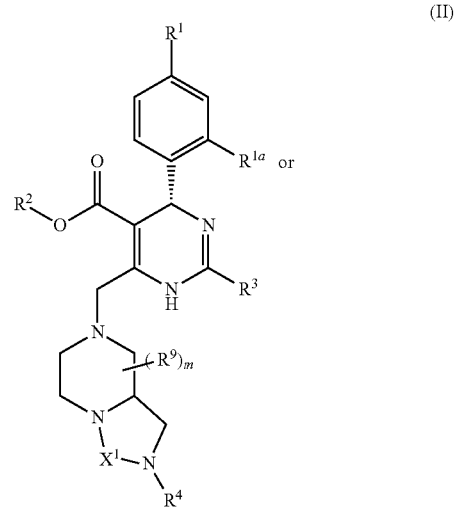

(II)

-continued (IIa)

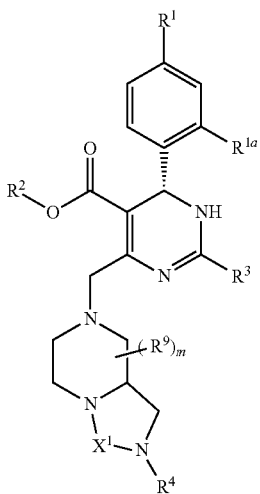

wherein each $R^1$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl; each $R^2$, $R^3$, $R^9$, $R^4$, $X^1$ and m is as defined herein.

In some embodiments, each $R^2$ is independently methyl, ethyl, n-propyl, i-propyl, $C_{1-4}$ haloalkyl, $C_{3-6}$ cycloalkyl-$C_{1-3}$ alkylene or 5-6 membered heterocyclyl-$C_{1-3}$ alkylene;

$R^3$ is phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of the phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with one, two, three, four or five substituents independently selected from deuterium, F, Cl, Br, OH, CN, $C_{1-4}$ alkyl, hydroxy-$C_{1-4}$ alkyl, $C_{1-4}$ alkyl-OC(=O)—, $C_{1-4}$ alkyl-OC(=O)—$C_{1-3}$ alkylene, HOOC—$C_{1-6}$ alkylene-, $C_{1-4}$ alkoxy-$C_{1-3}$ alkylene or $C_{1-4}$ alkyl-S(=O)$_2$—;

each $R^7$, $R^8$ and $R^9$ is independently H, deuterium, F, Cl, Br, methyl, ethyl, n-propyl, i-propyl, $NH_2C(=O)—$, $C_{1-4}$ alkyl-OC(=O)—, carboxy, carboxy-$C_{1-3}$ alkylene, hydroxy-$C_{1-4}$ alkyl or haloalkyl, or $R^7$ and $R^8$, together with the carbon atom to which they are attached, form cyclopropyl, cyclobutyl, cyclopentyl, cyclohexyl or carbonyl.

In some embodiments, $R^5$ is 5-10 membered heterocyclyl, $C_{3-6}$ cycloalkyl, $C_{2-8}$ alkynyl, 5-10 membered heteroaryl, phenyl or naphthyl, wherein each of the 5-10 membered heterocyclyl, $C_{3-6}$ cycloalkyl, $C_{2-8}$ alkynyl, 5-10 membered heteroaryl, phenyl and naphthyl is independently unsubstituted or substituted with one, two, three, four or five substituents independently selected from deuterium, F, Cl, Br, OH, CN, $C_{1-4}$ alkoxy, $C_{1-4}$ alkyl, HOOC—$(CR^7R^8)_h$— and $C_{1-4}$ alkoxy-C(=O)—;

$R^6$ is 5-10 membered heterocyclyl, $C_{3-6}$ cycloalkyl, $C_{2-8}$ alkynyl, 5-10 membered heteroaryl, phenyl or naphthyl, wherein each of the 5-10 membered heterocyclyl, $C_{3-6}$ cycloalkyl, $C_{2-8}$ alkynyl, 5-10 membered heteroaryl, phenyl and naphthyl is independently unsubstituted or substituted with one, two, three, four or five $R^w$;
wherein $R^7$, $R^8$, h and $R^w$ are as defined herein.

In some embodiments, $R^5$ is 5-6 membered heterocyclyl, $C_{3-6}$ cycloalkyl, $C_{2-6}$ alkynyl, 5-6 membered heteroaryl, 9-10 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, 9-10 membered heteroaryl, phenyl and naphthyl is independently unsubstituted or substituted with one, two, three, four or five substituents independently selected from deuterium, F, Cl, Br, OH, CN, $C_{1-3}$ alkoxy, $C_{1-3}$ alkyl, HOOC—$(CR^7R^8)_h$— and $C_{1-3}$ alkoxy-C(=O)—;

$R^6$ is 5-6 membered heterocyclyl, $C_{3-6}$ cycloalkyl, $C_{2-6}$ alkynyl, 5-6 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, phenyl and naphthyl is independently unsubstituted or substituted with one, two, three, four or five $R^w$;
wherein $R^7$, $R^8$, h and $R^w$ are as defined herein.

In some embodiments, $R^5$ is 5-6 membered heterocyclyl, $C_{3-6}$ cycloalkyl, $C_{2-6}$ alkynyl, 5-6 membered heteroaryl, 9 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, 9 membered heteroaryl, phenyl and naphthyl is independently unsubstituted or substituted with one, two, three, four or five substituents independently selected from deuterium, F, Cl, Br, OH, $C_{1-3}$ alkoxy, $C_{1-3}$ alkyl, HOOC—$(CR^7R^8)_h$— and $C_{1-3}$ alkoxy-C(=O)—;

$R^6$ is 5-6 membered heterocyclyl, $C_{3-6}$ cycloalkyl, $C_{2-6}$ alkynyl, 5-6 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, phenyl and naphthyl is independently unsubstituted or substituted with one, two, three, four or five $R^w$;
wherein $R^7$, $R^8$, h and $R^w$ are as defined herein.

In some embodiments, $R^5$ is pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzimidazolyl, benzofuranyl, benzothienyl, indolyl, purinyl, quinolyl, isoquinolyl, phenyl or naphthyl, wherein each of the pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzimidazolyl, benzofuranyl, benzothienyl, indolyl, purinyl, quinolyl, isoquinolyl, phenyl and naphthyl is independently unsubstituted or substituted with one, two, three, four or five substituents independently selected from deuterium, F, Cl Br, OH, CN, $C_{1-3}$ alkoxy, $C_{1-3}$ alkyl, HOOC—$(CR^7R^8)_h$— and $C_{1-3}$ alkoxy-C(=O)—;

$R^6$ is pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, phenyl or naphthyl, wherein each of the pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, phenyl and naphthyl is independently unsubstituted or substituted with one, two, three, four or five $R^w$;

wherein $R^7$, $R^8$, h and $R^w$ are as defined herein.

In some embodiments, each $R^w$ is independently deuterium, F, Cl, Br, OH, CN, HOOC—$(CR^7R^8)_h$—, $R^{11}C(=O)$—, $R^cR^dP(=O)$—, $R^{10}$—$S(=O)_t$—, $R^{13}O$—, $R^{12}$—$(CR^7R^8)_j$—, amino, $C_{1-6}$ alkoxy, $C_{3-6}$ cycloalkyl, $C_{1-6}$ alkoxy-$(CR^7R^8)_n$—O—, $C_{1-6}$ alkyl, hydroxy-$C_{1-6}$ alkyl, $C_{2-6}$ alkynyl, phenyl, naphthyl, 5-6 membered heterocyclyl or 5-6 membered heteroaryl, and wherein each of the amino, $C_{1-6}$ alkoxy, $C_{3-6}$ cycloalkyl, $C_{1-6}$ alkoxy of $C_{1-6}$ alkoxy-$(CR^7R^8)_n$—O—, $C_{1-6}$ alkyl, hydroxy-$C_{1-6}$ alkyl, $C_{2-6}$ alkynyl, phenyl, naphthyl, 5-6 membered heterocyclyl and 5-6 membered heteroaryl is independently unsubstituted or substituted with one, two, three, four or five $R^x$;

wherein $R^7$, $R^8$, h, t, n, j, $R^{11}$, $R^c$, $R^d$, $R^{10}$, $R^{13}$, $R^{12}$ and $R^x$ are as defined herein.

In some embodiments, each $R^w$ is independently deuterium, F, Cl, Br, OH, CN, HOOC—$(CR^7R^8)_h$—, $R^{11}C(=O)$—, $R^cR^dP(=O)$—, $R^{10}$—$S(=O)_t$—, $R^{13}O$—, $R^{12}$—$(CR^7R^8)_j$—, amino, $C_{1-4}$ alkoxy, $C_{3-6}$ cycloalkyl, $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl or piperazinyl, and wherein each of the amino, $C_{1-4}$ alkoxy, $C_{3-6}$ cycloalkyl, $C_{1-4}$ alkoxy of $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl and piperazinyl is independently unsubstituted or substituted with one, two, three, four or five $R^x$;

wherein $R^7$, $R^8$, h, t, n, j, $R^{11}$, $R^c$, $R^d$, $R^{10}$, $R^{13}$, $R^{12}$ and $R^x$ are as defined herein.

In some embodiments, each $R^{10}$ and $R^{11}$ is independently $R^aR^bN$—, $C_1$ alkyl, $C_{1-6}$ alkoxy, $C_{3-6}$ cycloalkyl, 5-6 membered heterocyclyl, phenyl, naphthyl or 5-6 membered heteroaryl, and wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five $R^y$;

each $R^{12}$ is independently OH, HOOC—, $C_{1-6}$ alkyl, $C_{1-6}$ alkoxy, $C_{3-6}$ cycloalkyl, 4 membered heterocyclyl, 5-6 membered heterocyclyl, phenyl, naphthyl or 5-6 membered heteroaryl, and wherein each of the $C_{1-6}$ alkyl, $C_{1-6}$ alkoxy, $C_{3-6}$ cycloalkyl, 4 membered heterocyclyl, 5-6 membered heterocyclyl, phenyl, naphthyl and 5-6 membered heteroaryl is independently unsubstituted or substituted with one, two, three, four or five $R^z$;

each $R^{13}$ is independently $C_{1-6}$ alkyl, $C_{3-6}$ cycloalkyl, 5-6 membered heteroaryl, phenyl, naphthyl or 5-6 membered heterocyclyl, and wherein each of the $C_{1-6}$ alkyl, $C_{3-6}$ cycloalkyl, 5-6 membered heteroaryl, phenyl, naphthyl and 5-6 membered heterocyclyl is independently unsubstituted or substituted with one, two, three, four or five $R^g$;

wherein $R^a$, $R^b$, $R^y$, $R^z$ and $R^g$ are as defined herein.

In some embodiments, each $R^{10}$ and $R^{11}$ is independently $R^aR^bN$—, $C_1$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^y$;

each $R^{12}$ is independently OH, HOOC—, $C_{1-4}$ alkyl, $C_{1-4}$ alkoxy, cyclopropyl, cyclobutyl, cyclopentyl, cyclohexyl, azetidinyl, oxetanyl, thietanyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, cyclohexyl, azetidinyl, oxetanyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^z$;

each $R^{13}$ is independently $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^g$;

wherein $R^a$, $R^b$, $R^y$, $R^z$ and $R^g$ are as defined herein.

In some embodiments, each $R^x$, $R^y$, $R^z$ and $R^g$ is independently deuterium, F, Cl, Br, OH, CN, HOOC—$(CR^7R^8)_h$—, $R^{14}C(=O)$—, $R^cR^dP(=O)$—, $R^{15}$—$S(=O)_t$—, $R^{17}$—$(CR^7R^8)_j$—, amino, $C_{1-6}$ alkoxy, $C_{3-6}$ cycloalkyl, $C_{1-6}$ alkoxy-$(CR^7R^8)_n$—O—, $C_{1-6}$ alkyl, hydroxy-$C_1$ alkyl, $C_{2-6}$ alkynyl, phenyl, naphthyl, 5-6 membered heterocyclyl or 5-6 membered heteroaryl, wherein each of the amino, $C_{1-6}$ alkoxy, $C_{3-6}$ cycloalkyl, $C_{1-6}$ alkoxy of $C_{1-6}$ alkoxy-$(CR^7R^8)_n$—O—, $C_{1-6}$ alkyl, hydroxy-$C_{1-6}$ alkyl, $C_{2-6}$ alkynyl, phenyl, naphthyl, 5-6 membered heterocyclyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, hydroxy-$C_{1-6}$ alkyl, HOOC—$(CR^7R^8)_h$— and $C_{1-6}$ alkoxy-$(CR^7R^8)_n$—O—;

wherein $R^7$, $R^8$, $R^{14}$, $R^{15}$, $R^{16}$, $R^{17}$, $R^c$, $R^d$, h, t, n and j are as defined herein.

In some embodiments, each $R^x$, $R^y$, $R^z$ and $R^g$ is independently deuterium, F, Cl, Br, OH, CN, HOOC—$(CR^7R^8)_h$—, $R^{14}C(=O)$—, $R^cR^dP(=O)$—, $R^{15}$—$S(=O)_j$—, $R^{16}O$—, $R^{17}$—$(CR^7R^8)_j$—, amino, $C_{1-4}$ alkoxy, $C_{3-6}$ cycloalkyl, $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl or piperazinyl, and wherein each of the amino, $C_{1-4}$ alkoxy, $C_{3-6}$ cycloalkyl, $C_{1-4}$ alkoxy of $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl and piperazinylis independently unsubstituted or substituted with one, two, three, four or five substituents independently selected from deuterium, F, Cl, Br, OH, $C_{1-4}$ alkoxy, $C_{1-4}$ alkyl, hydroxy-$C_{1-4}$ alkyl, HOOC—$(CR^7R^8)_h$— and $C_{1-4}$ alkoxy-$(CR^7R^8)_n$—O—;

wherein $R^7$, $R^8$, $R^{14}$, $R^{15}$, $R^{16}$, $R^{17}$, $R^c$, $R^d$, h, t, n and j are as defined herein.

In some embodiments, each $R^{14}$ and $R^{15}$ is independently $R^aR^bN$—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—;

each $R^{17}$ is independently OH, HOOC—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—;

each $R^{16}$ is independently $C_{1-6}$ alkyl, $C_{3-6}$ cycloalkyl, 5-6 membered heteroaryl, phenyl, naphthyl or 5-6 membered heterocyclyl, wherein each of the $C_{1-6}$ alkyl, $C_{3-6}$ cycloalkyl, 5-6 membered heteroaryl, phenyl, naphthyl and 5-6 membered heterocyclyl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—;

wherein $R^7$, $R^8$, $R^a$, $R^b$, h and n are as defined herein.

In some embodiments, each $R^{14}$ and $R^{15}$ is independently $R^aR^bN$—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-4}$ alkoxy, $C_{1-4}$ alkyl, HOOC—$(CR^7R^8)_h$— and $C_{1-4}$ alkoxy-$(CR^7R^8)_n$—O—;

each $R^{17}$ is independently OH, HOOC—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-4}$ alkoxy, $C_{1-4}$ alkyl, HOOC—$(CR^7R^8)_h$— and $C_{1-4}$ alkoxy-$(CR^7R^8)_n$—O—;

each $R^{16}$ is independently $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-4}$ alkoxy, $C_{1-4}$ alkyl, HOOC—$(CR^7R^8)_h$— and $C_{1-4}$ alkoxy-$(CR^7R^8)_n$—O—;

wherein $R^7$, $R^8$, $R^a$, $R^b$, h and n are as defined herein.

In some embodiments, each $R^a$, $R^b$, $R^c$ and $R^d$ is independently H, deuterium, $C_{1-6}$ alkyl, $C_{2-6}$ alkynyl, $C_{1-6}$ alkoxy, $C_{3-6}$ cycloalkyl, HOOC—$(CR^7R^8)_h$—, phenyl-$C_{1-3}$ alkylene or 5-6 membered heterocyclyl, wherein each of the $C_{1-6}$ alkyl, $C_{2-6}$ alkynyl, $C_{1-6}$ alkoxy, $C_{3-6}$ cycloalkyl, phenyl-$C_{1-3}$ alkylene and 5-6 membered heterocyclyl is independently unsubstituted or substituted with one, two, three, four or five substituents independently selected from deuterium, F, Cl, Br, OH, $C_{1-6}$ alkyl, $(C_{1-4}$ alkyl$)_2$NC(=O)—, $C_{1-6}$ alkoxy, HOOC—$(CR^7R^8)_h$— and $C_{1-6}$ alkoxy-$(CR^7R^8)_n$—O—;

wherein $R^7$, $R^b$, h and n are as defined herein.

In some embodiments, each $R^a$, $R^b$, $R^e$ and $R^d$ is independently H, deuterium, $C_{1-4}$ alkyl, $C_{2-4}$ alkynyl, $C_{1-4}$ alkoxy, cyclopropyl, cyclobutyl, cyclopentyl, cyclohexyl, HOOC—$(CR^7R^8)_h$—, phenyl-methylene, pyrrolidyl, pyrazolidyl, imidazolidinyl tetrahydrofuryl, tetrahydrothienyl, tetrahydropyranyl, tetraphydrothiopyranyl, piperidyl, morpholinyl, thiomorpholinyl or piperazinyl, and wherein each of the $C_{1-4}$ alkyl, $C_{2-4}$ alkynyl, $C_{1-4}$ alkoxy, cyclopropyl, cyclobutyl, cyclopentyl, cyclohexyl, phenyl-methylene, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl and piperazinyl is independently unsubstituted or substituted with one, two, three, four or five substituents independently selected from deuterium, F, Cl, Br, OH, $C_{1-4}$ alkyl, $(CH_3)_2$NC(=O)—, $(CH_2CH_3)_2$NC(=O)—, $CH_3CH_2N(CH_3)$C(=O)—, $C_{1-4}$ alkoxy, HOOC—$(CR^7R^8)_h$— and $C_{1-4}$ alkoxy-$(CR^7R^8)_n$—O—;

wherein $R^7$, $R^8$, h and n are as defined herein.

In other aspect, provided herein is a pharmaceutical composition comprising the compound disclosed herein and one or more pharmaceutically acceptable adjuvants.

In some embodiments, the pharmaceutical composition disclosed herein further comprises one or more other anti-HBV drugs.

In some embodiments of the pharmaceutical composition disclosed herein, wherein the other anti-HBV drug is an HBV polymerase inhibitor, immunomodulator or interferon.

In some embodiments of the pharmaceutical composition, wherein the other anti-HBV drug is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, Euforavac, rintatolimod, Phosphazid, Heplisav, interferon α-2b, levamisole, or propagermanium.

In another aspect, also provided herein is use of the compound or the pharmaceutical composition disclosed herein in the manufacture of a medicament for preventing, treating or lessening a virus disease in a patient.

In some embodiments of the use, wherein the virus disease disclosed herein is hepatitis B infection or a disease caused by hepatitis B infection.

In other embodiments of the use, the disease caused by hepatitis B infection disclosed herein is hepatic cirrhosis or hepatocellular carcinogenesis.

In other aspect, provided herein is use of the compound or the pharmaceutical composition in the manufacture of a medicament for preventing, treating or lessening an HBV disease in a patient, comprising administering to the patient a therapeutically effective amount of the compound or the pharmaceutical composition of the invention.

In other aspect, provided herein is a method of preventing, treating or lessening an HBV disease in a patient, comprising administering a therapeutically effective amount of a pharmaceutically acceptable effective amount of the compound to a patient.

In other aspect, provided herein is a method of preventing, managing, treating or lessening an HBV disease in a patient, comprising administering a therapeutically effective amount of a pharmaceutically acceptable effective amount of the composition of the compound disclosed herein to a patient.

In other aspect, provided herein is the compound disclosed herein for use in preventing, managing or treating an HBV disease in a patient, and lessening the severity thereof.

In other aspect, provided herein is the composition containing the compound disclosed herein for use in preventing, managing or treating an HBV disease in a patient, and lessening the severity thereof.

In other aspect, provided herein is a method of inhibiting HBV infection, comprising contacting cells with an effective amount of the compound or the composition to HBV. In other some embodiments, the method further comprises contacting cells with other anti-HBV therapeutic agent.

In other aspect, the present invention relates to a method of treating an HBV disease in a patient, comprising administrating a therapeutically effective amount of the compound or composition thereof to a patient. In other some embodiments, the method further comprises administrating a therapeutically effective amount of other anti-HBV therapeutic agent.

In other aspect, the present invention relates to a method of inhibiting an HBV infection in a patient, comprising administrating a therapeutically effective amount of the compound or composition thereof to a patient. In other some embodiments, the method further comprises administrating a therapeutically effective amount of other anti-HBV therapeutic agent.

In other aspect, provided herein is a method of preparing, separating or purifying the compound of Formula (I) or Formula (Ia).

The foregoing merely summarizes certain aspects disclosed herein and is not intended to be limiting in nature. These aspects and other aspects and embodiments are described more fully below.

DETAILED DESCRIPTION OF THE INVENTION

Definitions and General Terminology

Reference will now be made in detail to certain embodiments of the invention, examples of which are illustrated in the accompanying structures and formulas. The invention is intended to cover all alternatives, modifications, and equivalents that may be included within the scope disclosed herein as defined by the claims. One skilled in the art will recognize many methods and materials similar or equivalent to those described herein, which could be used in the practice of the present invention. The present invention is in no way limited to the methods and materials described herein. In the event that one or more of the incorporated literature, patents, and similar materials differs from or contradicts this application, including but not limited to defined terms, term usage, described techniques, or the like, this application controls.

As used herein, the following definitions shall be applied unless otherwise indicated. For purposes disclosed herein, the chemical elements are identified in accordance with the Periodic Table of the Elements, CAS version, and the Handbook of Chemistry and Physics, 75 th Ed. 1994. Additionally, general principles of organic chemistry are described in Sorrell et al., "Organic Chemistry", University Science Books, Sausalito: 1999, and "March's Advanced Organic Chemistry", by Michael B. Smith and Jerry March, John Wiley & Sons, New York: 2007, all of which are incorporated herein by reference in their entireties.

As described herein, compounds disclosed herein may optionally be substituted with one or more substituents, such as are illustrated generally below, or as exemplified by particular classes, subclasses, and species of the invention. In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. Wherein the substituent may be, but are not limited to, deuterium, F, Cl, Br, OH, $C_{1-8}$ alky, $C_{1-8}$ alkoxy, HOOC—$(CR^7R^8)_q$— or $C_{1-8}$ alkoxy-$(CR^7R^8)_k$—O—, and wherein q, k, $R^7$ and $R^8$ are as defined herein.

At various places in the present specification, substituents of compounds disclosed herein are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "alkyl" or "alkyl group" refers to a saturated linear or branched-chain monovalent hydrocarbon radical of 1 to 20 carbon atoms, wherein the alkyl radical may be optionally and independently substituted with one or more substituents described herein. In some embodiments, the alkyl group contains 1-12 carbon atoms. In other embodiments, the alkyl group contains 1-10 carbon atoms. In other embodiments, the alkyl group contains 1-8 carbon atoms. In still other embodiments, the alkyl group contains 1-6 carbon atoms. In yet other embodiments, the alkyl group contains 1-4 carbon atoms and in still yet other embodiments, the alkyl group contains 1-3 carbon atoms. Some non-limiting examples of the alkyl group further include, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), isobutyl (i-Bu, —$CH_2CH(CH_3)_2$), sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$ 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_{2,3}CH(CH_3)_2$), 3,3-dimethyl-2-butyl (—$CH(CH_3)C(CH_{3,3})_3$, n-heptyl and n-octyl, etc.

The term "alkylene" refers to a saturated divalent or multivalent hydrocarbon group derived from a straight or branched chain saturated hydrocarbon by the removal of two or multi hydrogen atoms. Unless otherwise specified, the alkylene group contains 1-12 carbon atoms. In some embodiments, the alkylene group contains 1-6 carbon atoms. In other embodiments, the alkylene group contains 1-4 carbon atoms. In still other embodiments, the alkylene group contains 1-3 carbon atoms. In yet other embodiments, the alkylene group contains 1-2 carbon atoms. And the alkylene group are exemplified by, but not limited to, methylene (—$CH_2$—), ethylene (—$CH_2CH_2$—), isopropylene (—$CH(CH_3)CH_2$—), and the like.

The term "hydroxyalkyl" or "hydroxyalkoxy" refers to alkyl or alkoxy, as the case may be, substituted with one or more hydroxy groups. Wherein some non-limiting examples of the hydroxyalkyl group include hydroxymethyl (—$CH_2OH$), hydroxyethyl (—$CH_2CH_2OH$, —$CHOHCH_3$), hydroxypropyl (—$CH_2CH_2CH_2OH$, —$CH_2CHOHCH_3$, —$CHOHCH_2CH_3$), hydroxymethoxy (—$OCH_2OH$), and the like.

The terms "haloalkyl", "haloalkenyl" or "haloalkoxy" refer to alkyl, alkenyl, or alkoxy, as the case may be, substituted with one or more halogen atoms. Wherein the alkyl, alkenyl and alkoxy are as defined herein. Some non-limiting examples of such groups include difluoroethyl (—$CH_2CHF_2$, —$CF_2CH_3$, —$CHFCH_2F$), trifluoroethyl (—$CH_2CF_3$, —$CF_2CH_2F$, —$CFHCHF_2$), trifluoromethyl (—$CF_3$), trifluoromethoxy (—$OCF_3$), fluoroethenyl (—$CH=CHF$, —$CF=CH_2$), and the like.

The term "alkenyl" refers to a linear or branched chain monovalent hydrocarbon radical of 2 to 12 carbon atoms, wherein at least one carbon-carbon bond is $sp^2$ double bond, wherein the alkenyl radical may be independently and optionally substituted with one or more substituents described herein, and includes radicals having "cis" and "trans" orientations, or alternatively, "E" and "Z" orientations. Examples of the alkenyl group include, but are not limited to, vinyl (—$CH=CH_2$), allyl (—$CH_2CH=CH_2$), and the like.

The term "alkoxy" refers to an alkyl group, as previously defined, attached to the parent molecular moiety via an oxygen atom. Unless otherwise specified, the alkoxy group contains 1-12 carbon atoms. In some embodiments, the alkoxy group contains 1-8 carbon atoms. In other embodiments, the alkoxy group contains 1-6 carbon atoms. In still other embodiments, the alkoxy group contains 1-4 carbon atoms. In yet other embodiments, the alkoxy group contains 1-3 carbon atoms. The alkoxy group may be optionally substituted with one or more substituents disclosed herein.

Some non-limiting examples of the alkoxy group include, but are not limited to, methoxy (MeO, —$OCH_3$), ethoxy (EtO, —$OCH_2CH_3$), 1-propoxy (n-PrO, n-propoxy, —$OCH_2CH_2CH_3$), 2-propoxy i-propoxy, —$OCH(CH_3)_2$), 1-butoxy (n-BuO, n-butoxy, —$OCH_2CH_2CH_3$), 2-methyl-1-propoxy i-butoxy, —$OCH_2CH(CH_3)_2$), 2-butoxy (s-BuO, s-butoxy, —$OCH(CH_3)CH_2CH_3$), 2-methyl-2-propoxy (t-BuO, t-butoxy, —$OC(CH_3)_3$), 1-pentoxy (n-pentoxy, —$OCH_2CH_2CH_2CH_2CH_3$), 2-pentoxy (—$OCH(CH_3)CH_2CH_2CH_3$), 3-pentoxy (—$OCH(CH_2CH_3)_2$), 2-methyl-2-butoxy (—$OC(CH_3)_2CH_2CH_3$), 3-methyl-2-butoxy (—$OCH(CH_3)CH(CH_3)_2$), 3-methyl-1-butoxy (—$OCH_2CH_2CH(CH_3)_2$), 2-methyl-1-butoxy (—$OCH_2CH(CH_3)CH_2CH_3$), and the like.

The term "alkynyl" refers to a linear or branched chain monovalent hydrocarbon radical of 2 to 12 carbon atoms, with at least one site of unsaturation, i.e., a carbon-carbon, sp triple bond, wherein the alkynyl radical is optionally substituted independently with one or more substituents described herein, in some embodiments, the alkynyl group contains 2 to 12 carbon atoms, in other embodiments, the alkynyl group contains 2 to 8 carbon atoms, in other embodiments, the alkynyl group contains 2 to 6 carbon atoms, in other embodiments, the alkynyl group contains 2 to 4 carbon atoms. Some specific examples include, but are not limited to, ethynyl (—C≡CH), propargyl (—$CH_2C≡CH$), propinyl (—C≡C—$CH_3$), butynyl (—$CH_2CH_2C≡CH$, —$CH_2C≡CCH_3$, —C≡$CCH_2CH_3$ and —CH($CH_3$)C≡CH) and pentynyl(-$CH_2CH_2CH_2C≡CH$, —$CH_2CH_2C≡CCH_3$, —$CH_2C≡CCH_2CH_3$, —C≡CCH$_2$CH$_2$CH$_3$, —CH$_2$CH(CH$_3$)C≡CH, —CH(CH$_3$)CH$_2$C≡CH, —C(CH$_3$)$_2$C≡CH, —CH(CH$_3$)C≡CCH$_3$ and —C≡CCH(CH$_3$)$_2$) and the like.

The term "cycloaliphatic", "carbocycle" and "carbocyclyl" can be used interchangeably, which refers to a monovalent or multivalent, non-aromatic, saturated or partially unsaturated ring consisting of 3-12 carbon atoms as a monocyclic ring or 7-12 carbon atoms as a bicyclic ring. Bicyclic carbocycles having 7-12 ring atoms can be arranged, for example, as a bicyclo[4,5], [5,5], [5,6] or [6,6] system, and bicyclic carbocycles having 9 or 10 ring atoms can be arranged as a bicyclo[5,6] or [6,6] system. Some non-limiting examples of the cycloaliphatic group include cycloalkyl, cycloalkenyl and cycloalkynyl. Further examples of the cycloaliphatic group include, but are not limited to, cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

The term "cycloalkyl" refers to a monovalent or multivalent saturated ring having 3 to 12 carbon atoms as a monocyclic, bicyclic, or tricyclic ring system. In some embodiments, the cycloalkyl group contains 3 to 12 carbon atoms. In other embodiments, the cycloalkyl group contains 3 to 8 carbon atoms. In other embodiments, the cycloalkyl group contains 3 to 7 carbon atoms. In still other embodiments, the cycloalkyl group contains 3 to 6 carbon atoms. The cycloalkyl group may be optionally substituted with one or more substituents disclosed herein.

The term "n-membered", where n is an integer typically describes the number of ring-forming atoms in a moiety where the number of ring-forming atoms is n. For example, piperidinyl is an example of 6-membered heterocyclyl.

The term "heterocyclyl" refers to a saturated or unsaturation, nonaromatic, monocyclic, bicyclic or tricyclic ring system in which at least one ring member is selected from nitrogen, sulfur or oxygen. Wherein, the heterocyclyl group may be optionally substituted with one or more substituents disclosed herein. Unless otherwise specified, the heterocyclyl group may be carbon or nitrogen linked, and a —CH$_2$— group can be optionally replaced by a —C(=O)— or —C(=S)— group. In which, the sulfur can be optionally oxygenized to S-oxide. And the nitrogen can be optionally oxygenized to N-oxide. In some embodiments, heterocyclyl may be 3-12 membered heterocyclyl; In some embodiments, heterocyclyl may be 5-10 membered heterocyclyl; In some embodiments, heterocyclyl may be 4-6 membered heterocyclyl; In some embodiments, heterocyclyl may be 5-6 membered heterocyclyl; In other embodiments, heterocyclyl may be 4 membered heterocyclyl. In other embodiments, heterocyclyl may be 5 membered heterocyclyl. In other embodiments, heterocyclyl may be 6 membered heterocyclyl.

Some non-limiting examples of the heterocyclyl group include pyrrolidyl, tetrahydrofuryl, dihydrofuryl, tetrahydrothienyl, tetrahydropyranyl, dihydropyranyl, tetraphydrothiopyranyl, piperidyl, morpholinyl, thiomorpholinyl, thioxanyl, piperazinyl, homopiperazinyl, azetidinyl, oxetanyl, thietanyl, homopiperidinyl, epoxypropyl, azapanyl, oxepanyl, thiepanyl, oxoazepinyl, diazepinyl, thiazepinyl, 2-pyrrolidinyl, 3-pyrrolidinyl, dihydroindolyl, 2H-pyranyl, 4H-pyranyl, dioxanyl, 1,3-dioxolanyl, pyrrazolidyl, dithianyl, dithiolanyl, dihydrothienyl, pyrazolidyl, imidazolinyl, imidazolidinyl, 1,2,3,4-tetrahydroisoquinolinyl, 3-azabicyclo[3.1.0]hexyl, 3-azabicyclo[4.1.0]heptyl, azabicyclo[2.2.2]hexyl, 3H-indolyl, quinolyl and N-pyridyl. Examples of the heterocyclyl group also include 1,1-dioxothiomorpholinyl, some examples, of which carbon atom replaced with oxo (=O), include but are not limited to pyrimidinyldione, 1,2,4-thiadiazolyl-5(4H)-one, 1,2,4-oxadiazolyl-5(4H)-one, 1H-1,2,4-triazolyl-5(4H)-one, and the like, some examples, of which carbon atom replaced with =S, include but are not limited to 1,2,4-oxadiazolyl-5(4H)-thione, 1,3,4-oxadiazolyl-2(3H)-thione, and the like.

The term "heterocyclylalkyl" or "heterocyclylalkylene" can be used interchangeably, which refers to heterocyclyl-substituted alkyl. Examples of such groups include, but are not limited to, pyrrolidin-2-ylmethyl, morpholin-4-ylmethyl, and the like.

The term "heterocyclylalkoxy" refers to heterocyclyl-substituted alkoxy, attached to the rest of molecular through an oxygen atom. Examples of such groups include, but are not limited to, pyrrolidin-2-ylmethoxy, morpholin-4-ylethoxy, and the like.

The term "heterocyclylalkylamino" refers to heterocyclyl-substituted alkylamino, attached to the rest of molecular through a nitrogen atom. Wherein the heterocyclyl, alkyl and alkylamino are defined as the invention described herein. Examples of such groups include, but are not limited to, 2-morpholin-ethylamino, and the like.

The term "heteroatom" refers to one or more of oxygen, sulfur, nitrogen, phosphorus and silicon, including any oxidized form of nitrogen, sulfur, or phosphorus; the primary, secondary, tertiary or quaternary ammonium salts; or a substitutable nitrogen of a heterocyclic ring, for example, N (as in 3,4-dihydro-2H-pyrrolyl), NH (as in pyrrolidinyl) or NR (as in N-substituted pyrrolidinyl).

The term "halogen" or "halo" or "halogen atom" refers to F (fluorine), Cl (chlorine), Br (bromine), or I (iodine).

The term "unsaturated" refers to a moiety having one or more units of unsaturation.

The term "aryl" refers to monocyclic, bicyclic and tricyclic carbocyclic ring systems having a total of six to fourteen ring members, or six to twelve ring members, or six to ten ring members, wherein at least one ring in the system is aromatic, wherein each ring in the system contains 3 to 7 ring members and that has a single point or multipoint of attachment to the rest of the molecule. The term "aryl" and "aromatic ring" can be used interchangeably herein. Examples of aryl ring may include phenyl, naphthyl and anthryl. The aryl group may be optionally and independently substituted with one or more substituents disclosed herein.

The term "heteroaryl" refers to monocyclic, bicyclic and tricyclic ring systems having a total of 5 to 12 ring members, or 5 to 10 ring members, or 9 to 10 ring members, or 9 ring members, or 5 to 6 ring members, wherein at least one ring in the system is aromatic, and in which at least one ring member is selected from heteroatom, and wherein each ring in the system contains 5 to 7 ring members and that has a single point or multipoint of attachment to the rest of the molecule. The term "heteroaryl" and "heteroaromatic ring" or "heteroaromatic compound" can be used interchangeably herein. In some embodiments, the heteroaryl group is a 5- to 12-membered heteroaryl comprising 1, 2, 3 or 4 heteroatoms independently selected from O, S and N. In other embodiments, the heteroaryl group is a 5- to 10-membered heteroaryl comprising 1, 2, 3 or 4 heteroatoms independently selected from O, S and N. In other embodiments, the heteroaryl group is a 9- to 10-membered heteroaryl comprising 1, 2, 3 or 4 heteroatoms independently selected from O, S and N. In other embodiments, the heteroaryl group is a 9-membered heteroaryl comprising 1, 2, 3 or 4 heteroatoms independently selected from O, S and N. In other embodiments, the heteroaryl group is a 5- to 6-membered heteroaryl comprising 1, 2, 3 or 4 heteroatoms independently selected from O, S and N. And the heteroaryl group may be substituted or unsubstituted, wherein the substituents may be, but are not limited to, deuterium, F, Cl, Br, OH, $C_{1-8}$ alky, $C_{1-8}$ alkoxy, HOOC—$(CR^7R^8)_q$— or $C_{1-8}$ alkoxy-$(CR^7R^8)_k$—O—, and wherein q, k, $R^7$ and $R^8$ are as defined herein.

Some non-limiting examples of the heteroaryl group include the following monocyclic ring, 1,2,4-oxadiazolyl-5 (4H)-thione, 1,2,4-thiadiazolyl-5(4H)-one, 1,2,4-oxadiazolyl-5(4H)-one, 1,3,4-oxadiazolyl-2(3H)-thione, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl, 5-triazolyl), 2-thienyl, 3-thienyl, pyranyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, diazolyl, thiadiazolyl triazinyl, and the following bicycles, but are not limited to: benzothiazolyl, benzimidazolyl, benzofuryl, benzothiophenyl, indolyl (e.g., 2-indolyl), purinyl, quinolinyl (e.g., 2-quinolinyl, 3-quinolinyl, 4-quinolinyl), isoquinolinyl (e.g., 1-isoquinolinyl, 3-isoquinolinyl or 4-isoquinolinyl), and the like.

The term "heteroarylalkyl" and "heteroarylalkylene" can be used interchangeably, which refers to an alkyl group substituted with one or more same or different heteroaryl groups, wherein the alkyl group and heteroaryl group are as defined herein. Some non-limiting examples of the heteroarylalkyl group include (pyrid-2-yl)ethyl, (thiazol-2-yl) methyl, (imidazol-2-yl)ethyl, (pyrimidin-2-yl)propyl, and the like.

The term "aralkyl" or "arylalkyl" can be used interchangeably, which refers to aryl-substituted alkyl, wherein the aryl and the alkyl are as defined herein. In some embodiments, the aralkyl or arylalkyl radical refers to a "lower aralkyl" radical, i.e. aryl attaches to $C_{1-6}$ alkyl. In other embodiments, aralkyl or arylalkyl refers to phenyl attaches to $C_{1-3}$ alkyl. Specific examples include phenylmethyl (i.e. benzyl), diphenylmethyl, phenylethyl, and the like. And aryl of the arylalkyl may be further substituted with the substituent selected from deuterium, F, Cl, Br, OH, $C_{1-8}$ alky, $C_{1-8}$ alkoxy, HOOC—$(CR^7R^8)_q$— or $C_{1-8}$ alkoxy-$(CR^7R^8)_k$—O—, and wherein q, k, $R^7$ and $R^8$ are as defined herein.

The term "alkylamino" refers to "N-alkylamino" and "N,N-dialkylamino" wherein amino groups are independently substituted with one alkyl radical or two alkyl radicals, respectively. In some embodiments, the alkylamino group is lower alkylamino group having one or two $C_{1-12}$ alkyl groups attached to nitrogen atom. In other embodiments, the alkylamino group is lower alkylamino group having one or two $C_{1-6}$ alkyl groups attached to nitrogen atom. In other embodiments, the alkylamino group is lower alkylamino group having one or two $C_{1-4}$ alkyl groups attached to nitrogen atom. In other embodiments, the alkylamino group is lower alkylamino group having one or two $C_{1-3}$ alkyl groups attached to nitrogen atom. Some non-limiting examples of suitable alkylamino radical include mono or dialkylamino. Some examples include, but not limited to, N-methylamino, N-ethylamino, N,N-dimethylamino and N,N-diethylamino, and the like.

The term "cycloalkylalkyl" and "cycloalkylalkylene" can be used interchangeably, which refers to an alkyl group substituted with one or more the same or different cycloalkyl groups, wherein the alkyl and cycloalkyl groups are as defined herein. Some non-limiting examples of such group include cyclohexylmethylene, cyclopropylethylene, etc.

The term "alkoxyalkyl" and "alkoxyalkylene" can be used interchangeably, which refers to an alkyl group substituted with one or more the same or different alkoxy groups, wherein the alkoxy and alkyl groups are as defined herein. Some non-limiting examples of such group include methoxymethyl, methoxyethyl, ethoxymethyl, etc.

As described herein, a bond drawn from a substituent to the center of one ring within a ring system (as shown in Formula b) represents substitution of the substituent at any substitutable or reasonable position on the ring, and optionally including any substitution case on an enantiomer, for example, as shown as formula b, c, d, e, f, g and h.

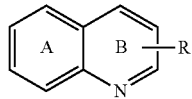

Formula a

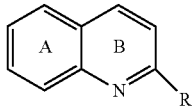

Formula b

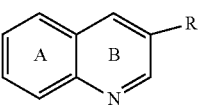

Formula c

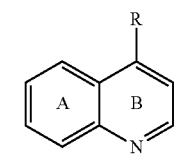

Formula d

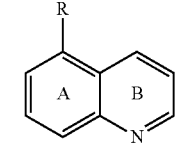

Formula e

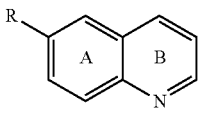

Formula f

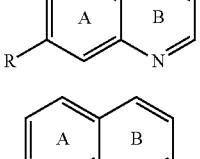

Formula g

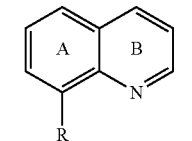

Formula h

Furthermore, unless otherwise stated, the phrase "each . . . is independently" is used interchangeably with the phrase "each (of) . . . and . . . is independently". It should be understood broadly that the specific options expressed by the same symbol are independently of each other in different radicals; or the specific options expressed by the same symbol are independently of each other in same radicals. Such as Formula (p), specific options of $R^9$ are not affect each other between multiple $R^9$.

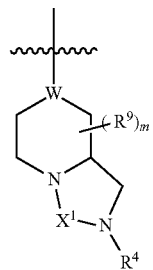

Formula p

As described herein, a system may have two attachment points attached to the rest of the molecule, for example, Formula q represents that it may connect with the rest of the molecule through either E or E, i.e. the two connect manners are interchangeable with each other in the case of reasonable molecular structure.

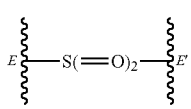

Formula q

Unless otherwise stated, structures depicted herein are also meant to include all isomeric (e.g., enantiomeric, diastereomeric, and geometric (conformational isomerism)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, or geometric mixtures of the present compounds are within the scope disclosed herein.

The term "prodrug" refers to a compound that is transformed in vivo into a compound of Formula (I). Such a transformation can be affected, for example, by hydrolysis of the prodrug form in blood or enzymatic transformation to the parent form in blood or tissue. Prodrugs of the compounds disclosed herein may be, for example, esters. Some common esters which have been utilized as prodrugs are phenyl esters, aliphatic ($C_1$-$C_{24}$) esters, acyloxymethyl esters, carbonates, carbamates and amino acid esters. For example, a compound disclosed herein that contains a hydroxy group may be acylated at this position in its prodrug form. Other prodrug forms include phosphates, such as, those phosphate compounds derived from the phosphonation of a hydroxy group on the parent compound. A thorough discussion of prodrugs is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, Nature Review Drug Discovery, 2008, 7, 255-270, and S. J. Hecker et al., Prodrugs of Phosphates and Phosphonates, Journal of Medicinal Chemistry, 2008, 51, 2328-2345, all of which are incorporated herein by reference in their entireties.

Unless otherwise stated, all tautomeric forms of the compounds disclosed herein are within the scope of the invention. Additionally, unless otherwise stated, structures depicted herein are also meant to include compounds that differ only in the presence of one or more isotopically enriched atoms.

A "metabolite" is a product produced through metabolism in the body of a specified compound or salt thereof. The metabolites of a compound may be identified using routine techniques known in the art and their activities determined using tests such as those described herein. Such products may result for example from oxidation, reduction, hydrolysis, amidation, deamidation, esterification, deesterification, enzyme cleavage, and the like, of the administered compound. Accordingly, the invention includes metabolites of compounds disclosed herein, including metabolites produced by contacting a compound disclosed herein with a mammal for a sufficient time period.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds disclosed herein may contain asymmetric or chiral centers, and therefore exist in different stereoisomeric forms. It is intended that all stereoisomeric forms of the compounds disclosed herein, including, but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The term "racemic mixture" or "racemate" refers to an equimolar mixture of two enantiomeric species, devoid of optical activity.

The term "tautomer" or "tautomeric form" refers to structural isomers of different energies which are interconvertible via a low energy barrier. Some non-limiting examples of proton tautomers (also known as prototropic tautomers) include interconversions via migration of a proton, such as keto-enol and imine-enamine isomerizations. Valence tautomers include interconversions by reorganization of some of the bonding electrons. Unless otherwise stated, all tautomeric forms of the compounds disclosed herein are within the scope of the invention.

A "pharmaceutically acceptable salt" refers to organic or inorganic salts of a compound disclosed herein. Pharmaceutically acceptable salts are well known in the art. For example, Berge et al., describe pharmaceutically acceptable salts in detail in J. Pharmacol Sci, 1977, 66:1-19, which is incorporated herein by reference. Some non-limiting examples of pharmaceutically acceptable and nontoxic salts include salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid and malonic acid or by using other methods used in the art such as ion exchange. Other pharmaceutically acceptable salts include adipate, 2-hydroxy propionate, alginate, ascorbate, aspartate, benzenesulfonate, benzoate, bisulfate, borate, butyrate, camphorate, camphorsulfonate, cyclopentanepropionate, digluconate, dodecylsulfate, ethanesulfonate, formate, fumarate, glucoheptonate, glycerophosphate, gluconate, hemisulfate, heptanoate, hexanoate, hydro iodide, 2-hydroxy-ethanesulfonate, lactobionate, lactate, laurate, laurylsulfate, malate, malonate, methanesulfonate, 2-naphthalenesulfonate, nicotinate, nitrate, oleate, palmitate, pamoate, pectinate, persulfate, 3-phenylpropionate, picrate, pivalate, propionate, stearate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. This invention also envisions the quaternization of any basic nitrogen-containing groups of the compounds disclosed herein. Water or oil soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate or aryl sulfonate.

The term "solvate" refers to an association or complex of one or more solvent molecules and a compound disclosed herein. Some non-limiting examples of the solvent that form solvates include water, isopropanol, ethanol, methanol, dimethylsulfoxide (DMSO), ethyl acetate, acetic acid and ethanolamine. The term "hydrate" refers to the complex where the solvent molecule is water.

The term "protecting group" or "PG" refers to a substituent that is commonly employed to block or protect a particular functionality while reacting with other functional groups on the compound. For example, an "amino-protecting group" is a substituent attached to an amino group that blocks or protects the amino functionality in the compound. Suitable amino-protecting groups include acetyl, trifluoroacetyl, t-butoxy-carbonyl (BOC, Boc), benzyloxycarbonyl (CBZ, Cbz) and 9-fluorenylmethylenoxy-carbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —CH$_2$CH$_2$SO$_2$Ph, cyanoethyl, 2-(trimethylsilyl)ethyl, 2-(trimethylsilyl) ethoxy-methy-1, 2-(p-toluenesulfonyl) ethyl, 2-(p-nitrophenylsulfenyl)-ethyl, 2-(diphenylphosphino)-ethyl, nitroethyl and the like. For a general description of protecting groups and their use, see T. W. Greene, Protective Groups in Organic Synthesis, John Wiley & Sons, New York, 1991; and P. J. Kocienski, Protecting Groups, Thieme, Stuttgart, 2005.

DESCRIPTION OF COMPOUNDS OF THE INVENTION

The compound and the pharmaceutically acceptable composition thereof of the present invention all can inhibit HBV infection effectively.

In one aspect, provided herein is a compound having Formula (I) or Formula (Ia) or a stereoisomer, a tautomer, an N-oxide, a solvate, a metabolite, a pharmaceutically acceptable salt or a prodrug thereof;

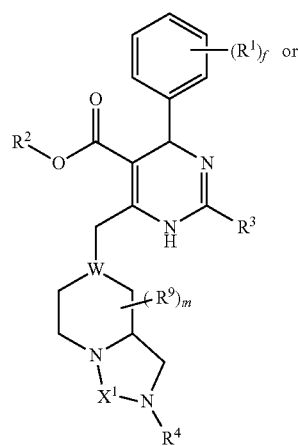

(I)

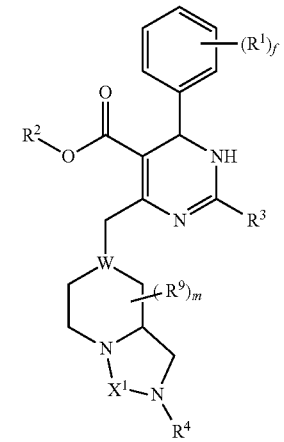

(Ia)

wherein each $R^1$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl;

each $R^2$ is independently $C_{1-6}$ alkyl, $C_{1-6}$ haloalkyl, $C_{3-6}$ cycloalkyl-$C_{1-6}$ alkylene or 5 to 6 membered heterocyclyl-$C_{1-6}$ alkylene;

each $R^3$ is independently $C_{6-10}$ aryl or 5-6 membered heteroaryl, wherein each of the $C_{6-10}$ aryl or 5-6 membered heteroaryl is independently unsubstituted or substituted with one, two, three, four or five substituents independently selected from deuterium, F, Cl, Br, OH, CN, $C_{1-6}$ alkyl, hydroxy-$C_{1-6}$ alkyl, $C_{1-6}$ alkyl-OC(=O)—, $C_{1-6}$ alkyl-OC(=O)—$C_{1-6}$ alkylene, HOOC—$C_{1-6}$ alkylene, $C_{1-6}$ alkoxy-$C_{1-6}$ alkylene and $C_{1-6}$ alkyl-S(=O)$_2$—;

each W is independently CH or N;

each $X^1$ is independently —C(=O)—, —S(=O)$_2$—, —(O=)P(OH)— or —(CR$^7$R$^8$)$_j$—;

each $R^4$ is independently —(CR$^7$R$^8$)$_j$—R$^5$-L-R$^6$;

$R^5$ is 3-12 membered heterocyclyl, $C_{3-7}$ cycloalkyl, $C_{2-12}$ alkynyl, 5-12 membered heteroaryl or $C_{6-10}$ aryl, wherein each of the 3-12 membered heterocyclyl, $C_{3-7}$ cycloalkyl, $C_{2-12}$ alkynyl, 5-12 membered heteroaryl and $C_{6-10}$ aryl is independently unsubstituted or substituted with one, two, three, four or five substituents independently selected from deuterium, F, Cl, Br, OH, CN, $C_{1-6}$ alkoxy, $C_{1-6}$ alkyl, HOOC—$(CR^7R^8)_h$— and $C_{1-6}$ alkoxy-C(=O)—;

$R^6$ is 3-12 membered heterocyclyl, $C_{3-7}$ cycloalkyl, $C_{2-12}$ alkynyl, 5-12 membered heteroaryl or $C_{6-10}$ aryl, wherein each of the 3-12 membered heterocyclyl, $C_{3-7}$ cycloalkyl, $C_{2-12}$ alkynyl, 5-12 membered heteroaryl and $C_{6-10}$ aryl is independently unsubstituted or substituted with one, two, three, four or five $R^w$;

L is a single bond, —O—, —S(=O)$_j$—, —C(=O)—, —NH—, —$(CR^7R^8)_j$— or —O—$(CR^7R^8)_j$—;

each $R^w$ is independently deuterium, F, Cl, Br, OH, CN, HOOC—$(CR^7R^8)_h$—, $R^eR^dP(=O)$—, $R^{10}$—S(=O)$_t$—, $R^{12}$—$(CR^7R^8)_j$—, amino, $C_{1-12}$ alkoxy, $C_{3-7}$ cycloalkyl, $C_{1-8}$ alkoxy-$(CR^7R^8)_n$—O—, $C_{1-8}$ alkyl, hydroxy-$C_{1-8}$ alkyl, $C_{2-12}$ alkynyl, $C_{6-10}$ aryl, 3-10 membered heterocyclyl or 5-10 membered heteroaryl, wherein each of the amino, $C_{1-12}$ alkoxy, $C_{3-7}$ cycloalkyl, $C_{1-8}$ alkoxy of $C_{1-8}$ alkoxy-$(CR^7R^8)_n$—O—, $C_{1-8}$ alkyl, hydroxy $C_{1-8}$ alkyl, $C_{2-12}$ alkynyl, $C_{6-10}$ aryl, 3-10 membered heterocyclyl and 5-10 membered heteroaryl is independently unsubstituted or substituted with one, two, three, four or five $R^x$;

each $R^{10}$ and $R^{11}$ is independently $R^aR^bN$—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five $R^y$;

each $R^{12}$ is independently OH, HOOC—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five $R^z$;

each $R^{13}$ is independently $C_{1-8}$ alkyl, $C_{3-7}$ cycloalkyl, 5-10 membered heteroaryl, $C_{6-10}$ aryl or 5-10 membered heterocyclyl, wherein each of the $C_{1-8}$ alkyl, $C_{3-7}$ cycloalkyl, 5-10 membered heteroaryl, $C_{6-10}$ aryl and 5-10 membered heterocyclyl is independently unsubstituted or substituted with one, two, three, four or five $R^g$;

each $R^x$, $R^y$, $R^z$ and $R^g$ is independently deuterium, F, Cl, Br, OH, CN, HOOC—$(CR^7R^8)_h$—, $R^{14}C(=O)$—, $R^cR^dP(=O)$—, $R^{15}$—S(=O)$_t$—, $R^{16}O$—, $R^{17}$—$(CR^7R^8)_j$—, amino, $C_{1-2}$ alkoxy, $C_{3-7}$ cycloalkyl, $C_{1-8}$ alkoxy-$(CR^7R^8)_n$—O—, $C_{1-8}$ alkyl, hydroxy-$C_{1-8}$ alkyl, $C_{2-12}$ alkynyl, $C_{6-10}$ aryl, 3-12 membered heterocyclyl or 5-10 membered heteroaryl, wherein each of the amino, $C_{1-12}$ alkoxy, $C_{3-7}$ cycloalkyl, $C_{1-8}$ alkoxy of $C_{1-8}$ alkoxy-$(CR^7R^8)_n$—O—, $C_{1-8}$ alkyl, hydroxy-$C_{1-8}$ alkyl, $C_{2-12}$ alkynyl, $C_{6-10}$ aryl, 3-12 membered heterocyclyl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, hydroxy-$C_{1-8}$ alkyl, HOOC—$(CR^7R^8)_h$— and $C_{1-8}$ alkoxy-$(CR^7R^8)_n$—O—;

each $R^{14}$ and $R^{15}$ is independently $R^aR^bN$—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, HOOC—$(CR^7R^8)_h$— and $C_{1-8}$ alkoxy-$(CR^7R^8)_n$—O—;

each $R^{17}$ is independently OH, HOOC—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, alkoxy, $C_{3-7}$ cycloalkyl, 3-12 membered heterocyclyl, $C_{6-10}$ aryl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, HOOC—$(CR^7R^8)_h$— and $C_{1-8}$ alkoxy-$(CR^7R^8)_n$—O—;

each $R^{16}$ is independently $C_{1-8}$ alkyl, $C_{3-7}$ cycloalkyl, 5-10 membered heteroaryl, $C_{6-10}$ aryl or 5-10 membered heterocyclyl, wherein each of the $C_{1-8}$ alkyl, $C_{3-7}$ cycloalkyl, 5-10 membered heteroaryl, $C_{6-10}$ aryl and 5-10 membered heterocyclyl is independently unsubstituted or substituted with one, two, three, four or five substituents independently selected from deuterium, F, Cl, Br, OH, $C_{1-8}$ alkoxy, $C_{1-8}$ alkyl, HOOC—$(CR^7R^8)_h$— and $C_{1-8}$ alkoxy-$(CR^7R^8)_n$—O—;

each $R^a$, $R^b$, $R^c$ and $R^d$ is independently H, deuterium, $C_{1-8}$ alkyl, $C_{2-8}$ alkynyl, $C_{1-8}$ alkoxy, $C_{3-7}$ cycloalkyl, HOOC—$(CR^7R^8)_h$—, $C_{6-10}$ aryl-$C_{1-4}$ alkylene or 3-12 membered heterocyclyl, wherein each of the $C_{1-8}$ alkyl, $C_{2-8}$ alkynyl, $C_{1-8}$ alkoxy, $C_{3-7}$ cycloalkyl, $C_{6-10}$ aryl of $C_{6-10}$ aryl-$C_{1-4}$ alkylene and 3-12 membered heterocyclyl is independently unsubstituted or substituted with one, two, three, four or five substituents independently selected from deuterium, F, Cl, Br, OH, $C_{1-8}$ alkyl, $(C_{1-6}$ alkyl$)_2$NC(=O)—, $C_{1-8}$ alkoxy, HOOC—$(CR^7R^8)_h$— and $C_{1-8}$ alkoxy-$(CR^7R^8)_{11}$—O—;

each $R^7$, $R^8$ and $R^9$ is independently H, deuterium, F, Cl, Br, $C_{1-6}$ alkyl, $NH_2C(=O)$—, $C_{1-6}$ alkyl-OC(=O)—, carboxy, carboxy-$C_{1-6}$ alkylene, hydroxy-$C_1$ alkyl or $C_{1-6}$ haloalkyl, or $R^7$ and $R^8$, together with the carbon atom to which they are attached, form $C_{3-6}$ cycloalkyl or carbonyl;

each f, m and h is independently 0, 1, 2, 3, or 4;

each n is independently 1, 2, 3 or 4;

each t is independently 0, 1 or 2;

each j is independently 0, 1, 2 or 3.

In some embodiments, provided herein is a compound having Formula (II) or Formula (IIa):

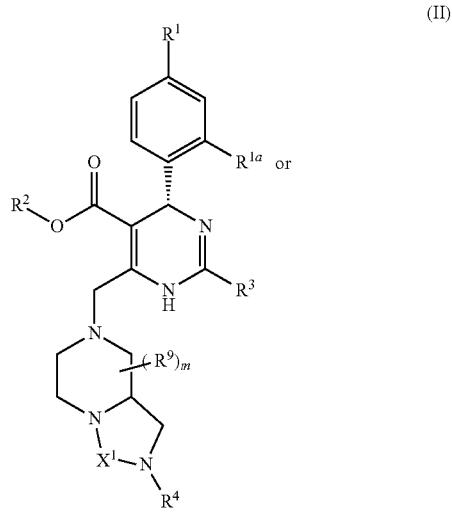

-continued (IIa)

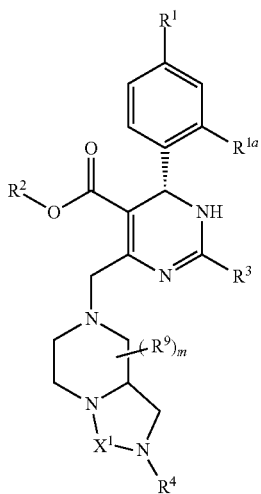

wherein each $R^1$ and $R^{1a}$ is independently H, deuterium, F, Cl, Br, I, cyano, methyl, ethyl, methoxy, ethoxy, methylamino, ethylamino, nitro, 4-trifluoromethylphenyl, 3,5-di(trifluoromethyl)phenyl or trifluoromethyl; each $R^2$, $R^3$, $R^9$, $R^4$, $X^1$ and m is as defined herein.

In some embodiments, each $R^2$ is independently methyl, ethyl, n-propyl, i-propyl, $C_{1-4}$ haloalkyl, $C_{3-6}$ cycloalkyl-$C_{1-3}$ alkylene or 5-6 membered heterocyclyl-$C_{1-3}$ alkylene;

$R^3$ is phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl or pyrimidinyl, wherein each of the phenyl, furyl, pyrrolyl, pyridyl, pyrazolyl, imidazolyl, triazolyl, tetrazolyl, oxazolyl, oxadiazolyl, 1,3,5-triazinyl, thiazolyl, thienyl, pyrazinyl, pyridazinyl and pyrimidinyl is independently unsubstituted or substituted with one, two, three, four or five substituents independently selected from deuterium, F, Cl, Br, OH, CN, $C_{1-4}$ alkyl, hydroxy-$C_{1-4}$ alkyl, $C_{1-4}$ alkyl-OC(=O)—, $C_{1-4}$alkyl-OC(=O)—$C_{1-3}$ alkylene, HOOC—$C_{1-6}$ alkylene, $C_{1-4}$alkoxy-$C_{1-3}$ alkylene or $C_{1-4}$ alkyl-S(=O)$_2$—;

each $R^7$, $R^8$ and $R^9$ is independently H, deuterium, F, Cl, Br, methyl, ethyl, n-propyl, i-propyl, $NH_2C(=O)$—, $C_{1-4}$ alkyl-OC(=O)—, carboxy, carboxy-$C_{1-3}$ alkylene, hydroxy-$C_{1-4}$ alkyl or $C_{1-4}$ haloalkyl, or $R^7$ and $R^8$, together with the carbon atom to which they are attached, form cyclopropyl, cyclobutyl, cyclopentyl, cyclohexyl or carbonyl;

In some embodiments, $R^5$ is 5-10 membered heterocyclyl, $C_{3-6}$ cycloalkyl, $C_{2-8}$alkynyl, 5-10 membered heteroaryl, phenyl or naphthyl, wherein each of the 5-10 membered heterocyclyl, $C_{3-6}$ cycloalkyl, $C_{2-8}$ alkynyl, 5-10 membered heteroaryl, phenyl and naphthyl is independently unsubstituted or substituted with one, two, three, four or five substituents independently selected from deuterium, F, Cl, Br, OH, CN, $C_{1-4}$ alkoxy, $C_{1-4}$ alkyl, HOOC—$(CR^7R^8)_h$— and $C_{1-4}$ alkoxy-C(=O)—;

$R^6$ is 5-10 membered heterocyclyl, $C_{3-6}$ cycloalkyl, $C_{2-8}$alkynyl, 5-10 membered heteroaryl, phenyl or naphthyl, wherein each of the 5-10 membered heterocyclyl, $C_{3-6}$ cycloalkyl, $C_{2-8}$ alkynyl, 5-10 membered heteroaryl, phenyl and naphthyl is independently unsubstituted or substituted with one, two, three, four or five $R^w$.

In some embodiments, $R^5$ is 5-6 membered heterocyclyl, $C_{3-6}$ cycloalkyl, $C_{2-6}$ alkynyl, 5-6 membered heteroaryl, 9-10 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, 9-10 membered heteroaryl, phenyl and naphthyl is independently unsubstituted or substituted with one, two, three, four or five substituents independently selected from deuterium, F, Cl, Br, OH, CN, $C_{1-3}$ alkoxy, $C_{1-3}$ alkyl, HOOC—$(CR^7R^8)_h$— and $C_{1-3}$ alkoxy-C(=O)—;

$R^6$ is 5-6 membered heterocyclyl, $C_{3-6}$ cycloalkyl, $C_{2-6}$ alkynyl, 5-6 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, phenyl and naphthyl is independently unsubstituted or substituted with one, two, three, four or five $R^w$;

wherein $R^7$, $R^8$, h and $R^w$ are as defined herein.

In some embodiments, $R^5$ is 5-6 membered heterocyclyl, $C_{3-6}$ cycloalkyl, $C_{2-6}$ alkynyl, 5-6 membered heteroaryl, 9 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, 9 membered heteroaryl, phenyl and naphthyl is independently unsubstituted or substituted with one, two, three, four or five substituents independently selected from deuterium, F, Cl, Br, OH, CN, $C_{1-3}$ alkoxy, $C_{1-3}$ alkyl, HOOC—$(CR^7R^8)_h$— and $C_{1-3}$ alkoxy-C(=O)—;

$R^6$ is 5-6 membered heterocyclyl, $C_{3-6}$ cycloalkyl, $C_{2-6}$ alkynyl, 5-6 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, phenyl and naphthyl is independently unsubstituted or substituted with one, two, three, four or five $R^w$;

wherein $R^7$, $R^8$, h and $R^w$ are as defined herein.

In some embodiments, $R^5$ is pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzimidazolyl, benzofuranyl, benzothienyl, indolyl, purinyl, quinolyl, isoquinolyl, phenyl or naphthyl, wherein each of the pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzimidazolyl, benzofuranyl, benzothienyl, indolyl, purinyl, quinolyl, isoquinolyl, phenyl and naphthyl is independently unsubstituted or substituted with one, two, three, four or five substituents independently selected from deuterium, F, Cl, Br, OH, CN, $C_{1-3}$ alkoxy, $C_{1-3}$ alkyl, HOOC—$(CR^7R^8)_h$— and $C_{1-3}$ alkoxy-C(=O)—;

$R^6$ is pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, phenyl or naphthyl, wherein each of the pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, phenyl and naphthyl is independently unsubstituted or substituted with one, two, three, four or five $R^w$;

wherein $R^7$, $R^8$, h and $R^w$ are as defined herein.

In some embodiments, each $R^w$ is independently deuterium, F, Cl, Br, OH, CN, HOOC—$(CR^7R^8)_h$—, $R^{11}C(=O)$—, $R^cR^dP(=O)$—, $R^{10}$—$S(=O)_t$—, $R^{13}O$—, $R^{12}$—$(CR^7R^8)_j$—, amino, $C_{1-6}$ alkoxy, $C_{3-6}$ cycloalkyl, $C_{1-6}$ alkoxy-$(CR^7R^8)_n$—O—, $C_1$ alkyl, hydroxy-$C_{1-6}$ alkyl, $C_{2-6}$ alkynyl, phenyl, naphthyl, 5-6 membered heterocyclyl or 5-6 membered heteroaryl, and wherein each of the amino, $C_{1-6}$ alkoxy, $C_{3-6}$ cycloalkyl, $C_{1-6}$ alkoxy of $C_{1-6}$ alkoxy-$(CR^7R^8)_n$—O—, $C_{1-6}$ alkyl, hydroxy-$C_{1-6}$ alkyl, $C_{2-6}$ alkynyl, phenyl, naphthyl, 5-6 membered heterocyclyl and 5-6 membered heteroaryl is independently unsubstituted or substituted with one, two, three, four or five $R^x$;

wherein $R^7$, $R^8$, h, t, n, j, $R^{11}$, $R^c$, $R^d$, $R^{10}$, $R^{13}$, $R^{12}$ and $R^x$ are as defined herein.

In some embodiments, each $R^w$ is independently deuterium, F, Cl, Br, OH, CN, HOOC—$(CR^7R^8)_h$—, $R^{11}C(=O)$—, $R^cR^dP(=O)$—, $R^{10}$—$S(=O)_t$—, $R^{13}O$—, $R^{12}$—$(CR^7R^8)_j$—, amino, $C_{1-4}$ alkoxy, $C_{3-6}$ cycloalkyl, alkoxy, $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, naphthyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl or piperazinyl, and wherein each of the amino, $C_{1-4}$ alkoxy, $C_{3-6}$ cycloalkyl, $C_{1-4}$ alkoxy of $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, naphthyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl and piperazinylis independently unsubstituted or substituted with one, two, three, four or five $R^x$;

wherein $R^7$, $R^8$, h, t, n, j, $R^{11}$, $R^c$, $R^d$, $R^{10}$, $R^{13}$, $R^{12}$ and $R^x$ are as defined herein.

In some embodiments, each $R^{10}$ and $R^{11}$ is independently $R^aR^bN$—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, and wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five $R^y$;

each $R^{12}$ is independently OH, HOOC—, $C_{1-6}$ alkyl, $C_{1-6}$ alkoxy, $C_{3-6}$ cycloalkyl, 4 membered heterocyclyl, 5-6 membered heterocyclyl, phenyl, naphthyl or 5-6 membered heteroaryl, and wherein each of the $C_{1-6}$ alkyl, $C_{1-6}$ alkoxy, $C_{3-6}$ cycloalkyl, 4 membered heterocyclyl, 5-6 membered heterocyclyl, phenyl, naphthyl and 5-6 membered heteroaryl is independently unsubstituted or substituted with one, two, three, four or five $R^z$;

each $R^{13}$ is independently $C_{1-6}$ alkyl, $C_{3-6}$ cycloalkyl, 5-6 membered heteroaryl, phenyl, naphthyl or 5-6 membered heterocyclyl, and wherein each of the $C_{1-6}$ alkyl, $C_{3-6}$ cycloalkyl, 5-6 membered heteroaryl, phenyl, naphthyl and 5-6 membered heterocyclyl is independently unsubstituted or substituted with one, two, three, four or five $R^g$;

wherein $R^a$, $R^b$, $R^y$, $R^z$ and $R^g$ are as defined herein.

In some embodiments, each $R^{10}$ and $R^{11}$ is independently $R^aR^bN$—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, naphthyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, naphthyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^y$;

each $R^{12}$ is independently OH, HOOC—, $C_{1-4}$ alkyl, $C_{1-4}$ alkoxy, cyclopropyl, cyclobutyl, cyclopentyl, cyclohexyl, azetidinyl, oxetanyl, thietanyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, cyclohexyl, azetidinyl, oxetanyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^z$;

each $R^{13}$ is independently $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^g$;

wherein $R^a$, $R^b$, $R^y$, $R^z$ and $R^g$ are as defined herein.

In some embodiments, each $R^x$, $R^y$, $R^z$ and $R^g$ is independently deuterium, F, Cl, Br, OH, CN, HOOC—$(CR^7R^8)_h$—, $R^{14}C(=O)$—, $R^cR^dP(=O)$—, $R^{15}$—$S(=O)_t$—, $R^{16}O$—, $R^{17}$—$(CR^7R^8)_j$—, amino, $C_{1-6}$ alkoxy, $C_{3-6}$ cycloalkyl, $C_{1-6}$ alkoxy-$(CR^7R^8)_n$—O—, $C_{1-6}$ alkyl, hydroxy-$C_1$ alkyl, $C_{2-6}$ alkynyl, phenyl, naphthyl, 5-6 membered heterocyclyl or 5-6 membered heteroaryl, wherein each of the amino, $C_{1-6}$ alkoxy, $C_{3-6}$ cycloalkyl, $C_{1-6}$ alkoxy of $C_{1-6}$ alkoxy-$(CR^7R^8)_n$—O—, $C_{1-6}$ alkyl, hydroxy-$C_{1-6}$ alkyl, $C_{2-6}$ alkynyl, phenyl, naphthyl, 5-6 membered heterocyclyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, hydroxy-$C_{1-6}$ alkyl, HOOC—$(CR^7R^8)_h$— and $C_{1-6}$ alkoxy-$(CR^7R^8)_n$—O—;

wherein $R^7$, $R^8$, $R^{14}$, $R^{15}$, $R^{16}$, $R^{17}$, $R^c$, $R^d$, h, t, n and j are as defined herein.

In some embodiments, each $R^x$, $R^y$, $R^z$ and $R^g$ is independently deuterium, F, Cl, Br, OH, CN, HOOC—$(CR^7R^8)_h$—, $R^{14}C(=O)$—, $R^cR^dP(=O)$—, $R^{15}$—S$(=O)_t$—, $R^{16}O$—, $R^{17}$—$(CR^7R^8)_j$—, amino, $C_{1-4}$ alkoxy, $C_{3-6}$ cycloalkyl, $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl or piperazinyl, and wherein each of the amino, $C_{1-4}$ alkoxy, $C_{3-6}$ cycloalkyl, $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl and piperazinylis independently unsubstituted or substituted with one, two, three, four or five substituents independently selected from deuterium, F, Cl, Br, OH, $C_{1-4}$ alkoxy, $C_{1-4}$ alkyl, hydroxy-$C_{1-4}$ alkyl, HOOC—$(CR^7R^8)_h$— and $C_{1-4}$ alkoxy-$(CR^7R^8)_n$—O—;

wherein $R^7$, $R^8$, $R^{14}$, $R^{15}$, $R^{16}$, $R^{17}$, $R^c$, $R^d$, h, t, n and j are as defined herein.

In some embodiments, each $R^{14}$ and $R^{15}$ is independently $R^aR^bN$—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—;

each $R^{17}$ is independently OH, HOOC—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—;

each $R^{16}$ is independently $C_{1-6}$ alkyl, $C_{3-6}$ cycloalkyl, 5-6 membered heteroaryl, phenyl, naphthyl or 5-6 membered heterocyclyl, wherein each of the $C_{1-6}$ alkyl, $C_{3-6}$ cycloalkyl, 5-6 membered heteroaryl, phenyl, naphthyl and 5-6 membered heterocyclyl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—;

wherein $R^7$, $R^8$, $R^a$, $R^b$, h and n are as defined herein.

In some embodiments, each $R^{14}$ and $R^{15}$ is independently $R^aR^bN$—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-4}$ alkoxy, $C_{1-4}$ alkyl, HOOC—$(CR^7R^8)_h$— and $C_{1-4}$ alkoxy-$(CR^7R^8)_n$—O—;

each $R^{17}$ is independently OH, HOOC—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-4}$ alkoxy, $C_{1-4}$ alkyl, HOOC—$(CR^7R^8)_h$— and $C_{1-4}$ alkoxy-$(CR^7R^8)_n$—O—;

each $R^{16}$ is independently $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-4}$ alkoxy-$(CR^7R^8)_n$—O—;

wherein $R^7$, $R^8$, $R^a$, $R^b$, h and n are as defined herein.

In some embodiments, each $R^a$, $R^b$, $R^e$ and $R^d$ is independently H, deuterium, $C_{1-6}$ alkyl, $C_{2-6}$ alkynyl, $C_{1-6}$ alkoxy, $C_{3-6}$ cycloalkyl, HOOC—$(CR^7R^8)_h$—, phenyl-$C_{1-3}$ alkylene or 5-6 membered heterocyclyl, wherein each of the $C_{1-6}$ alkyl, $C_{2-6}$ alkynyl, $C_{1-6}$ alkoxy, $C_{3-6}$ cycloalkyl, phenyl-$C_{1-3}$ alkylene and 5-6 membered heterocyclyl is independently unsubstituted or substituted with one, two, three, four or five substituents independently selected from deuterium, F, Cl, Br, OH, $C_{1-6}$ alkyl, $(C_{1-4}$ alkyl$)_2$NC(=O)—, $C_{1-6}$ alkoxy, HOOC—$(CR^7R^8)_h$— and $C_{1-6}$ alkoxy-$(CR^7R^8)_n$—O—;

wherein $R^7$, $R^8$, h and n are as defined herein.

In some embodiments, each $R^a$, $R^b$, $R^c$ and $R^d$ is independently H, deuterium, $C_{1-4}$ alkyl, $C_{2-4}$ alkynyl, $C_{1-4}$ alkoxy, cyclopropyl, cyclobutyl, cyclopentyl, cyclohexyl, HOOC—$(CR^7R^8)_h$—, phenyl-methylene, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl or piperazinyl, and wherein each of the $C_{1-4}$ alkyl, $C_{2-4}$ alkynyl, $C_{1-4}$ alkoxy, cyclopropyl, cyclobutyl, cyclopentyl, cyclohexyl, phenyl-methylene, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl and piperazinyl is independently unsubstituted or substituted with one, two, three, four or five substituents independently selected from deuterium, F, Cl, Br, OH, $C_{1-4}$ alkyl, $(CH_3)_2$NC(=O)—, $(CH_2CH_3)_2$NC(=O)—, $CH_3CH_2N(CH_3)C(=O)$—, $C_{1-4}$ alkoxy, HOOC—$(CR^7R^8)_h$— and $C_{1-4}$ alkoxy-$(CR^7R^8)_n$—O—;

wherein $R^7$, $R^8$, h and n are as defined herein.

In still some embodiments, provided herein is a compound having one of the following structures, or a stereoisomer, a tautomer, an N-oxide, a solvate, a metabolite, a pharmaceutically acceptable salt or a prodrug thereof but not limited to these compounds:

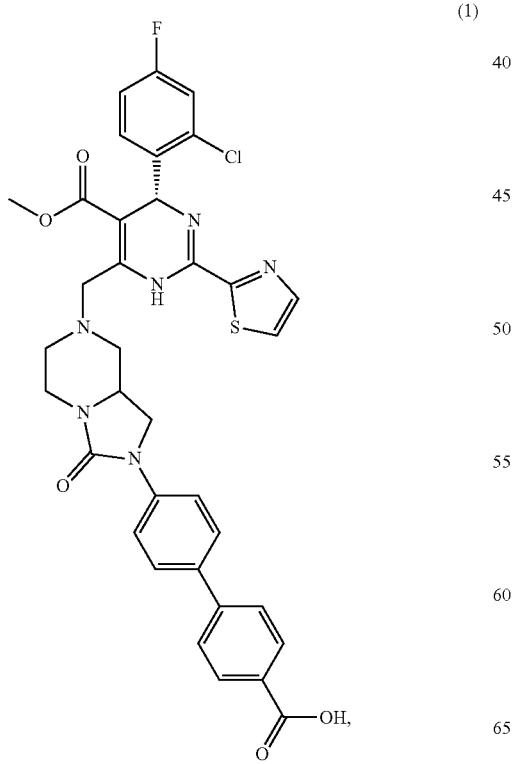

(1)

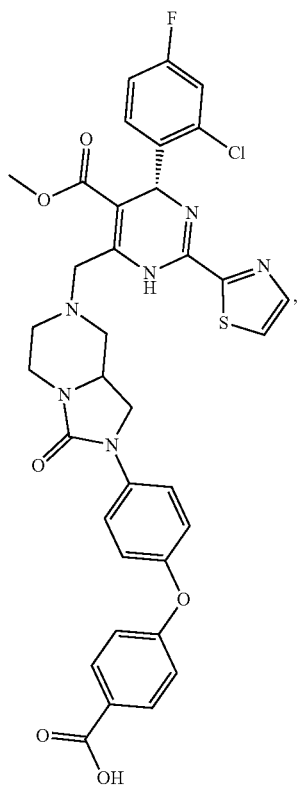

(2)

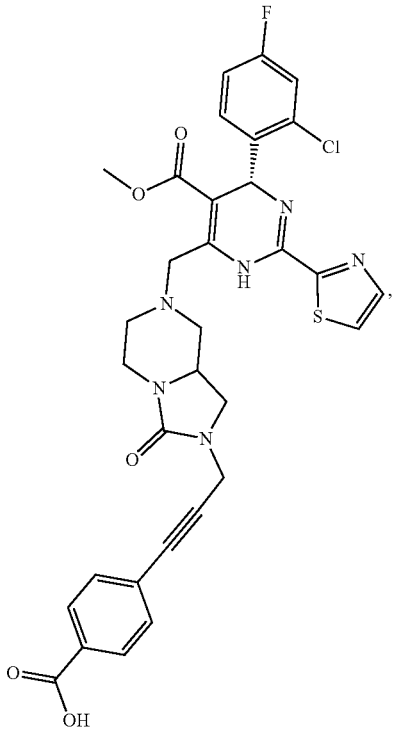

(3)

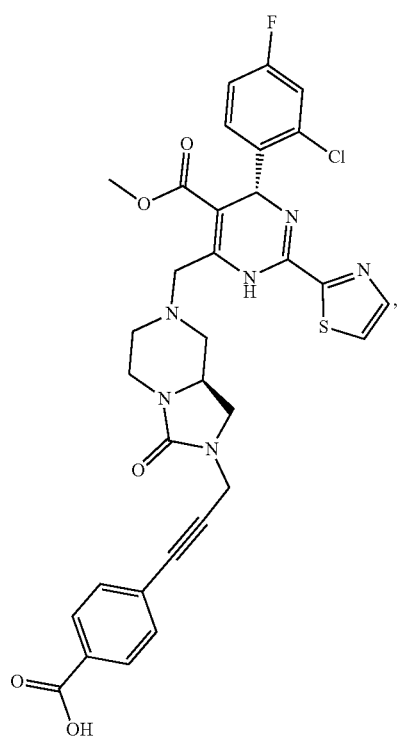
(4)
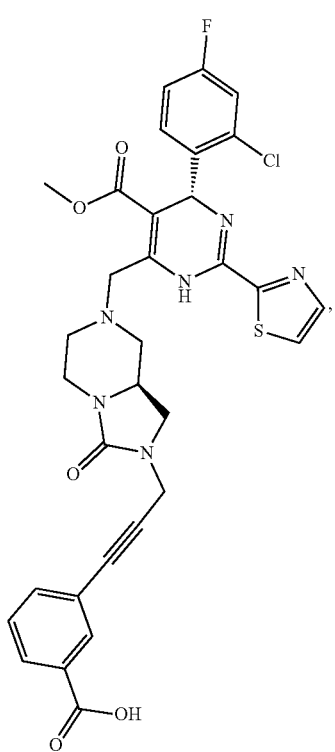
(6)
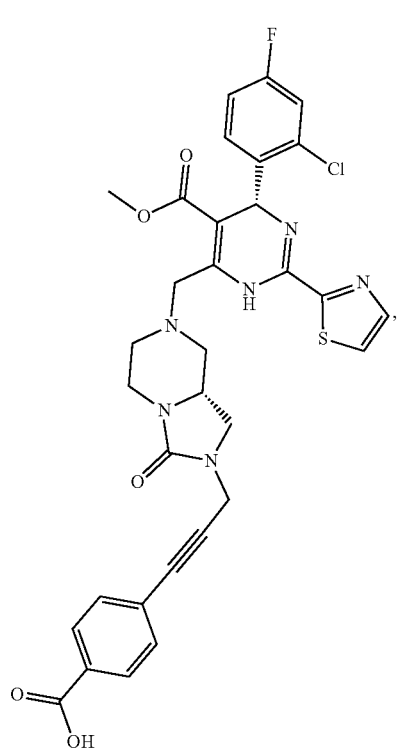
(5)
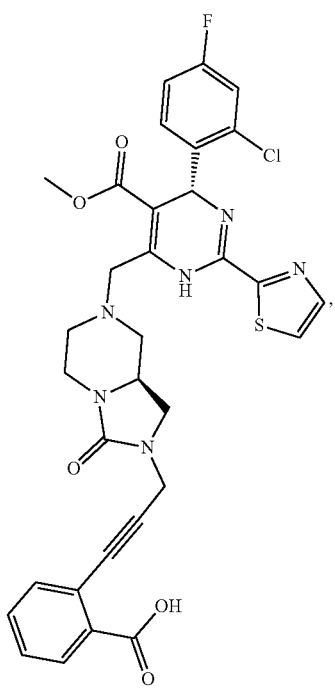
(7)

(8)
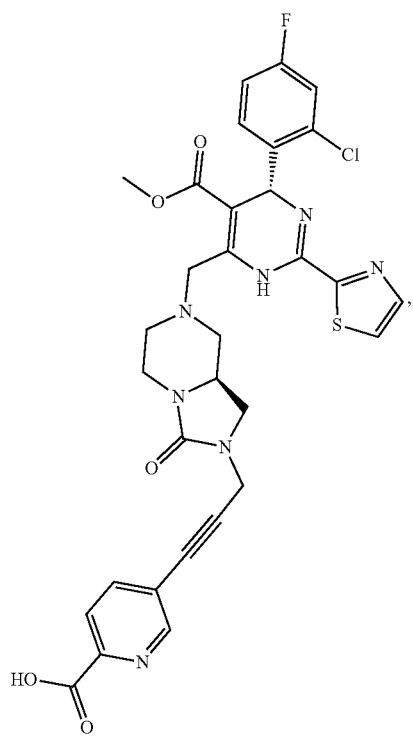
(9)
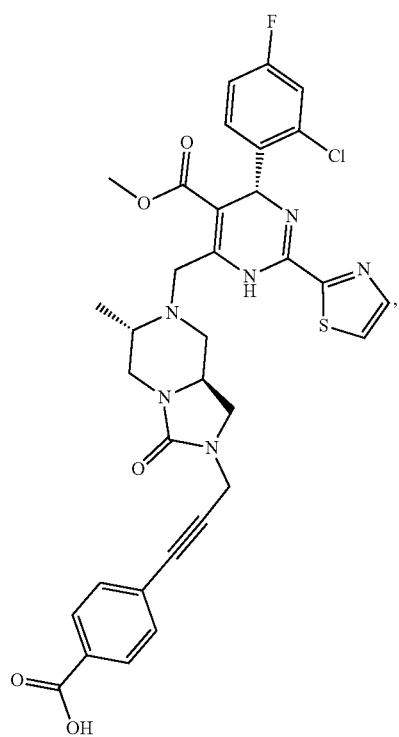
(10)
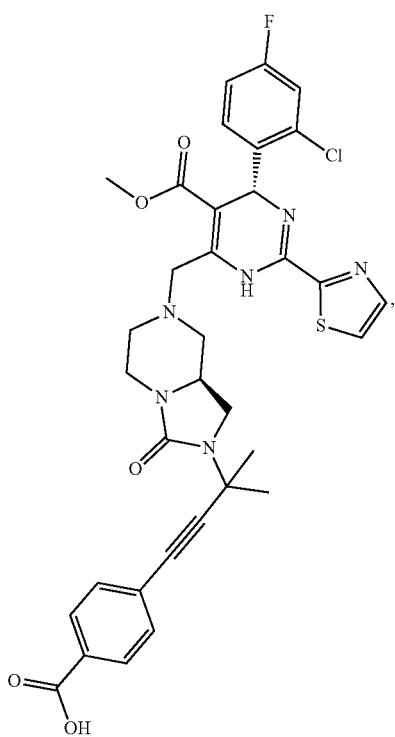
(11)
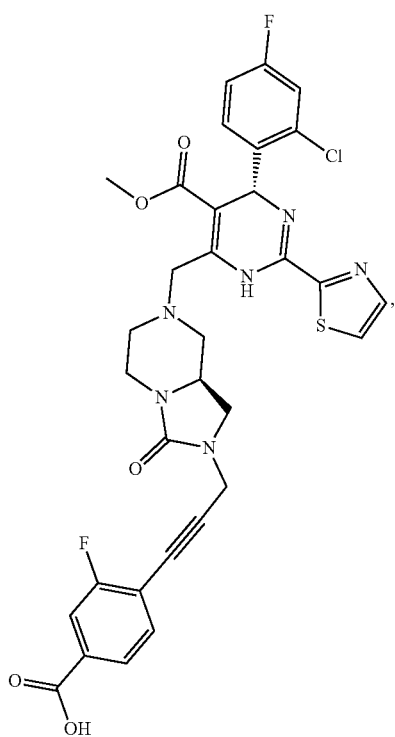

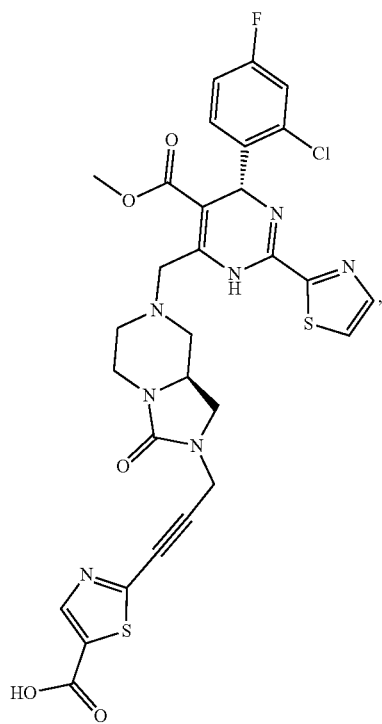
(12)
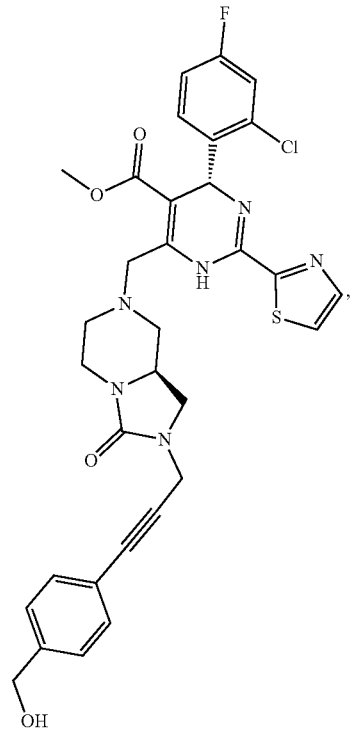
(14)
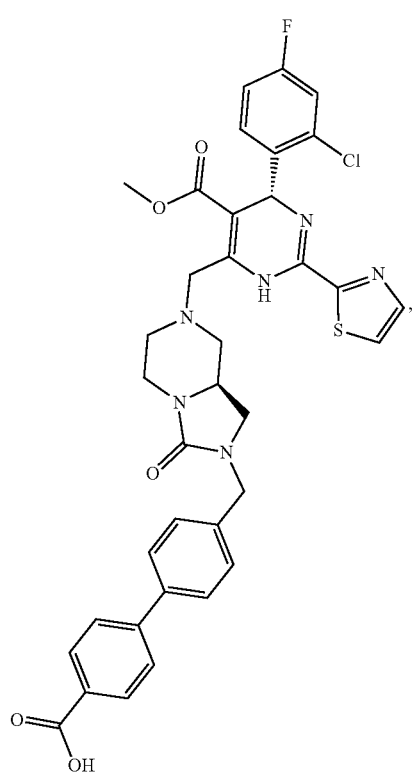
(13)
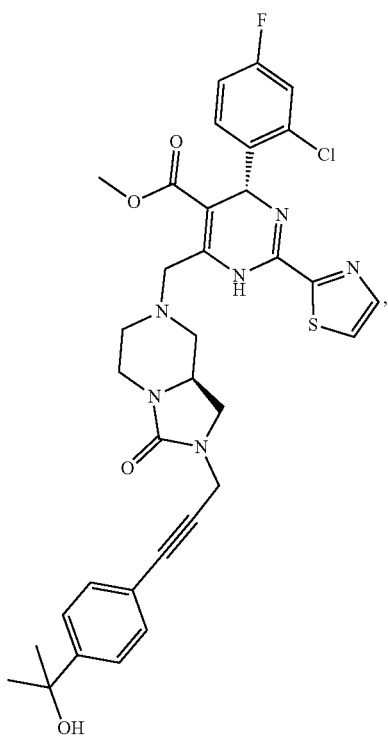
(15)

-continued
(16)
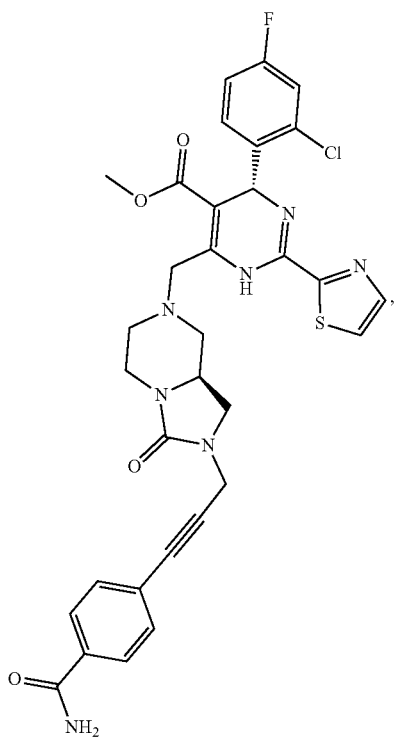
(17)
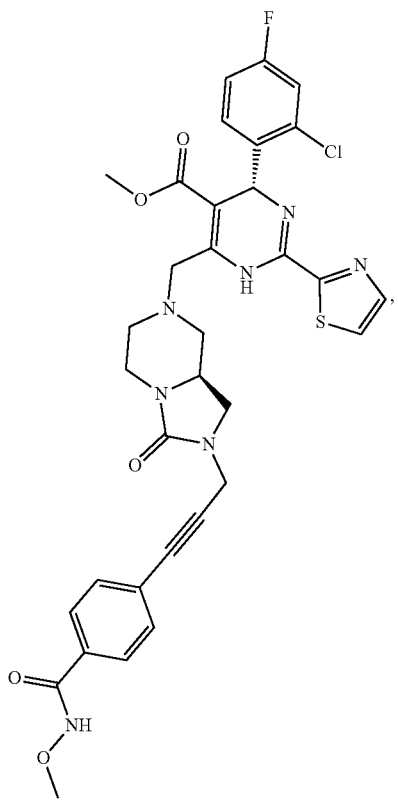
-continued
(18)
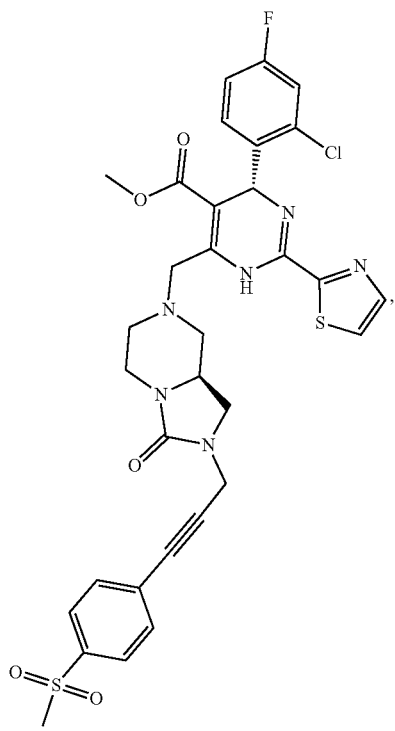
(19)
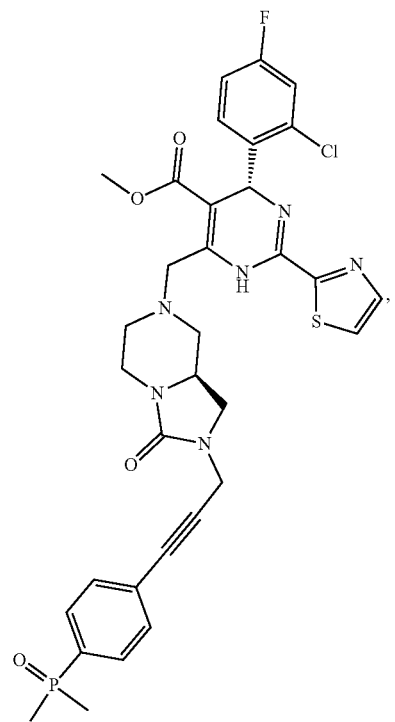

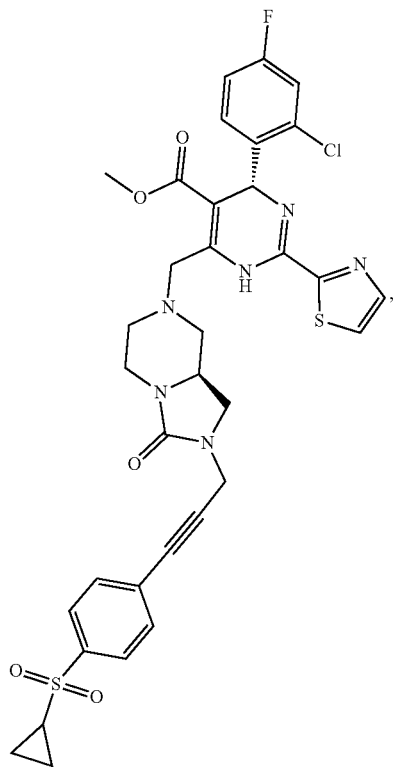
(20)
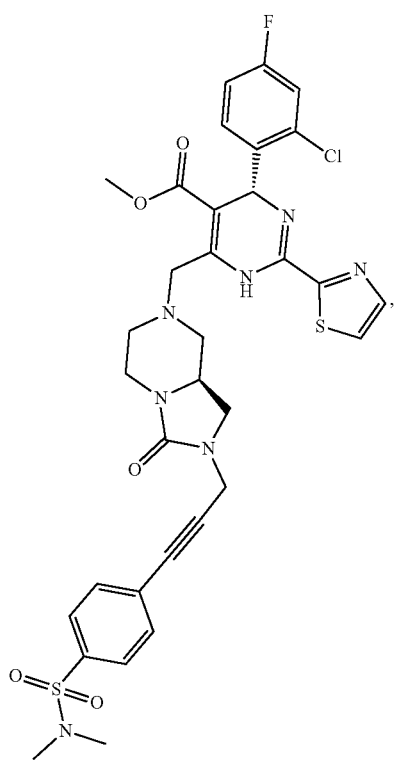
(22)
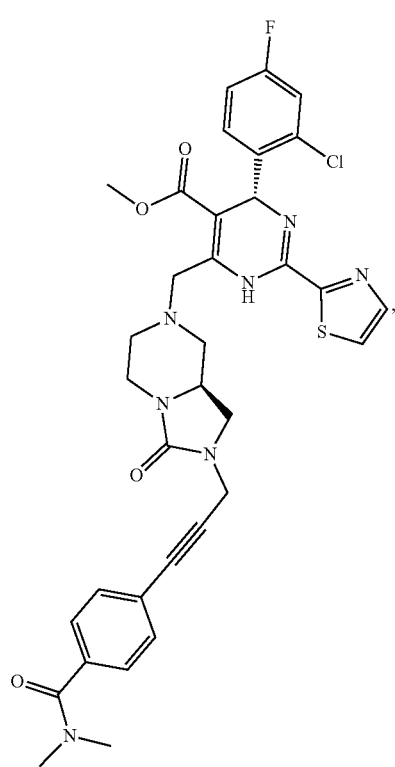
(21)
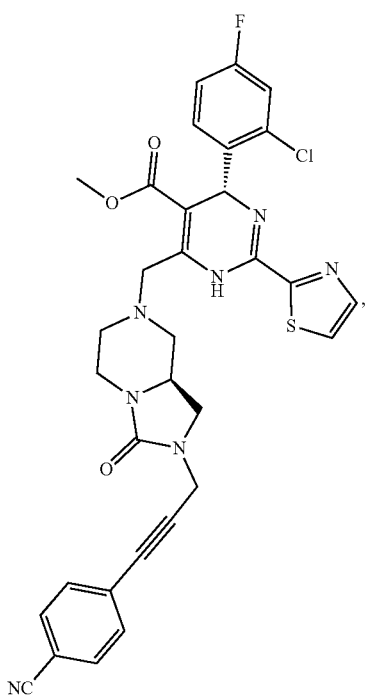
(23)

(24)
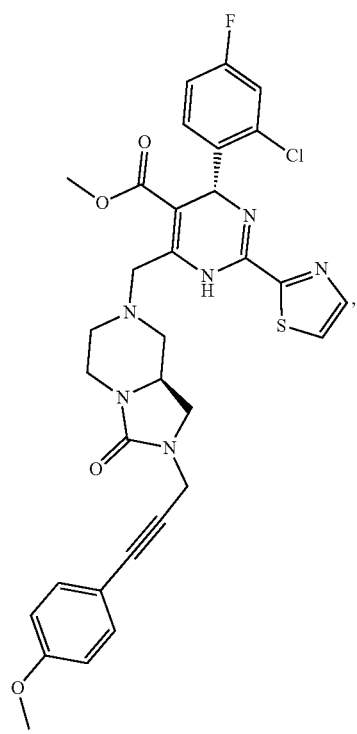
(26)
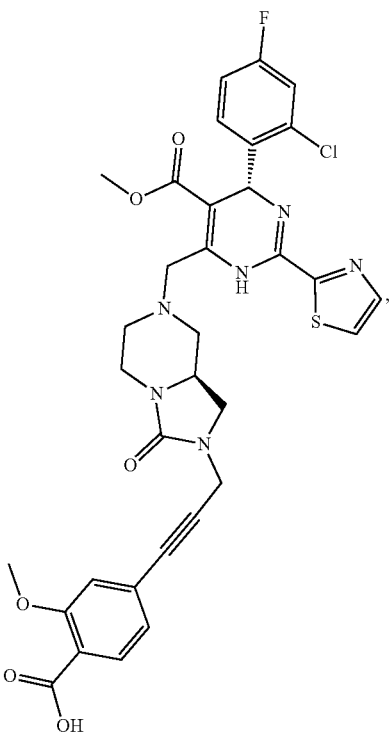
(25)
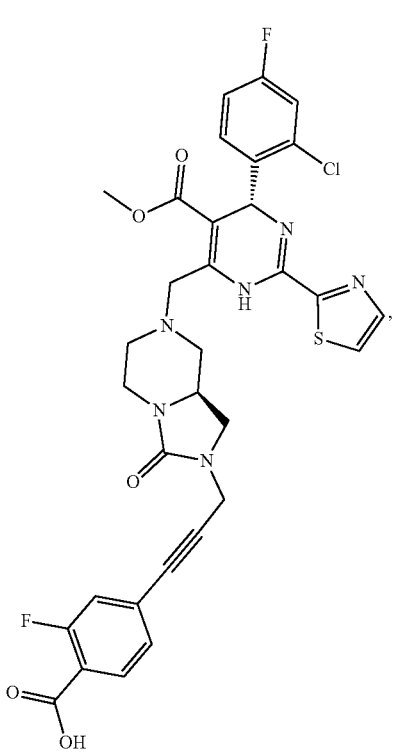
(27)
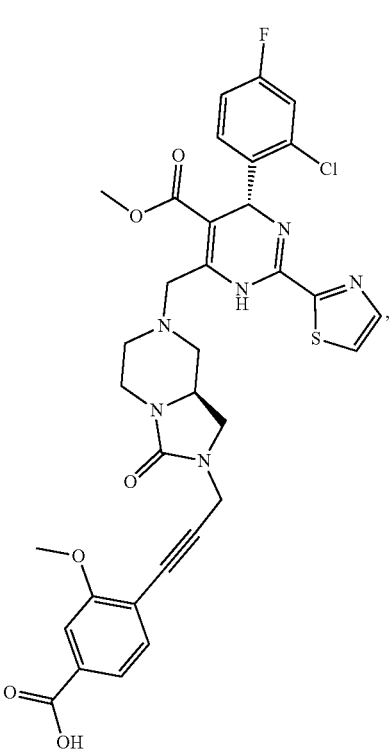

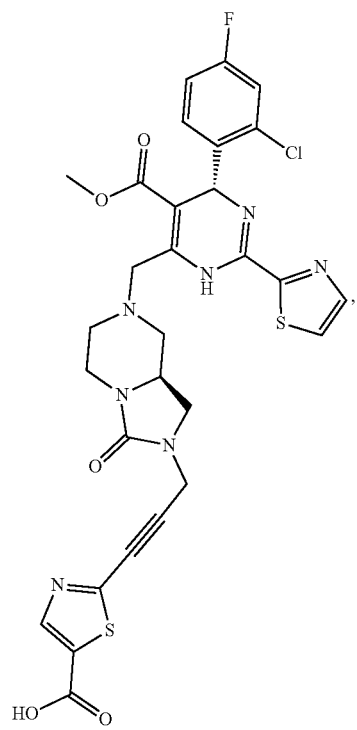
(28)
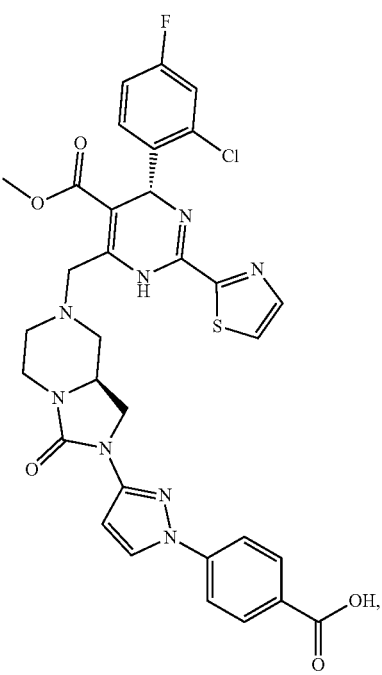
(30)
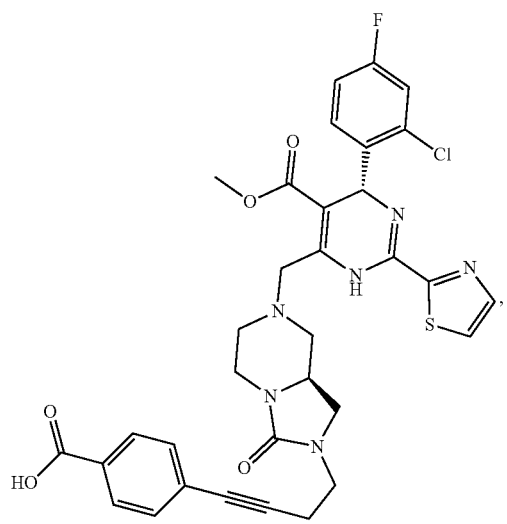
(29)
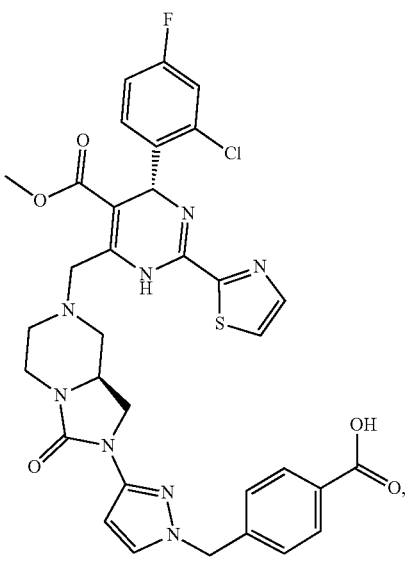
(31)

(32)
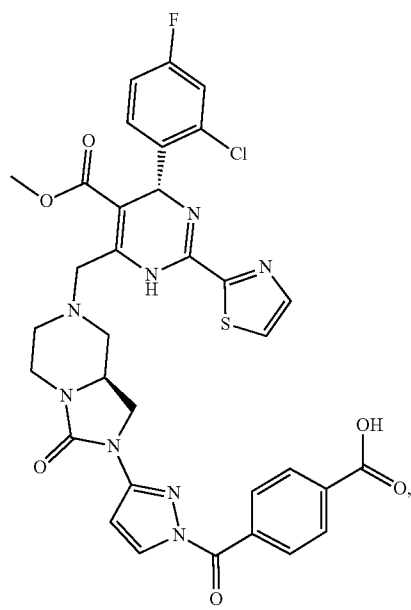
(34)
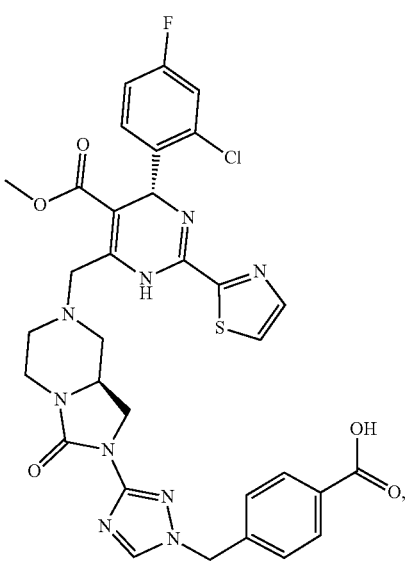
(33)
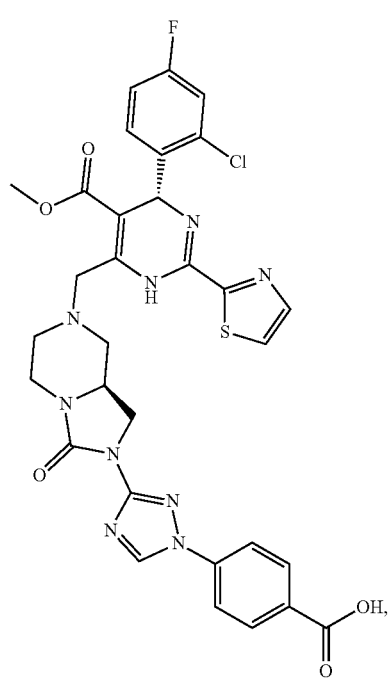
(35)
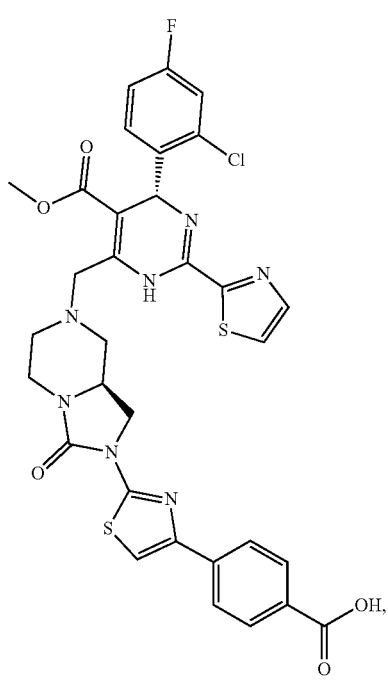

-continued
(36)
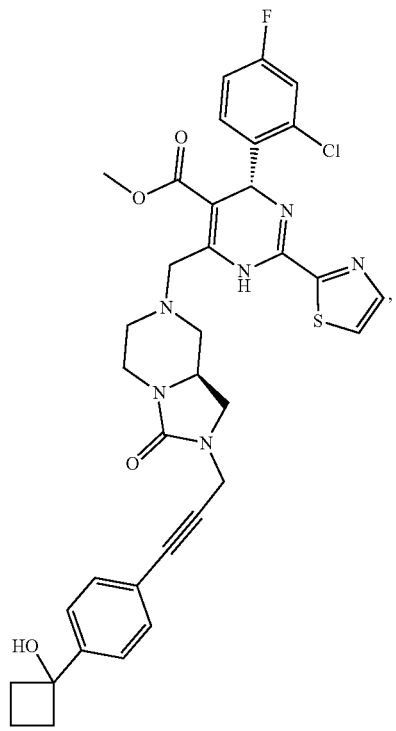
(38)
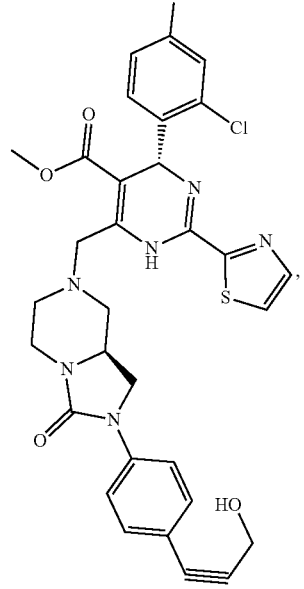
(37)
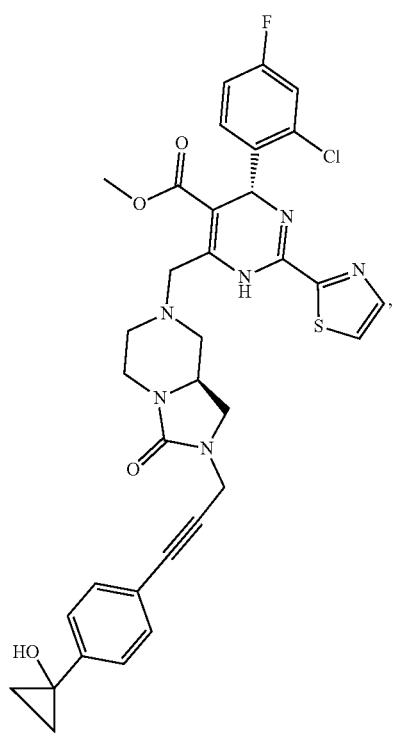
(39)
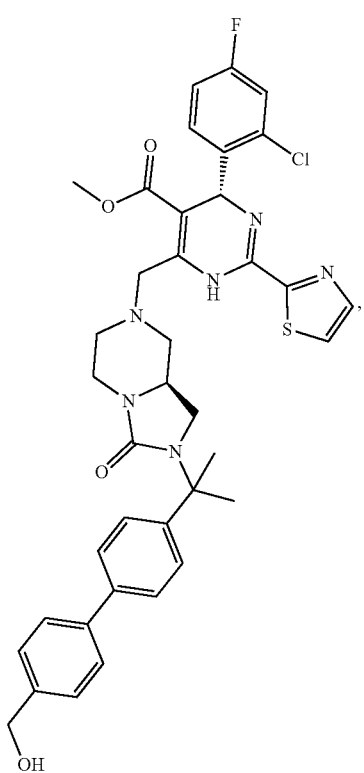

(40)
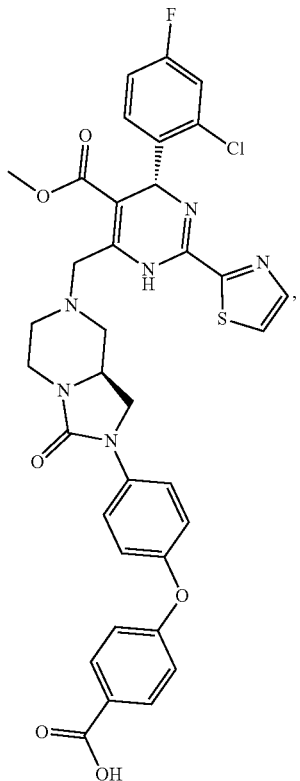
(41)
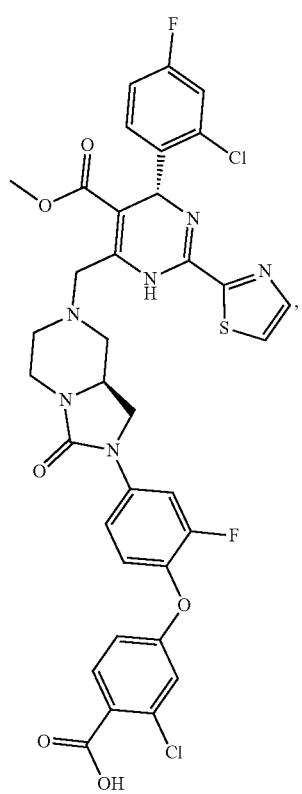
(42)
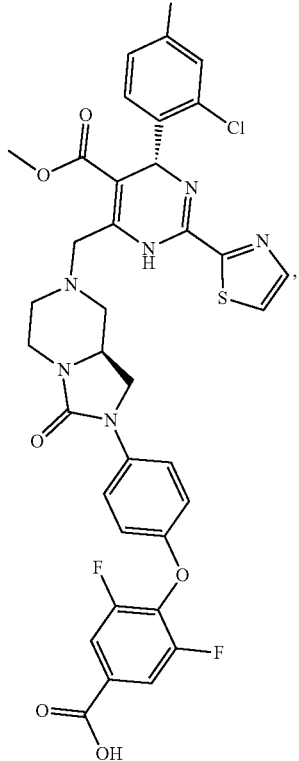
(43)
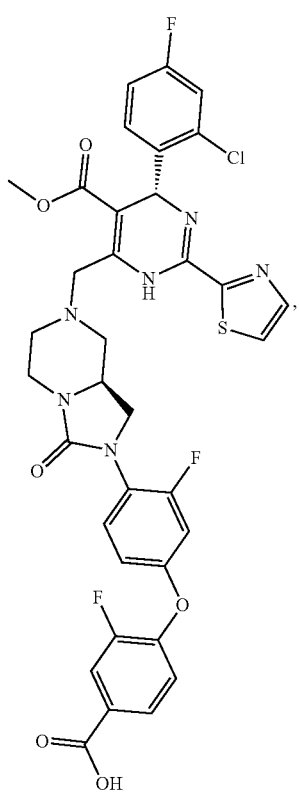

(44)
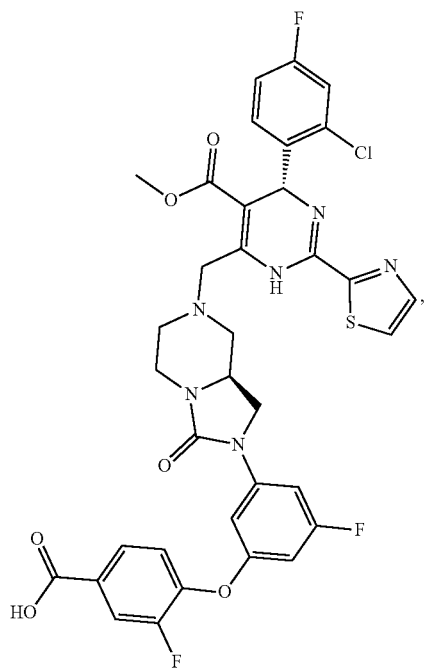
(45)
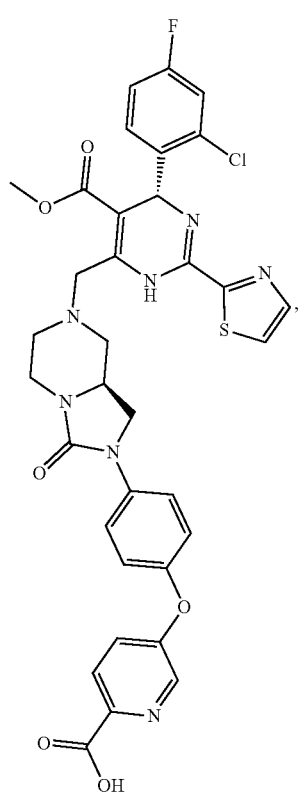
(46)
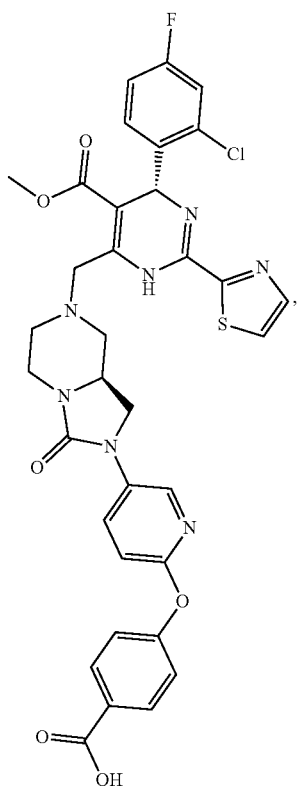
(47)
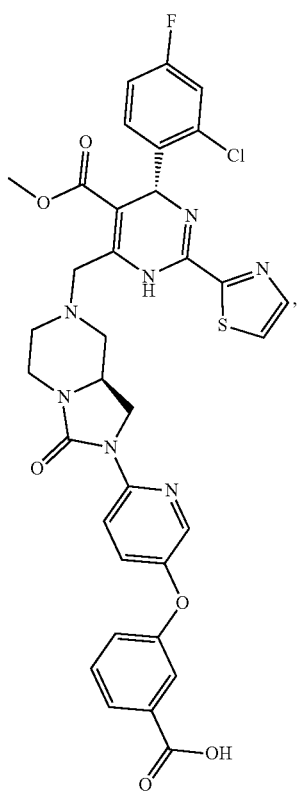

(48)
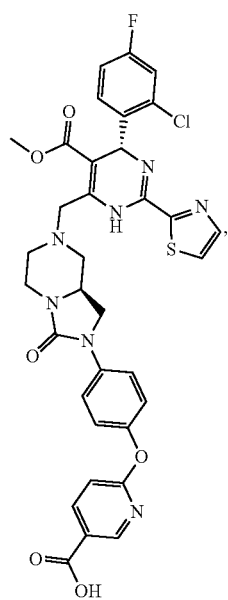
(50)
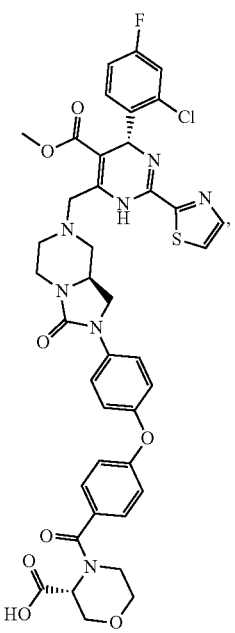
(49)
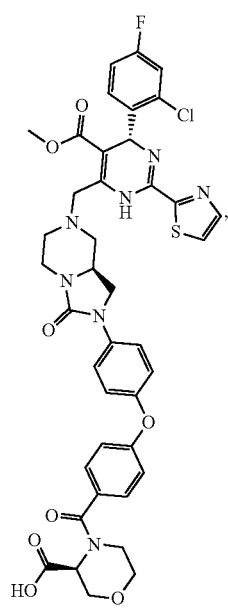
(51)
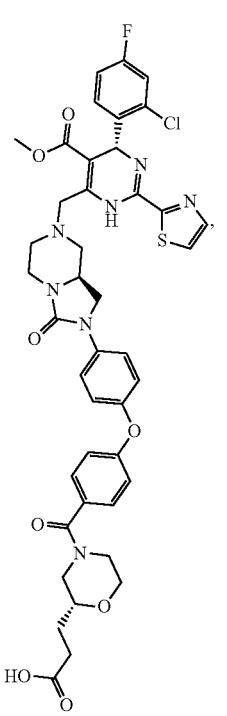

-continued
(52)
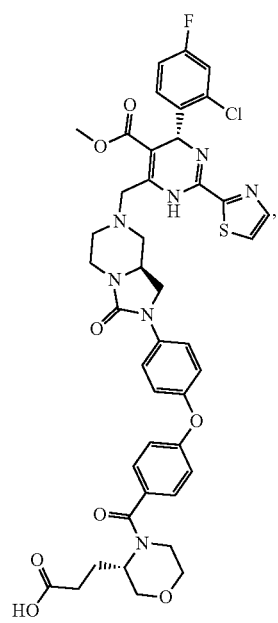
(54)
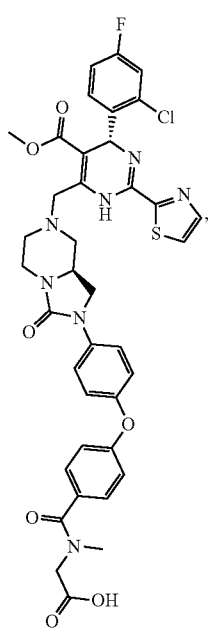
(53)
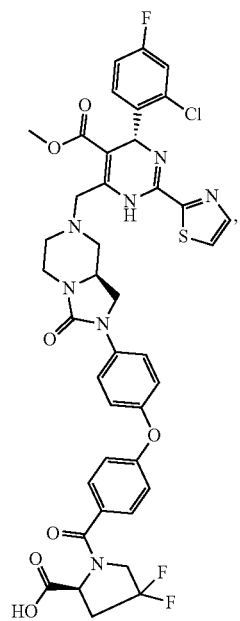
(55)
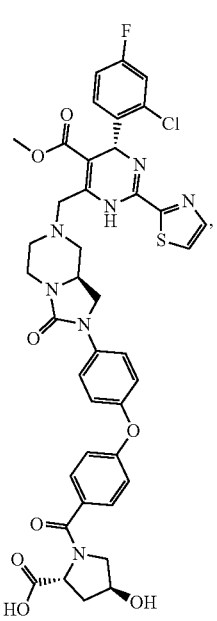

-continued
(56)
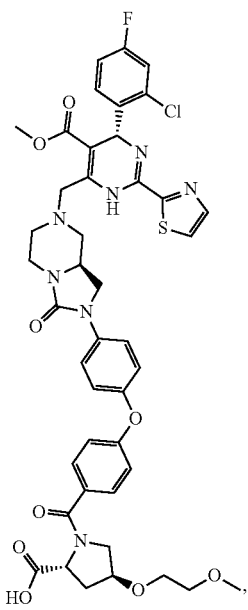
(57)
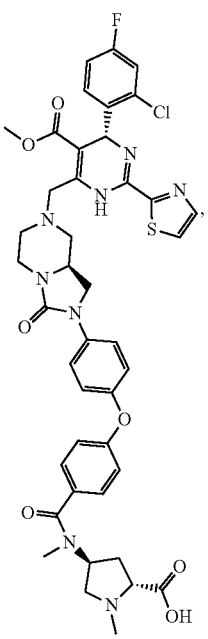
-continued
(58)
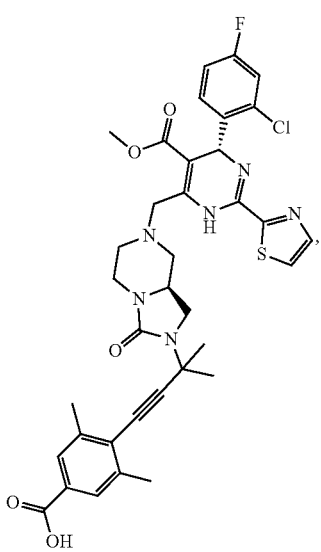
(59)
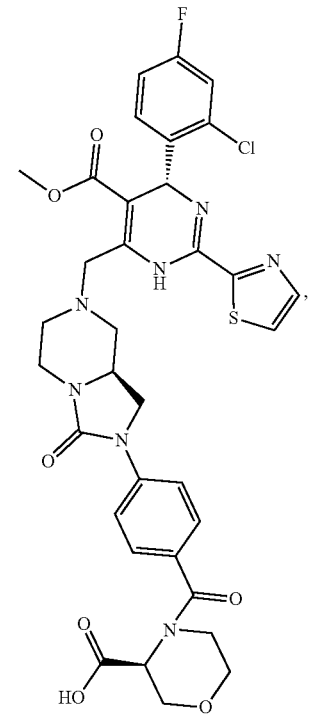

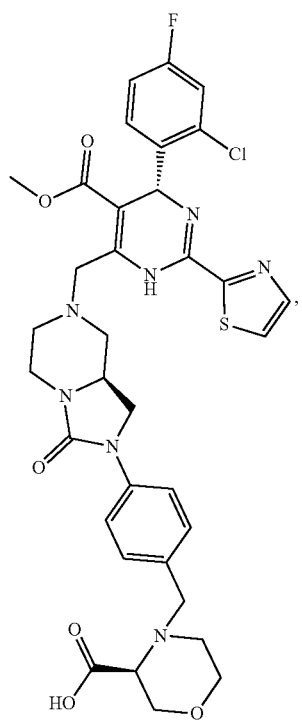
(60)
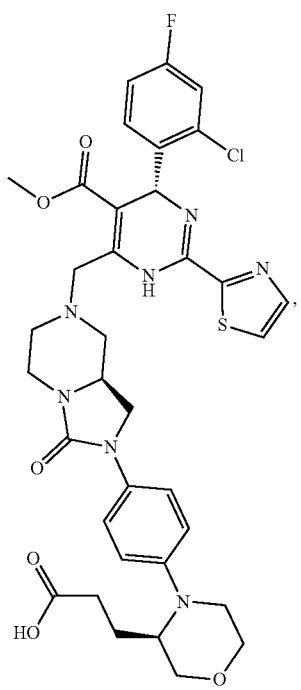
(62)
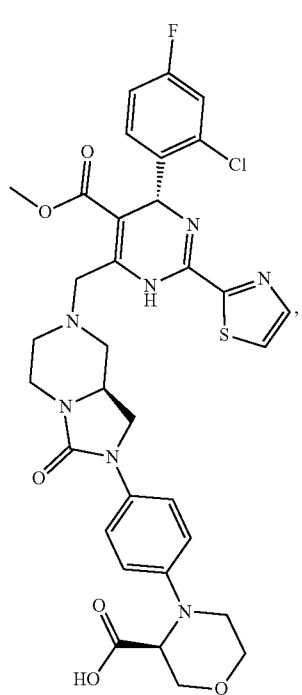
(61)
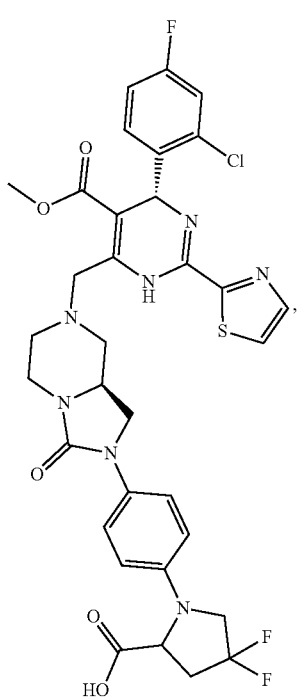
(63)

(64)
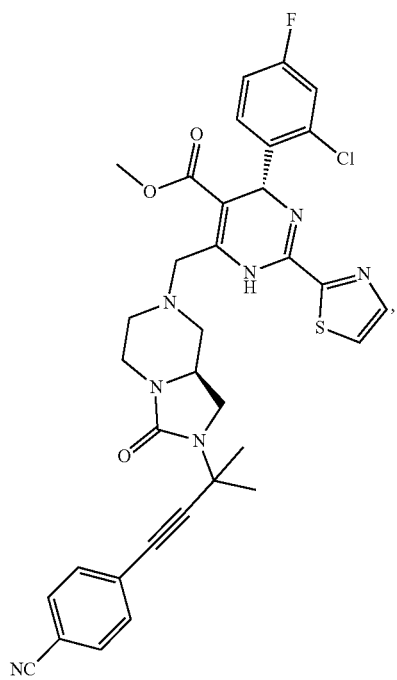
(65)
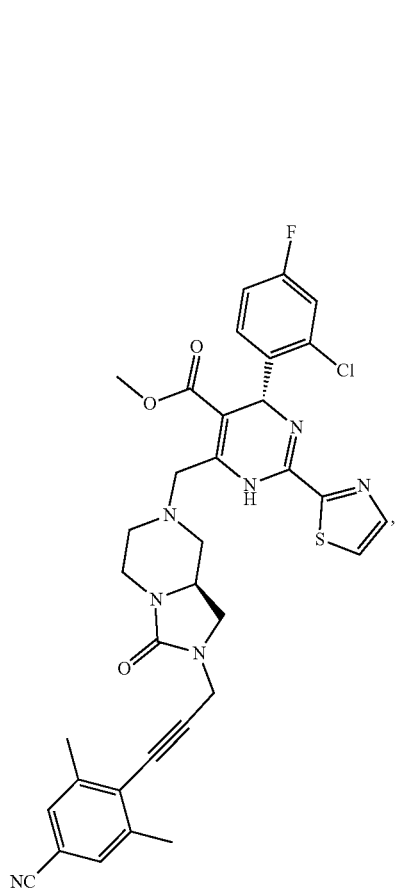
(66)
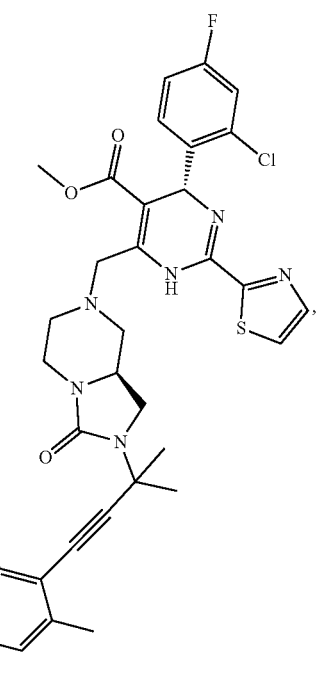
(67)
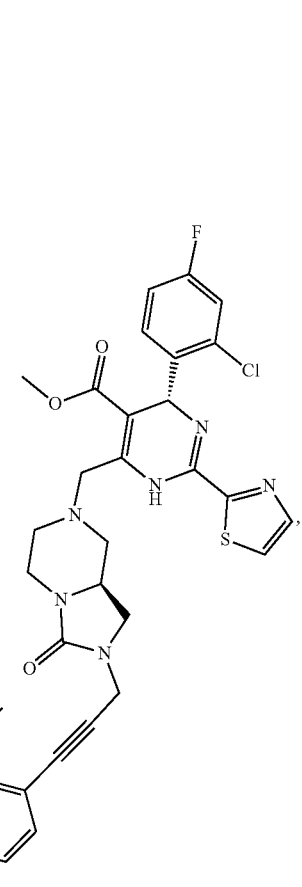

(68)
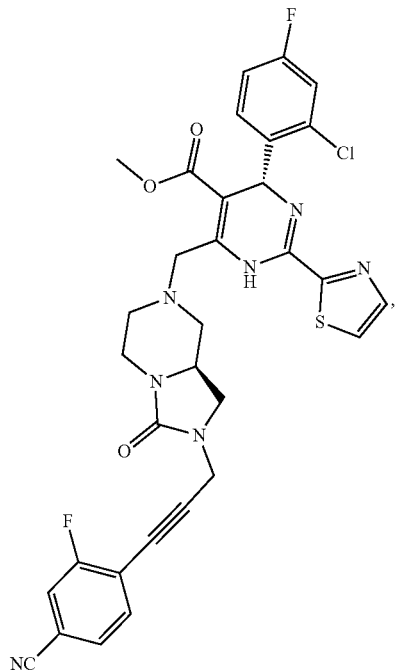
(69)
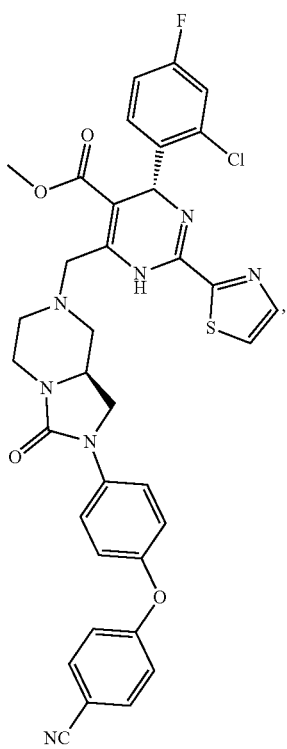
(70)
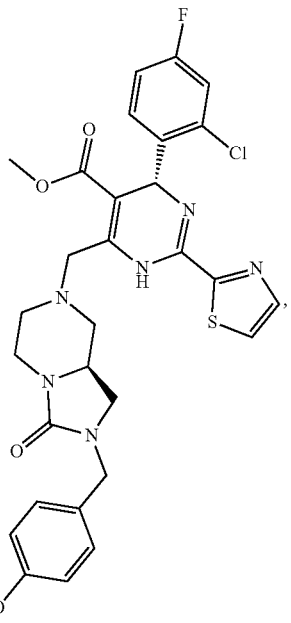
(71)
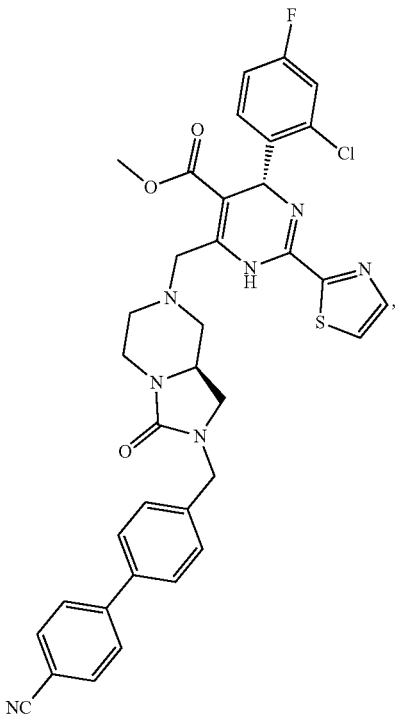

(72)
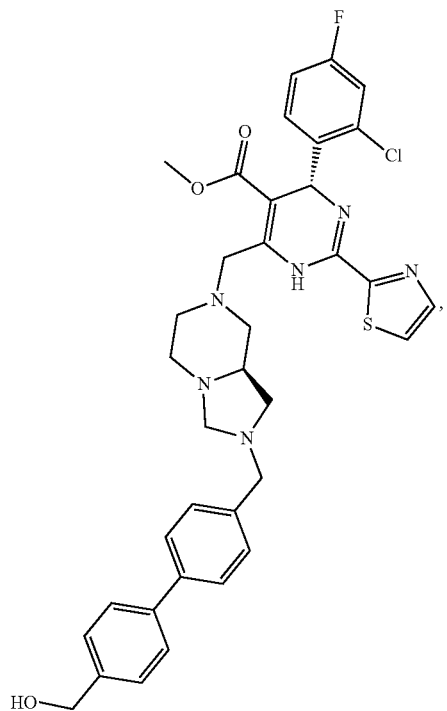
(73)
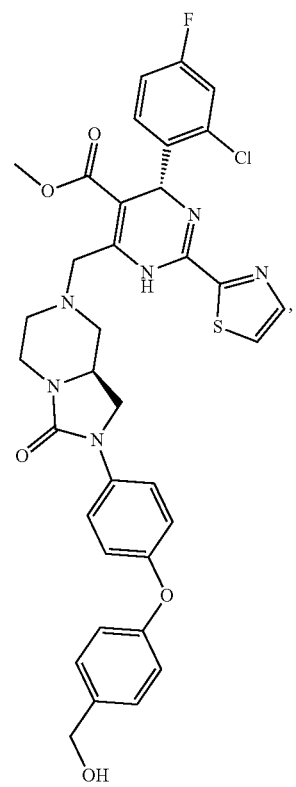
(74)
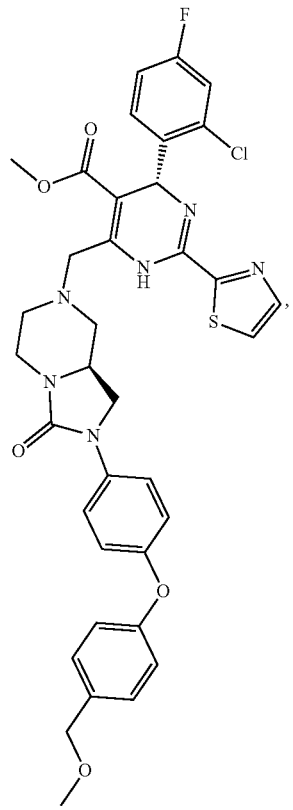
(75)
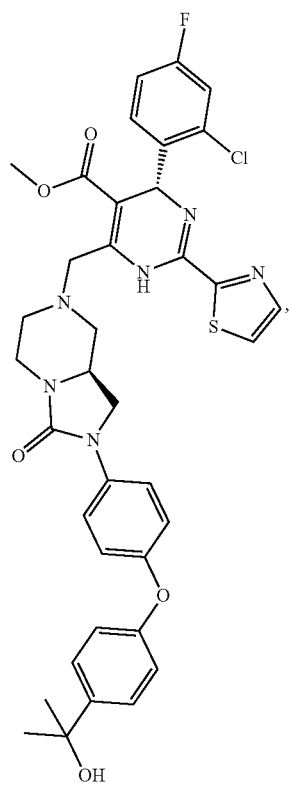

(76)
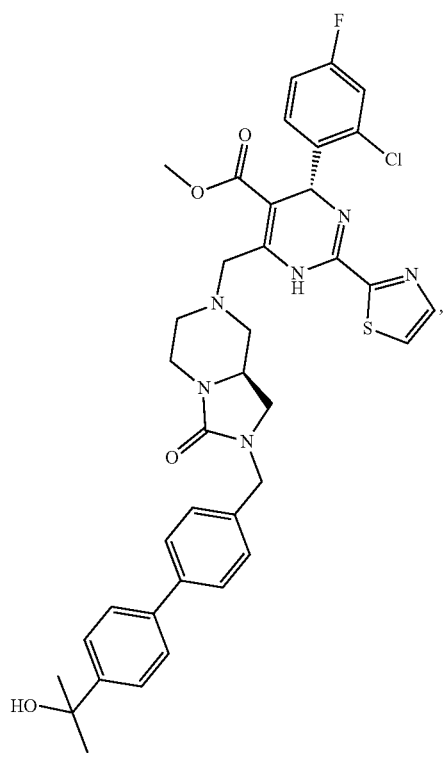
(77)
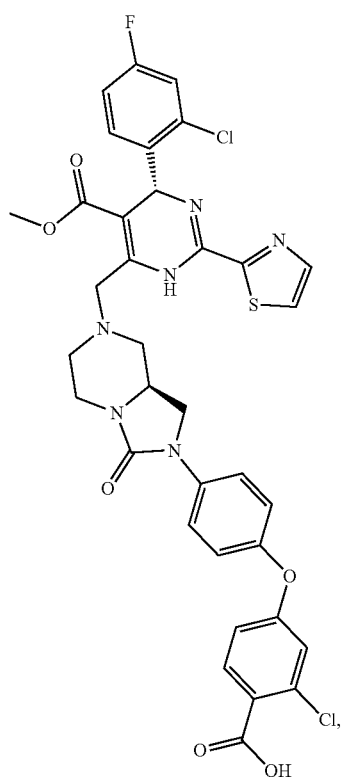
(78)
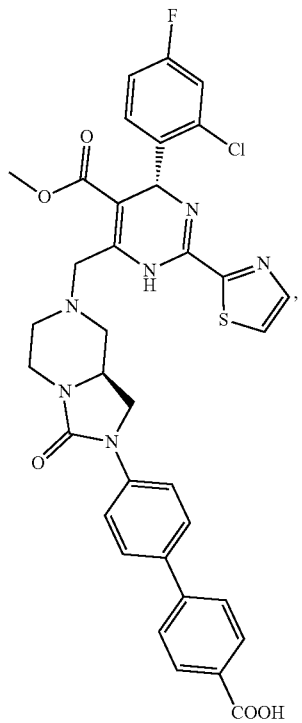
(79)
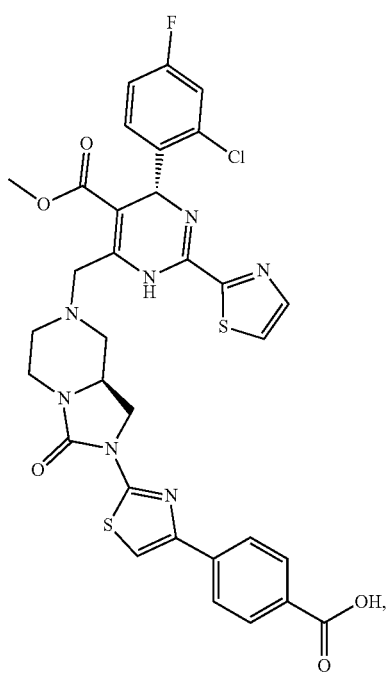

71
-continued
(80)
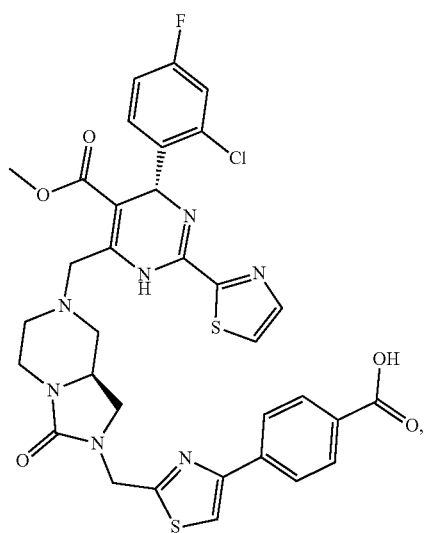
(81)
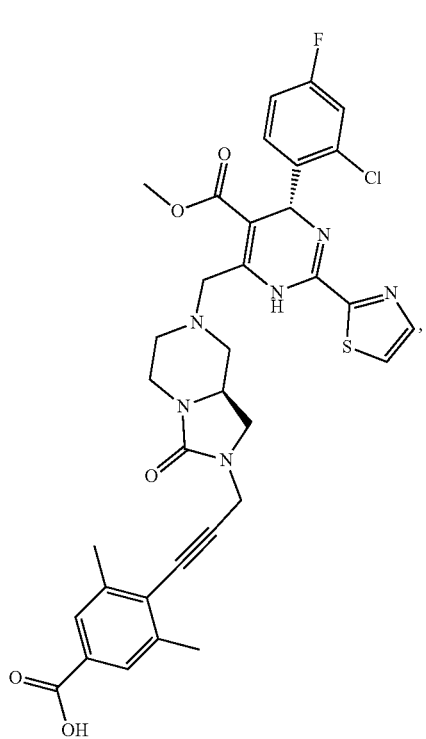
72
-continued
(82)
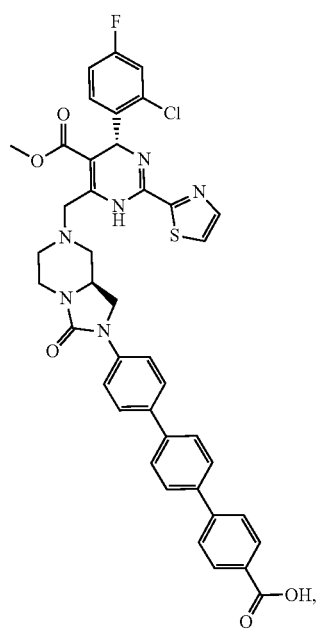
(83)
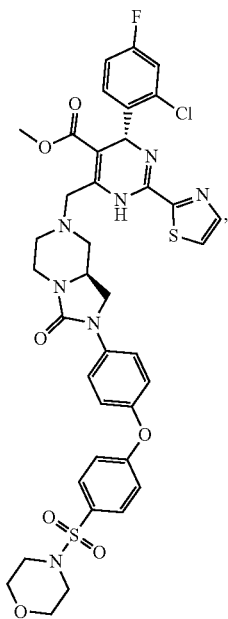

(84)
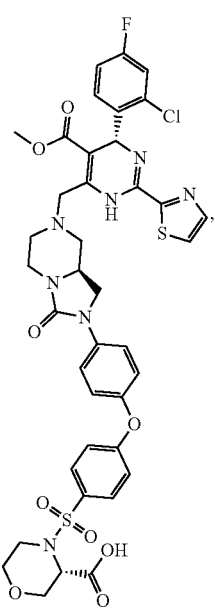
(85)
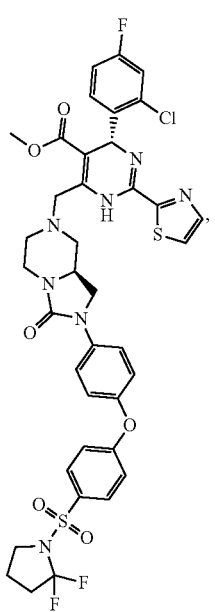
(86)
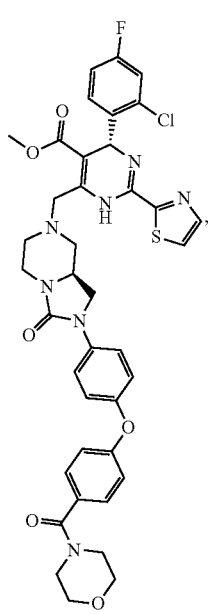
(87)
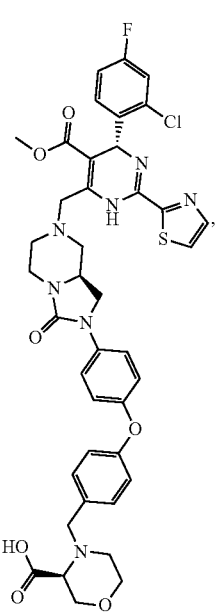

-continued
(88)
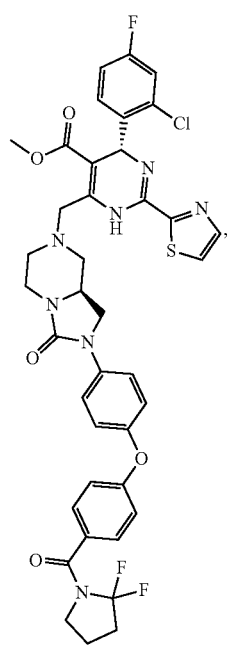
(89)
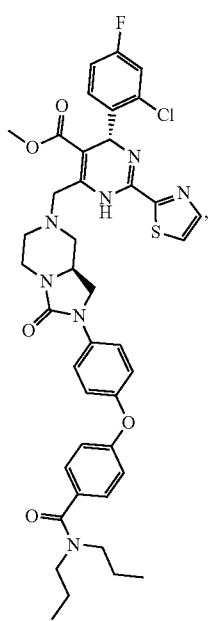
(90)
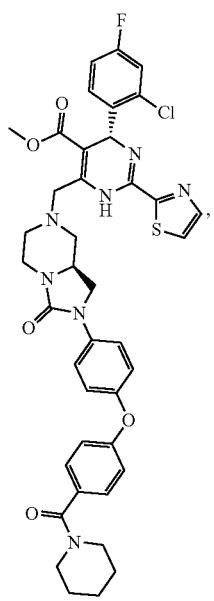
(91)
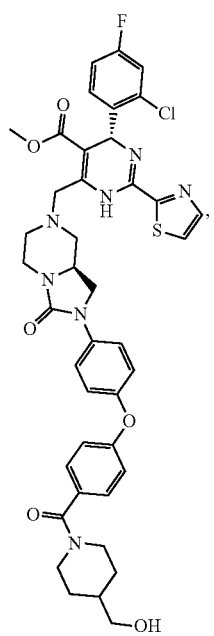

(92)
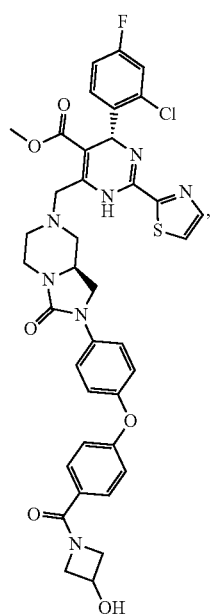
(93)
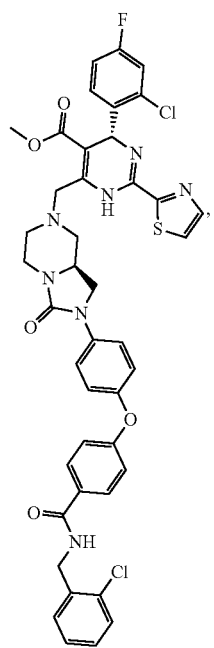
(94)
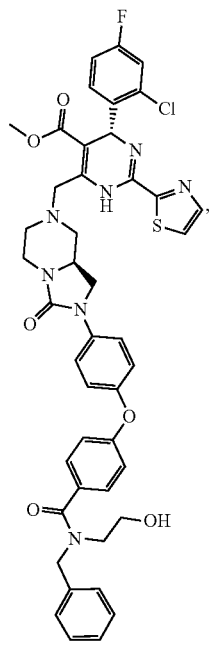
(95)
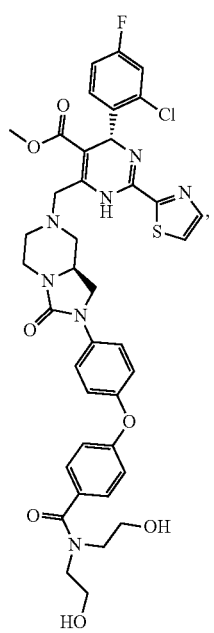

-continued
(96)
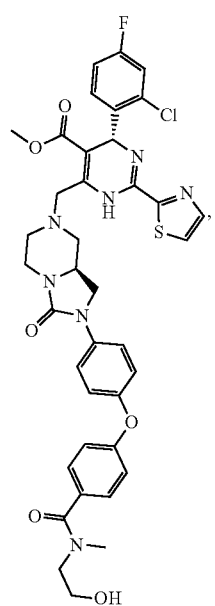
(97)
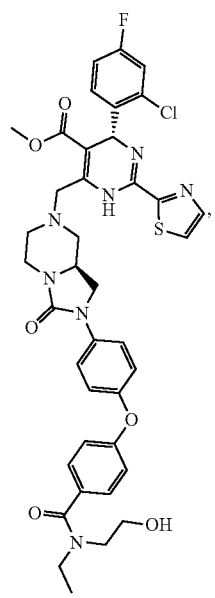
(98)
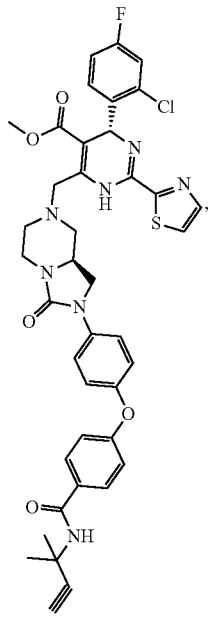
(99)
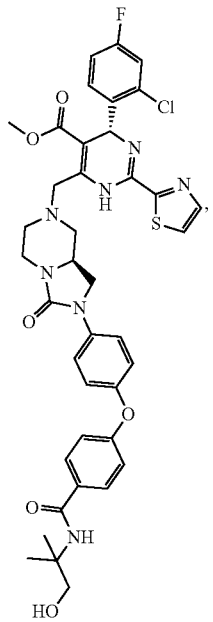

(100)
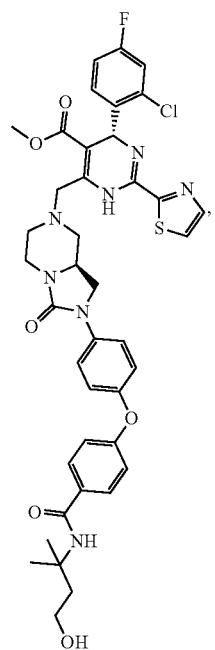
(102)
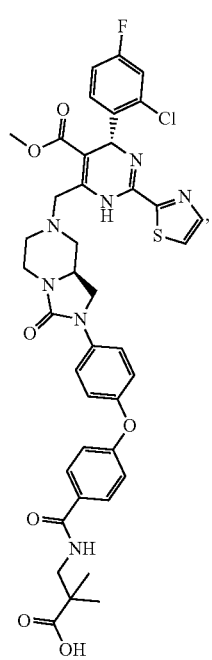
(101)
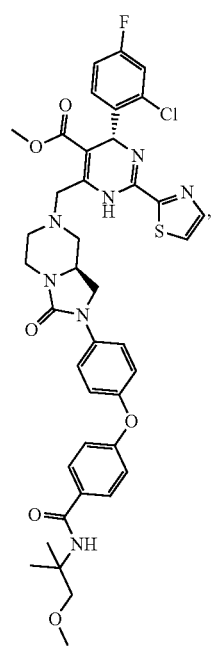
(103)
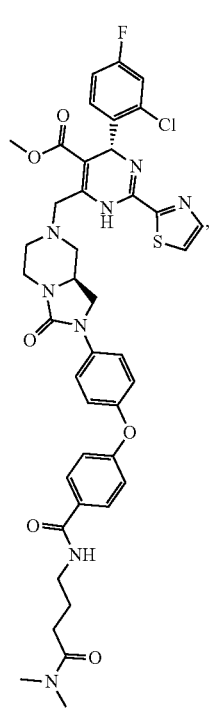

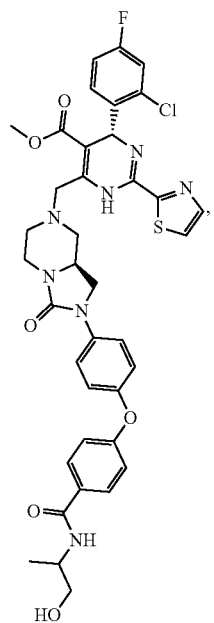
(104)
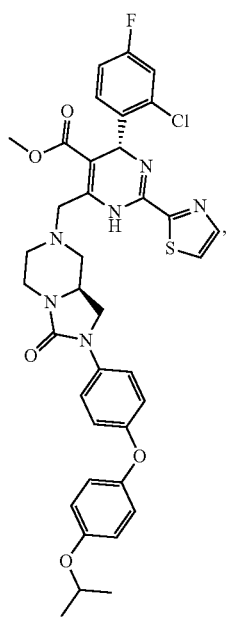
(106)
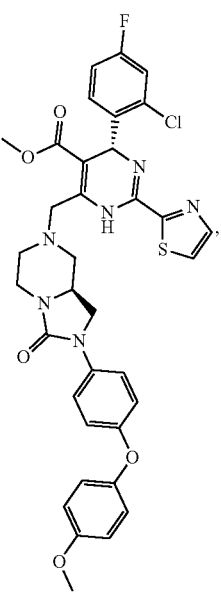
(105)
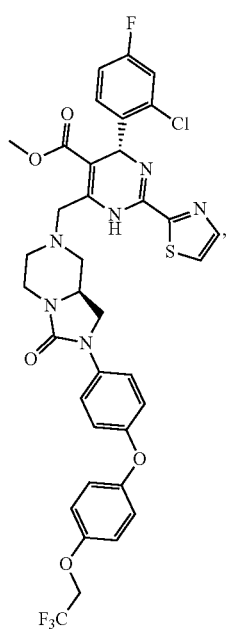
(107)

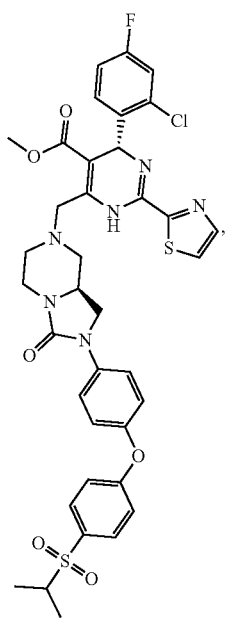
(108)
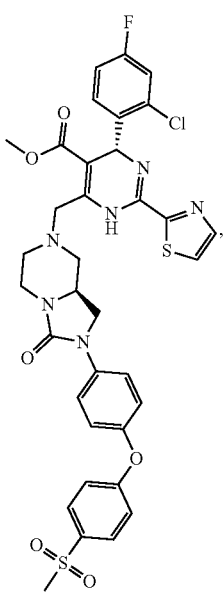
(109)
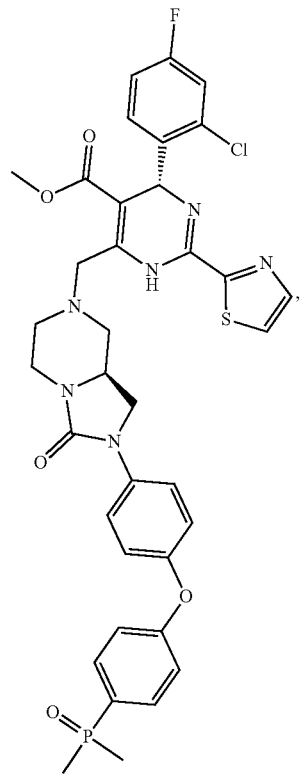
(110)
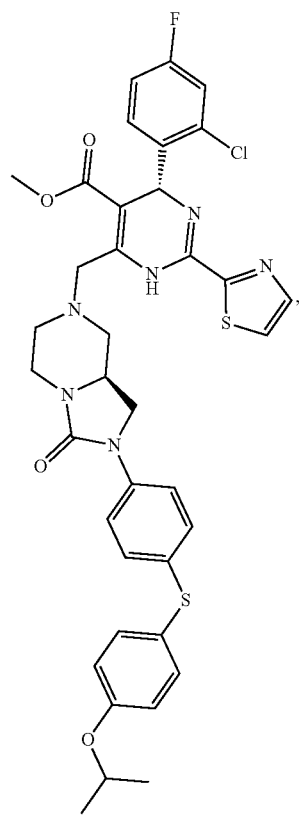
(111)

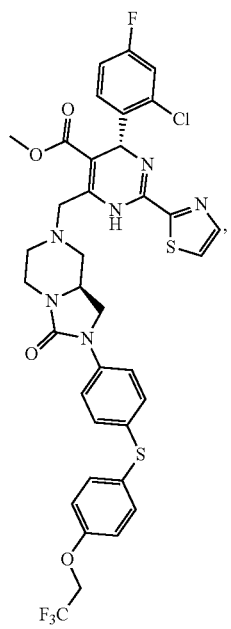
(112)
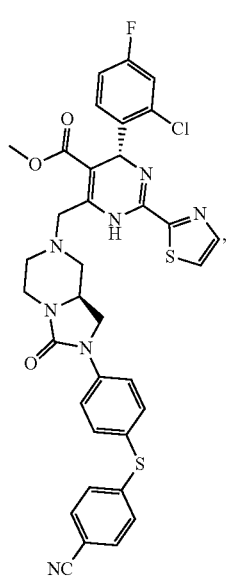
(114)
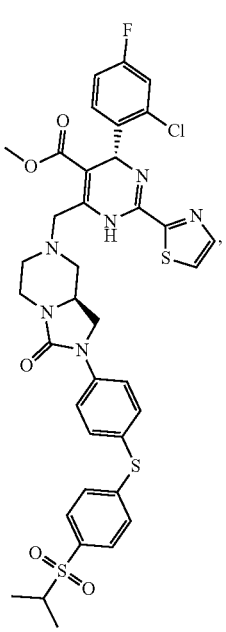
(113)
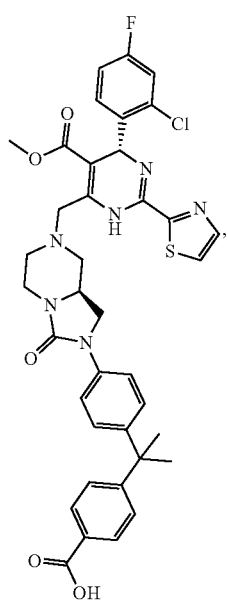
(115)

(116)
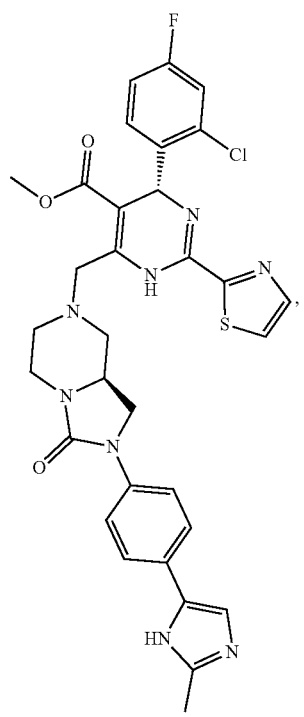
(117)
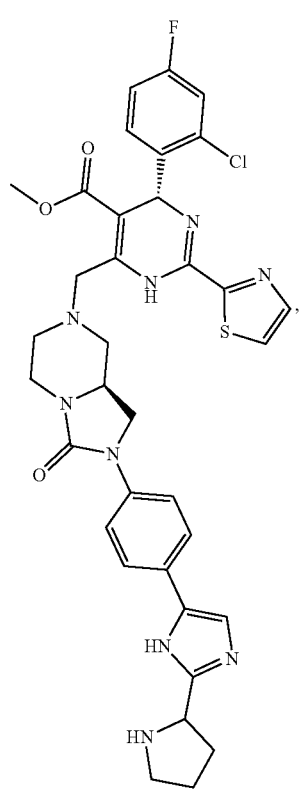
(118)
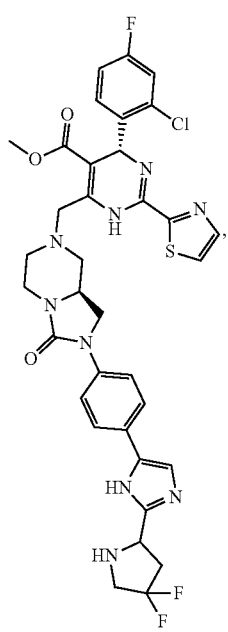
(119)
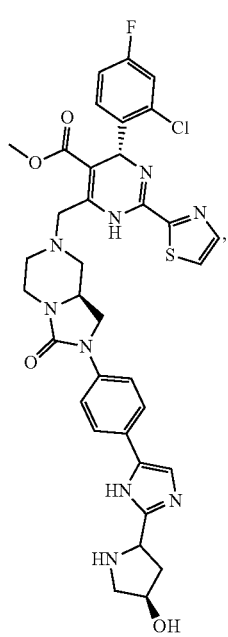

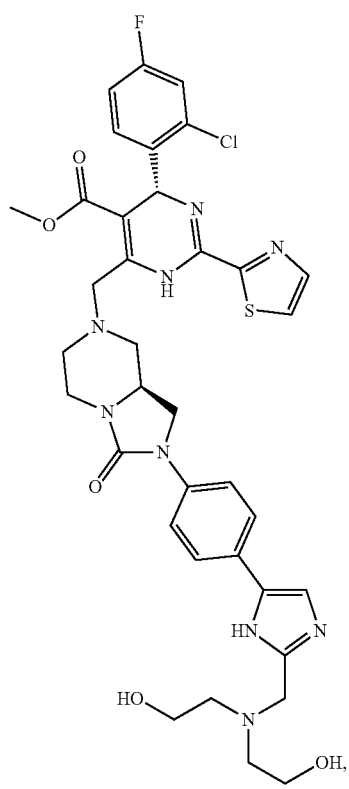
(120)
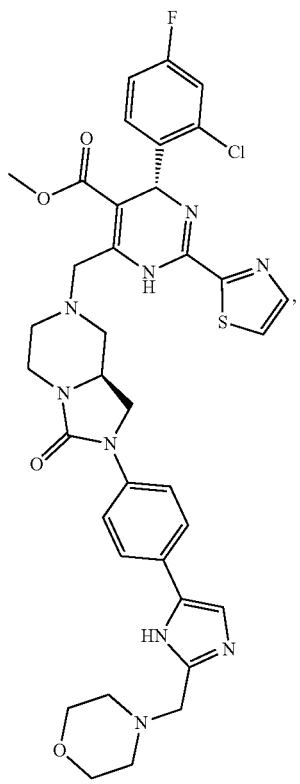
(121)
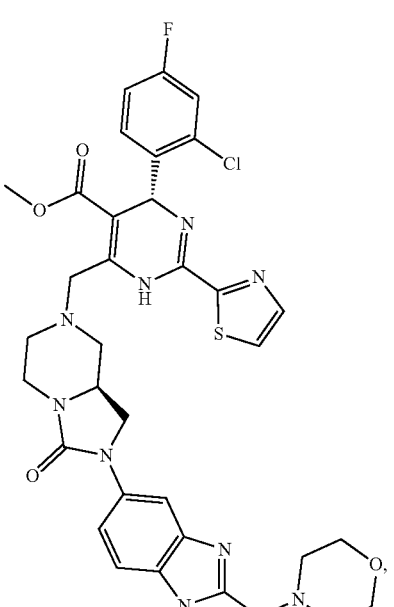
(122)
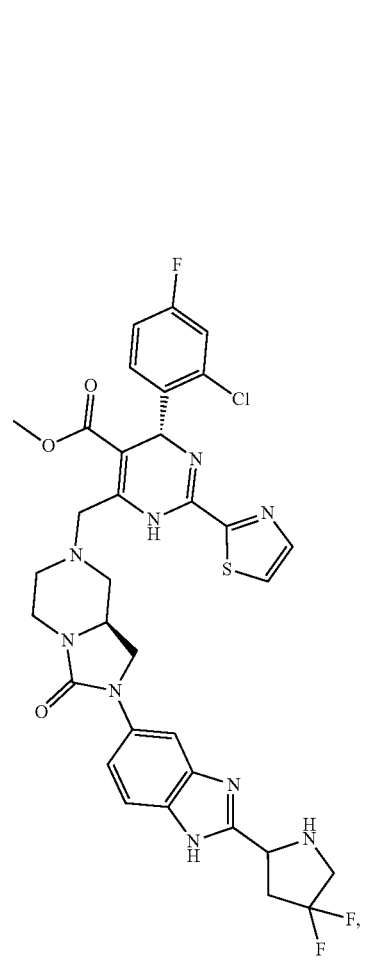
(123)

-continued
(124)
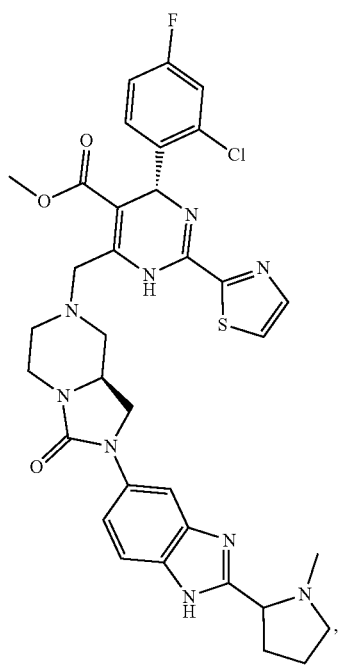
(125)
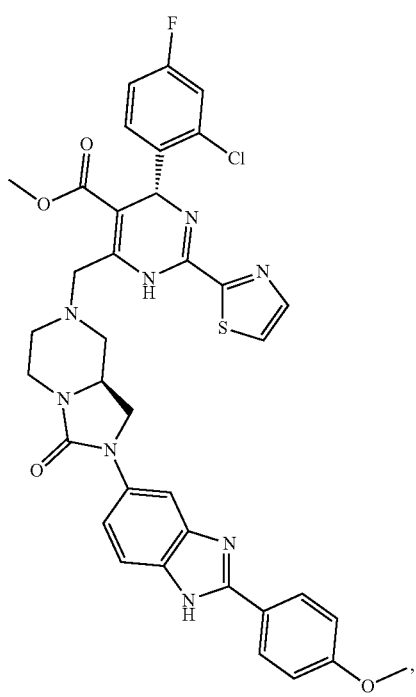
(126)
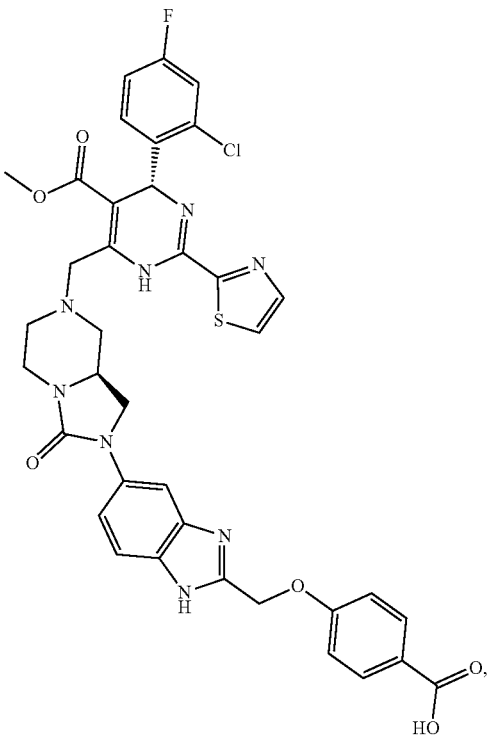
(127)
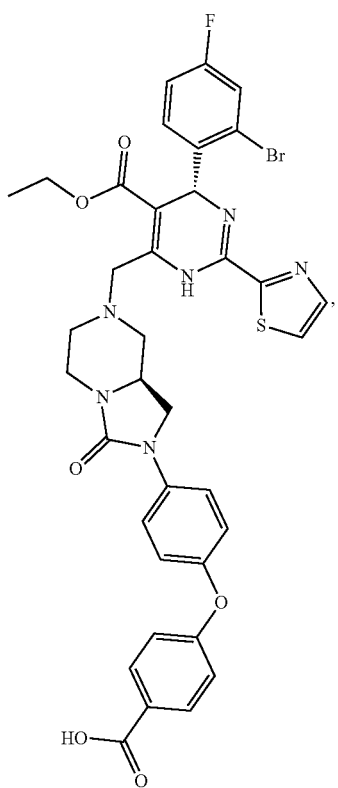

(128)
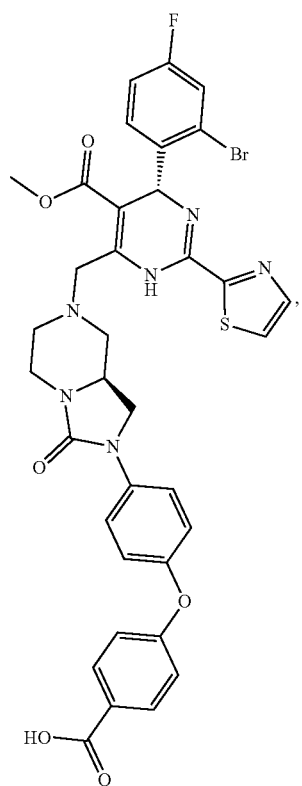
(129)
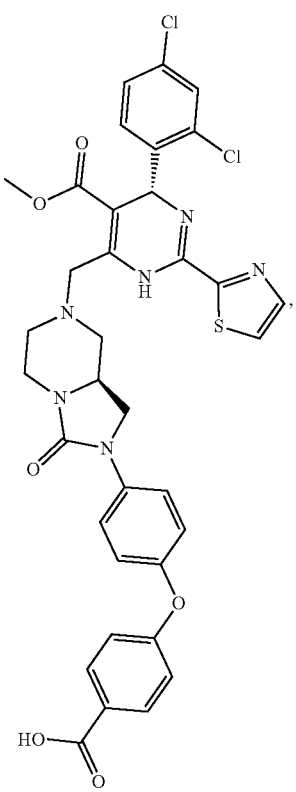
(130)
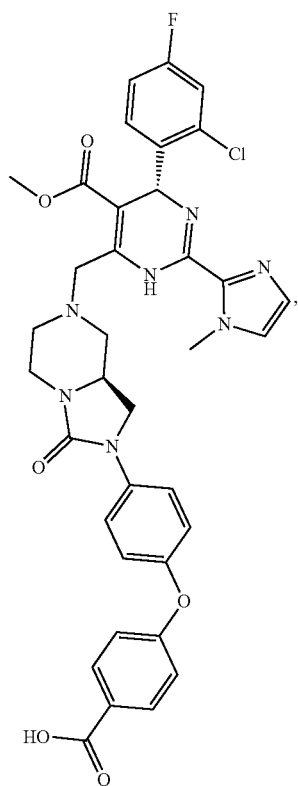
(131)
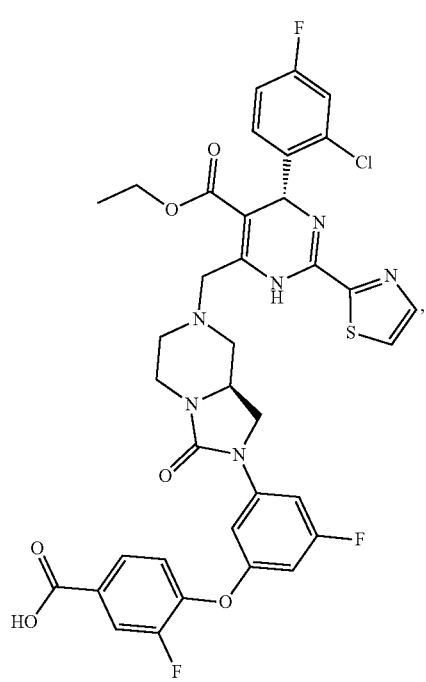

(132)
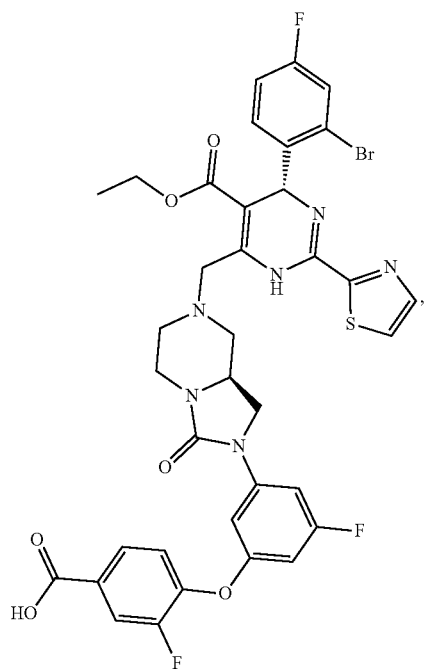
(133)
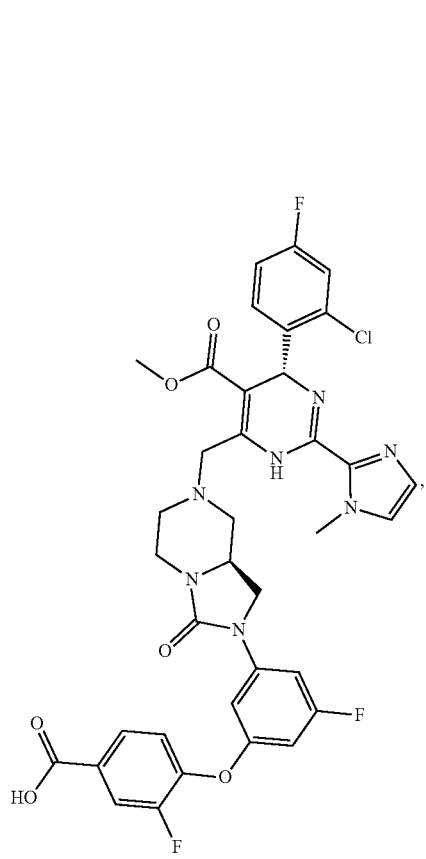
(134)
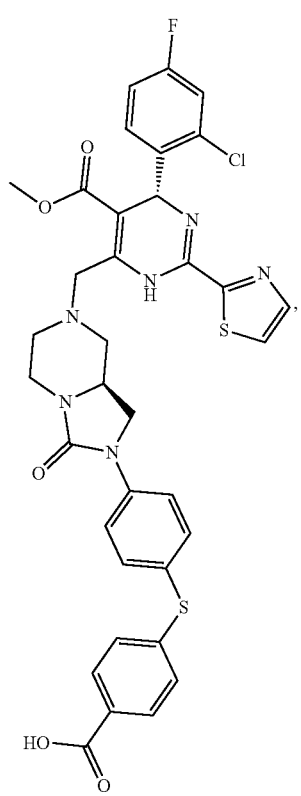
(135)
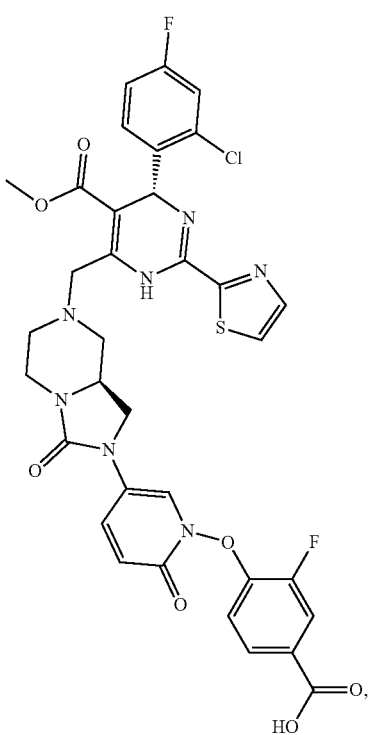

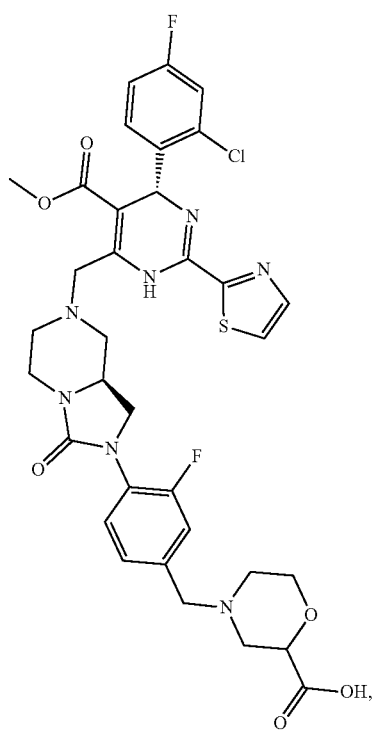
(136)
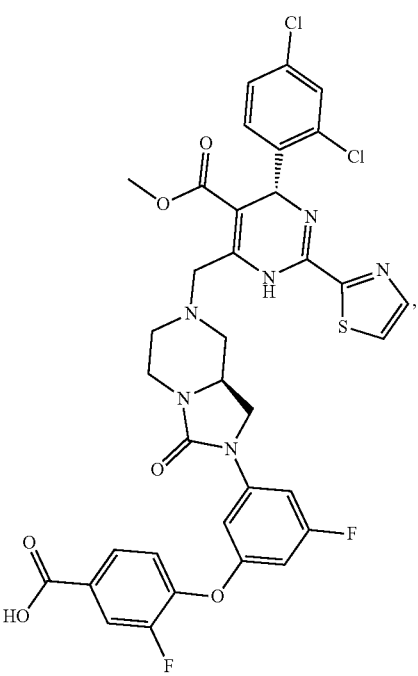
(138)
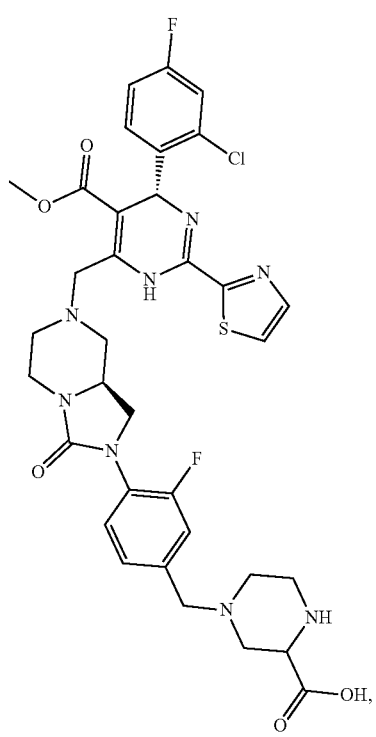
(137)
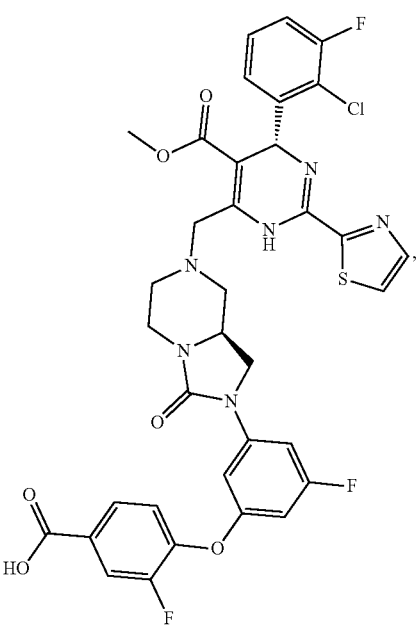
(139)

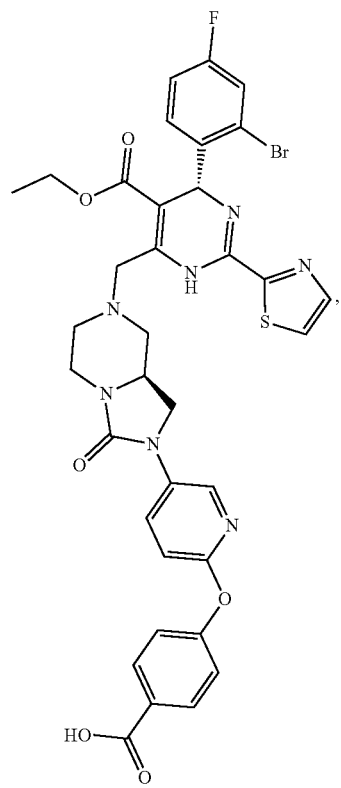
(140)
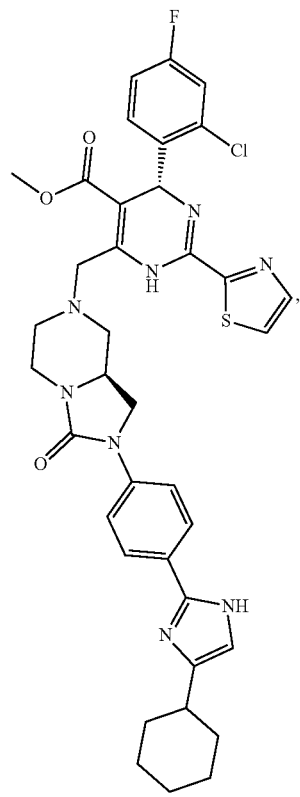
(142)
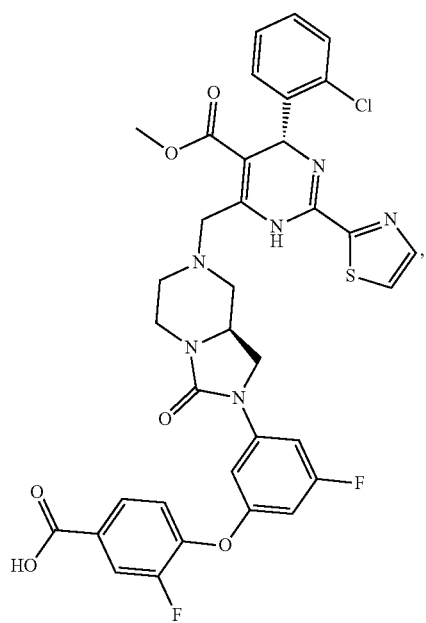
(141)
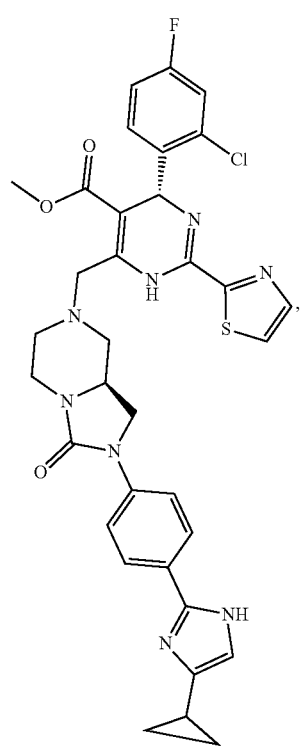
(143)

(144)
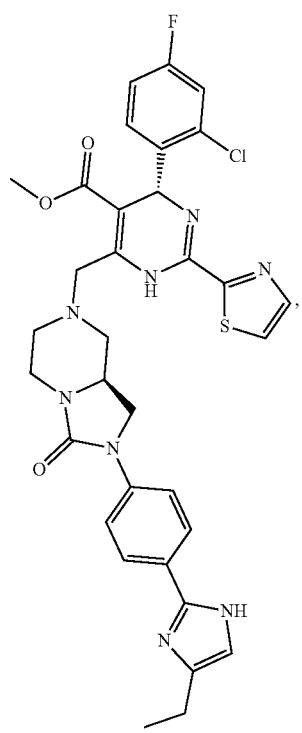
(145)
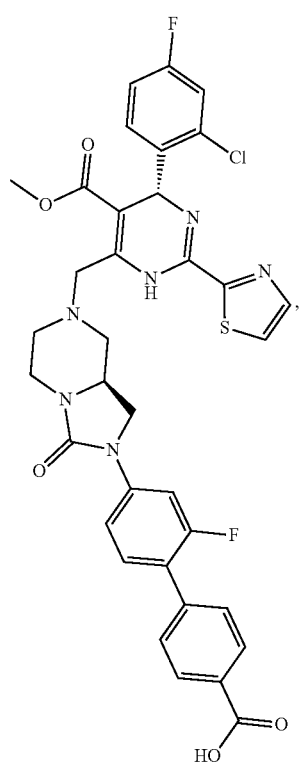
(146)
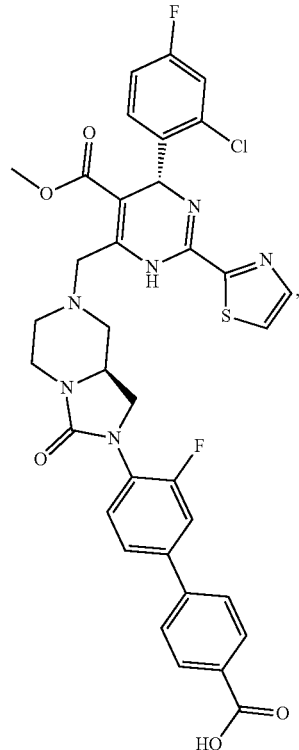
(147)
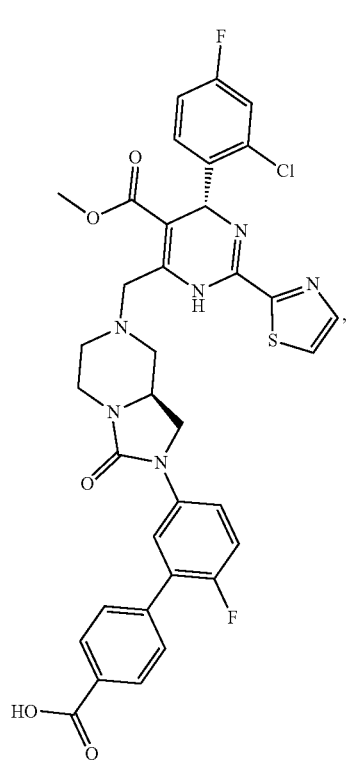

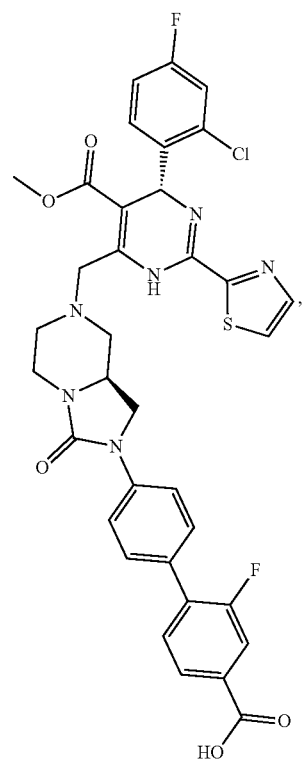
(148)
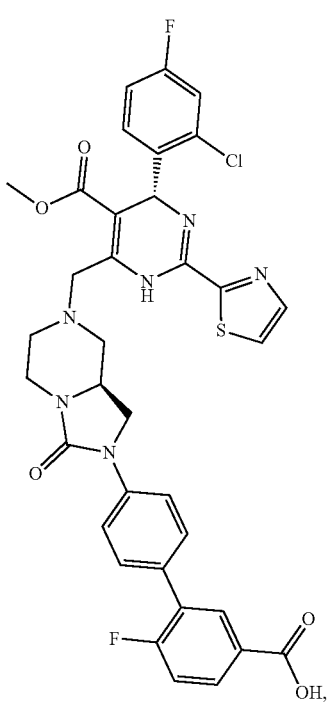
(150)
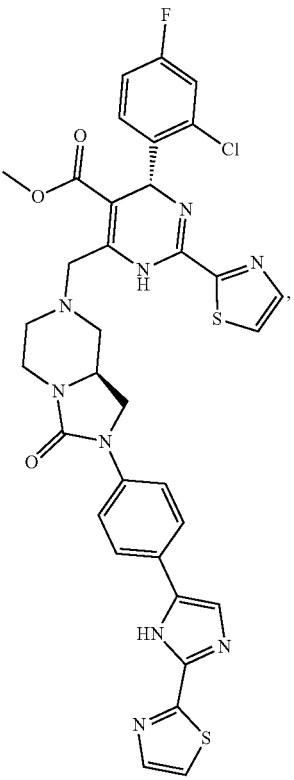
(151)
(149)

(152)
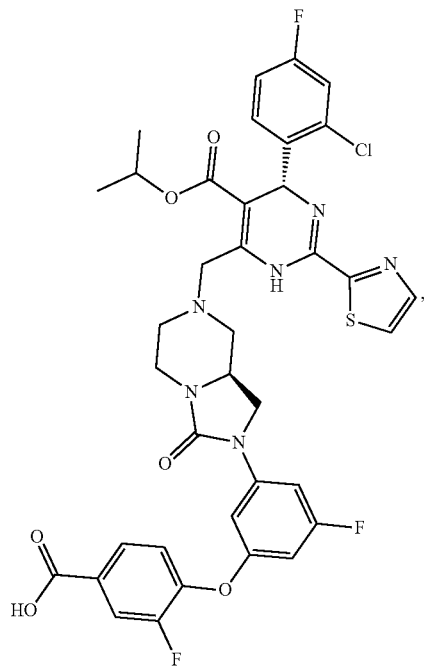
(153)
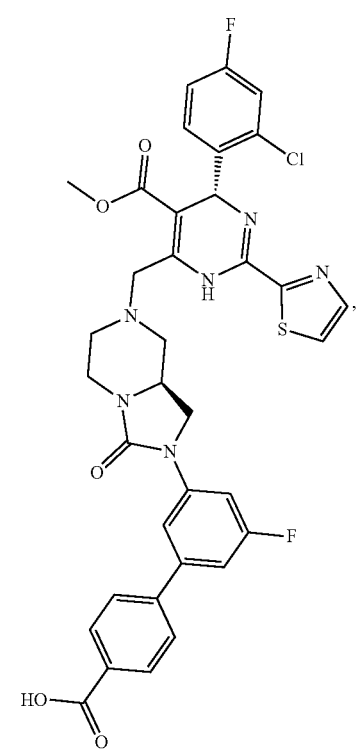
(154)
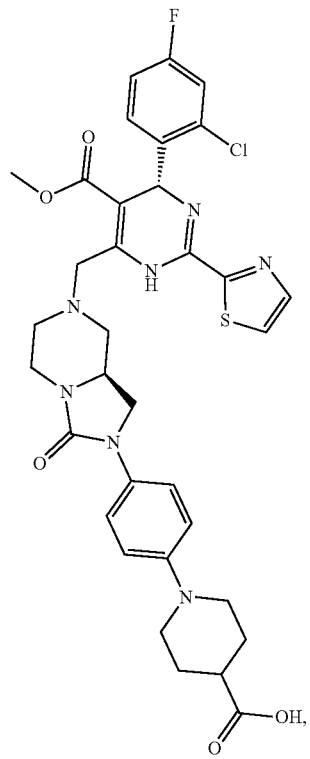
(155)
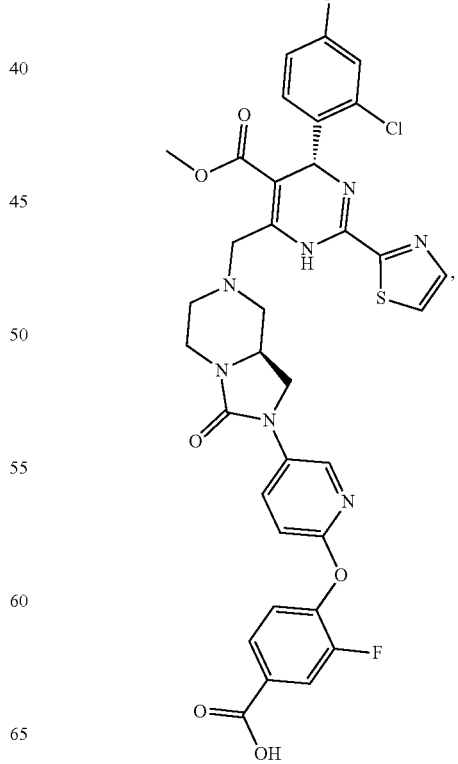

(156)
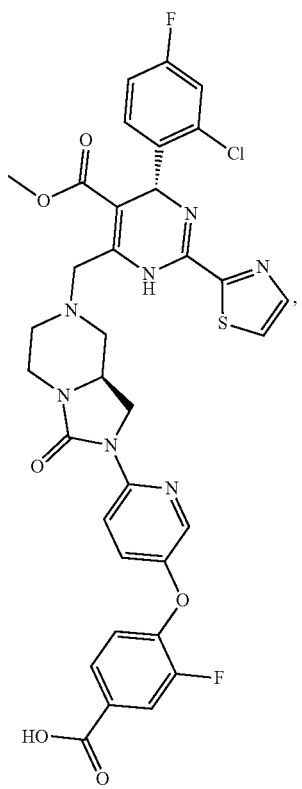
(157)
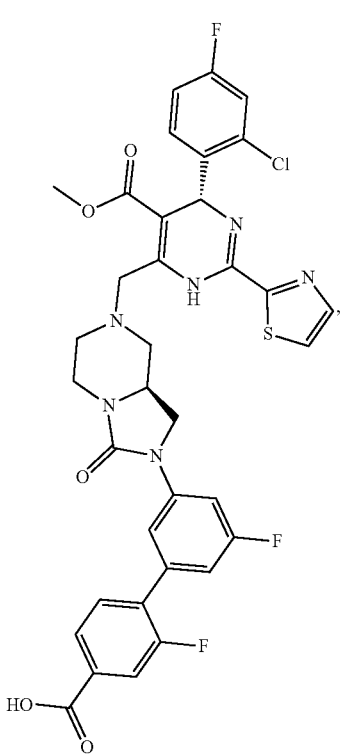
(158)
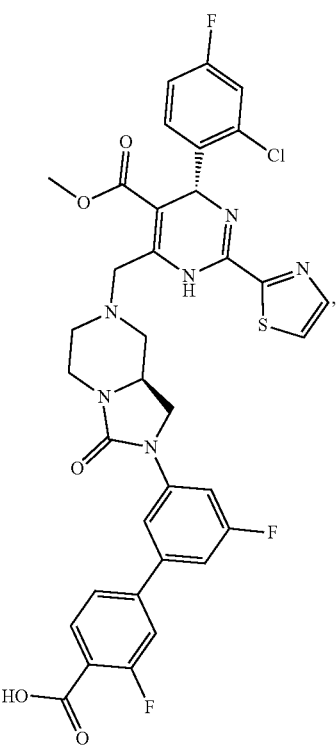
(159)
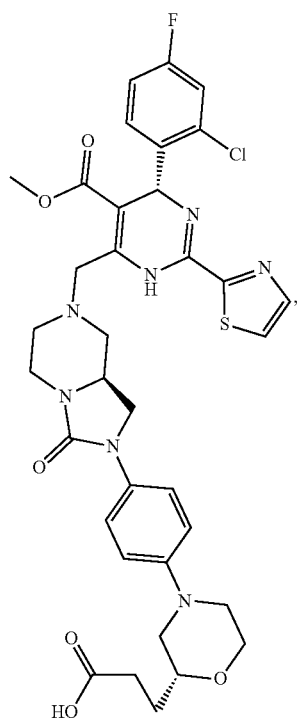

(160)
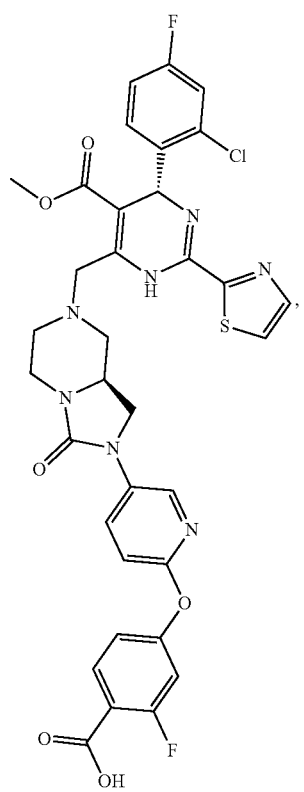
(161)
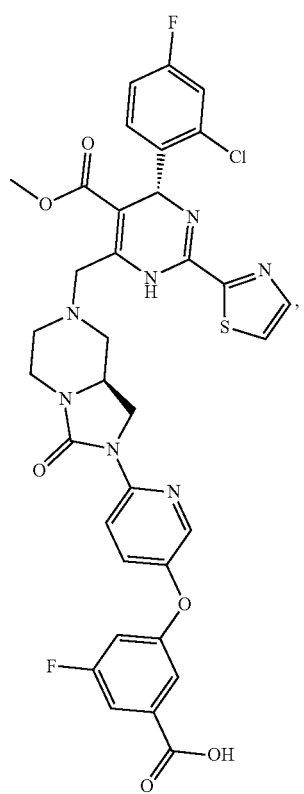
(162)
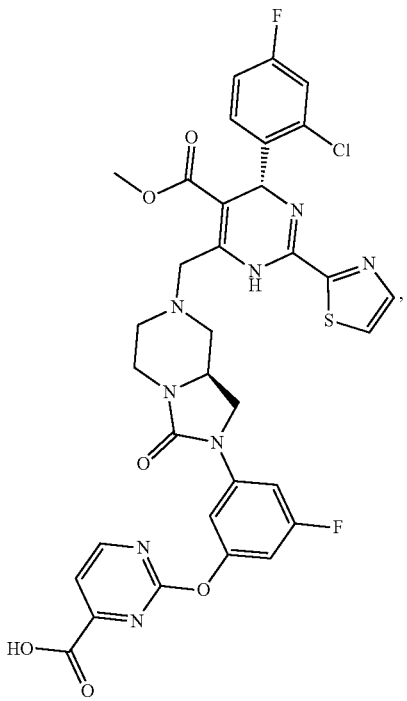
(163)
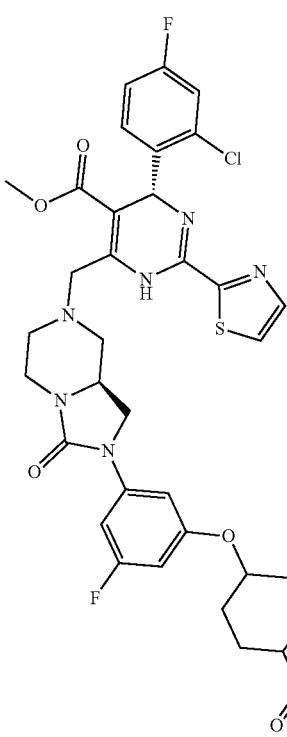

(164)
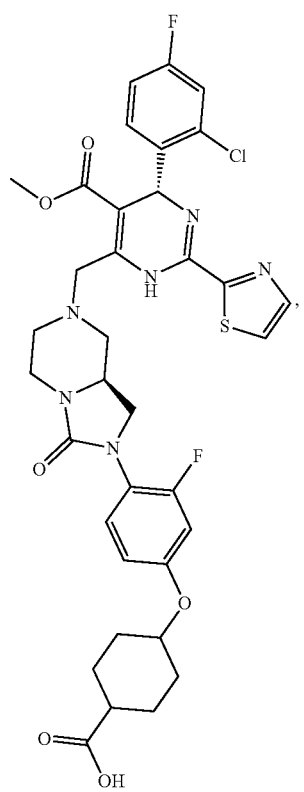
(165)
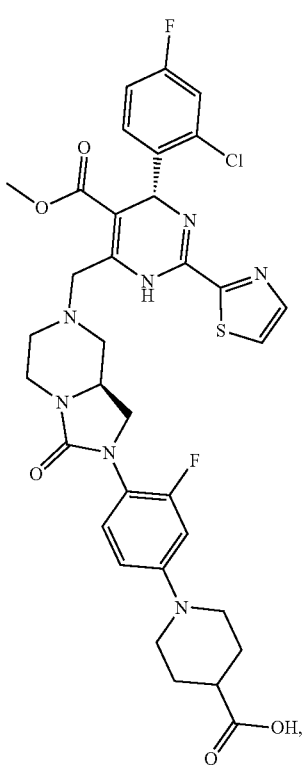
(166)
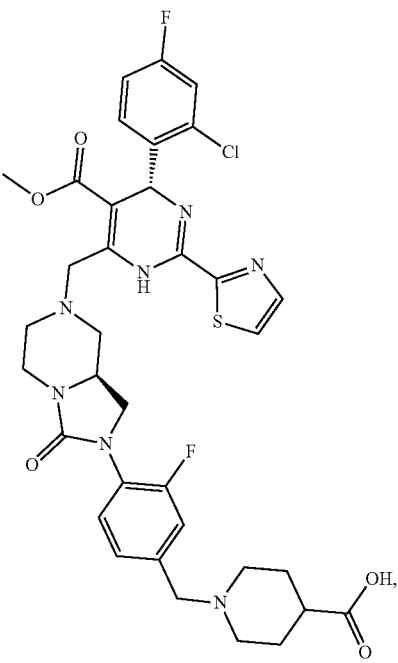
(167)
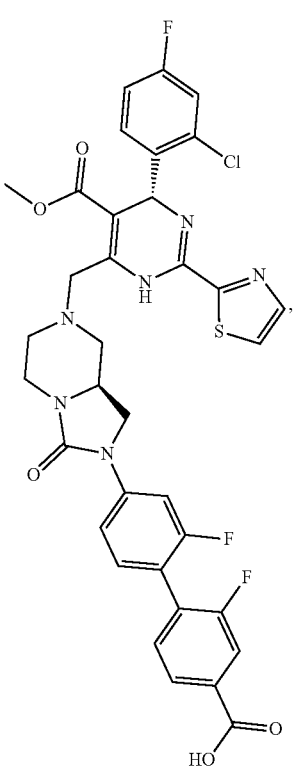

(168)
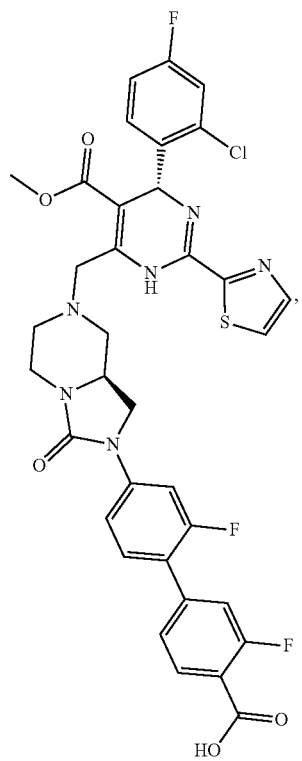
(169)
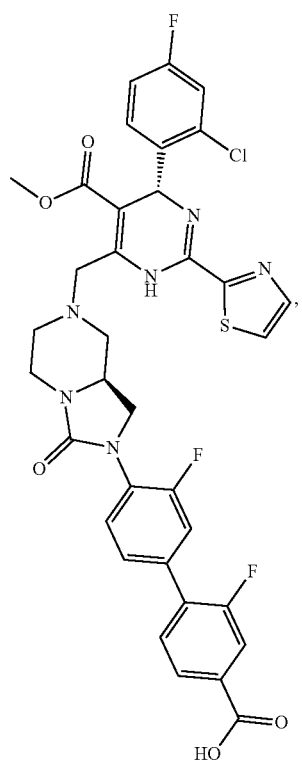
(170)
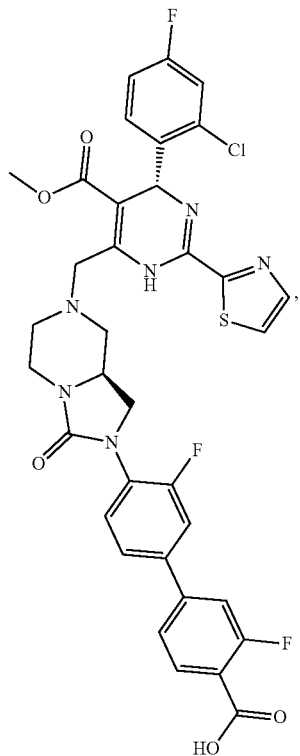
(171)
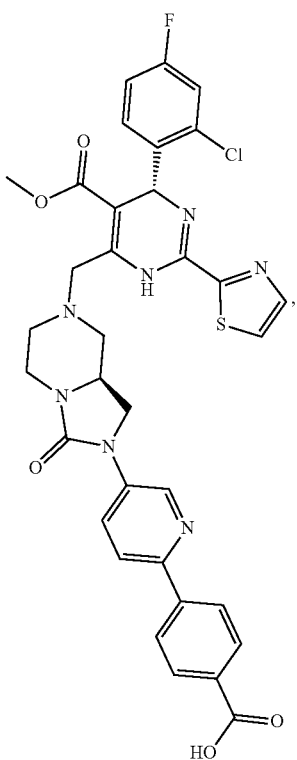

-continued
(172)
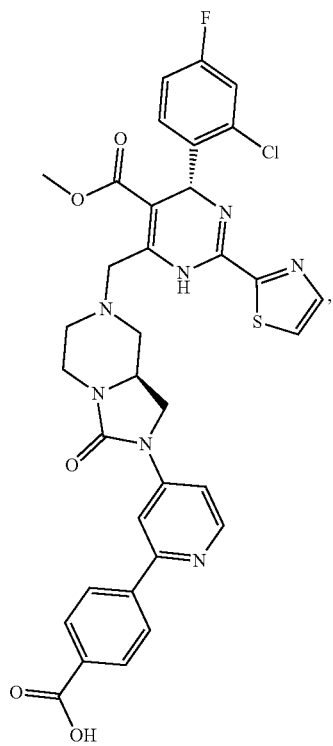
(173)
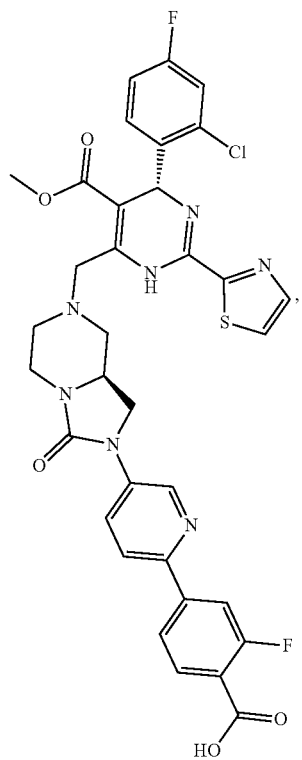
-continued
(174)
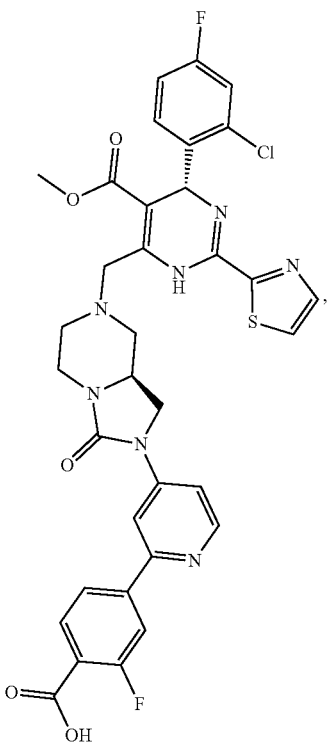
(175)
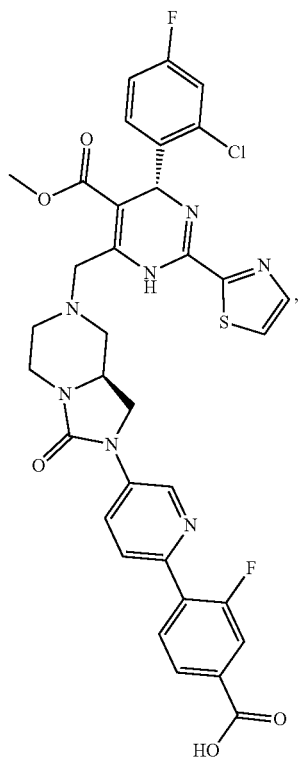

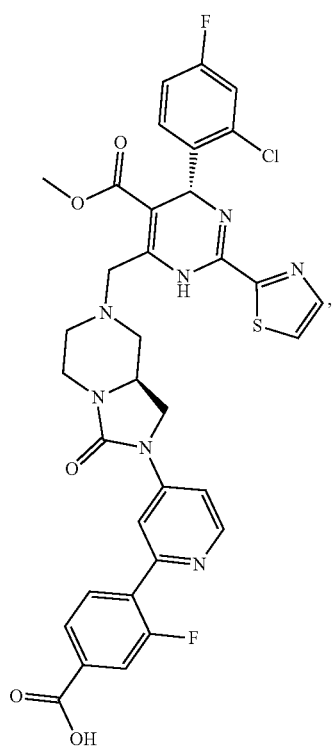
(176)
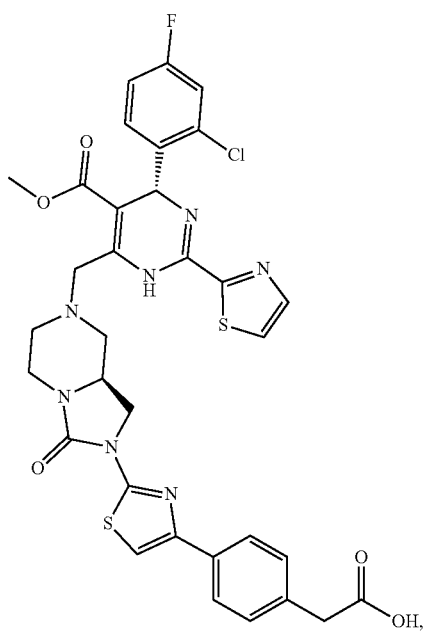
(178)
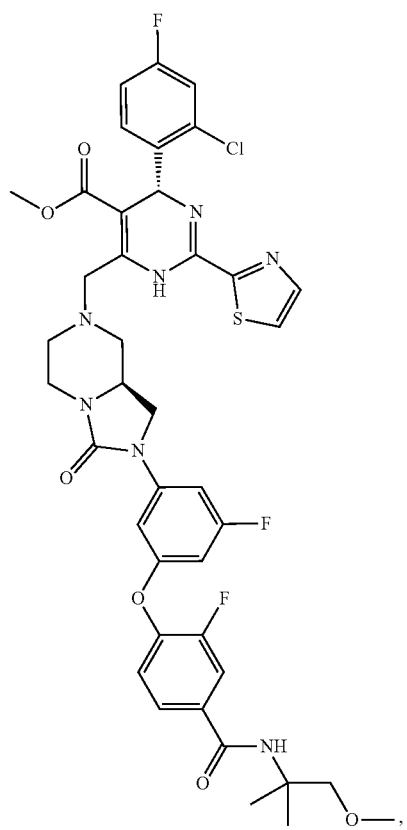
(177)
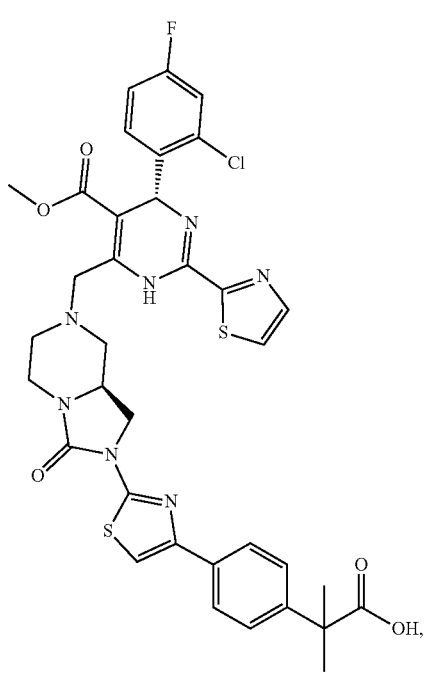
(179)

121
-continued
(180)
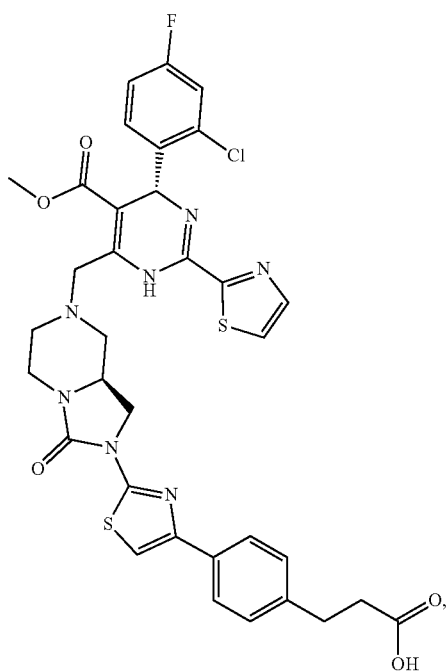
(181)
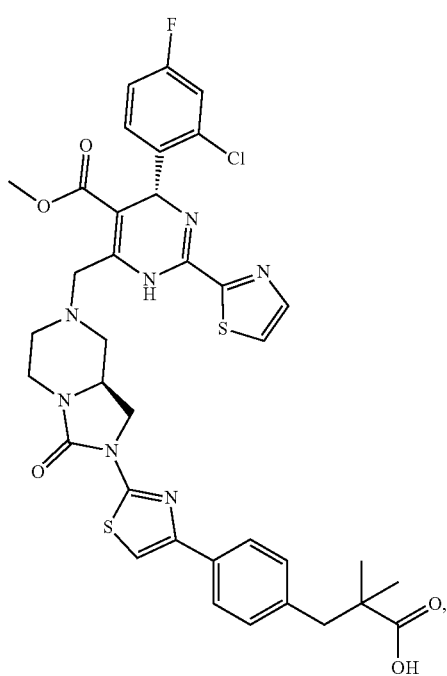
122
-continued
(182)
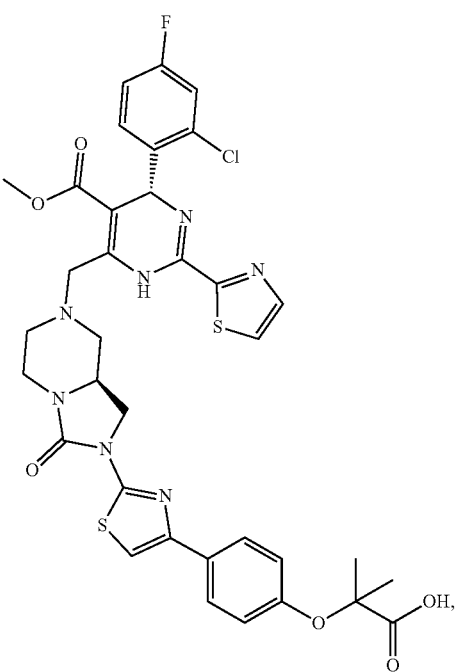
(183)
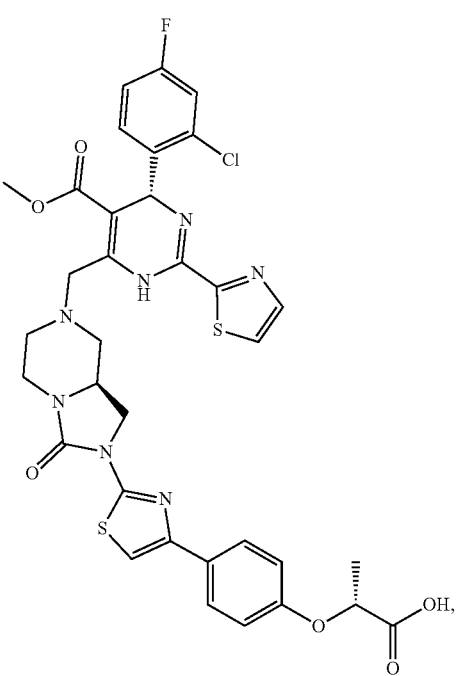

(184)
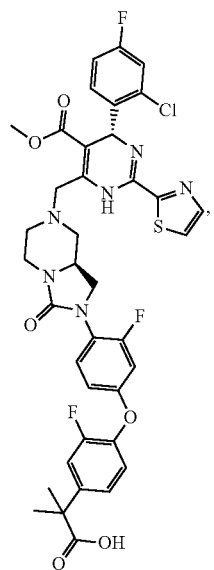
(186)
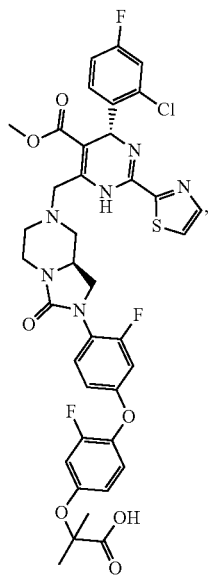
(185)
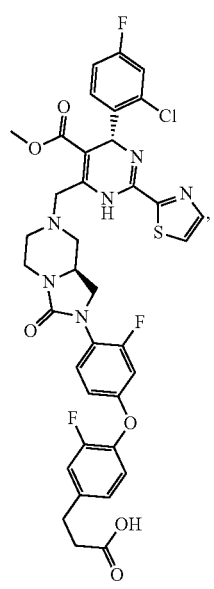
(187)
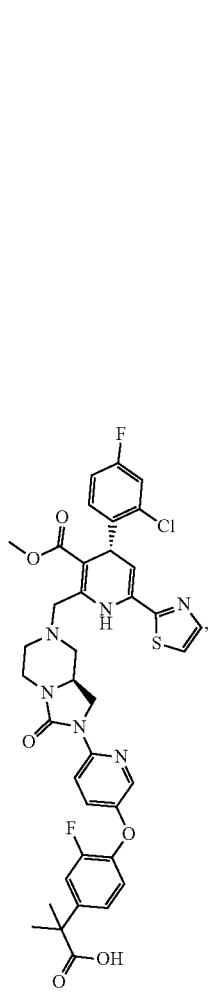

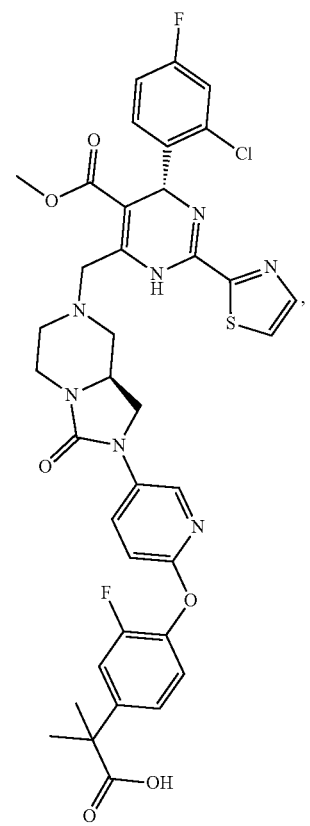
(188)
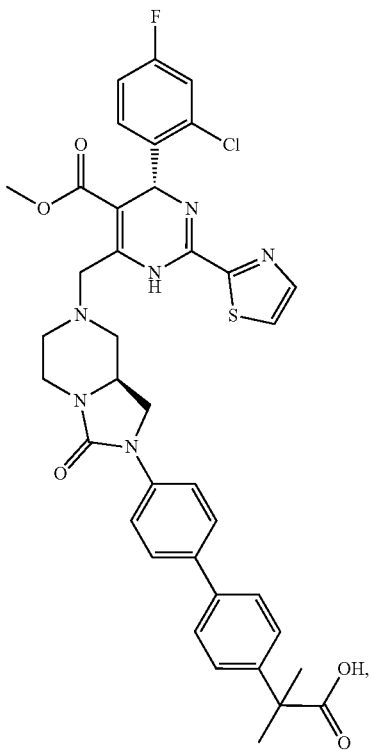
(190)
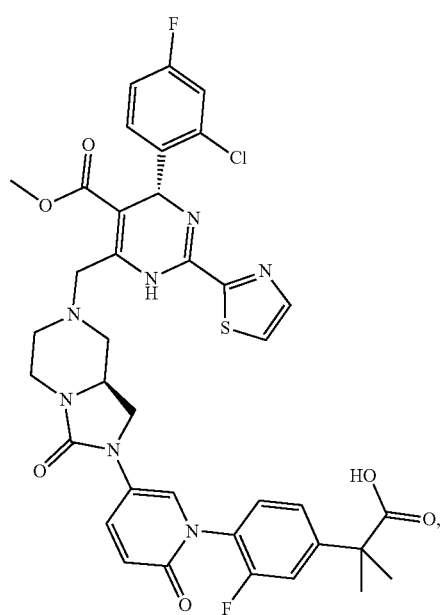
(189)
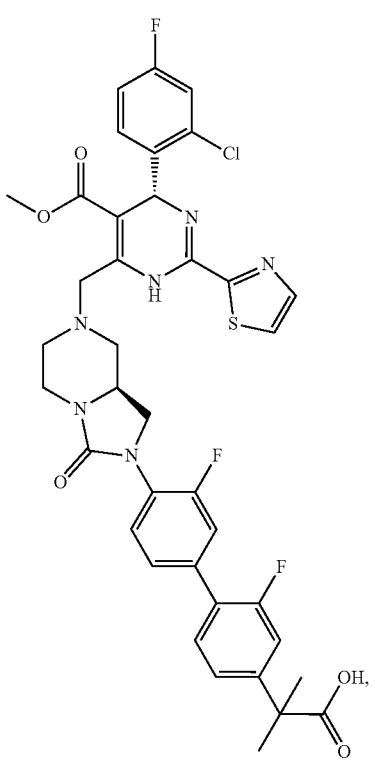
(191)

127
-continued
(192)
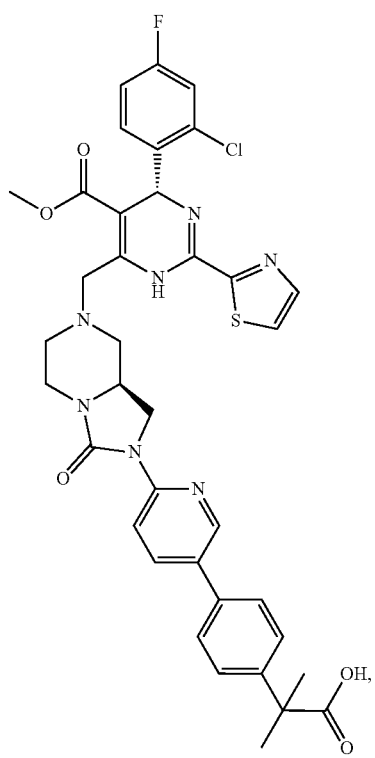
128
-continued
(194)
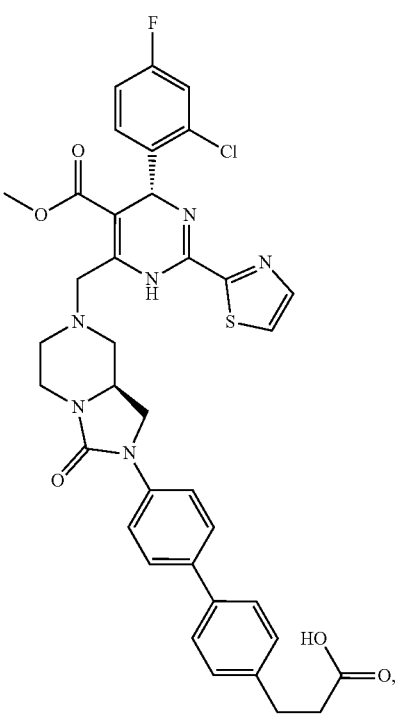
(193)
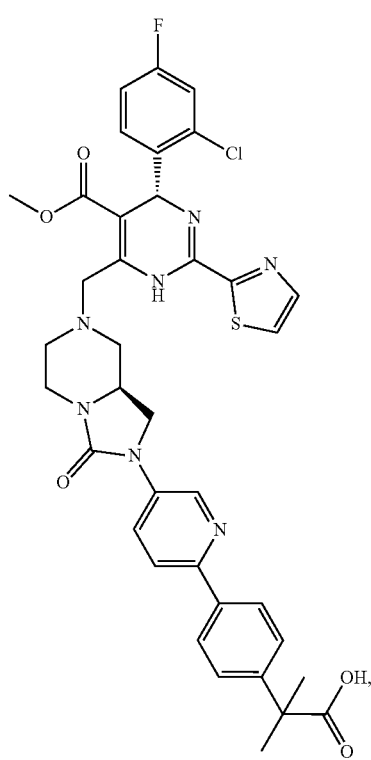
(195)
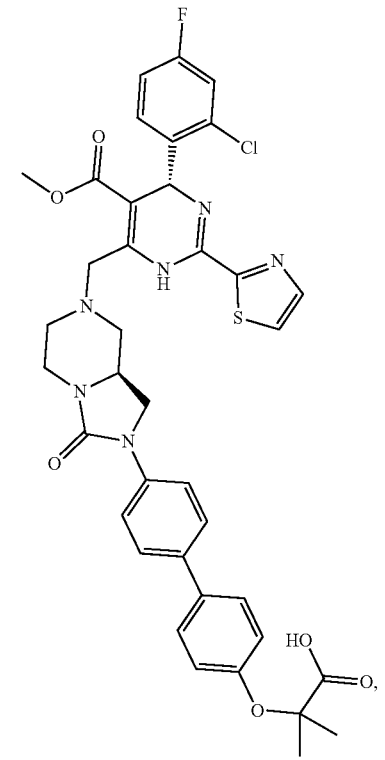

(196)
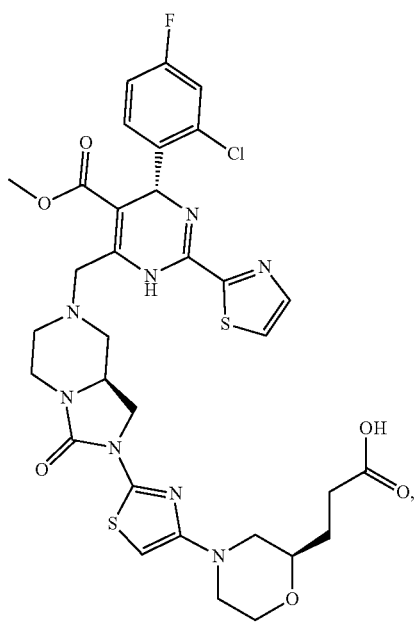
(197)
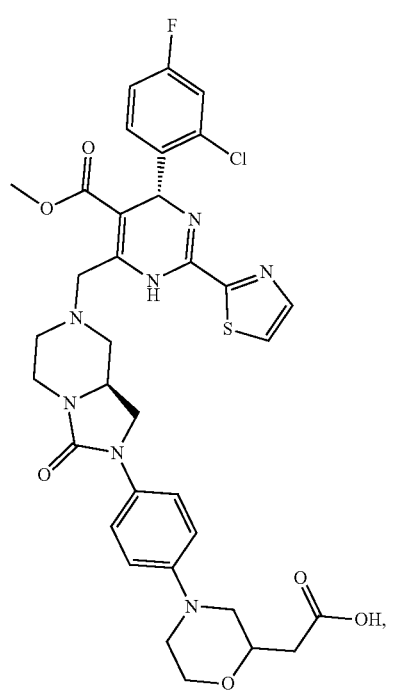
(198)
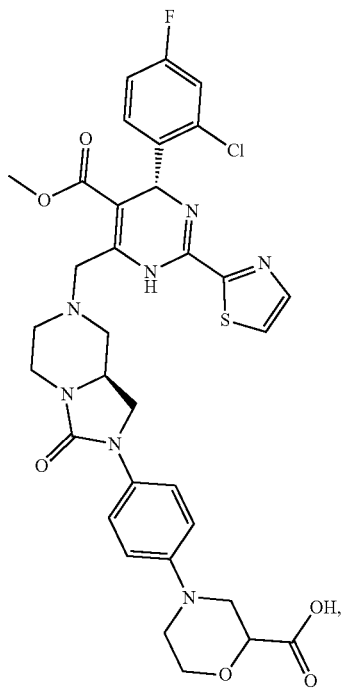
(199)
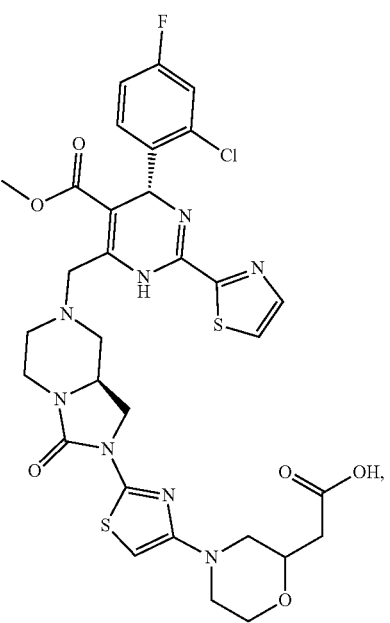

(200)
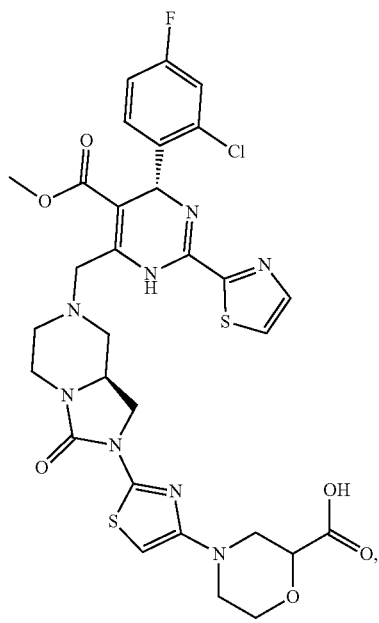
(201)
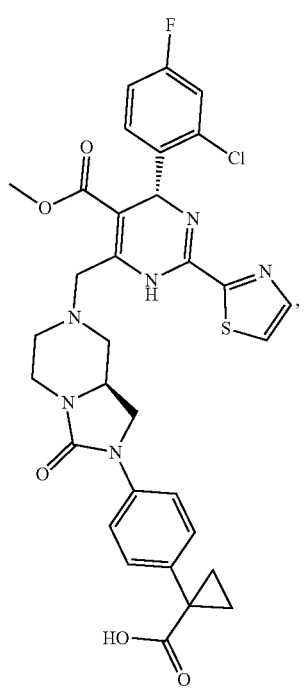
(202)
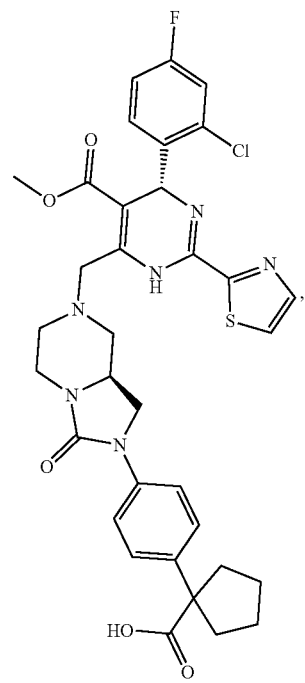
(203)
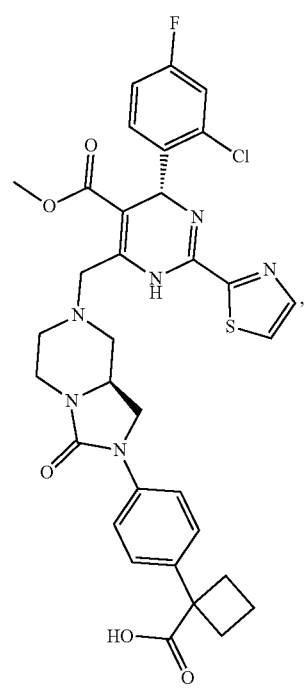

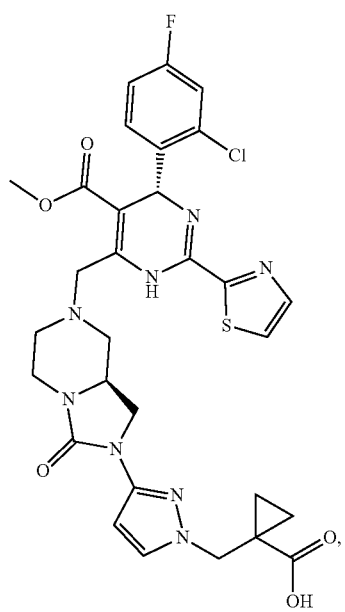
(204)
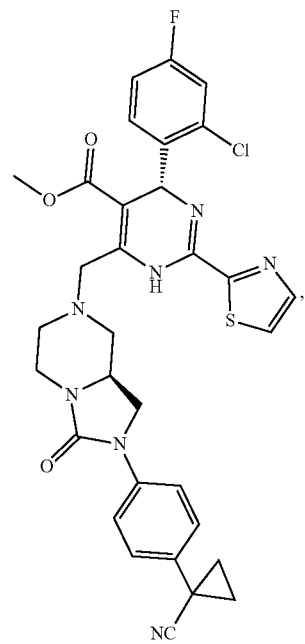
(206)
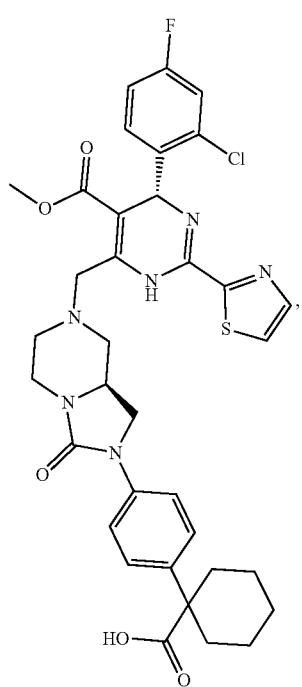
(205)
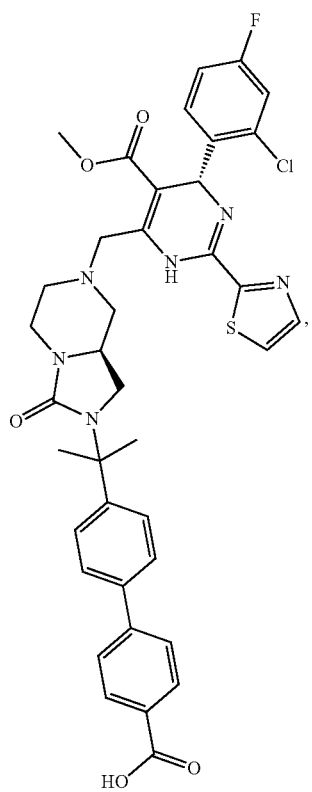
(207)

(208)
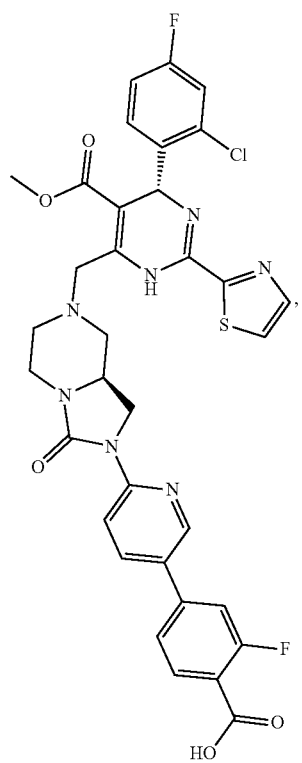
(209)
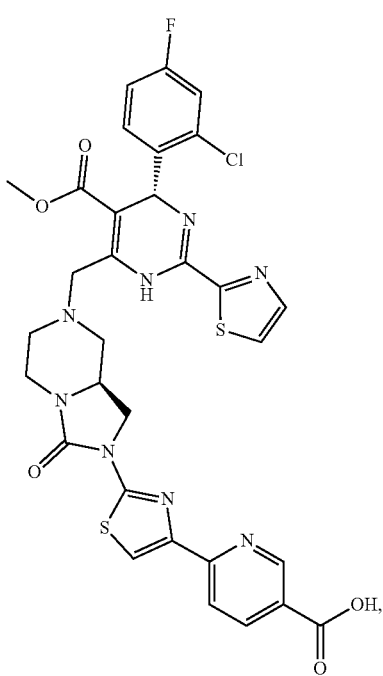
(210)
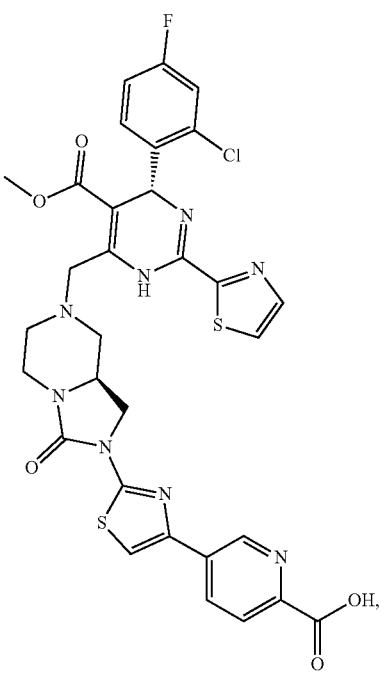
(211)
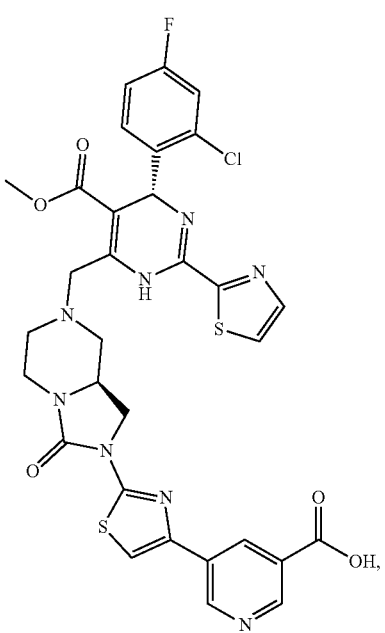

(212)
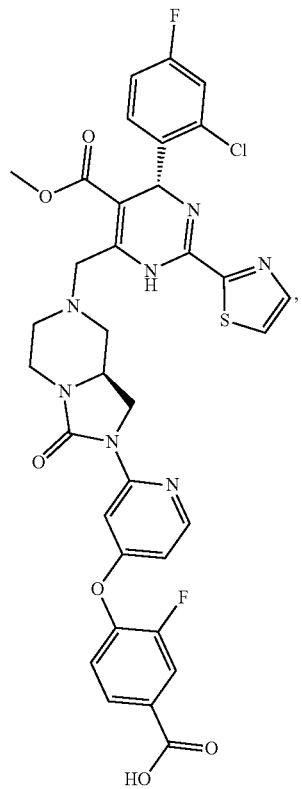
(213)
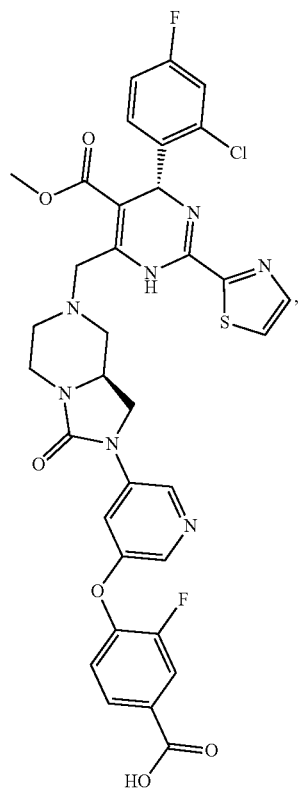
(214)
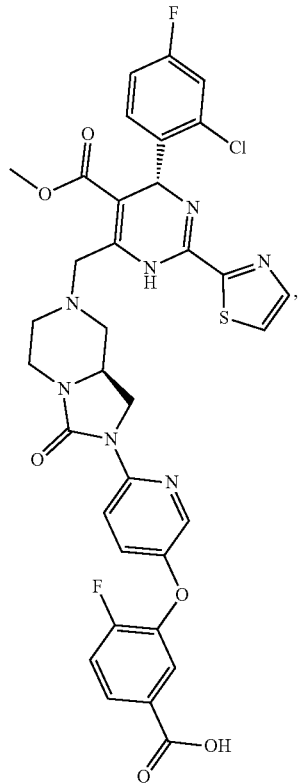
(215)
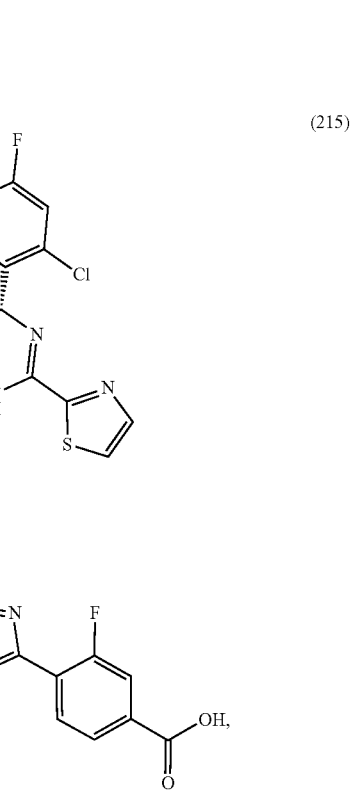

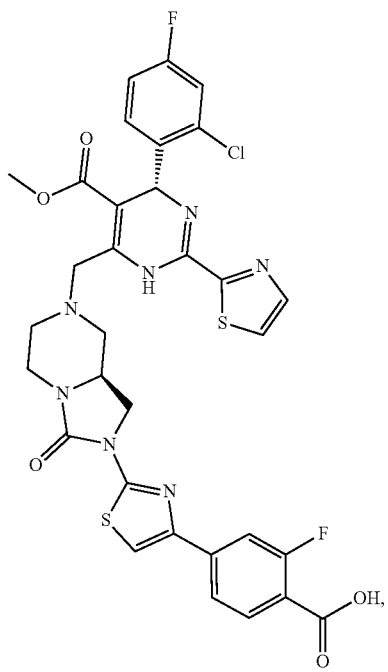
(216)
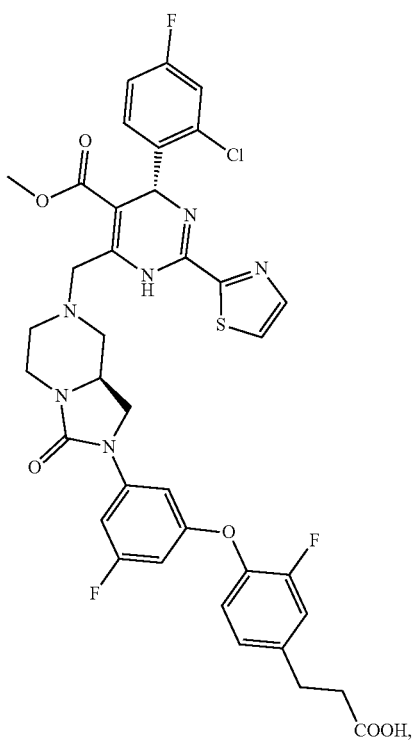
(217)
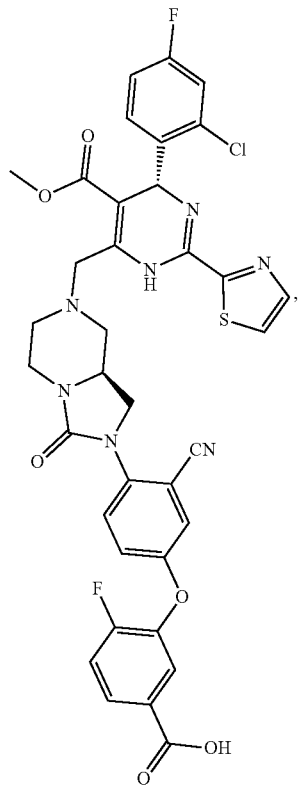
(218)
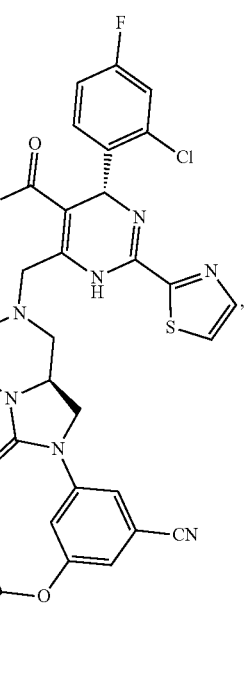
(219)

-continued
(220)
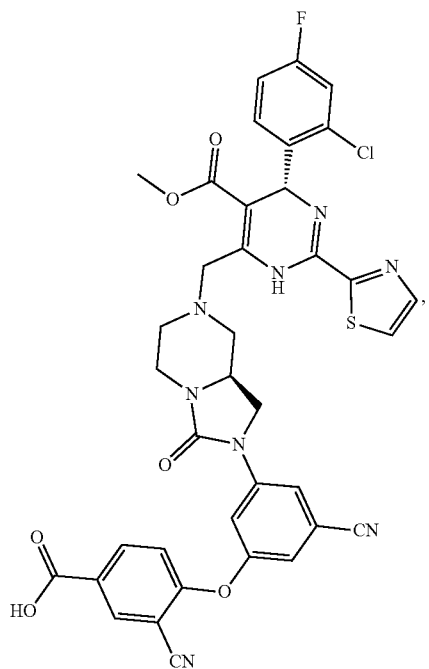
(222)
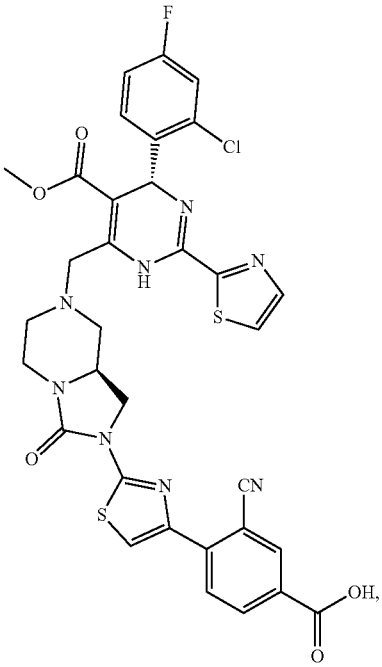
(221)
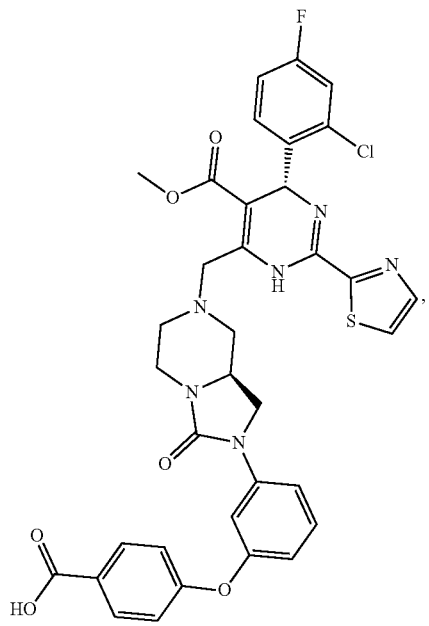
(223)
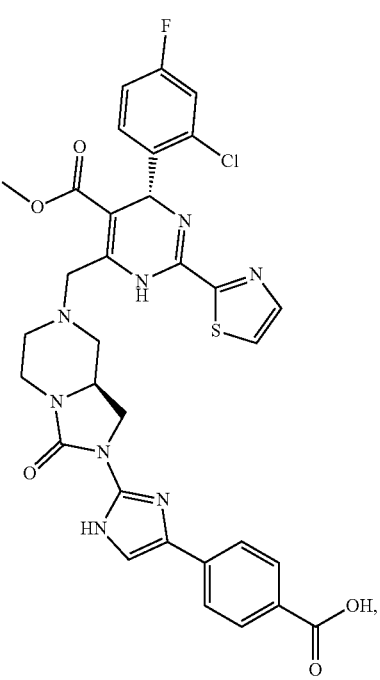

(224)
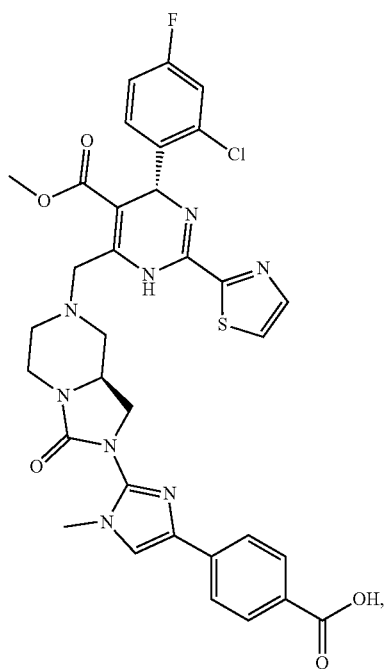
(225)
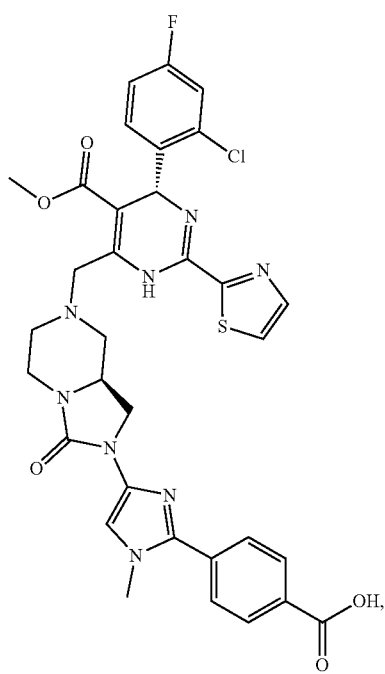
(226)
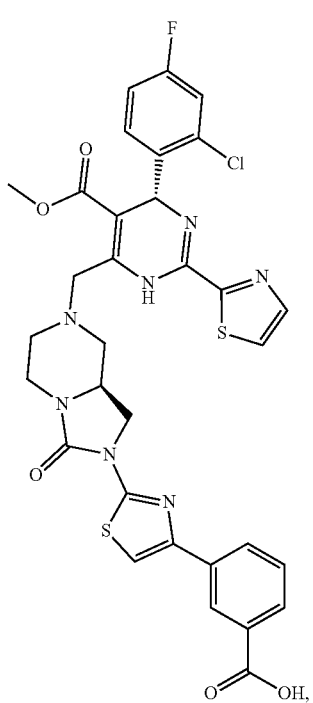
(227)
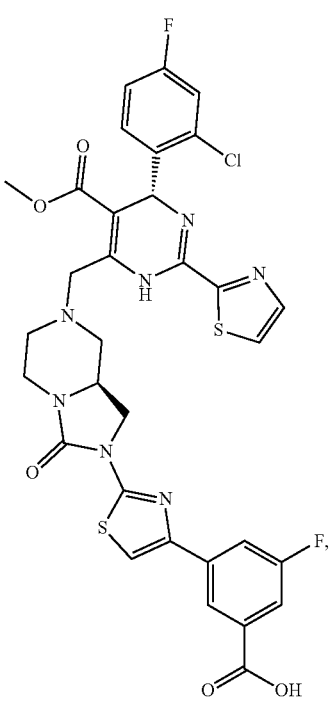

-continued
(228)
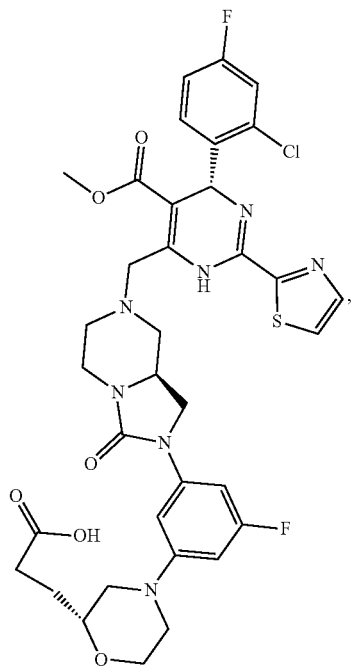
(229)
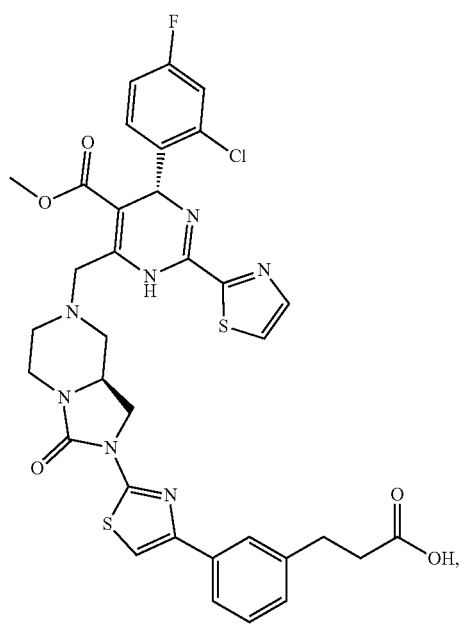
-continued
(230)
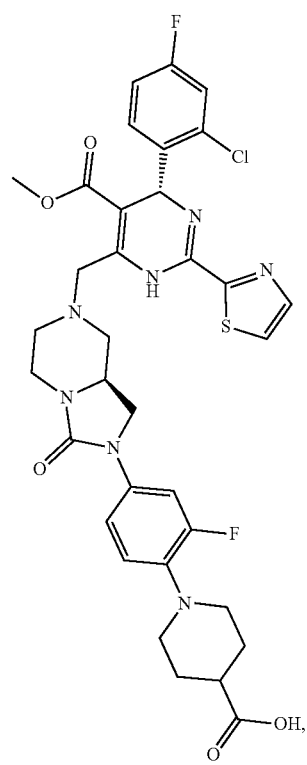
(231)
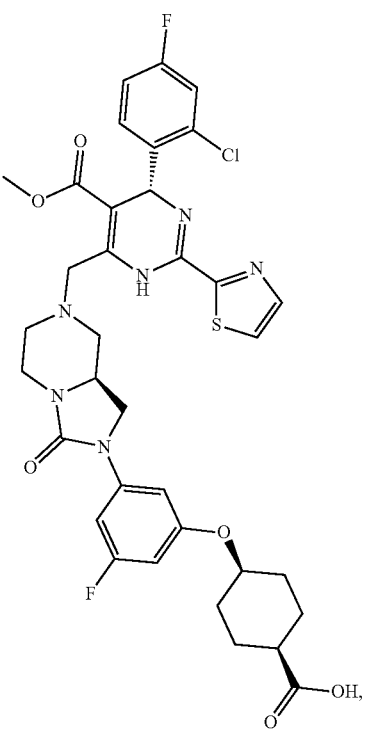

(232)
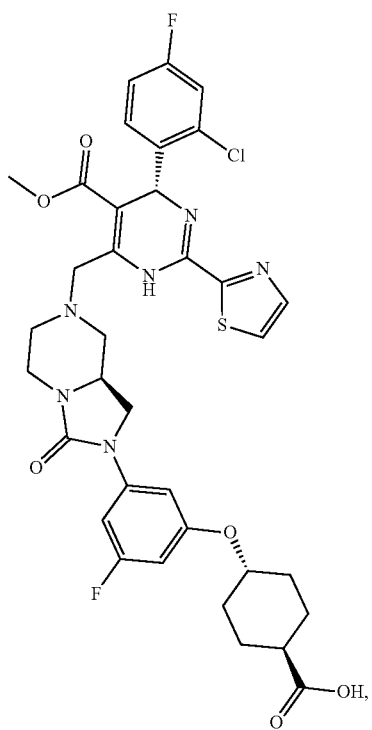
(233)
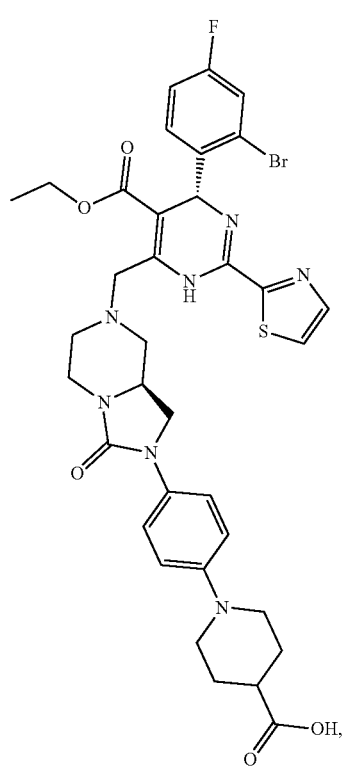
(234)
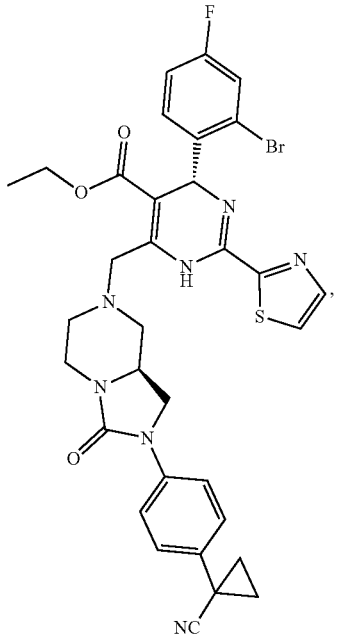
(235)
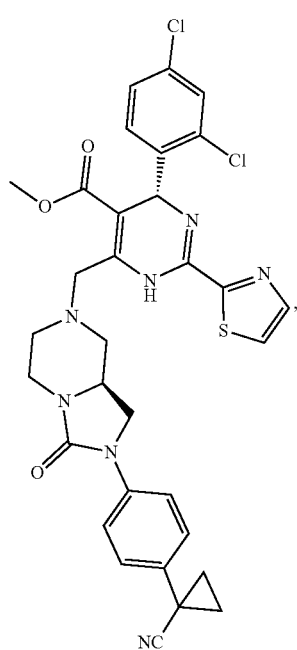

(236)
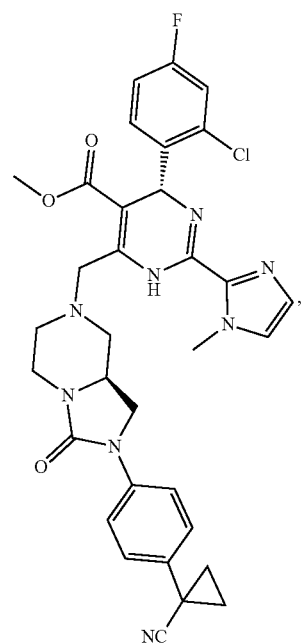
(237)
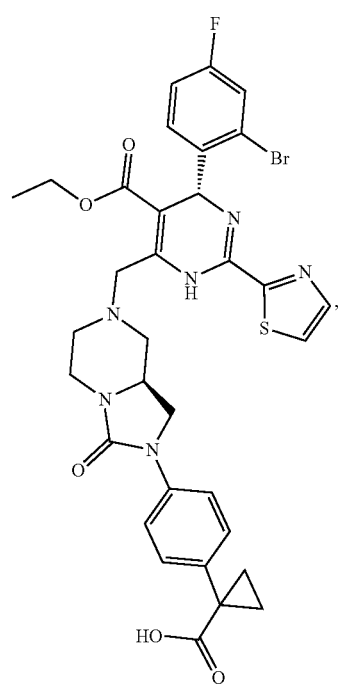
(238)
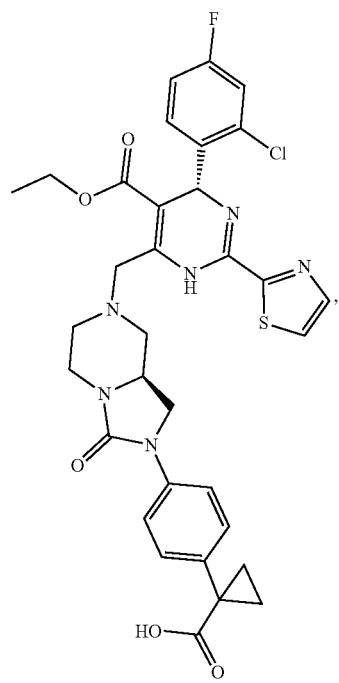
(239)
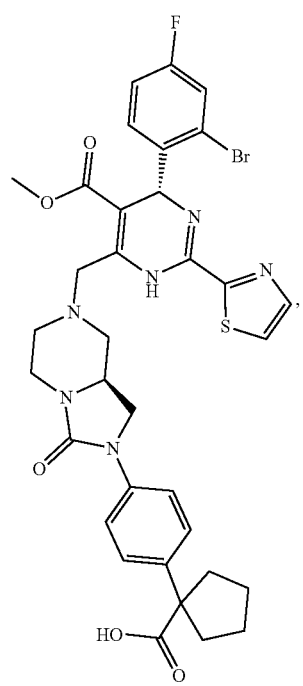

-continued
(240)
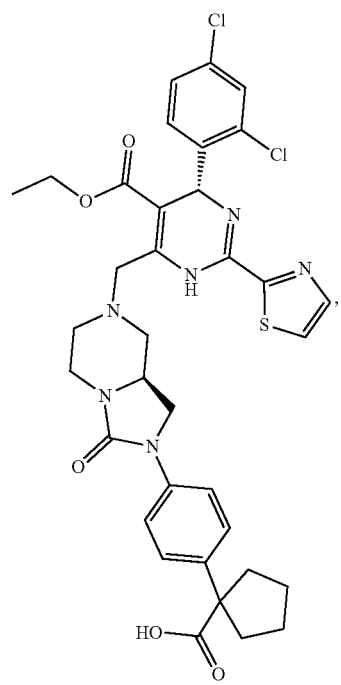
(241)
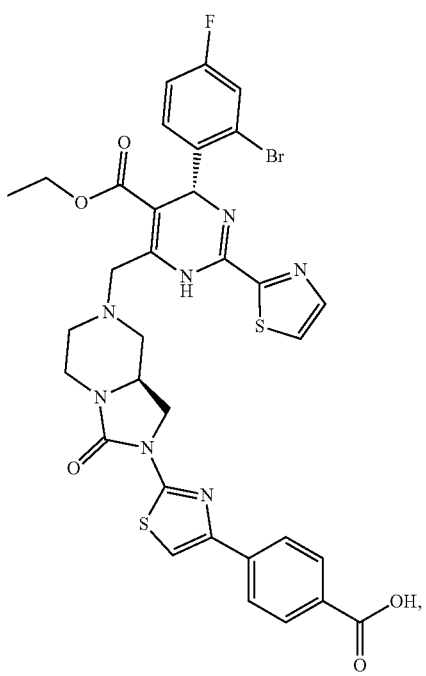
(242)
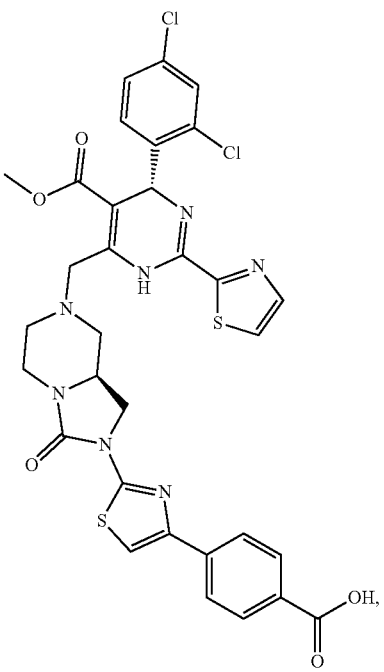
(243)
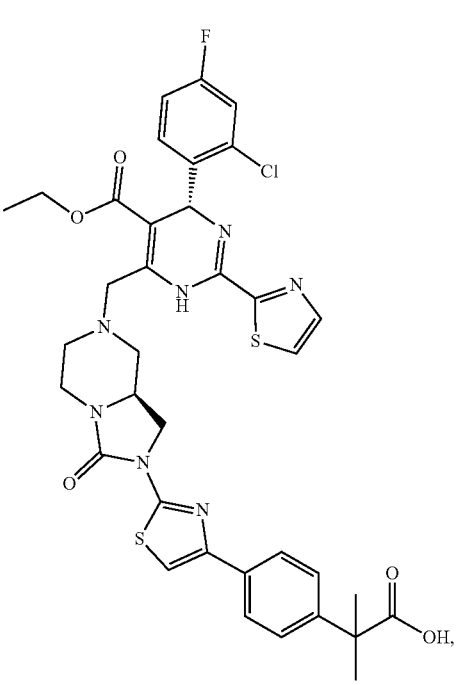

(244)
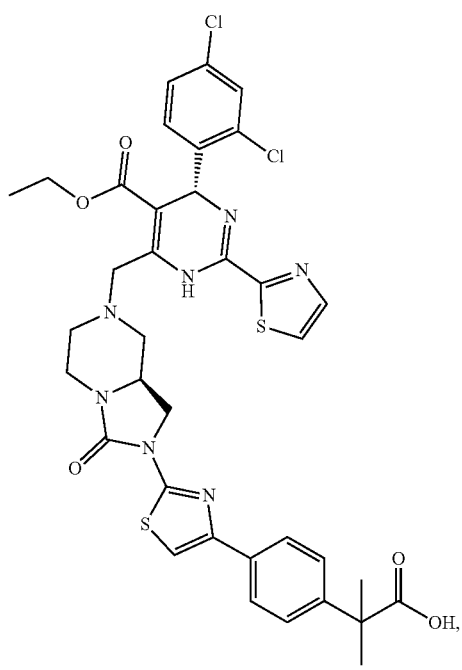
(245)
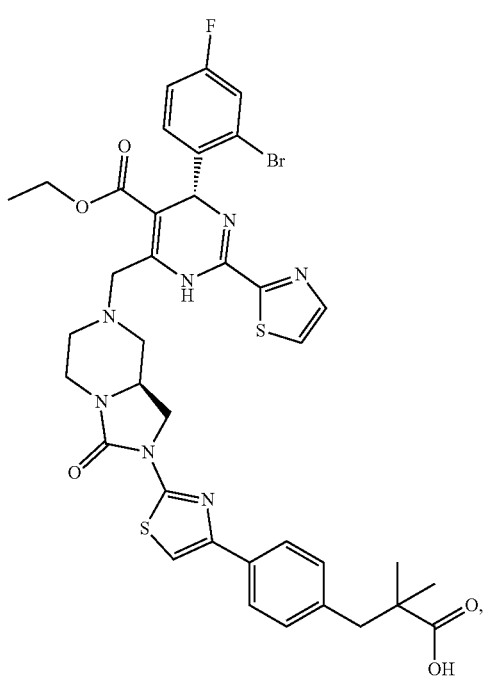
(246)
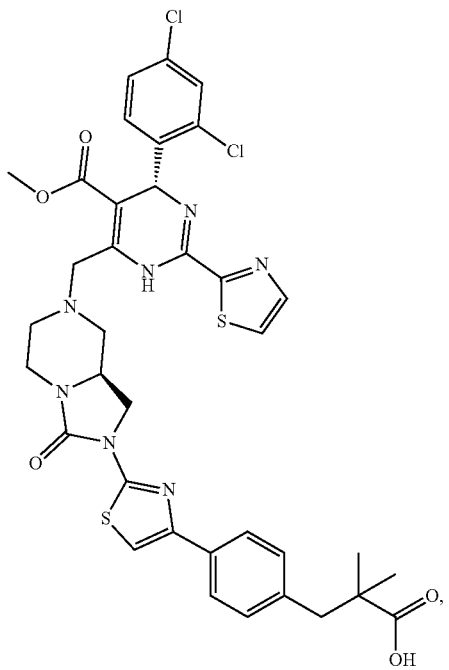
(247)
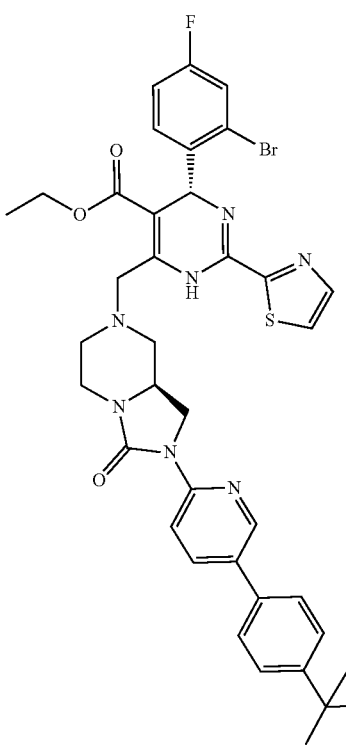

(248)
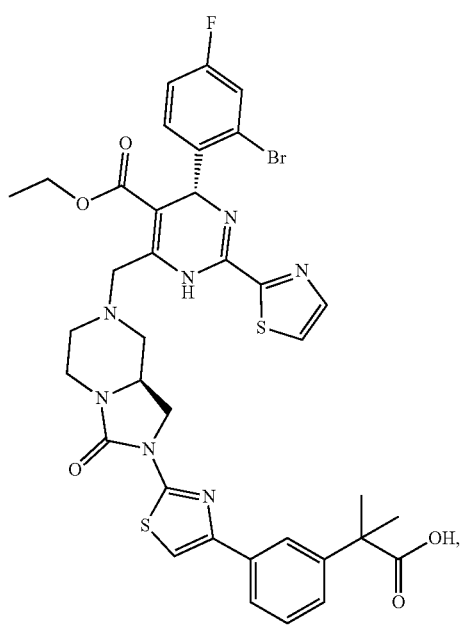
(249)
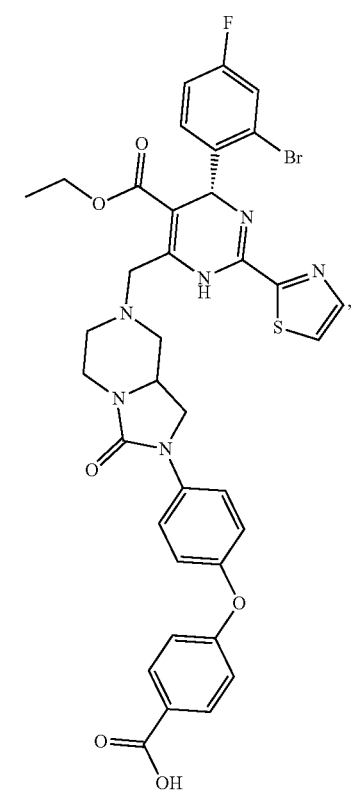
(250)
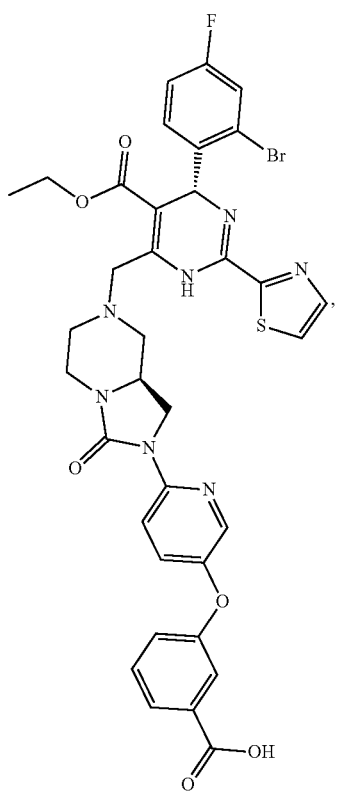
(251)
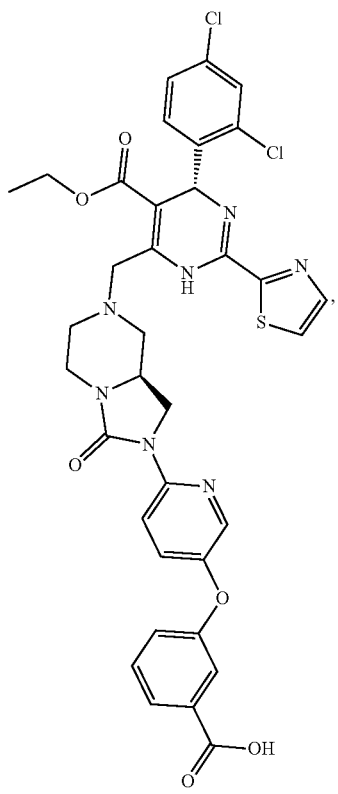

157
-continued
(252)
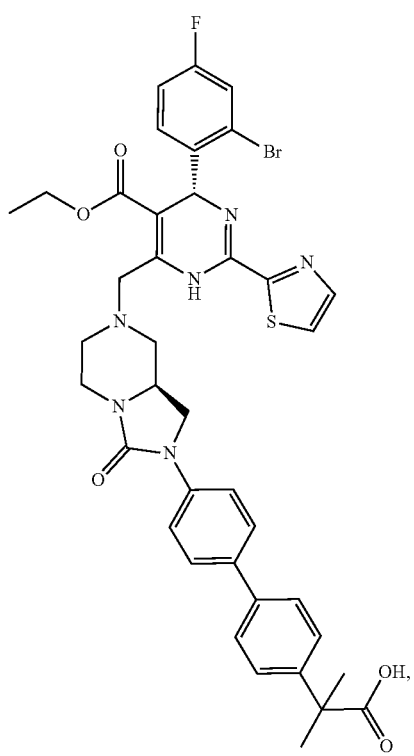
158
-continued
(254)
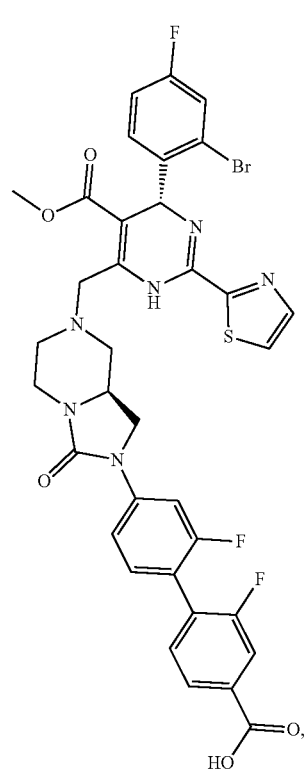
(253)
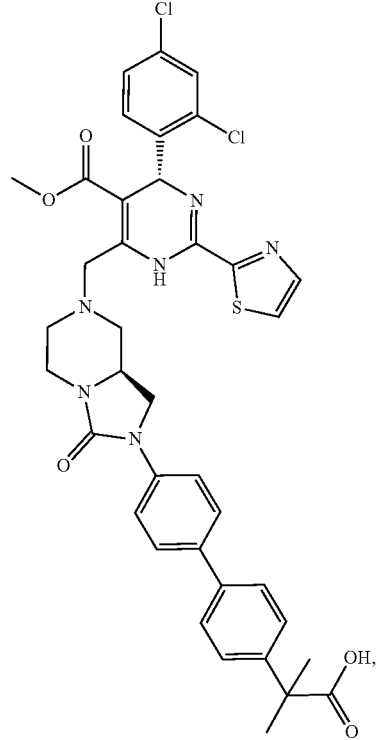
(255)
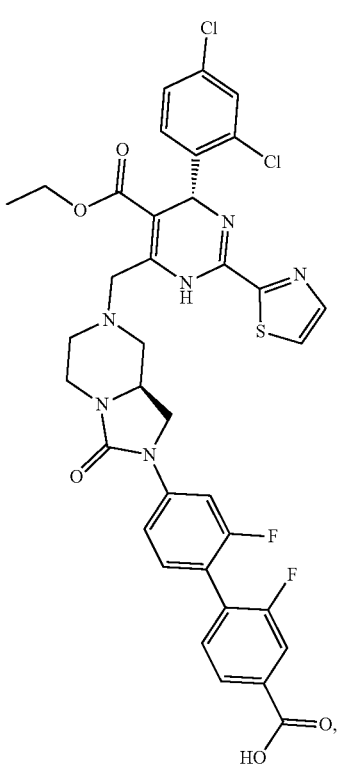

(256)
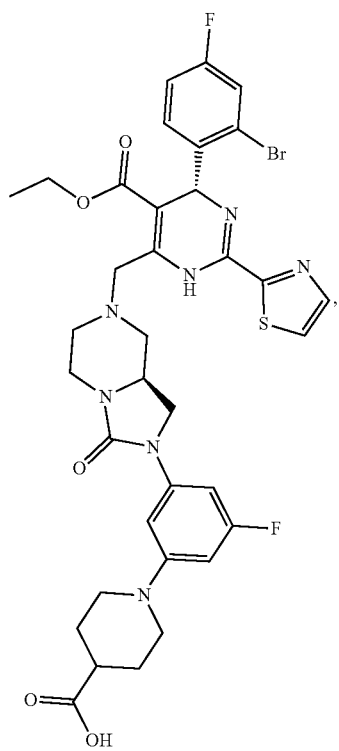
(257)
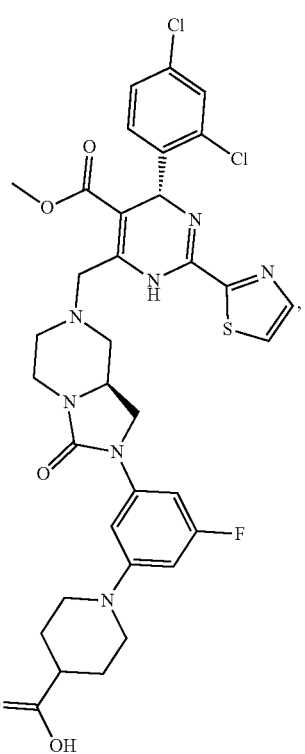
(258)
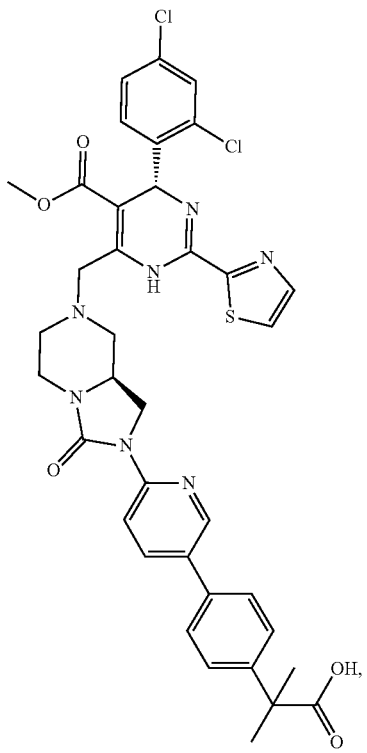
(259)
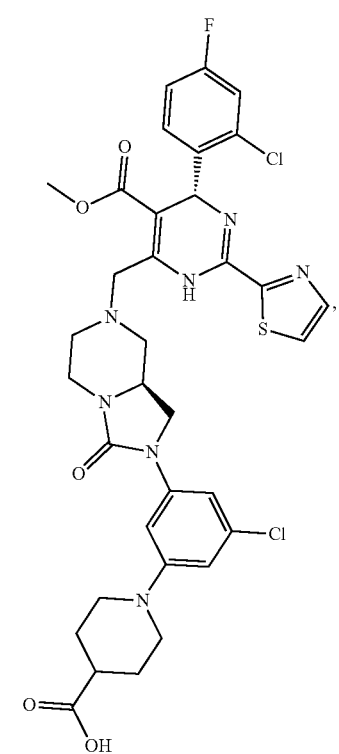

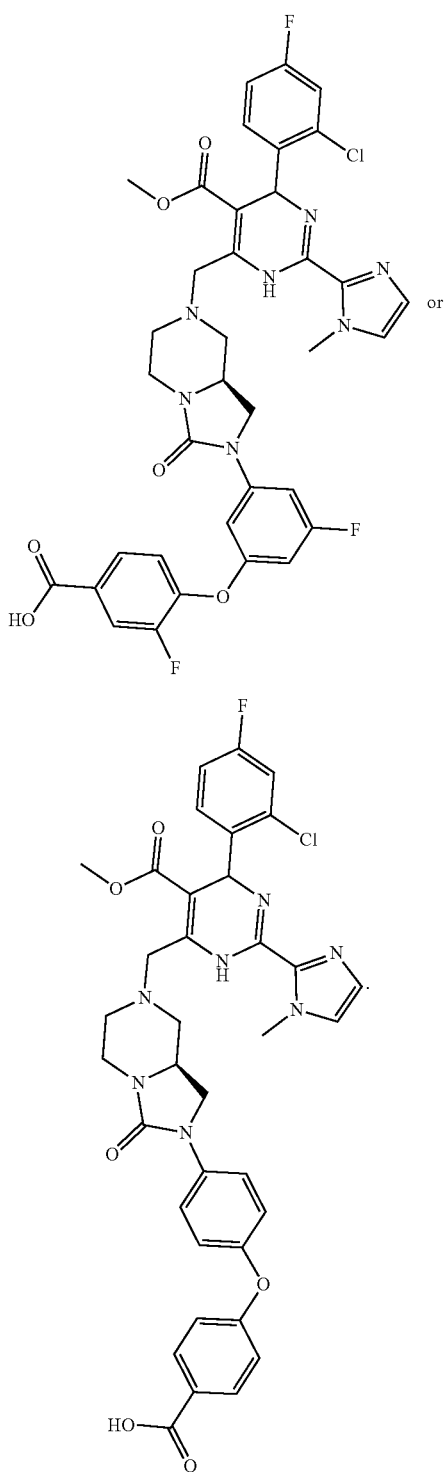

In other aspect, provided herein is a pharmaceutical composition comprising the compound disclosed herein and one or more pharmaceutically acceptable adjuvants.

In some embodiments, the pharmaceutical composition disclosed herein further comprises one or more other anti-HBV drugs.

In some embodiments of the pharmaceutical composition disclosed herein, wherein the other anti-HBV drug is an HBV polymerase inhibitor, immunomodulator or interferon.

In some embodiments of the pharmaceutical composition, wherein the other anti-HBV drug is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, Euforavac, rintatolimod, Phosphazid, Heplisav, interferon α-2b, levamisole, or propagermanium.

In other aspect, also provided herein is use of the compound or the pharmaceutical composition disclosed herein in the manufacture of a medicament for preventing, treating or lessening a virus disease in a patient.

In some embodiments of the use, wherein the virus disease disclosed herein is hepatitis B infection or a disease caused by hepatitis B infection.

In other embodiments of the use, the disease caused by hepatitis B infection disclosed herein is hepatic cirrhosis or hepatocellular carcinogenesis.

In other aspect, provided herein is the compound or the pharmaceutical composition disclosed herein for use in preventing, managing, treating or lessening a virus disease in a patient.

In some embodiments, the use of the compound or the pharmaceutical composition disclosed herein, wherein the virus disease disclosed herein is hepatitis B infection or a disease caused by hepatitis B infection.

In other embodiments, the use of the compound or the pharmaceutical composition disclosed herein, wherein the disease caused by hepatitis B infection disclosed herein is hepatic cirrhosis or hepatocellular carcinogenesis.

In other embodiments, the present invention relates to a method of preventing, treating or lessening a virus disease in a patient, comprising administering a pharmaceutically acceptable effective amount of the compound or pharmaceutical composition to a patient.

In some embodiments, the method of the present invention, wherein the virus disease disclosed herein is hepatitis B infection or a disease caused by hepatitis B infection.

In other embodiments, the method of the present invention, wherein the disease caused by hepatitis B infection disclosed herein is hepatic cirrhosis or hepatocellular carcinogenesis.

In other aspect, also provided herein is use of the compound or the pharmaceutical composition disclosed herein in the manufacture of a medicament for preventing, treating or lessening a HBV disease in a patient.

In other embodiments, the present invention relates to a method of preventing, managing, treating or lessening an HBV disease in a patient, comprising administering a pharmaceutically acceptable effective amount of the compound to a patient.

In other embodiments, the present invention relates to a method of preventing, managing, treating or lessening an HBV disease in a patient, comprising administering a pharmaceutically acceptable effective amount of the compound to a patient.

In other aspect, provided herein is use of the compound disclosed herein in the manufacture of a medicament for preventing, managing or treating an HBV disease in a patient, and lessening the severity thereof.

In other aspect, provided herein is use of the composition containing the compound disclosed herein in the manufacture of a medicament for preventing, managing or treating an HBV disease in a patient, and lessening the severity thereof.

In some embodiments, the organism is a mammal. In other embodiments, the organism is human. In other embodiments, the method further comprises contacting kinases with other anti-HBV therapeutic agent.

In other embodiments, provided herein is a method of inhibiting HBV infection, comprising contacting cells with an effective amount of the compound or the composition to HBV. In other some embodiments, the method further comprises contacting cells with other anti-HBV therapeutic agent.

In other aspect, the present invention relates to a method of treating an HBV disease in a patient, comprising administrating a therapeutically effective amount of the compound or composition thereof to a patient.

In other some embodiments, the method further comprises administrating other anti-HBV therapeutic agents.

In other aspect, the present invention relates to a method of inhibiting an HBV infection in a patient, comprising administrating a therapeutically effective amount of the compound or composition thereof to a patient. In other embodiments, the method further comprises administrating a therapeutically effective amount of other anti-HBV therapeutic agent.

In other aspect, provided herein is a method of preparing, separating or purifying the compound of Formula (I) or Formula (Ia).

The present invention also comprises uses of the compound and pharmaceutically acceptable salts thereof in the manufacture of a medicament for effectively inhibiting HBV infection including those described in the invention. Use of the compound disclosed herein in the manufacture of a medicament for effectively inhibiting HCV infection. The compound disclosed herein also can be used in the manufacture of a medicament for lessening, preventing, managing or treating a HBV disease in a patient. The present invention provides a pharmaceutical composition comprising a therapeutically effective amount of the compound of Formula (I) or (Ia), and at least one of pharmaceutically acceptable adjuvants.

The present invention also provides a method of effectively inhibiting or lessening a HBV infection disease in a patient comprising administering to the patient a therapeutically effective amount of the compound of Formula (I) or (Ia).

Unless otherwise stated, all stereoisomers, geometric isomers, tautomers, N-oxides, hydrates, solvates, metabolites, salts and pharmaceutically acceptable prodrugs of the compounds disclosed herein are within the scope of the invention.

Specifically, the salt is a pharmaceutically acceptable salt. The phrase "pharmaceutically acceptable" refers to that the substance or composition must be compatible chemically and/or toxicologically, with the other ingredients comprising a formulation, and/or the mammal being treated therewith.

The compounds disclosed herein also include salts of the compounds which are not necessarily pharmaceutically acceptable salts, and which may be useful as intermediates for preparing and/or purifying compounds of Formula (I) or (Ia), and/or for separating enantiomers of compounds of Formula (I) or (Ia).

If the compound disclosed herein is a base, the desired salt may be prepared by any suitable method available in the art, for example, treatment of the free base with an inorganic acid, such as hydrochloric acid, hydrobromic acid, sulfuric acid, nitric acid, phosphoric acid, and the like, or with an organic acid, such as acetic acid, maleic acid, succinic acid, mandelic acid, fumaric acid, malonic acid, pyruvic acid, malic acid, 2-hydroxypropionic acid, citric acid, oxalic acid, glycolic acid and salicylic acid; a pyranosidyl acid, such as glucuronic acid and galacturonic acid; an alpha-hydroxy acid, such as citric acid and tartaric acid; an amino acid, such as aspartic acid and glutamic acid; an aromatic acid, such as benzoic acid and cinnamic acid; a sulfonic acid, such as p-toluenesulfonic acid, benzenesulfonic acid, methanesulfonic acid, ethanesulfonic acid, trifluoromethanesulfonic acid, and the like; or the combination thereof.

If the compound disclosed here in is an acid, the desired salt may be prepared by any suitable method, for example, treatment of the free acid with an inorganic or organic base, such as an amine (primary, secondary or tertiary), an alkali metal hydroxide, ammonium, $N^+(R^{14})_4$ salt or alkaline earth metal hydroxide, and the like. Some non-limiting examples of suitable salts include organic salts derived from amino acids, such as glycine and arginine; ammonia, such as primary, secondary and tertiary amine, $N^+(R^{14})_4$ salt, wherein $R^{14}$ is H, $C_{1-4}$ alkyl, $C_{6-10}$ aryl, $C_{6-10}$ aryl-$C_{1-4}$-alkyl, and the like; and cyclic amines, such as piperidine, morpholine and piperazine, and inorganic salts derived from sodium, calcium, potassium, magnesium, manganese, iron, copper, zinc, aluminum, lithium, and the like, and further include, when appropriate, nontoxic ammonium, quaternary ammonium and amine cations formed using counterions such as halide, hydroxide, carboxylate, sulfate, phosphate, nitrate, $C_{1-8}$ sulfonate or aryl sulfonate.

Compositions of the Compound, Formulation, Administration and Use of the Compounds and Pharmaceutical Compositions According to other aspect, the characteristic of the pharmaceutical composition disclosed herein comprise the compound having Formula (I) or (Ia), the compound listed in the specification, or compounds of examples, and a pharmaceutically acceptable adjuvant. The compound in the pharmaceutical compositions disclosed herein can inhibit hepatitis B virus (HBV) effectively, and suitable for treating diseases induced by viruses in a patient, especially acute and chronic persistent HBV infections. Chronic viral diseases induced by HBV can worsen the morbidity and the chronic HBV infection can cause liver cirrhosis and/or hepatocellular carcinogenesis in many cases.

Areas of indication which may be mentioned for the compounds of the invention are, for example: the treatment of acute and chronic viral infections which may lead to infectious hepatitis, for example infections with hepatitis B viruses. The compounds of the invention are particularly suitable for the treatment of chronic hepatitis B infections and the treatment of acute and chronic hepatitis B viral infections.

The present invention includes pharmaceutical preparations which, besides nontoxic, inert pharmaceutically suitable carriers, comprise one or more compounds (I) or (Ia) or a combination of the invention or which consist of one or more active ingredients (I) or (Ia) or of a combination of the invention.

The pharmaceutical preparations mentioned above may also comprise other active pharmaceutical ingredients apart from the compounds (I) and (Ia).

It will also be appreciated that certain of the compounds disclosed herein can exist in free form for treatment, or where appropriate, as a pharmaceutically acceptable derivative thereof. According to the invention, the pharmaceutically acceptable derivatives include pharmaceutically acceptable prodrugs, salts, esters, salts of such esters, or any other adducts or derivatives which upon administration to a patient in need is capable of providing, directly or indirectly, a compound as otherwise described herein, or a metabolite or residue thereof.

As described above, the pharmaceutical compositions disclosed herein comprises any one of the compound of formula (I) or (Ia), and further comprise a pharmaceutically acceptable an adjuvant, such adjuvant, which, as used herein, includes any and all solvents, solid excipients, diluents, binders, disintegrants, or other liquid excipients, dispersion, corrigents or suspension aids, surface active agents, isotonic agents, thickening or emulsifying agents, preservatives, solid binders, lubricants and the like, as suited to the particular dosage form desired. As the following described: In Remington: The Science and Practice of Pharmacy, 21st ed., 2005, Lippincott Williams & Wilkins, Philadelphia, and Swarbrick et al., Encyclopedia of Pharmaceutical Technology, eds. 1988-1999, Marcel Dekker, New York, both of which are herein incorporated by reference in their entireties, discloses various excipients used in formulating pharmaceutically acceptable compositions and known techniques for the preparation thereof. Except insofar as any conventional adjuvant incompatible with the compounds disclosed herein, such as by producing any undesirable biological effect or otherwise interacting in a deleterious manner with any other components of the pharmaceutically acceptable composition, its use is contemplated to be within the scope of this invention.

Some non-limiting examples of materials which can serve as pharmaceutically acceptable adjuvants include ion exchangers; aluminium; aluminum stearate; lecithin; serum proteins such as human serum albumin; buffer substances such as phosphates; glycine; sorbic acid; potassium sorbate; partial glyceride mixtures of saturated vegetable fatty acids; water; salts or electrolytes such as protamine sulfate, disodium hydrogen phosphate, potassium hydrogen phosphate, sodium chloride and zinc salts; colloidal silica; magnesium trisilicate; polyvinyl pyrrolidone; polyacrylates; waxes; polyethylene-polyoxypropylene-block polymers; wool fat; sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol and polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants.

The pharmaceutical composition of the compound disclosed herein may be administered in any of the following routes: orally, inhaled by spray, locally, rectally, nasally, locally, vaginally, parenterally such as subcutaneous, intravenous, intramuscular, intraperitoneal, intrathecal, intraventricular, intrasternal, or intracranial injection or infusion, or administered with the aid of an explanted reservoir. Administration routes by orally, intramuscular, intraperitoneal or intravenous injection are preferred.

The compound and pharmaceutically composition thereof may be administered in a unit dosage form. The dosage form may be in a liquid form, or a solid form. The liquid form includes true solutions, colloids, particulates, suspensions. Other dosage forms include tablets, capsules, dropping pills, aerosols, pills, powders, solutions, suspensions, emulsions, granules, suppositories, freeze-dried powder injection, clathrates, implants, patches, liniments and the like.

Oral tablets and capsules may comprise excipients, e.g., binders, such as syrup, Arabic gum, sorbitol, tragacanth or polyvinylpyrrolidone; fillers, such as lactose, sucrose, corn starch, calcium phosphate, sorbitol, glycine; lubricants such as magnesium stearate, talc, polyethylene glycol, silica; disintegrating agents, such as potato starch, or acceptable moisturizing agents such as sodium lauryl sulfate. Tablets may be coated by using known methods in pharmaceutics.

Oral solution may be made as a suspension of water and oil, a solution, an emulsion, syrup or an elixir, or made as a dried product to which water or other suitable medium is added before use. This liquid preparation may comprise conventional additives, e.g., suspending agents such as sorbitol, cellulose methyl ether, glucose syrup, gel, hydroxyethyl cellulose, carboxymethyl cellulose, aluminum stearate gel, hydrogenated edible greases; emulsifying agents such as lecithin, sorbitan monoleate, Arabic gum; or non-aqueous carriers (possibly including edible oil), such as almond oil, grease such as glycerin, ethylene glycol, or ethanol; antiseptics such as methyl or propyl p-hydroxybenzoate, sorbic acid. If desired, a flavoring agent or a colorant may be added.

Suppositories may comprise a conventional suppository base, such as cocoa butter or other glyceride.

For parenteral administration, the liquid dosage form is usually made from the compound and a sterilized adjuvant. The first selection of adjuvant is water. According to the difference of selected adjuvant and drug concentration, the compound can be either dissolved in the adjuvant or made into a supernatant solution. When being made into a solution for injection, the compound is firstly dissolved in water, and then filtered and sterilized before being packaged into an sealed bottle or an ampoule.

For application topically to the skin, the compound disclosed herein may be made into a suitable form of ointments, lotions or creams, wherein the active ingredient is suspended or dissolved in one or more adjuvant(s). Wherein adjuvants used for an ointment preparation include, but are not limited to: mineral oil, liquid vaseline, white vaseline, propylene glycol, polyoxyethylene, polyoxypropylene, emulsified wax and water; carriers used for a lotion and a cream include, but are not limited to: mineral oil, sorbitan monostearate, Tween 60, cetyl ester wax, hexadecylene aromatic alcohol, 2-octyl dodecanol, benzyl alcohol and water.

In general, it has proved to be advantageous in either human medicine or veterinary medicine, the total administrated dose of the active compound disclosed herein is about 0.5 to 500 mg every 24 hours, preferably 1 to 100 mg/kg body weight. If appropriate, the drug is administrated in single dose for multiple times, to achieve the desired effect. The amount of the active compound in a single dose is preferably about 1 to 80 mg, more preferably 1 to 50 mg/kg body weight. Nevertheless, the dose may also be varied according to the kind and the body weight of treatment objects, the nature and the severity of diseases, the type of preparations and the method of administration of drugs, and administration period or time interval.

The pharmaceutical composition provided herein further comprises anti-HBV drugs. Wherein the anti-HBV drug is an HBV polymerase inhibitor, immunomodulator or interferon.

The anti HBV agent is lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, euforavac, veldona, rintatolimod, phosphazid, heplisav, interferon α-2b, levamisole, or propagermanium, and the like.

In another aspect, provided herein is a use of the compound disclosed herein or pharmaceutical compositions thereof in the manufacture of a medicament for preventing, treating or lessening HBV diseases in a patient, comprising administering a pharmaceutically acceptable effective amount to a patient. The HBV disease is a hepatic disease caused by hepatitis B virus infection or hepatitis B infection, including acute hepatitis, chronic hepatitis, cirrhosis and hepatocellular carcinoma. The symptoms of acute hepatitis B virus infection may be asymptomatic or manifested as acute hepatitis symptoms. A patient with chronic virus infection suffers an active disease, which can progress to cirrhosis and liver cancer.

The anti HBV agents may be administered separately from the composition disclosed herein as part of a multiple dosage regimen. Alternatively, those agents may be part of a single dosage form, mixed together with the compound disclosed herein in a single composition. If administered as part of a multiple dosage regimen, the two active agents may be submitted simultaneously, sequentially or within a period of time from one another which would result in the desired activity of the agents.

The amount of both the compound and the composition (in those comprise one composition as described above) that may be combined with the adjuvant materials to produce a single dosage form will vary depending upon the host treated and the particular mode of administration Normally, the amount of the composition disclosed herein will be no more than the amount that would normally be administered in a composition as the only active agent. In other embodiments, the amount of the presently disclosed compositions will range from about 50% to 100% of the amount normally present in a composition comprising that agent as the only therapeutically active agent. In those compositions, that the composition and the compound disclosed herein may act synergistically.

The compounds disclosed herein show a strong antiviral activity. These compounds have unexpected antiviral activity for HBV, therefore which are suitable for the treatment of various diseases caused by virus, especially for the disease caused by acute and chronic persistent HBV virus infection. Chronic viral diseases caused by HBV may lead to a variety of symptoms with different severity, as everyone knows, the chronic HBV infection may lead to liver cirrhosis and/or hepatocellular carcinoma.

Some examples of indications treated with the compounds of the invention include acute and chronic viral infections which may lead to infectious hepatitis, for example HBV infection. More preferably, chronic hepatitis B infection and acute hepatitis B virus infection.

The present invention also relates to use of the compound and composition disclosed herein in the manufacture of a medicament for treating and preventing viral diseases, especially hepatitis B.

General Synthetic Procedures

Generally, the compounds disclosed herein may be prepared by methods described herein, wherein the substituents are as defined for Formula (I) or (Ia) above, except where further noted. The following non-limiting schemes and examples are presented to further exemplify the invention.

Persons skilled in the art will recognize that the chemical reactions described may be readily adapted to prepare a number of other compounds disclosed herein, and alternative methods for preparing the compounds disclosed herein are deemed to be within the scope disclosed herein. For example, the synthesis of non-exemplified compounds according to the invention may be successfully performed by modifications apparent to those skilled in the art, e.g., by appropriately protecting interfering groups, by utilizing other suitable reagents known in the art other than those described, and/or by making routine modifications of reaction conditions. Alternatively, other reactions disclosed herein or known in the art will be recognized as having applicability for preparing other compounds disclosed herein.

In the examples described below, unless otherwise indicated all temperatures are set forth in degrees Celsius. Reagents were purchased from commercial suppliers such as Aldrich Chemical Company, Arco Chemical Company and Alfa Chemical Company, and were used without further purification unless otherwise indicated. Common solvents were purchased from commercial suppliers such as Shantou XiLong Chemical Factory, Guangdong Guanghua. Reagent Chemical Factory Co. Ltd., Guangzhou Reagent Chemical Factory, Tianjin YuYu Fine Chemical Ltd., Qingdao Tenglong Reagent Chemical Ltd., and Qingdao Ocean Chemical Factory.

Column chromatography was conducted using a silica gel column. Silica gel (200-300 mesh) was purchased from Qingdao Ocean Chemical Factory. $^1$H NMR spectra were obtained by using CDCl$_3$, DMSO-d$_6$, CD$_3$OD or acetone-d$_6$ solutions (reported in ppm), with TMS (0 ppm) or chloroform (7.25 ppm) as the reference standard. When peak multiplicities were reported, the following abbreviations were used: s (singlet), d (doublet), t (triplet), m (multiplet), br (broadened), dd (doublet of doublets), dt (doublet of triplets), br.s (broadened singlet). Coupling constants J, when given, were reported in Hertz (Hz).

Low-resolution mass spectral (MS) data were also determined on an Agilent 6320 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Low-resolution mass spectral (MS) data were also determined on an Agilent 6120 series LC-MS spectrometer equipped with G1312A binary pumps, a G1316A TCC (Temperature Control of Column, maintained at 30° C.), a G1329A autosampler and a G1315B DAD detector were used in the analysis. An ESI source was used on the LC-MS spectrometer.

Both LC-MS spectrometers were equipped with an Agilent Zorbax SB-C18, 2.1×30 mm, 5 μm column. Injection volume was decided by the sample concentration. The flow rate was 0.6 mL/min. The HPLC peaks were recorded by UV-Vis wavelength at 210 nm and 254 nm. The mobile phase was 0.1% formic acid in acetonitrile (phase A) and 0.1% formic acid in ultrapure water (phase B). The gradient elution conditions were showed in Table 1: The gradient elution conditions were showed in Table 1:

TABLE 1

| Time (min) | A (CH₃CN, 0.1% HCOOH) | B (H₂O, 0.1% HCOOH) |
|---|---|---|
| 0-3 | 5-100 | 95-0 |
| 3-6 | 100 | 0 |
| 6-6.1 | 100-5 | 0-95 |
| 6.1-8 | 5 | 95 |

Purities of compounds were assessed by Agilent 1100 Series high performance liquid chromatography (HPLC) with UV detection at 210 nm and 254 nm (Zorbax SB-C18, 2.1×30 mm, 4 micorn, 10 min, 0.6 mL/min flow rate, 5 to 95% (0.1% formic acid in CH₃CN) in (0.1% formic acid in H₂O). Column was operated at 40° C.

The following abbreviations are used throughout the specification:
MeCN, CH₃CN acetonitrile
MTBE tert-Butyl methyl ether
DCM, CH₂Cl₂ dichloromethane
CHCl₃ chloroform, trichloromethane
CDCl₃ chloroform-d
CbzCl Carbobenzoxy Chloride
CBZ, Cbz carbobenzoxy
PPh₃ triphenylphosphine
Pd(PPh₃)₄ tetrakis(triphenylphosphine)palladium(0)
LiOH.H₂O Lithium hydroxide monohydrate
LDA lithium diisopropylamide
tBuXPhos 2-di-t-butylphosphino-2',4',6'-tri-i-propyl-1,1'-biphenyl
TEA triethylamine
TFA trifluoroacetic acid
(dppf)PdCl₂ [1,1'-bis(diphenylphosphino)ferrocene]dichloropalladium(II)
X-Phos 2-(dicyclohexylphosphino)-2',4',6'-tri-i-propyl-1,1'-biphenyl
Xantphos dimethylbisdiphenylphosphinoxanthene
CCl₄ tetrachloromethane
Pd/C Palladium on activated carbon
Pd₂(dba)₃ tris(dibenzylideneacetone)dipalladium
BOC, Boc tert-butoxycarbonyl
PE petroleum ether
EA, EtOAc ethyl acetate
EtOH ethyl alcohol
HCl hydrochloric acid
K₂CO₃ potassium carbonate
NaHCO₃ sodium bicarbonate
NaOH sodium hydroxide
NaCl sodium chloride
Na₂SO₄ sodium sulfate
Et₃N, TEA triethylamine
NBS N-bromosuccinimide
D₂O heavy water
H₂O water
mL, ml milliliter
RT rt room temperature
Rt retention time
1 atm 101.325 kPa
h hour, hours
H₂ hydrogen
HC/EA, HCl/EtOAc a hydrogen chloride solution in ethyl acetate
HOAT 1-hydroxy-7-azabenzotriazole
DIPEA ethyldiisopropylamine
DCC N,N'-dicyclohexylcarbodiimide
DIAD diisopropyl azodicarboxylate
DMF N,N-dimethylformamide
THF tetrahydrofuran
DMSO dimethylsulfoxide
CuCN cuprous cyanide
CH₃OH, MeOH methanol
N₂ nitrogen
NH₄Cl ammonium chloride
Ac₂O acetic anhydride
$t_{1/2}$ half life
AUC area under the curve
Vss apparent volume of distribution
CL clearance
F, absolute bioavailability biological availability
Dose dose
$T_{max}$ time to peak
$C_{max}$ maximum concentration
hr*ng/mL blood concentration*time Synthetic Methods The following schemes represent the synthetic steps of the compounds of the invention, wherein each $R^1$, $R^2$, $R^4$, $R^9$, $X^1$, m and f is as defined herein.

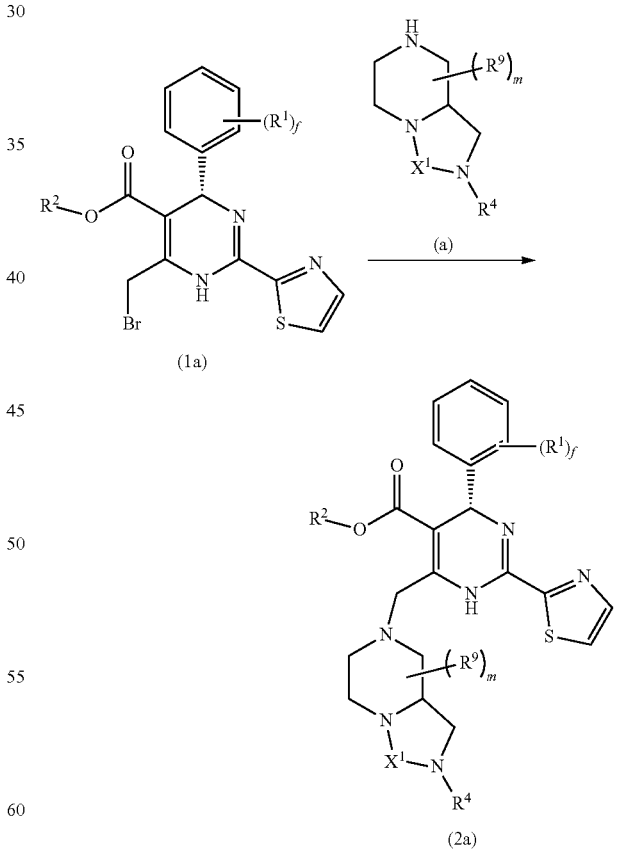

Scheme 1

Compound (2a) can be prepared by a method as illustrated in scheme 1, compound (Ia) (prepared by the method as shown in scheme 1 of WO2015074546 and specific examples therein) and compound (a) in the present of a base (e.g. potassium carbonate, etc) and in a suitable solvent (e.g. ethanol, etc) can react to get compound (2a).
EXAMPLES
The structure and number of each example are listed in table 2.
Table 2 the structure and number of each example of the present invention
| Example No. | Structure |
|---|---|
| 1 | 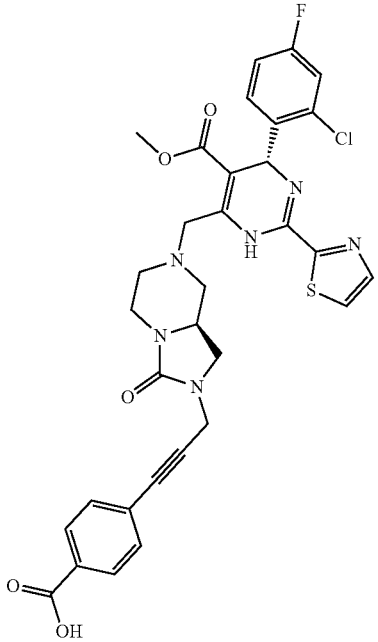 [SMILES: COC(=O)C1=C(CN2CCN3C(=O)N(CC#Cc4ccc(C(=O)O)cc4)C[C@@H]3C2)NC(c2nccs2)=N[C@H]1c1ccc(F)cc1Cl] |
| 2 | 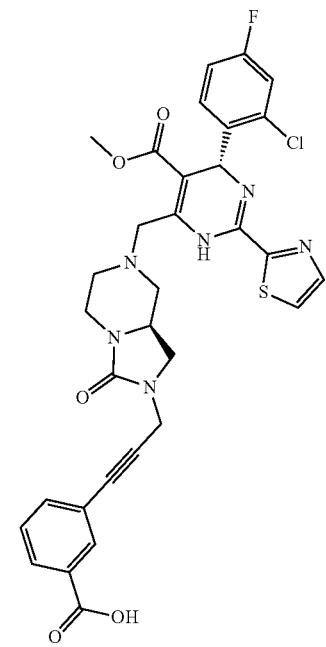 [SMILES: COC(=O)C1=C(CN2CCN3C(=O)N(CC#Cc4cccc(C(=O)O)c4)C[C@@H]3C2)NC(c2nccs2)=N[C@H]1c1ccc(F)cc1Cl] |
| 3 | 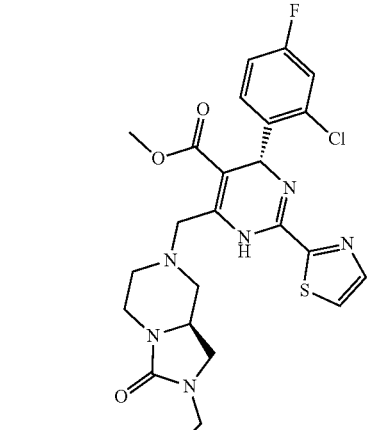 |
| 4 | 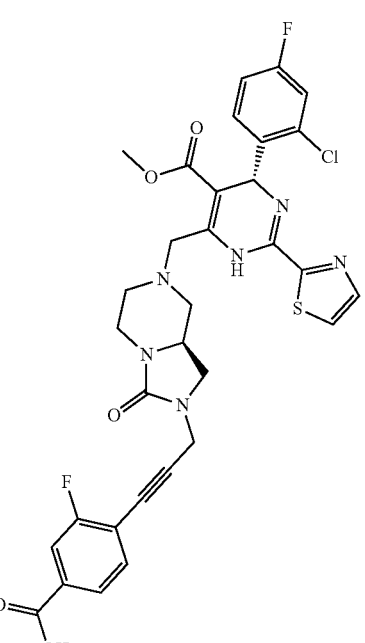 |

-continued
| Example No. | Structure |
|---|---|
| 5 | 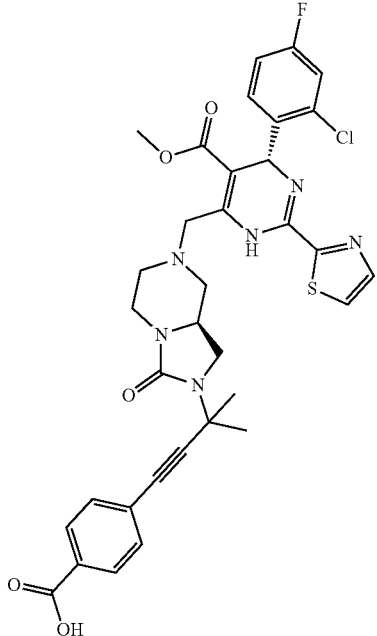 [SMILES: COC(=O)C1=C(CN2CCN3C(=O)N(C(C)(C)C#Cc4ccc(C(=O)O)cc4)C[C@@H]3C2)NC(c2nccs2)=N[C@H]1c1ccc(F)cc1Cl] |
| 6 | 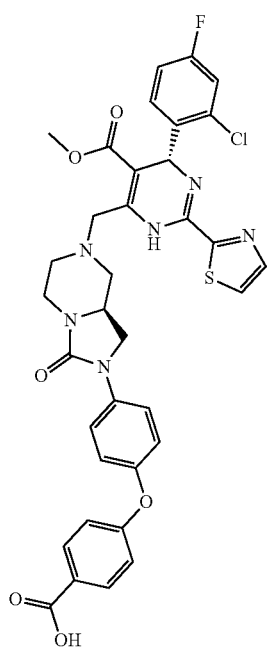 [SMILES: COC(=O)C1=C(CN2CCN3C(=O)N(c4ccc(Oc5ccc(C(=O)O)cc5)cc4)C[C@@H]3C2)NC(c2nccs2)=N[C@H]1c1ccc(F)cc1Cl] |
-continued
| Example No. | Structure |
|---|---|
| 7 | 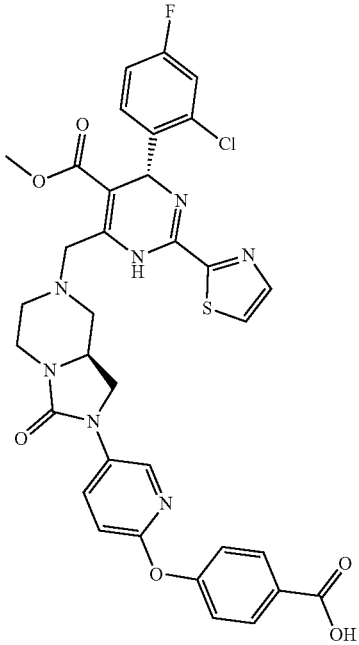 [SMILES: COC(=O)C1=C(CN2CCN3C(=O)N(c4ccc(Oc5ccc(C(=O)O)cc5)nc4)C[C@@H]3C2)NC(c2nccs2)=N[C@H]1c1ccc(F)cc1Cl] |
| 8 | 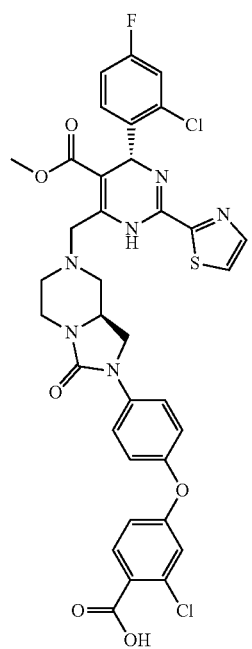 [SMILES: COC(=O)C1=C(CN2CCN3C(=O)N(c4ccc(Oc5ccc(C(=O)O)c(Cl)c5)cc4)C[C@@H]3C2)NC(c2nccs2)=N[C@H]1c1ccc(F)cc1Cl] |

| Example No. | Structure |
|---|---|
| 9 | 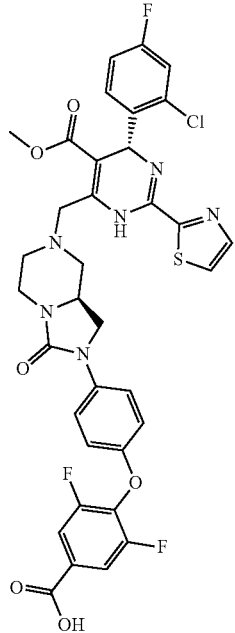 [SMILES: COC(=O)C1=C(CN2CCN3C(=O)N(c4ccc(Oc5c(F)cc(C(=O)O)cc5F)cc4)C[C@@H]3C2)NC(c2nccs2)=N[C@H]1c1ccc(F)cc1Cl] |
| 10 | 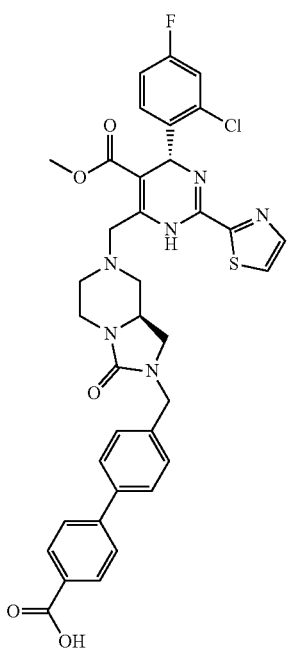 [SMILES: COC(=O)C1=C(CN2CCN3C(=O)N(Cc4ccc(-c5ccc(C(=O)O)cc5)cc4)C[C@@H]3C2)NC(c2nccs2)=N[C@H]1c1ccc(F)cc1Cl] |
| Example No. | Structure |
|---|---|
| 11 | 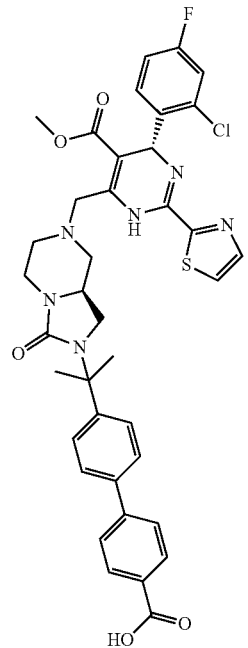 [SMILES: COC(=O)C1=C(CN2CCN3C(=O)N(C(C)(C)c4ccc(-c5ccc(C(=O)O)cc5)cc4)C[C@@H]3C2)NC(c2nccs2)=N[C@H]1c1ccc(F)cc1Cl] |
| 12 | 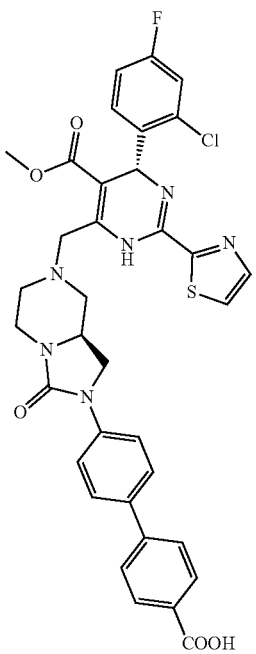 [SMILES: COC(=O)C1=C(CN2CCN3C(=O)N(c4ccc(-c5ccc(C(=O)O)cc5)cc4)C[C@@H]3C2)NC(c2nccs2)=N[C@H]1c1ccc(F)cc1Cl] |

-continued
| Example No. | Structure |
|---|---|
| 13 | 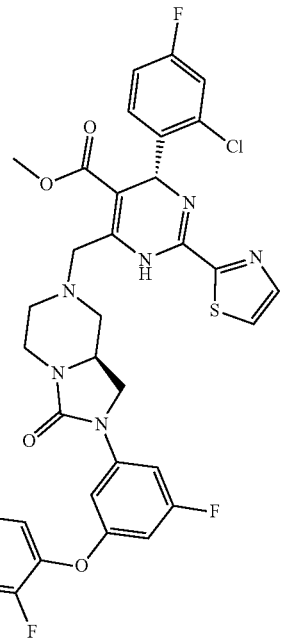 |
| 14 | 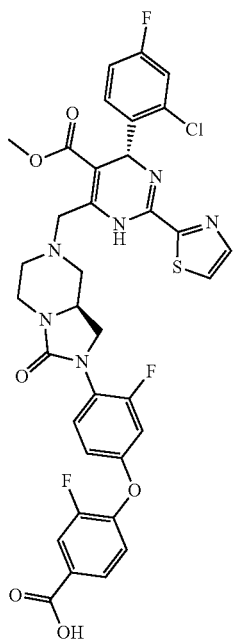 [SMILES: COC(=O)C1=C(CN2CCN3C(=O)N(c4ccc(Oc5ccc(C(=O)O)cc5F)cc4F)C[C@@H]3C2)NC(c2nccs2)=N[C@H]1c1ccc(F)cc1Cl] |
-continued
| Example No. | Structure |
|---|---|
| 15 | 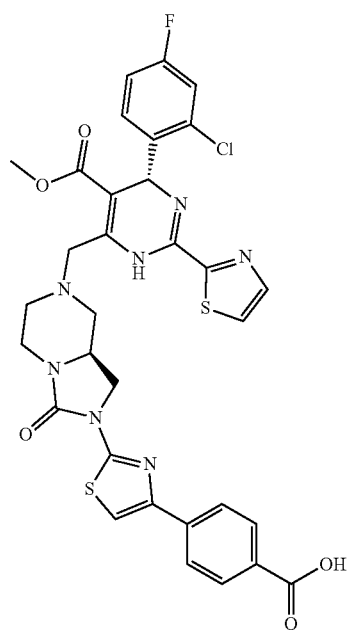 [SMILES: COC(=O)C1=C(CN2CCN3C(=O)N(c4nc(-c5ccc(C(=O)O)cc5)cs4)C[C@@H]3C2)NC(c2nccs2)=N[C@H]1c1ccc(F)cc1Cl] |
| 16 | 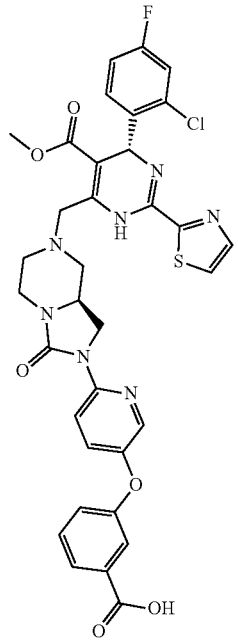 [SMILES: COC(=O)C1=C(CN2CCN3C(=O)N(c4ccc(Oc5cccc(C(=O)O)c5)cn4)C[C@@H]3C2)NC(c2nccs2)=N[C@H]1c1ccc(F)cc1Cl] |

179
-continued
| Example No. | Structure |
|---|---|
| 17 | 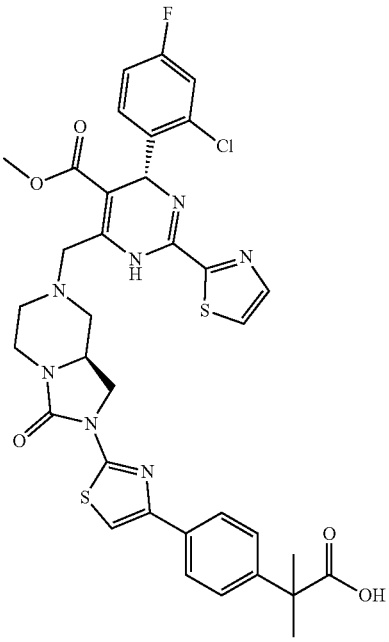 [SMILES: COC(=O)C1=C(CN2CCN3C(=O)N(c4nc(-c5ccc(C(C)(C)C(=O)O)cc5)cs4)C[C@@H]3C2)NC(c2nccs2)=N[C@H]1c1ccc(F)cc1Cl] |
| 18 | 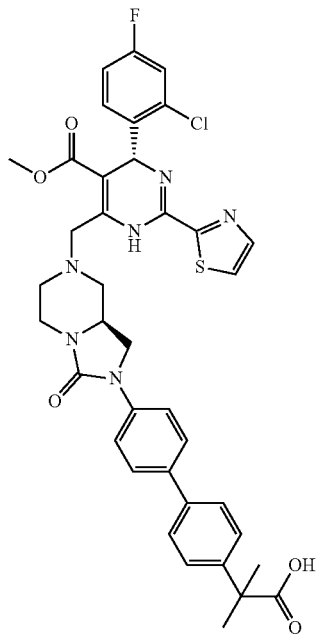 [SMILES: COC(=O)C1=C(CN2CCN3C(=O)N(c4ccc(-c5ccc(C(C)(C)C(=O)O)cc5)cc4)C[C@@H]3C2)NC(c2nccs2)=N[C@H]1c1ccc(F)cc1Cl] |
180
-continued
| Example No. | Structure |
|---|---|
| 19 | 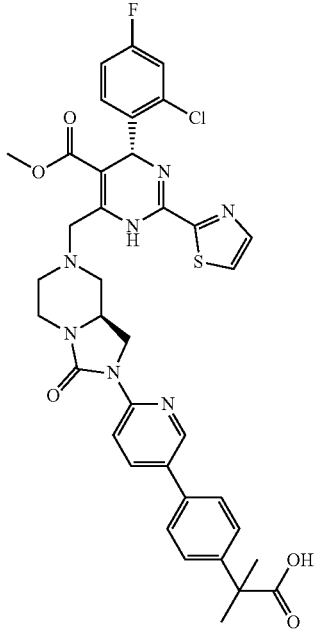 [SMILES: COC(=O)C1=C(CN2CCN3C(=O)N(c4ccc(-c5ccc(C(C)(C)C(=O)O)cc5)cn4)C[C@@H]3C2)NC(c2nccs2)=N[C@H]1c1ccc(F)cc1Cl] |
| 20 | 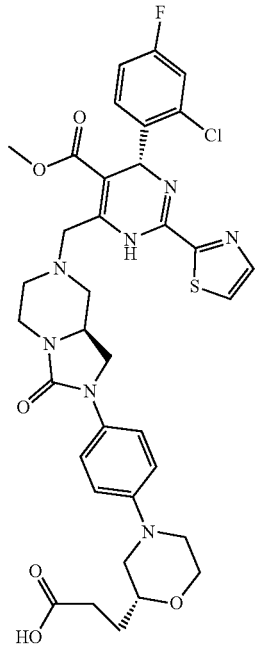 [SMILES: COC(=O)C1=C(CN2CCN3C(=O)N(c4ccc(N5CCO[C@H](CCC(=O)O)C5)cc4)C[C@@H]3C2)NC(c2nccs2)=N[C@H]1c1ccc(F)cc1Cl] |

| Example No. | Structure |
|---|---|
| 21 | 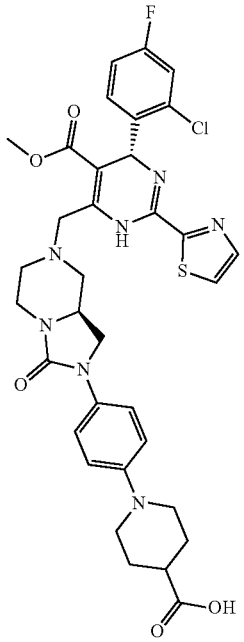 [SMILES: COC(=O)C1=C(CN2CCN3C(=O)N(c4ccc(N5CCC(C(=O)O)CC5)cc4)C[C@@H]3C2)NC(c2nccs2)=N[C@H]1c1ccc(F)cc1Cl] |
| 22 | 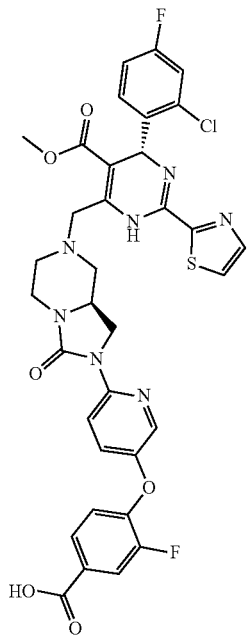 [SMILES: COC(=O)C1=C(CN2CCN3C(=O)N(c4ccc(Oc5ccc(C(=O)O)cc5F)cn4)C[C@@H]3C2)NC(c2nccs2)=N[C@H]1c1ccc(F)cc1Cl] |
| Example No. | Structure |
|---|---|
| 23 | 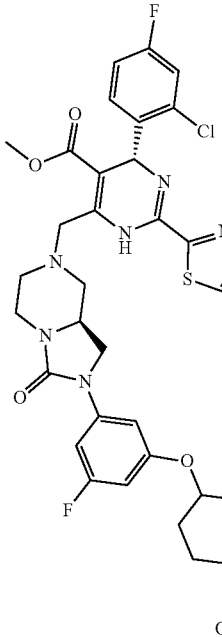 |
| 24 | 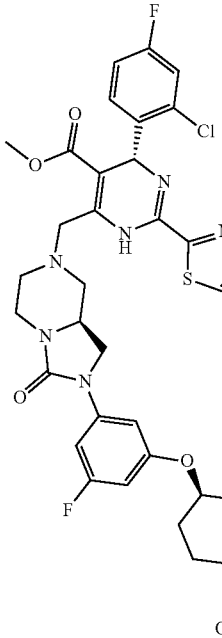 |

| Example No. | Structure |
|---|---|
| 25 | 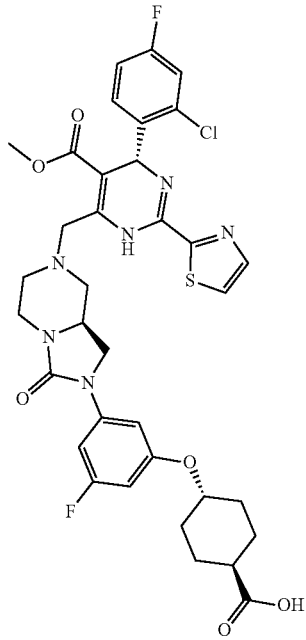 [SMILES: COC(=O)C1=C(CN2CCN3C(=O)N(c4cc(F)cc(O[C@H]5CC[C@H](C(=O)O)CC5)c4)C[C@@H]3C2)NC(c2nccs2)=N[C@H]1c1ccc(F)cc1Cl] |
| 26 | 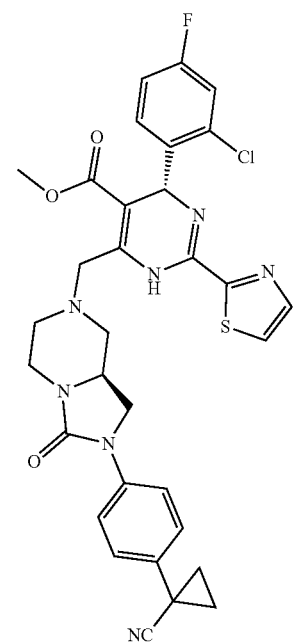 [SMILES: COC(=O)C1=C(CN2CCN3C(=O)N(c4ccc(C5(C#N)CC5)cc4)C[C@@H]3C2)NC(c2nccs2)=N[C@H]1c1ccc(F)cc1Cl] |
| Example No. | Structure |
|---|---|
| 27 | 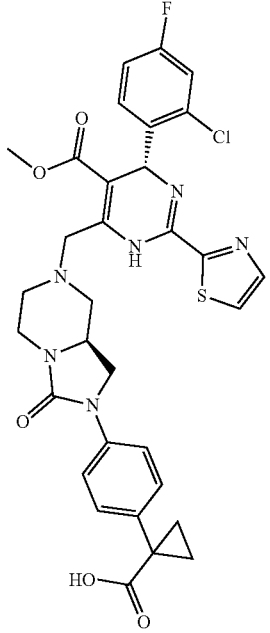 [SMILES: COC(=O)C1=C(CN2CCN3C(=O)N(c4ccc(C5(C(=O)O)CC5)cc4)C[C@@H]3C2)NC(c2nccs2)=N[C@H]1c1ccc(F)cc1Cl] |
| 28 | 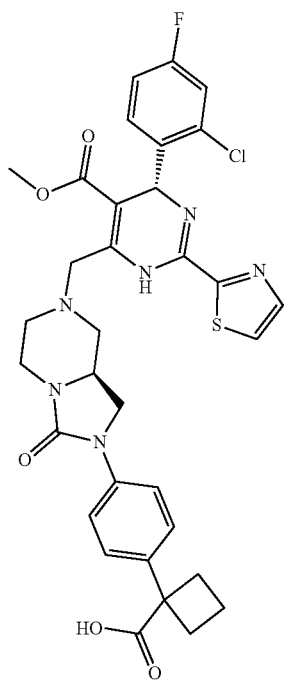 [SMILES: COC(=O)C1=C(CN2CCN3C(=O)N(c4ccc(C5(C(=O)O)CCC5)cc4)C[C@@H]3C2)NC(c2nccs2)=N[C@H]1c1ccc(F)cc1Cl] |

| Example No. | Structure |
|---|---|
| 29 | 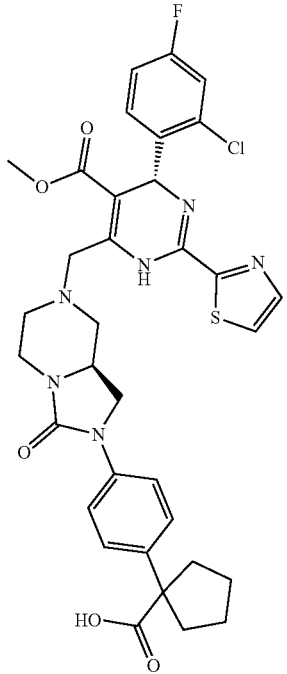 [SMILES: COC(=O)C1=C(CN2CCN3C(=O)N(c4ccc(C5(C(=O)O)CCCC5)cc4)C[C@@H]3C2)NC(c2nccs2)=N[C@H]1c1ccc(F)cc1Cl] |
| 30 | 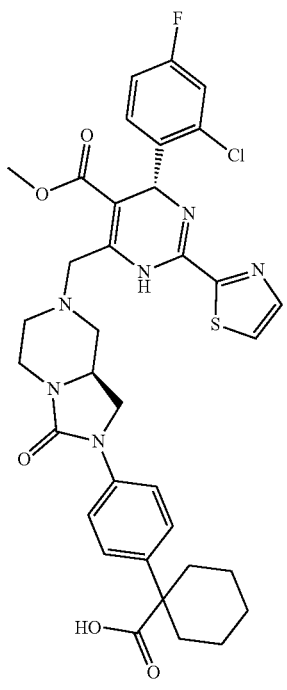 [SMILES: COC(=O)C1=C(CN2CCN3C(=O)N(c4ccc(C5(C(=O)O)CCCCC5)cc4)C[C@@H]3C2)NC(c2nccs2)=N[C@H]1c1ccc(F)cc1Cl] |
| Example No. | Structure |
|---|---|
| 31 | 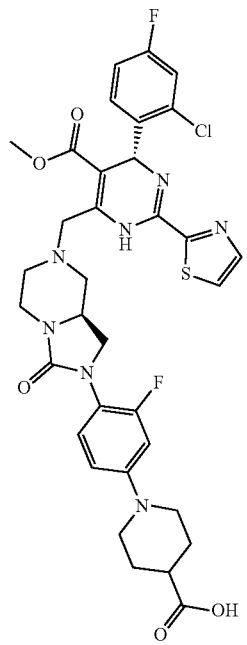 [SMILES: COC(=O)C1=C(CN2CCN3C(=O)N(c4ccc(N5CCC(C(=O)O)CC5)cc4F)C[C@@H]3C2)NC(c2nccs2)=N[C@H]1c1ccc(F)cc1Cl] |
| 32 | 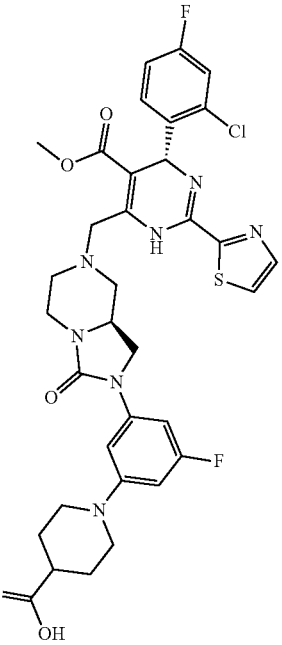 |

-continued
| Example No. | Structure |
|---|---|
| 33 | 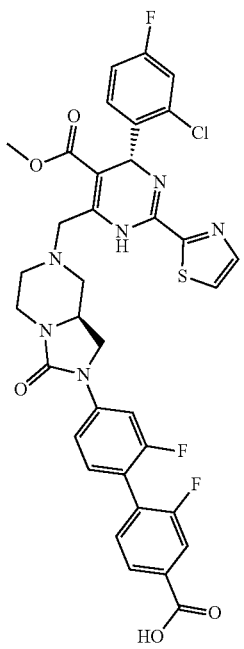 [SMILES: COC(=O)C1=C(CN2CCN3C(=O)N(c4ccc(-c5ccc(C(=O)O)cc5F)c(F)c4)C[C@@H]3C2)NC(c2nccs2)=N[C@H]1c1ccc(F)cc1Cl] |
| 34 | 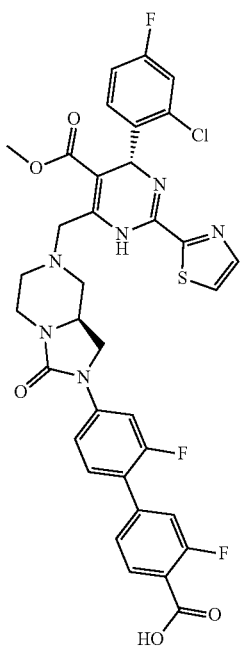 [SMILES: COC(=O)C1=C(CN2CCN3C(=O)N(c4ccc(-c5ccc(C(=O)O)c(F)c5)c(F)c4)C[C@@H]3C2)NC(c2nccs2)=N[C@H]1c1ccc(F)cc1Cl] |
| 35 | 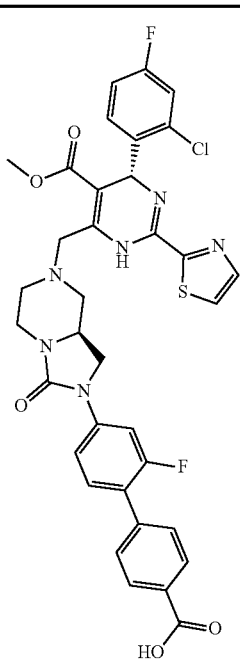 |
| 36 | 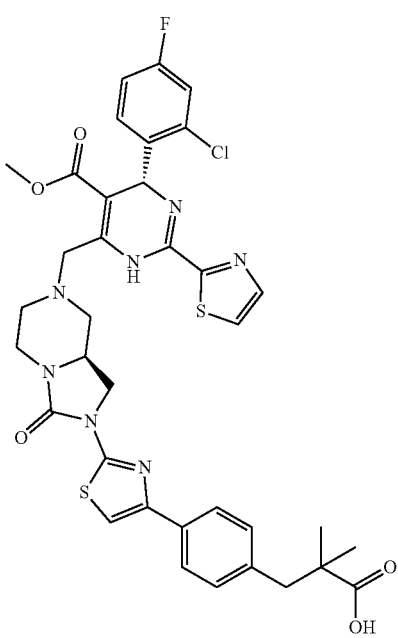 [SMILES: COC(=O)C1=C(CN2CCN3C(=O)N(c4nc(-c5ccc(CC(C)(C)C(=O)O)cc5)cs4)C[C@@H]3C2)NC(c2nccs2)=N[C@H]1c1ccc(F)cc1Cl] |

| Example No. | Structure |
|---|---|
| 37 | 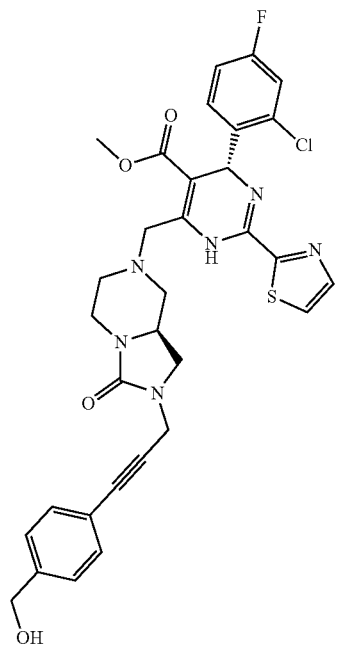 [SMILES: COC(=O)C1=C(CN2CCN3C(=O)N(CC#Cc4ccc(CO)cc4)C[C@@H]3C2)NC(c2nccs2)=N[C@H]1c1ccc(F)cc1Cl] |
| 38 | 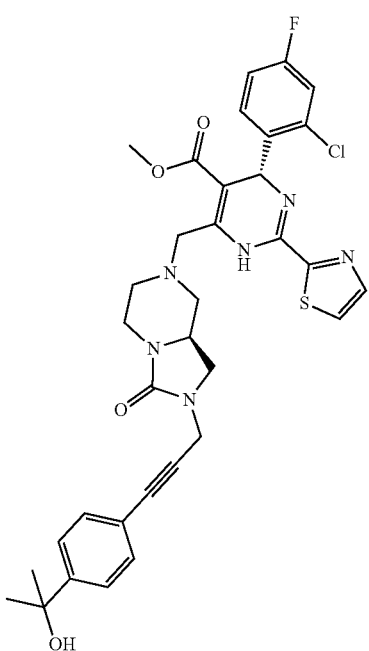 [SMILES: COC(=O)C1=C(CN2CCN3C(=O)N(CC#Cc4ccc(C(C)(C)O)cc4)C[C@@H]3C2)NC(c2nccs2)=N[C@H]1c1ccc(F)cc1Cl] |
| Example No. | Structure |
|---|---|
| 39 | 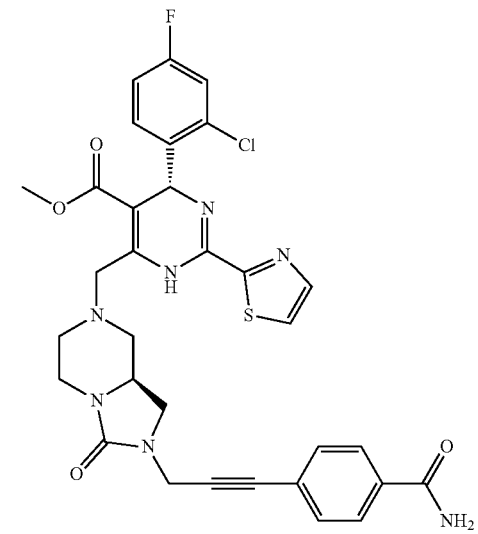 [SMILES: COC(=O)C1=C(CN2CCN3C(=O)N(CC#Cc4ccc(C(N)=O)cc4)C[C@@H]3C2)NC(c2nccs2)=N[C@H]1c1ccc(F)cc1Cl] |
| 40 | 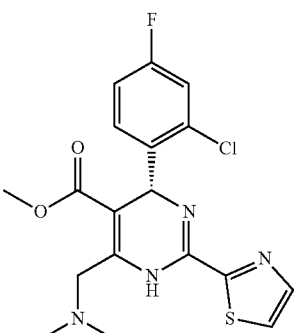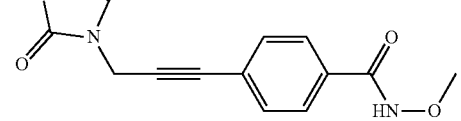 |
| 41 | 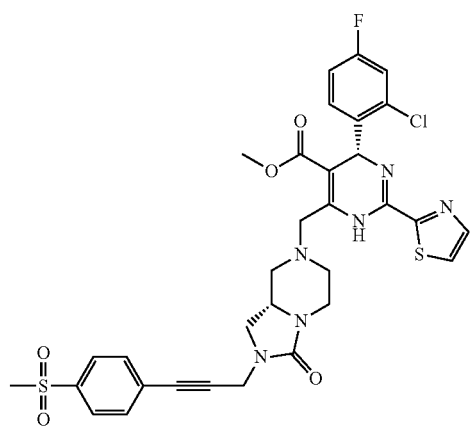 [SMILES: COC(=O)C1=C(CN2CCN3C(=O)N(CC#Cc4ccc(S(C)(=O)=O)cc4)C[C@@H]3C2)NC(c2nccs2)=N[C@H]1c1ccc(F)cc1Cl] |

-continued
| Example No. | Structure |
|---|---|
| 42 | 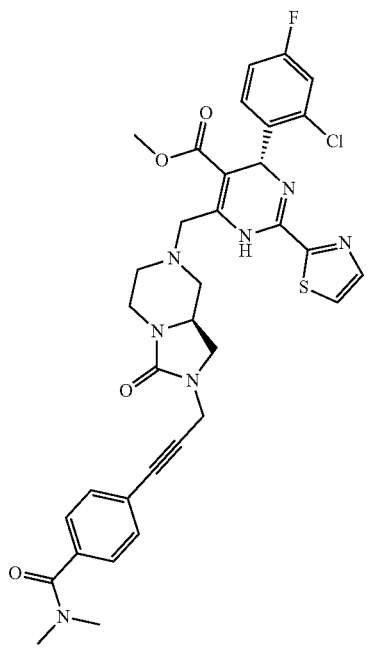 [SMILES: COC(=O)C1=C(CN2CCN3C(=O)N(CC#Cc4ccc(C(=O)N(C)C)cc4)C[C@@H]3C2)NC(c2nccs2)=N[C@H]1c1ccc(F)cc1Cl] |
| 43 | 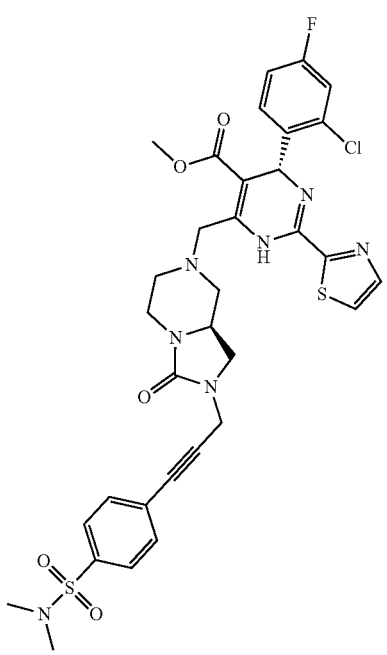 [SMILES: COC(=O)C1=C(CN2CCN3C(=O)N(CC#Cc4ccc(S(=O)(=O)N(C)C)cc4)C[C@@H]3C2)NC(c2nccs2)=N[C@H]1c1ccc(F)cc1Cl] |
-continued
| Example No. | Structure |
|---|---|
| 44 | 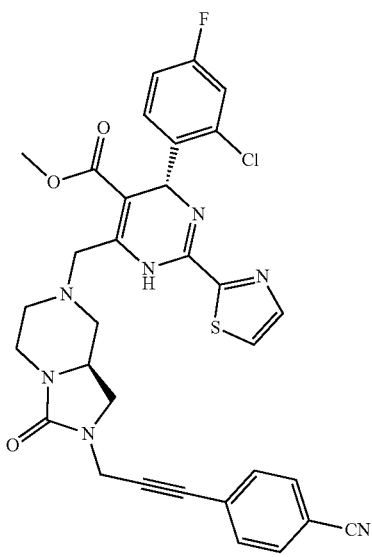 [SMILES: COC(=O)C1=C(CN2CCN3C(=O)N(CC#Cc4ccc(C#N)cc4)C[C@@H]3C2)NC(c2nccs2)=N[C@H]1c1ccc(F)cc1Cl] |
| 45 | 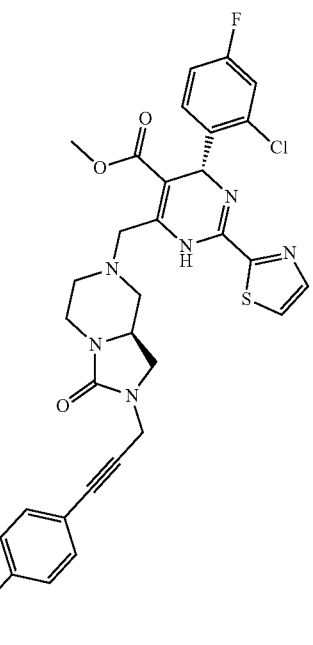 |

-continued
| Example No. | Structure |
|---|---|
| 46 | 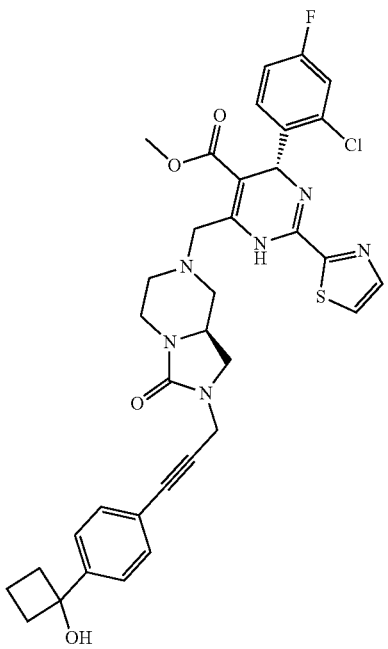 [SMILES: COC(=O)C1=C(CN2CCN3C(=O)N(CC#Cc4ccc(C5(O)CCC5)cc4)C[C@@H]3C2)NC(c2nccs2)=N[C@H]1c1ccc(F)cc1Cl] |
| 47 | 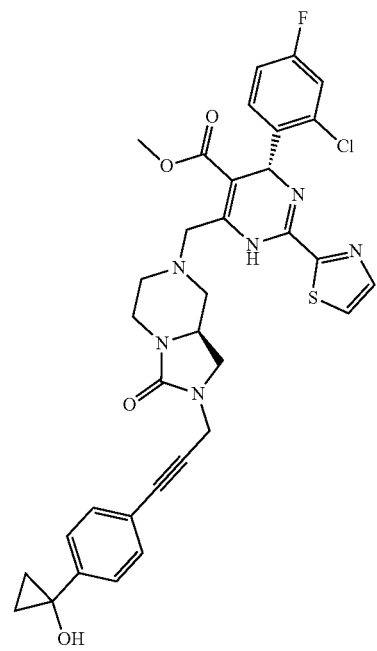 [SMILES: COC(=O)C1=C(CN2CCN3C(=O)N(CC#Cc4ccc(C5(O)CC5)cc4)C[C@@H]3C2)NC(c2nccs2)=N[C@H]1c1ccc(F)cc1Cl] |
-continued
| Example No. | Structure |
|---|---|
| 48 | 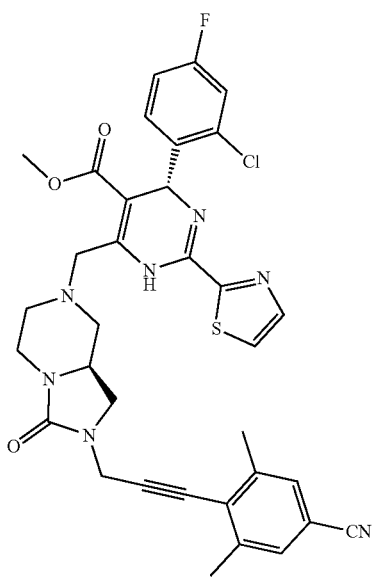 [SMILES: COC(=O)C1=C(CN2CCN3C(=O)N(CC#Cc4c(C)cc(C#N)cc4C)C[C@@H]3C2)NC(c2nccs2)=N[C@H]1c1ccc(F)cc1Cl] |
| 49 | 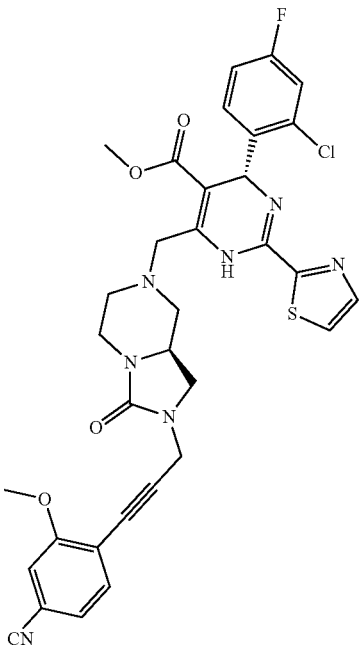 [SMILES: COC(=O)C1=C(CN2CCN3C(=O)N(CC#Cc4ccc(C#N)cc4OC)C[C@@H]3C2)NC(c2nccs2)=N[C@H]1c1ccc(F)cc1Cl] |

| Example No. | Structure |
|---|---|
| 50 | 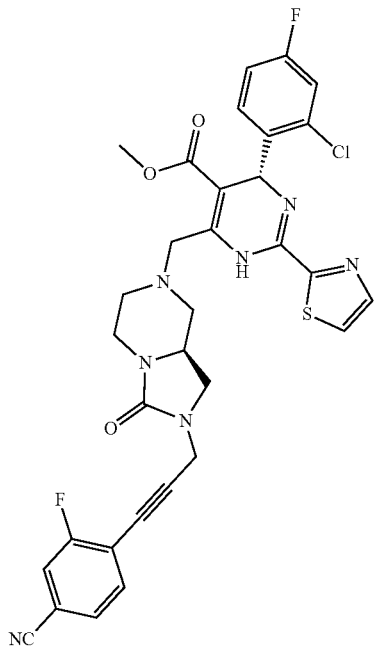 [SMILES: COC(=O)C1=C(CN2CCN3C(=O)N(CC#Cc4ccc(C#N)cc4F)C[C@@H]3C2)NC(c2nccs2)=N[C@H]1c1ccc(F)cc1Cl] |
| 51 | 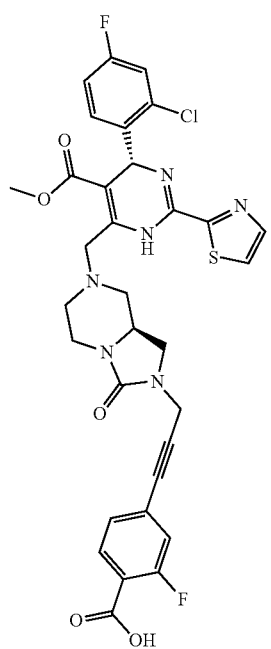 [SMILES: COC(=O)C1=C(CN2CCN3C(=O)N(CC#Cc4ccc(C(=O)O)c(F)c4)C[C@@H]3C2)NC(c2nccs2)=N[C@H]1c1ccc(F)cc1Cl] |
| Example No. | Structure |
|---|---|
| 52 | 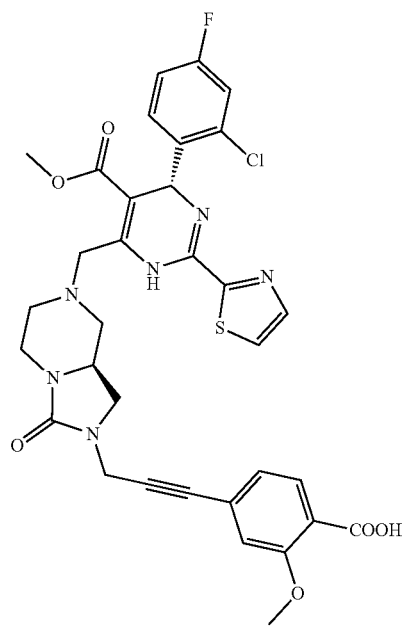 [SMILES: COC(=O)C1=C(CN2CCN3C(=O)N(CC#Cc4ccc(C(=O)O)c(OC)c4)C[C@@H]3C2)NC(c2nccs2)=N[C@H]1c1ccc(F)cc1Cl] |
| 53 | 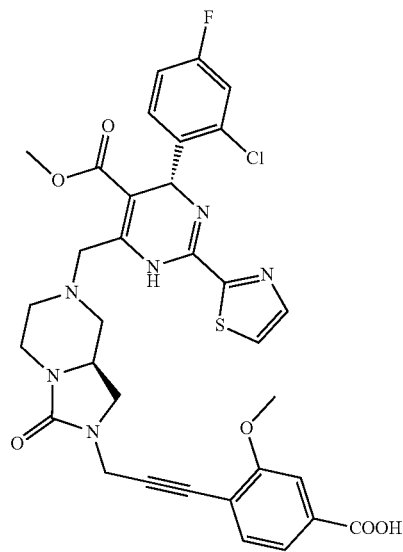 [SMILES: COC(=O)C1=C(CN2CCN3C(=O)N(CC#Cc4ccc(C(=O)O)cc4OC)C[C@@H]3C2)NC(c2nccs2)=N[C@H]1c1ccc(F)cc1Cl] |

TABLE-continued
| Example No. | Structure |
|---|---|
| 54 | 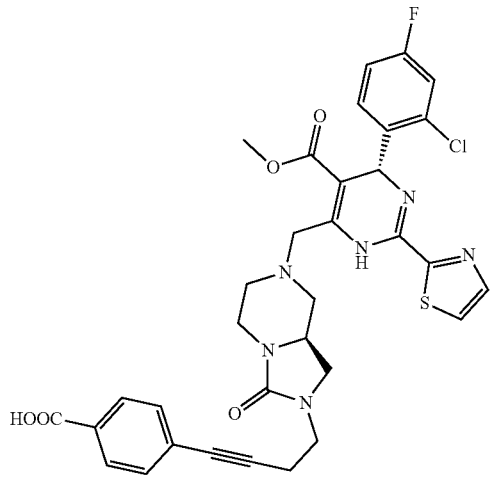 [SMILES: COC(=O)C1=C(CN2CCN3C(=O)N(CCC#Cc4ccc(C(=O)O)cc4)C[C@@H]3C2)NC(c2nccs2)=N[C@H]1c1ccc(F)cc1Cl] |
| 55 | 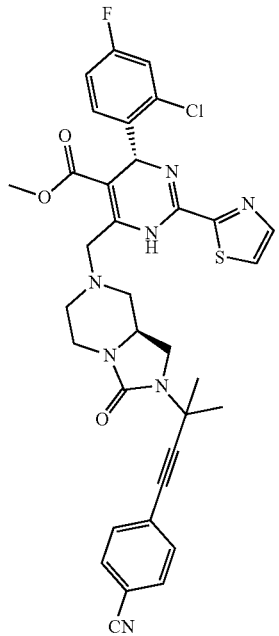 [SMILES: COC(=O)C1=C(CN2CCN3C(=O)N(C(C)(C)C#Cc4ccc(C#N)cc4)C[C@@H]3C2)NC(c2nccs2)=N[C@H]1c1ccc(F)cc1Cl] |
| 56 | 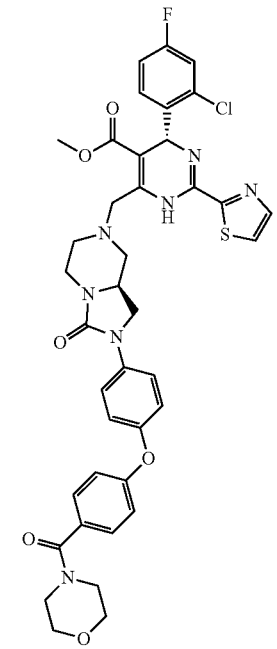 [SMILES: COC(=O)C1=C(CN2CCN3C(=O)N(c4ccc(Oc5ccc(C(=O)N6CCOCC6)cc5)cc4)C[C@@H]3C2)NC(c2nccs2)=N[C@H]1c1ccc(F)cc1Cl] |
| 57 | 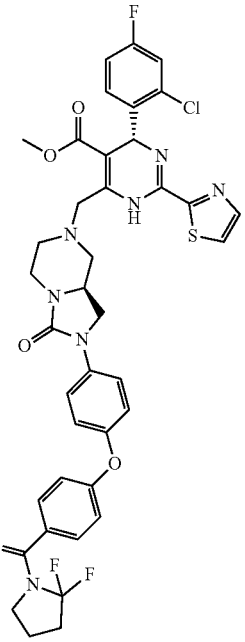 |

-continued
| Example No. | Structure |
|---|---|
| 58 | 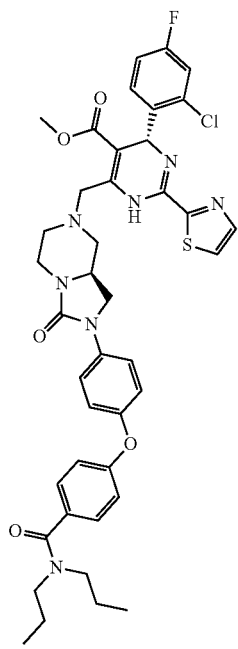 [SMILES: CCCN(CCC)C(=O)c1ccc(Oc2ccc(N3C[C@@H]4CN(CC5=C(C(=O)OC)[C@H](c6ccc(F)cc6Cl)N=C(c6nccs6)N5)CCN4C3=O)cc2)cc1] |
| 59 | 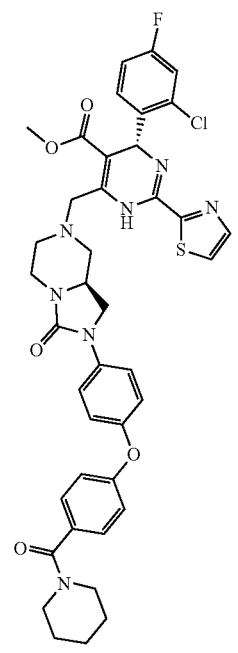 [SMILES: COC(=O)C1=C(CN2CCN3C(=O)N(c4ccc(Oc5ccc(C(=O)N6CCCCC6)cc5)cc4)C[C@@H]3C2)NC(c2nccs2)=N[C@H]1c1ccc(F)cc1Cl] |
-continued
| Example No. | Structure |
|---|---|
| 60 | 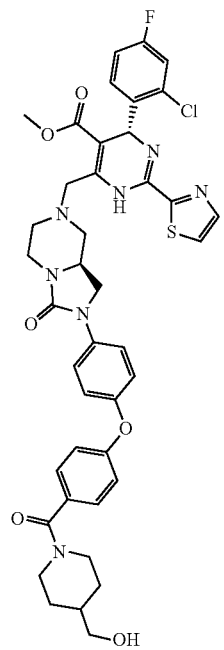 [SMILES: COC(=O)C1=C(CN2CCN3C(=O)N(c4ccc(Oc5ccc(C(=O)N6CCC(CO)CC6)cc5)cc4)C[C@@H]3C2)NC(c2nccs2)=N[C@H]1c1ccc(F)cc1Cl] |
| 61 | 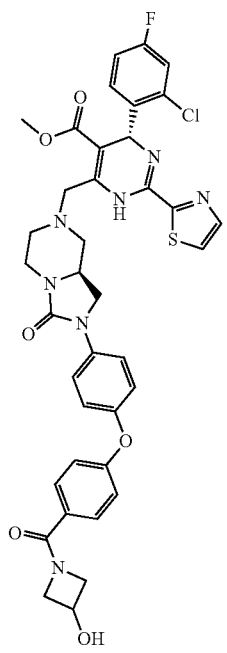 [SMILES: COC(=O)C1=C(CN2CCN3C(=O)N(c4ccc(Oc5ccc(C(=O)N6CC(O)C6)cc5)cc4)C[C@@H]3C2)NC(c2nccs2)=N[C@H]1c1ccc(F)cc1Cl] |

| Example No. | Structure |
|---|---|
| 62 | 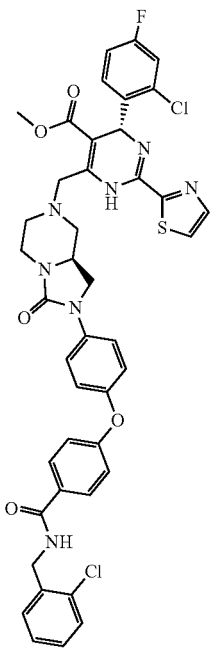 [SMILES: COC(=O)C1=C(CN2CCN3C(=O)N(c4ccc(Oc5ccc(C(=O)NCc6ccccc6Cl)cc5)cc4)C[C@@H]3C2)NC(c2nccs2)=N[C@H]1c1ccc(F)cc1Cl] |
| 63 | 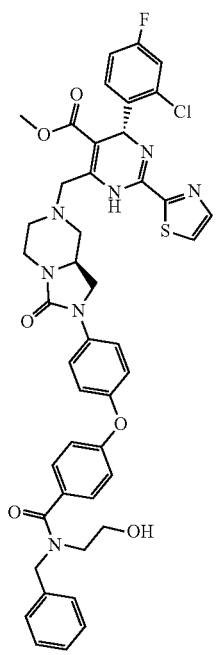 [SMILES: COC(=O)C1=C(CN2CCN3C(=O)N(c4ccc(Oc5ccc(C(=O)N(CCO)Cc6ccccc6)cc5)cc4)C[C@@H]3C2)NC(c2nccs2)=N[C@H]1c1ccc(F)cc1Cl] |
| Example No. | Structure |
|---|---|
| 64 | 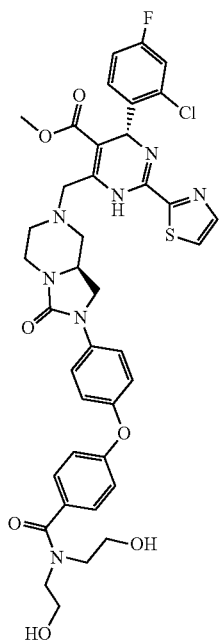 [SMILES: COC(=O)C1=C(CN2CCN3C(=O)N(c4ccc(Oc5ccc(C(=O)N(CCO)CCO)cc5)cc4)C[C@@H]3C2)NC(c2nccs2)=N[C@H]1c1ccc(F)cc1Cl] |
| 65 | 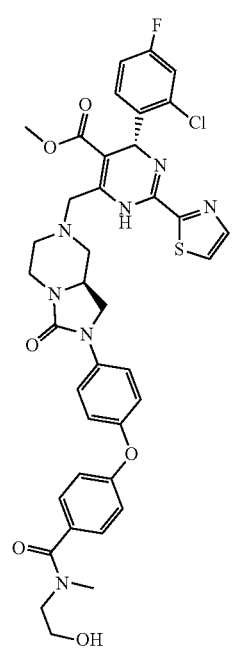 |

| Example No. | Structure |
|---|---|
| 66 | 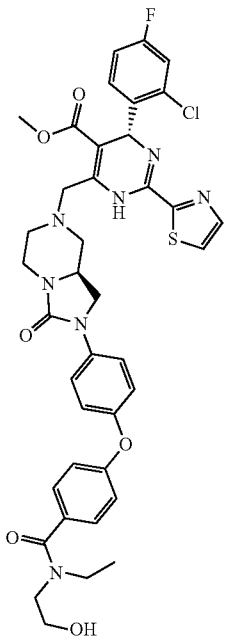 [SMILES: CCN(CCO)C(=O)c1ccc(Oc2ccc(N3C[C@@H]4CN(CC5=C(C(=O)OC)[C@H](c6ccc(F)cc6Cl)N=C(c6nccs6)N5)CCN4C3=O)cc2)cc1] |
| 67 | 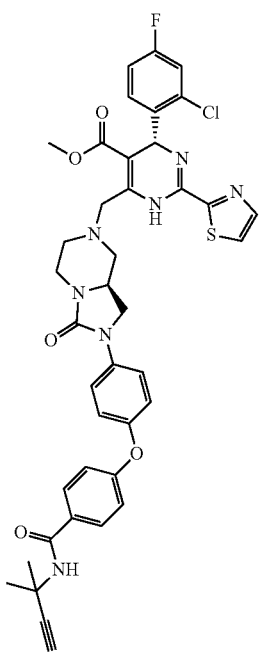 [SMILES: C#CC(C)(C)NC(=O)c1ccc(Oc2ccc(N3C[C@@H]4CN(CC5=C(C(=O)OC)[C@H](c6ccc(F)cc6Cl)N=C(c6nccs6)N5)CCN4C3=O)cc2)cc1] |
| Example No. | Structure |
|---|---|
| 68 | 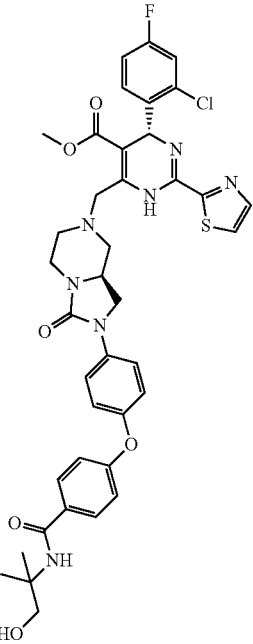 |
| 69 | 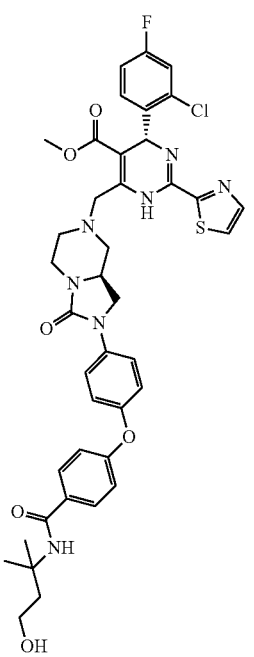 [SMILES: COC(=O)C1=C(CN2CCN3C(=O)N(c4ccc(Oc5ccc(C(=O)NC(C)(C)CCO)cc5)cc4)C[C@@H]3C2)NC(c2nccs2)=N[C@H]1c1ccc(F)cc1Cl] |

| Example No. | Structure |
|---|---|
| 70 | 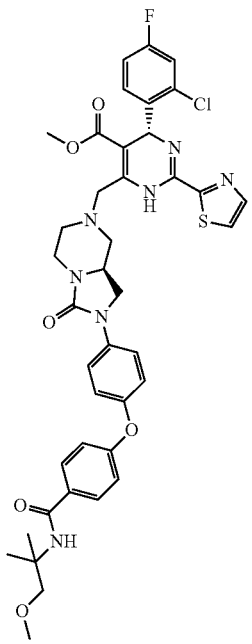 [SMILES: COCC(C)(C)NC(=O)c1ccc(Oc2ccc(N3C[C@@H]4CN(CC5=C(C(=O)OC)[C@H](c6ccc(F)cc6Cl)N=C(c6nccs6)N5)CCN4C3=O)cc2)cc1] |
| 71 | 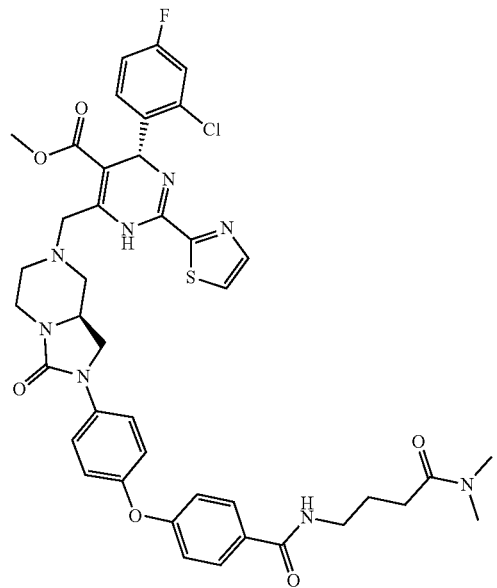 |
| Example No. | Structure |
|---|---|
| 72 | 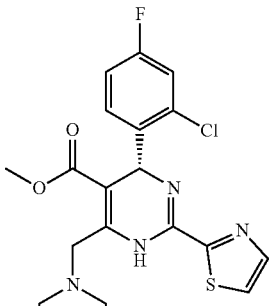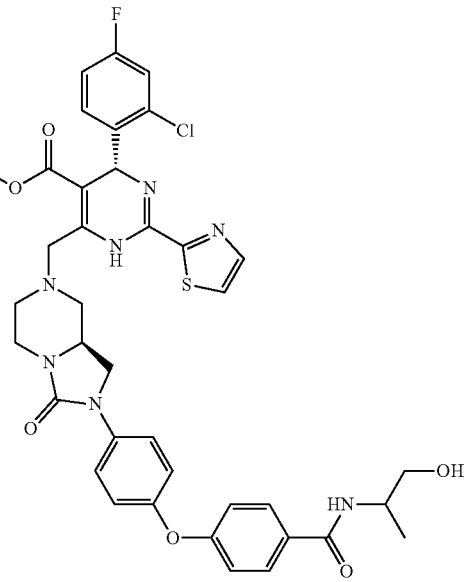 |
| 73 | 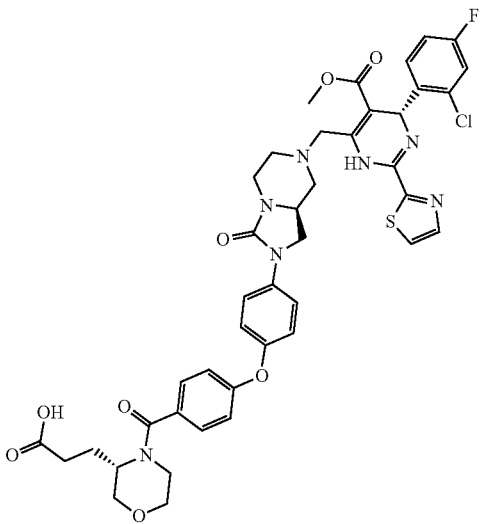 [SMILES: COC(=O)C1=C(CN2CCN3C(=O)N(c4ccc(Oc5ccc(C(=O)N6CCOC[C@@H]6CCC(=O)O)cc5)cc4)C[C@@H]3C2)NC(c2nccs2)=N[C@H]1c1ccc(F)cc1Cl] |

| Example No. | Structure |
|---|---|
| 74 | 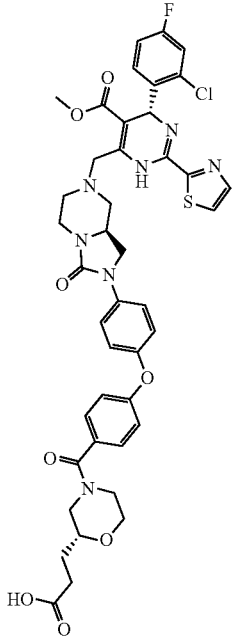 [SMILES: COC(=O)C1=C(CN2CCN3C(=O)N(c4ccc(Oc5ccc(C(=O)N6CCO[C@H](CCC(=O)O)C6)cc5)cc4)C[C@@H]3C2)NC(c2nccs2)=N[C@H]1c1ccc(F)cc1Cl] |
| 75 | 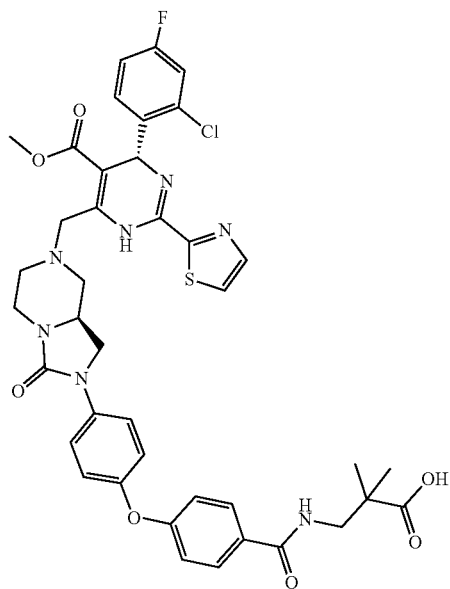 [SMILES: COC(=O)C1=C(CN2CCN3C(=O)N(c4ccc(Oc5ccc(C(=O)NCC(C)(C)C(=O)O)cc5)cc4)C[C@@H]3C2)NC(c2nccs2)=N[C@H]1c1ccc(F)cc1Cl] |
| 76 | 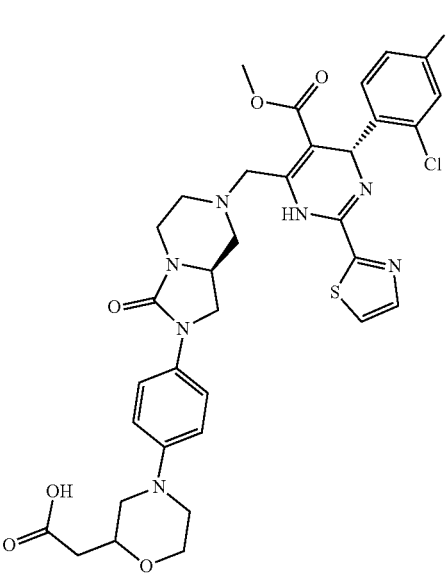 |
| 77 | 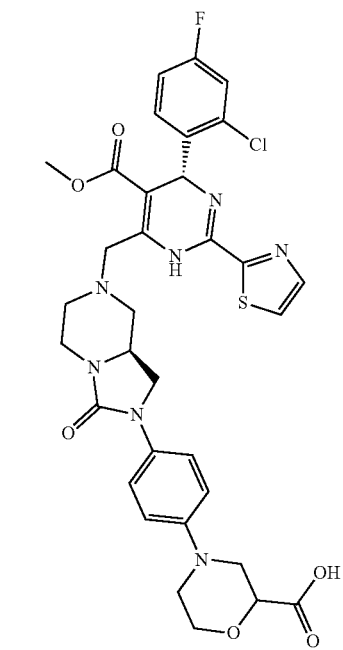 [SMILES: COC(=O)C1=C(CN2CCN3C(=O)N(c4ccc(N5CCOC(C(=O)O)C5)cc4)C[C@@H]3C2)NC(c2nccs2)=N[C@H]1c1ccc(F)cc1Cl] |

TABLE-continued
| Example No. | Structure |
|---|---|
| 78 | 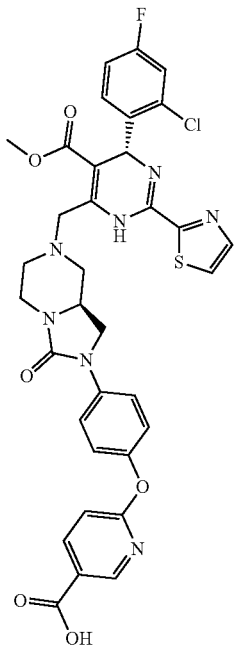 [SMILES: COC(=O)C1=C(CN2CCN3C(=O)N(c4ccc(Oc5ccc(C(=O)O)cn5)cc4)C[C@@H]3C2)NC(c2nccs2)=N[C@H]1c1ccc(F)cc1Cl] |
| 79 | 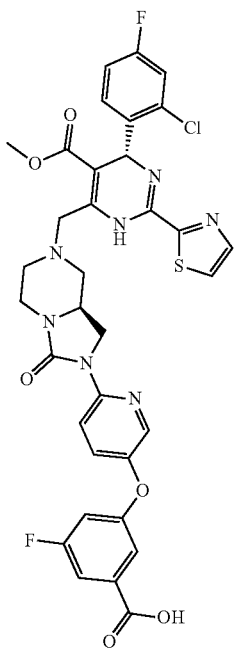 [SMILES: COC(=O)C1=C(CN2CCN3C(=O)N(c4ccc(Oc5cc(F)cc(C(=O)O)c5)cn4)C[C@@H]3C2)NC(c2nccs2)=N[C@H]1c1ccc(F)cc1Cl] |
| 80 | 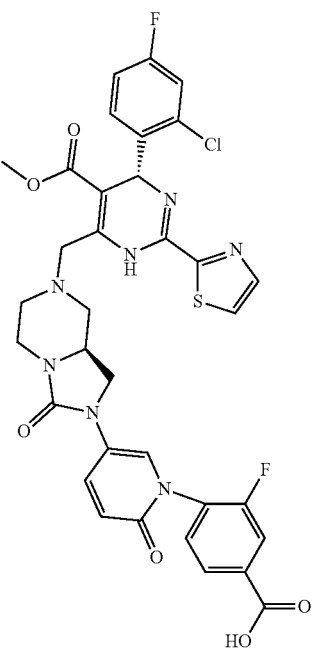 [SMILES: COC(=O)C1=C(CN2CCN3C(=O)N(c4ccc(=O)n(-c5ccc(C(=O)O)cc5F)c4)C[C@@H]3C2)NC(c2nccs2)=N[C@H]1c1ccc(F)cc1Cl] |
| 81 | 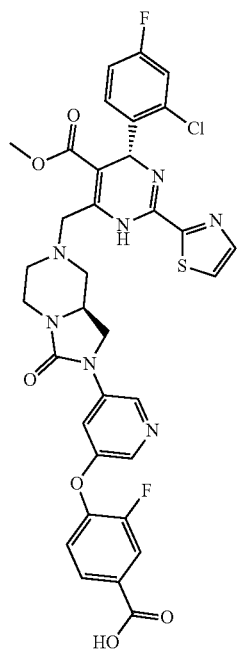 [SMILES: COC(=O)C1=C(CN2CCN3C(=O)N(c4cncc(Oc5ccc(C(=O)O)cc5F)c4)C[C@@H]3C2)NC(c2nccs2)=N[C@H]1c1ccc(F)cc1Cl] |

| Example No. | Structure |
|---|---|
| 82 | 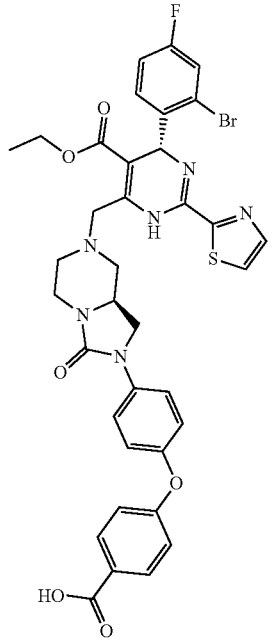 [SMILES: CCOC(=O)C1=C(CN2CCN3C(=O)N(c4ccc(Oc5ccc(C(=O)O)cc5)cc4)C[C@@H]3C2)NC(c2nccs2)=N[C@H]1c1ccc(F)cc1Br] |
| 83 | 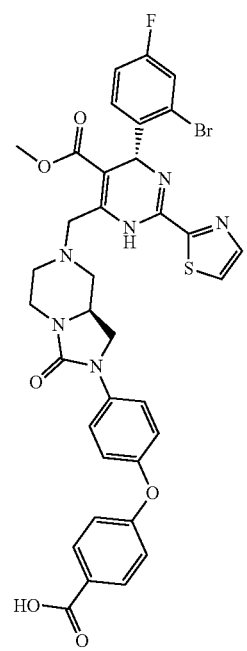 [SMILES: COC(=O)C1=C(CN2CCN3C(=O)N(c4ccc(Oc5ccc(C(=O)O)cc5)cc4)C[C@@H]3C2)NC(c2nccs2)=N[C@H]1c1ccc(F)cc1Br] |
| Example No. | Structure |
|---|---|
| 84 | 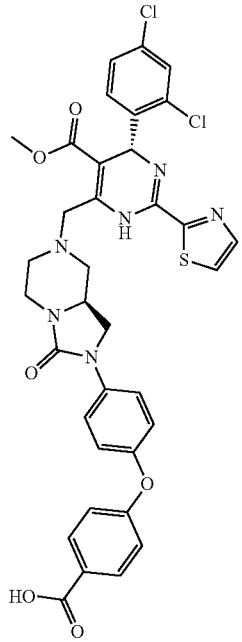 [SMILES: COC(=O)C1=C(CN2CCN3C(=O)N(c4ccc(Oc5ccc(C(=O)O)cc5)cc4)C[C@@H]3C2)NC(c2nccs2)=N[C@H]1c1ccc(Cl)cc1Cl] |
| 85 | 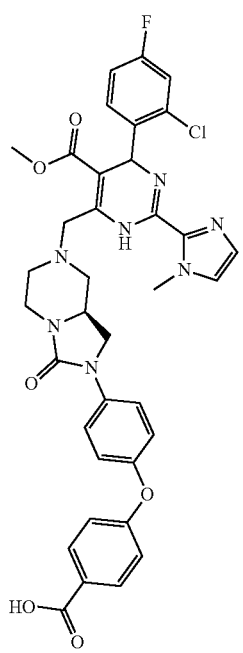 [SMILES: COC(=O)C1=C(CN2CCN3C(=O)N(c4ccc(Oc5ccc(C(=O)O)cc5)cc4)C[C@@H]3C2)NC(c2nccn2C)=NC1c1ccc(F)cc1Cl] |

| Example No. | Structure |
|---|---|
| 86 | 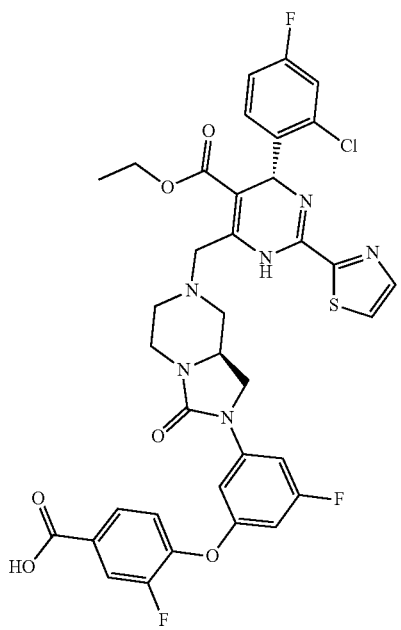 [SMILES: CCOC(=O)C1=C(CN2CCN3C(=O)N(c4cc(F)cc(Oc5ccc(C(=O)O)cc5F)c4)C[C@@H]3C2)NC(c2nccs2)=N[C@H]1c1ccc(F)cc1Cl] |
| 87 | 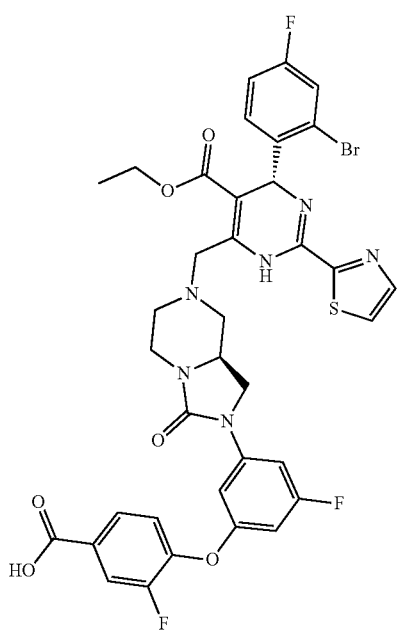 |
| Example No. | Structure |
|---|---|
| 88 | 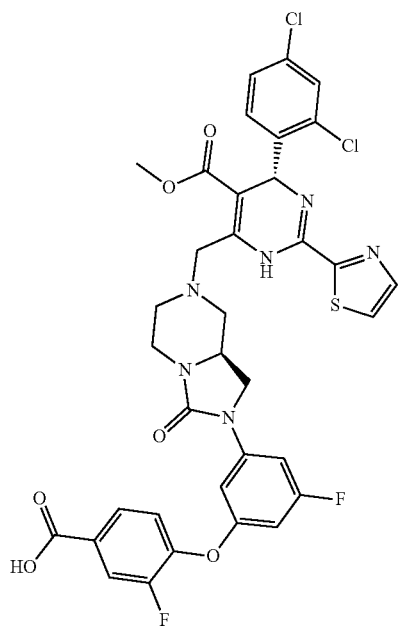 [SMILES: COC(=O)C1=C(CN2CCN3C(=O)N(c4cc(F)cc(Oc5ccc(C(=O)O)cc5F)c4)C[C@@H]3C2)NC(c2nccs2)=N[C@H]1c1ccc(Cl)cc1Cl] |
| 89 | 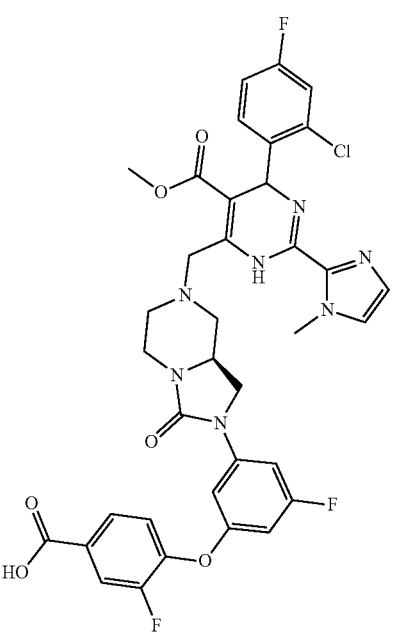 [SMILES: COC(=O)C1=C(CN2CCN3C(=O)N(c4cc(F)cc(Oc5ccc(C(=O)O)cc5F)c4)C[C@@H]3C2)NC(c2nccn2C)=NC1c1ccc(F)cc1Cl] |

215
-continued
| Example No. | Structure |
|---|---|
| 90 | 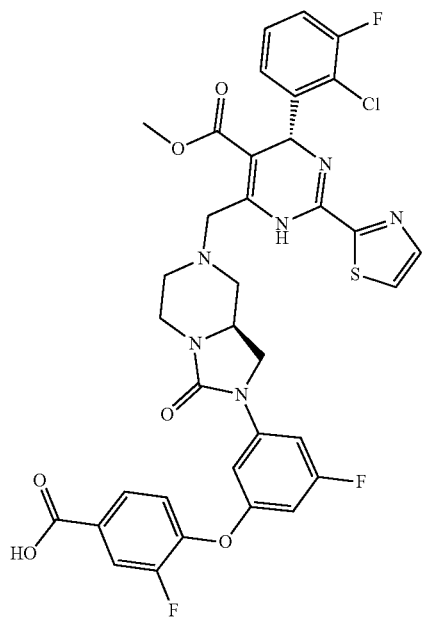 [SMILES: COC(=O)C1=C(CN2CCN3C(=O)N(c4cc(F)cc(Oc5ccc(C(=O)O)cc5F)c4)C[C@@H]3C2)NC(c2nccs2)=N[C@H]1c1cccc(F)c1Cl] |
| 91 | 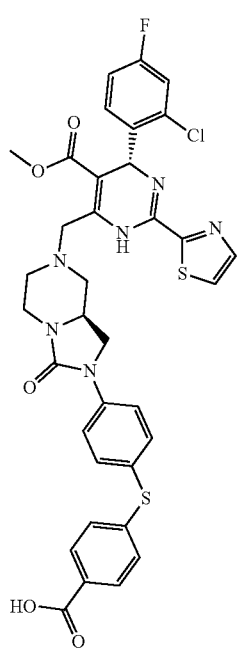 [SMILES: COC(=O)C1=C(CN2CCN3C(=O)N(c4ccc(Sc5ccc(C(=O)O)cc5)cc4)C[C@@H]3C2)NC(c2nccs2)=N[C@H]1c1ccc(F)cc1Cl] |
216
-continued
| Example No. | Structure |
|---|---|
| 92 | 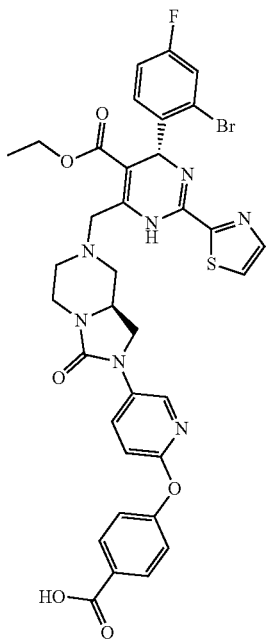 [SMILES: CCOC(=O)C1=C(CN2CCN3C(=O)N(c4ccc(Oc5ccc(C(=O)O)cc5)nc4)C[C@@H]3C2)NC(c2nccs2)=N[C@H]1c1ccc(F)cc1Br] |
| 93 | 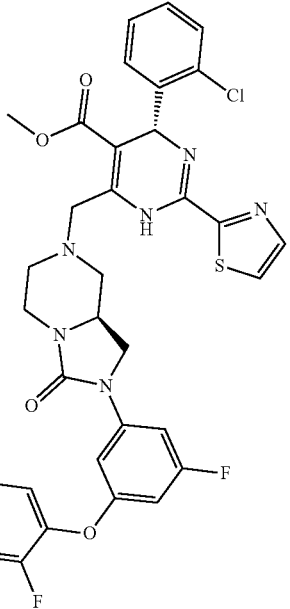 |

TABLE-continued
| Example No. | Structure |
|---|---|
| 94 | 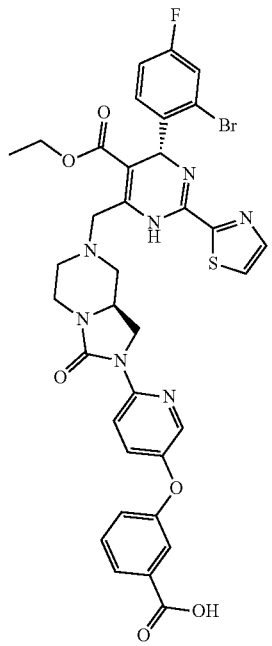 [SMILES: CCOC(=O)C1=C(CN2CCN3C(=O)N(c4ccc(Oc5cccc(C(=O)O)c5)cn4)C[C@@H]3C2)NC(c2nccs2)=N[C@H]1c1ccc(F)cc1Br] |
| 95 | 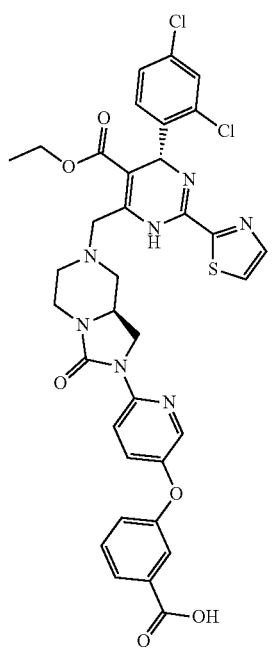 [SMILES: CCOC(=O)C1=C(CN2CCN3C(=O)N(c4ccc(Oc5cccc(C(=O)O)c5)cn4)C[C@@H]3C2)NC(c2nccs2)=N[C@H]1c1ccc(Cl)cc1Cl] |
| Example No. | Structure |
|---|---|
| 96 | 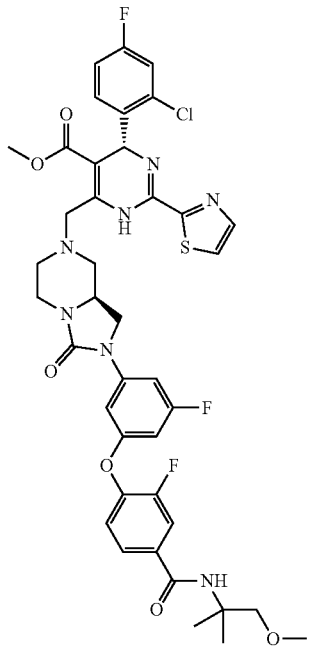 |
| 97 | 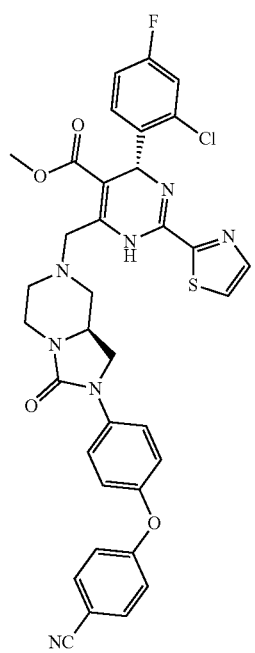 [SMILES: COC(=O)C1=C(CN2CCN3C(=O)N(c4ccc(Oc5ccc(C#N)cc5)cc4)C[C@@H]3C2)NC(c2nccs2)=N[C@H]1c1ccc(F)cc1Cl] |

| Example No. | Structure |
|---|---|
| 98 | 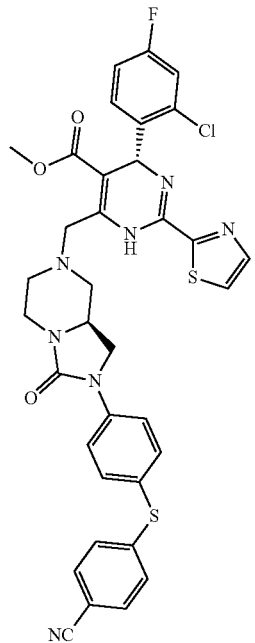 [SMILES: COC(=O)C1=C(CN2CCN3C(=O)N(c4ccc(Sc5ccc(C#N)cc5)cc4)C[C@@H]3C2)NC(c2nccs2)=N[C@H]1c1ccc(F)cc1Cl] |
| 99 | 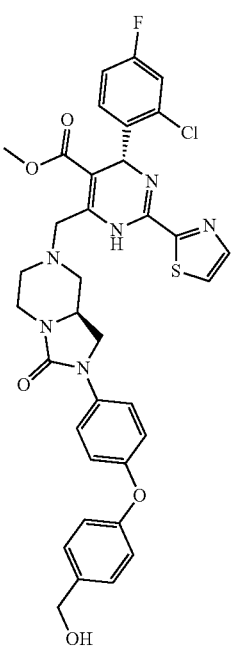 [SMILES: COC(=O)C1=C(CN2CCN3C(=O)N(c4ccc(Oc5ccc(CO)cc5)cc4)C[C@@H]3C2)NC(c2nccs2)=N[C@H]1c1ccc(F)cc1Cl] |
| Example No. | Structure |
|---|---|
| 100 | 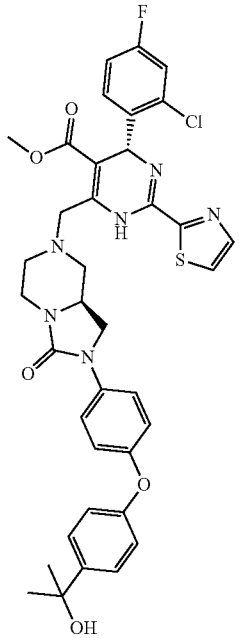 [SMILES: COC(=O)C1=C(CN2CCN3C(=O)N(c4ccc(Oc5ccc(C(C)(C)O)cc5)cc4)C[C@@H]3C2)NC(c2nccs2)=N[C@H]1c1ccc(F)cc1Cl] |
| 101 | 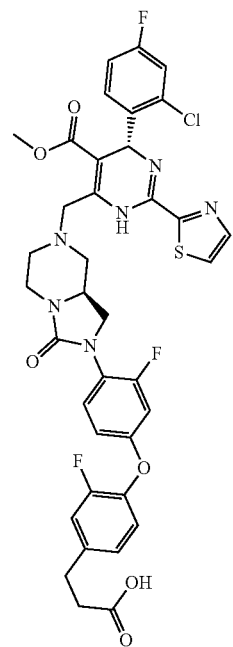 [SMILES: COC(=O)C1=C(CN2CCN3C(=O)N(c4ccc(Oc5ccc(CCC(=O)O)cc5F)cc4F)C[C@@H]3C2)NC(c2nccs2)=N[C@H]1c1ccc(F)cc1Cl] |

| Example No. | Structure |
|---|---|
| 102 | 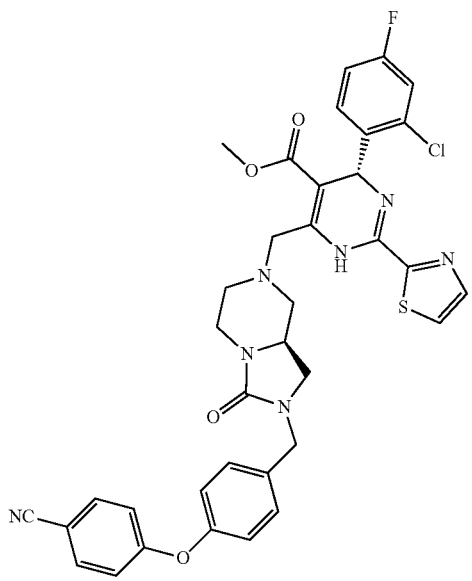 [SMILES: COC(=O)C1=C(CN2CCN3C(=O)N(Cc4ccc(Oc5ccc(C#N)cc5)cc4)C[C@@H]3C2)NC(c2nccs2)=N[C@H]1c1ccc(F)cc1Cl] |
| 103 | 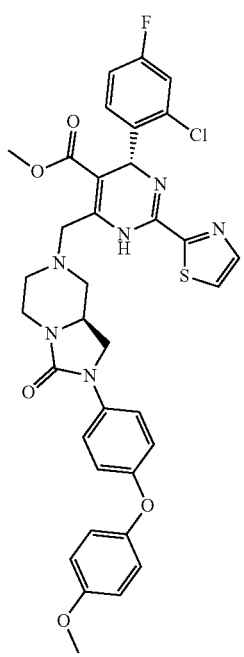 [SMILES: COC(=O)C1=C(CN2CCN3C(=O)N(c4ccc(Oc5ccc(OC)cc5)cc4)C[C@@H]3C2)NC(c2nccs2)=N[C@H]1c1ccc(F)cc1Cl] |
| Example No. | Structure |
|---|---|
| 104 | 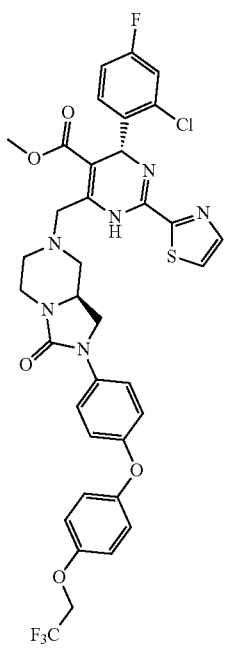 [SMILES: COC(=O)C1=C(CN2CCN3C(=O)N(c4ccc(Oc5ccc(OCC(F)(F)F)cc5)cc4)C[C@@H]3C2)NC(c2nccs2)=N[C@H]1c1ccc(F)cc1Cl] |
| 105 | 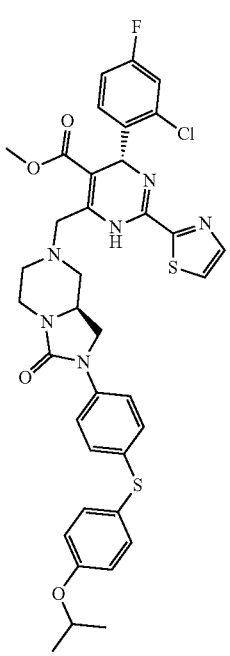 [SMILES: COC(=O)C1=C(CN2CCN3C(=O)N(c4ccc(Sc5ccc(OC(C)C)cc5)cc4)C[C@@H]3C2)NC(c2nccs2)=N[C@H]1c1ccc(F)cc1Cl] |

-continued
| Example No. | Structure |
|---|---|
| 106 | 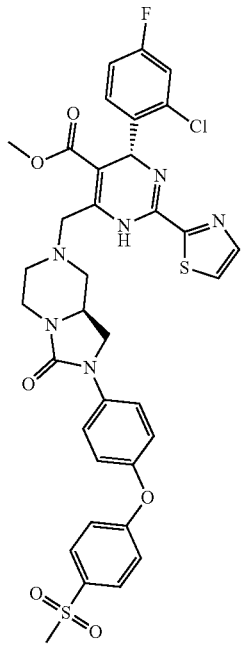 [SMILES: COC(=O)C1=C(CN2CCN3C(=O)N(c4ccc(Oc5ccc(S(C)(=O)=O)cc5)cc4)C[C@@H]3C2)NC(c2nccs2)=N[C@H]1c1ccc(F)cc1Cl] |
| 107 | 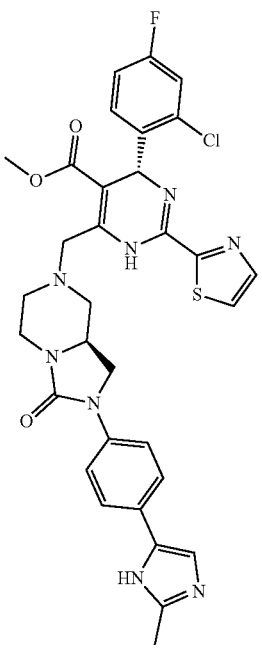 [SMILES: COC(=O)C1=C(CN2CCN3C(=O)N(c4ccc(-c5cnc(C)[nH]5)cc4)C[C@@H]3C2)NC(c2nccs2)=N[C@H]1c1ccc(F)cc1Cl] |
-continued
| Example No. | Structure |
|---|---|
| 108 | 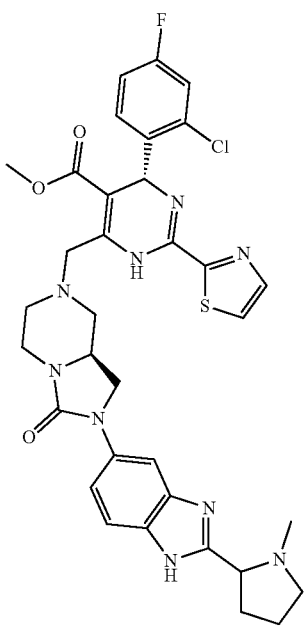 [SMILES: COC(=O)C1=C(CN2CCN3C(=O)N(c4ccc5[nH]c(C6CCCN6C)nc5c4)C[C@@H]3C2)NC(c2nccs2)=N[C@H]1c1ccc(F)cc1Cl] |
| 109 | 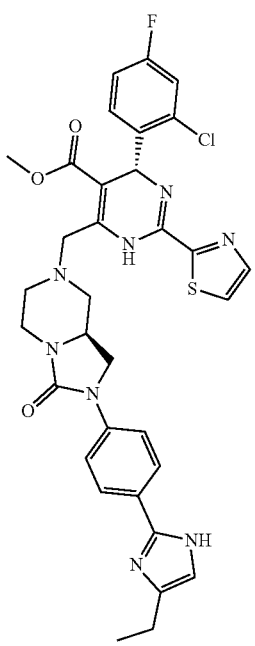 [SMILES: CCc1c[nH]c(-c2ccc(N3C[C@@H]4CN(CC5=C(C(=O)OC)[C@H](c6ccc(F)cc6Cl)N=C(c6nccs6)N5)CCN4C3=O)cc2)n1] |

| Example No. | Structure |
|---|---|
| 110 | 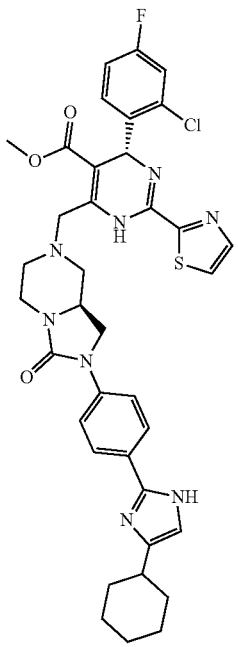 [SMILES: COC(=O)C1=C(CN2CCN3C(=O)N(c4ccc(-c5nc(C6CCCCC6)c[nH]5)cc4)C[C@@H]3C2)NC(c2nccs2)=N[C@H]1c1ccc(F)cc1Cl] |
| 111 | 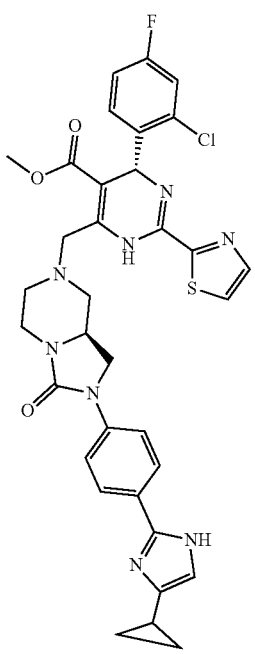 [SMILES: COC(=O)C1=C(CN2CCN3C(=O)N(c4ccc(-c5nc(C6CC6)c[nH]5)cc4)C[C@@H]3C2)NC(c2nccs2)=N[C@H]1c1ccc(F)cc1Cl] |
| Example No. | Structure |
|---|---|
| 112 | 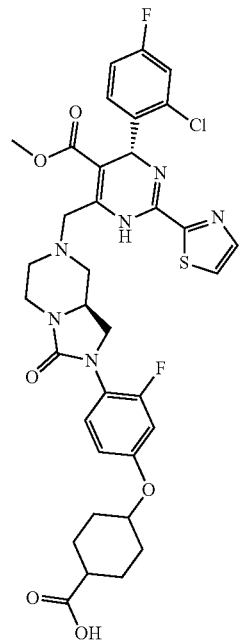 [SMILES: COC(=O)C1=C(CN2CCN3C(=O)N(c4ccc(OC5CCC(C(=O)O)CC5)cc4F)C[C@@H]3C2)NC(c2nccs2)=N[C@H]1c1ccc(F)cc1Cl] |
| 113 | 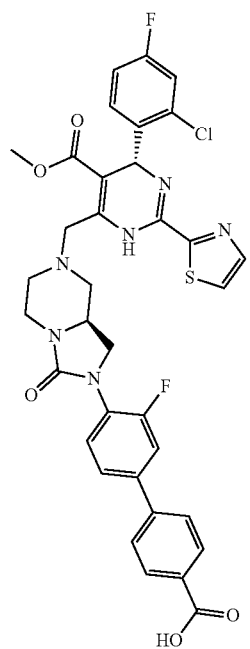 [SMILES: COC(=O)C1=C(CN2CCN3C(=O)N(c4ccc(-c5ccc(C(=O)O)cc5)cc4F)C[C@@H]3C2)NC(c2nccs2)=N[C@H]1c1ccc(F)cc1Cl] |

227
-continued
| Example No. | Structure |
|---|---|
| 114 | 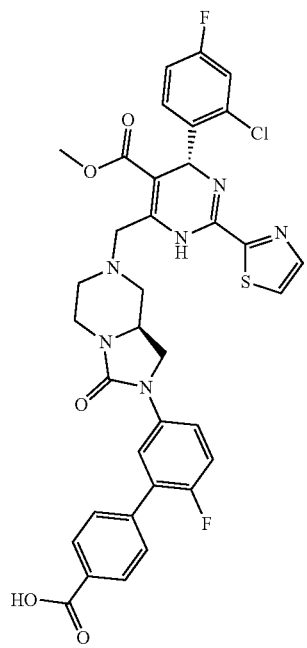 [SMILES: COC(=O)C1=C(CN2CCN3C(=O)N(c4ccc(F)c(-c5ccc(C(=O)O)cc5)c4)C[C@@H]3C2)NC(c2nccs2)=N[C@H]1c1ccc(F)cc1Cl] |
| 115 | 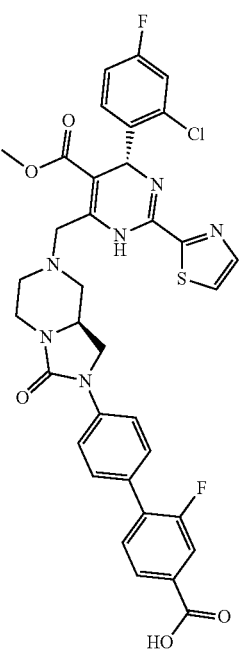 [SMILES: COC(=O)C1=C(CN2CCN3C(=O)N(c4ccc(-c5ccc(C(=O)O)cc5F)cc4)C[C@@H]3C2)NC(c2nccs2)=N[C@H]1c1ccc(F)cc1Cl] |
228
-continued
| Example No. | Structure |
|---|---|
| 116 | 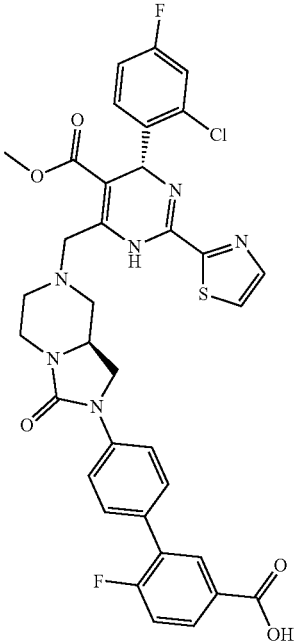 [SMILES: COC(=O)C1=C(CN2CCN3C(=O)N(c4ccc(-c5cc(C(=O)O)ccc5F)cc4)C[C@@H]3C2)NC(c2nccs2)=N[C@H]1c1ccc(F)cc1Cl] |
| 117 | 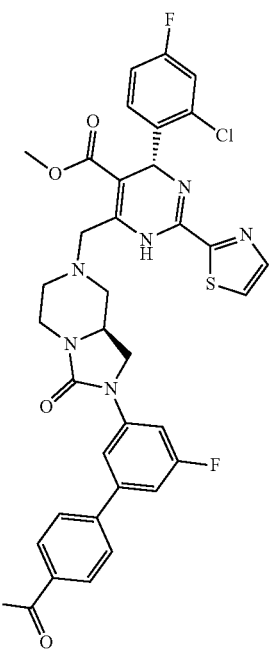 |

-continued
| Example No. | Structure |
|---|---|
| 118 | 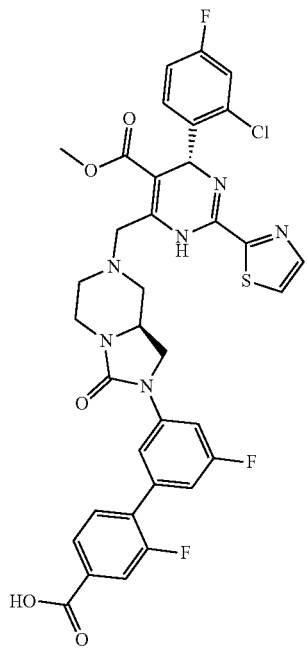 [SMILES: COC(=O)C1=C(CN2CCN3C(=O)N(c4cc(F)cc(-c5ccc(C(=O)O)cc5F)c4)C[C@@H]3C2)NC(c2nccs2)=N[C@H]1c1ccc(F)cc1Cl] |
| 119 | 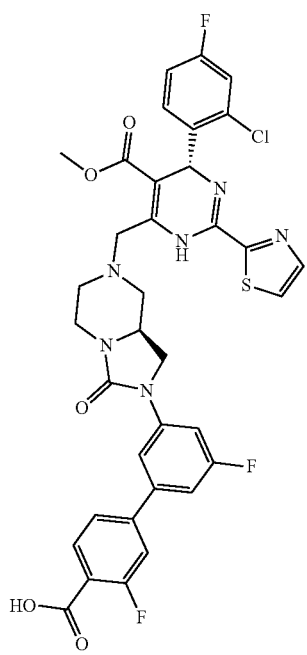 [SMILES: COC(=O)C1=C(CN2CCN3C(=O)N(c4cc(F)cc(-c5ccc(C(=O)O)c(F)c5)c4)C[C@@H]3C2)NC(c2nccs2)=N[C@H]1c1ccc(F)cc1Cl] |
-continued
| Example No. | Structure |
|---|---|
| 120 | 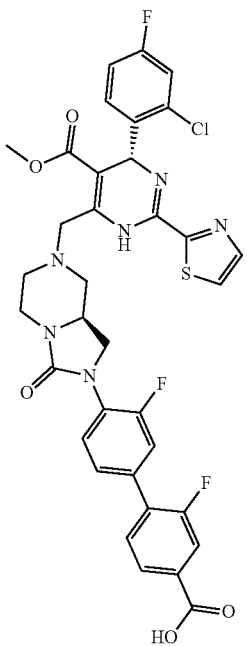 [SMILES: COC(=O)C1=C(CN2CCN3C(=O)N(c4ccc(-c5ccc(C(=O)O)cc5F)cc4F)C[C@@H]3C2)NC(c2nccs2)=N[C@H]1c1ccc(F)cc1Cl] |
| 121 | 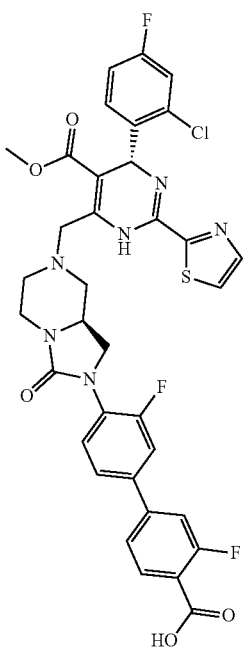 [SMILES: COC(=O)C1=C(CN2CCN3C(=O)N(c4ccc(-c5ccc(C(=O)O)c(F)c5)cc4F)C[C@@H]3C2)NC(c2nccs2)=N[C@H]1c1ccc(F)cc1Cl] |

| Example No. | Structure |
|---|---|
| 122 | 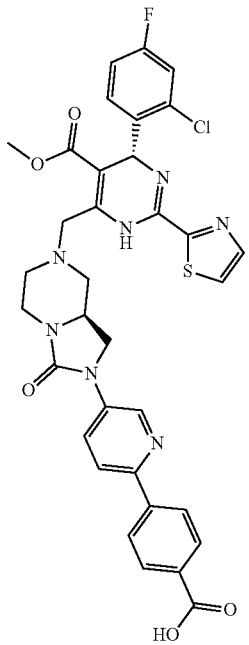 [SMILES: COC(=O)C1=C(CN2CCN3C(=O)N(c4ccc(-c5ccc(C(=O)O)cc5)nc4)C[C@@H]3C2)NC(c2nccs2)=N[C@H]1c1ccc(F)cc1Cl] |
| 123 | 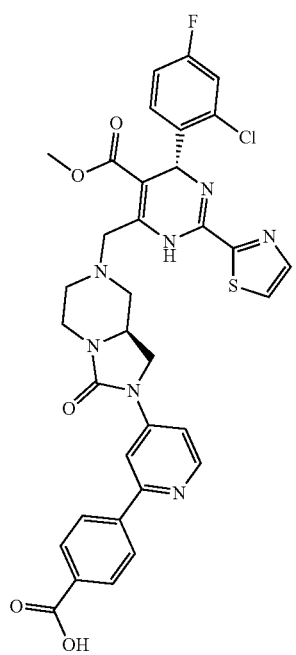 [SMILES: COC(=O)C1=C(CN2CCN3C(=O)N(c4ccnc(-c5ccc(C(=O)O)cc5)c4)C[C@@H]3C2)NC(c2nccs2)=N[C@H]1c1ccc(F)cc1Cl] |
| Example No. | Structure |
|---|---|
| 124 | 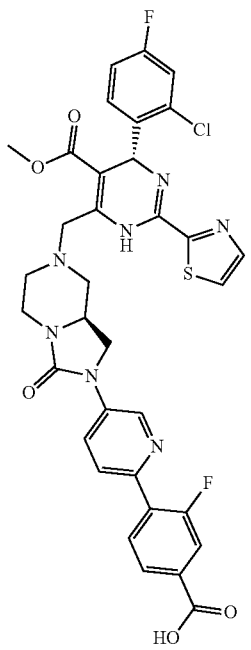 [SMILES: COC(=O)C1=C(CN2CCN3C(=O)N(c4ccc(-c5ccc(C(=O)O)cc5F)nc4)C[C@@H]3C2)NC(c2nccs2)=N[C@H]1c1ccc(F)cc1Cl] |
| 125 | 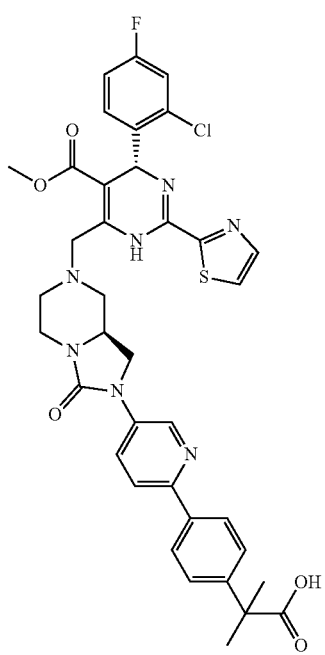 [SMILES: COC(=O)C1=C(CN2CCN3C(=O)N(c4ccc(-c5ccc(C(C)(C)C(=O)O)cc5)nc4)C[C@@H]3C2)NC(c2nccs2)=N[C@H]1c1ccc(F)cc1Cl] |

| Example No. | Structure |
|---|---|
| 126 | 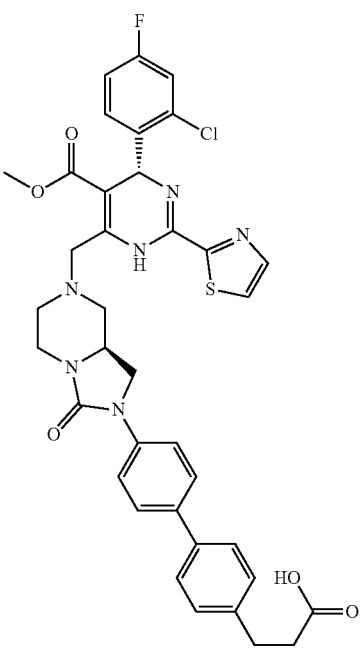 [SMILES: COC(=O)C1=C(CN2CCN3C(=O)N(c4ccc(-c5ccc(CCC(=O)O)cc5)cc4)C[C@@H]3C2)NC(c2nccs2)=N[C@H]1c1ccc(F)cc1Cl] |
| 127 | 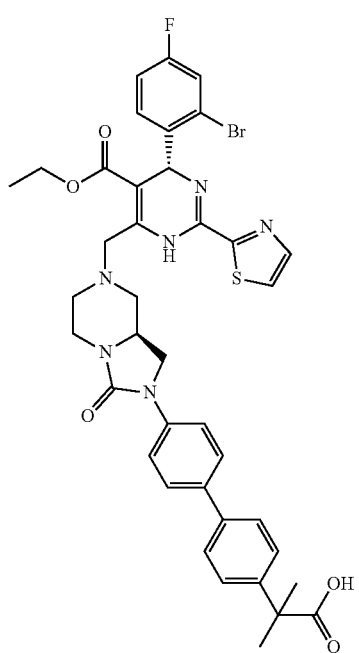 [SMILES: CCOC(=O)C1=C(CN2CCN3C(=O)N(c4ccc(-c5ccc(C(C)(C)C(=O)O)cc5)cc4)C[C@@H]3C2)NC(c2nccs2)=N[C@H]1c1ccc(F)cc1Br] |
| Example No. | Structure |
|---|---|
| 128 | 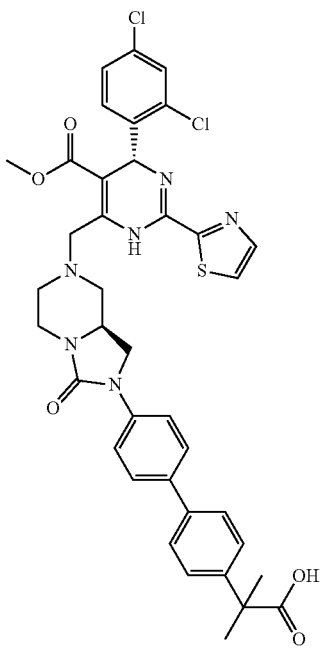 [SMILES: COC(=O)C1=C(CN2CCN3C(=O)N(c4ccc(-c5ccc(C(C)(C)C(=O)O)cc5)cc4)C[C@@H]3C2)NC(c2nccs2)=N[C@H]1c1ccc(Cl)cc1Cl] |
| 129 | 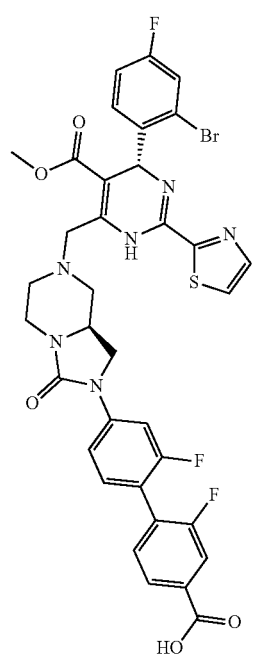 [SMILES: COC(=O)C1=C(CN2CCN3C(=O)N(c4ccc(-c5ccc(C(=O)O)cc5F)c(F)c4)C[C@@H]3C2)NC(c2nccs2)=N[C@H]1c1ccc(F)cc1Br] |

| Example No. | Structure |
|---|---|
| 130 | 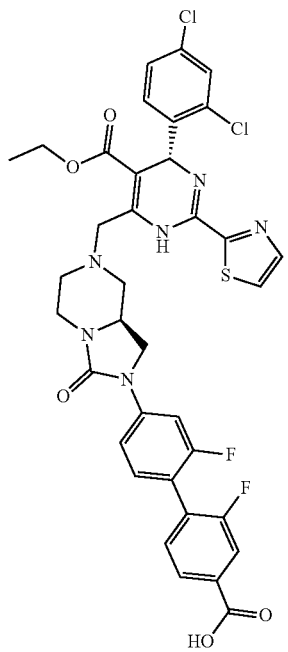 [SMILES: CCOC(=O)C1=C(CN2CCN3C(=O)N(c4ccc(-c5ccc(C(=O)O)cc5F)c(F)c4)C[C@@H]3C2)NC(c2nccs2)=N[C@H]1c1ccc(Cl)cc1Cl] |
| 131 | 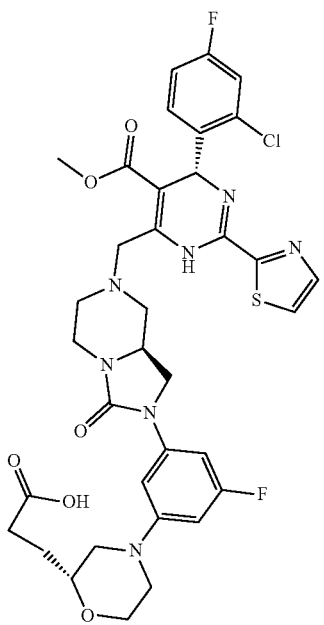 [SMILES: COC(=O)C1=C(CN2CCN3C(=O)N(c4cc(F)cc(N5CCO[C@H](CCC(=O)O)C5)c4)C[C@@H]3C2)NC(c2nccs2)=N[C@H]1c1ccc(F)cc1Cl] |
| Example No. | Structure |
|---|---|
| 132 | 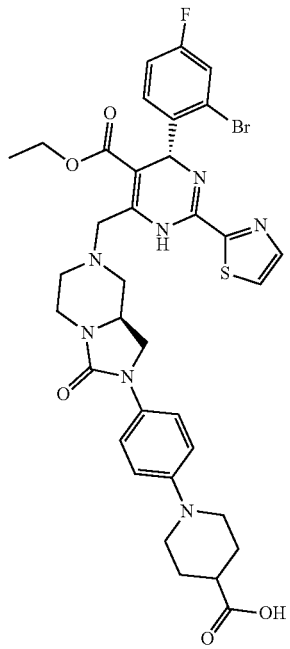 [SMILES: CCOC(=O)C1=C(CN2CCN3C(=O)N(c4ccc(N5CCC(C(=O)O)CC5)cc4)C[C@@H]3C2)NC(c2nccs2)=N[C@H]1c1ccc(F)cc1Br] |
| 133 | 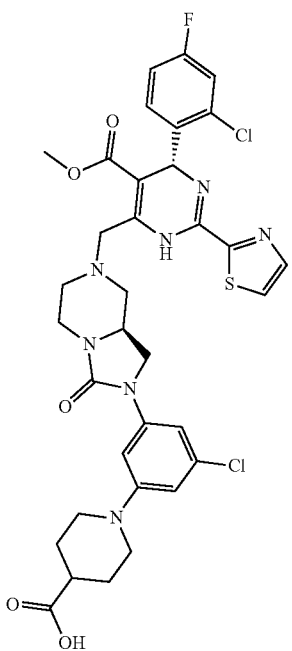 [SMILES: COC(=O)C1=C(CN2CCN3C(=O)N(c4cc(Cl)cc(N5CCC(C(=O)O)CC5)c4)C[C@@H]3C2)NC(c2nccs2)=N[C@H]1c1ccc(F)cc1Cl] |

-continued
| Example No. | Structure |
|---|---|
| 134 | 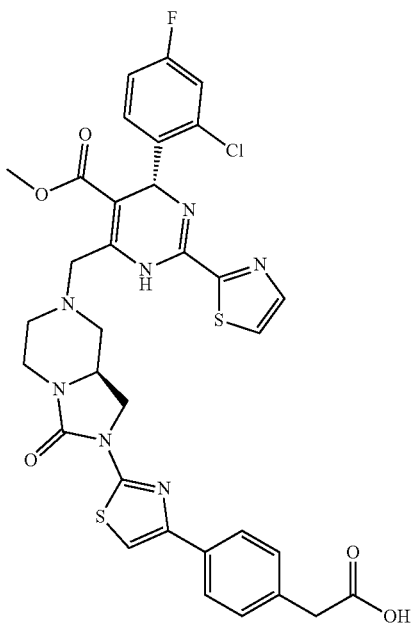 [SMILES: COC(=O)C1=C(CN2CCN3C(=O)N(c4nc(-c5ccc(CC(=O)O)cc5)cs4)C[C@@H]3C2)NC(c2nccs2)=N[C@H]1c1ccc(F)cc1Cl] |
| 135 | 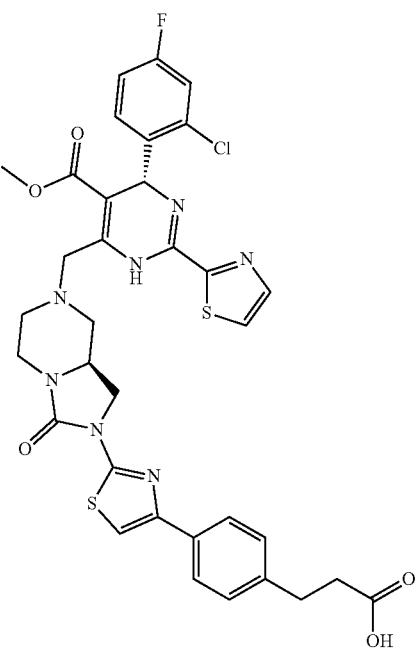 [SMILES: COC(=O)C1=C(CN2CCN3C(=O)N(c4nc(-c5ccc(CCC(=O)O)cc5)cs4)C[C@@H]3C2)NC(c2nccs2)=N[C@H]1c1ccc(F)cc1Cl] |
-continued
| Example No. | Structure |
|---|---|
| 136 | 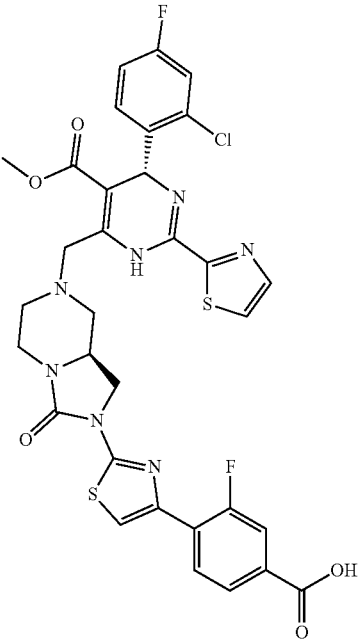 [SMILES: COC(=O)C1=C(CN2CCN3C(=O)N(c4nc(-c5ccc(C(=O)O)cc5F)cs4)C[C@@H]3C2)NC(c2nccs2)=N[C@H]1c1ccc(F)cc1Cl] |
| 137 | 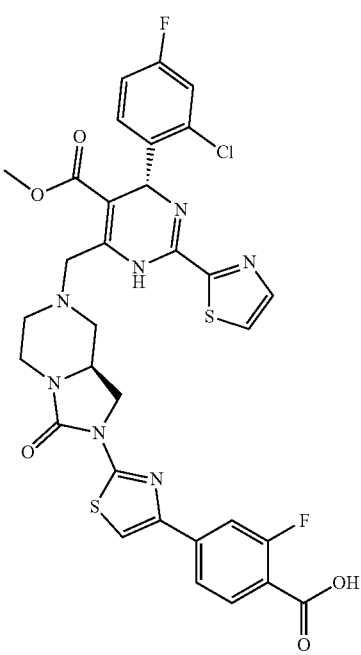 [SMILES: COC(=O)C1=C(CN2CCN3C(=O)N(c4nc(-c5ccc(C(=O)O)c(F)c5)cs4)C[C@@H]3C2)NC(c2nccs2)=N[C@H]1c1ccc(F)cc1Cl] |

| Example No. | Structure |
|---|---|
| 138 | 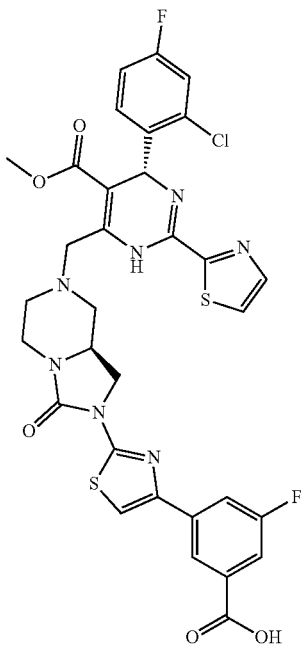 [SMILES: COC(=O)C1=C(CN2CCN3C(=O)N(c4nc(-c5cc(F)cc(C(=O)O)c5)cs4)C[C@@H]3C2)NC(c2nccs2)=N[C@H]1c1ccc(F)cc1Cl] |
| 139 | 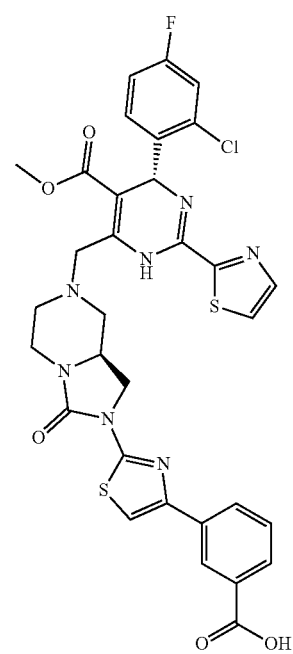 [SMILES: COC(=O)C1=C(CN2CCN3C(=O)N(c4nc(-c5cccc(C(=O)O)c5)cs4)C[C@@H]3C2)NC(c2nccs2)=N[C@H]1c1ccc(F)cc1Cl] |
| Example No. | Structure |
|---|---|
| 140 | 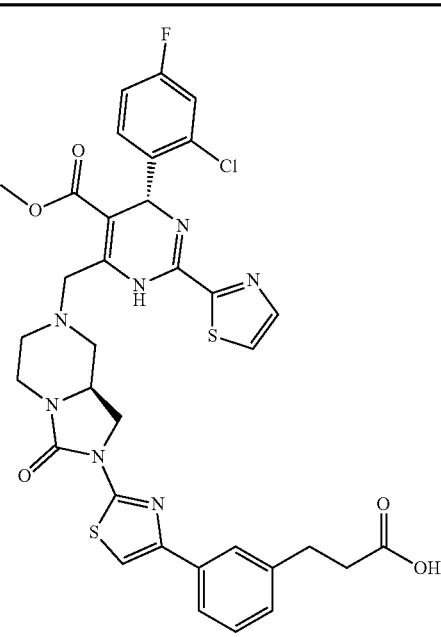 |
| 141 | 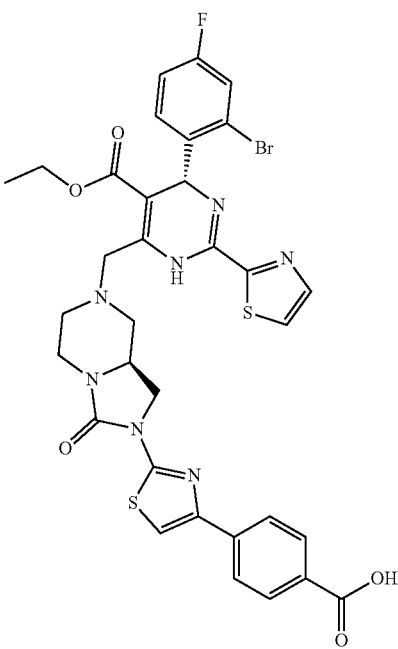 [SMILES: CCOC(=O)C1=C(CN2CCN3C(=O)N(c4nc(-c5ccc(C(=O)O)cc5)cs4)C[C@@H]3C2)NC(c2nccs2)=N[C@H]1c1ccc(F)cc1Br] |

| Example No. | Structure |
|---|---|
| 142 | 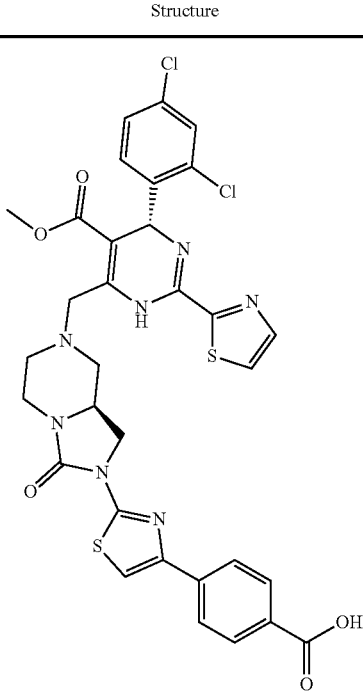 |
| 143 | 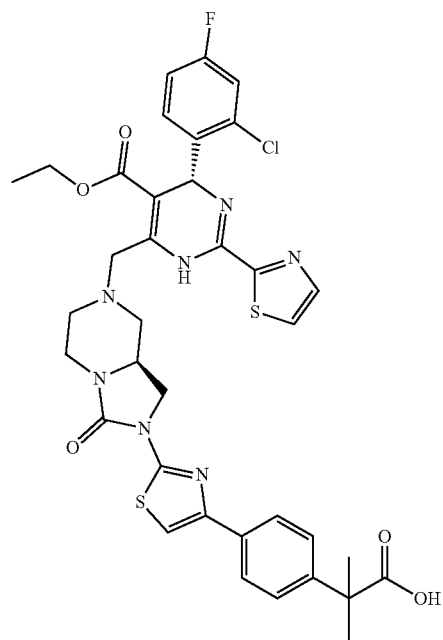 [SMILES: CCOC(=O)C1=C(CN2CCN3C(=O)N(c4nc(-c5ccc(C(C)(C)C(=O)O)cc5)cs4)C[C@@H]3C2)NC(c2nccs2)=N[C@H]1c1ccc(F)cc1Cl] |
| Example No. | Structure |
|---|---|
| 144 | 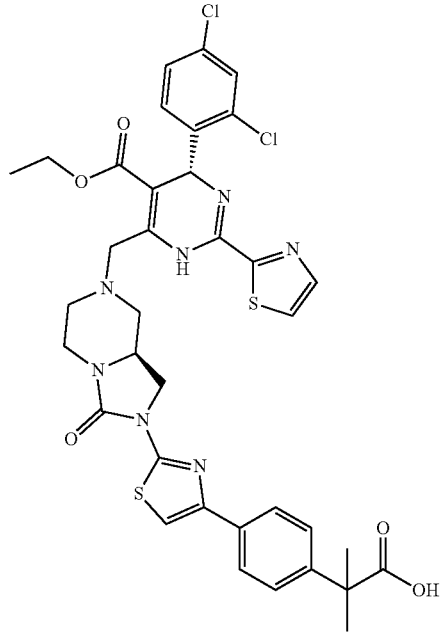 [SMILES: CCOC(=O)C1=C(CN2CCN3C(=O)N(c4nc(-c5ccc(C(C)(C)C(=O)O)cc5)cs4)C[C@@H]3C2)NC(c2nccs2)=N[C@H]1c1ccc(Cl)cc1Cl] |
| 145 | 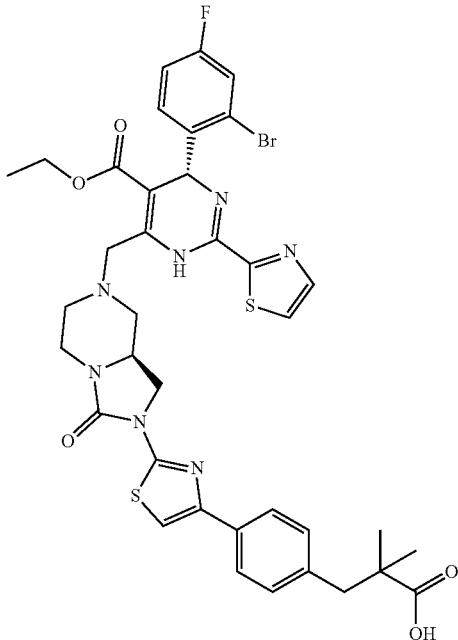 [SMILES: CCOC(=O)C1=C(CN2CCN3C(=O)N(c4nc(-c5ccc(CC(C)(C)C(=O)O)cc5)cs4)C[C@@H]3C2)NC(c2nccs2)=N[C@H]1c1ccc(F)cc1Br] |

| Example No. | Structure |
|---|---|
| 146 | 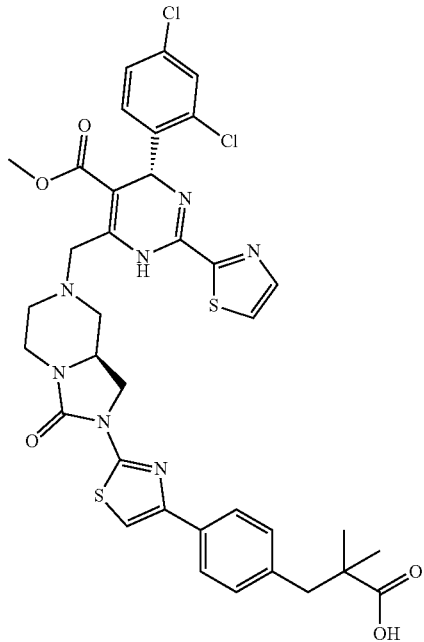 [SMILES: COC(=O)C1=C(CN2CCN3C(=O)N(c4nc(-c5ccc(CC(C)(C)C(=O)O)cc5)cs4)C[C@@H]3C2)NC(c2nccs2)=N[C@H]1c1ccc(Cl)cc1Cl] |
| 147 | 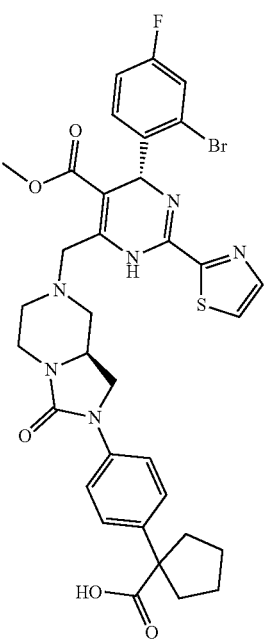 [SMILES: COC(=O)C1=C(CN2CCN3C(=O)N(c4ccc(C5(C(=O)O)CCCC5)cc4)C[C@@H]3C2)NC(c2nccs2)=N[C@H]1c1ccc(F)cc1Br] |
| Example No. | Structure |
|---|---|
| 148 | 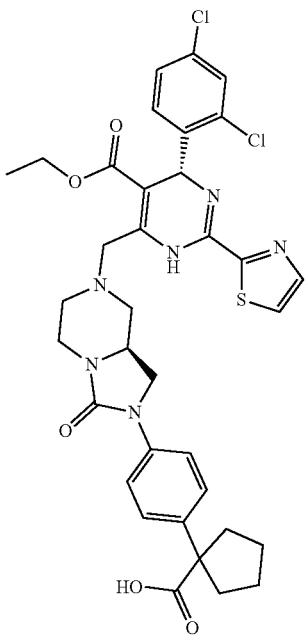 [SMILES: CCOC(=O)C1=C(CN2CCN3C(=O)N(c4ccc(C5(C(=O)O)CCCC5)cc4)C[C@@H]3C2)NC(c2nccs2)=N[C@H]1c1ccc(Cl)cc1Cl] |
| 149 | 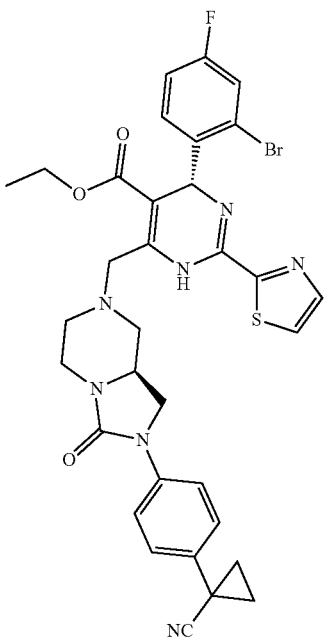 [SMILES: CCOC(=O)C1=C(CN2CCN3C(=O)N(c4ccc(C5(C#N)CC5)cc4)C[C@@H]3C2)NC(c2nccs2)=N[C@H]1c1ccc(F)cc1Br] |

| Example No. | Structure |
|---|---|
| 150 | 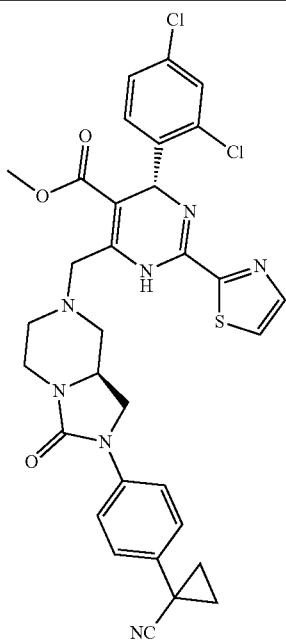 |

Example 1 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)benzoic acid Step 1: (R)-tert-butyl 3-oxo-2-(prop-2-yn-1-yl)hexahydroimidazo[1,5-a]pyrazine-7(1H)-carboxylate

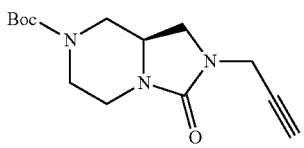 [SMILES: C#CCN1C[C@@H]2CN(C(=O)OC(C)(C)C)CCN2C1=O]

To a 25 mL two-neck flask were added (R)-tert-butyl 3-oxohexahydroimidazo[1,5-a]pyrazine-7(1H)-carboxylate (503 mg, 2.0846 mmol) and anhydrous DMF (8 mL), the mixture was stirred at 0° C. under N₂. And then sodium hydride (130 mg, 3.25 mmol, 60 mass %) was added, the mixture was further stirred for 30 min, and then a solution of 3-bromopropyne (320 mg, 2.69 mmol) in anhydrous THF (1 mL) was added, the resulting mixture was maintained at the reaction temperature and stirred for 5 hours. After the reaction was complete, the reaction mixture was partitioned between EtOAc (30 mL) and water (15 mL). The water phase was extracted with EtOAc (20 mL). The organic layers were combined. The combined organic layers were washed with saturated brine (45 mL), dried over anhydrous Na₂SO₄, and concentrated in vacuo. The residue was purified by silica gel column chromatography (PE/EtOAc (v/v)= 4/1) to give the title compound as a light yellow solid (500 mg, 85.88%). MS (ESI, pos. ion) m/z: 302.1 [M+Na]⁺.

Step 2: (R)-tert-butyl 2-((3-(4-((methoxycarbonyl)phenyl)prop-2-yn-1-yl)-3-oxohexahydro imidazo[1,5-a]pyrazine-7(1H)-carboxylate

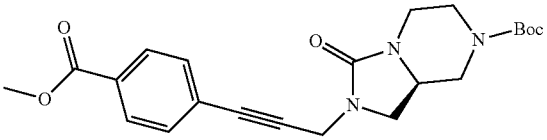 [SMILES: COC(=O)c1ccc(C#CCN2C[C@@H]3CN(C(=O)OC(C)(C)C)CCN3C2=O)cc1]

To a 50 mL two-neck flask were added methyl 4-iodobenzoate (900 mg, 3.44 mmol), dichlorobis(triphenylphosphine)palladium (100 mg, 0.1425 mmol), cuprous iodide (81 mg, 0.43 mmol), triethylamine (0.8 mL, 6 mmol) and (R)-tert-butyl 3-oxo-2-((prop-2-yn-1-yl) hexahydroimidazo [1,5-a]pyrazine-7(1H)-carboxylate (800 mg, 2.864 mmol). To the mixture was added anhydrous THF (10 mL) under N₂, and the air in the reactor was replaced with nitrogen 5 times, and then the mixture was stirred at 30° C. under N₂ for 5 hours. The reaction mixture was concentrated in vacuo. The residue was purified by silica gel column chromatography (PE/EtOAc (v/v)=3/1) to give the title compound as a light yellow solid (963 mg, 81.31%). MS (ESI, pos. ion) m/z: 436.1[M+Na]⁺.

Step 3: (R)-4-(3-(7-(tert-butoxycarbonyl)-3-oxohexahydroimidazo[1,5-a]pyrazin-2(3H)-yl) prop-1-yn-1-yl)benzoic acid

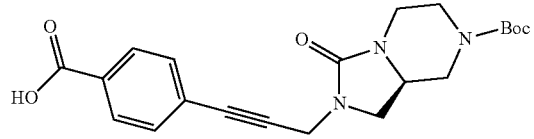 [SMILES: CC(C)(C)OC(=O)N1CCN2C(=O)N(CC#Cc3ccc(C(=O)O)cc3)C[C@@H]2C1]

To a 50 mL single neck flask were added (R)-tert-butyl 2-(3-((4-((methoxycarbonyl)phenyl)prop-2-yn-1-yl)-3-oxohexahydroimidazo[1,5-a]pyrazine-7(1H)-carboxylate (963 mg, 2.329 mmol, 100 mass %), methanol (8 mL), water (2.5 mL) and lithium hydroxide monohydrate (127 mg, 3.027 mmol). The reaction mixture was stirred at 35° C. for 4 hours, and then partitioned between water (25 mL) and EtOAc (10 mL). The organic layer was discarded. The water phase was adjusted with dilute hydrochloric acid to pH 5, and the resulting mixture was extracted with EtOAc (30 mL), and the EtOAc layer was washed with saturated aqueous NaCl and dried over anhydrous sodium sulfate. The mixture was filtered and the filtrate was concentrated in vacuo to give the title compound as a gray solid (910 mg, 97.83%). MS (ESI, pos. ion) m/z: 422.4 [M+Na]⁺.

Step 4: (S)-4-(3-(3-oxohexahydroimidazo[1,5-a]pyrazin-2(3H)-yl)prop-1-yn-1-yl)benzoic acid trifluoroacetate

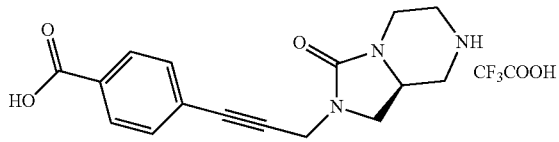

To a 25 mL single neck flask were added (R)-4-(3-(7-(butoxycarbonyl)-3-oxohexahydroimidazo[1,5-a]pyrazin-2(3H)-yl)prop-1-yn-1-yl) benzoic acid (910 mg, 2.278 mmol), DCM (9 mL) and TFA (3 mL), the mixture was stirred at rt for 2 hours. After the reaction was complete, the reaction mixture was concentrated in vacuo to give the title compound as a light yellow oil (941 mg, 99.90%). The oil was used in the next step without further purification. MS (ESI, pos. ion) m/z: 300.1 [M+H]$^+$.

Step 5: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)benzoic acid

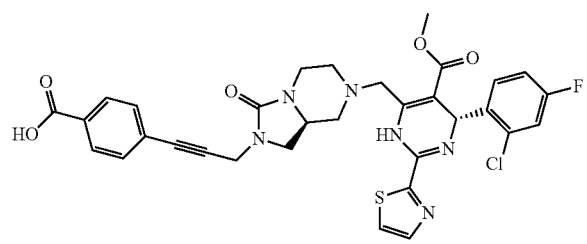 [SMILES: COC(=O)C1=C(CN2CCN3C(=O)N(CC#Cc4ccc(C(=O)O)cc4)C[C@@H]3C2)NC(c2nccs2)=N[C@H]1c1ccc(F)cc1Cl]

To a 50 mL single neck flask were added (S)-4-(3-(3-oxohexahydroimidazo [1,5-a]pyrazin-2(3H)-yl)prop-1-yn-1-yl)benzoic acid trifluoroacetate (941 mg, 2.276 mmol), anhydrous ethanol (20 mL) and (R)-methyl 6-(bromomethyl)-4-(2-chloro-4-fluorophenyl)-2-(thiazol-2-yl)-1,4-dihydropyrimidine-5-carboxylate (0.9 g, 2.02 mmol) (prepared by the method refer to scheme 1 of WO2015074546 and example 1 and example 15 therein), and then potassium carbonate (842 mg, 6.09 mmol) was added to adjust pH to 8 to 9. The reaction mixture was stirred at rt for 6 hours. After the reaction was complete, the reaction mixture was diluted with water (60 mL), and the resulting mixture was extracted with EtOAc (20 mL). The organic layer was discarded. To the water phase was added EtOAc (60 mL), and adjusted with concentrated hydrochloric acid to pH 5. The EtOAc layer was washed with saturated aqueous NaCl and dried over anhydrous sodium sulfate. The mixture was filtered and the filtrate was concentrated in vacuo to give the title compound as a yellow solid (612 mg, 45.6%). MS (ESI, pos. ion) m/z: 663.0 [M+H]$^+$; $^1$H NMR (400 MHz, CDCl$_3$) 9.64 (br.s., 1H), 8.01 (d, J=8.1 Hz, 2H), 7.83 (d, J=3.1 Hz, 1H), 7.51-7.42 (m, 3H), 7.30-7.25 (m, 1H), 7.12 (dd, J=8.6, 2.6 Hz, 1H), 6.91 (td, J=8.4, 2.8 Hz, 1H), 6.20 (s, 1H), 4.35 (d, J=18.0 Hz, 1H), 4.24 (d, J=17.6 Hz, 1H), 4.10 (d, J=17.2 Hz, 1H), 4.02-3.96 (m, 1H), 3.96-3.89 (m, 1H), 3.86 (d, J=17.2 Hz, 1H), 3.62 (d, J=8.2 Hz, 1H), 3.59 (s, 3H), 3.29-3.16 (m, 1H), 3.10 (dd, J=8.9, 4.5 Hz, 1H), 2.91-2.72 (m, 2H), 2.46 (td, J=11.5, 3.1 Hz, 1H), 2.27 (t, J=10.8 Hz, 1H).

Example 2 3-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)benzoic acid

Step 1: (R)-tert-butyl 2-(3-(3-(methoxycarbonyl)phenyl)prop-2-yn-1-yl)-3-oxohexahydroimidazo[1,5-a]pyrazine-7(1H)-carboxylate

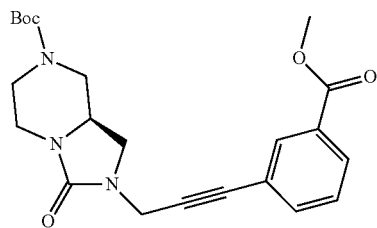 [SMILES: COC(=O)c1cccc(C#CCN2C[C@@H]3CN(C(=O)OC(C)(C)C)CCN3C2=O)c1]

(R)-tert-Butyl 3-oxo-2-(prop-2-yn-1-yl)hydroimidazo[1,5-a]pyrazine-7(1H)-carboxylate (500 mg, 1.79 mmol), methyl 3-bromobenzoate (390 mg, 1.81 mmol), cuprous iodide (17 mg, 0.09 mmol) and dichlorobis(triphenylphosphine)palladium (62 mg, 0.09 mmol) were dissolved in a mixed solvent of triethylamine (25 mL) and DMF (4 mL) under N$_2$, the reaction mixture was stirred at 50° C. for 23 hours. After the mixture was complete, the reaction was quenched with water (10 mL). The resulting mixture was extracted with ethyl acetate (10 mL×4). The combined organic phases were dried over anhydrous sodium sulfate, filtered and the filtrate was concentrated in vacuo. The residue was purified by silica gel chromatograph (PE/EtOAc (V/V)=4/1) to give the title compound as an off-white solid (115 mg, 15.6%). MS (ESI. pos) m/z: 358.5 [M+H−56]$^+$.

Step 2: (R)-3-(3-(7-(tert-butoxycarbonyl)-3-oxohexahydroimidazo[1,5-a]pyrazin-2(3H)-yl)prop-1-yn-1-yl)benzoic acid

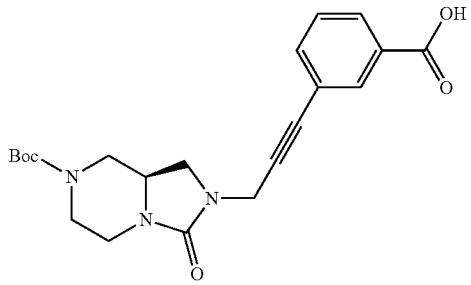 [SMILES: CC(C)(C)OC(=O)N1CCN2C(=O)N(CC#Cc3cccc(C(=O)O)c3)C[C@@H]2C1]

The title compound was obtained as a white solid (50 mg, 44.7%) according to step 3 of example 1 by using (R)-tert-butyl 2-(3-(3-(methoxycarbonyl)phenyl)prop-2-yn-1-yl)-3-oxohexahydroimidazo[1,5-a]pyrazine-7(1H)-carboxylate (115 mg, 0.28 mmol), methanol (5 mL) and water (3 mL) as materials. MS (ESI. pos)m/z: 344.1[M+H−56]$^+$.

Step 3: (S)-3-(3-(3-oxohexahydroimidazo[1,5-a]piperazin-2(3H)-yl)prop-1-yn-1-yl)benzoic acid trifluoroacetate

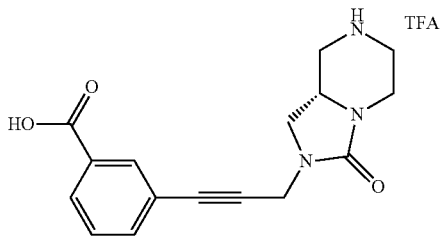 [SMILES: O=C(O)c1cccc(C#CCN2C[C@@H]3CNCCN3C2=O)c1]

The title compound was obtained as a brown oil (66 mg, 100%) according to step 4 of example 1 by using (R)-3-(3-(7-(tert-butoxycarbonyl)-3-oxohexahydroimidazo[1,5-a]pyrazin-2(3H)-yl)prop-1-yn-1-yl)benzoic acid (62 mg, 0.16 mmol), DCM (2 mL) and TFA (0.5 mL, 7 mmol) as materials.

Step 4: 3-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)benzoic acid

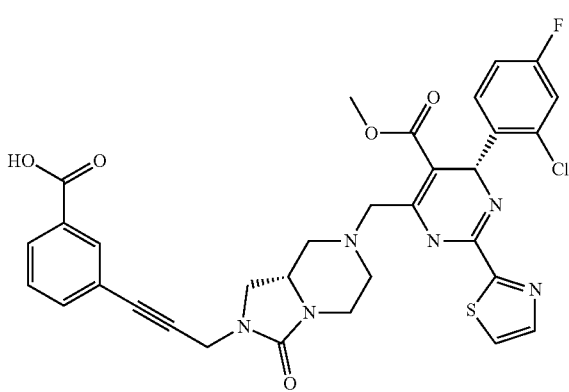 [SMILES: COC(=O)C1=C(CN2CCN3C(=O)N(CC#Cc4cccc(C(=O)O)c4)C[C@@H]3C2)NC(c2nccs2)=N[C@H]1c1ccc(F)cc1Cl]

The title compound was obtained as a yellow solid (85 mg, 83.4%) according to step 5 of example 1 by using (S)-3-(3-(3-oxohexahydroimidazo[1,5-a]piperazin-2(3H)-yl) prop-1-yn-1-yl)benzoic acid trifluoroacetate (62 mg, 0.15 mmol), (R)-methyl 6-(bromomethyl)-4-(2-chloro-4-fluorophenyl)-2-(thiazol-2-yl)-1,4-dihydropyrimidine-5-carboxylate (68 mg, 0.15 mmol), potassium carbonate (52 mg, 0.38 mmol) and anhydrous ethanol (3 mL) as materials. MS (ESI. pos) m/z: 664.05 [M+H]$^+$; $^1$H NMR (400 MHz, CDCl$_3$) 9.67 (br.s., 1H), 8.16 (s, 1H), 8.05 (d, J=7.3 Hz, 1H), 7.86 (d, J=2.9 Hz, 1H), 7.63 (d, J=7.4 Hz, 1H), 7.47 (d, J=2.8 Hz, 1H), 7.42 (t, J=7.6 Hz, 1H), 7.31 (overlap, 1H), 7.15 (dd, J=8.4, 2.2 Hz, 1H), 6.93 (td, J=8.4, 2.0 Hz, 1H), 6.22 (s, 1H), 4.35 (d, J=17.7 Hz, 1H), 4.25 (d, J=17.7 Hz, 1H), 4.17-4.10 (m, 1H), 4.04-3.92 (m, 2H), 3.88 (d, J=17.3 Hz, 1H), 3.63 (overlap, 1H), 3.61 (s, 3H), 3.28-3.20 (m, 1H), 3.12 (dd, J=8.6, 4.2 Hz, 1H), 2.84 (br, 2H), 2.53-2.44 (m, 1H), 2.29 (t, J=10.8 Hz, 1H).

Example 3 5-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl) pyridine carboxylic acid Step 1: (R)-tert-butyl 2-(3-(6-(methoxycarbonyl)pyridin-3-yl)prop-2-yn-1-yl)-3-oxohexahydro imidazo[1,5-a]pyrazine-7(1H)-carboxylate

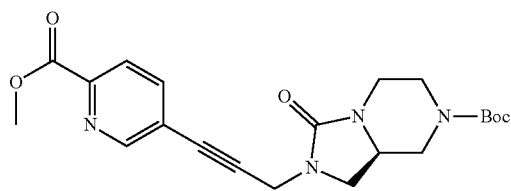 [SMILES: COC(=O)c1ccc(C#CCN2C[C@@H]3CN(C(=O)OC(C)(C)C)CCN3C2=O)cn1]

To a 25 mL two-neck flask were added (R)-tert-butyl 3-oxo-2-(prop-2-yn-1-yl)hexahydroimidazo[1,5-a]pyrazine-7(1H)-carboxylate (201 mg, 0.72 mmol), methyl 4-bromopyridine carboxylate (173 mg, 0.80 mmol, 100 mass %), tetrabutylammonium acetate (326 mg, 1.081 mmol), tris(dibenzylideneacetone)dipalladium (39 mg, 0.04 mmol) and DMF (5 mL). The reaction mixture was stirred at 50° C. for 7 hours under nitrogen. After the reaction was complete, the mixture was partitioned between ethyl acetate (20 mL) and water (10 mL). The organic phase was washed with saturated brine (150 mL), dried over anhydrous sodium sulfate, filtered, and the filtrate was concentrated in vacuo. The residue was purified by silica gel chromatograph (DCM/CH$_3$OH (V/V)=20/1) to give the title compound as a white solid (105 mg, 35.21%). MS (ESI, pos. ion) m/z: 415.2[M+H]$^+$.

Step 2: (R)-5-(3-(7-(tert-butoxycarbonyl)-3-oxohexahydroimidazo[1,5-a]pyrazin-2(3H)prop-1-yn-1-yl)pyridine carboxylic acid

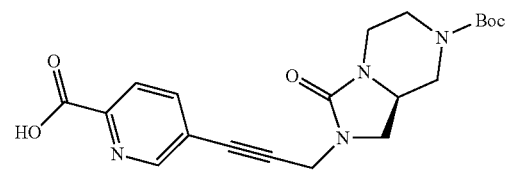 [SMILES: CC(C)(C)OC(=O)N1CCN2C(=O)N(CC#Cc3ccc(C(=O)O)nc3)C[C@@H]2C1]

The title compound was obtained as a light yellow foam solid (104 mg, 87.51%) according to step 3 of example 1 by using (R)-tert-butyl 2-(3-(6-(methoxycarbonyl) pyridin-3-yl)prop-2-yn-1-yl)-3-oxo hexahydroimidazo[1,5-a]pyrazine-7(1H)-carboxylate (123 mg, 0.3 mmol), methanol (3 mL), water (1 mL) and lithium hydroxide monohydrate (16 mg, 0.38 mmol) as materials. MS (ESI, pos. ion) m/z: 401.6[M+H]$^+$.

Step 3: (S)-5-(3-(3-oxohexahydroimidazo[1,5-a]pyrazin-2(3H)-yl)prop-1-yn-1-yl)pyridine carboxylic acid trifluoroacetate

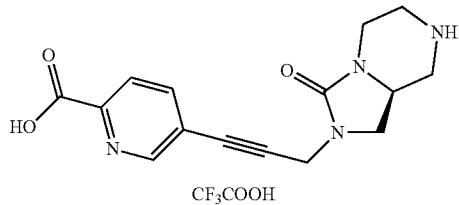

CF₃COOH

The title compound was obtained as a yellow oil (100 mg, 99.35%) according to step 4 of example 1 by using (R)-5-(3-(7-(tert-butoxycarbonyl)-3-oxohexahydroimidazo[1,5-a]pyrazin-2(3H)-yl)prop-1-yn-1-yl)pyridine carboxylic acid (102 mg, 0.25 mmol), DCM (3 mL) and TFA (2 mL) as materials. MS (ESI, pos. ion) m/z: 301.1[M+H]⁺.

Step 4: 5-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)pyridine carboxylic acid

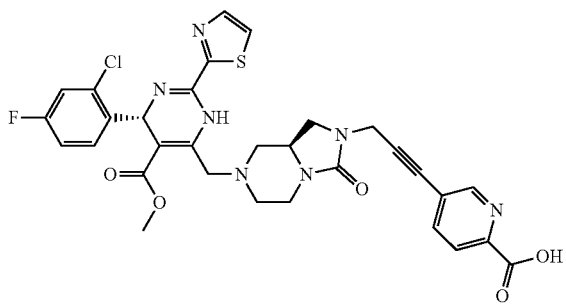 [SMILES: COC(=O)C1=C(CN2CCN3C(=O)N(CC#Cc4ccc(C(=O)O)nc4)C[C@@H]3C2)NC(c2nccs2)=N[C@H]1c1ccc(F)cc1Cl]

The title compound was obtained as a yellow solid (86 mg, 57.02%) according to step 5 of example 1 by using (S)-5-(3-(3-oxohexahydroimidazo[1,5-a]piperazin-2(3H)-yl) prop-1-yn-1-yl)pyridine carboxylic acid trifluoroacetate (76 mg, 0.25 mmol), potassium carbonate (77 mg, 0.56 mmol), anhydrous ethanol (3 mL) and (R)-methyl 6-(bromomethyl)-4-(2-chloro-4-fluorophenyl)-2-(thiazol-2-yl)-1,4-dihydropyrimidine-5-carboxylate (101 mg, 0.23 mmol) and as materials. MS (ESI, pos. ion) m/z: 664.7[M+H]⁺; ¹H NMR (600 MHz, CDCl₃) 8.64 (br.s., 1H), 8.14 (br.s., 1H), 7.90 (d, J=5.5 Hz, 1H), 7.81 (br.s., 1H), 7.46 (br.s., 1H), 7.27 (overlap, 1H), 7.12 (d, J=7.1 Hz, 1H), 6.91 (t, J=7.1 Hz, 1H), 6.15 (s, 1H), 4.43-4.30 (m, 1H), 4.29-4.19 (m, 1H), 4.18-4.07 (m, 1H), 4.01-3.83 (m, 3H), 3.57 (overlap, 4H), 3.31-3.23 (m, 1H), 3.14-3.06 (m, 1H), 2.98-2.83 (m, 2H), 2.55-2.45 (m, 1H), 2.35-2.25 (m, 1H).

Example 4 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)-3-fluorobenzoic acid

Step 1: (R)-tert-butyl 2-(3-(2-fluoro-4-(methoxycarbonyl)phenyl)prop-2-yn-1-yl)-3-oxohexahydroimidazo[1,5-a]pyrazine-7(1H)-carboxylate

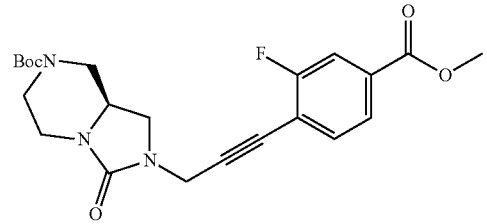 [SMILES: COC(=O)c1ccc(C#CCN2C[C@@H]3CN(C(=O)OC(C)(C)C)CCN3C2=O)c(F)c1]

To a 10 mL single neck flask were added (R)-tert-butyl 3-oxo-2-(prop-2-yn-1-yl)hexahydroimidazo[1,5-a]pyrazine-7(1H)-carboxylate (100 mg, 0.36 mmol), methyl 4-bromo-3-fluorobenzoate (100 mg, 0.43 mmol), tris(dibenzylideneacetone)dipalladium (15 mg, 0.02 mmol) and cuprous iodide (3.4 mg, 0.02 mmol), the air in the reactor was replaced with nitrogen 3 times, and then TEA (1 mL) was added. The reaction mixture was heated to 85° C. and stirred for 2 hours. After the reaction was complete, to the reaction mixture were added EtOAc (20 mL) and hydrochloric acid (1 M, 20 mL) in turn, the mixture was stood and layered. The organic layer was concentrated in vacuo. The residue was purified by silica gel chromatograph (PE/EtOAc (V/V)=1/1) to give the tile compound as a white solid (123 mg, 79.62%). ¹H NMR (400 MHz, CDCl₃) δ 7.80-7.69 (m, 2H), 7.51-7.42 (m, 1H), 4.31 (s, 2H), 4.28-4.14 (m, 1H), 4.11-4.02 (m, 1H), 3.92 (s, 3H), 3.88-3.83 (m, 1H), 3.69-3.52 (m, 2H), 3.24-3.07 (m, 1H), 2.98-2.89 (m, 1H), 2.85-2.75 (m, 1H), 2.73-2.63 (m, 1H), 1.47 (s, 9H).

Step 2: (R)-4-(3-(7-(tert-butoxycarbonyl)-3-oxohexahydroimidazo[1,5-a]pyrazin-2(3H)-yl) prop-1-yn-1-yl)-3-fluorobenzoic acid

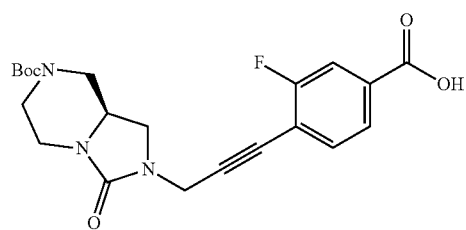 [SMILES: CC(C)(C)OC(=O)N1CCN2C(=O)N(CC#Cc3ccc(C(=O)O)cc3F)C[C@@H]2C1]

The title compound was obtained as an off-white solid (300 mg, 87.86%) according to step 3 of example 1 by using (R)-tert-butyl 2-(3-(2-fluoro-4-(methoxycarbonyl)phenyl)prop-2-yn-1-yl)-3-oxohexahydroimidazo[1,5-a]pyrazine-7(1H)-carboxylate (353 mg, 0.8181 mmol), lithium hydroxide monohydrate (123 mg, 2.9286 mmol), methanol (3 mL) and water (1 mL) as materials. MS (ESI, pos. ion) m/z: 362.5 [M+H−55]⁺.

Step 3: (S)-3-fluoro-4-(3-(3-oxohexahydroimidazo[1,5-a]pyrazin-2(3H)-yl)prop-1-yn-1-yl) benzoic acid hydrochloride

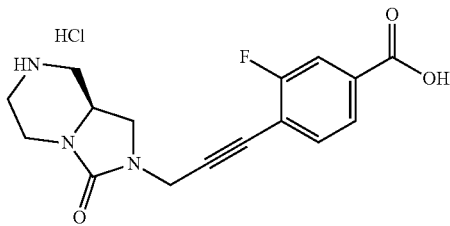 [SMILES: O=C(O)c1ccc(C#CCN2C[C@@H]3CNCCN3C2=O)c(F)c1 ; Cl]

To a 50 mL single neck flask were added (R)-4-(3-(7-(tert-butoxycarbonyl)-3-oxohexahydroimidazo[1,5-a]pyrazin-2(3H)-yl)prop-1-yn-1-yl)-3-fluorobenzoic acid (300 mg, 0.7187 mmol) and a solution of hydrogen chloride in EtOAc (4 mol/L, 10 mL). The reaction mixture was stirred at rt for 4 hours. After the reaction was complete, the reaction mixture was concentrated in vacuo to get the title compound as a white solid (250 mg, 98.31%). MS (ESI, pos. ion) m/z: 318.4 [M+H]$^+$.

Step 4: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)-3-fluorobenzoic acid

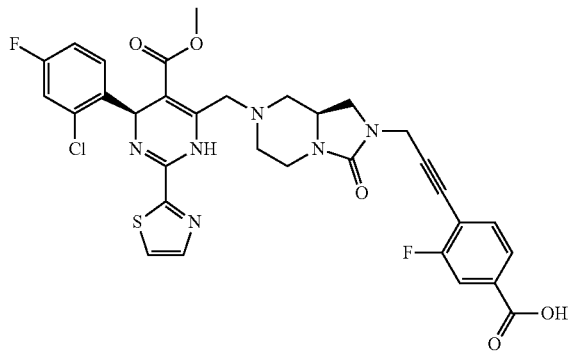 [SMILES: COC(=O)C1=C(CN2CCN3C(=O)N(CC#Cc4ccc(C(=O)O)cc4F)C[C@@H]3C2)NC(c2nccs2)=N[C@H]1c1ccc(F)cc1Cl]

To a dry flask were added (R)-methyl 6-(bromomethyl)-4-(2-chloro-4-fluorophenyl)-2-(thiazol-2-yl)-1,4-dihydropyrimidine-5-carboxylate (345 mg, 0.78 mmol), (S)-3-fluoro-4-(3-(3-oxohexahydroimidazo[1,5-a]pyrazin-2(3H)-yl)prop-1-yn-1-yl)benzoic acid hydrochloride (250 mg, 0.71 mmol), potassium carbonate (487 mg, 3.53 mmol) and ethanol (10 mL). The reaction mixture was stirred at rt for 24 hours and concentrated in vacuo, to the residue were added water (30 mL) and ethyl acetate (20 mL). The resulting mixture was statically separated, the organic layer was abandoned. To the water phase was added EtOAc (30 mL), and adjusted with concentrated hydrochloric acid to pH 5-6 under stirring. The organic layer was dried over anhydrous sodium sulfate. The mixture was filtered and the filtrate was concentrated in vacuo to give the title compound as a yellow solid (332 mg, 68.98%). MS (ESI, pos. ion) m/z: 681.1 [M+H]$^+$. $^1$H NMR (400 MHz, CDCl$_3$) δ 9.66 (s, 1H), 7.86 (d, J=3.1 Hz, 1H), 7.79 (dd, J=21.0, 8.4 Hz, 2H), 7.48 (d, J=3.1 Hz, 2H), 7.33-7.29 (m, 1H), 7.15 (dd, J=8.6, 2.5 Hz, 1H), 6.93 (td, J=8.3, 2.6 Hz, 1H), 6.22 (s, 1H), 4.35 (q, J=17.9 Hz, 3H), 4.13 (d, J=17.1 Hz, 1H), 4.05-3.86 (m, 3H), 3.65 (d, J=8.7 Hz, 1H), 3.61 (s, 3H), 3.27-3.21 (m, 1H), 3.14 (dd, J=8.9, 4.6 Hz, 1H), 2.89-2.83 (m, 2H), 2.53-2.45 (m, 1H), 2.30 (t, J=10.9 Hz, 1H).

Example 5 4-(3-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-3-methylbut-1-yn-1-yl) benzoic acid

Step 1: (R)-di-tert-butyl 2-(((2-methylbut-3-yn-2-yl)amino)methyl)piperazine-1,4-dicarboxylic

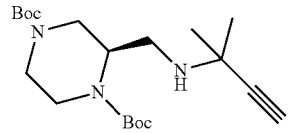 [SMILES: C#CC(C)(C)NC[C@@H]1CNCCN1C(=O)OC(C)(C)C]

To a dry flask were added 2-methylbut-3-yn-2-amine (2 mL, 19 mmol), (2S)-di-tert-butyl 2-formylpiperazine-1,4-dicarboxylate (5 g 15.90 mmol), acetic acid (0.2 mL, 3 mmol) and methanol (50 mL) in turn. The reaction mixture was stirred at rt for 3 hours and cooled to 0° C., to the mixture was added sodium cyanoborohydride (2 g 31.83 mmol). After the addition, the resulting mixture was heated to rt and stirred overnight. After the reaction was complete, the mixture was concentrated and quenched with a saturated aqueous sodium bicarbonate solution (20 mL), and extracted with methyl tert-butyl ether (100 mL). The organic layer was extracted with hydrochloric acid (1 M, 100 mL). The water phase was adjusted with a saturated aqueous sodium bicarbonate solution to pH 8-9, and then the resulting mixture was extracted with methyl tert-butyl ether (100 mL). The separated organic layer was dried over anhydrous sodium sulfate and filtered. The filtrate was concentrated in vacuo to get the title compound as colorless oil (2.5 g 41%).

Step 2: (R)-tert-butyl 2-(2-methylbut-3-yn-2-yl)-3-oxohexahydroimidazo[1,5-a]pyrazine-7(1H)-carboxylate

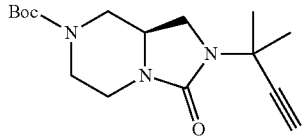 [SMILES: C#CC(C)(C)N1C[C@@H]2CN(C(=O)OC(C)(C)C)CCN2C1=O]

To a dry flask were added (R)-di-tert-butyl 2-(((2-methylbut-3-yn-2-yl)amino)methyl)piperazine-1,4-dicarboxylate (4.2 g 11 mmol), TFA (10 mL, 134.63 mmol) and DCM (10 mL) in turn. The reaction mixture was stirred at rt for 10 hours and concentrated in vacuo to remove trifluoroacetic acid to get a white solid (5.8 g 100%). To the above solid was added DCM (15 mL), the mixture was cooled to 0° C., and then TEA (7.7 mL, 56 mmol) and (Boc)$_2$O (2.7 g 12 mmol) were added. The reaction mixture was stirred at 0° C. for 12 hours and a solution of triphosgene (1.6 g 5.4 mmol) in DCM (30 mL) was added dropwise at 0° C. After the reaction was complete, the reaction was quenched with hydrochloric acid (1 M, 10 mL). The resulting mixture was extracted with DCM (30 mL). The separated organic phase was dried over anhydrous sodium sulfate, filtered and the filtrate was concentrated in vacuo. The residue was purified by silica gel chromatograph (PE/EtOAc (V/V)=3/1) to give the title compound as an off-white solid (1 g 30%). $^1$H NMR (400 MHz, CDCl$_3$) δ 4.14 (dd, J=14.2, 7.1 Hz, 1H), 4.02 (s, 1H), 3.80 (d, J=9.6 Hz, 1H), 3.58 (t, J=8.3 Hz, 1H), 3.54-3.44 (m, 1H), 3.11 (dd, J=8.7, 5.3 Hz, 1H), 2.82 (d, J=9.9 Hz, 2H), 2.66 (s, 1H), 2.37 (s, 1H), 1.71 (d, J=6.4 Hz, 6H), 1.49 (s, 9H).

Step 3: (R)-tert-butyl 2-(4-(4-(methoxycarbonyl)phenyl)-2-methylbut-3-yn-2-yl)-3-oxohexahydroimidazo[1,5-a]pyrazine-7(1H)-carboxylate

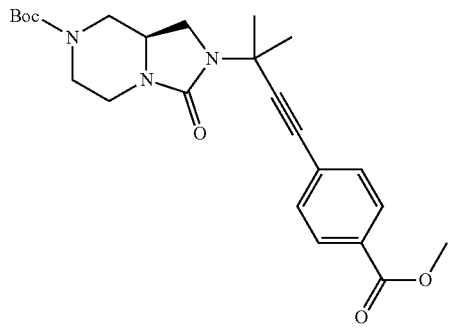 [SMILES: COC(=O)c1ccc(C#CC(C)(C)N2C[C@@H]3CN(C(=O)OC(C)(C)C)CCN3C2=O)cc1]

To a dry flask were added (R)-tert-butyl 2-(2-methylbut-3-yn-2-yl)-3-oxohexahydroimidazo[1,5-a]pyrazine-7(1H)-carboxylate (500 mg, 1.63 mmol), methyl 4-iodidebenzoate (511 mg, 1.95 mmol), cuprous iodide (81 mg, 0.27 mmol) and dichlorobis(triphenylphosphine)palladium (97 mg, 0.14 mmol), triethylamine (0.45 mL, 3.3 mmol) and THF (5 mL) in turn. The reaction mixture was heated to 65° C. and stirred for 12 hours under nitrogen. After the reaction was complete, the reaction mixture was concentrated in vacuo. The residue was purified by silica gel column chromatography (PE/EtOAc (v/v)=2/1) to give the title compound as a white solid (480 mg, 66.84%). $^1$H NMR (400 MHz, CDCl$_3$) δ 7.99 (d, J=8.4 Hz, 2H), 7.49 (d, J=8.4 Hz, 2H), 4.16-4.03 (m, 2H), 3.94 (s, 3H), 3.80 (t, J=7.3 Hz, 1H), 3.66 (t, J=8.4 Hz, 1H), 3.52 (td, J=11.6, 5.3 Hz, 1H), 3.18 (dd, J=8.8, 5.4 Hz, 1H), 2.85-2.79 (m, 2H), 1.80 (s, 6H), 1.49 (s, 9H).

Step 4: (R)-4-(3-(7-(tert-butoxycarbonyl)-3-oxohexahydroimidazo[1,5-a]pyrazin-2(3H)-yl)-3-methylbut-1-yn-1-yl)benzoic acid

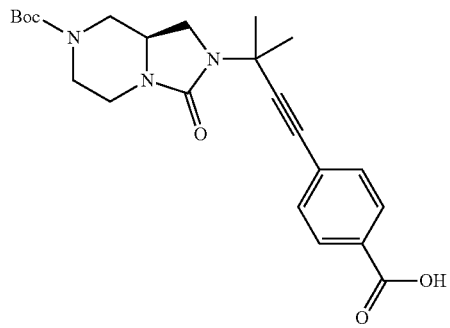 [SMILES: CC(C)(C)OC(=O)N1CCN2C(=O)N(C(C)(C)C#Cc3ccc(C(=O)O)cc3)C[C@@H]2C1]

To a dry flask were added (R)-tert-butyl 2-(4-(4-(methoxycarbonyl)phenyl)-2-methylbut-3-yn-2-yl)-3-oxohexahydroimidazo[1,5-a]pyrazine-7(1H)-carboxylate (480 mg, 1.09 mmol), lithium hydroxide monohydrate (228 mg, 5.43 mmol), methanol (30 mL) and water (10 mL) in turn. The mixture was refluxed for 2 hours. After the reaction was complete, the mixture was concentrated in vacuo. To the residue was added EtOAc (100 mL), and adjusted with concentrated hydrochloric acid (1 M) to pH 5-6. The organic layer was dried over anhydrous sodium sulfate. The mixture was filtered and the filtrate was concentrated in vacuo to give the title compound as an off-white solid (460 mg, 98.97%). MS (ESI, pos. ion) m/z: 428.2 [M+H]$^+$.

Step 5: (S)-4-(3-methyl-3-(3-oxohexahydroimidazo[1,5-a]pyrazin-2(3H)-yl)but-1-yn-1-yl) benzoic acid hydrochloride

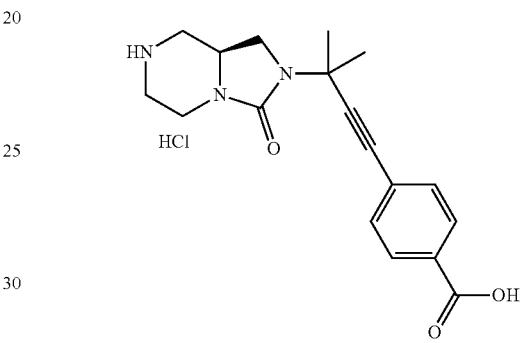

To a dry flask were added (R)-4-(3-(7-(tert-butoxycarbonyl)-3-oxohexahydroimidazo [1,5-a]pyrazin-2(3H)-yl)-3-methylbut-1-yn-1-yl)benzoic acid (460 mg, 1.08 mmol) and a solution of hydrogen chloride in EtOAc (4 mol/L, 20 mL). The reaction mixture was stirred at rt for 6 hours. After the reaction was complete, the reaction mixture was filtered to get the title compound as an off-white solid (280 mg, 71.53%). MS (ESI, pos. ion) m/z: 328.3 [M+H]$^+$.

Step 6: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-methylbut-1-yn-1-yl) benzoic acid

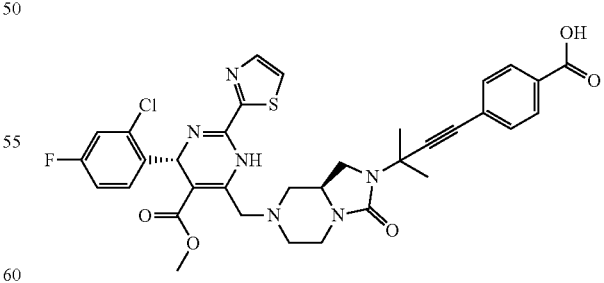

To a dry flask were added (S)-4-(3-methyl-3-(3-oxohexahydroimidazo[1,5-a]pyrazin-2(3H)-yl)but-1-yn-1-yl)benzoic acid hydrochloride (280 mg, 0.77 mmol), potassium carbonate (531 mg, 3.85 mmol), ethanol (8.4 mL) and (R)-methyl 6-(bromomethyl)-4-(2-chloro-4-fluorophenyl)-(2-thiazol-2-yl)-1,4-dihydropyrimidine-5-carboxylate (519 mg, 0.92 mmol) in turn, the reaction mixture was stirred at rt for 20 hours and concentrated in vacuo. The residue was diluted with ethyl acetate (100 mL) and adjusted with hydrochloric acid (1 M) to pH 6 to 7 under stirring. The mixture was stood and layered. The organic phase was dried over anhydrous sodium sulfate, filtered and the filtrate was concentrated in vacuo. The residue was purified by silica gel chromatograph (DCM/CH$_3$OH (V/V)=10/1) to get the title compound as a yellow solid (300 mg, 18.80%). MS (ESI, pos. ion) m/z: 691.1 [M+H]$^+$; $^1$H NMR (400 MHz, CDCl$_3$) δ 9.66 (s, 1H), 7.97 (d, J=7.9 Hz, 2H), 7.86 (d, J=3.0 Hz, 1H), 7.53-7.42 (m, 3H), 7.31 (overlap, 1H), 7.15 (dd, J=8.5, 2.3 Hz, 1H), 6.94 (dd, J=11.2, 5.2 Hz, 1H), 6.22 (s, 1H), 4.14 (d, J=17.1 Hz, 1H), 3.98 (d, J=12.2 Hz, 1H), 3.86 (d, J=17.2 Hz, 1H), 3.83-3.76 (m, 1H), 3.65 (d, J=8.5 Hz, 1H), 3.62 (s, 3H), 3.20-3.14 (m, 2H), 2.91-2.76 (m, 2H), 2.54-2.44 (m, 1H), 2.29 (t, J=10.6 Hz, 1H), 1.80 (d, J=1.7 Hz, 6H).

Example 6 4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy) benzoic acid Step 1: (R)-tert-butyl 2-(4-(4-(methoxycarbonyl) phenoxy)phenyl)-3-oxohexahydroimidazo[1,5-a] pyrazine-7(1H)-carboxylate

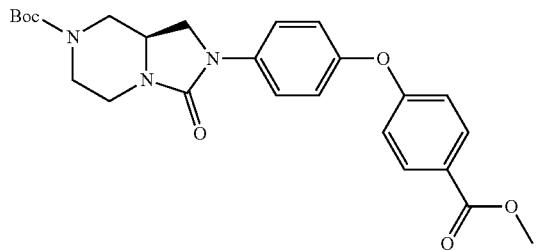 [SMILES: COC(=O)c1ccc(Oc2ccc(N3C[C@@H]4CN(C(=O)OC(C)(C)C)CCN4C3=O)cc2)cc1]

To a dry flask were added methyl 4-(4-bromophenoxy) benzoate (400 mg, 1.30 mmol), (R)-tert-butyl 3-oxohexahydroimidazo[1,5-a]pyrazine-7(1H)-carboxylate (345 mg, 1.43 mmol), palladiumacetate (60 mg, 0.26 mmol), tBuX-Phos (226 mg, 0.52 mmol), cesium carbonate (849 mg, 2.60 mmol) and 1,4-dioxane (10 mL). The reaction mixture was degassed 3 times with nitrogen, and stirred at 90° C. for 12 hours. After the reaction was complete, the reaction mixture was filtered and the filtrate was concentrated in vacuo. The residue was purified by silica gel column chromatography (PE/EtOAc (v/v)=2/1) to give the title compound as a light brown (455 mg, 74%). MS (ESI, pos. ion) m/z: 468.2 [M+H]$^+$.

Step 2: (R)-4-(4-(7-(tert-butoxycarbonyl)-3-oxohexahydroimidazo[1,5-a]pyrazin-2(3H)-yl) phenoxy)benzoic acid

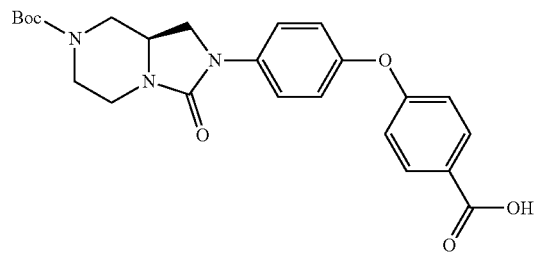 [SMILES: CC(C)(C)OC(=O)N1CCN2C(=O)N(c3ccc(Oc4ccc(C(=O)O)cc4)cc3)C[C@@H]2C1]

(R)-tert-Butyl 2-(4-(4-(methoxycarbonyl)phenoxy)phenyl)-3-oxohexahydroimidazo [1,5-a]pyrazine-7(1H)-carboxylate (500 mg, 1.07 mmol) was dissolved in 1,4-dioxane (20 mL), to the solution was added a solution of lithium hydroxide monohydrate (225 mg, 5.36 mmol) in water (5 mL), the mixture was stirred at rt for 6 hours. After the reaction was complete, the mixture was adjusted with hydrochloric acid (1 M) to pH 2 to 3, and extracted with ethyl acetate (3×20 mL). The combined organic layers were dried over anhydrous sodium sulfate and filtered. The filtrate was concentrated in vacuo to get the title compound as a white solid (453 mg, 93%). MS (ESI, pos. ion) m/z: 476 [M+Na]$^+$.

Step 3: (S)-4-(4-(3-oxohexahydroimidazo[1,5-a] pyrazin-2(3H)-yl)phenoxy)benzoic acid trifluoroacetate

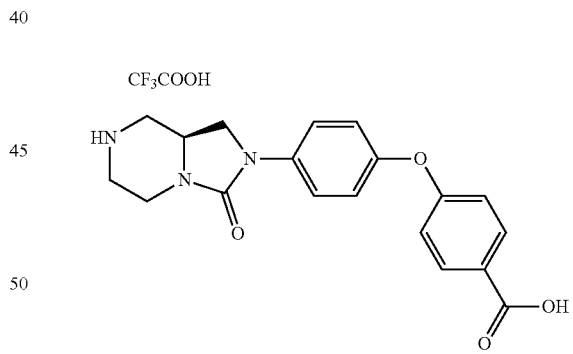

(R)-4-(4-(7-(tert-Butoxycarbonyl)-3-oxohexahydroimidazo[1,5-a]pyrazin-2(3H)-yl) phenoxy)benzoic acid (500 mg, 1.10 mmol) was dissolved in DCM (10 mL), to the solution was added trifluoroacetic acid (10 ml), the mixture was stirred at rt for 6 hours. After the reaction was complete, the reaction mixture was concentrated in vacuo to give the title compound as a light brown oil. The oil was used in the next step without further purification. MS (ESI, pos. ion) m/z: 354[M+H]$^+$.

Step 4: 4-(4-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)phenoxy)benzoic acid

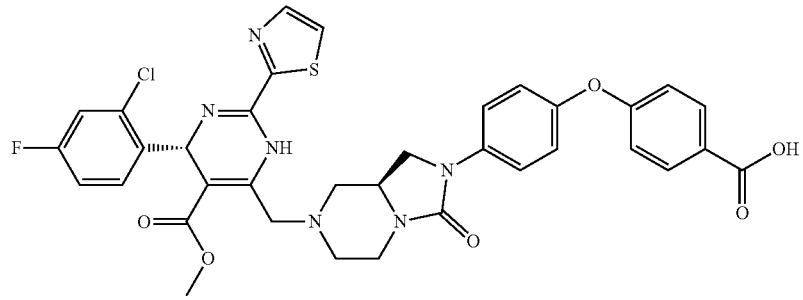 [SMILES: COC(=O)C1=C(CN2CCN3C(=O)N(c4ccc(Oc5ccc(C(=O)O)cc5)cc4)C[C@@H]3C2)NC(c2nccs2)=N[C@H]1c1ccc(F)cc1Cl]

To a solution of (S)-4-(4-(3-oxohexahydroimidazo[1,5-a]pyrazin-2(3H)-yl)phenoxy) benzoic acid trifluoroacetate (500 mg, 1.07 mmol) in ethanol (50 mL) was added potassium carbonate (443 mg, 3.20 mmol), the mixture was stirred for 5 min and (R)-methyl 6-(bromomethyl)-4-(2-chloro-4-fluorophenyl)-2-(thiazol-2-yl)-1,4-dihydropyrimidine-5-carboxylate (475 mg, 1.07 mmol) was added. The reaction mixture was stirred at room temperature for 12 hours and concentrated in vacuo. The residue was diluted with water (50 mL) and adjusted with hydrochloric acid (1 M) to pH 5 to 6. The mixture was extracted with EtOAc (4×50 mL). The combined organic layers were washed with saturated aqueous sodium chloride (100 mL), dried over anhydrous sodium sulfate, and filtered. The filtrate was concentrated in vacuo, and the residue was purified by silica gel column chromatography (DCM/MeOH=20/1) to give the title compound as a light yellow solid (460 mg, 60%). MS (ESI, pos. ion) m/z: 717 [M+H]$^+$; $^1$H NMR (400 MHz, CDCl$_3$) δ 9.65 (s, 1H), 8.05 (d, J=6.7 Hz, 2H), 7.87 (s, 1H), 7.58 (d, J=7.1 Hz, 2H), 7.48 (s, 1H), 7.34-7.26 (m, 1H), 7.20-7.13 (m, 1H), 7.13-7.04 (m, 2H), 7.03-6.85 (m, 3H), 6.23 (s, 1H), 4.20-4.00 (m, 3H), 3.85-3.40 (m, 2H), 3.62 (s, 3H), 3.50-3.40 (m, 1H), 3.35-3.20 (m, 1H), 3.00-2.80 (m, 2H), 2.60-2.45 (m, 1H), 2.35-2.25 (m, 1H).

Example 7 4-((5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-2-yl)oxy) benzoic acid Step 1: methyl 4-((5-bromopyridin-2-yl)oxy)benzoate

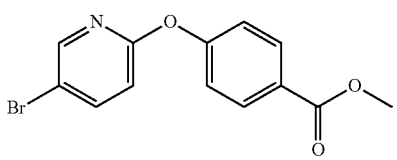 [SMILES: COC(=O)c1ccc(Oc2ccc(Br)cn2)cc1]

To a dry flask were added methyl 4-hydroxybenzoate (1.93 g 12.6 mmol), K$_2$CO$_3$ (2.36 g, 16.9 mmol), 2,5-dibromopyridine (2.00 g 8.44 mmol) and DMF (20 mL). The reaction mixture was heated at 120° C. for 24 hours. The mixture was cooled to rt and filtered. The filter cake was washed with EtOAc (10 mL). The filtrate was diluted with EtOAc (40 mL) and water (20 mL), and stood and layered. The water phase was extracted with EtOAc (20 mL). The organic layers were combined. The combined organic layers were washed with saturated aqueous NaHCO$_3$ (20 mL×3), hydrochloric acid (0.5 M, 20 mL) and saturated aqueous NaCl (20 mL) in turn, and then dried over anhydrous Na$_2$SO$_4$ and concentrated in vacuo. The residue was purified by silica gel column chromatography (PE/EtOAc (V/V)=20/1) to give the title compound as a white solid (1.23 g, 47%). MS (ESI, pos. ion) m/z: 308.0[M+H].

Step 2: (R)-tert-butyl 2-(6-(4-(methoxycarbonyl)phenoxy)pyridin-3-yl)-3-oxohexahydroimidazo [1,5-a]pyrazin-7(1H)-carboxylate

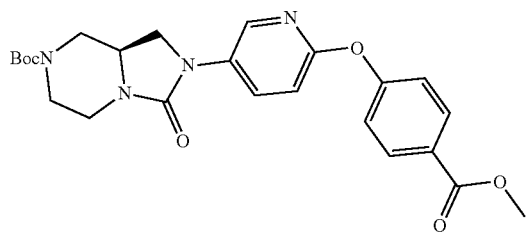 [SMILES: COC(=O)c1ccc(Oc2ccc(N3C[C@@H]4CN(C(=O)OC(C)(C)C)CCN4C3=O)cn2)cc1]

To a two-neck flask were added methyl 4-(5-bromopyridin-2-yl)oxy)benzoate (128 mg, 0.42 mmol), (R)-tert-butyl 3-oxohexahydroimidazo[1,5-a]pyrazine-7(1H)-carboxylate (100 mg, 0.41 mmol), tris(dibenzylideneacetone)dipalladium (23 mg, 0.03 mmol), Xantphos (24 mg, 0.04 mmol), cesium carbonate (270 mg, 0.83 mmol) and dioxane (10 mL). The mixture was stirred at 100° C. for 23 hours under nitrogen, and then cooled to rt and filtered. The filter cake was washed with EtOAc (5 mL). The filtrate was diluted with EtOAc (15 mL) and water (10 mL), and stood and layered. The water was extracted with EtOAc (10 mL). The combined organic layers were dried over anhydrous Na$_2$SO$_4$ and concentrated in vacuo. The residue was purified by silica gel column chromatography (PE/EtOAc (v/v)=2/1) to give the title compound as a beige solid (184 mg, 94.76%). MS (ESI, pos. ion) m/z: 469.1 [M+H]$^+$.

Step 3: (R)-4-((5-(7-(tert-butoxycarbonyl)-3-oxo-hexahydroimidazo[1,5-a]pyrazin-2(3H)-yl) pyridin-2-yl)oxy)benzoic acid

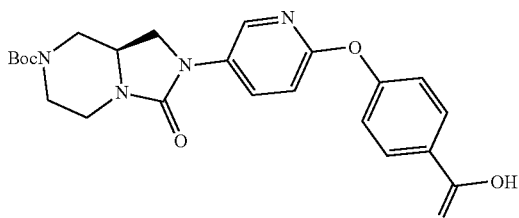

To a 50 mL single neck flask were added (R)-tert-butyl 2-(6-(4-(methoxycarbonyl) phenoxy)pyridin-3-yl)-3-oxo-hexahydroimidazo[1,5-a]pyrazin-7(1H)-carboxylate (184 mg, 0.39 mmol), THF (2 mL) and methanol (2 mL), and then a solution of lithium hydroxide monohydrate (85 mg, 2.03 mmol) in water (2 mL) was added. The reaction mixture was stirred at rt for 5 hours and adjusted with hydrochloric acid (6 M) to pH 7, and then concentrated in vacuo to remove THF and MeOH. The residue was diluted with water (5 mL) and EtOAc (2 mL), and then adjusted with saturated aqueous K₂CO₃ to pH 9-10, the organic phase was abandoned, the water phase was adjusted with hydrochloric acid (6 M) to pH 6 and a large amount of solid precipitated out. The mixture was filtered by suction. The filter cake was washed with water (mL) and dried at rt under vacuum overnight to get the title compound as a white solid (142 mg, 79.55%). MS (ESI, pos. ion) m/z: 455.3 [M+H]⁺.

Step 4: (S)-4-((5-(3-oxohexahydroimidazo[1,5-a]piperazin-2(3H)-yl)pyrazin-2-yl)oxy)benzoic acid trifluoroacetate

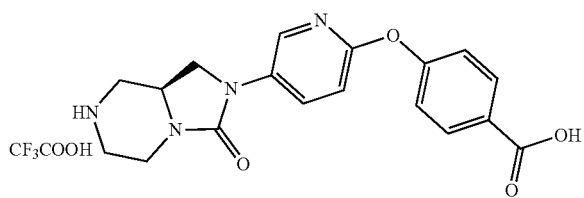 [SMILES: "CF3COOH" ; O=C(O)c1ccc(Oc2ccc(N3C[C@@H]4CNCCN4C3=O)cn2)cc1]

To a 50 mL single neck flask were added (R)-4-((5-(7-(tert-butoxycarbonyl)-3-oxohexahydroimidazo[1,5-a]pyrazin-2(3H)-yl)pyridin-2-yl)oxy)benzoic acid (142 mg, 0.31 mmol) and DCM (2 mL), and then TFA (2 mL, 26.66 mmol) was added. The reaction mixture was stirred at rt for 12 hours. The mixture was concentrated in vacuo to get a yellow oil. To the yellow oil was added MTBE (10 mL), and a white solid precipitated out immediately, the mixture was filtered by suction, the filter cake was washed with MTBE (5 mL) and dried at rt under vacuum for 1 hour to get the title compound as a brown yellow solid (146 mg, 99.77%). MS (ESI, pos. ion) m/z: 355.1[M+H]⁺.

Step 5): 4-((5-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)pyridin-2-yl)oxy)benzoic acid

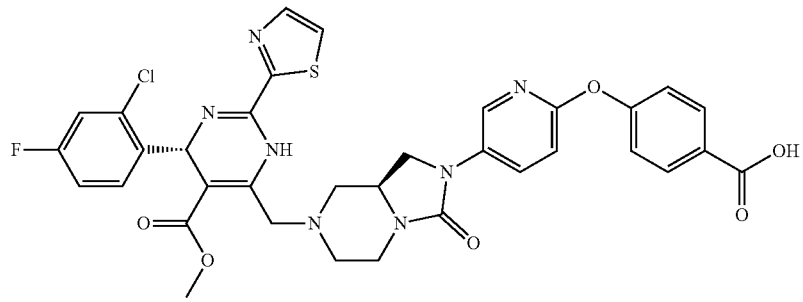 [SMILES: COC(=O)C1=C(CN2CCN3C(=O)N(c4ccc(Oc5ccc(C(=O)O)cc5)nc4)C[C@@H]3C2)NC(c2nccs2)=N[C@H]1c1ccc(F)cc1Cl]

To a 50 mL single neck flask were added (S)-4-((5-(3-oxohexahydroimidazo[1,5-a]piperazin-2(3H)-yl)pyrazin-2-yl)oxy)benzoic acid trifluoroacetate (146 mg, 0.31 mmol), (R)-methyl 6-(bromomethyl)-4-(2-chloro-4-fluorophenyl)-2-(thiazol-2-yl)-1,4-dihydro pyrimidine-5-carboxylate (200 mg, 0.43 mmol), potassium carbonate (87 mg, 0.62 mmol) and ethanol (10 mL). The reaction mixture was stirred at room temperature for 16 h. The mixture was filtered by suction. The filter cake was washed with EtOH (5 mL), the filtrate was concentrated. The residue was diluted with water (10 mL) and EtOAc (10 mL), and then adjusted with hydrochloric acid (6 M) to pH 2 to 3, the mixture was stood and layered, the organic layer was washed with saturated aqueous NaCl (10 mL) and concentrated in vacuo. The residue was purified by silica gel column chromatography (CH₂Cl₂/MeOH (V/V)=15/1) to give the title compound as a yellow solid (73 mg, 32.61%). MS (ESI, pos. ion) m/z: 719.0 [M+H]⁺; ¹H NMR (400 MHz, CD₃OD) δ 8.34 (d, J=2.7 Hz, 1H), 8.17-8.14 (m, 1H), 8.02 (d, J=8.7 Hz, 2H), 7.98-7.94 (m, 1H), 7.77-7.74 (m, 1H), 7.45-7.42 (m, 1H), 7.26-7.21 (m, 1H), 7.08-7.04 (m, 3H), 7.02-6.98 (m, 1H), 6.18 (s, 1H), 4.15 (d, J=16.9 Hz, 1H), 4.11-4.02 (m, 1H), 4.02-3.91 (m, 3H), 3.61 (s, 3H), 3.56-3.53 (m, 1H), 330-3.23 (m, 1H), 3.00 (d, J=11.3 Hz, 2H), 2.46 (t, J=11.5 Hz, 1H), 2.27 (t, J=10.8 Hz, 1H).

Example 8: 2-chloro-4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)benzoic acid Step 1: 4-(4-bromophenoxy)-2-chloro benzoic acid

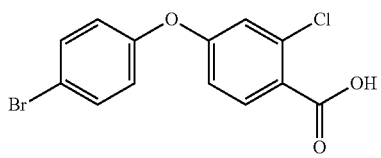 [SMILES: O=C(O)c1ccc(Oc2ccc(Br)cc2)cc1Cl]

To a dry flask were added methyl 2-chloro-4-fluorobenzoate (500 mg, 2.65 mmol), 4-bromophenol (504 mg, 2.9131 mmol), potassium carbonate (731 mg, 5.2971 mmol) and DMAc (5 mL), the reaction mixture was heated at 120° C. for 12 h under nitrogen and cooled to rt, and then diluted with water (20 mL) and ethyl acetate (20 mL). The mixture was stood and layered. The water phase was adjusted with hydrochloric acid (1 M) to pH 3 to 4, and then ethyl acetate (15 mL) was added, a white solid precipitated. The mixture was filtered by suction. The filter cake was washed with ethyl acetate (5 mL) to get the tilte compound as a white solid (230 mg, 27%). $^1$H NMR (400 MHz, DMSO-d$_6$) δ 7.87 (d, J=8.7 Hz, 1H), 7.68-7.58 (m, 2H), 7.19-7.09 (m, 3H), 7.01 (dd, J=8.7, 2.5 Hz, 1H).

Step 2: (R)-4-(4-(7-(tert-butoxycarbonyl)-3-oxohexahydroimidazo[1,5-a]pyrazin-2(3H)-yl)phenoxy)-2-chloro benzoic acid

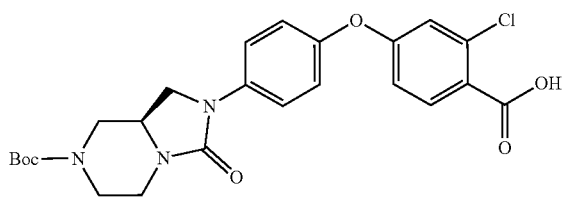 [SMILES: CC(C)(C)OC(=O)N1CCN2C(=O)N(c3ccc(Oc4ccc(C(=O)O)c(Cl)c4)cc3)C[C@@H]2C1]

A mixture of (R)-tert-butyl 3-oxohexahydroimidazo[1,5-a]pyrazine-7(1H)-carboxylate (100 mg, 0.41 mmol), 4-(4-bromophenoxy)-2-chloro benzoic acid (157 mg, 0.48 mmol), tBuXPhos (35 mg, 0.08 mmol), Pd(OAc)$_2$ (9.2 mg, 0.041 mmol), Cs$_2$CO3 (405 mg, 1.24 mmol) and 1,4-dioxane (5 mL) was degassed with nitrogen 3 times. After the reaction was carried out at 90° C. for 12 hours, the mixture was concentrated in vacuo and adjusted with hydrochloric acid (1 M) to pH 4 to 5. The resulting mixture was extracted with ethyl acetate (3×20 mL). The combined organic phases were dried over anhydrous sodium sulfate, filtered, and the filtrate was concentrated in vacuo. The residue was purified by silica gel chromatograph (DCM/CH$_3$OH (V/V)=10/1) to give the title compound as a white solid (150 mg, 74.2%). MS (ESI, pos. ion) m/z: 432.0 [M+H−55]$^+$; $^1$H NMR (400 MHz, CDCl$_3$) δ 8.01 (d, J=8.8 Hz, 1H), 7.62 (d, J=9.1 Hz, 2H), 7.09 (d, J=9.0 Hz, 2H), 7.01 (d, J=2.4 Hz, 1H), 6.89 (dd, J=8.8, 2.4 Hz, 1H), 4.31 (s, 1H), 4.12 (s, 1H), 3.97-3.93 (m, 2H), 3.84-3.77 (m, 1H), 3.49 (dd, J=9.2, 5.2 Hz, 1H), 3.00 (td, J=12.7, 3.1 Hz, 1H), 2.87 (s, 1H), 2.72 (s, 1H), 1.52 (s, 9H).

Step 3: (S)-2-chloro-4-(4-(3-oxohexahydroimidazo[1,5-a]pyrazin-2(3H)-yl)phenoxy)benzoic acid trifluoroacetate

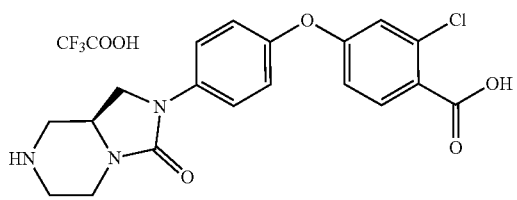 [SMILES: "CF3COOH" ; O=C(O)c1ccc(Oc2ccc(N3C[C@@H]4CNCCN4C3=O)cc2)cc1Cl]

A mixture of (R)-4-(4-(7-(tert-butoxycarbonyl)-3-oxohexahydroimidazo[1,5-a]pyrazin-2(3H)-yl)phenoxy)-2-chloro benzoic acid (150 mg, 0.31 mmol), DCM (5 mL) and TFA (5 mL) was stirred at rt for 3 hours and concentrated in vacuo to get the title compound as a colorless oil (143 mg, 92.26%). MS (ESI, pos. ion) m/z: 388.0 [M+H]$^+$.

Step 4: 2-chloro-4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)benzoic acid

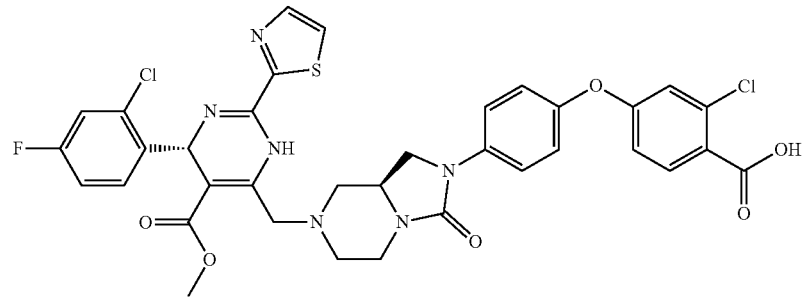 [SMILES: COC(=O)C1=C(CN2CCN3C(=O)N(c4ccc(Oc5ccc(C(=O)O)c(Cl)c5)cc4)C[C@@H]3C2)NC(c2nccs2)=N[C@H]1c1ccc(F)cc1Cl]

To a mixture of (S)-2-chloro-4-(4-(3-oxohexahydroimidazo[1,5-a]pyrazin-2(3H)-yl)phenoxy)benzoic acid trifluoroacetate (143 mg, 0.28 mmol), ethanol (5 mL) and potassium carbonate (195 mg, 1.41 mmol) was added (R)-methyl 6-(bromomethyl)-4-(2-chloro-4-fluorophenyl)-2-(thiazol-2- yl)-1,4-dihydropyrimidine-5-carboxy late (151 mg, 0.34 mmol). The reaction mixture was stirred at rt for 24 hours and concentrated in vacuo, the residue was adjusted with hydrochloric acid (1 M) to pH 5. The resulting mixture was extracted with ethyl acetate (3×20 mL). The combined organic phases were dried over anhydrous sodium sulfate, filtered, and the filtrate was concentrated in vacuo. The residue was purified by silica gel chromatograph (DCM/CH$_3$OH (V/V)=10/1) to give the title compound as a yellow solid (50 mg, 23.45%). MS (ESI, pos. ion) m/z: 751.0 [M+H]$^+$; $^1$H NMR (400 MHz, CDCl$_3$) δ 7.97 (d, J=8.8 Hz, 1H), 7.90 (d, J=3.0 Hz, 1H), 7.63-7.53 (m, 3H), 7.35 (dd, J=8.6, 5.9 Hz, 1H), 7.17 (dd, J=8.2, 2.4 Hz, 1H), 7.08 (d, J=8.9 Hz, 2H), 7.04-6.97 (m, 2H), 6.88 (dd, J=8.8, 2.3 Hz, 1H), 6.19 (s, 1H), 6.19 (s, 1H), 4.87 (d, J=14.6 Hz, 1H), 4.63-4.51 (m, 2H), 4.22 (dd, J=14.5, 2.7 Hz, 1H), 4.07 (t, J=9.0 Hz, 1H), 3.91 (d, J=12.0 Hz, 1H), 3.84 (d, J=11.8 Hz, 1H), 3.75-3.66 (m, 1H), 3.64 (s, 3H), 3.55 (dd, J=9.6, 2.7 Hz, 1H), 3.18-3.00 (m, 2H).

Example 9: 4-(4-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)phenoxy)-3, 5-difluorobenzoic acid Step 1: 4-(4-bromophenoxy)-3,5-difluoromethyl benzoate

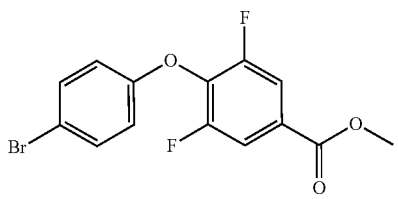 [SMILES: COC(=O)c1cc(F)c(Oc2ccc(Br)cc2)c(F)c1]

A mixture of methyl 3,4,5-trifluorobenzoate (500 mg, 2.63 mmol), 4-bromophenol (500 mg, 2.89 mmol), potassium carbonate (1 g 7.25 mmol) and DMF (5 mL) was degassed with nitrogen 3 times and stirred at 120° C. for 12 hours. The mixture was cooled to rt and diluted with tert-butyl methyl ether (20 mL) and water (20 mL). The reaction mixture was stood and layered, the organic layer was concentrated in vacuo to get the title compound as a white solid (650 mg, 59.79%). $^1$H NMR (400 MHz, DMSO-d$_6$) δ 7.87-7.80 (m, 2H), 7.60-7.53 (m, 2H), 7.08-7.00 (m, 2H), 3.90 (s, 3H).

Step 2: (R)-tert-butyl 2-(4-(2,6-difluoro-4-(methoxycarbonyl)phenoxy)phenyl)-3-oxohexahydro imidazo[1,5-a]pyrazin-7(1H)-carboxylate

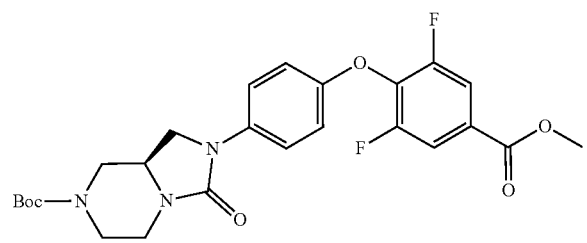 [SMILES: COC(=O)c1cc(F)c(Oc2ccc(N3C[C@@H]4CN(C(=O)OC(C)(C)C)CCN4C3=O)cc2)c(F)c1]

A mixture of (R)-tert-butyl 3-oxohexahydroimidazo[1,5-a]pyrazine-7(1H)-carboxylate (100 mg, 0.41 mmol), methyl 4-(4-bromophenoxy)-3,5-difluoro benzoate (223 mg, 0.45 mmol), tBuXPhos (35 mg, 0.08 mmol), Pd(OAc)$_2$ (9.2 mg, 0.04 mmol), Cs$_2$CO$_3$ (405 mg, 1.24 mmol) and 1,4-dioxane (5 mL) was degassed with nitrogen 3 times. After the reaction was carried out at 90° C. for 24 hours, the mixture was concentrated in vacuo and adjusted with hydrochloric acid (1 M) to pH 45. The resulting mixture was extracted with ethyl acetate (3×20 mL). The combined organic phases were dried over anhydrous sodium sulfate, filtered, and the filtrate was concentrated in vacuo. The residue was purified by silica gel chromatograph (PE/EtOAc (V/V)=10/1) to give the title compound as a white solid (164 mg, 78.59%). MS (ESI, pos. ion) m/z: 526.1 [M+Na]$^+$.

Step 3: (R)-4-(4-(7-(tert-butoxycarbonyl)-3-oxohexahydroimidazo[1,5-a]pyrazin-2(3H)-yl) phenoxy)-3,5-difluorobenzoic acid

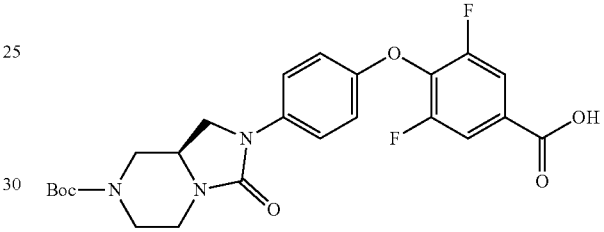

A mixture of (R)-tert-butyl 2-(4-(2,6-difluoro-4-(methoxycarbonyl)phenoxy)phenyl)-3-oxohexahydroimidazo[1,5-a]pyrazin-7(1H)-carboxylate (164 mg, 0.33 mmol), lithium hydroxide monohydrate (68 mg, 1.62 mmol), methanol (6 mL) and water (2 mL) was stirred at rt for 4 hours. The mixture was concentrated in vacuo and adjusted with hydrochloric acid (1 M) to pH 5. The resulting mixture was extracted with ethyl acetate (3×20 mL). The combined organic phases were dried over anhydrous sodium sulfate, filtered, and the filtrate was concentrated in vacuo to give the title compound as a white solid (150 mg, 94.08%). MS (ESI, pos. ion) m/z: 512.1 [M+Na]$^+$.

Step 4: (S)-3,5-difluoro-4-(4-(3-oxohexahydroimidazo[1,5-a]pyrazin-2(3H)-yl)phenoxy)benzoic acid trifluoroacetate

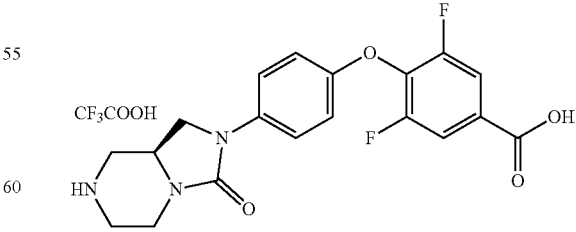

To a dry flask were added (R)-4-(4-(7-(tert-butoxycarbonyl)-3-oxohexahydroimidazo [1,5-a]pyrazin-2(3H)-yl)phenoxy)-3,5-difluorobenzoic acid (150 mg, 0.3 mmol), DCM (5 mL) and TFA (5 mL), the mixture was stirred at rt for 12 hours and concentrated in vacuo to get the title compound as a gray solid (151 mg, 100%). MS (ESI, pos. ion) m/z: 390.1 [M+H]+.

Step 5: 4-(4-(((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)phenoxy)-3, 5-difluorobenzoic acid

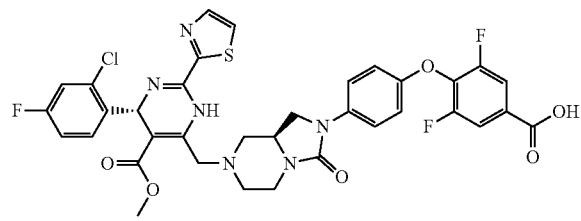 [SMILES: COC(=O)C1=C(CN2CCN3C(=O)N(c4ccc(Oc5c(F)cc(C(=O)O)cc5F)cc4)C[C@@H]3C2)NC(c2nccs2)=N[C@H]1c1ccc(F)cc1Cl]

A mixture of (S)-3,5-difluoro-4-(4-(3-oxohexahydroimidazo[1,5-a]pyrazin-2(3H)-yl)phenoxy)benzoic acid trifluoroacetate (151 mg, 0.3 mmol), (R)-methyl 6-(bromomethyl)-4-(2-chloro-4-fluorophenyl)-(2-thiazol-2-yl)-1,4-dihydropyrimidine-5-carboxy late (165 mg, 0.37 mmol), potassium carbonate (212 mg, 1.54 mmol) in ethanol (5 mL) was stirred at rt for 24 hours and concentrated in vacuo. The residue was adjusted with hydrochloric acid (1 M) to pH 5 to 6 and extracted with ethyl acetate (3×20 mL). The combined organic phases were dried over anhydrous sodium sulfate, filtered and the filtrate was concentrated in vacuo. The residue was purified by silica gel chromatograph (DCM/CH₃OH (V/V)=10/1) to get the title compound as a yellow solid (50 mg, 21.54%). MS (ESI, pos. ion) m/z: 753.2 [M+H]+; ¹H NMR (400 MHz, CDCl₃) δ 7.88 (d, J=2.9 Hz, 1H), 7.71 (d, J=7.8 Hz, 2H), 7.54 (d, J=3.0 Hz, 1H), 7.48 (d, J=9.0 Hz, 2H), 7.34 (dd, J=8.5, 6.1 Hz, 1H), 7.17 (dd, J=8.3, 2.4 Hz, 1H), 7.03-6.93 (m, 3H), 6.19 (s, 1H), 4.69 (d, J=15.2 Hz, 1H), 4.46-4.39 (m, 2H), 4.34 (d, J=15.1 Hz, 1H), 4.15 (d, J=14.8 Hz, 1H), 4.00 (t, J=8.9 Hz, 1H), 3.65-3.55 (m, 5H), 3.48 (dd, J=9.5, 3.1 Hz, 1H), 3.00-2.85 (m, 2H).

Example 10 4'-(((S)-7-(((R)-6-(2-chloro-4-fluorophenyl)-5-(methoxycarbonyl)-2-(thiazol-2-yl)-3,6-dihydroprimidin-4-yl)methyl)-3-oxohexahydroimidazo[1,5-a]pyrazin-2(3H)-yl)methyl)-[1,1'-diphenyl]-4-carboxylic acid Step 1: (R)-tert-butyl 2-(4-bromobenzyl)-3-oxohexahydroimidazo[1,5-a]pyrazine-7(1H)-carboxylate

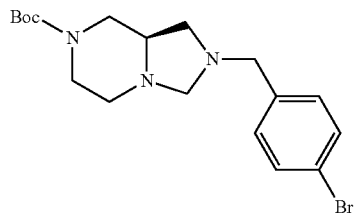 [SMILES: CC(C)(C)OC(=O)N1CCN2CN(Cc3ccc(Br)cc3)C[C@@H]2C1]

To a two-neck flask was added (R)-tert-butyl 3-oxohexahydroimidazo[1,5-a]pyrazine-7(1H)-carboxylate (100 mg, 0.41 mmol), and the flask was degassed with nitrogen 3 times, and then DMF (2 mL) and THF (2 mL) were added, and then NaH (40 mg, 1.0 mmol) was added at 0° C. The mixture was stirred at rt for 1 hour and 1-bromo-4-(bromomethyl)benzene (207 mg, 0.83 mmol) was added. The resulting mixture was stirred at 60° C. for 12 hours and cooled to rt. The reaction was quenched with hydrochloric acid (1 M, 2 mL), and then extracted with ethyl acetate (6 mL×3). The combined organic phases were dried over anhydrous sodium sulfate, filtered and the filtrate was concentrated in vacuo. The residue was purified by silica gel chromatograph (PE/EtOAc (V/V)=1/1) to give the title compound as a white solid (153 mg, 90%). MS (ESI, pos. ion) m/z: 434.5 [M+Na]+.

Step 2: (R)-tert-butyl 2-((4'-(methoxycarbonyl)-[1,1'-diphenyl]-4-yl)methyl-3-oxohexahydro imidazo[1,5-a]pyrazine-7(1H)-carboxylate

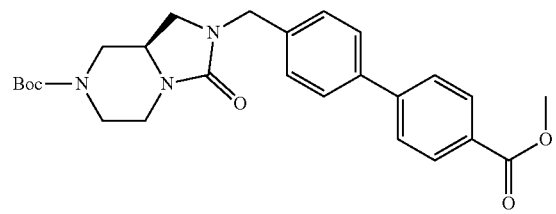 [SMILES: COC(=O)c1ccc(-c2ccc(CN3C[C@@H]4CN(C(=O)OC(C)(C)C)CCN4C3=O)cc2)cc1]

(R)-tert-Butyl 2-(4-bromobenzyl)-3-oxohexahydroimidazo[1,5-a]pyrazine-7(1H)-carboxylate (150 mg, 0.37 mmol), 4-(methoxycarbonyl)benzeneboronic acid (98 mg, 0.54 mmol) and Pd(PPh₃)₄ (21 mg, 0.02 mmol) were dissolved in a mixed toluene (3 mL) and ethanol (1 mL) solvent, the solution was degassed with nitrogen 3 times and heated at 80° C. for 24 hours. The reaction mixture was cooled to rt and concentrated in vacuo. The residue was purified by silica gel column chromatography (PE/EtOAc (v/v)=2/1) to give the title compound as a white solid (136 mg, 80%). MS (ESI, pos. ion) m/z: 410.6 [M+H−56]+.

Step 3: (R)-4'-((7-(tert-butoxycarbonyl)-3-oxohexahydroimidazo[1,5-a]pyrazin-2(3H)-yl) methyl)-[1,1'-diphenyl]-4-carboxylic acid

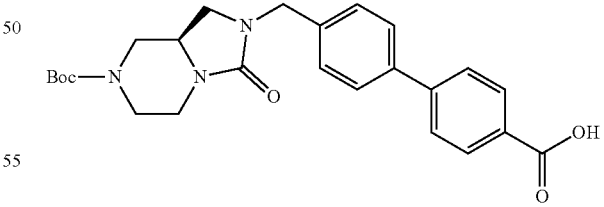

(R)-tert-Butyl 2-((4'-(methoxycarbonyl)-[1,1'-diphenyl]-4-yl)methyl)-3-oxohexahydro imidazo[1,5-a]pyrazine-7(1H)-carboxylate (136 mg, 0.29 mmol), lithium hydroxide monohydrate (60 mg, 1.43 mmol) were dissolved in a mixed methanol (6 mL) and water (2 mL) solvent. The mixture was stirred at 50° C. for 4 hours and concentrated in vacuo. The residue was adjusted with hydrochloric acid (1 M) to pH 5 to 6 and extracted with ethyl acetate (3×6 mL). The combined organic phases were dried over anhydrous sodium sulfate, filtered and the filtrate was concentrated in vacuo to get the title compound as a white solid (100 mg, 76%).

Step 4: (S)-4'-((3-oxohexahydroimidazo[1,5-a]pyrazin-2(3H)-yl)methyl)-[1,1'-diphenyl]-4-carboxylic acid hydrochloride

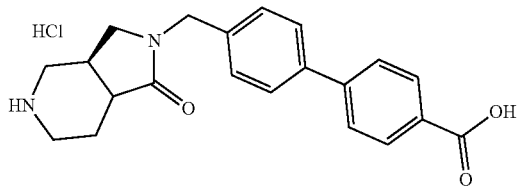

To a dry flask were added (R)-4'-((7-(tert-butoxycarbonyl)-3-oxohexahydroimidazo [1,5-a]pyrazin-2(3H)-yl)methyl)-[1,1'-diphenyl]-4-carboxylic acid (100 mg, 0.22 mmol) and a solution of HCl in EtOAc (4 mol/L, 10 mL), the mixture was stirred at rt for 8 hours and concentrated in vacuo to get the title compound as a white solid (86 mg, 100%). MS (ESI, pos. ion): m/z 352.1 [M+H]$^+$.

Step 5: 4'-(((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)methyl)-[1,1'-diphenyl]-4-carboxylic acid

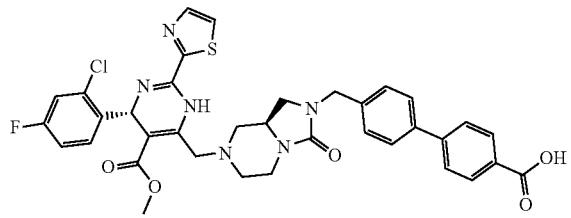 [SMILES: COC(=O)C1=C(CN2CCN3C(=O)N(Cc4ccc(-c5ccc(C(=O)O)cc5)cc4)C[C@@H]3C2)NC(c2nccs2)=N[C@H]1c1ccc(F)cc1Cl]

A mixture of (R)-methyl 6-(bromomethyl)-4-(2-chloro-4-fluorophenyl)-(2-thiazol-2-yl)-1,4-dihydropyrimidine-5-carboxylate (117 mg, 0.26 mmol), (S)-4'-((3-oxohexahydroimidazo [1,5-a]pyrazin-2(3H)-yl)methyl)-[1,1'-diphenyl]-4-carboxylic acid hydrochloride (93 mg, 0.24 mmol), potassium carbonate (165 mg, 1.20 mmol) in ethanol (10 mL) was stirred at rt for 24 hours and concentrated in vacuo. The residue was adjusted with hydrochloric acid (1 M) to pH 5 to 4 and extracted with ethyl acetate (3×20 mL). The combined organic phases were dried over anhydrous sodium sulfate, filtered and the filtrate was concentrated in vacuo. The residue was purified by silica gel chromatograph (DCM/CH$_3$OH (V/V)=10/1) to get the title compound as a yellow solid (77 mg, 45%). MS (ESI, pos. ion) m/z: 715.1 [M+H]$^+$; $^1$H NMR (400 MHz, CDCl$_3$) δ 9.64 (s, 1H), 8.18 (d, J=8.3 Hz, 2H), 7.84 (d, J=3.1 Hz, 1H), 7.69 (d, J=8.3 Hz, 2H), 7.62 (d, J=8.1 Hz, 2H), 7.46 (d, J=3.1 Hz, 1H), 7.38 (d, J=8.1 Hz, 2H), 7.33-7.25 (m, 1H), 7.15 (dd, J=8.6, 2.5 Hz, 1H), 6.94 (td, J=8.4, 2.5 Hz, 1H), 6.21 (s, 1H), 4.48 (s, 2H), 4.15-4.02 (m, 2H), 3.96-3.85 (m, 2H), 3.61 (s, 3H), 3.37 (t, J=8.8 Hz, 1H), 3.27 (td, J=12.9, 2.7 Hz, 1H), 2.88 (dd, J=9.0, 4.0 Hz, 2H), 2.76 (d, J=9.0 Hz, 1H), 2.51 (td, J=11.2, 2.7 Hz, 1H), 2.24 (t, J=10.8 Hz, 1H).

Example 11 4'-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-2-yl)-[1,1'-diphenyl]-4-carboxylic acid Step 1: 2-(4-bromophenyl)propane-2-amine

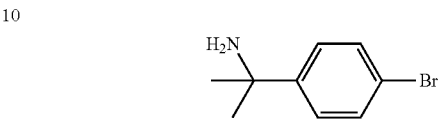

To a solution of 4-bromobenzylcyanide (10 g, 54.93 mmol) in THF (100 mL) was added methyl magnesium bromide (54 mL, 162 mmol) at rt under nitrogen, after the mixture was stirred for 30 min, tetraisopropoxy titanium (16 mL, 54 mmol) was added. The obtained mixture was heated to 50° C. and stirred for 12 hours, and then an aqueous sodium hydroxide solution (10%, 150 mL) was added, and the resulting mixture was stirred for 15 min and filtered to remove solid, the filtrate was extracted with tert-butyl methyl ether (300 mL), the organic layer was washed with an aqueous sodium hydroxide solution (10%, 100 mL) and saturated aqueous sodium chloride solution (100 mL) in turn, and then to the organic layer was added hydrochloric acid (1 M, 200 mL), the mixture was layered. The water layer was extracted with tert-butyl methyl ether (100 mL×2) and adjusted with an aqueous sodium hydroxide solution (10%) to pH 8 to 9, and then the resulting mixture was extracted with methyl tert-butyl ether (100 mL×3). The combined organic layers were dried over anhydrous sodium sulfate and filtered. The filtrate was concentrated in vacuo to get the title compound as yellow oil (8.5 g, 72%). $^1$H NMR (400 MHz, CDCl$_3$) δ 7.49-7.44 (m, 2H), 7.43-7.39 (m, 2H), 1.49 (s, 6H).

Step 2: (R)-di-tert-butyl 2-(((2-(4-bromophenyl)prop-2-yl)amino)methyl)piperazine-1,4-dicarboxylate

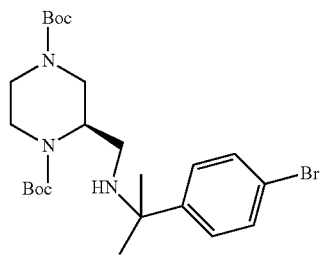 [SMILES: CC(C)(C)OC(=O)N1CCN(C(=O)OC(C)(C)C)[C@H](CNC(C)(C)c2ccc(Br)cc2)C1]

A solution of 2-(4-bromophenyl)propane-2-amine (2.25 g, 10.5 mmol), (2S)-di-tert-butyl2-formylpiperazine-1,4-dicarboxylate (3 g 9.54 mmol) and acetic acid (0.1 mL, 2 mmol) in methanol (30 mL) was stirred at rt for 2 hours and cooled to 0° C., and then sodium cyanoborohydrid (1.2 g 19 mmol) was added. After the addition, the mixture was stirred at rt for 3 hours. The mixture was concentrated in vacuo, the reaction was quenched with saturated aqueous sodium bicarbonate solution (20 mL). The resulting mixture was extracted with ethyl acetate (30 mL×3). The combined organic phases were dried over anhydrous sodium sulfate, filtered and the filtrate was concentrated in vacuo. The residue was purified by silica gel chromatograph (PE/EtOAc (V/V)=8/1) to give the title compound as colorless oil (1.56 g 32%). MS (ESI, pos. ion) m/z: 514.3 [M+H]⁺.

Step 3: (R)-benzyl 2-(2-(4-bromophenyl)prop-2-yl)-3-oxohexahydroimidazo[1,5-a]pyrazine-7(1H)-carboxylate

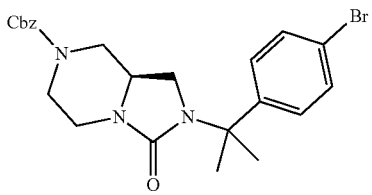 [SMILES: CC(C)(c1ccc(Br)cc1)N1C[C@@H]2CN(C(=O)OCc3ccccc3)CCN2C1=O]

(R)-di-tert-Butyl 2-(((2-(4-bromophenyl)prop-2-yl)amino)methyl)piperazine-1,4-dicarboxylate (1.56 g 3.04 mmol) was dissolved in DCM (5 mL), and to the solution was added TFA (5 mL). The mixture was stirred at rt for 3 hours and concentrated in vacuo. To the residue were added TEA (3.3 mL, 24 mmol) and DCM (15 mL), the resulting mixture was cooled to 0° C. and a solution of CbzCl (0.9 g 5 mmol) in DCM (15 mL) was added. The reaction mixture was stirred at 0° C. for 12 h, and then a solution of triphosgene (453 mg, 1.53 mmol) in DCM (15 mL) was added, the resulting mixture was stirred for 3 h. After the reaction was complete, the reaction was quenched with hydrochloric acid (1 M, 5 mL). The resulting mixture was extracted with DCM (30 mL×3). The combined organic phases were dried over anhydrous sodium sulfate, filtered and the filtrate was concentrated in vacuo. The residue was purified by silica gel chromatograph (PE/EtOAc (V/V)=3/1) to give the title compound as a white solid (160 mg, 12%). MS (ESI, pos. ion) m/z: 474.2 [M+H]⁺.

Step 4: (R)-benzyl 2-(2-(4'-(methoxycarbonyl)-[1,1'-diphenyl]-4-yl)propan2-yl)-3-oxohexahydro imidazo[1,5-a]pyrazine-7(1H)-carboxylate

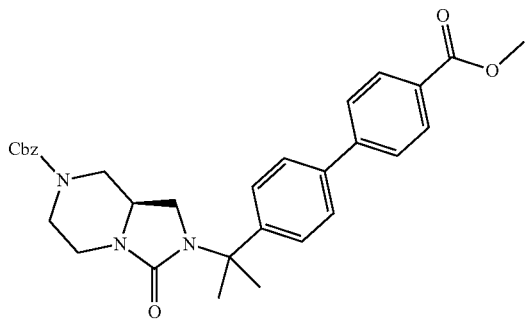 [SMILES: COC(=O)c1ccc(-c2ccc(C(C)(C)N3C[C@@H]4CN(C(=O)OCc5ccccc5)CCN4C3=O)cc2)cc1]

To a single neck flask were added (4-methoxycarbonyl)benzeneboronic acid (123 mg, 0.68 mmol), tetrakis(triphenylphosphine)palladium (66 mg, 0.06 mmol) and potassium carbonate (236 mg, 1.71 mmol), the mixture was degassed with nitrogen 3 times, and a solution of (R)-benzyl 2-(2-(4-bromophenyl)prop-2-yl)-3-oxohexahydroimidazo[1,5-a]pyrazine-7(1H)-carboxylate (160 mg, 0.37 mmol) in a mixed tolene (6 mL) and ethanol (2 mL) solvent was added, the resulting mixture was degassed with nitrogen 3 times and heated to 80° C. and stirred for 24 hours. After the reaction was complete, the reaction mixture was concentrated in vacuo. The residue was purified by silica gel column chromatography (PE/EtOAc (v/v)=3/1) to give the title compound as a white solid (147 mg, 49%). MS (ESI, pos. ion) m/z: 528.1 [M+H]⁺.

Step 5: (R)-4'-(2-(7-((benzyloxy)carbonyl)-3-oxohexahydroimidazo[1,5-a]pyrazin-2(3H)-yl) prop-2-yl)-[1,1'-diphenyl]-4-carboxylic acid

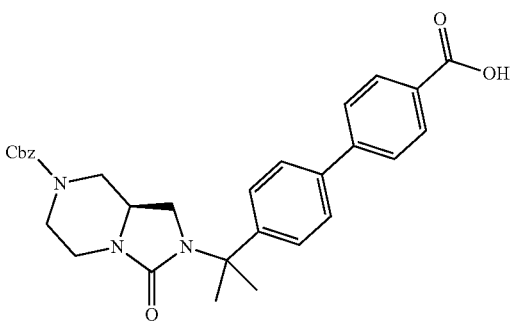 [SMILES: CC(C)(c1ccc(-c2ccc(C(=O)O)cc2)cc1)N1C[C@@H]2CN(C(=O)OCc3ccccc3)CCN2C1=O]

(R)-Benzyl 2-(2-(4'-(methoxycarbonyl)-[1,1'-diphenyl]-4-yl)prop-2-yl)-3-oxohexahydroimidazo[1,5-a]pyrazine-7(1H)-carboxylate (147 mg, 0.28 mmol), lithium hydroxide monohydrate (58 mg, 1.38 mmol) were dissolved in a mixed methanol (3 mL) and water (2 mL) solvent. The mixture was stirred at 50° C. for 4 hours and concentrated in vacuo. The residue was adjusted with hydrochloric acid (1 M) to pH 5-6 and extracted with ethyl acetate (3×20 mL). The combined organic phases were dried over anhydrous sodium sulfate, filtered and the filtrate was concentrated in vacuo to get the title compound as a white solid (130 mg, 91%). MS (ESI, pos. ion) m/z: 514.1 [M+H]⁺.

Step 6: (S)-4'-(2-(3-oxohexahydroimidazo[1,5-a]pyrazin-2(3H)-yl)prop-2-yl)-[1,1'-diphenyl]-4-carboxylic acid

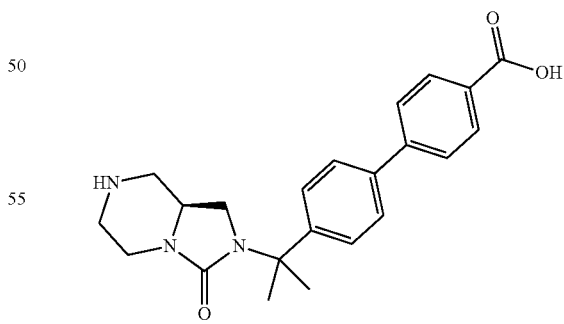

To a dry flask were added (R)-4'-(2-(7-((benzyloxy)carbonyl)-3-oxohexahydro imidazo[1,5-a]pyrazin-2(3H)-yl) prop-2-yl)-[1,1'-diphenyl]-4-carboxylic acid (110 mg, 0.21 mmol), methanol (5 mL) and palladium on carbon (41 mg, 0.04 mmol), the mixture was stirred at rt under H₂ for 12 hours and filtered, the filtrate was concentrated in vacuo to get the title compound as a white solid (70 mg, 86%). MS (ESI, pos. ion) m/z: 380.3 [M+H]+.

Step 7: 4'-(2-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)prop-2-yl)-[1,1'-diphenyl]-4-carboxylic acid

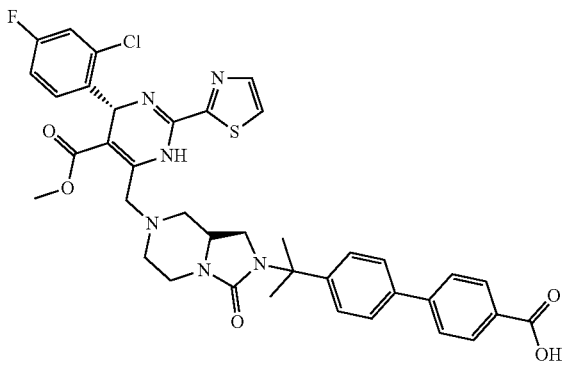

A mixture of (R)-methyl 6-(bromomethyl)-4-(2-chloro-4-fluorophenyl)-2-(thiazol-2-yl)-1,4-dihydropyrimidine-5-carboxylate (130 mg, 0.23 mmol), (S)-4'-(2-(3-oxohexahydroimidazo[1,5-a]pyrazin-2(3H)-yl)prop-2-yl)-[1,1'-diphenyl]-4-carboxylic acid (73 mg, 0.19 mmol), ethanol (5 mL) and potassium carbonate (130 mg, 0.94 mmol) was stirred at rt for 24 hours. The mixture was concentrated in vacuo and adjusted with hydrochloric acid (1 M) to pH 5 to 6. The resulting mixture was extracted with ethyl acetate (3×10 mL). The combined organic phases were dried over anhydrous sodium sulfate, filtered, and the filtrate was concentrated in vacuo. The residue was purified by silica gel chromatograph (DCM/CH$_3$OH (V/V)=10/1) to give the title compound as a yellow solid (45 mg, 31%). MS (ESI, pos. ion) m/z: 743.2 [M+H]+; $^1$H NMR (400 MHz, CDCl$_3$) δ 9.67 (s, 1H), 8.06 (d, J=8.2 Hz, 2H), 7.87 (d, J=3.0 Hz, 1H), 7.60 (d, J=8.2 Hz, 4H), 7.52-7.44 (m, 3H), 7.32-7.29 (m, 1H), 7.15 (dd, J=8.5, 2.4 Hz, 1H), 6.93 (td, J=8.4, 2.4 Hz, 1H), 6.22 (s, 1H), 4.24-4.10 (m, 1H), 4.00-3.85 (m, 3H), 3.71-3.65 (m, 1H), 3.63 (s, 3H), 3.54 (t, J=8.7 Hz, 1H), 3.23-3.15 (m, 1H), 3.06 (dd, J=8.9, 4.0 Hz, 1H), 2.90-2.78 (m, 1H), 2.60-2.45 (m, 1H), 2.40-2.27 (m, 1H), 1.75 (d, J=7.1 Hz, 6H).

Example 12 4'-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-[1,1'-diphenyl]-4-carboxylic acid Step 1: methyl 4'-bromo-[1,1'-diphenyl]-4-carboxylate

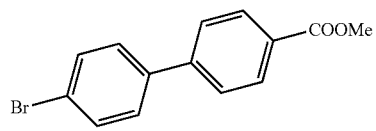 [SMILES: COC(=O)c1ccc(-c2ccc(Br)cc2)cc1]

To a dry flask were added 4-bromophenylboronic acid (460 mg, 2.3 mmol), methyl 4-iodobenzoate (500 mg, 1.91 mmol), potassium carbonate (528 mg, 3.82 mmol), (dppf)PdCl$_2$ (140 mg, 0.19 mmol) and toluene (10 mL) in turn, the mixture was stirred at 90° C. under nitrogen for 12 hours. After the reaction was complete, the reaction mixture was filtered and the filtrate was concentrated in vacuo. The residue was purified by silica gel column chromatography (PE/EtOAc (v/v)=50/1) to give the title compound as a white solid (520 mg, 93.62%).

Step 2: 4'-bromo-[1,1'-diphenyl]-4-carboxylic acid

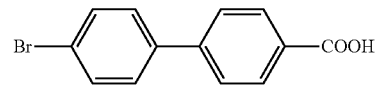

To a dry flask were added methyl 4'-bromo-[1,1'-diphenyl]-4-carboxylate (500 mg, 1.718 mmol), methanol (5 mL), a solution of lithium hydroxide monohydrate (216 mg, 5.15 mmol) in water (1 mL) in turn, the mixture was stirred at rt for 12 hours. After the reaction was complete, the reaction mixture was concentrated in vacuo. To the residue was added water (20 mL) and the mixture was adjusted with hydrochloric acid (1 M) to pH 2-3 under stirring and then filtered to get the title compound as a white solid (450 mg, 94.55%).

Step 3: (R)-4'-(7-(tert-butoxycarbonyl)-3-oxohexahydroimidazo[1,5-a]pyrazin-2(3H)-yl)-[1,1'-diphenyl]-4-carboxylic acid

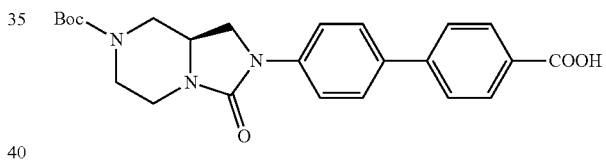

To a dry flask were added 4'-bromo-[1,1'-diphenyl]-4-carboxylic acid (700 mg, 2.53 mmol), (R)-tert-butyl 3-oxohexahydroimidazo[1,5-a]pyrazine-7(1H)-carboxylate (730 mg, 3.03 mmol), palladiumacetate (118 mg, 0.510 mmol), X-PHOS (500 mg, 1.02 mmol), cesium carbonate (1.65 g 5.06 mmol) and 1,4-dioxane (20 mL) in turn, the mixture was stirred at 90° C. under nitrogen for 12 hours. After the reaction was complete, the reaction mixture was concentrated in vacuo. The residue was purified by silica gel column chromatography (DCM/MeOH (V/V)=15/1) to give the title compound as a white solid (620 mg, 56.10%). MS (ESI, pos. ion) m/z: 460.3 [M+H−55]+.

Step 4: (S)-4'-(3-oxohexahydroimidazo[1,5-a]pyrazin-2(3H)-yl)-[1,1'-diphenyl]-4-carboxylic acid trifluoroacetate

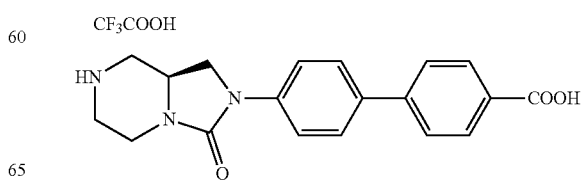

To a dry flask were added (R)-4'-(7-(tert-butoxycarbonyl)-3-oxohexahydro imidazo[1,5-a]pyrazin-2(3H)-yl)-[1,1'-diphenyl]-4-carboxylic acid (600 mg, 1.37 mmol), DCM (20 mL) and trifluoroacetic acid (20 ml) in turn, the mixture was stirred at rt for 12 hours. The most solvent was removed by rotary evaporation in vacuo, and to the residue was added toluene (30 mL), and then the mixture was concentrated again to get the tile compound as colorless oil (588 mg, 94.98%). MS (ESI, pos. ion) m/z: 338.1 [M+H]+.

Step 5: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-[1,1'-diphenyl]-4-carboxylic acid

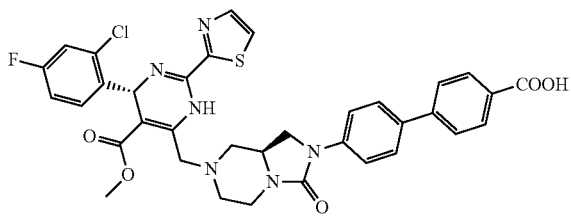 [SMILES: COC(=O)C1=C(CN2CCN3C(=O)N(c4ccc(-c5ccc(C(=O)O)cc5)cc4)C[C@@H]3C2)NC(c2nccs2)=N[C@H]1c1ccc(F)cc1Cl]

To a dry flask were added (S)-4'-(3-oxohexahydroimidazo[1,5-a]pyrazin-2(3H)-yl)-[1,1'-diphenyl]-4-carboxylic acid trifluoroacetate (600 mg, 1.329 mmol), 1,2-dichloroethane (50 mL), N,N-diisopropylethylamine (517 mg, 3.99 mmol) and (R)-methyl 6-(bromomethyl)-4-(2-chloro-4-fluorophenyl)-(2-thiazol-2-yl)-1,4-dihydropyrimidine-5-carboxy late (592 mg, 1.331 mmol) in turn, the reaction mixture was stirred at rt for 12 hours and concentrated in vacuo. The residue was diluted with water (10 mL) and washed with ethyl acetate (10 mL×3). The organic phases were abandoned. The water phase was adjusted with hydrochloric acid (1 M) to pH 5 to 6 and extracted with EtOAc (10 mL×4). The combined organic layers were washed with saturated aqueous sodium chloride (40 mL), dried over anhydrous sodium sulfate, and filtered. The filtrate was concentrated in vacuo, and the residue was purified by silica gel column chromatography (DCM/CH$_3$OH=25/1) to give the title compound as a yellow solid (300 mg, 32.19%). MS (ESI, pos. ion) m/z: 701.0 [M+H]+; $^1$H NMR (400 MHz, DMSO-d$_6$) δ 9.72 (s, 1H), 8.04 (d, J=3.0 Hz, 1H), 7.99 (d, J=8.2 Hz, 2H), 7.95 (d, J=2.8 Hz, 1H), 7.78 (d, J=8.1 Hz, 2H), 7.75-7.65 (m, 4H), 7.47-7.36 (m, 2H), 7.24-7.10 (m, 1H), 6.06 (s, 1H), 4.07-3.93 (m, 3H), 3.91-3.82 (m, 2H), 3.52 (s, 3H), 3.14-3.01 (m, 2H), 3.00-2.88 (m, 2H), 2.39-2.27 (m, 1H), 2.17 (t, J=10.8 Hz, 1H).

Example 13: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid Step 1: methyl 4-(3-bromo-5-fluorophenoxy)-3-fluorobenzoate

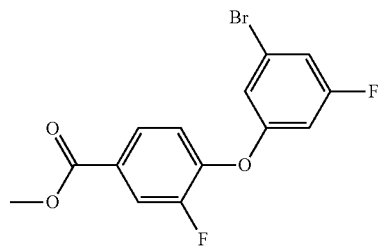 [SMILES: COC(=O)c1ccc(Oc2cc(F)cc(Br)c2)c(F)c1]

To a 25 mL single neck flask was added methyl 3,4-difluorobenzoate (211 mg, 1.23 mmol), 3-bromo-5-fluorophenol (256 mg, 1.34 mmol), potassium carbonate (539 mg, 3.9 mmol) and anhydrous DMF (4 mL), the mixture was stirred at 120° C. for 8 hours. After the reaction was complete, the mixture was cooled to rt, and diluted with EtOAc (30 mL) and water (15 mL). The separated organic layer was washed with saturated aqueous NaCl 4 times and dried over anhydrous sodium sulfate. The mixture was filtered and the filtrate was concentrated in vacuo to give the title compound as a white solid (310 mg, 73.71%). $^1$H NMR (400 MHz, DMSO-d$_6$) δ 7.87 (dd, J=11.3, 1.8 Hz, 1H), 7.83-7.77 (m, 1H), 7.76-7.70 (m, 1H), 7.33-7.22 (m, 2H), 6.92 (dd, J=8.8, 2.0 Hz, 1H), 3.85 (s, 3H).

Step 2: (R)-tert-butyl 2-(3-fluoro-5-(2-fluoro-4-(methoxycarbonyl)phenoxy)phenyl)-3-oxohexahydroimidazo[1,5-a]pyrazine-7(1H)-carboxylate

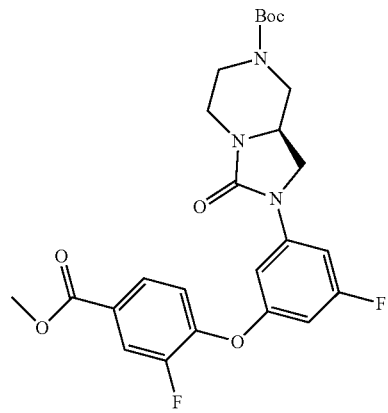 [SMILES: COC(=O)c1ccc(Oc2cc(F)cc(N3C[C@@H]4CN(C(=O)OC(C)(C)C)CCN4C3=O)c2)c(F)c1]

To a 25 mL two-neck flask were added methyl 4-(3-bromo-5-fluorophenoxy)-3-fluorobenzoate (245 mg, 0.71 mmol), (R)-tert-butyl 3-oxohexahydroimidazo[1,5-a]pyrazine-7(1H)-carboxylate (150 mg, 0.62 mmol), 2-di-tert-butylphosphino-2',4',6'-trisopropylbinphenyl (52 mg, 0.12 mmol), palladiumacetate (13 mg, 0.06 mmol), cesium carbonate (405 mg, 1.24 mmol), and 1,4-dioxane (6 mL) was added in turn under nitrogen, the mixture was degassed with nitrogen 4 times and stirred at 90° C. under nitrogen for 16 hours. After the reaction was complete, the mixture was cooled to rt and diluted with water (15 mL) and ethyl acetate (20 mL), the water phase was extracted with ethyl acetate (10 mL×1), the organic layers were combined. The organic layer was washed with saturated brine once, dried over anhydrous sodium sulfate and filtered. The filtrate was concentrated in vacuo to dry and the residue was purified by silica gel column chromatography (PE/EtOAc (v/v)=3/1) to give the title compound as a white foam solid (171 mg, 54.63%). MS (ESI, pos. ion) m/z: 526.1 [M+Na]+.

Step 3: (R)-4-(3-(7-(tert-butoxycarbonyl)-3-oxo-hexahydroimidazo[1,5-a]pyrazin-2(3H)-yl)-5-fluorophenoxy)-3-fluorobenzoic acid

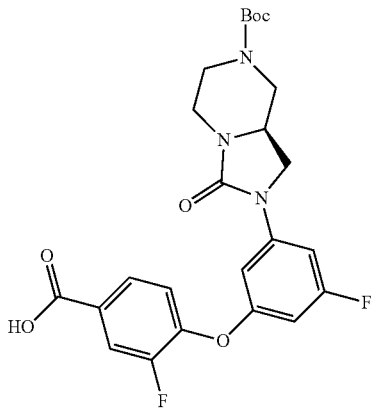 [SMILES: CC(C)(C)OC(=O)N1CCN2C(=O)N(c3cc(F)cc(Oc4ccc(C(=O)O)cc4F)c3)C[C@@H]2C1]

To a 25 mL single neck flask were added (R)-tert-butyl 2-(3-fluoro-5-(2-fluoro-4-(methoxycarbonyl)phenoxy)phenyl)-3-oxohexahydroimidazo[1,5-a]pyrazine-7(1H)-carboxylate (170 mg, 0.34 mmol), methanol (22 mL), water (1 mL) and lithium hydroxide monohydrate (143 mg, 3.41 mmol), the mixture was stirred at rt for 24 hours and concentrated in vacuo to remove the solvent, and then DCM (30 mL) and water (20 mL) were added to dilute the residue, and the resulting mixture was adjusted with dilute hydrochloric acid (2 M) to pH 3. The organic layer was separated and washed with saturated brine once, dried over anhydrous sodium sulfate and filtered. The filtrate was concentrated in vacuo to give the title compound as a white foam solid (165 mg, 99.83%). MS (ESI, pos. ion) m/z: 512.2[M+Na]$^+$.

Step 4: (S)-3-fluoro-4-(3-fluoro-5-(3-oxohexahydroimidazo[1,5-a]pyrazin-2(3H)-yl)phenoxy) benzoic acid trifluoroacetate

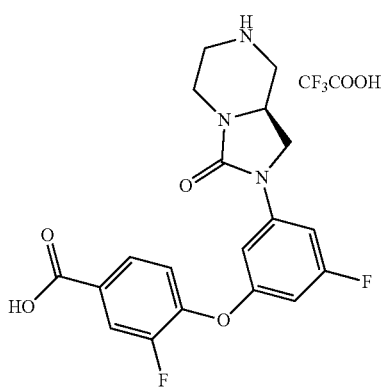 [SMILES: O=C(O)c1ccc(Oc2cc(F)cc(N3C[C@@H]4CNCCN4C3=O)c2)c(F)c1 ; "CF3COOH"]

To a 50 mL single neck flask were added (R)-4-(3-(7-(tert-butoxycarbonyl)-3-oxohexahydroimidazo[1,5-a]pyrazin-2(3H)-yl)-5-fluorophenoxy)-3-fluorobenzoic acid (165 mg, 0.34 mmol), DCM (3 mL) and TFA (4 mL), the mixture was stirred at rt for 4 hours. After the reaction was complete, the reaction mixture was concentrated in vacuo to get the title compound as light yellow oil (131 mg, 76.6%). MS (ESI, pos. ion) m/z: 390.0 [M+H]$^+$.

Step 5: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid

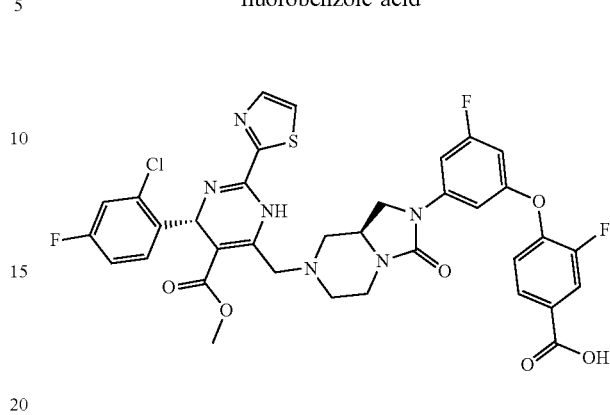

To a 50 mL single neck flask were added (S)-3-fluoro-4-(3-fluoro-5-(3-oxohexahydroimidazo[1,5-a]pyrazin-2(3H)-yl)phenoxy)benzoic acid trifluoroacetate (130 mg, 0.33 mmol), (R)-methyl 6-(bromomethyl)-4-(2-chloro-4-fluorophenyl)-2-(thiazol-2-yl)-1,4-dihydropyrimidine-5-carboxylate (140 mg, 0.32 mmol), anhydrous ethanol (8 mL) and potassium carbonate (130 mg, 0.94 mmol). The mixture was stirred at rt for 20 hours. After the reaction was complete, the mixture was concentrated in vacuo and diluted with water (40 mL) and ethyl acetate (30 mL), the organic phase was extracted with water (10 mL×3), the water layers were combined. To the combined water phases was added ethyl acetate (40 mL), and the mixture was adjusted with dilute hydrochloric acid (2 M) to pH 5, and the water phase was abandoned, The organic layer was washed with saturated brine once, dried over anhydrous sodium sulfate and filtered. The filtrate was concentrated in vacuo to dry and the residue was purified by silica gel column chromatography (DCM/MeOH (V/V)=12/1) to give the title compound as a yellow foam solid (85 mg, 35.85%). MS (ESI, pos. ion) m/z: 753.1 [M+H]$^+$; $^1$H NMR (400 MHz, CDCl$_3$) δ 9.58 (s, 1H), 7.93-7.78 (m, 3H), 7.50-7.42 (m, 1H), 7.32-7.23 (m, 1H), 7.18-7.03 (m, 4H), 6.91 (t, J=7.2 Hz, 1H), 6.44 (d, J=8.7 Hz, 1H), 6.20 (s, 1H), 4.14 (d, J=16.9 Hz, 1H), 4.07-3.95 (m, 2H), 3.92-3.80 (m, 2H), 3.59 (s, 3H), 3.42-3.31 (m, 1H), 3.24 (t, J=11.5 Hz, 1H), 2.97-2.81 (m, 2H), 2.48 (t, J=10.1 Hz, 1H), 2.24 (t, J=10.5 Hz, 1H).

Example 14: 4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenoxy)-3-fluorobenzoic acid Step 1: methyl 4-(4-bromo-3-fluorophenoxy)-3-fluorobenzoate

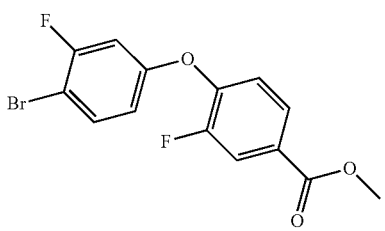 [SMILES: COC(=O)c1ccc(Oc2ccc(Br)c(F)c2)c(F)c1]

To a 50 mL single neck flask was added methyl 3,4-difluorobenzoate (1.00 g 5.81 mmol), 4-bromo-3-fluorophenol (1.22 g 6.39 mmol), potassium carbonate (2.41 g 17.4 mmol) and anhydrous DMF (15 mL). The reaction mixture was heated to 120° C. and stirred for 7 hours under nitrogen. After the reaction was complete, the mixture was cooled to rt and diluted with ethyl acetate (50 mL) and water (20 mL). The organic layer was separated and washed with saturated brine 4 times, dried over anhydrous sodium sulfate and filtered. The filtrate was concentrated in vacuo to give the title compound as a white solid (1.70 g, 85.3%). $^1$H NMR (400 MHz, DMSO-d$_6$) δ 7.89 (dd, J=11.2, 1.8 Hz, 1H), 7.85-7.80 (m, 1H), 7.43-7.38 (m, 1H), 7.33 (t, J=8.3 Hz, 1H), 7.21-7.17 (m, 1H), 7.10 (dt, J=10.0, 2.1 Hz, 1H), 3.87 (s, 3H).

Step 2: (R)-tert-butyl 2-(2-fluoro-4-(2-fluoro-4-(methoxycarbonyl)phenoxy)phenyl)-3-oxohexahydroimidazo[1,5-a]pyrazine-7(1H)-carboxylate

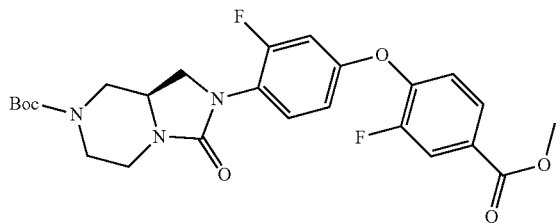 [SMILES: COC(=O)c1ccc(Oc2ccc(N3C[C@@H]4CN(C(=O)OC(C)(C)C)CCN4C3=O)c(F)c2)c(F)c1]

To a 25 mL two-neck flask were added methyl 4-(4-bromo-3-fluorophenoxy)-3-fluorobenzoate (550 mg, 1.60 mmol), (R)-tert-butyl 3-oxohexahydroimidazo[1,5-a]pyrazine-7(1H)-carboxylate (320 mg, 1.33 mmol), bis(benzonitrile)palladium chloride (50 mg, 0.13 mmol), X-Phos (94 mg, 0.2 mmol), cesium carbonate (864 mg, 2.65 mmol), and 1,4-dioxane (5 mL) was added in turn under nitrogen, the mixture was degassed with nitrogen additional 4 times and stirred at 95° C. under nitrogen for 20 hours. After the reaction was complete, the mixture was cooled to rt, and diluted with water (20 mL) and EtOAc (30 mL). The separated organic layer was washed with saturated aqueous NaCl once and dried over anhydrous sodium sulfate. The mixture was filtered and the filtrate was concentrated in vacuo. The residue was purified by silica gel column chromatography (PE/EtOAc (V/V)=2/1) to give the title compound as a white solid (81 mg, 12.13%). MS (ESI, pos. ion) m/z: 447.8 [M+H−56]$^+$.

Step 3: (S)-methyl 3-fluoro-4-(3-fluoro-4-(3-oxohexahydroimidazo[1,5-a]pyrazin-2(3H)-yl) phenoxy)benzoate trifluoroacetate

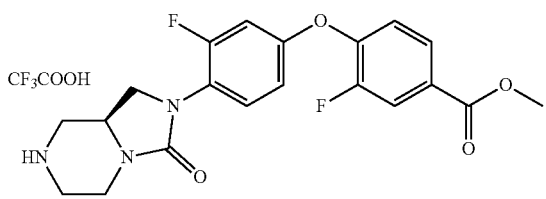 [SMILES: "CF3COOH" ; COC(=O)c1ccc(Oc2ccc(N3C[C@@H]4CNCCN4C3=O)c(F)c2)c(F)c1]

To a 25 mL single neck flask were added (R)-tert-butyl 2-(2-fluoro-4-(2-fluoro-4-(methoxycarbonyl)phenoxy)phenyl)-3-oxohexahydroimidazo[1,5-a]pyrazine-7(1H)-carboxylate (81 mg, 0.16 mmol), DCM (3 mL) and TFA (1 mL), the mixture was stirred at rt for 1 hour. After the reaction was complete, the reaction mixture was concentrated in vacuo to get the title compound as light yellow oil (81.6 mg, 98.62%).

Step 4: (R)-methyl 4-(2-chloro-4-fluorophenyl)-6-(((S)-2-(2-fluoro-4-(2-fluoro-4-(methoxy carbonyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate

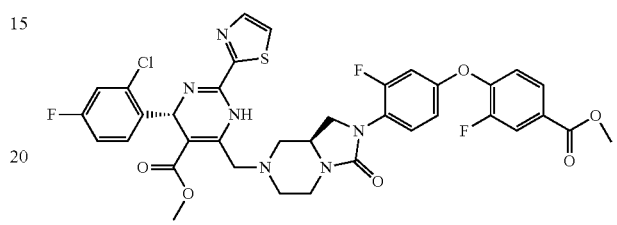

To a 25 mL single neck flask were added (S)-methyl 3-fluoro-4-(3-fluoro-4-(3-oxohexahydroimidazo[1,5-a]pyrazin-2(3H)-yl)phenoxy)benzoate trifluoroacetate (64 mg, 0.16 mmol), (R)-methyl 6-(bromomethyl)-4-(2-chloro-4-fluorophenyl)-2-(thiazol-2-yl)-1,4-dihydropyrimidine-5-carboxylate (65 mg, 0.15 mmol), potassium carbonate (60 mg, 0.43 mmol) and anhydrous ethanol (4 mL). The mixture was stirred at rt for 4 hours. After the reaction was complete, the mixture was diluted with EtOAc (25 mL) and water (15 mL). The separated organic layer was washed with saturated brine once, dried over anhydrous sodium sulfate and filtered. The filtrate was concentrated in vacuo to dry and the residue was purified by silica gel column chromatography (PE/EtOAc (v/v)=2/3) to give the title compound as a yellow foam solid (80 mg, 71.34%). MS (ESI, pos. ion) m/z: 767.2 [M+H]$^+$.

Step 5: 4-(4-(((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenoxy)-3-fluorobenzoic acid

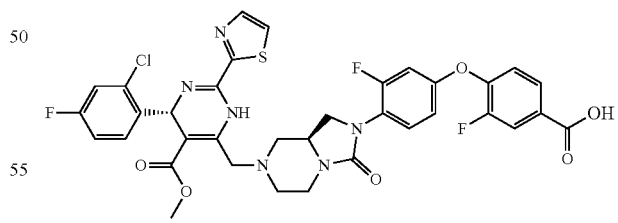

To a 25 mL single neck flask were added (R)-methyl 4-(2-chloro-4-fluorophenyl)-6-(((S)-2-(2-fluoro-4-(2-fluoro-4-(methoxycarbonyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate (80 mg, 0.10 mmol), methanol (3 mL), water (0.5 mL) and lithium hydroxide monohydrate (13 mg, 0.31 mmol), the mixture was stirred at rt for 3 hours. After the reaction was complete, the mixture was concentrated in vacuo and diluted with EtOAc (25 mL) and water (20 mL). The mixture was adjusted with dilute hydrochloric acid (2 M) to pH 5. The water layer was extracted with EtOAc (10 mL) once. The combined organic layers were washed with saturated brine once, dried over anhydrous sodium sulfate and filtered. The filtrate was concentrated in vacuo to dry and the residue was purified by silica gel column chromatography (DCM/MeOH (V/V)=15/1) to give the title compound as a yellow foam solid (42 mg, 53.48%). MS (ESI, pos. ion) m/z: 753.3 [M+H]$^+$; $^1$H NMR (400 MHz, CDCl$_3$) δ 9.64 (s, 1H), 8.00-7.74 (m, 3H), 7.55-7.40 (m, 2H), 7.33-7.26 (m, 1H), 7.13 (d, J=7.3 Hz, 1H), 7.10-6.99 (m, 1H), 6.97-6.87 (m, 1H), 6.82 (d, J=9.4 Hz, 2H), 6.21 (s, 1H), 4.20-4.09 (m, 1H), 4.08-3.97 (m, 2H), 3.94-3.82 (m, 2H), 3.60 (s, 3H), 3.53-3.41 (m, 1H), 3.28 (t, J=11.1 Hz, 1H), 2.97-2.78 (m, 2H), 2.53 (t, J=9.2 Hz, 1H), 2.37 (t, J=8.0 Hz, 1H).

Example 15: 4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)benzoic acid Step 1: (S)-tert-butyl 2-(4-bromothiazol-2-yl)-3-oxohexahydroimidazo[1,5-a]pyrazine-7(1H)-carboxylate

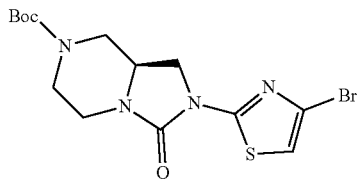 [SMILES: CC(C)(C)OC(=O)N1CCN2C(=O)N(c3nc(Br)cs3)C[C@@H]2C1]

(R)-tert-Butyl 3-oxohexahydroimidazo[1,5-a]pyrazine-7(1H)-carboxylate (500 mg, 2.07 mmol), 2,4-dibromo-thiazol (503 mg, 2.07 mmol), tris(dibenzylideneacetone)dipalladium (193 mg, 0.21 mmol), 4,5-bis(diphenylphosphino)-9,9-diMethylxanthene (247 mg, 0.41 mmol) and cesium carbonate (1.35 g 4.14 mmol) were dissolved in 1,4-dioxane (20 mL) under N$_2$, the mixture was heated to 90° C. and stirred for 12 hours and concentrated in vacuo. The residue was purified by silica gel column chromatography (PE/EtOAc (V/V)=3/1) to get the title compound as a white solid (618 mg, 74%). MS (ESI, pos. ion) m/z: 403.0 [M+H]$^+$.

Step 2: (S)-tert-butyl 2-(4-(4-(methoxycarbonyl)phenyl)thiazol-2-yl)-3-oxohexahydroimidazo [1,5-a]pyrazine-7(1H)-carboxylate

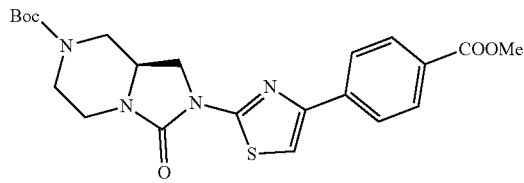 [SMILES: COC(=O)c1ccc(-c2csc(N3C[C@@H]4CN(C(=O)OC(C)(C)C)CCN4C3=O)n2)cc1]

(S)-tert-Butyl 2-(4-bromothiazol-2-yl)-3-oxohexahydroimidazo[1,5-a]pyrazine-7(1H)-carboxylate (300 mg, 0.74 mmol), 4-(methoxycarbonyl)benzeneboronic acid (160 mg, 0.89 mmol), tetrakis(triphenylphosphine)palladium (431 mg, 0.37 mmol) and cesium carbonate (728 mg, 2.23 mmol) were dissolved in 1,4-dioxane (10 mL) under N$_2$, the mixture was heated to 100° C. and stirred for 4 hours. After the reaction was complete, the reaction mixture was concentrated in vacuo. The residue was purified by silica gel column chromatography (PE/EtOAc (v/v)=2/1) to give the title compound as a white solid (230 mg, 67%). MS (ESI, pos. ion) m/z: 459.2 [M+H]$^+$.

Step 3: (S)-4-(2-(7-(tert-butoxycarbonyl)-3-oxohexahydroimidazo[1,5-a]pyrazin-2(3H)-yl) thiazol-4-yl)benzoic acid

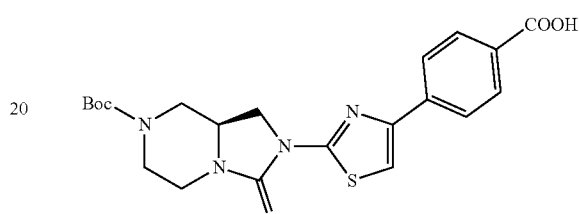

(S)-tert-Butyl 2-(4-(4-(methoxycarbonyl)phenyl)thiazol-2-yl)-3-oxohexahydroimidazo [1,5-a]pyrazine-7(1H)-carboxylate (150 mg, 0.33 mmol) was dissolved in methanol (3 mL), to the solution was added a solution of lithium hydroxide monohydrate (41 mg, 0.98 mmol) in water (3 mL), the mixture was stirred at 40° C. for 4 hours. After the reaction was complete, the mixture was concentrated in vacuo and diluted with water (10 mL). The mixture was adjusted with hydrochloric acid (1 N) to pH 3-4 and extracted with EtOAc (20 mL×3). The combined organic layers were washed with saturated brine, dried over anhydrous sodium sulfate and filtered. The filtrate was concentrated in vacuo to give the title compound as a white solid (120 mg, 83%). MS (ESI, pos. ion) m/z: 445.0 [M+H]$^+$.

Step 4: (S)-4-(2-(3-oxohexahydroimidazo[1,5-a]pyrazin-2(3H)-yl)thiazol-4-yl)benzoic acid trifluoroacetate

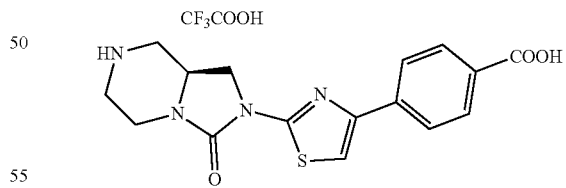

(S)-4-(2-(7-(tert-Butoxycarbonyl)-3-oxohexahydroimidazo[1,5-a]pyrazin-2(3H)-yl)thiazol-4-yl)benzoic acid (120 mg, 0.27 mmol) was dissolved in DCM (3 mL), to the solution was added trifluoroacetic acid (3 ml), the mixture was stirred at rt for 2 hours. After the reaction was complete, the most solvent was removed by rotary evaporation in vacuo, and to the residue was added toluene (10 mL), and then the mixture was concentrated again to get the tile compound as colorless oil (120 mg, 97%). MS (ESI, pos. ion) m/z: 345.1 [M+H]$^+$.

Step 5: 4-(2-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)thiazol-4-yl)benzoic acid

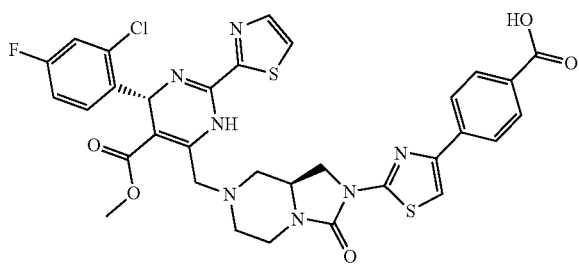 [SMILES: COC(=O)C1=C(CN2CCN3C(=O)N(c4nc(-c5ccc(C(=O)O)cc5)cs4)C[C@@H]3C2)NC(c2nccs2)=N[C@H]1c1ccc(F)cc1Cl]

(S)-4-(2-(3-Oxohexahydroimidazo[1,5-a]pyrazin-2(3H)-yl)thiazol-4-yl)benzoic acid trifluoroacetate (150 mg, 0.33 mmol) and potassium carbonate (136 mg, 0.98 mmol) was dissolved in ethanol (10 mL), and to the mixture was added (R)-methyl 6-(bromomethyl)-4-(2-chloro-4-fluorophenyl)-2-(thiazol-2-yl)-1,4-dihydropyrimidine-5-carboxylate (145 mg, 0.33 mmol), the resulting mixture was stirred at rt for 5 hours. And then the mixture was concentrated in vacuo. The residue was purified by silica gel column chromatography (DCM/MeOH (V/V)=15/1) to get a crude product, the crude product was purified by TLC (DCM/CH$_3$OH (V/V)=10/1) to give the title compound as a yellow solid (150 mg, 65%). MS (ESI, pos. ion) m/z: 708.2 [M+H]$^+$; $^1$H NMR (400 MHz, CDCl$_3$) δ 9.60 (s, 1H), 8.13 (d, J=8.2 Hz, 2H), 7.95 (d, J=8.2 Hz, 2, 7.88 (d, J=3.0 Hz, 1H), 7.49 (d, J=3.0 Hz, 1H), 7.34-7.26 (m, 2H), 7.16 (dd, J=8.5, 2.4 Hz, 1H), 6.95 (td, J=8.3, 2.3 Hz, 1H), 6.24 (s, 1H), 4.30 (t, J=9.7 Hz, 1H), 4.18-4.08 (m, 3H), 3.95 (d, J=17.1 Hz, 1H), 3.85 (dd, J=10.6, 4.8 Hz, 1H), 3.62 (s, 3H), 3.35 (td, J=12.9, 2.8 Hz, 1H), 3.05-2.90 (m, 2H), 2.60-2.48 (m, 1H), 2.33 (t, J=10.7 Hz, 1H).

Example 16: 3-((6-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)oxy) benzoic acid Step 1: methyl 3-((6-bromopyridin-3-yl)oxy)benzoate

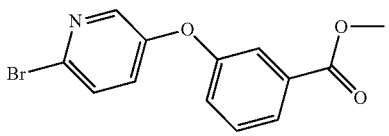 [SMILES: COC(=O)c1cccc(Oc2ccc(Br)nc2)c1]

To a single neck flask were added 2-bromo-5-fluoropyridine (2.0 g 11.4 mmol), methyl 3-hydroxybenzoate (1.9 g 12.5 mmol), DMF (15 mL) and potassium carbonate (3.14 g 22.7 mmol). The reaction mixture was stirred at 130° C. for 24 hours and cooled to 25° C., and then diluted with water (30 mL), the resulting mixture was extracted with ethyl acetate (100 mL). The organic layer was washed with saturated brine, dried over anhydrous sodium sulfate and filtered. The filtrate was concentrated in vacuo. The residue was purified by silica gel column chromatography (PE/EtOAc (V/V)=20/1) to give the title compound as colorless oil (0.71 g 20%). MS (ESI, pos. ion) m/z: 307.9 [M+H]$^+$.

Step 2: (R)-tert-butyl 2-(5-(3-(methoxycarbonyl)phenoxy)pyridin-2-yl)-3-oxohexahydroimidazo [1,5-a]pyrazin-7(1H)-carboxylat

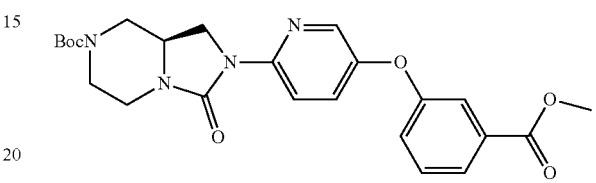

To a flask were added (R)-tert-butyl 3-oxohexahydroimidazo[1,5-a]pyrazine-7(1H)-carboxylate (510 mg, 1.96 mmol), methyl 3-((6-bromopyridin-3-yl)oxy)benzoate (550 mg, 1.79 mmol), tris(dibenzylideneacetone)dipalladium (169 mg, 0.18 mmol), 2-di-tert-butylphosphino-2',4',6'-trisopropylbinphenyl (207 mg, 0.36 mmol), cesium carbonate (1.17 g 3.57 mmol) and 1,4-dioxane (30 mL). The mixture was stirred at 100° C. for 5 hours and concentrated. The residue was purified by silica gel column chromatography (PE/EtOAc (V/V)=2/1) to give the title compound as a white solid (0.7 g 80%). MS (ESI, pos. ion) m/z: 469.3 [M+H]$^+$.

Step 3: (R)-3-((6-(7-(tert-butoxycarbonyl)-3-oxohexahydroimidazo[1,5-a]pyrazin-2(3H)-yl) pyridin-3-yl)oxy)benzoic acid

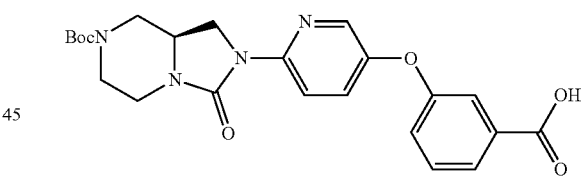

To a flask were added (R)-tert-butyl 2-(5-(3-(methoxycarbonyl)phenoxy)pyridin-2-yl)-3-oxohexahydroimidazo[1,5-a]pyrazin-7(1H)-carboxylate (0.70 g 1.5 mmol), methanol (5 mL), water (5 mL) and lithium hydroxide monohydrate (0.31 g 7.4 mmol). The reaction mixture was stirred at 25° C. for 5 hours and concentrated in vacuo, and then diluted with water (20 mL) and EtOAc (10 mL), the organic layer was abandoned. To the water phase was added EtOAc (30 mL), the mixture was adjusted with dilute hydrochloric acid (2 M) to pH 4 and extracted with EtOAc (30 mL). The organic layers were combined. The combined organic layers were washed with saturated brine, dried over anhydrous sodium sulfate and filtered. The filtrate was concentrated in vacuo to give the title compound as a white solid (0.52 g 77%). MS (ESI, pos. ion) m/z: 455.3 [M+H]$^+$.

Step 4: (S)-3-((6-(3-oxohexahydroimidazo[1,5-a]pyrazin-2(3H)-yl)pyridin-3-yl)oxy)benzoic acid hydrochloride

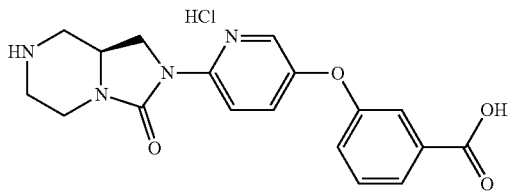 [SMILES: Cl ; O=C(O)c1cccc(Oc2ccc(N3C[C@@H]4CNCCN4C3=O)nc2)c1]

To a single neck flask were added (R)-3-((6-(7-(tert-butoxycarbonyl)-3-oxohexahydro imidazo[1,5-a]pyrazin-2(3H)-yl)pyridin-3-yl)oxy)benzoic acid (0.52 g 1.1 mmol) and a solution of HCl in 1,4-dioxane (4 mol/L, 20 mL), the mixture was stirred at 25° C. for 16 hours and filtered, the filtrate was concentrated in vacuo to get the title compound as a white solid (0.40 g 90%).

Step 5: 3-((6-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)oxy)benzoic acid

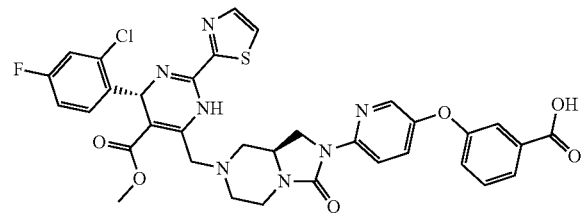 [SMILES: COC(=O)C1=C(CN2CCN3C(=O)N(c4ccc(Oc5cccc(C(=O)O)c5)cn4)C[C@@H]3C2)NC(c2nccs2)=N[C@H]1c1ccc(F)cc1Cl]

To a flask were added (S)-3-((6-(3-oxohexahydroimidazo[1,5-a]pyrazin-2(3H)-yl) pyridin-3-yl)oxy)benzoic acid hydrochloride (0.35 g, 0.89 mmol), (R)-methyl 6-(bromomethyl)-4-(2-chloro-4-fluorophenyl)-2-(thiazol-2-yl)-1,4-dihydropyrimidine-5-carboxy late (0.4 g 0.89 mmol), potassium carbonate (250 mg, 1.79 mmol) and ethanol (10 mL). The mixture was stirred at 35° C. for 4 hours and filtered, the filter cake was washed with EA (5 mL), the combined filtrates were concentrated, the residue was diluted with EA (20 mL) and water (10 mL), the mixture was adjusted with concentrated hydrochloric acid to pH 5, the water phase was abandoned, the organic layers was washed with saturated aqueous NaCl (10 mL) and concentrated, the residue was purified by silica gel column chromatography (DCM/MeOH (V/V)=25/1) to give the title compound as a yellow solid (0.30 g 46.6%). MS (ESI, pos. ion) m/z: 718.3 [M+H]+; 1H NMR (400 MHz, CD3OD) δ 8.28 (d, J=9.2 Hz, 1H), 8.09 (d, J=2.7 Hz, 1H), 7.97 (d, J=3.1 Hz, 1H), 7.81-7.75 (m, 2H), 7.57 (s, 1H), 752-7.42 (m, 3H), 7.28-7.21 (m, 2H), 7.07 (td, J=8.4, 2.6 Hz, 1H), 6.19 (s, 1H), 4.19-4.12 (m, 2H), 4.09-3.95 (m, 3H), 3.75 (dd, J=10.8, 4.6 Hz, 1H), 3.61 (s, 3H), 3.35-3.25 (m, 1H), 3.05 (t, J=9.3 Hz, 2H), 2.51 (td, J=11.5, 2.7 Hz, 1H), 2.29 (t, J=10.8 Hz, 1H).

Example 17: 2-(4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydro-imidazo[1,5-a]pyrazin-2(3H)-yl)thiazol-4-yl)phenyl)-2-methylpropionic acid

Step 1: methyl 2-(4-bromophenyl)acetate

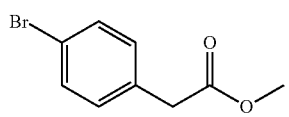

2-(4-Bromobenzene)acetic acid (5 g 23.3 mmol) was dissolved in methanol (50 mL), and to the solution was added thionyl chloride (3.4 mL, 46 mmol) in an ice bath, the mixture was stirred at rt for 12 hours and concentrated in vacuo to get the title compound as colorless oil (5.01 g 94.1%).

Step 2: methyl 2-(4-bromophenyl)-2-methylpropanoate

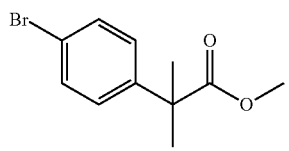

NaH (140 mg, 3.50 mmol, 60 mass %) was dissolved in N,N-dimethylformamide (10 mL) under N2, to the mixture was added methyl 2-(4-bromophenyl)acetate (200 mg, 0.87 mmol) in an ice bath, after the resulting mixture was stirred for 30 min, iodomethane (0.33 mL, 5.2 mmol) was added. The mixture was stirred at rt for 12 hours, and the reaction was quenched with water (20 mL) in an ice bath, the resulting mixture was extracted with EtOAc (20 mL×3), the organic layer was washed with water (50 mL×2) and saturated aqueous NaCl (50 mL), dried over anhydrous sodium sulfate, and then concentrated in vacuo to get the title compound as colorless oil (150 mg, 67%). 1H NMR (400 MHz, CDCl3) δ 7.45 (d, J=8.6 Hz, 2H), 7.22 (d, J=8.6 Hz, 2H), 3.66 (s, 3H), 1.57 (s, 6H).

Step 3: methyl 2-methyl-2-(4-(4,4,5,5-tetramethyl-1,3,2-dioxaborolan-2-yl)phenyl)propanoate

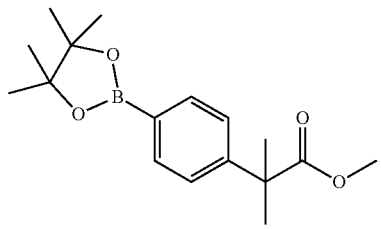

Methyl 2-(4-Bromophenyl)-2-methylpropionate (1 g 3.89 mmol), (dppf)PdCl2 (158 mg, 0.19 mmol), potassium acetate (1.15 g 11.7 mmol) and bis(pinacolato)diboron (1.5 g 5.8 mmol) were dissolved in 1,4-dioxane (20 mL) under N₂. The reaction mixture was stirred at 90° C. for 5 hours and concentrated in vacuo. The residue was purified by silica gel column chromatography (PE/EtOAc (v/v)=50/1) to give the title compound as a white solid (0.75 g 63%). MS (ESI, pos. ion): m/z 305.1 [M+H]⁺.

Step 4: (S)-tert-butyl 2-(4-(4-(1-methoxy-2-methyl-1-oxoprop-2-yl)phenyl)thiazol-2-yl)-3-oxohexahydroimidazo[1,5-a]pyrazin-7-(1H)-carboxylate

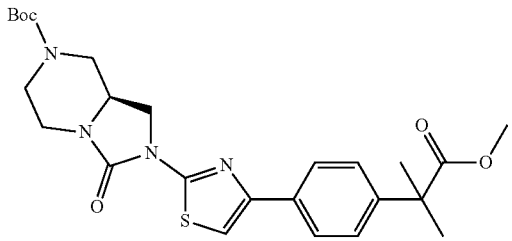 [SMILES: COC(=O)C(C)(C)c1ccc(-c2csc(N3C[C@@H]4CN(C(=O)OC(C)(C)C)CCN4C3=O)n2)cc1]

(S)-tert-Butyl 2-(4-bromothiazol-2-yl)-3-oxohexahydroimidazo[1,5-a]pyrazine-7(1H)-carboxylate (300 mg, 0.74 mmol), methyl 2-methyl-2-(4-(4,4,5,5-tetramethyl-1,3,2-dioxaborolan-2-yl)phenyl)propanoate (271 mg, 0.89 mmol), tetrakis(triphenylphosphine)palladium (172 mg, 0.15 mmol) and cesium carbonate (727 mg, 2.23 mmol) were dissolved in 1,4-dioxane (10 mL) under N₂. The mixture was heated to 90° C. and stirred for 5 hours, and then concentrated in vacuo. The residue was purified by silica gel column chromatography (PE/EtOAc (V/V)=2/1) to give the title compound as a white solid (230 mg, 62%). MS (ESI, pos. ion): m/z 501.4 [M+H]⁺.

Step 5: (S)-2-(4-(2-(7-(tert-butoxycarbonyl)-3-oxohexahydroimidazo[1,5-a]pyrazin-2(3H)-yl) thiazol-4-yl)phenyl)-2-methyl propionic acid

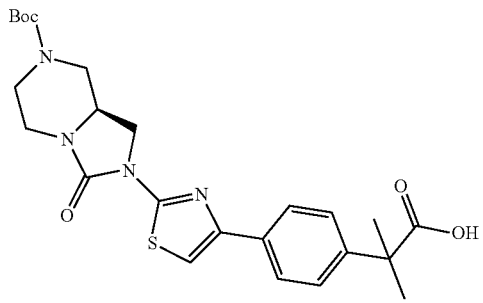 [SMILES: CC(C)(C)OC(=O)N1CCN2C(=O)N(c3nc(-c4ccc(C(C)(C)C(=O)O)cc4)cs3)C[C@@H]2C1]

(S)-tert-Butyl 2-(4-(4-(1-methoxy-2-methyl-1-oxoprop-2-yl)phenyl)thiazol-2-yl)-3-oxohexahydroimidazo[1,5-a]pyrazin-7-(1H)-carboxylate (120 mg, 0.24 mmol) was dissolved in methanol (5 mL), to the solution was added a solution of sodium hydroxide (96 mg, 2.40 mmol) in water (1 mL). The mixture was stirred at 50° C. for 12 hours and concentrated in vacuo, and then adjusted with hydrochloric acid (1 M) to pH 4. The resulting mixture was extracted with ethyl acetate (10 mL×3), the organic layers were combined. The combined organic layers were washed with saturated brine (20 mL), dried over anhydrous sodium sulfate and filtered. The filtrate was concentrated in vacuo to give the title compound as a gray solid (85 mg, 73%). MS (ESI, pos. ion): m/z 487.4 [M+H]⁺.

Step 6: (S)-2-methyl-2-(4-(2-(3-oxohexahydroimidazo[1,5-a]pyrazin-2(3H)-yl)thiazol-4-yl) phenyl) propionic acid trifluoroacetate

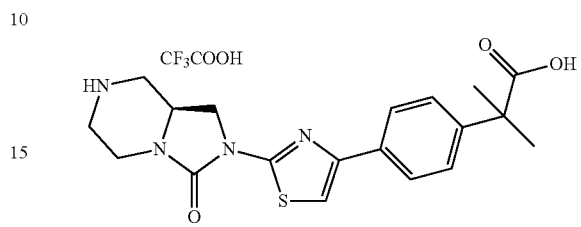

(S)-2-(4-(2-(7-(tert-Butoxycarbonyl)-3-oxohexahydroimidazo[1,5-a]pyrazin-2(3H)-yl)thiazol-4-yl)phenyl)-2-methyl propionic acid (80 mg, 0.15 mmol) was dissolved in DCM (5 mL), to the solution was added trifluoroacetic acid (5 ml). The mixture was stirred at rt for 1 hour, the most solvent was removed by rotary evaporation in vacuo, and to the residue was added toluene (10 mL), and then the mixture was concentrated again to get the title compound as brown oil (60 mg, 94%). MS (ESI, pos. ion): m/z 387.3 [M+H]⁺.

Step 7: 2-(4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl)-2-methyl propionic acid

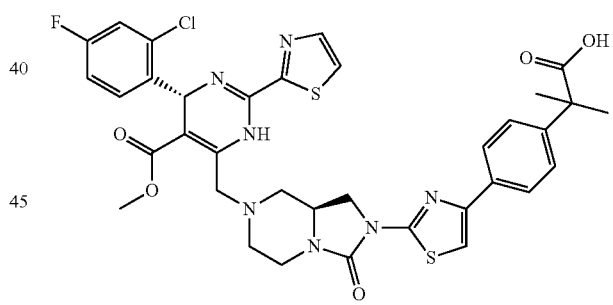

(S)-2-Methyl-2-(4-(2-(3-oxohexahydroimidazo[1,5-a]pyrazin-2(3H)-yl)thiazol-4-yl)phenyl) propionic acid trifluoroacetate (76 mg, 0.17 mmol) and potassium carbonate (64 mg, 0.46 mmol) was dissolved in ethanol (10 mL), and to the mixture was added (R)-methyl 6-(bromomethyl)-4-(2-chloro-4-fluorophenyl)-2-(thiazol-2-yl)-1,4-dihydropyrimidine-5-carboxy late (76 mg, 0.17 mmol). The resulting mixture was stirred at rt for 12 hours, the reaction mixture was concentrated in vacuo. The residue was purified by silica gel column chromatography (DCM/MeOH (V/V)=10/1) to give the title compound as a yellow solid (60 mg, 52%). MS (ESI, pos. ion): m/z 750.3 [M+H]⁺; ¹H NMR (400 MHz, CDCl₃) δ 9.59 (s, 1H), 7.88 (d, J=3.1 Hz, 1H), 7.81 (d, J=8.2 Hz, 2H), 7.49 (d, J=3.1 Hz, 1H), 7.44 (d, J=8.2 Hz, 2H), 7.34-7.29 (m, 1H), 7.16 (dd, J=8.6, 2.5 Hz, 1H), 7.06 (s, 1H), 6.94 (td, J=8.3, 2.5 Hz, 1H), 6.23 (s, 1H), 4.27 (t, J=9.7 Hz, 1H), 4.16-4.04 (m, 3H), 3.92 (d, J=17.1 Hz, 1H), 3.81 (dd, J=10.5, 4.5 Hz, 1H), 3.62 (s, 3H), 3.31 (t, J=11.2 Hz, 1H), 2.99-2.85 (m, 2H), 2.59-2.44 (m, 1H), 2.29 (t, J=10.9 Hz, 1H), 1.63 (s, 6H).

Example 18: 2-(4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-[1,1'-di phenyl]-4-yl)-2-methyl propionic acid Step 1: methyl 2-(4'-bromo-[1,1'-diphenyl]-4-yl)-2-methylpropionate

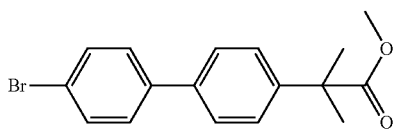

Bromo-4-iodo benzene (500 mg, 1.77 mmol), methyl 2-methyl-2-(4-(4,4,5,5-tetramethyl-1,3,2-dioxaborolan-2-yl)phenyl)propanoate (591 mg, 1.94 mmol), tetrakis(triphenylphosphine)palladium (205 mg, 0.18 mmol) and cesium carbonate (1.72 g 5.28 mmol) were dissolved in toluene (10 mL) under N₂. The reaction mixture was stirred at 90° C. for 5 hours and concentrated in vacuo. The residue was purified by silica gel column chromatography (PE/EtOAc (v/v)=50/1) to give the title compound as a white solid (430 mg, 73%).

Step 2: (R)-tert-butyl 2-(4'-(1-methoxy-2-methyl-1-oxoprop-2-yl)-[1,1'-diphenyl]-4-yl)-3-oxohexahydroimidazo[1,5-a]pyrazine-7(1H)-carboxylate

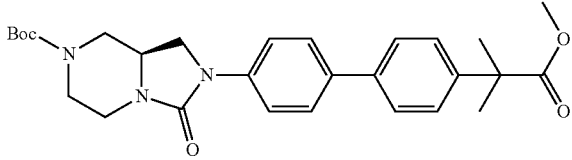 [SMILES: COC(=O)C(C)(C)c1ccc(-c2ccc(N3C[C@@H]4CN(C(=O)OC(C)(C)C)CCN4C3=O)cc2)cc1]

(R)-tert-Butyl 2-oxohexahydroimidazo[1,5-a]pyrazine-7 (1H)-carboxylate (300 mg, 1.24 mmol), methyl 2-(4'-bromo-[1,1'-diphenyl]-4-yl)-2-methylpropionate (456 mg, 1.37 mmol), tris(dibenzylideneacetone)dipalladium (116 mg, 0.12 mmol), 4,5-bis(diphenylphosphino)-9,9-dimethylxanthene (148 mg, 0.25 mmol) and cesium carbonate (810 mg, 2.49 mmol) were dissolved in 1,4-dioxane (10 mL). The reaction mixture was stirred at 90° C. for 6 hours and concentrated in vacuo. The residue was purified by silica gel column chromatography (PE/EtOAc (v/v)=3/1) to give the title compound as a white solid (350 mg, 57%).

Step 3: (R)-2-(4'-(7-(tert-butoxycarbonyl)-3-oxohexahydroimidazo[1,5-a]pyrazin-2(3H)-yl)-[1,1'-diphenyl]-4-yl)-2-methyl propionic acid

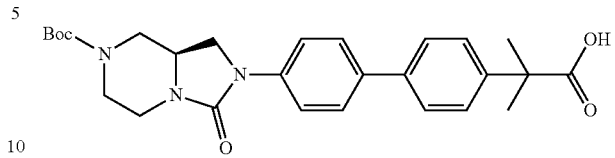

(R)-tert-Butyl 2-(4'-(1-methoxy-2-methyl-1-oxoprop-2-yl)-[1,1'-diphenyl]-4-yl)-3-oxohexahydroimidazo[1,5-a]pyrazine-7(1H)-carboxylate (150 mg, 0.30 mmol) was dissolved in methanol (10 mL), to the solution was added a solution of sodium hydroxide (24 mg, 0.60 mmol) in water (1 mL). The mixture was stirred at rt for 5 hours and adjusted with hydrochloric acid (1 M) to pH 3-4, the resulting mixture was extracted with EtOAc (20 mL×3). The combined organic layers were dried over anhydrous sodium sulfate and filtered. The filtrate was concentrated in vacuo to give the title compound as a white solid (140 mg, 96%). MS (ESI, pos. ion): m/z 480.3 [M+H]⁺.

Step 4: (S)-2-methyl-2-(4'-(3-oxohexahydroimidazo[1,5-a]pyrazin-2(3H)-yl)-[1,1'-diphenyl]-4-yl)propionic acid trifluoroacetate

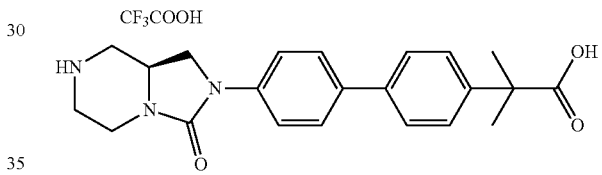

(R)-2-(4'-(7-(tert-Butoxycarbonyl)-3-oxohexahydroimidazo[1,5-a]pyrazin-2(3H)-yl)-[1, 1'-diphenyl]-4-yl)-2-methyl propionic acid (150 mg, 0.31 mmol) was dissolved in DCM (5 mL), to the solution was added trifluoroacetic acid (5 mL). The mixture was stirred at rt for 1 hour, the most solvent was removed by rotary evaporation in vacuo, and to the residue was added toluene (10 mL), and then the mixture was concentrated again to get the title compound as brown oil (150 mg, 97%).

Step 5: 2-(4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-[1,1'-diphenyl]-4-yl)-2-methylpropionic acid

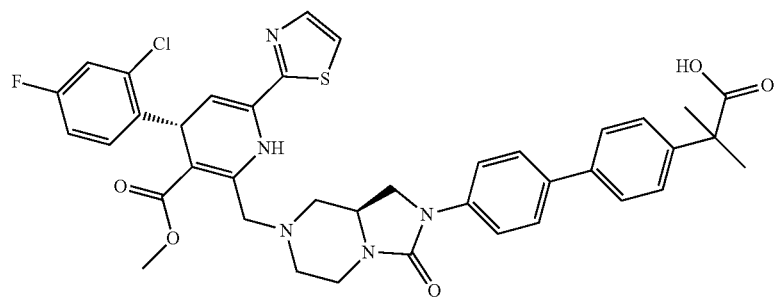 [SMILES: COC(=O)C1=C(CN2CCN3C(=O)N(c4ccc(-c5ccc(C(C)(C)C(=O)O)cc5)cc4)C[C@@H]3C2)NC(c2nccs2)=C[C@H]1c1ccc(F)cc1Cl]

(S)-2-Methyl-2-(4'-(3-oxohexahydroimidazo[1,5-a]pyrazin-2(3H)-yl)-[1,1'-diphenyl]-4-yl)propionic acid trifluoroacetate (100 mg, 0.26 mmol) and potassium carbonate (72 mg, 0.52 mmol) was dissolved in ethanol (10 mL), and to the mixture was added (R)-methyl 6-(bromomethyl)-4-(2-chloro-4-fluorophenyl)-2-(thiazol-2-yl)-1,4-dihydropyrimidine-5-carboxylate (128 mg, 0.29 mmol). The resulting mixture was stirred at rt for 12 hours, the reaction mixture was concentrated in vacuo. The residue was purified by silica gel column chromatography (DCM/MeOH (V/V)=10/1) to give the title compound as a yellow solid (120 mg, 61%). MS (ESI, pos. ion): m/z 743.4 [M+H]$^+$; $^1$H NMR (400 MHz, CDCl$_3$) δ 9.66 (s, 1H), 7.88 (d, J=3.1 Hz, 1H), 7.62-7.53 (m, 6H), 7.50-7.44 (m, 3H), 7.31 (dd, J=8.6, 6.2 Hz, 1H), 7.16 (dd, J=8.6, 2.5 Hz, 1H), 6.94 (td, J=8.3, 2.5 Hz, 1H), 6.23 (s, 1H), 4.17-4.09 (m, 2H), 4.08-3.97 (m, 1H), 3.96-3.88 (m, 2H), 3.62 (s, 3H), 3.47 (dd, J=8.9, 4.5 Hz, 1H), 3.32-3.23 (m, 1H), 2.90 (d, J=9.7 Hz, 2H), 2.52 (td, J=11.5, 3.0 Hz, 1H), 2.29 (t, J=10.6 Hz, 1H), 1.65 (s, 6H).

Example 19: 2-(4-(6-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)phenyl)-2-methylpropionic acid Step 1: (R)-tert-butyl 2-(5-bromopyridin-2-yl)-3-oxohexahydroimidazo[1,5-a]pyrazine-7(1H)-carboxylate

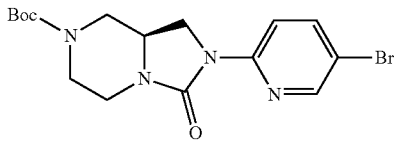

(R)-tert-Butyl 3-oxohexahydroimidazo[1,5-a]pyrazine-7(1H)-carboxylate (500 mg, 2.07 mmol), 2,5-dibromopyridine (539 mg, 2.27 mmol), tris(dibenzylideneacetone)dipalladium (193 mg, 0.21 mmol), 4,5-bis(diphenylphosphino)-9,9-dimethylxanthene (247 mg, 0.41 mmol) and cesium carbonate (1.35 mg, 4.14 mmol) were dissolved in 1,4-dioxane (20 mL). The reaction mixture was stirred at 90° C. for 6 hours and concentrated in vacuo. The residue was purified by silica gel column chromatography (PE/EtOAc (v/v)=3/1) to give the title compound as a white solid (520 mg, 63%). MS (ESI, pos. ion): m/z 397.0 [M+H]$^+$, 399.0 [M+2]$^+$.

Step 2: (R)-tert-butyl 2-(5-(4-(1-methoxy-2-methyl-1-oxoprop-2-yl)phenyl)pyridin-2-yl)-3-oxohexahydroimidazo[1,5-a]pyrazine-7-(1H)-carboxylate

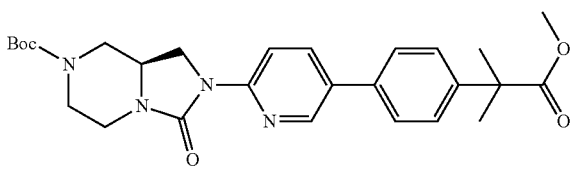 [SMILES: COC(=O)C(C)(C)c1ccc(-c2ccc(N3C[C@@H]4CN(C(=O)OC(C)(C)C)CCN4C3=O)nc2)cc1]

(R)-tert-Butyl 2-(5-bromopyridin-2-yl)-3-oxohexahydroimidazo[1,5-a]pyrazine-7(1H)-carboxylate (500 mg, 1.26 mmol), methyl 2-methyl-2-(4-(4,4,5,5-tetramethyl-1,3,2-dioxaborolan-2-yl)phenyl)propanoate (421 mg, 1.38 mmol), tetrakis(triphenylphosphine)palladium (145 mg, 0.13 mmol) and cesium carbonate (1.23 g 3.78 mmol) were dissolved in 1,4-dioxane (20 mL) under N$_2$. The mixture was stirred at 90° C. for 3 hours and concentrated in vacuo. The residue was purified by silica gel column chromatography (PE/EtOAc (V/V)=2/1) to give the title compound as a white solid (320 mg, 52%). MS (ESI, pos. ion): m/z 495.1[M+H]$^+$.

Step 3: (R)-2-(4-(6-(7-(tert-butoxycarbonyl)-3-oxohexahydroimidazo[1,5-a]pyrazin-2(3H)-yl)pyridin-3-yl)phenyl)-2-methyl propionic acid

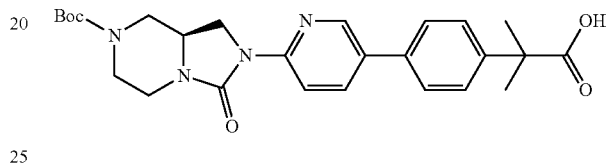

(R)-tert-Butyl 2-(5-(4-(1-methoxy-2-methyl-1-oxoprop-2-yl)phenyl)pyridin-2-yl)-3-oxohexahydroimidazo[1,5-a]pyrazin-7-(1H)-carboxylate (150 mg, 0.30 mmol) was dissolved in methanol (10 mL), to the solution was added a solution of sodium hydroxide (24 mg, 0.60 mmol) in water (1 mL). The mixture was stirred at rt for 5 hours and adjusted with hydrochloric acid (1 M) to pH 3-4, the resulting mixture was extracted with EtOAc (20 mL×3). The combined organic layers were dried over anhydrous sodium sulfate and filtered. The filtrate was concentrated in vacuo to give the title compound as a white solid (130 mg, 89%). MS (ESI, pos. ion): m/z 481.1 [M+H]$^+$.

Step 4: (S)-2-methyl-2-(4-(6-(3-oxohexahydroimidazo[1,5-a]pyrazin-2(3H)-yl)pyridin-3-yl) phenyl) propionic acid trifluoroacetate

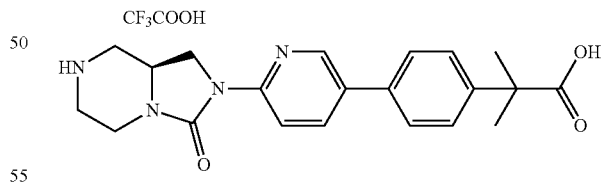

(R)-2-(4-(6-(7-(tert-Butoxycarbonyl)-3-oxohexahydroimidazo[1,5-a]pyrazin-2(3H)-yl) pyridin-3-yl)phenyl)-2-methyl propionic acid (180 mg, 0.37 mmol) was dissolved in DCM (5 mL), to the solution was added trifluoroacetic acid (5 ml). The mixture was stirred at rt for 1 hour, the most solvent was removed by rotary evaporation in vacuo, and to the residue was added toluene (10 mL), and then the mixture was concentrated again to get the title compound as brown oil (180 mg, 97%).

Step 5: 2-(4-(6-((S)-7-(((R)-6-(2-chloro-4-fluoro-phenyl)-5-(methoxycarbonyl)-2-(thiazol-2-yl)-3,6-dihydropyrimidin-4-yl)-3-oxohexahydroimidazo[1,5-a]pyrazin-2(3H)-yl)pyridin-3-yl)phenyl)-2-methyl propionic acid

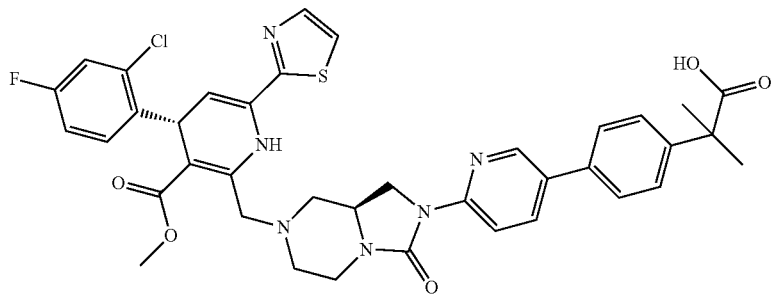 [SMILES: COC(=O)C1=C(CN2CCN3C(=O)N(c4ccc(-c5ccc(C(C)(C)C(=O)O)cc5)cn4)C[C@@H]3C2)NC(c2nccs2)=C[C@H]1c1ccc(F)cc1Cl]

(S)-2-Methyl-2-(4-(6-(3-oxohexahydroimidazo[1,5-a]pyrazin-2(3H)-yl)pyridin-3-yl)phenyl)propionic acid trifluoroacetate (150 mg, 0.39 mmol) and potassium carbonate (263 mg, 1.90 mmol) was dissolved in ethanol (10 mL), and to the mixture was added (R)-methyl 6-(bromomethyl)-4-(2-chloro-4-fluorophenyl)-2-(thiazol-2-yl)-1,4-dihydropyrimidine-5-carboxylate (192 mg, 0.43 mmol). The resulting mixture was stirred at rt for 12 hours, the reaction mixture was concentrated in vacuo. The residue was purified by silica gel column chromatography (DCM/MeOH (V/V)=10/1) to give the title compound as a yellow solid (180 mg, 61%). MS (ESI, pos. ion): m/z 744.2 [M+H]+; 1H NMR (400 MHz, CDCl3) δ 9.65 (s, 1H), 8.49 (d, J=2.0 Hz, 1H), 8.36 (d, J=8.8 Hz, 1H), 7.91-7.84 (m, 2H), 7.57-7.48 (m, 4H), 7.48 (d, J=3.1 Hz, 1H), 7.31 (dd, J=8.8, 6.4 Hz, 1H), 7.15 (dd, J=8.6, 2.5 Hz, 1H), 6.94 (td, J=8.3, 2.5 Hz, 1H), 6.23 (s, 1H), 4.20-4.07 (m, 3H), 4.05-3.98 (m, 1H), 3.93 (d, J=17.2 Hz, 1H), 3.75 (dd, J=10.8, 4.9 Hz, 1H), 3.61 (s, 3H), 3.29 (td, J=12.9, 2.7 Hz, 1H), 2.93 (t, J=8.3 Hz, 2H), 2.52 (dd, J=11.6, 8.4 Hz, 1H), 2.29 (t, J=10.8 Hz, 1H), 1.63 (d, J=15.6 Hz, 6H).

Example 20: 3-((R)-4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)morpholin-2-yl)propionic acid Step 1: (R)-tert-butyl 2-(4-bromophenyl)-3-oxo-hexahydroimidazo[1,5-a]pyrazine-7(1H)-carboxylate

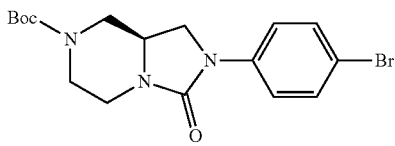 [SMILES: CC(C)(C)OC(=O)N1CCN2C(=O)N(c3ccc(Br)cc3)C[C@@H]2C1]

To a dry flask were added bromo-4-iodo benzene (1.33 g 4.56 mmol), (R)-tert-butyl 3-oxohexahydroimidazo[1,5-a]pyrazine-7(1H)-carboxylate (1 g 4.14 mmol), xantphos (370 mg, 0.62 mmol), Pd2(dba)3 (293 mg, 0.31 mmol), cesium carbonate (2.97 g 9.12 mmol) and 1,4-dioxane (50 mL). The mixture was stirred at 80° C. for 12 hours under N2 and cooled to rt, and then filtered by suction, the filtrate was concentrated in vacuo. The residue was purified by silica gel column chromatography (PE/EtOAc (V/V)=3/1) to give the title compound as a white solid (1.42 g 86.5%). MS (ESI, pos. ion) m/z: 418.0 [M+Na]+.

Step 2: (R)-tert-butyl 2-(4-((R)-2-(3-methoxy-3-oxopropyl)morpholinyl)phenyl)-3-oxohexahydroimidazo[1,5-a]pyrazine-7(1H)-carboxylate

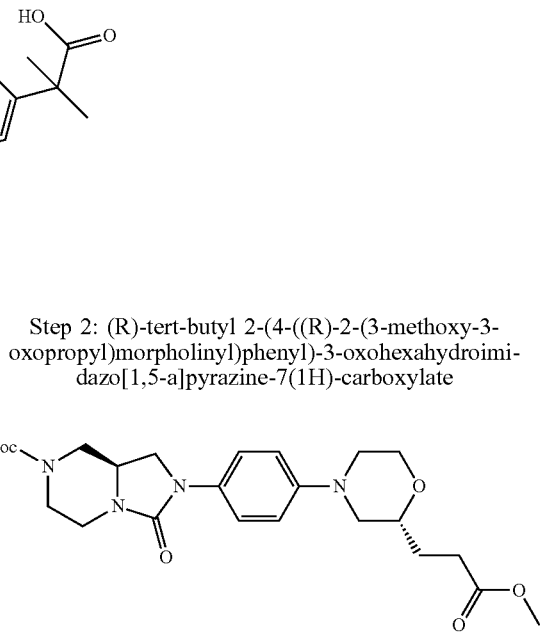

To a dry flask were added (R)-tert-butyl 2-(4-bromophenyl)-3-oxohexahydroimidazo [1,5-a]pyrazine-7(1H)-carboxylate (416 mg, 1.05 mmol), methyl (R)-3-(morpholin-2-yl)propionate hydrochloride (200 mg, 0.754 mmol), palladiumacetate (43 mg, 0.188 mmol), tBuXPhos (167 mg, 0.381 mmol), cesium carbonate (1.25 g 3.84 mmol) and 1,4-dioxane (25 mL). The mixture was stirred at 90° C. for 12 hours under N2 and cooled to rt, and then filtered by suction, the filtrate was concentrated in vacuo. The residue was purified by silica gel column chromatography (PE/EtOAc (V/V)=2/3) to give the title compound as a yellow solid (228 mg, 49.02%). MS (ESI, pos. ion) m/z: 489.4 [M+H]+.

Step 3: 3-((R)-4-(4-((R)-7-(tert-butoxycarbonyl)-3-oxohexahydroimidazo[1,5-a]pyrazin-2(3H)-yl)phenyl)morpholin-2-yl)propionic acid

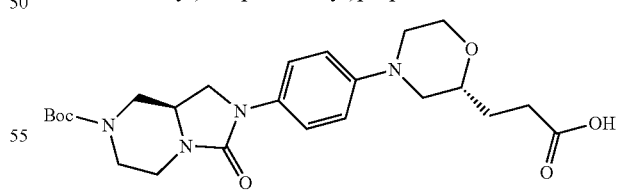

(R)-tert-Butyl 2-(4-((R)-2-(3-methoxy-3-oxopropyl)morpholinyl)phenyl)-3-oxohexahydroimidazo[1,5-a]pyrazine-7(1H)-carboxylate (309 mg, 0.63 mmol) was dissolved in methanol (12 mL) in a dry flask, to the solution was added a solution of sodium hydroxide (133 mg, 3.170 mmol) in water (4 mL). The mixture was stirred at 45° C. for 12 hours and concentrated in vacuo, the residue was diluted with water (60 mL) and adjusted with hydrochloric acid (1 M) to pH 5, the resulting mixture was stirred for 30 min and filtered by suction. The filter cake was dried by rotary evaporation in vacuo to get the title compound as a white solid (230 mg, 76.63%). MS (ESI, pos. ion) m/z: 475.1 [M+H]⁺.

Step 4: 3-((R)-4-(4-((S)-3-oxohexahydroimidazo[1,5-a]pyrazin-2(3H)-yl)phenyl)morpholin-2-yl)propionic acid trifluoroacetate

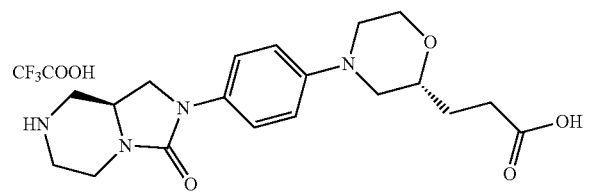 [SMILES: "CF3COOH" ; O=C(O)CC[C@@H]1CN(c2ccc(N3C[C@@H]4CNCCN4C3=O)cc2)CCO1]

To a dry flask were added 3-((R)-4-(4-((R)-7-(tert-butoxycarbonyl)-3-oxohexahydroimidazo[1,5-a]pyrazin-2(3H)-yl)phenyl)morpholin-2-yl)prop ionic acid (209 mg, 0.44 mmol), DCM (9 mL) and trifluoroacetic acid (3 ml). The mixture was stirred for 6 hours, and then concentrated in vacuo. The residue was diluted with toluene (5 mL), the resulting mixture was concentrated in vacuo, the operation was repeated 3 time to get the title compound as aubergine oil (215 mg, 100%). MS (ESI, pos. ion) m/z: 375.1 [M+H]⁺.

Step 5: 3-((R)-4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)morpholin-2-yl) propionic acid

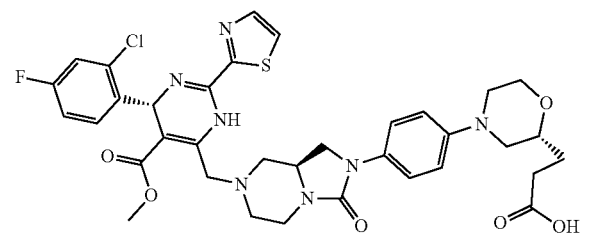 [SMILES: COC(=O)C1=C(CN2CCN3C(=O)N(c4ccc(N5CCO[C@H](CCC(=O)O)C5)cc4)C[C@@H]3C2)NC(c2nccs2)=N[C@H]1c1ccc(F)cc1Cl]

To a dry flask were added 3-((R)-4-(4-((S)-3-oxohydroimidazo[1,5-a]pyrazin-2(3H)-yl)phenyl)morpholin-2-yl) propionic acid trifluoroacetate (215 mg, 0.44 mmol), ethanol (15 mL), potassium carbonate (274 mg, 1.98 mmol) and (R)-methyl 6-(bromomethyl)-4-(2-chloro-4-fluorophenyl)-2-(thiazol-2-yl)-1,4-dihydropyrimidine-5-carboxylate (205 mg, 0.46 mmol). The mixture was stirred at rt for 12 hours and concentrated in vacuo to remove the most ethanol, the residue was diluted with water (30 mL) and EtOAc (30 mL), and then adjusted with hydrochloric acid to pH 4-5. The mixture was partitioned, the water phase was extracted with EtOAc (30 mL×2). The combined organic layers were washed with saturated brine, dried over anhydrous Na₂SO₄ and filtered. The filtrate was concentrated in vacuo. The residue was purified by silica gel column chromatography (DCM/MeOH (V/V)=18/1) to give the title compound as a yellow solid (174 mg, 53.56%). MS (ESI, pos. ion) m/z: 738.0 [M+H]⁺; ¹H NMR (400 MHz, DMSO-d₆) δ 12.09 (s, 1H), 9.72 (s, 1H), 8.04 (d, J=3.1 Hz, 1H), 7.95 (d, J=2.8 Hz, 1H), 7.46-7.37 (m, 4H), 7.18 (td, J=8.4, 2.4 Hz, 1H), 6.93 (d, J=9.0 Hz, 2H), 6.06 (s, 1H), 4.01 (d, J=16.8 Hz, 1H), 3.95-3.89 (m, 2H), 3.87-3.79 (m, 3H), 3.60 (td, J=11.5, 2.1 Hz, 1H), 3.55-3.46 (m, 5H), 3.43-3.38 (m, 2H), 3.05 (td, J=12.4, 2.6 Hz, 1H), 2.91 (d, J=11.1 Hz, 2H), 2.59 (td, J=11.5, 2.8 Hz, 1H), 2.44-2.25 (m, 4H), 2.14 (t, J=10.5 Hz, 1H), 1.81-1.61 (m, 2H).

Example 21: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl) piperidine-4-carboxylic acid Step 1: (R)-tert-butyl 2-(4-(4-(methoxycarbonyl)piperidin-1-yl)phenyl)-3-oxohexahydroimidazo [1,5-a]pyrazine-7(1H)-carboxylate

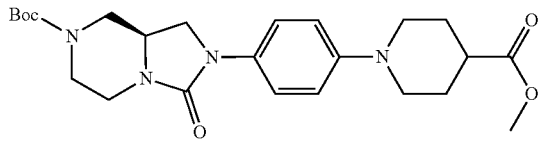 [SMILES: COC(=O)C1CCN(c2ccc(N3C[C@@H]4CN(C(=O)OC(C)(C)C)CCN4C3=O)cc2)CC1]

To a dry flask were added (R)-tert-butyl 2-(4-bromophenyl)-3-oxohexahydroimidazo [1,5-a]pyrazine-7(1H)-carboxylate (913 mg, 2.304 mmol), methyl 4-isonipecotinate (300 mg, 2.095 mmol), palladiumacetate (96 mg, 0.419 mmol), tBuXPhos (367 mg, 0.838 mmol), cesium carbonate (2.39 g 7.34 mmol) and 1,4-dioxane (40 mL). The mixture was stirred at 90° C. for 16 hours under N₂ and cooled to rt, and then filtered by suction, the filtrate was concentrated in vacuo. The residue was purified by silica gel column chromatography (PE/EtOAc (v/v)=1/1) to give the title compound as a light yellow solid (497 mg, 51.72%). MS(ESI, pos. ion) m/z: 459.4 [M+H]⁺.

Step 2: (R)-1-(4-(7-(tert-butoxycarbonyl)-3-oxohexahydroimidazo[1,5-a]pyrazin-2(3H)-yl) phenyl) piperidine-4-carboxylic acid

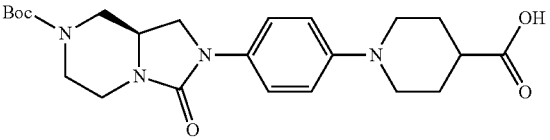 [SMILES: CC(C)(C)OC(=O)N1CCN2C(=O)N(c3ccc(N4CCC(C(=O)O)CC4)cc3)C[C@@H]2C1]

To a flask were added (R)-tert-butyl 2-(4-(4-(methoxycarbonyl)piperidin-1-yl) phenyl)-3-oxohexahydroimidazo [1,5-a]pyrazine-7(1H)-carboxylate (495 mg, 1.079 mmol), methanol (12 mL), tetrahydrofuran (12 mL) and a solution of lithium hydroxide monohydrate (230 mg, 5.48 mmol) in water (4 mL). The mixture was stirred at rt for 12 hours, and then concentrated in vacuo. The residue was diluted with water (60 mL) and adjusted with hydrochloric acid (1 M) to pH 4-5, the resulting mixture was stirred for 30 min and filtered by suction. The filter cake was dried by rotary evaporation in vacuo to get the title compound as a gray solid (440 mg, 91.71%). MS(ESI, pos. ion) m/z: 445.3 [M+H]⁺.

Step 3: (S)-1-(4-(3-oxohexahydroimidazo[1,5-a]pyrazin-2(3H)-yl)phenyl)piperidine-4-carboxylic acid trifluoroacetate

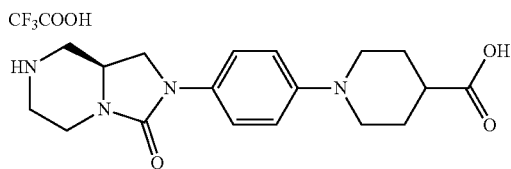 [SMILES: "CF3COOH" ; O=C(O)C1CCN(c2ccc(N3C[C@@H]4CNCCN4C3=O)cc2)CC1]

To a dry flask were added (R)-1-(4-(7-(tert-butoxycarbonyl)-3-oxohexahydroimidazo [1,5-a]pyrazin-2(3H)-yl)phenyl)piperidine-4-carboxylic acid (205 mg, 0.461 mmol), DCM (10 mL) and trifluoroacetic acid (20 ml) in turn, the mixture was stirred for 12 hours. The mixture was concentrated in vacuo, and the residue was diluted with toluene (5 mL), the resulting mixture was concentrated in vacuo, the operation was repeated 3 times to get the title compound as brownish red oil (211 mg, 99.81%). MS(ESI, pos. ion) m/z: 345.3 $[M+H]^+$.

Step 4: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo [1,5-a]pyrazin-2(3H)-yl)phenyl) piperidine-4-carboxylic acid

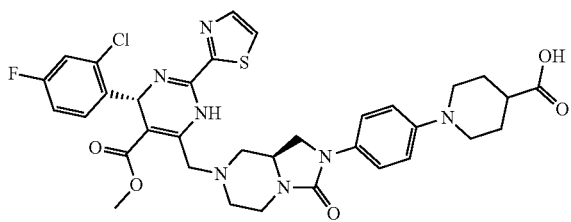 [SMILES: COC(=O)C1=C(CN2CCN3C(=O)N(c4ccc(N5CCC(C(=O)O)CC5)cc4)C[C@@H]3C2)NC(c2nccs2)=N[C@H]1c1ccc(F)cc1Cl]

To a dry flask were added (S)-1-(4-(3-oxohexahydroimidazo[1,5-a]pyrazin-2(3H)-yl)phenyl)piperidine-4-carboxylic acid trifluoroacetate (211 mg, 0.46 mmol), ethanol (15 mL), potassium carbonate (222 mg, 1.61 mmol) and (R)-methyl 6-(bromomethyl)-4-(2-chloro-4-fluorophenyl)-2-(thiazol-2-yl)-1,4-dihydropyrimidine-5-carboxylate (215 mg, 0.48 mmol). The mixture was stirred at rt for 12 hours and concentrated in vacuo to remove the most ethanol, the residue was diluted with water (20 mL) and DCM (20 mL), and then adjusted with hydrochloric acid to pH 4 to 5. The mixture was partitioned, the water phase was extracted with DCM (30 mL×2). The combined organic layers were washed with saturated brine, dried over anhydrous $Na_2SO_4$ and filtered. The filtrate was concentrated in vacuo. The residue was purified by silica gel column chromatography (DCM/MeOH (V/V)=15/1) to give the title compound as a yellow solid (132 mg, 40.49%). $^1$H NMR (400 MHz, $CDCl_3$) δ 9.66 (s, 1H), 7.87 (d, J=3.0 Hz, 1H), 7.48 (d, J=3.0 Hz, 1H), 7.43 (d, J=8.9 Hz, 2H), 7.35-7.29 (m, 1H), 7.16 (dd, J=8.6, 2.4 Hz, 1H), 7.00-6.90 (m, 3H), 6.22 (s, 1H), 4.12 (d, J=17.2 Hz, 1H), 4.07 (d, J=13.9 Hz, 1H), 4.03-3.95 (m, 1H), 3.91 (s, 1H), 3.88 (d, J=7.7 Hz, 1H), 3.62 (s, 3H), 3.60-3.54 (m, 2H), 3.41 (dd, J=9.0, 4.5 Hz, 1H), 3.26 (td, J=12.9, 3.0 Hz, 1H), 2.87 (t, J=8.9 Hz, 2H), 2.82-2.74 (m, 2H), 2.56-2.44 (m, 2H), 2.29 (t, J=10.7 Hz, 1H), 2.12-2.05 (m, 2H), 1.99-1.85 (m, 2H).

Example 22 4-((6-((S)-7-(((R)-6-(2-chloro-4-fluorophenyl)-5-(methoxycarbonyl)-2-(thiazol-2-yl)-3,6-dihydro pyrimidin-4-yl)methyl)-3-oxohexahydroimidazo[1,5-a]pyrazin-2(3H)-yl)pyridin-3-yl)oxy)-3-fluorobenzoic acid Step 1: methyl 4-((6-bromopyridin-3-yl)oxy)-3-fluorobenzoate

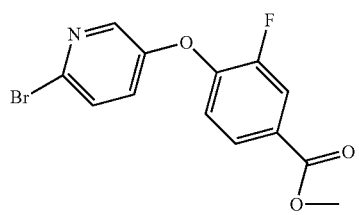 [SMILES: COC(=O)c1ccc(Oc2ccc(Br)nc2)c(F)c1]

To a 25 mL single neck flask were added 2-bromo-5-hydroxypyridine (0.30 g 1.7 mmol), methyl 3,4-fluorobenzoate (0.33 g 1.9 mmol), DMF (10 mL) and potassium carbonate (0.48 g 3.5 mmol). The reaction mixture was stirred at 120° C. for 10 hours and cooled to 25° C., and then diluted with water (20 mL), the resulting mixture was extracted with ethyl acetate (50 mL). The organic layer was washed with saturated brine once, dried over anhydrous sodium sulfate and filtered. The filtrate was concentrated in vacuo and the residue was purified by silica gel column chromatography (PE/EtOAc (v/v)=10/1) to give the title compound as colorless oil (0.53 g 94%). MS (ESI, pos. ion) m/z: 325.9 $[M+H]^+$.

Step 2: (R)-tert-butyl 2-(5-(2-fluoro-4-(methoxycarbonyl)phenoxy)pyridin-2-yl)-3-oxohexahydroimidazo[1,5-a]pyrazin-7(1H)-carboxylate

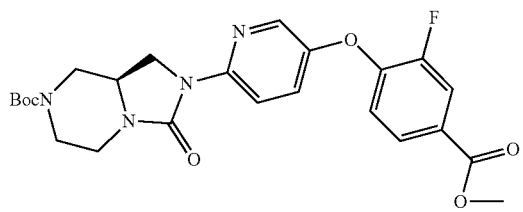 [SMILES: COC(=O)c1ccc(Oc2ccc(N3C[C@@H]4CN(C(=O)OC(C)(C)C)CCN4C3=O)nc2)c(F)c1]

To a 100 mL two-neck flask were added (R)-tert-butyl 4-oxohexahydroimidazo[1,5-a]pyrazine-7(1H)-carboxylate (320 mg, 1.33 mmol), methyl 4-((6-bromopyridin-3-yl)oxy)-3-fluorobenzoate (432 mg, 1.33 mmol), tris(dibenzylideneacetone)dipalladium (121 mg, 0.13 mmol), 4,5-bis(diphenylphosphino)-9,9-dimethylxanthene (153 mg, 0.26 mmol), cesium carbonate (0.86 g 2.65 mmol) and 1,4-dioxane (20 mL). The reaction mixture was stirred at 100° C. for 3 hours and concentrated in vacuo. The residue was purified by silica gel column chromatography (PE/EtOAc (v/v)=2/1) to give the title compound as a white solid (0.40 g 62%). MS (ESI, pos. ion) m/z: 487.1 $[M+H]^+$.

Step 3: (R)-4-((6-(7-(tert-butoxycarbonyl)-3-oxo-hexahydroimidazo[1,5-a]pyrazin-2(3H)-yl) pyridin-3-yl)oxy)-3-fluorobenzoic acid

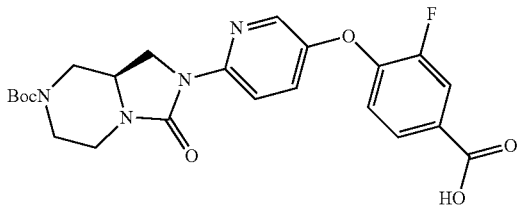 [SMILES: CC(C)(C)OC(=O)N1CCN2C(=O)N(c3ccc(Oc4ccc(C(=O)O)cc4F)cn3)C[C@@H]2C1]

To a 50 mL single neck flask were added (R)-tert-butyl 2-(5-(2-fluoro-4-(methoxycarbonyl)phenoxy)pyridin-2-yl)-3-oxohexahydroimidazo[1,5-a]pyrazin-7(1H)-carboxylate (0.40 g 0.82 mmol), methanol (10 mL), water (10 mL) and lithium hydroxide monohydrate (0.17 g 4.1 mmol). The mixture was stirred at 50° C. for 1 hour and concentrated in vacuo, the residue was diluted with water (10 mL) and EtOAc (4 mL), and then adjusted with hydrochloric acid (2 M) to pH 6. A solid precipitated out and the mixture was stirred additional 0.5 hour and filtered, the filter cake was dried to get the title compound as a light yellow solid (0.30 g 77%). MS (ESI, pos. ion) m/z: 473.1.3 [M+H]$^+$.

Step 4: (S)-3-fluoro-4-((6-(3-oxohexahydroimidazo[1,5-a]pyrazin-2(3H)-yl)pyridin-3-yl)oxy) benzoic acid hydrochloride

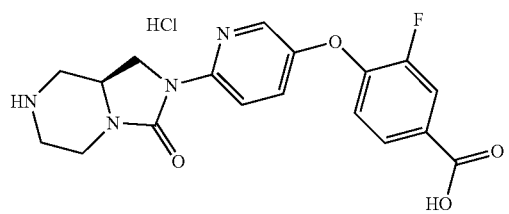 [SMILES: O=C(O)c1ccc(Oc2ccc(N3C[C@@H]4CNCCN4C3=O)nc2)c(F)c1 ; Cl]

To a 25 mL single neck flask were added (R)-4-((6-(7-(tert-butoxycarbonyl)-3-oxohexahydroimidazo[1,5-a]pyrazin-2(3H)-yl)pyridin-3-yl)oxy)-3-fluorobenzoic acid (0.28 g 0.59 mmol) and a solution of HCl in 1,4-dioxane (4 mol/L, 10 mL). The reaction mixture was stirred at 25° C. for 16 hours and concentrated in vacuo to get the title compound as a white solid (0.24 g 99%).

Step 5: 4-((6-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)oxy)-3-fluorobenzoic acid

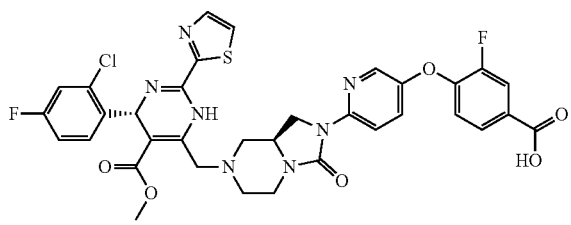 [SMILES: COC(=O)C1=C(CN2CCN3C(=O)N(c4ccc(Oc5ccc(C(=O)O)cc5F)cn4)C[C@@H]3C2)NC(c2nccs2)=N[C@H]1c1ccc(F)cc1Cl]

To a 50 mL flask were added (S)-3-fluoro-4-((6-(3-oxohexahydroimidazo[1,5-a]pyrazin-2(3H)-yl)pyridin-3-yl)oxy)benzoic acid hydrochloride (0.24 g 0.59 mmol), (R)-methyl 6-(bromomethyl)-4-(2-chloro-4-fluorophenyl)-2-(thiazol-2-yl)-1,4-dihydropyrimidine-5-carboxylate (0.26 g 0.59 mmol), potassium carbonate (160 mg, 1.20 mmol) and EtOH (30 mL). The mixture was stirred at 35° C. for 4 hours and filtered, the filter cake was washed with EA (5 mL). The combined filtrates were concentrated, the residue was diluted with EA (20 mL) and water (10 mL), the mixture was adjusted with concentrated hydrochloric acid to pH 5, the water phase was abandoned, the organic layers was washed with saturated aqueous NaCl (10 mL) and concentrated, the residue was purified by silica gel column chromatography (DCM/MeOH (V/V)=15/1) to give the title compound as a yellow solid (0.20 g 46.0%). MS (ESI, pos. ion) m/z: 736.3 [M+H]$^+$; $^1$H NMR (600 MHz, CD$_3$OD) δ 8.29 (d, J=9.2 Hz, 1H), 8.12 (d, J=2.6 Hz, 1H), 7.98 (d, J=2.8 Hz, 1H), 7.85 (dd, 15.8, 10.2 Hz, 2H), 7.77 (d, J=2.8 Hz, 1H), 7.53 (dd, J=9.2, 2.6 Hz, 1H), 7.45 (dd, J=8.4, 6.2 Hz, 1H), 7.25 (dd, J=8.6, 2.1 Hz, 1H), 7.10-7.04 (m, 2H), 6.19 (s, 1H), 4.22-4.13 (m, 2H), 4.08-3.95 (m, 3H), 3.75 (dd, J=10.8, 4.5 Hz, 1H), 3.61 (s, 3H), 3.31-3.28 (m, 1H), 3.08-3.02 (m, 2H), 2.54-2.47 (m, 1H), 2.32-2.25 (m, 1H).

Example 23: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy) cyclohexane carboxylic acid Step 1: methyl 4-(3-bromo-5-fluoropheoxy)cyclohexanecarboxylate

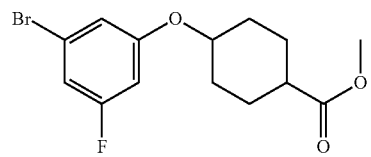 [SMILES: COC(=O)C1CCC(Oc2cc(F)cc(Br)c2)CC1]

To a 25 mL three-neck flask were added 3-bromo-5-fluoro-phenol (110 mg, 0.58 mmol), methyl 4-hydroxycyclohexanecarboxylate (100 mg, 0.631 mmol), triphenylphosphine (208 mg, 0.79 mmol) and anhydrous THF (3 mL). To the mixture was added a solution of DIAD (178 mg, 0.86 mmol) in THF (2.0 mL) dropwise under N$_2$ in an ice bath. After the addition, the mixture was warmed naturally to rt and stirred for 10 hours. After the reaction was complete, the mixture was concentrated. The residue was purified by silica gel column chromatography (PE/EtOAc (V/V)=20/1) to give the title compound as colorless oil (62 mg, 32.50%). $^1$H NMR (400 MHz, CDCl$_3$) δ 6.90-6.76 (m, 2H), 6.62-6.50 (m, 1H), 4.52-4.35 (m, 1H), 3.71 (s, 3H), 2.50-2.32 (m, 1H), 2.21-2.05 (m, 1H), 2.04-1.85 (m, 3H), 1.84-1.71 (m, 2H), 1.71-1.58 (m, 2H).

Step 2: (R)-methyl 4-(2-chloro-4-fluorophenyl)-6-(((S)-2-(3-fluoro-5-((4-(methoxycarbonyl) cyclohexyl)oxy)phenyl)-3-oxohexahydroimidazo[1,5-a]pyrazin-7(1H)-yl)methyl)-2-me (thiazol-2-yl)-1,4-dihydropyrimidine-5-carboxylate

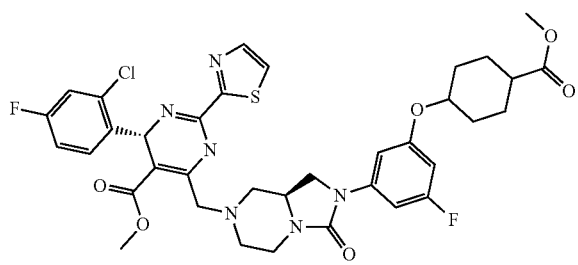 [SMILES: COC(=O)C1=C(CN2CCN3C(=O)N(c4cc(F)cc(OC5CCC(C(=O)OC)CC5)c4)C[C@@H]3C2)NC(c2nccs2)=N[C@H]1c1ccc(F)cc1Cl]

To a two-neck flask were added methyl 4-(3-bromo-5-fluoropheoxy)cyclohexanecarboxylate (793 mg, 2.40 mmol), (R)-methyl 4-(2-chloro-4-fluorophenyl)-6-(((R)-3-oxohexahydroimidazo[1,5-a]pyrazin-7(1H)-yl)methyl)-2-(thiazol-2-yl)-1,4-dihydropyrimidine-5-carboxylate (1.00 g, 1.98 mmol), tris(dibenzylideneacetone)dipalladium (181 mg, 0.20 mmol), XantPhos (229 mg, 0.40 mmol), cesium carbonate (1.29 g 3.96 mmol) and dioxane (15 mL). The reaction mixture was stirred at 90° C. for 8 hours and diluted with EtOAc (60 mL) and water (30 mL). The organic layer was washed with saturated brine, dried over anhydrous $Na_2SO_4$, and concentrated in vacuo. The residue was purified by silica gel column chromatography (PE/EtOAc (V/V)= 2/1) to give the title compound as a yellow foam solid (435 mg, 29.1%). MS (ESI, pos. ion) m/z: 755.0 $[M+H]^+$.

Step 3: 4-(3-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-5-fluorophenyloxy)cyclohexanecarboxylic acid

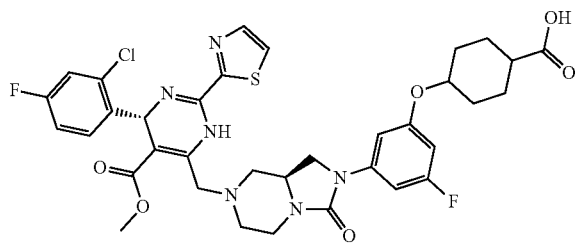 [SMILES: COC(=O)C1=C(CN2CCN3C(=O)N(c4cc(F)cc(OC5CCC(C(=O)O)CC5)c4)C[C@@H]3C2)NC(c2nccs2)=N[C@H]1c1ccc(F)cc1Cl]

To a flask were added (R)-methyl 4-(2-chloro-4-fluorophenyl)-6-(((S)-2-(3-fluoro-5-((4-(methoxycarbonyl)cyclohexyl)oxy)phenyl)-3-oxohexahydroimidazo[1,5-a]pyrazin-7(1H)-yl) methyl)-2-(thiazol-2-yl)-1,4-dihydropyrimidine-5-carboxylate (420 mg, 0.56 mmol), THF (4 mL), water (1 mL) and lithium hydroxide monohydrate (48 mg, 1.14 mmol), the mixture was stirred at 45° C. for 7 hours, and water (15 mL) was added, the resulting mixture was extracted with petroleum ether (7 mL), the organic layer was abandoned, to the water phase was added EtOAc (30 mL), and the mixture was adjusted with dilute hydrochloric acid to pH 5, the organic layer was washed with saturated aqueous NaCl once and dried over anhydrous sodium sulfate, and then concentrated in vacuo, the residue was purified by silica gel column chromatography (DCM/MeOH (V/V)=20/1) to give the title compound as a yellow foam solid (270 mg, 65.50%). MS (ESI, pos. ion) m/z: 741.4 $[M+H]^+$; $^1H$ NMR (400 MHz, $CDCl_3$) δ 9.60 (s, 1H), 7.85 (d, J=3.1 Hz, 1H), 7.46 (d, J=3.1 Hz, 1H), 7.31-7.26 (m, 1H), 7.13 (dd, J=8.6, 2.5 Hz 1H), 7.01 (s, 1H), 6.95-6.83 (m, 2H), 6.31 (d, J=10.5 Hz, 1H), 6.20 (s, 1H), 4.47 (s, 1H), 4.11 (d, 1H), 4.07-3.94 (m, 2H), 3.92-3.81 (m, 2H), 3.59 (s, 3H), 3.37 (dd, J=9.1, 4.7 Hz, 1H), 3.29-3.21 (m, 1H), 2.88 (d, J=10.0 Hz, 2H), 2.53-2.39 (m, 2H), 2.24 (t, J=10.8 Hz, 1H), 2.06-1.87 (m, 4H), 1.83-1.73 (m, 2H), 1.70-1.58 (m, 2H).

Example 24: (1R,4s)-4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenyloxy)cyclohexane carboxylic acid Step 1: methyl (1r,4r)-4-hydroxycyclohexane carboxylate

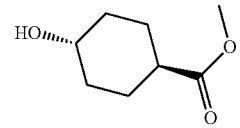

(1r,4r)-Methyl 4-hydroxycyclohexanecarboxylate (1.57 g 10.9 mmol) was dissolved in MeOH (9.0 mL), and to the solution was added $H_2SO_4$ (0.08 mL) slowly under $N_2$ at rt, after the addition, the mixture was warmed up to 60° C. slowly and stirred for 12 hours. After that, the reaction was quenched with saturated aqueous sodium bicarbonate solution (20 mL) and extracted with EA (20 mL×3). The combined organic layers were dried over anhydrous sodium sulfate and concentrated in vacuo to get the title compound as yellow oil (1.38 g 80.10%).

Step 2: methyl (1s,4s)-4-(3-bromo-5-fluorophenyloxy)cyclohexane carboxylate

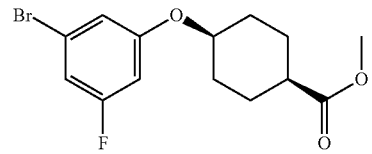 [SMILES: COC(=O)[C@H]1CC[C@@H](Oc2cc(F)cc(Br)c2)CC1]

3-Bromo-5-fluoro-phenol (1.39 g 7.28 mmol) was dissolved in anhydrous THF (25 mL), to the solution was added (1r,4r)-methyl 4-hydroxycyclohexanecarboxylate (1.38 g 8.72 mmol), $PPh_3$ (2.34 g, 8.74 mmol) and DIAD (1.80 g 8.72 mmol) under $N_2$ in one portion. The reaction mixture was stirred at rt for 12 hours under $N_2$ and concentrated in vacuo. The residue was purified by silica gel column chromatography (PE/EtOAc (v/v)=20/1) to give the title compound as colorless (1.61 g 66.80%). $^1H$ NMR (400 MHz, $CDCl_3$) δ 6.88-6.78 (m, 2H), 6.58-6.53 (m, 1H), 4.43 (s, 1H), 3.69 (s, 3H), 2.46-2.37 (m, 1H), 2.03-1.86 (m, 4H), 1.82-1.71 (m, 2H), 1.64 (t, J=12.5 Hz, 2H).

Step 3: (R)-tert-butyl 2-(3-fluoro-5-(((1s,4S)-4-(methoxycarbonyl)cyclohexyl)oxy)phenyl)-3-oxohexahydroimidazo[1,5-a]pyrazine-7(1H)-carboxylate

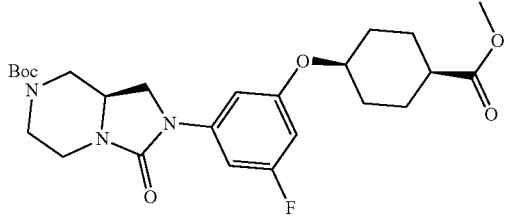 [SMILES: COC(=O)[C@H]1CC[C@@H](Oc2cc(F)cc(N3C[C@@H]4CNCCN4C3=O)c2)CC1]

Methyl (1s,4s)-4-(3-bromo-5-fluorophenyloxy)cyclohexane carboxylate (1.61 g 4.86 mmol), (R)-tert-butyl 3-oxohexahydroimidazo[1,5-a]pyrazine-7(1H)-carboxylate (1.29 g 5.35 mmol), Pd$_2$(dba)$_3$ (229 mg, 0.24 mmol), Xantphos (290 mg, 0.49 mmol) and Cs$_2$CO$_3$ (3.14 g 9.63 mmol) were added to 1,4-dioxane (60 mL). The mixture was stirred at 90° C. for 4 hours and EA (50 mL) was added. The organic layer was washed with water (50 mL), and the water phase was extracted with EA (30 mL). The organic layers were combined. The combined organic layers were dried over anhydrous sodium sulfate and filtered. The filtrate was concentrated in vacuo to dry and the residue was purified by silica gel column chromatography (PE/EtOAc (v/v)=2/1) to give the title compound as a light yellow foam solid (1.57 g 65.70%). MS (ESI, pos. ion) m/z: 436.1 [M−56+H]$^+$.

Step 4: (1S,4s)-4-(3-((R)-7-(tert-butoxycarbonyl)-3-oxohexahydroimidazo[1,5-a]pyrazin-2(3H)-yl)-5-fluorophenoxy)cyclohexanecarboxylic acid

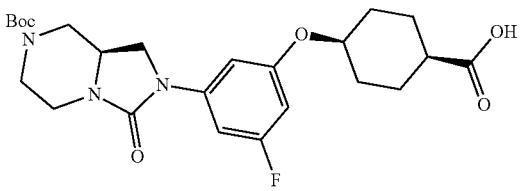 [SMILES: O=C1N(c2cc(F)cc(O[C@H]3CC[C@@H](C(=O)O)CC3)c2)C[C@@H]2CNCCN12]

(R)-tert-Butyl 2-(3-fluoro-5-(((1s,4S)-4-(methoxycarbonyl)cyclohexyl)oxy)phenyl)-3-oxohexahydroimidazo[1,5-a]pyrazine-7(1H)-carboxylate (1.57 g 3.19 mmol) was dissolved in THF (25 mL). To the solution were added MeOH (15 mL) and a solution of NaOH (640 mg, 16 mmol) in H$_2$O (15 mL), the mixture was stirred at 60° C. for 2.5 hours and adjusted with dilute hydrochloric acid (1 M) to pH 5 to 6, the resulting mixture was extracted with (30 mL×2). The combined organic layers were dried over anhydrous sodium sulfate and filtered. The filtrate was concentrated in vacuo to give the title compound as a white-yellow foam solid (1.47 g 96.40%).

Step 5: (1R,4s)-4-(3-fluoro-5-((S)-3-oxohexahydroimidazo[1,5-a]pyrazin-2(3H)-yl)phenoxy) cyclohexanecarboxylic acid trifluoroacetate

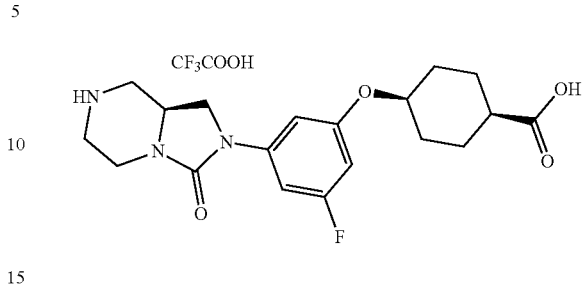

(1S,4s)-4-(3-((R)-7-(tert-Butoxycarbonyl)-3-oxohexahydroimidazo[1,5-a]pyrazin-2(3H)-yl)-5-fluorophenoxy)cyclohexanecarboxylic acid (1.47 g 3.08 mmol), was dissolved in DCM (3 mL), and TFA (5 mL) was added. The mixture was stirred at rt for 1 hour and concentrated in vacuo to get the title compound as yellow oil (1.51 g 99.74%).

Step 6: (1R,4s)-4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy) cyclohexane carboxylic acid

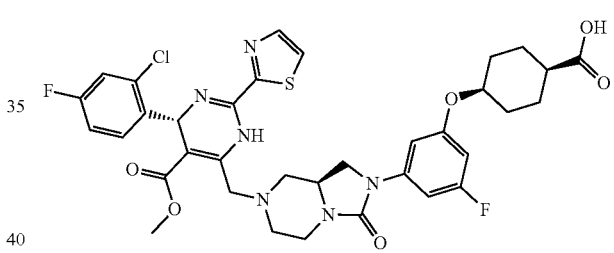

To a dry flask were added (1R,4s)-4-(3-fluoro-5-((S)-3-oxohexahydroimidazo[1,5-a]pyrazin-2(3H)-yl)phenoxy)cyclohexanecarboxylic acid trifluoroacetate (1.2 g 2.45 mmol), (R)-methyl 6-(bromomethyl)-4-(2-chloro-4-fluorophenyl)-2-(thiazol-2-yl)-1,4-dihydro pyrimidine-5-carboxylate (1.09 g 2.45 mmol), potassium carbonate (1.70 g 12.3 mmol) and ethanol (40 mL). The reaction mixture was stirred at rt for 12 hours and diluted with EA (50 mL) and water (50 mL), and then adjusted with hydrochloric acid (1 M) to pH 5-6. The water phase was extracted with ethyl acetate (30 mL). The combined organic phases were dried over anhydrous sodium sulfate, filtered, and the filtrate was concentrated in vacuo. The residue was purified by silica gel chromatograph (DCM/CH$_3$OH (V/V)=40/1) to give the title compound as a yellow solid (1.16 g 50.90%). MS (ESI, pos. ion) m/z: 741.1[M+H]$^+$. $^1$H NMR (400 MHz, CDCl$_3$) δ 7.86 (d, J=3.0 Hz, 1H), 7.52 (d, J=3.0 Hz, 1H), 7.32 (dd, J=8.6, 6.0 Hz, 1H), 7.15 (dd, J=8.4, 2.4 Hz, 1H), 7.01-6.93 (m, 2H), 6.92-6.87 (m, 1H), 6.37-6.32 (m, 1H), 6.17 (s, 1H), 4.61 (d, J=15.4 Hz, 1H), 4.47 (s, 1H), 4.39-4.24 (m, 2H), 4.15-4.08 (m, 1H), 3.94 (t, J=9.0 Hz, 1H), 3.61 (s, 3H), 3.55-3.47 (m, 2H), 3.42 (dd, J=9.7, 3.4 Hz, 2H), 2.92-2.76 (m, 2H), 2.50-2.42 (m, 1H), 2.06-1.99 (m, 2H), 1.98-1.87 (m, 2H), 1.83-1.74 (m, 2H), 1.69-1.62 (m, 2H).

Example 25: (1S,4r)-4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)cyclohexanecarboxylic acid Step 1: methyl (1s,4s)-4-hydroxycyclohexane carboxylate

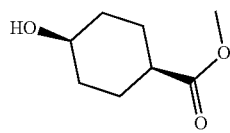

(1s,4s)-4-Hydroxycyclohexane carboxylic acid (1.57 g 10.9 mmol) was dissolved in MeOH (9.0 mL), to the solution was added $H_2SO_4$ (0.08 mL) slowly under $N_2$ at rt, after the addition, the mixture was warmed up to 60° C. and stirred for 12 hours. The reaction was quenched with saturated aqueous sodium bicarbonate solution (20 mL) and extracted with EA (20 mL×3). The combined organic layers were dried over anhydrous sodium sulfate and filtered. The filtrate was concentrated in vacuo to give the title compound as yellow oil (1.36 g 78.90%).

Step 2: methyl (1r,4r)-4-(3-bromo-5-fluorophenoxy)cyclohexane carboxylate

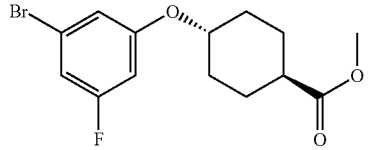 [SMILES: COC(=O)[C@H]1CC[C@H](Oc2cc(F)cc(Br)c2)CC1]

3-Bromo-5-fluoro-phenol (1.37 g 7.17 mmol) was dissolved in anhydrous THF (25 mL), to the solution was added (1s,4s)-methyl 4-hydroxycyclohexanecarboxylate (1.36 g 8.60 mmol), $PPh_3$ (2.30 g 8.59 mmol) and DIAD (1.78 g 8.63 mmol) under $N_2$. The reaction mixture was stirred at rt for 12 hours under $N_2$ and concentrated in vacuo. The residue was purified by silica gel column chromatography (PE/EtOAc (v/v)=20/1) to give the title compound as colorless (1.05 g 44.2%). $^1$H NMR (400 MHz, $CDCl_3$) b 6.86-6.79 (m, 2H), 6.56-6.50 (m, 1H), 4.43 (s, 1H), 3.69 (s, 3H), 2.43-2.37 (m, 1H), 2.03-1.87 (m, 4H), 1.81-1.72 (m, 2H), 1.69-1.60 (m, 2H).

Step 3: (R)-tert-butyl 2-(3-fluoro-5-(((1r,4R)-4-(methoxycarbonyl)cyclohexyl)oxy)phenyl)-3-oxohexahydroimidazo[1,5-a]pyrazin-7(1H)-carboxylate

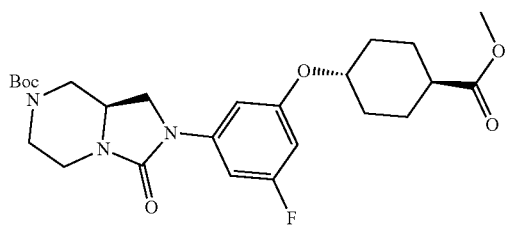 [SMILES: COC(=O)[C@H]1CC[C@H](Oc2cc(F)cc(N3C[C@@H]4CNCCN4C3=O)c2)CC1]

To a 100 mL flask were added methyl (1 r,4r)-4-(3-bromo-5-fluorophenyloxy)cyclohexane carboxylate (1.05 g, 3.17 mmol), (R)-tert-butyl 3-oxohexahydroimidazo[1,5-a]pyrazine-7(1H)-carboxylate (841 mg, 3.49 mmol), $Pd_2(dba)_3$ (150 mg, 0.16 mmol), Xantphos (189 mg, 0.32 mmol) and $Cs_2CO_3$ (2.05 g 6.29 mmol) in turn, and then 1,4-dioxane (40 mL) was added under $N_2$. The reaction mixture was stirred at 90° C. for 4 hours and diluted with EA (50 mL), the organic layer was washed with water (50 mL) and the water phase was extracted with EA (30 mL). The combined organic phases were dried over anhydrous sodium sulfate, filtered, and the filtrate was concentrated in vacuo. The residue was purified by silica gel chromatograph (PE/EA (V/V)=2/1) to give the title compound as a light yellow form solid (1.03 g 66.1%). MS (ESI, pos. ion) m/z: 436.1 [M−56+H]$^+$.

Step 4: (1R,4r)-4-(3-((R)-7-(tert-butoxycarbonyl)-3-oxohexahydroimidazo[1,5-a]pyrazin-2(3H)-yl)-5-fluorophenoxy)cyclohexane carboxylic acid

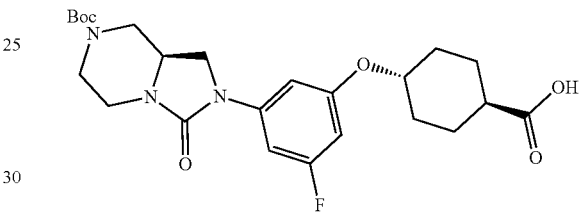

(R)-tert-Butyl 2-(3-fluoro-5-(((1r,4R)-4-(methoxycarbonyl)hexyl)oxy)phenyl)-3-oxohexahydroimidazo[1,5-a]pyrazine-7(1H)-carboxylate (1.03 g 2.10 mmol) was dissolved in THF (15 mL). To the solution were added MeOH (15 mL) and a solution of NaOH (420 mg, 10.5 mmol) in $H_2O$ (15 mL) in turn. The mixture was stirred at rt for 1 hour and adjusted with dilute hydrochloric acid (1 M) to pH 5 to 6, the resulting mixture was extracted with EA (30 mL×2). The organic layers were combined. The combined organic layers were dried over anhydrous sodium sulfate and filtered. The filtrate was concentrated in vacuo to give the title compound as a white-yellow foam solid (830 mg, 83.0%).

Step 5: (1S,4r)-4-(3-fluoro-5-((S)-3-oxohexahydroimidazo[1,5-a]pyrazin-2(3H)-yl)phenoxy) cyclohexane carboxylic acid trifluoroacetate

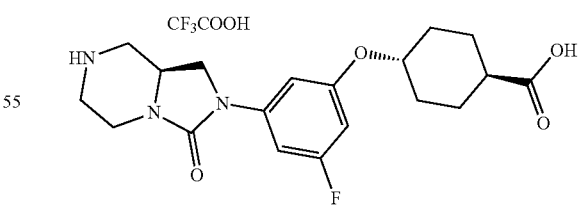

(1R,4r)-4-(3-((R)-7-(tert-Butoxycarbonyl)-3-oxohexahydroimidazo[1,5-a]pyrazin-2(3H)-yl)-5-fluorophenoxy)cyclohexane carboxylic acid (830 mg, 1.74 mmol) was dissolved in DCM (10 mL), and TFA (5 mL) was added, the mixture was stirred at rt for 2.5 hours and concentrated in vacuo to get the title compound as yellow oil (845 mg, 98.9%).

Step 6: (1S,4r)-4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)cyclohexane carboxylic acid

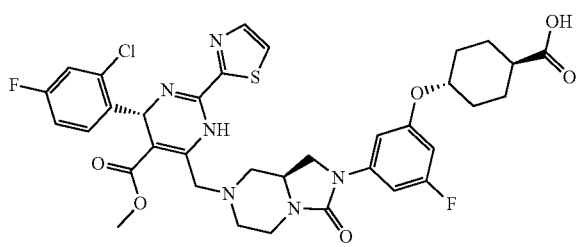 [SMILES: COC(=O)C1=C(CN2CCN3C(=O)N(c4cc(F)cc(O[C@H]5CC[C@H](C(=O)O)CC5)c4)C[C@@H]3C2)NC(c2nccs2)=N[C@H]1c1ccc(F)cc1Cl]

(1S,4r)-4-(3-Fluoro-5-((S)-3-oxohexahydroimidazo[1,5-a]pyrazin-2(3H)-yl)phenoxy)cyclohexanecarboxylic acid trifluoroacetate (845 mg, 1.72 mmol) was dissolved in EtOH (20 mL), (R)-methyl 6-(bromomethyl)-4-(2-chloro-4-fluorophenyl)-2-(thiazol-2-yl)-1,4-dihydro pyrimidine-5-carboxylate (842 mg, 1.89 mmol) and potassium carbonate (950 mg, 6.88 mmol) were added. The reaction mixture was stirred at rt for 12 hours and diluted with EA (50 mL) and water (50 mL), and then adjusted with hydrochloric acid (1 M) to pH 5-6. The water phase was extracted with ethyl acetate (30 mL). The organic layers were combined. The combined organic layers were dried over anhydrous sodium sulfate and filtered. The filtrate was concentrated in vacuo and the residue was purified by silica gel column chromatography (DCM/CH$_3$OH (V/V)=40/1) to give the title compound as a yellow solid (945 mg, 74.03%). MS (ESI, pos. ion) m/z: 741.1[M+H]$^+$; $^1$H NMR (400 MHz, CDCl$_3$) δ 7.87 (d, J=3.1 Hz, 1H), 7.53 (d, J=3.1 Hz, 1H), 7.35-7.29 (m, 1H), 7.15 (dd, J=8.3, 2.5 Hz, 1H), 7.02-6.93 (m, 2H), 6.85 (d, J=11.0 Hz, 1H), 6.34 (d, J=10.5 Hz, 1H), 6.17 (s, 1H), 4.62 (d, J=15.4 Hz, 1H), 4.41-4.25 (m, 2H), 4.24-4.16 (m, 1H), 4.15-4.09 (m, 1H), 3.94 (t, J=9.1 Hz, 1H), 3.61 (s, 3H), 3.57-3.48 (m, 3H), 3.41 (dd, J=9.6, 3.2 Hz, 2H), 2.93-2.79 (m, 1H), 2.43-2.35 (m, 1H), 2.15 (dd, J=26.3, 12.0 Hz, 4H), 1.69-1.58 (m, 2H), 1.54-1.43 (m, 2H).

Example 26: (R)-methyl 4-(2-chloro-4-fluorophenyl)-6-(((S)-2-(4-(1-cyanocyclopropyl)phenyl)-3-oxohexahydroimidazo[1,5-a]pyrazin-7(1H)-yl)methyl)-2-thiazol-2-yl)-1,4-dihydropyrimidine-5-carboxylate Step 1: (R)-tert-butyl 2-(4-(1-cyanocyclopropyl)phenyl)-3-oxohexahydroimidazo[1,5-a]pyrazine-7(1H)-carboxylate

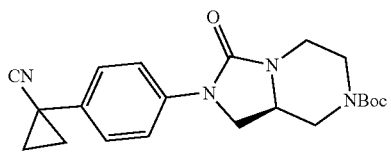 [SMILES: CC(C)(C)OC(=O)N1CCN2C(=O)N(c3ccc(C4(C#N)CC4)cc3)C[C@@H]2C1]

1-(4-Bromophenyl)cyclopropanecarbonitrile (200 mg, 0.9 mmol), (R)-tert-butyl 3-oxohexahydroimidazo[1,5-a]pyrazine-7(1H)-carboxylate (239 mg, 0.99 mmol), palladiumacetate (42 mg, 0.178 mmol), 2-di-tert-butylphosphino-2',4',6'-trisopropylbinphenyl (157 mg, 0.36 mmol), cesium carbonate (881 mg, 2.70 mmol) were dissolved in 1,4-dioxane (10 mL) under N$_2$. The reaction mixture was stirred at 90° C. for 12 hours and filtered. The filtrate was concentrated in vacuo. The residue was purified by silica gel column chromatography (PE/EtOAc (v/v)=4/1) to give the title compound as a white solid (300 mg, 87.09%). MS (ESI. pos) m/z: 405.30 [M+Na]$^+$.

Step 2: (S)-1-(4-(3-oxohexahydroimidazo[1,5-a]pyrazin-2(3H)-yl)phenyl)cyclopropane carbonitrile trifluoroacetate

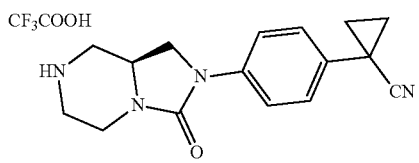 [SMILES: "CF3COOH" ; N#CC1(c2ccc(N3C[C@@H]4CNCCN4C3=O)cc2)CC1]

(R)-tert-Butyl 2-(4-(1-cyanocyclopropyl)phenyl)-3-oxohexahydroimidazo[1,5-a]pyrazine-7(1H)-carboxylate (300 mg, 0.78 mmol) was dissolved in DCM (6 mL) at rt, and TFA (1 mL) was added. The mixture was stirred at rt for 2 hour and concentrated in vacuo to get the title compound as brown oil (310 mg, 100%). MS (ESI. pos) m/z: 283.20 [M+H]$^+$.

Step 3: (R)-methyl 4-(2-chloro-4-fluorophenyl)-6-(((S)-2-(4-(1-cyanopropyl)phenyl)-3-oxohexahydroimidazo[1,5-a]pyrazin-7(1H)-yl)methyl)-2-(thiazol-2-yl)-1,4-dihydropyrimidine-5-carboxylate

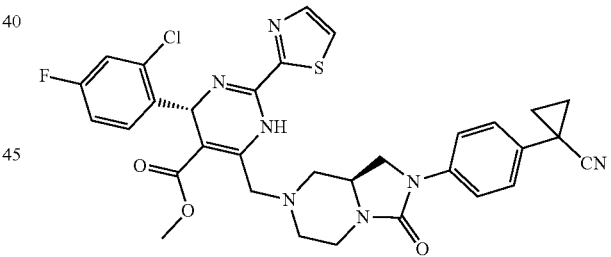

To a dry flask were added (S)-1-(4-(3-oxohexahydroimidazo[1,5-a]pyrazin-2(3H)-yl) phenyl)cyclopropanecarbonitrile trifluoroacetate (310 mg, 0.78 mmol), anhydrous ethanol (10 mL), DMF (4 mL), potassium carbonate (324 mg, 2.34 mmol) and (R)-methyl 6-(bromomethyl)-4-(2-chloro-4-fluorophenyl)-2-(thiazol-2-yl)-1,4-dihydropyrimidine-5-carboxy late (382 mg, 0.86 mmol). The mixture was stirred at rt for 13 hours and diluted with water (2 mL), the mixture was stirred for additional 30 min and filtered to get a crude product. To the crude product was added ethanol (8 mL), and the mixture was stirred at rt for 4 hours and filtered to get the title compound as a yellow solid (450 mg, 89.06%). MS (ESI. pos) m/z: 647.10 [M+H]$^+$; $^1$H NMR (400 MHz, CDCl$_3$) δ 9.62 (s, 1H), 7.87 (d, J=2.7 Hz, 1H), 7.55 (d, J=8.5 Hz, 2H), 7.48 (d, J=2.7 Hz, 1H), 7.33-7.24 (m, 3H), 7.15 (d, J=8.3 Hz, 1H), 6.97-6.91 (m, 1H), 6.22 (s, 1H), 4.19-3.97 (m, 3H), 3.95-3.82 (m, 2H), 3.61 (s, 3H), 3.43 (dd, J=8.7, 4.6

Hz, 1H), 3.27 (t, J=11.1 Hz, 1H), 2.90 (d, J=10.3 Hz, 2H), 2.52 (t, J=10.2 Hz, 1H), 2.27 (t, J=10.7 Hz, 1H), 1.74-1.65 (m, 2H), 1.40-1.33 (m, 2H).

Example 27: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)cyclopropane carboxylic acid Step 1: (R)-tert-butyl 2-(4-(1-(methoxycarbonyl)cyclopropyl)phenyl)-3-oxohexahydroimidazo [1,5-a]pyrazine-7(1H)-carboxylate

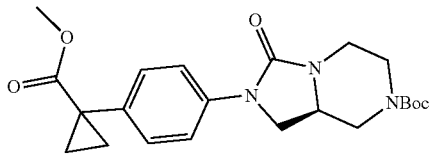 [SMILES: COC(=O)C1(c2ccc(N3C[C@@H]4CN(C(=O)OC(C)(C)C)CCN4C3=O)cc2)CC1]

Methyl 1-(4-bromophenyl)cyclopropanecarboxylate (200 mg, 0.78 mmol), (R)-tert-butyl 3-oxohexahydroimidazo[1,5-a]pyrazine-7(1H)-carboxylate (208 mg, 0.86 mmol), palladium acetate (37 mg, 0.16 mmol), 2-di-tert-butylphosphino-2',4',6'-trisopropylbinphenyl (137 mg, 0.31 mmol), cesium carbonate (767 mg, 2.35 mmol) were dissolved in 1,4-dioxane (20 mL) under $N_2$. The reaction mixture was stirred at 90° C. for 17 hours and filtered. The filtrate was concentrated in vacuo. The residue was purified by silica gel column chromatography (PE/EtOAc (v/v)=4/1) to give the title compound as a white solid (225 mg, 70%). MS (ESI, pos. ion) m/z: 438.10 [M+Na]$^+$.

Step 2: (R)-1-(4-(7-(tert-butoxycarbonyl)-3-oxohexahydroimidazo[1,5-a]pyrazin-2(3H)-yl) phenyl)cyclopropane carboxylic acid

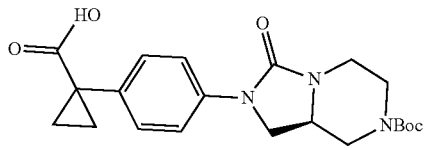 [SMILES: CC(C)(C)OC(=O)N1CCN2C(=O)N(c3ccc(C4(C(=O)O)CC4)cc3)C[C@@H]2C1]

(R)-tert-Butyl 2-(4-(1-(methoxycarbonyl)cyclopropyl)phenyl)-3-oxohexahydroimidazo [1,5-a]pyrazine-7(1H)-carboxylate (365 mg, 0.8785 mmol) was dissolved in a mixed methanol (8 mL) and THF (12 mL) solvent, to the solution was added a solution of sodium hydroxide (185 mg, 4.44 mmol) in water (5 mL). The reaction mixture was stirred at 50° C. for 0.5 hours and concentrated in vacuo, and then diluted with water (10 mL) and EtOAc (10 mL), the organic layer was abandoned. To the water phase was added DCM (10 mL), the mixture was adjusted with dilute hydrochloric acid (1 M) to pH 5, the water phase was extracted with DCM (10 mL×3). The combined organic layers were dried over anhydrous sodium sulfate and concentrated in vacuo to get the title compound as a white solid (307 mg, 87.04%). MS (ESI, pos. ion) m/z: 424.10 [M+Na]$^+$.

Step 3: (S)-1-(4-(3-oxohexahydroimidazo[1,5-a]pyrazin-2(3H)-yl)phenyl)cyclopropane carboxylic acid trifluoroacetate

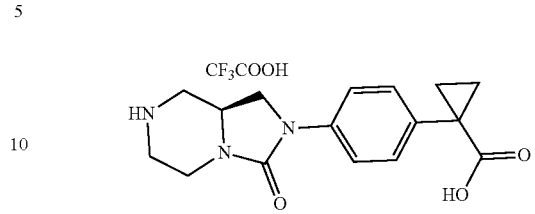

To a dry flask were added (R)-1-(4-(7-(tert-butoxycarbonyl)-3-oxohexahydroimidazo [1,5-a]pyrazin-2(3H)-yl)phenyl)cyclopropane carboxylic acid (310 mg, 0.77 mmol) and DCM (6 mL) in turn, and then trifluoroacetic acid (3 ml) was added. The mixture was stirred at rt for 1 hour and concentrated in vacuo to get the title compound as brown liquid (320 mg, 99.77%). MS (ESI, pos. ion) m/z: 302.10 [M+H]$^+$.

Step 4: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo [1,5-a]pyrazin-2(3H)-yl)phenyl)cyclopropane carboxylic acid

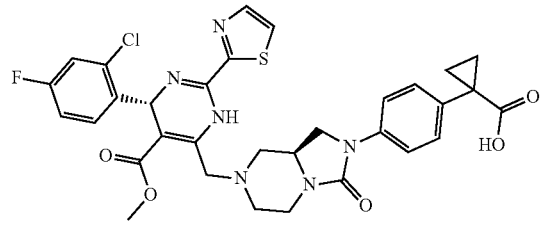 [SMILES: COC(=O)C1=C(CN2CCN3C(=O)N(c4ccc(C5(C(=O)O)CC5)cc4)C[C@@H]3C2)NC(c2nccs2)=N[C@H]1c1ccc(F)cc1Cl]

To a dry flask were added (S)-1-(4-(3-oxohexahydroimidazo[1,5-a]pyrazin-2(3H)-yl)phenyl)cyclopropane carboxylic acid trifluoroacetate (320 mg, 0.77 mmol), anhydrous ethanol (10 mL), DMF (4 mL), potassium carbonate (320 mg, 2.32 mmol) and (R)-methyl 6-(bromomethyl)-4-(2-chloro-4-fluorophenyl)-2-(thiazol-2-yl)-1,4-dihydropyrimidine-5-carboxylate (376 mg, 0.85 mmol). The mixture was stirred at rt for 16 hours. The reaction mixture was diluted with water (10 mL) and EtOAc (10 mL) and adjusted with dilute hydrochloric acid (1 M) to pH 5, the water phase was extracted with EtOAc (20 mL×2). The combined organic layers were dried over anhydrous sodium sulfate and filtered. The filtrate was concentrated in vacuo and the residue was purified by silica gel column chromatography (DCM/CH$_3$OH (V/V)=30/1) to give the title compound as a yellow solid (209 mg, 40.79%). MS (ESI, pos. ion) m/z: 666.10 [M+H]$^+$; $^1$H NMR (400 MHz, CDCl$_3$) δ 9.64 (s, 1H), 7.87 (d, J=3.1 Hz, 1H), 7.55-7.46 (m, 3H), 7.35-7.29 (m, 3H), 7.16 (dd, J=8.6, 2.5 Hz, 1H), 6.94 (td, J=8.3, 2.6 Hz, 1H), 6.22 (s, 1H), 4.09 (d, J=15.7 Hz, 1H), 4.09-4.05 (m, 1H), 4.02-3.95 (m, 1H), 3.94-3.86 (m, 2H), 3.62 (s, 3H), 3.42 (dd, J=9.0, 4.5 Hz, 1H), 3.31-3.21 (m, 1H), 2.88 (d, J=10.5 Hz, 2H), 2.55-2.44 (m, 1H), 2.25 (t, J=10.8 Hz, 1H), 1.68-1.62 (m, 2H), 1.26-1.19 (m, 2H).

Example 28: 1-(4-((S)-7-(((R)-6-(2-chloro-4-fluorophenyl)-5-(methoxycarbonyl)-2-(thiazol-2-yl)-3,6-dihydroprimidin-4-yl)methyl)-3-oxohexahydroimidazo[1,5-a]pyrazin-2(3H)-yl)phenyl) cyclopropane carboxylic acid

Step 1: methyl 1-(4-bromophenyl)cyclopropane carboxylate

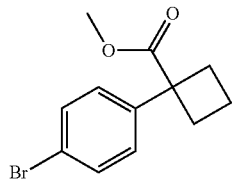

To a 250 mL two-neck flask were added methyl 2-(4-bromophenyl)acetate (3.0 g 13 mmol) and THF (50 mL), the mixture was cooled to 0° C. and lithium bis(trimethylsilyl) amide in THF (32 mL, 32 mmol, 1 mol/L) was added dropwise. The resulting mixture was stirred for 10 min and 1,4-dibromopropane (1.70 mL, 17 mmol) was added. The mixture was stirred at rt for 24 hours, and saturated aqueous ammonium chloride solution was added, the resulting mixture was extracted with EA (100 mL). The organic layer was washed with saturated brine (40 mL), dried over anhydrous sodium sulfate and filtered. The filtrate was concentrated in vacuo and the residue was purified by silica gel column chromatography (PE/EtOAc (v/v)=50/1) to give the title compound as colorless oil (2.0 g 57%).

Step 2: (R)-tert-butyl 2-(4-(1-(methoxycarbonyl)cyclobutyl)phenyl)-3-oxohexahydroimidazo [1,5-a]pyrazine-7(1H)-carboxylate

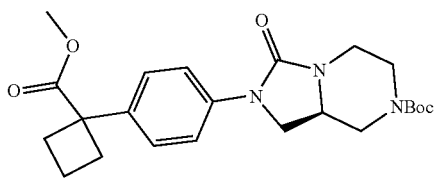 [SMILES: COC(=O)C1(c2ccc(N3C[C@@H]4CN(C(=O)OC(C)(C)C)CCN4C3=O)cc2)CCC1]

Methyl 1-(4-bromophenyl)cyclopropane carboxylate (1.3 g 4.8 mmol), (R)-tert-butyl 3-oxohexahydroimidazo[1,5-a]pyrazine-7(1H)-carboxylate (1.2 g, 4.8 mmol), tris(dibenzylideneacetone)dipalladium (440 mg, 0.48 mmol), 2-di-tert-butylphosphino-2',4',6'-trisopropylbinphenyl (410 mg, 0.97 mmol), cesium carbonate (3.1 g 9.5 mmol) were dissolved in 1,4-dioxane (30 mL) under $N_2$. The reaction mixture was stirred at 90° C. for 12 hours and filtered. The filtrate was concentrated in vacuo. The residue was purified by silica gel column chromatography (PE/EtOAc (v/v)=4/1) to give the title compound as a white solid (770 mg, 37%). MS (ESI, pos. ion) m/z: 430.2 [M+H]$^+$.

Step 3: (R)-1-(4-(7-(tert-butoxycarbonyl)-3-oxohexahydroimidazo[1,5-a]pyrazin-2(3H)-yl) phenyl) cyclobutane carboxylic acid

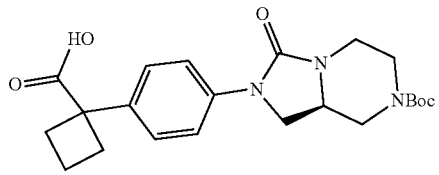 [SMILES: CC(C)(C)OC(=O)N1CCN2C(=O)N(c3ccc(C4(C(=O)O)CCC4)cc3)C[C@@H]2C1]

(R)-tert-Butyl 2-(4-(1-(methoxycarbonyl)cyclobutyl)phenyl)-3-oxohexahydroimidazo [1,5-a]pyrazine-7(1H)-carboxylate (770 mg, 1.8 mmol) was dissolved in a mixed methanol (10 mL), water (10 mL) and THF (10 mL) solvent, to the solution was added sodium hydroxide (360 mg, 9.0 mmol). The reaction mixture was stirred at 50° C. for 4 hours and concentrated in vacuo, and then diluted with water (20 mL) and EtOAc (10 mL), the organic layer was abandoned. To the water phase was added EtOAc (40 mL), and adjusted with concentrated hydrochloric acid to pH 5. The organic layer was washed with saturated aqueous NaCl (20 mL) and dried over anhydrous sodium sulfate. The mixture was filtered and the filtrate was concentrated in vacuo to give the title compound as a white solid (350 mg, 47%). MS (ESI, pos. ion) m/z: 438.4 [M+Na]$^+$.

Step 4: (S)-1-(4-(3-oxohexahydroimidazo[1,5-a]pyrazin-2(3H)-yl)phenyl)cyclobutane carboxylic acid hydrochloride

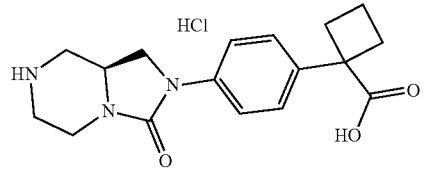 [SMILES: O=C1N(c2ccc(C3(C(=O)O)CCC3)cc2)C[C@@H]2CNCCN12 ; Cl]

(R)-1-(4-(7-(tert-Butoxycarbonyl)-3-oxohexahydroimidazo[1,5-a]pyrazin-2(3H)-yl)phenyl) cyclobutane carboxylic acid (350 mg, 0.84 mmol) was dissolved in a solution of HCl in 1,4-dioxane (4 mol/L, 10 mL). The mixture was stirred at rt for 12 hour and concentrated in vacuo to get the title compound as a white solid (290 mg, 98.0%).

Step 5: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)cyclobutane carboxylic acid

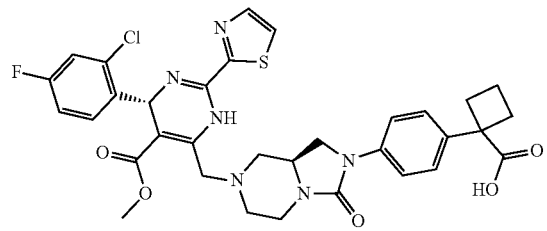 [SMILES: COC(=O)C1=C(CN2CCN3C(=O)N(c4ccc(C5(C(=O)O)CCC5)cc4)C[C@@H]3C2)NC(c2nccs2)=N[C@H]1c1ccc(F)cc1Cl]

To a single neck flask were added (S)-1-(4-(3-oxohexahydroimidazo[1,5-a]pyrazin-2(3H)-yl)phenyl)cyclobutane carboxylic acid hydrochloride (0.29 g 0.82 mmol), (R)-methyl 6-(bromomethyl)-4-(2-chloro-4-fluorophenyl)-2-(thiazol-2-yl)-1,4-dihydropyrimidine-5-carboxylate (0.37 g 0.83 mmol), potassium carbonate (160 mg, 1.20 mmol) and EtOH (20 mL). The mixture was stirred at 35° C. for 3 hours and filtered, the filter cake was washed with EA (5 mL), the combined filtrates were concentrated, the residue was diluted with EA (20 mL) and water (5 mL), the mixture was adjusted with dilute hydrochloric acid (1 M) to pH 6 and extracted with EA (10 mL), the water phase was abandoned, the organic layer was washed with saturated aqueous NaCl (10 mL) and concentrated, the residue was purified by silica gel column chromatography (DCM/MeOH (V/V)=40/1) to give the title compound as a yellow solid (290 mg, 52%). MS (ESI, pos. ion) m/z: 679.1 [M+H]$^+$; $^1$H NMR (400 MHz, CD$_3$OD) δ 7.97 (d, J=3.1 Hz, 1H), 7.76 (d, J=3.1 Hz, 1H), 7.52 (d, J=8.7 Hz, 2H), 7.44 (dd, J=8.7, 6.1 Hz, 1H), 7.31 (d, J=8.7 Hz, 2H), 7.24 (dd, J=8.7, 2.6 Hz, 1H), 7.06 (td, J=8.4, 2.6 Hz, 1H), 6.19 (s, 1H), 4.16 (d, J=17.0 Hz, 1H), 4.07-4.01 (m, 1H), 4.00-3.92 (m, 3H), 3.54 (dd, J=9.2, 4.3 Hz 1H), 3.28-3.23 (m, 1H), 3.00 (d, J=9.5 Hz, 2H), 2.86-2.76 (m, 2H), 2.55-2.45 (m, 3H), 2.27 (t, J=10.5 Hz, 1H), 2.06-1.98 (m, 1H), 1.91-1.82 (m, 1H).

Example 29: 1-(4-((S)-7-(((R)-6-(2-chloro-4-fluorophenyl)-5-(methoxycarbonyl)-2-(thiazol-2-yl)-3,6-dihydroprimidin-4-yl)methyl)-3-oxohexahydroimidazo[1,5-a]pyrazin-2(3H)-yl)phenyl) cyclopentane carboxylic acid Step 1: methyl 1-(4-bromophenyl)cyclopentane carboxylate

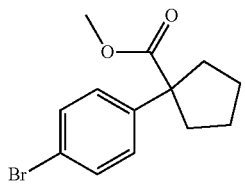 [SMILES: COC(=O)C1(c2ccc(Br)cc2)CCCC1]

To a two-neck flask were added methyl 4-bromophenylacetate (1.0 g 4.4 mmol) and THF (20 mL), the mixture was cooled to 0° C. and lithium bis(trimethylsilyl)amide in THF (10.4 mL, 10.4 mmol, 1 mol/L) was added dropwise. The resulting mixture was stirred for 10 min and 1,4-dibromobutane (0.70 mL, 5.7 mmol) was added. The mixture was stirred at rt for 24 hours, and saturated aqueous ammonium chloride solution (20 mL) was added, the resulting mixture was extracted with EA (100 mL). The organic layer was washed with saturated brine (40 mL), dried over anhydrous sodium sulfate and filtered. The filtrate was concentrated in vacuo and the residue was purified by silica gel column chromatography (PE/EtOAc (v/v)=50/1) to give the title compound as a white solid (400 mg, 32%). MS (ESI, pos. ion) m/z: 283.0 [M+H]$^+$; $^1$H NMR (400 MHz, CDCl$_3$) δ 7.45 (d, J=8.6 Hz, 2H), 7.28 (d, J=7.3 Hz, 2H), 3.63 (s, 3H), 2.64 (dd, J=7.2, 4.5 Hz, 2H), 1.94-1.84 (m, 2H), 1.78-1.71 (m, 4H).

Step 2: (R)-tert-butyl 2-(4-(1-(methoxycarbonyl)cyclopentyl)phenyl)-3-oxohexahydroimidazo [1,5-a]pyrazine-7(1H)-carboxylate

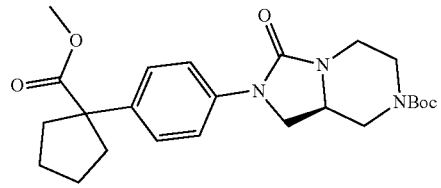 [SMILES: COC(=O)C1(c2ccc(N3C[C@@H]4CN(C(=O)OC(C)(C)C)CCN4C3=O)cc2)CCCC1]

Methyl 1-(4-bromophenyl)cyclopentane carboxylate (340 mg, 1.2 mmol), (R)-tert-butyl 3-oxohexahydroimidazo[1,5-a]pyrazine-7(1H)-carboxylate (290 mg, 1.2 mmol), tris(dibenzylideneacetone)dipalladium (110 mg, 0.12 mmol), 2-di-tert-butylphosphino-2',4',6'-trisopropylbinphenyl (100 mg, 0.24 mmol), cesium carbonate (780 mg, 2.40 mmol) were dissolved in 1,4-dioxane (30 mL) under N$_2$. The reaction mixture was stirred at 90° C. for 4 hours and filtered. The filtrate was concentrated in vacuo. The residue was purified by silica gel column chromatography (PE/EtOAc (v/v)=4/1) to give the title compound as a white solid (460 mg, 86%). MS (ESI, pos. ion) m/z: 466.1 [M+Na]$^+$.

Step 3: (R)-1-(4-(7-(tert-butoxycarbonyl)-3-oxohexahydroimidazo[1,5-a]pyrazin-2(3H)-yl) phenyl) cyclopentane carboxylic acid

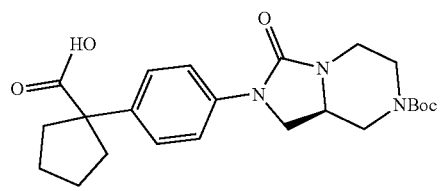 [SMILES: CC(C)(C)OC(=O)N1CCN2C(=O)N(c3ccc(C4(C(=O)O)CCCC4)cc3)C[C@@H]2C1]

(R)-tert-Butyl 2-(4-(1-(methoxycarbonyl)cyclopentyl)phenyl)-3-oxohexahydroimidazo [1,5-a]pyrazine-7(1H)-carboxylate (450 mg, 1.0 mmol) was dissolved in a mixed methanol (10 mL), water (10 mL) and THF (10 mL) solvent, to the solution was added sodium hydroxide (200 mg, 5.0 mmol). The reaction mixture was stirred at 50° C. for 24 hours and concentrated in vacuo, and then diluted with water (20 mL) and EtOAc (10 mL), the organic layer was abandoned. To the water phase was added EtOAc (40 mL), and adjusted with concentrated hydrochloric acid to pH 5. The organic layer was washed with saturated aqueous NaCl (20 mL) and dried over anhydrous sodium sulfate. The mixture was filtered and the filtrate was concentrated in vacuo to give the title compound as a white solid (400 mg, 92%). MS (ESI, pos. ion) m/z: 452.1 [M+Na]$^+$.

Step 4: (S)-1-(4-(3-oxohexahydroimidazo[1,5-a]pyrazin-2(3H)-yl)phenyl)cyclopentane carboxylic acid hydrochloride

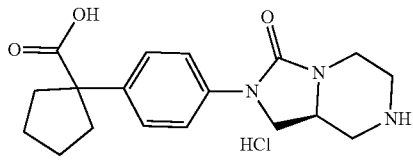 [SMILES: O=C1N(c2ccc(C3(C(=O)O)CCCC3)cc2)C[C@@H]2CNCCN12 ; Cl]

(R)-1-(4-(7-(tert-Butoxycarbonyl)-3-oxohexahydroimidazo[1,5-a]pyrazin-2(3H)-yl)phenyl) cyclopentane carboxylic acid (400 mg, 0.77 mmol) was dissolved in a solution of HCl in 1,4-dioxane (4 mol/L, 10 mL). The mixture was stirred at rt for 12 hour and concentrated in vacuo to get the title compound as a white solid (340 mg, 99.80%).

Step 5: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)cyclopentane carboxylic acid

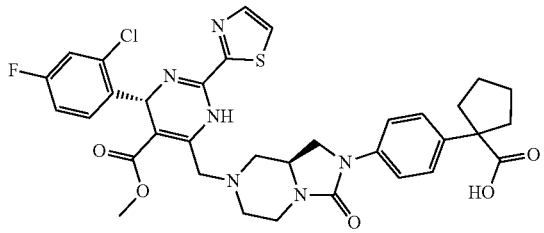 [SMILES: COC(=O)C1=C(CN2CCN3C(=O)N(c4ccc(C5(C(=O)O)CCCC5)cc4)C[C@@H]3C2)NC(c2nccs2)=N[C@H]1c1ccc(F)cc1Cl]

To a 100 mL single neck flask were added (S)-1-(4-(3-oxohexahydroimidazo[1,5-a]pyrazin-2(3H)-yl)phenyl)cyclopentane carboxylic acid hydrochloride (0.40 g 1.1 mmol), (R)-methyl 6-(bromomethyl)-4-(2-chloro-4-fluorophenyl)-2-(thiazol-2-yl)-1,4-dihydro pyrimidine-5-carboxylate (0.49 g 1.1 mmol), potassium carbonate (450 mg, 3.30 mmol) and EtOH (20 mL). The mixture was stirred at 35° C. for 5 hours and filtered, the filter cake was washed with EA (5 mL), the combined organic layers were concentrated in vacuo. The residue was diluted with EA (20 mL) and water (5 mL), the mixture was adjusted with dilute hydrochloric acid to pH 6 and extracted with EA (10 mL), the water phase was abandoned, the organic layers was washed with saturated aqueous NaCl (10 mL) and concentrated, the residue was purified by silica gel column chromatography (DCM/MeOH (V/V)=40/1) to give the title compound as a yellow solid (200 mg, 26%). MS (ESI, pos. ion) m/z: 693.4 [M+H]$^+$; $^1$H NMR (400 MHz, CDCl$_3$) δ 9.64 (s, 1H), 7.87 (d, J=3.1 Hz, 1H), 7.53-7.47 (m, 3H), 7.38 (d, J=8.7 Hz, 2H), 7.33-7.29 (m, 1H), 7.16 (dd, J=8.6, 2.5 Hz, 1H), 6.94 (td, J=8.4, 2.5 Hz, 1H), 6.23 (s, 1H), 4.12 (d, J=17.2 Hz, 1H), 4.09-4.44 (m, 1H), 4.02-3.96 (m, 1H), 3.94-3.86 (m, 2H), 3.62 (s, 3H), 3.42 (dd, J=9.0, 4.6 Hz, 1H), 3.26 (td, J=13.2, 3.0 Hz, 1H), 2.88 (d, J=10.9 Hz, 2H), 2.70-2.60 (m, 2H), 2.50 (td, J=11.6, 3.2 Hz, 1H), 2.25 (t, J=10.7 Hz, 1H), 1.97-1.87 (m, 2H), 1.79-1.72 (m, 4H).

Example 30: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl) cyclohexanecarboxylic acid

Step 1: methyl 1-(4-bromophenyl)cyclohexane carboxylate

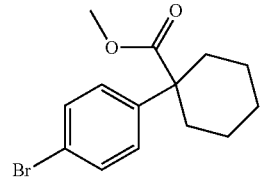 [SMILES: COC(=O)C1(c2ccc(Br)cc2)CCCCC1]

To a 250 mL two-neck flask were added methyl 2-(4-bromophenyl)acetate (3.0 g 13 mmol) and THF (50 mL), the mixture was cooled to 0° C. and lithium bis(trimethylsilyl) amide in THF (32 mL, 32 mmol, 1 mol/L) was added dropwise. The resulting mixture was stirred for 10 min and 1,4-dibromopentane (2.2 mL, 17 mmol) was added. The mixture was stirred at rt for 24 hours and saturated aqueous ammonium chloride solution (40 mL) was added, the resulting mixture was extracted EA (100 mL). The organic layer was washed with saturated brine (40 mL) once, dried over anhydrous sodium sulfate and concentrated in vacuo, the residue was purified by silica gel column chromatography (PE/EtOAc (v/v)=50/1) to give the title compound as colorless oil (2.0 g 51%).

Step 2: (R)-tert-butyl 2-(4-(1-(methoxcarbonyl)cyclohexyhenyl)phenyl)-3-oxohexahydroimidazo [1,5-a]pyrazine-7(1H)-carboxylate

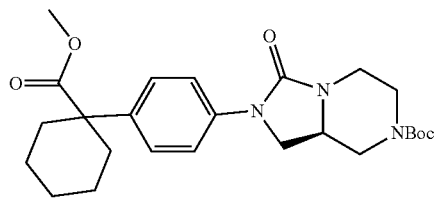 [SMILES: COC(=O)C1(c2ccc(N3C[C@@H]4CN(C(=O)OC(C)(C)C)CCN4C3=O)cc2)CCCCC1]

Methyl 1-(4-bromophenyl)cyclohexane carboxylate (1.0 g 3.4 mmol), (R)-tert-butyl 3-oxohexahydroimidazo[1,5-a]pyrazine-7(1H)-carboxylate (0.81 g, 3.4 mmol), tris(dibenzylideneacetone)dipalladium (310 mg, 0.34 mmol), 2-di-tert-butylphosphino-2',4',6'-trisopropylbinphenyl (290 mg, 0.68 mmol), cesium carbonate (2.2 g 6.8 mmol) were dissolved in 1,4-dioxane (40 mL) under N$_2$. The reaction mixture was stirred at 90° C. for 12 hours and concentrated in vacuo. The residue was purified by silica gel column chromatography (PE/EtOAc (v/v)=4/1) to give the title compound as a white solid (700 mg, 45%). MS (ESI, pos. ion) m/z: 480.2 [M+Na]$^+$.

Step 3: (R)-1-(4-(7-(tert-butoxycarbonyl)-3-oxo-hexahydroimidazo[1,5-a]pyrazin-2(3H)-yl) phenyl) cyclohexanecarboxylic acid

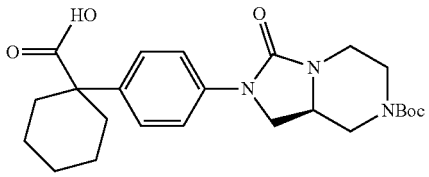 [SMILES: CC(C)(C)OC(=O)N1CCN2C(=O)N(c3ccc(C4(C(=O)O)CCCCC4)cc3)C[C@@H]2C1]

(R)-tert-Butyl 2-(4-(1-(methoxycarbonyl)cyclohexyl) phenyl)-3-oxohexahydroimidazo [1,5-a]pyrazine-7(1H)-carboxylate (770 mg, 1.7 mmol) was dissolved in a mixed methanol (10 mL), water (10 mL) and THF (10 mL) solvent, to the solution was added sodium hydroxide (340 mg, 8.5 mmol). The reaction mixture was stirred at 60° C. for 32 hours and concentrated in vacuo, the residue was diluted with water (20 mL) and EtOAc (10 mL), the organic layer was abandoned. To the water phase was added EtOAc (40 mL), and adjusted with concentrated hydrochloric acid to pH 5. The organic layer was washed with saturated aqueous NaCl (20 mL) and dried over anhydrous sodium sulfate. The mixture was filtered and the filtrate was concentrated in vacuo to give the title compound as a white solid (400 mg, 54%). MS (ESI, pos. ion) m/z: 466.4 [M+Na]+.

Step 4: (S)-1-(4-(3-oxohexahydroimidazo[1,5-a] pyrazin-2(3H)-yl)phenyl)cyclohexane carboxylic acid hydrochloride

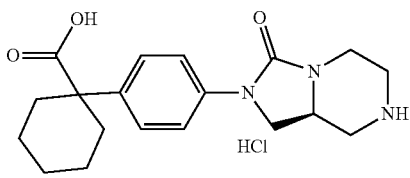 [SMILES: O=C1N(c2ccc(C3(C(=O)O)CCCCC3)cc2)C[C@@H]2CNCCN12 ; Cl]

(R)-1-(4-(7-(tert-Butoxycarbonyl)-3-oxohexahydroimidazo[1,5-a]pyrazin-2(3H)-yl) phenyl)cyclohexanecarboxylic acid (400 mg, 0.90 mmol) was dissolved in a solution of HCl in 1,4-dioxane (4 mol/L, 10 mL), the mixture was stirred at rt for 12 hours and concentrated in vacuo to get the title compound as a white solid (340 mg, 99.0%).

Step 5: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl) cyclohexane carboxylic acid

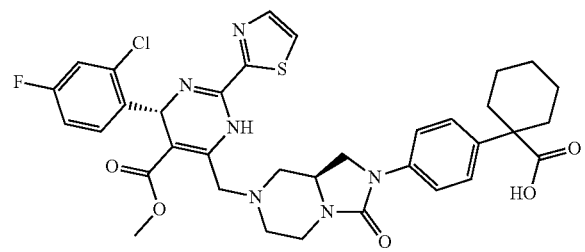 [SMILES: COC(=O)C1=C(CN2CCN3C(=O)N(c4ccc(C5(C(=O)O)CCCCC5)cc4)C[C@@H]3C2)NC(c2nccs2)=N[C@H]1c1ccc(F)cc1Cl]

To a single neck flask were added (S)-1-(4-(3-oxohexahydroimidazo[1,5-a]pyrazin-2(3H)-yl)phenyl)cyclohexane carboxylic acid hydrochloride (0.34 g 0.89 mmol), (R)-methyl 6-(bromomethyl)-4-(2-chloro-4-fluorophenyl)-2-(thiazol-2-yl)-1,4-dihydropyrimidine-5-carboxy late (0.40 g 0.90 mmol), potassium carbonate (370 mg, 2.70 mmol) and EtOH (20 mL). The mixture was stirred at 35° C. for 16 hours and filtered, the filter cake was washed with EA (5 mL). The combined organic layers were concentrated. The residue was diluted with EA (20 mL) and water (5 mL), the mixture was adjusted with dilute hydrochloric acid to pH 6 and extracted with EA (10 mL), the water phase was abandoned, the organic layers was washed with saturated aqueous NaCl (10 mL) and concentrated, the residue was purified by silica gel column chromatography (DCM/MeOH (V/V)=40/1) to give the title compound as a yellow solid (320 mg, 51%). MS (ESI, pos. ion) m/z: 707.4 [M+H]+; 1H NMR (400 MHz, CD3OD) δ 7.97 (d, J=3.1 Hz, 1H), 7.77 (d, J=3.1 Hz, 1H), 7.51 (d, J=8.8 Hz, 2H), 7.46-7.40 (m, 3H), 7.24 (dd, J=8.7, 2.5 Hz, 1H), 7.06 (td, J=8.4, 2.5 Hz, 1H), 6.19 (s, 1H), 4.21-4.13 (m, 1H), 4.06-3.93 (m, 4H), 3.61 (s, 3H), 3.53 (dd, J=9.3, 4.3 Hz, 1H), 3.27-3.23 (m, 1H), 3.01 (s, 2H), 2.50-2.40 (m, 3H), 2.29 (s, 1H), 1.75-1.68 (m, 4H), 1.61-1.51 (m, 2H), 1.35-1.27 (m, 2H).

Example 31: 1-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenyl) piperidine-4-carboxylic acid Step 1: methyl 1-(4-bromo-3-fluorophenyl)piperidine-4-carboxylate

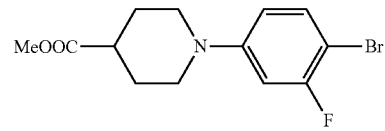 [SMILES: COC(=O)C1CCN(c2ccc(Br)c(F)c2)CC1]

1-Bromo-2-fluoro-4-iodobenzene (500 mg, 1.66 mmol), methyl piperidine-4-carboxylate hydrochloride (299 mg, 1.66 mmol), tris(dibenzylideneacetone)dipalladium (155 mg, 0.16 mmol), 4,5-bis(diphenylphosphino)-9,9-dimethylxanthene (198 mg, 0.33 mmol) and cesium carbonate (1.09 g 3.35 mmol) were dissolved in 1,4-dioxane (10 mL). The mixture was stirred at 110° C. for 12 hours and concentrated in vacuo. The residue was purified by silica gel column chromatography (PE/EtOAc (V/V)=10/1) to give the title compound as yellow oil (390 mg, 74%). MS (ESI, pos. ion): m/z 316.2 [M+H]+.

Step 2: (R)-tert-butyl 2-(2-fluoro-4-(4-(methoxycarbonyl)piperidin-1-yl)phenyl)-3-oxohexa hydroimidazo[1,5-a]pyrazin-7(1H)-carboxylate

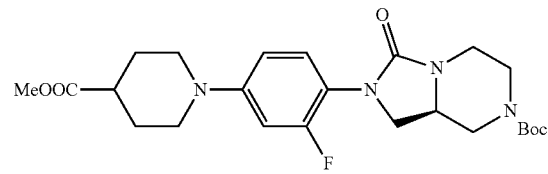 [SMILES: COC(=O)C1CCN(c2ccc(N3C[C@@H]4CNCCN4C3=O)c(F)c2)CC1 ; "Boc"]

(R)-tert-Butyl 3-oxohexahydroimidazo[1,5-a]pyrazine-7 (1H)-carboxylate (300 mg, 1.24 mmol), methyl 1-(4-bromo-3-fluorophenyl)piperidine-4-carboxylate (393 mg, 1.24 mmol), tris(dibenzylideneacetone)dipalladium (116 mg, 0.12 mmol), 4,5-bis(diphenylphosphino)-9,9-dimethylxanthene (148 mg, 0.25 mmol) and cesium carbonate (810 mg, 2.49 mmol) were dissolved in 1,4-dioxane (20 mL). The reaction mixture was stirred at 110° C. for 12 hours and concentrated in vacuo. The residue was purified by silica gel column chromatography (PE/EtOAc (v/v)=1/1) to give the title compound as a gray solid (320 mg, 54%). MS (ESI, pos. ion): m/z 477.1 [M+H]⁺.

Step 3: (R)-1-(4-(7-(tert-butoxycarbonyl)-3-oxo-hexahydroimidazo[1,5-a]pyrazin-2(3H)-yl)-3-fluoro-phenyl)piperidine-4-carboxylic acid

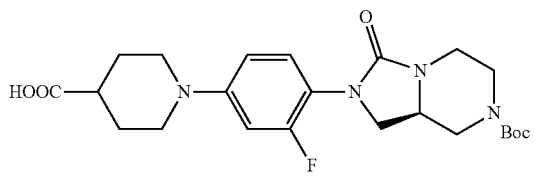 [SMILES: O=C(O)C1CCN(c2ccc(N3C[C@@H]4CNCCN4C3=O)c(F)c2)CC1 ; "Boc"]

(R)-tert-Butyl 2-(2-fluoro-4-(4-(methoxycarbonyl)piperidin-1-yl)phenyl)-3-oxohexa hydroimidazo[1,5-a]pyrazin-7(1H)-carboxylate (200 mg, 0.42 mmol) was dissolved in methanol (10 mL), to the solution was added a solution of lithium hydroxide monohydrate (88 mg, 2.1 mmol) in water (2 mL). The mixture was stirred at 50° C. for 2 hours and adjusted with hydrochloric acid (1 M) to pH 3 to 4, the resulting mixture was extracted with EtOAc (20 mL×3). The combined organic layers were dried over anhydrous sodium sulfate and concentrated in vacuo to give the title compound as a white solid (180 mg, 93%). MS (ESI, pos. ion): m/z 463.1 [M+H]⁺.

Step 4: (S)-1-(3-fluoro-4-(3-oxohexahydroimidazo [1,5-a]pyrazin-2(3H)-yl)phenyl)piperidine-4-carboxylic acid trifluoroacetate

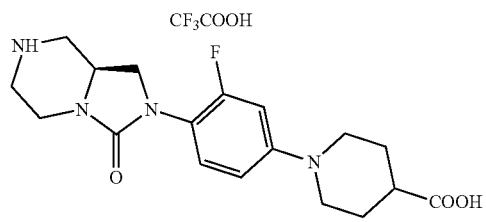 [SMILES: O=C(O)C1CCN(c2ccc(N3C[C@@H]4CNCCN4C3=O)c(F)c2)CC1 ; "CF3COOH"]

(R)-1-(4-(7-(tert-Butoxycarbonyl)-3-oxohexahydroimidazo[1,5-a]pyrazin-2(3H)-yl)-3-fluorophenyl)piperidine-4-carboxylic acid (150 mg, 0.32 mmol) was dissolved in DCM (5 mL), to the solution was added trifluoroacetic acid (5 ml). The mixture was stirred at rt for 1 hour and concentrated in vacuo to get the title compound as brown oil (110 mg, 94%).

Step 5: 1-(4-((S)-7-(((R)-6-(2-chloro-4-fluorophenyl)-5-(methoxycarbonyl)-2-(thiazol-2-yl)-3,6-dihydropyrimidin-4-yl)methyl-3-oxohexahydroimidazo [1,5-a]pyrazin-2(3H)-yl)-3-fluorophenyl)piperidine-4-carboxylic acid

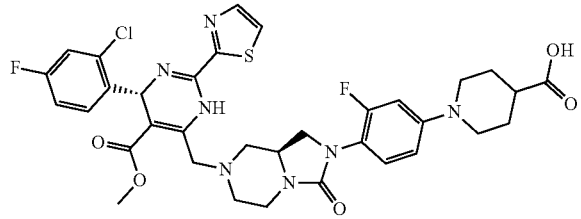 [SMILES: COC(=O)C1=C(CN2CCN3C(=O)N(c4ccc(N5CCC(C(=O)O)CC5)cc4F)C[C@@H]3C2)NC(c2nccs2)=N[C@H]1c1ccc(F)cc1Cl]

(S)-1-(3-Fluoro-4-(3-oxohexahydroimidazo[1,5-a] pyrazin-2(3H)-yl)phenyl)piperidine-4-carboxylic acid trifluoroacetate (100 mg, 0.28 mmol) and potassium carbonate (114 mg, 0.82 mmol) was dissolved in ethanol (10 mL), and to the mixture was added (R)-methyl 6-(bromomethyl)-4-(2-chloro-4-fluorophenyl)-2-(thiazol-2-yl)-1,4-dihydropyrimidine-5-carboxy late (135 mg, 0.30 mmol). The resulting mixture was stirred at rt for 12 hours, the reaction mixture was concentrated in vacuo. The residue was purified by silica gel column chromatography (DCM/MeOH (V/V)=10/1) to give the title compound as a yellow solid (120 mg, 60%). MS (ESI, pos. ion): m/z 726.3 [M+H]⁺; ¹H NMR (400 MHz, CDCl₃) δ 9.68 (s, 1H), 7.88 (d, J=3.1 Hz, 1H), 7.48 (d, J=3.1 Hz, 1H), 7.33-7.29 (m, 1H), 7.26 (d, J=9.1 Hz, 1H), 7.15 (dd, J=8.6, 2.6 Hz, 1H), 6.94 (td, J=8.4, 2.6 Hz, 1H), 6.71-6.61 (m, 2H), 6.22 (s, 1H), 4.16-4.10 (m, 1H), 4.07-3.97 (m, 2H), 3.92-3.81 (m, 2H), 3.65-3.59 (m, 5H), 3.40 (dd, J=9.0, 4.6 Hz, 1H), 3.31-3.22 (m, 1H), 2.92-2.77 (m, 4H), 2.58-2.44 (m, 2H), 2.39 (t, J=10.8 Hz, 1H), 2.06-2.00 (m, 2H), 1.91-1.78 (m, 2H).

Example 32: 1-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenyl) piperidine-4-carboxylic acid Step 1: (R)-tert-butyl 2-(3-bromo-5-fluorophenyl)-3-oxohexahydroimidazo[1,5-a]pyrazine-7(1H)-carboxylate

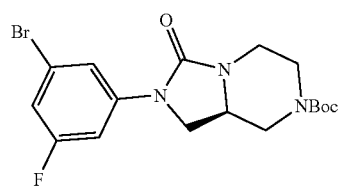 [SMILES: CC(C)(C)OC(=O)N1CCN2C(=O)N(c3cc(F)cc(Br)c3)C[C@@H]2C1]

To a dry flask were added (R)-tert-butyl 3-oxohexahydroimidazo[1,5-a]pyrazine-7(1H)-carboxylate (1.6 g, 6.6 mmol), 1-bromo-3-fluoro-5-iodobenzene (2 g 6.65 mmol), Pd₂(dba)₃ (630 mg, 0.67 mmol), Xantphos (590 mg, 0.99 mmol), Cs₂CO₃ (4.3 g 13 mmol) and 1,4-dioxane (40 mL) in turn. The mixture was stirred at 90° C. for 12 hours and filtered, the filtrate was concentrated, the residue was diluted with EA (100 mL). The organic layer was washed with saturated brine, dried over anhydrous sodium sulfate and concentrated in vacuo, the residue was purified by silica gel column chromatography (PE/EtOAc (v/v)=10/1 to 5/1) to give the title compound as a light brown solid (1.8 g 65%). MS (ESI, pos. ion) m/z: 358.0[M+H–56]$^+$.

Step 2: (R)-tert-butyl 2-(3-fluoro-5-(4-(methoxycarbonyl)piperidin-1-yl)phenyl)-3-oxohexa hydroimidazo[1,5-a]pyrazine-7(1H)-carboxylate

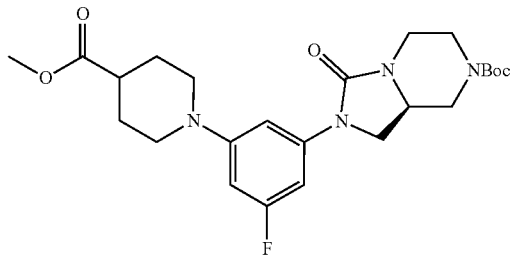 [SMILES: COC(=O)C1CCN(c2cc(F)cc(N3C[C@@H]4CN(C(=O)OC(C)(C)C)CCN4C3=O)c2)CC1]

To a dry flask were added (R)-tert-butyl 2-(3-bromo-5-fluorophenyl)-3-oxohexa hydroimidazo[1,5-a]pyrazine-7(1H)-carboxylate (0.6 g, 1 mmol), methyl piperidine-4-carboxylate (250 mg, 1.75 mmol), palladiumacetate (33 mg, 0.14 mmol), 2-di-tert-butylphosphino-2',4',6'-trisopropylbinphenyl (95 mg, 0.22 mmol), Cs$_2$CO$_3$ (0.94 g 2.9 mmol) and 1,4-dioxane (30 mL). The mixture was stirred at 90° C. for 12 hours under N$_2$ and filtered. The filtrate was concentrated in vacuo, to the residue was added EA (100 mL). The organic layer was washed with saturated brine, dried over anhydrous sodium sulfate and filtered.

The filtrate was concentrated in vacuo to dry and the residue was purified by silica gel column chromatography (PE/EtOAc (v/v)=3/1 to 1/1) to give the title compound as a white solid (0.51 g, 70%). MS (ESI, pos. ion) m/z: 477.2 [M+H]$^+$.

Step 3: (R)-1-(3-(7-(tert-butoxycarbonyl)-3-oxohexahydroimidazo[1,5-a]pyrazin-2(3H)-yl)-5-fluorophenyl)piperidine-4-carboxylic acid

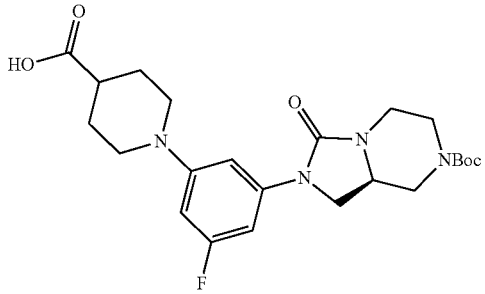 [SMILES: CC(C)(C)OC(=O)N1CCN2C(=O)N(c3cc(F)cc(N4CCC(C(=O)O)CC4)c3)C[C@@H]2C1]

To a flask were added (R)-tert-butyl 2-(3-fluoro-5-(4-(methoxycarbonyl)piperidin-1-yl)phenyl)-3-oxohexahydroimidazo[1,5-a]pyrazine-7(1H)-carboxylate (390 mg, 0.82 mmol), tetrahydrofuran (3 mL) and CH$_3$OH (3 mL), the mixture was stirred until dissolving completely, and a solution of NaOH (330 mg, 8.25 mmol) in H$_2$O (1 mL) was added. The mixture was stirred at rt for 12 hours and concentrated in vacuo. To the residue was added water, the water phase was extracted with EA (20 mL×2), the organic layer was abandoned. To the water phase was added EtOAc (30 mL), and adjusted with concentrated hydrochloric acid to pH 5 under stirring. The mixture was stood and layered. The organic layer was washed with saturated aqueous NaCl and dried over anhydrous sodium sulfate. The mixture was filtered and the filtrate was concentrated in vacuo to give the title compound as a white solid (0.3 g 80%).

Step 4: (S)-1-(3-fluoro-5-(3-oxohexahydroimidazo[1,5-a]pyrazin-2(3H)-yl)phenyl)piperidine-4-carboxylic acid hydrochloride

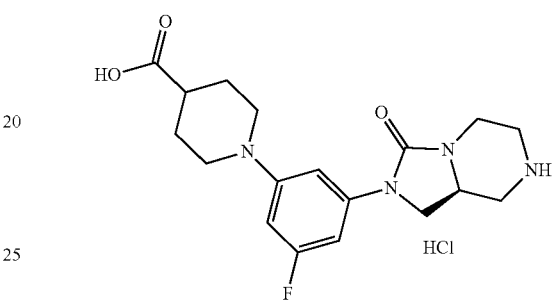

To a 50 mL single neck flask were added (R)-1-(3-(7-(tert-butoxycarbonyl)-3-oxohexahydroimidazo[1,5-a]pyrazin-2(3H)-yl)-5-fluorophenyl)piperidine-4-carboxylic acid (286 mg, 0.62 mmol) and a solution of HCl in 1,4-dioxane (3 mL, 12 mmol, 4 mol/L). The reaction mixture was stirred at rt for 8 hours and filtered by suction to get the title compound as a white solid (226 mg, 91.62%). MS (ESI, pos. ion) m/z: 363.1 [M+H]$^+$.

Step 5: 1-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenyl)piperidine-4-carboxylic acid

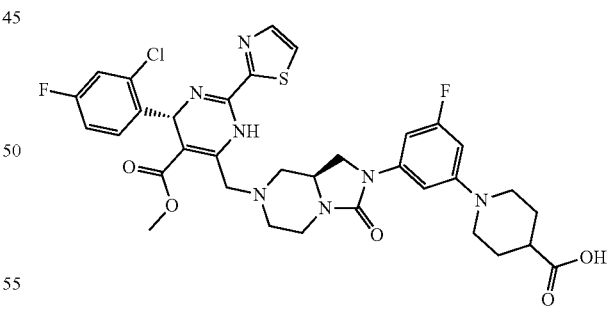

To a 50 mL single neck flask were added (S)-1-(3-fluoro-5-(3-oxohexahydroimidazo [1,5-a]pyrazin-2(3H)-yl)phenyl)piperidine-4-carboxylic acid hydrochloride (219 mg, 0.55 mmol), (4R)-methyl 6-(bromomethyl)-4-(2-chloro-4-fluorophenyl)-2-(thiazol-2-yl)-1,4-dihydro pyrimidine-5-carboxylate (244 mg, 0.55 mmol), potassium carbonate (153 mg, 1.1 mmol) and EtOH (20 mL). The mixture was stirred at rt for 12 hours and filtered by suction, the filter cake was washed with EtOAc (10 mL). The combined filtrates were concentrated in vacuo. The residue was diluted with EtOAc (30 mL) and water (15 mL), the mixture was adjusted with hydrochloric acid (6 M) to pH 6. The water phase was extracted with EtOAc (15 mL) once, the combined organic layers were concentrated in vacuo and the residue was purified by silica gel column chromatography (DCM/CH$_3$OH (V/V)=50/1) to give the title compound as a yellow solid (154 mg, 38.63%). MS (ESI, pos. ion) m/z: 727.5 [M+H]$^+$; $^1$H NMR (400 MHz, DMSO-d$_6$) δ 9.64 (s, 1H), 7.87 (d, J=3.0 Hz, 1H), 7.49 (d, J=2.9 Hz, 1H), 7.33-7.29 (m, 1H), 7.21 (s, 1H), 7.16 (dd, J=8.5, 2.3 Hz, 1H), 6.98-6.89 (m, 1H), 6.58 (d, J=10.8 Hz, 1H), 6.34 (d, J=11.8 Hz, 1H), 6.23 (s, 1H), 4.18-3.97 (m, 3H), 3.94-3.85 (m, 2H), 3.71-3.65 (m, 2H), 3.62 (s, 3H), 3.46-3.37 (m, 1H), 3.27 (t, J=11.2 Hz, 1H), 2.96-2.81 (m, 4H), 2.52 (t, J=9.6 Hz, 2H), 2.26 (t, J=10.5 Hz, 1H), 2.05 (d, J=11.0 Hz, 2H), 1.96-1.80 (m, 2H).

Example 33: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2,2'-difluoro-[1,1'-diphenyl]-4-carboxylic acid Step 1: methyl 4'-bromo-2,2'-difluoro-[1,1'-diphenyl]-4-carboxylate

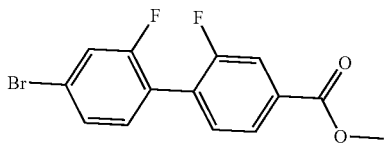 [SMILES: COC(=O)c1ccc(-c2ccc(Br)cc2F)c(F)c1]

To a 100 mL single neck flask were added 4-bromo-2-fluorobenzene boronic acid (0.50 g, 2.28 mmol), methyl 3-fluoro-4-iodobenzene carboxylate (0.57 g, 2.06 mmol), potassium carbonate (0.95 g 6.87 mmol), [1,1'-bis(diphenylphosphino)ferrocene]dichloropalladium (84 mg, 0.11 mmol) and 1,4-dioxane (20 mL). The reaction mixture was stirred at 100° C. for 12 hours and concentrated in vacuo. The residue was purified by silica gel column chromatography (PE/EtOAc (v/v)=100/1) to give the title compound as colorless (0.40 g 54%). $^1$H NMR (400 MHz, DMSO-d$_6$) δ 7.91 (dd, J=8.0, 1.5 Hz, 1H), 7.84 (dd, J=10.4, 1.3 Hz, 1H), 7.76 (dd, J=9.8, 1.7 Hz, 1H), 7.66 (t, J=7.7 Hz, 1H), 7.60 (dd, J=8.3, 1.7 Hz, 1H), 7.50 (t, J=8.1 Hz, 1H), 3.91 (s, 3H).

Step 2: (R)-tert-butyl 2-(2,2'-difluoro-4'-(methoxycarbonyl)-[1,1'-diphenyl]-4-yl)-3-oxohexahydroimidazo[1,5-a]pyrazine-7(1H)-carboxylate

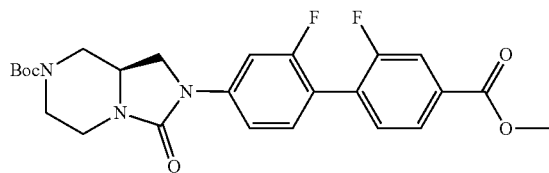 [SMILES: COC(=O)c1ccc(-c2ccc(N3C[C@@H]4CN(C(=O)OC(C)(C)C)CCN4C3=O)cc2F)c(F)c1]

To a 100 mL two-neck flask were added (R)-tert-butyl 4-oxohexahydroimidazo[1,5-a]pyrazine-7(1H)-carboxylate (221 mg, 0.92 mmol), methyl 4'-bromo-2,2'-difluoro-[1,1'-diphenyl-4-carboxylate (300 mg, 0.92 mmol), tris(dibenzylideneacetone)dipalladium (85 mg, 0.093 mmol), 2-di-tert-butylphosphino-2',4',6'-trisopropylbinphenyl (80 mg, 0.19 mmol), cesium carbonate (0.60 g 1.84 mmol) and 1,4-dioxane (20 mL). The reaction mixture was stirred at 90° C. for 12 hours and concentrated in vacuo. The residue was purified by silica gel column chromatography (PE/EtOAc (v/v)=1/1) to give the title compound as a white solid (310 mg, 69%). MS (ESI, pos. ion) m/z: 510.1 [M+Na]$^+$.

Step 3: (R)-4'-(7-(tert-butoxycarbonyl)-3-oxohexahydroimidazo[1,5-a]pyrazin-2(3H)-yl)-2,2'-difluoro-[1,1'-diphenyl]-4-carboxylic acid

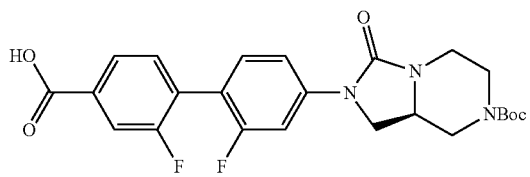 [SMILES: CC(C)(C)OC(=O)N1CCN2C(=O)N(c3ccc(-c4ccc(C(=O)O)cc4F)c(F)c3)C[C@@H]2C1]

To a single neck flask were added (R)-tert-butyl 2-(2,2'-difluoro-4'-(methoxycarbonyl)-[1,1'-diphenyl]-4-yl)-3-oxohexahydroimidazo[1,5-a]pyrazine-7(1H)-carboxylate (310 mg, 0.64 mmol), methanol (10 mL), water (2 mL) and lithium hydroxide monohydrate (140 mg, 3.3 mmol). The mixture was stirred at 25° C. for 2 hours, and then concentrated in vacuo. The residue was diluted with water (5 mL) and EtOAc (10 mL), and the mixture was adjusted with dilute hydrochloric acid (1 M) to pH 5, and the water phase was extracted with EtOAc (10 mL), and the combined organic layers were washed with saturated aqueous NaCl and dried over anhydrous sodium sulfate. The mixture was filtered and the filtrate was concentrated in vacuo to give the title compound as a white solid (0.18 g 60%).

Step 4: (S)-2,2'-difluoro-4'-(3-oxohexahydroimidazo[1,5-a]pyrazin-2(3H)-yl)-[1,1'-diphenyl]-4-carboxylic acid trifluoroacetate To a single neck flask were added (R)-4'-(7-(tert-butoxycarbonyl)-3-oxohexa hydroimidazo[1,5-a]pyrazin-2(3H)-yl)-2,2'-difluoro-[1,1'-diphenyl]-4-carboxylic acid (0.18 g 0.38 mmol), DCM (5 mL) and trifluoroacetic acid (5 mL). The reaction mixture was stirred at 25° C. for 2 hours and concentrated in vacuo to get the title compound as brown oil (0.18 g 100%).

Step 5: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2,2'-difluoro-[1,1'-diphenyl]-4-carboxylic acid

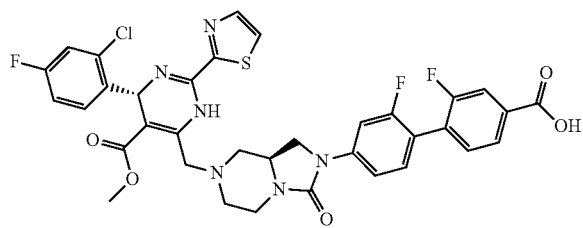 [SMILES: COC(=O)C1=C(CN2CCN3C(=O)N(c4ccc(-c5ccc(C(=O)O)cc5F)c(F)c4)C[C@@H]3C2)NC(c2nccs2)=N[C@H]1c1ccc(F)cc1Cl]

To a two neck flask were added (S)-2,2'-difluoro-4'-(3-oxohexahydroimidazo [1,5-a]pyrazin-2(3H)-yl)-[1,1'-diphenyl]-4-carboxylic acid trifluoroacetate (0.18 g 0.37 mmol), (R)-methyl 6-(bromomethyl)-4-(2-chloro-4-fluorophenyl)-2-(thiazol-2-yl)-1,4-dihydro pyrimidine-5-carboxylate (0.16 g 0.37 mmol), potassium carbonate (200 mg, 1.45 mmol) and EtOH (10 mL). The mixture was stirred at 35° C. for 12 hours and filtered, the filter cake was washed with EA (5 mL). The combined organic layers were concentrated. The residue was diluted with EA (20 mL) and water (5 mL), the mixture was adjusted with dilute hydrochloric acid to pH 6 and the water phase was extracted with EA (10 mL), the water phase was abandoned, the combined organic layers were washed with saturated aqueous NaCl (10 mL) and concentrated, the residue was purified by silica gel column chromatography (DCM/MeOH (V/V)=25/1) to give the title compound as a yellow solid (60 mg, 22.0%). MS (ESI, pos. ion) m/z: 737.3 [M+H]$^+$; $^1$H NMR (400 MHz, CD$_3$OD) δ 7.98 (d, J=3.1 Hz, 1H), 7.92 (dd, J=8.1, 0.9 Hz, 1H), 7.82-7.76 (m, 2H), 7.72-7.66 (m, 1H), 7.53 (t, J=7.6 Hz, 1H), 7.47-7.40 (m, 3H), 7.25 (dd, J=8.7, 2.6 Hz, 1H), 7.07 (td, J=8.4, 2.6 Hz, 1H), 6.19 (s, 1H), 4.18 (d, J=16.8 Hz, 1H), 4.12-4.06 (m, 1H), 4.05-3.95 (m, 3H), 3.68-3.65 (m, 1H), 3.61 (s, 3H), 3.59-3.56 (m, 1H), 3.04 (d, J=11.2 Hz, 2H), 2.51 (td, J=11.7, 3.2 Hz, 1H), 2.33-2.26 (m, 1H).

Example 34: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2',3-difluoro-[1,1'-diphenyl]-4-carboxylic acid Step 1: methyl 4'-bromo-2',3-difluoro-[1,1'-diphenyl]-4-carboxylate

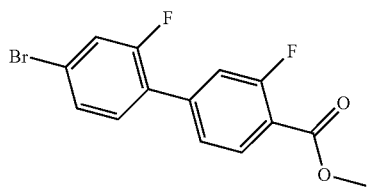 [SMILES: COC(=O)c1ccc(-c2ccc(Br)cc2F)cc1F]

To a single neck flask were added 4-bromo-2-fluorobenzene boronic acid (0.50 g 2.28 mmol), methyl 2-fluoro-4-iodobenzene carboxylate (0.57 g, 2.06 mmol), potassium carbonate (0.95 g 6.87 mmol) and [1,1'-bis(diphenylphosphino)ferrocene]dichloropalladium (84 mg, 0.11 mmol). The reaction mixture was stirred at 100° C. for 1 hour and concentrated in vacuo. The residue was purified by silica gel column chromatography (PE/EtOAc (v/v)=100/1) to give the title compound as colorless (0.39 g 52%).

Step 2: (R)-tert-butyl 2-(2,3'-difluoro-4'-(methoxycarbonyl)-[1,1'-diphenyl]-4-yl)-3-oxohexahydroimidazo[1,5-a]pyrazine-7(1H)-carboxylate

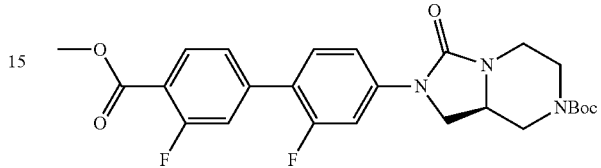

To a two-neck flask were added (R)-tert-butyl 3-oxohexahydroimidazo[1,5-a]pyrazine-7(1H)-carboxylate (251 mg, 1.04 mmol), methyl 4'-bromo-2,3'-difluoro-[1,1'-diphenyl]-4-carboxylate (340 mg, 1.04 mmol), tris(dibenzylideneacetone)dipalladium (96 mg, 0.10 mmol), 4,5-bis(diphenylphosphino)-9,9-dimethylxanthene (120 mg, 0.21 mmol), cesium carbonate (0.68 g 2.1 mmol) and 1,4-dioxane (30 mL). The reaction mixture was stirred at 90° C. for 12 hours and concentrated in vacuo. The residue was purified by silica gel column chromatography (PE/EtOAc (v/v)=4/1) to give the title compound as a white solid (310 mg, 61%). MS (ESI, pos. ion) m/z: 510.0 [M+Na]$^+$.

Step 3: (R)-4'-(7-(tert-butoxycarbonyl)-3-oxohexahydroimidazo[1,5-a]pyrazin-2(3H)-yl)-2',3-difluoro-[1,1'-diphenyl]-4-carboxylic acid

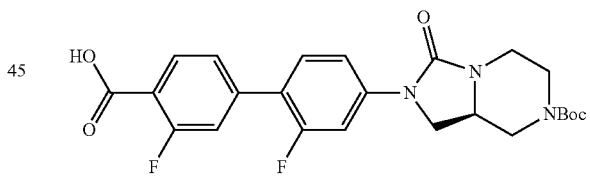

To a 50 mL single neck flask were added (R)-tert-butyl 2-(2,3'-difluoro-4'-(methoxycarbonyl)-[1,1'-diphenyl]-4-yl)-3-oxohexahydroimidazo[1,5-a]pyrazine-7(1H)-carboxylate (310 mg, 0.64 mmol), methanol (10 mL), water (2 mL) and lithium hydroxide monohydrate (140 mg, 3.3 mmol). The mixture was stirred at 25° C. for 2 hours, and then concentrated in vacuo. The residue was diluted with water (5 mL) and EtOAc (10 mL), and the mixture was adjusted with dilute hydrochloric acid (1 M) to pH 5, and the water phase was extracted with EtOAc (10 mL), and the combined organic layers were washed with saturated aqueous NaCl and dried over anhydrous sodium sulfate, and then concentrated in vacuo to give the title compound as a white solid (0.23 g 49%). MS (ESI, pos. ion) m/z: 496.1 [M+Na]$^+$.

Step 4: (S)-2',3-difluoro-4'-(3-oxohexahydroimidazo[1,5-a]pyrazin-2(3H)-yl)-[1,1'-diphenyl]-4-carboxylic acid trifluoroacetate

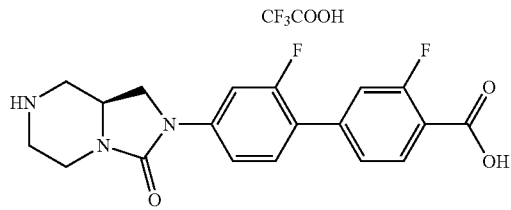 [SMILES: O=C(O)c1ccc(-c2ccc(N3C[C@@H]4CNCCN4C3=O)cc2F)cc1F ; "CF3COOH"]

To a single neck flask were added (R)-4'-(7-(tert-butoxycarbonyl)-3-oxohexahydroimidazo[1,5-a]pyrazin-2(3H)-yl)-2',3-difluoro-[1,1'-diphenyl]-4-carboxylic acid (0.19 g 0.40 mmol), DCM (5 mL) and trifluoroacetic acid (5 ml). The reaction mixture was stirred at 25° C. for 2 hours and concentrated in vacuo to get the title compound as brown oil (0.19 g 100%).

Step 5: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2',3-difluoro-[1,1'-diphenyl]-4-carboxylic acid

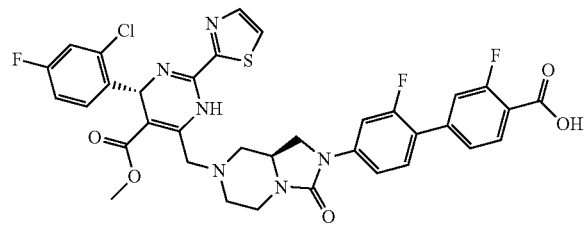 [SMILES: COC(=O)C1=C(CN2CCN3C(=O)N(c4ccc(-c5ccc(C(=O)O)c(F)c5)c(F)c4)C[C@@H]3C2)NC(c2nccs2)=N[C@H]1c1ccc(F)cc1Cl]

To a single neck flask were added (S)-2',3-difluoro-4'-(3-oxohexahydroimidazo [1,5-a]pyrazin-2(3H)-yl)-[1,1'-diphenyl]-4-carboxylic acid trifluoroacetate (0.195 g 0.40 mmol), (R)-methyl 6-(bromomethyl)-4-(2-chloro-4-fluorophenyl)-2-(thiazol-2-yl)-1,4-dihydro pyrimidine-5-carboxylate (0.18 g 0.40 mmol), potassium carbonate (200 mg, 1.45 mmol) and EtOH (10 mL). The mixture was stirred at 35° C. for 5 hours and filtered, the filter cake was washed with EA (5 mL). The combined filtrates were concentrated, the residue was diluted with EA (20 mL) and water (5 mL), the mixture was adjusted with dilute hydrochloric acid to pH 6 and the water phase was extracted with EA (10 mL), the combined organic layers were washed with saturated aqueous NaCl (10 mL) and concentrated, the residue was purified by silica gel column chromatography (DCM/MeOH (V/V)=15/1) to give the title compound as a yellow solid (60 mg, 22.3%). MS (ESI, pos. ion) m/z: 737.3 [M+H]$^+$; $^1$H NMR (400 MHz, CD$_3$OD) δ 8.03-7.95 (m, 2H), 7.77 (d, J=3.1 Hz, 1H), 7.70 (dd, J=14.0, 1.6 Hz, 1H), 7.55 (t, J=8.8 Hz, 1H), 7.48-7.43 (m, 2H), 7.42-7.37 (m, 2H), 7.25 (dd, J=8.7, 2.5 Hz, 1H), 7.07 (td, J=8.4, 2.5 Hz, 1H), 6.19 (s, 1H), 4.17 (d, J=17.2 Hz, 1H), 4.13-4.07 (m, 1H), 4.05-3.94 (m, 2H), 3.68-3.65 (m, 1H), 3.61 (s, 3H), 3.60-3.56 (m, 1H), 3.03 (d, J=11.1 Hz, 2H), 2.50 (td, J=11.4, 2.8 Hz, 1H), 2.33-2.25 (m, 1H), 2.08-2.02 (m, 1H).

Example 35: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2'-fluoro-[1,1'-diphenyl]-4-carboxylic acid Step 1: methyl 4'-bromo-2'-fluoro-[1,1'-diphenyl]-4-carboxylate

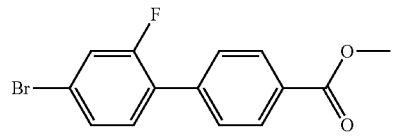 [SMILES: COC(=O)c1ccc(-c2ccc(Br)cc2F)cc1]

4-Bromo-2-fluorobenzene boronic acid (500 mg, 2.29 mmol), methyl 4-iodobenzene carboxylate (500 mg, 1.94 mmol), potassium carbonate (0.95 g 6.87 mmol) and (dppf)PdCl$_2$ (130 mg, 0.18 mmol) were dissolved in toluene (20 mL) under N$_2$. The reaction mixture was stirred at 90° C. for 5 hours and filtered. The filtrate was concentrated in vacuo. The residue was purified by silica gel column chromatography (PE/EtOAc (v/v)=50/1) to give the title compound as a white solid (430 mg, 73%).

Step 2: (R)-tert-butyl 2-(2-fluoro-4'-(methoxycarbonyl)-[1,1'-diphenyl]-4-yl)-3-oxohexahydro imidazo [1,5-a]pyrazine-7(1H)-carboxylate

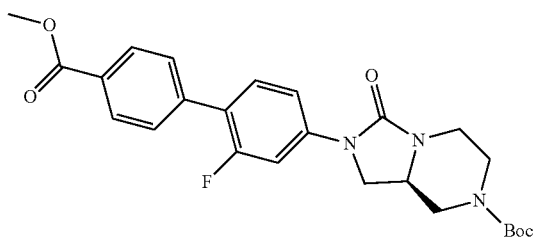 [SMILES: COC(=O)c1ccc(-c2ccc(N3C[C@@H]4CN(C(=O)OC(C)(C)C)CCN4C3=O)cc2F)cc1]

Methyl 4'-bromo-2'-fluoro-[1,1'-diphenyl]-4-carboxylate (200 mg, 0.65 mmol), (R)-tert-butyl 3-oxohexahydroimidazo[1,5-a]pyrazine-7(1H)-carboxylate (171 mg, 0.71 mmol), palladiumacetate (15 mg, 0.06 mmol), 2-di-tert-butylphosphino-2',4',6'-trisopropylbinphenyl (56 mg, 0.13 mmol), cesium carbonate (421 mg, 1.29 mmol) were dissolved in 1,4-dioxane (20 mL) under N$_2$. The mixture was stirred at 90° C. for 12 h. The mixture was concentrated in vacuo. The residue was purified by silica gel column chromatography (PE/EtOAc (V/V)=2/1) to give the title compound as a white solid (220 mg, 72%). MS (ESI, pos. ion): m/z 414.2 [M−56+H]$^+$.

Step 3: (R)-4'-(7-(tert-butoxycarbonyl)-3-oxohexahydroimidazo[1,5-a]pyrazin-2(3H)-yl)-2'-fluoro-[1,1'-diphenyl]-4-carboxylic acid

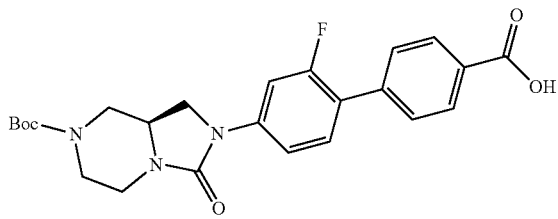 [SMILES: CC(C)(C)OC(=O)N1CCN2C(=O)N(c3ccc(-c4ccc(C(=O)O)cc4)c(F)c3)C[C@@H]2C1]

(R)-tert-Butyl 2-(2-fluoro-4'-(methoxycarbonyl)-[1,1'-diphenyl]-4-yl)-3-oxohexahydro imidazo[1,5-a]pyrazine-7(1H)-carboxylate (200 mg, 0.43 mmol) was dissolved in methanol (10 mL), to the solution was added a solution of lithium hydroxide monohydrate (225 mg, 5.36 mmol) in water (2 mL). The mixture was stirred at 50° C. for 5 hours and adjusted with hydrochloric acid (1 M) to pH 3-4, and then extracted with EtOAc (20 mL×3). The combined organic layers were washed with saturated brine (50 mL), dried over anhydrous sodium sulfate and concentrated in vacuo to give the title compound as a white solid (180 mg, 93%). MS (ESI, pos. ion): m/z 400.1 [M−56+H]+.

Step 4: (S)-2'-fluoro-4'-(3-oxohexahydroimidazo[1,5-a]pyrazin-2(3H)-yl)-[1,1'-diphenyl]-4-carboxylic acid trifluoroacetate

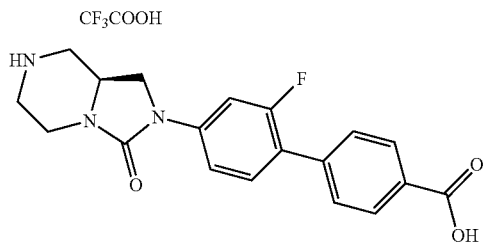 [SMILES: O=C(O)c1ccc(-c2ccc(N3C[C@@H]4CNCCN4C3=O)cc2F)cc1 ; "CF3COOH"]

(R)-4'-(7-(tert-Butoxycarbonyl)-3-oxohexahydroimidazo[1,5-a]pyrazin-2(3H)-yl)-2'-fluoro-[1,1'-diphenyl]-4-carboxylic acid (180 mg, 0.40 mmol) was dissolved in DCM (5 mL), to the solution was added trifluoroacetic acid (5 ml). The mixture was stirred at rt for 1 hour and concentrated in vacuo to get the title compound as brown oil (130 mg, 93%).

Step 5: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2'-fluoro-[1,1'-diphenyl]-4-carboxylic acid

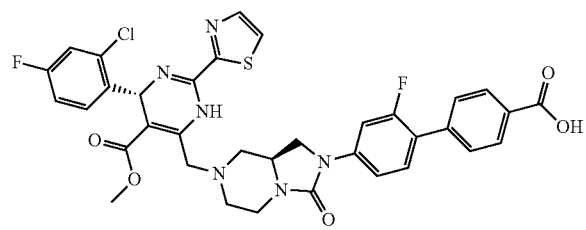 [SMILES: COC(=O)C1=C(CN2CCN3C(=O)N(c4ccc(-c5ccc(C(=O)O)cc5)c(F)c4)C[C@@H]3C2)NC(c2nccs2)=N[C@H]1c1ccc(F)cc1Cl]

(S)-2'-Fluoro-4'-(3-oxohexahydroimidazo[1,5-a]pyrazin-2(3H)-yl)-[1,1'-diphenyl]-4-carboxylic acid trifluoroacetate (120 mg, 0.34 mmol) and potassium carbonate (213 mg, 1.54 mmol) was dissolved in ethanol (10 mL), and to the mixture was added (R)-methyl 6-(bromomethyl)-4-(2-chloro-4-fluorophenyl)-2-(thiazol-2-yl)-1,4-dihydropyrimidine-5-carboxy late (252 mg, 0.57 mmol). The resulting mixture was stirred at rt for 12 hours, the reaction mixture was concentrated in vacuo. The residue was purified by silica gel column chromatography (DCM/MeOH (V/V)=10/1) to give the title compound as a yellow solid (120 mg, 49%). MS (ESI, pos. ion): m/z 719.0 [M+H]+; 1H NMR (400 MHz, DMSO-d6) δ 8.09-7.99 (m, 4H), 772-7.65 (m, 3H), 7.59 (t, J=8.9 Hz, 1H), 7.54-7.47 (m, 1H), 7.46-7.36 (m, 2H), 7.21 (td, J=8.4, 2.1 Hz, 1H), 6.03 (s, 1H), 4.45-4.30 (m, 1H), 4.23-4.16 (m, 1H), 4.05 (t, J=9.2 Hz, 2H), 3.97 (d, J=13.2 Hz, 2H), 3.65 (d, J=5.7 Hz, 1H), 3.55 (s, 3H), 3.47-3.35 (m, 2H), 3.06-2.72 (m, 2H).

Example 36: 3-(4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl)-2,2-dimethylpropionic acid Step 1: methyl 2,2-dimethyl-3-(4-(4,4,5,5-tetramethyl-1,3,2-dioxaborolan-2-yl)phenyl) propanoate

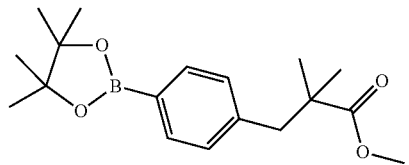

Methyl 3-(4-bromophenyl)-2,2-dimethylpropionate (740 mg, 2.73 mmol) and bis(pinacolato)diboron (1.04 g 4.10 mmol) dissolved in 1,4-dioxane (40 mL), (dppf)PdCl2 (63 mg, 0.08 mmol) and KOAc (800 mg, 8.16 mmol) were added under N2, the mixture was degassed with N2 3 times and stirred at 90° C. for 12 hours under N2. After the reaction was complete, EA (50 mL) was added. The organic layer was washed with water (30 mL) and saturated brine (30 mL) in turn, dried over anhydrous sodium sulfate and concentrated in vacuo. The residue was purified by silica gel column chromatography (PE/EtOAc (v/v)=10/1) to give the title compound as a light yellow solid (233 mg, 26.83%). MS (ESI, pos. ion) m/z: 319.1[M+H]+.

Step 2: (S)-tert-butyl 2-(4-(4-(3-methoxy-2,2-dimethyl-3-oxopropyl)phenyl)thiazol-2-yl)-3-oxohexahydroimidazo[1,5-a]pyrazin-7(1H)-carboxylate

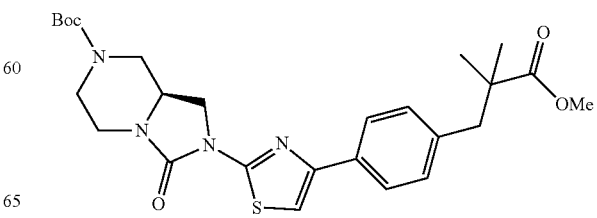

To a 50 mL two neck flask were added (S)-tert-Butyl 2,2-(4-bromothiazol-2-yl)-3-oxohexahydroimidazo[1,5-a]pyrazine-7(1H)-carboxylate (324 mg, 0.80 mmol), methyl 2,2-dimethyl-3-(4-(4,4,5,5-tetramethyl-1,3,2-dioxaborolan-2-yl)phenyl)propanoate (223 mg, 0.73 mmol), Pd(PPh$_3$)$_4$ (85 mg, 0.07 mmol) and Cs$_2$CO$_3$ (430 mg, 1.32 mmol), and 1,4-dioxane (15 mL) was added under N$_2$. The mixture was stirred at 90° C. for 12 hours and EA (50 mL) was added. The organic layer was washed with water (30 mL) and saturated brine (30 mL) in turn, dried over anhydrous sodium sulfate and concentrated in vacuo. The residue was purified by silica gel column chromatography (PE/EtOAc (v/v)=20/1-4/1) to give the title compound as a white solid (250 mg, 66.35%). MS (ESI, pos. ion) m/z: 515.1 [M+H]$^+$.

Step 3: (S)-3-(4-(2-(7-(tert-butoxycarbonyl)-3-oxohexahydroimidazo[1,5-a]pyrazin-2(3H)-yl) thiazol-4-yl)phenyl)-2,2-dimethyl propionic acid

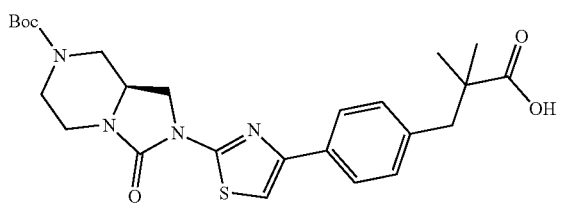 [SMILES: CC(C)(C)OC(=O)N1CCN2C(=O)N(c3nc(-c4ccc(CC(C)(C)C(=O)O)cc4)cs3)C[C@@H]2C1]

(S)-tert-Butyl 2-(4-(4-(3-methoxy-2,2-dimethyl-3-oxopropanyl)phenyl)thiazol-2-yl)-3-oxohexahydroimidazo[1,5-a]pyrazin-7-(1H)-carboxylate (250 mg, 0.49 mmol) was dissolved in THF (10 mL), to the solution was added MeOH (10 mL) and a solution of sodium hydroxide (76 mg, 1.90 mmol) in water (1 mL). The mixture was stirred at 50° C. for 3 hours and adjusted with dilute hydrochloric acid (1 M) to pH 5 to 6, the resulting mixture was extracted with EA (30 mL). The organic layer was washed with saturated brine (30 mL), dried over anhydrous sodium sulfate and filtered. The filtrate was concentrated in vacuo to give the title compound as a white solid (243 mg, 99.92%). MS (ESI, pos. ion) m/z: 501.2 [M+H]$^+$.

Step 4: (S)-2,2-dimethyl-3-(4-(2-(3-oxohexahydroimidazo[1,5-a]pyrazin-2(3H)-yl)thiazol-4-yl)phenyl)propionic acid trifluoroacetate

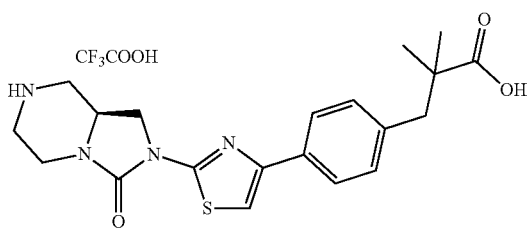 [SMILES: CC(C)(Cc1ccc(-c2csc(N3C[C@@H]4CNCCN4C3=O)n2)cc1)C(=O)O ; "CF3COOH"]

(S)-3-(4-(2-(7-(tert-Butoxycarbonyl)-3-oxohexahydroimidazo[1,5-a]pyrazin-2(3H)-yl) thiazol-4-yl)phenyl)-2,2-dimethyl propionic acid (243 mg, 0.49 mmol) was dissolved in DCM (10 mL), to the solution was added trifluoroacetic acid (5 mL) slowly. The mixture was stirred at rt for 1 hour and concentrated in vacuo to get the title compound as red brown oil (252 mg, 99.79%).

Step 5: 3-(4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl)-2,2-dimethylprop ionic acid

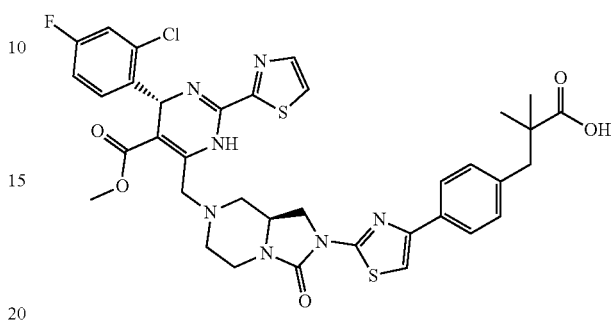

(S)-2,2-dimethyl-3-(4-(2-(3-oxohexahydroimidazo[1,5-a]pyrazin-2(3H)-yl)thiazol-4-yl) phenyl)propionic acid trifluoroacetate (252 mg, 0.49 mmol) was dissolved in EtOH (10 mL), and to the mixture was added (R)-methyl 6-(bromomethyl)-4-(2-chloro-4-fluorophenyl)-2-(thiazol-2-yl)-1,4-dihydropyrimidine-5-carboxylate (194 mg, 0.53 mmol) and potassium carbonate (64 mg, 0.46 mmol). The reaction mixture was stirred at rt for 12 hours and diluted with water (20 mL) and EA (30 mL), and then adjusted with dilute hydrochloric acid (1 M) to pH 5-6, the organic layer was washed with water (30 mL) and the water phase was extracted with EA (20 mL). The combined organic phases were concentrated in vacuo. The residue was purified by silica gel chromatograph (DCM/MeOH (V/V)=10/1) to give the title compound as a yellow solid (172 mg, 46%). MS (ESI, pos. ion) m/z: 764.4 [M+H]$^+$; $^1$H NMR (400 MHz, CDCl$_3$) δ 9.60 (s, 1H), 7.87 (d, J=3.1 Hz, 1H), 7.78 (d, J=8.1 Hz, 2H), 7.49 (d, J=3.1 Hz, 1H), 7.33-7.29 (m, 1H), 7.21 (d, J=8.1 Hz, 2H), 7.16 (dd, J=8.6, 2.5 Hz, 1H), 7.05 (s, 1H), 6.98-6.91 (m, 1H), 6.24 (s, 1H), 4.32-4.24 (m, 1H), 4.17-4.07 (m, 3H), 3.93 (d, J=17.3 Hz, 1H), 3.83 (dd, J=10.5, 4.9 Hz, 1H), 3.62 (s, 3H), 3.38-3.29 (m, 1H), 2.97-2.91 (m, 4H), 2.57-2.49 (m, 1H), 2.29 (t, J=10.9 Hz, 1H), 1.24 (d, J=1.7 Hz, 6H).

Example 37: (R)-methyl 4-(2-chloro-4-fluorophenyl)-6-(((S)-2-(3-(4-(hydroxymethyl)phenyl) prop-2-yn-1-yl)-3-oxohexahydroimidazo[1,5-a]pyrazin-7(1H)-yl)methyl)-2-(thiazol-2-yl)-1,4-dihydropyrimidine-5-carboxylate

Step 1: (R)-tert-butyl 2-(3-(4-(hydroxymethyl)phenyl)prop-2-yn-1-yl)-3-oxohexahydroimidazo [1,5-a]pyrazine-7(1H)-carboxylate

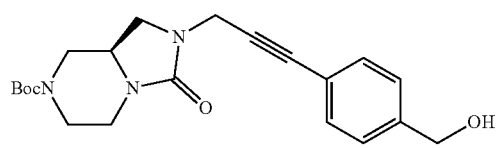 [SMILES: CC(C)(C)OC(=O)N1CCN2C(=O)N(CC#Cc3ccc(CO)cc3)C[C@@H]2C1]

To a flask were added (R)-tert-butyl 3-oxo-2-(2-propyn-1-yl)hexahydroimidazo[1,5-a]pyrazine-7(1H)-carboxylate (230 mg, 0.82 mmol), (4-iodophenyl)methanol (230 mg, 0.99 mmol), bis(triphenylphosphine)palladium(II) chloride (29 mg, 0.041 mmol), cuprous iodide (23 mg, 0.12 mmol), tetrahydrofuran (5 mL) and triethylamine (0.3 mL) in turn. The mixture was stirred at rt for 1 hour and concentrated. The residue was purified by silica gel chromatograph (EA/PE (V/V)=1/1) to get the title compound as light brown oil (0.27 g, 85%). MS (ESI, pos. ion) m/z: 386.1. [M+H]$^+$.

Step 2: (S)-2-(3-(4-(hydroxymethyl)phenyl)prop-2-yn-1-yl)hexahydroimidazo[1,5-a]pyrazine-3(2H)-one hydrochloride

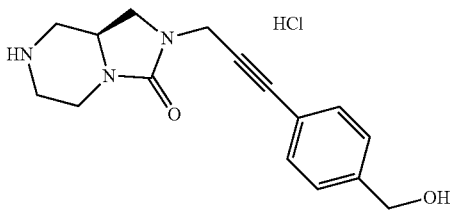 [SMILES: O=C1N(CC#Cc2ccc(CO)cc2)C[C@@H]2CNCCN12 ; Cl]

To a flask were added (R)-tert-butyl 2-(3-(4-(hydroxymethyl)phenyl)prop-2-yn-1-yl)-3-oxohexahydroimidazo[1,5-a]pyrazine-7(1H)-carboxylate (0.27 g, 2.17 mmol) and a solution of HCl in EtOAc (4 mol/L, 4 mL), the mixture was stirred at rt for 5 hours and concentrated. The residue was used in the next step without further purification. MS (ESI, pos. ion) m/z: 286.1 [M+H]$^+$.

Step 3: (R)-methyl 4-(2-chloro-4-fluorophenyl)-6-(((S)-2-(3-(4-(hydroxymethyl)phenyl)prop-2-yn-1-yl)-3-oxohexahydroimidazo[1,5-a]pyrazin-7(1H)-yl)methyl)-2-(thiazol-2-yl)-1,4-dihydro pyrimidine-5-carboxylate

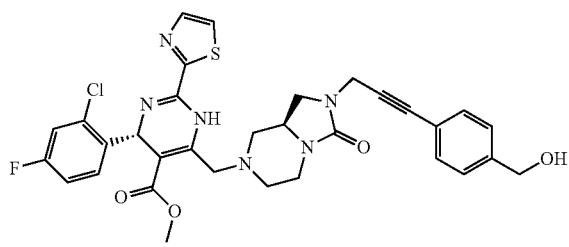 [SMILES: COC(=O)C1=C(CN2CCN3C(=O)N(CC#Cc4ccc(CO)cc4)C[C@@H]3C2)NC(c2nccs2)=N[C@H]1c1ccc(F)cc1Cl]

To a flask were added (S)-2-(3-(4-(hydroxymethyl)phenyl)prop-2-yn-1-yl) hexahydroimidazo[1,5-a]pyrazine-3(2H)-one hydrochloride (180 mg, 0.59 mmol), (R)-methyl 6-(bromomethyl)-4-(2-chloro-4-fluorophenyl)-2-(thiazol-2-yl)-1,4-dihydropyrimidine-5-carboxylate (0.26 g 0.59 mmol), potassium carbonate (160 mg, 1.12 mmol) and ethanol (10 mL). The mixture was stirred at 35° C. for 16 hours. The mixture was filtered and concentrated. The residue was purified by silica gel column chromatography (PE/EtOAc (v/v)=3/1) to give the title compound as a yellow solid (51 mg, 14%). MS (ESI, pos. ion) m/z: 649.1 [M+H]$^+$; $^1$H NMR (400 MHz, MeOH-d$_4$) δ 7.97 (d, J=3.1 Hz, 1H), 7.76 (d, J=3.1 Hz, 1H), 7.47-7.38 (m, 3H), 7.34 (d, J=8.2 Hz, 2H), 7.24 (dd, J=8.7, 2.6 Hz, 1H), 7.06 (td, J=8.4, 2.5 Hz, 1H), 6.18 (s, 1H), 4.61 (s, 2H), 4.25 (d, J=8.4 Hz, 2H), 4.14 (d, J=16.5 Hz, 1H), 4.00-3.87 (m, 3H), 3.66 (t, J=8.9 Hz, 1H), 3.61 (s, 3H), 3.25-3.18 (m, 2H), 2.96 (s, 2H), 2.42 (s, 1H), 2.27 (s, 1H).

Example 38: (R)-methyl 4-(2-chloro-4-fluorophenyl)-6-(((S)-2-(3-(4-(2-hydroxyprop-2-yl) phenyl)-2-propyn-1-yl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (118 mg, 41%) was prepared by the method according to example 37 by the replacement of (4-iodophenyl)methanol with 2-(4-iodophenyl)-2-propanol (0.134 g 0.51 mmol) in step 1 of example 37.

MS (ESI, pos. ion) m z: 677.3 [M+H]$^+$; $^1$H NMR (400 MHz, MeOH-d$_4$) δ 7.96 (d, J=3.1 Hz, 1H), 7.75 (d, J=3.1 Hz, 1H), 7.51-7.36 (m, 5H), 7.24 (dd, J=8.7, 2.6 Hz, 1H), 7.06 (td, J=8.4, 2.6 Hz, 1H), 6.17 (s, 1H), 4.25 (m, 2H), 4.11 (m, 1H), 3.98-3.86 (m, 3H), 3.65 (t, J=8.8 Hz, 1H), 3.60 (s, 3H), 3.24-3.16 (m, 2H), 2.94 (d, J=10.7 Hz, 2H), 2.43-2.36 (m, 1H), 2.23 (t, J=10.2 Hz, 1H), 1.53 (s, 6H).

Example 39: (R)-methyl 6-(((S)-2-(3-(4-carbamoylphenyl)prop-2-yn-1-yl)-3-oxohexahydro imidazo[1,5-a]pyrazin-7(1H)-yl)methyl)-4-(2-chloro-4-fluorophenyl)-2-(thiazol-2-yl)-1,4-dihydropyrimidine-5-carboxylate The title compound as a yellow solid (76 mg, 50.57%) was prepared by the method according to example 37 by the replacement of (4-iodophenyl)methanol with 4-iodobenzamide (89 mg, 0.36 mmol) in step 1 of example 37. MS (ESI, pos. ion) m/z: 662.1 [M+H]$^+$; $^1$H NMR (400 MHz, CDCl$_3$) δ 9.64 (s, 1H), 7.92-7.72 (m, 3H), 7.49 (d, J=8.1 Hz, 3H), 7.28 (s, 1H), 7.14 (d, J=6.8 Hz, 1H), 6.93 (s, 1H), 6.30 (s, 1H), 6.20 (s, 1H), 5.95 (s, 1H), 4.36-4.21 (m, 2H), 4.15-4.05 (m, 2H), 3.99-3.83 (m, 2H), 3.60 (s, 4H), 3.23 (s, 1H), 3.11 (s, 1H), 2.83 (s, 2H), 2.45 (s, 1H), 2.27 (s, 1H).

Example 40: (R)-methyl 4-(2-chloro-4-fluorophenyl)-6-(((S)-2-(3-(4-(methoxycarbamoyl)phenyl)prop-2-yn-1-yl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (257 mg, 45.45%) was prepared by the method according to example 37 by the replacement of (4-iodophenyl)methanol with 4-iodo-N-methoxybenzamide (340 mg, 1.22 mmol) in step 1 of example 37. MS (ESI, pos. ion) m/z: 692.2 [M+H]$^+$; 1H NMR (400 MHz, CDCl$_3$) δ 10.13 (s, 1H), 9.62 (s, 1H), 7.92-7.69 (m, 3H), 7.44 (d, J=8.0 Hz, 3H), 7.28 (s, 1H), 7.12 (d, J=7.5 Hz, 1H), 6.91 (s, 1H), 6.19 (s, 1H), 4.32-4.17 (m, 2H), 4.14-4.03 (m, 2H), 3.94 (d, J=12.4 Hz, 1H), 3.86 (s, 4H), 3.58 (s, 4H), 3.20 (t, J=11.1 Hz, 1H), 3.09 (s, 1H), 2.80 (s, 2H), 2.48-2.33 (m, 1H), 2.30-2.17 (m, 1H).

Example 41: (R)-methyl 4-(2-chloro-4-fluorophenyl)-6-(((S)-2-(3-(4-(methylsulfonyl)phenyl)-2-propyn-1-yl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (150 mg, 66.3%) was prepared by the method according to example 37 by the replacement of (4-iodophenyl)methanol with 1-iodo-4-

(methylsulfonyl)benzene (262 mg, 0.93 mmol) in step 1 of example 37. MS (ESI, pos. ion) m/z: 697.0[M+H]+; $^1$H NMR (400 MHz, CDCl$_3$) δ 9.63 (br, 1H), 7.91 (d, J=8.5 Hz, 2H), 7.86 (d, J=3.1 Hz, 1H), 7.61 (d, J=8.5 Hz, 2H), 7.47 (d, J=3.1 Hz, 1H), 7.28 (d, J=6.2 Hz, 1H), 7.15 (dd, J=8.6, 2.6 Hz, 1H), 6.97-6.89 (m, 1H), 6.21 (s, 1H), 4.37 (d, J=18 Hz, 1H), 4.26 (d, J=18 Hz, 1H), 4.14-4.07 (m, 1H), 4.03-3.90 (m, 2H), 3.90-3.83 (m, 1H), 3.64-3.56 (m, 4H), 3.28-3.17 (m, 1H), 3.12-3.08 (m, 1H), 3.07 (s, 3H), 2.87-2.74 (m, 2H), 2.51-2.38 (m, 1H), 2.26 (t, J=10.8 Hz, 1H).

Example 42: (R)-methyl 4-(2-chloro-4-fluorophenyl)-6-(((S)-2-(3-(4-(dimethylcarbamoyl) phenyl) prop-2-yn-1-yl)-3-oxohexahydroimidazo[1,5-a] pyrazin-7(1H)-yl)methyl)-2-(thiazol-2-yl)-1,4-dihydropyrimidine-5-carboxylate The title compound as a yellow solid (121 mg, 72.2%) was prepared by the method according to example 37 by the replacement of (4-iodophenyl)methanol with 4-iodo-N,N-dimethylbenzamide (201 mg, 0.73067 mmol) in step 1 of example 37. MS (ESI, pos. ion) m/z: 690.2 [M+H]+; $^1$H NMR (400 MHz, CDCl$_3$) δ 9.62 (s, 1H), 7.83 (d, J=3.1 Hz, 1H), 7.46-7.41 (m, 3H), 7.37-7.33 (m, 2H), 7.29-7.21 (m, 1H), 7.12 (dd, J=8.6, 2.6 Hz, 1H), 6.90 (td, J=8.3, 2.6 Hz, 1H), 6.18 (s, 1H), 4.31 (d, J=17.6 Hz, 1H), 4.21 (d, J=17.6 Hz, 1H), 4.11-4.04 (m, 1H), 3.96 (dd, J=13.2, 2.2 Hz, 1H), 3.93-3.87 (m, 1H), 3.84 (d, J=17.3 Hz, 1H), 3.62-3.55 (m, 4H), 3.20 (td, J=12.9, 3.3 Hz, 1H), 3.12-3.04 (m, 4H), 2.96 (s, 3H), 2.84-2.74 (m, 2H), 2.43 (td, J=11.5, 3.2 Hz, 1H), 2.24 (t, J=10.9 Hz, 1H).

Example 43: (R)-methyl 4-(2-chloro-4-fluorophenyl)-6-(((S)-2-(3-(4-(N,N-dimethylamino sulfonyl) phenyl)prop-2-yn-1-yl)-3-oxohexahydroimidazo[1, 5-a]pyrazin-7(1H)-yl)methyl)-2-(thiazol-2-yl)-1,4-dihydropyrimidine-5-carboxylate The title compound as a yellow solid (210 mg, 76.5%) was prepared by the method according to example 37 by the replacement of (4-iodophenyl)methanol with 4-iodo-N,N-dimethylbenzenesulfonamide (200 mg, 0.64 mmol) in step 1 of example 37. MS (ESI, pos. ion) m/z: 726.3[M+H]+; 1H NMR (400 MHz, CDCl$_3$) δ 9.60 (s, 1H), 7.83 (d, J=3.1 Hz, 1H), 7.70 (d, J=8.4 Hz, 2H), 7.55 (d, J=8.4 Hz, 2H), 7.45 (d, J=3.1 Hz, 1H), 7.26 (t, J=7.4 Hz, 1H), 7.12 (dd, J=8.6, 2.6 Hz, 1H), 6.90 (td, J=8.3, 2.6 Hz, 1H), 6.18 (s, 1H), 4.33 (d, J=17.6 Hz, 1H), 4.23 (d, J=18.0 Hz, 1H), 4.13-4.04 (m, 1H), 4.00-3.93 (m, 1H), 3.93-3.87 (m, 1H), 3.84 (d, J=17.3 Hz, 1H), 3.58 (t, J=8.6 Hz, 4H), 3.20 (td, J=12.9, 3.2 Hz, 1H), 3.09-3.06 (m, 1H), 2.80 (t, J=11.0 Hz, 2H), 2.70 (s, 6H), 2.43 (td, J=11.5, 3.2 Hz, 1H), 2.24 (t, J=10.9 Hz, 1H).

Example 44: (R)-methyl 4-(2-chloro-4-fluorophenyl)-6-(((S)-2-(3-(4-cyanophenyl)prop-2-yn-1-yl)-3-oxohexahydroimidazo[1,5-a]pyrazin-7(1H)-yl) methyl)-2-(thiazol-2-yl)-1,4-dihydropyrimidine-5-carboxylate The title compound as a yellow solid (210 mg, 64.3%) was prepared by the method according to example 37 by the replacement of (4-iodophenyl)methanol with 4-iodobenzonitrile (165 mg, 0.72 mmol) in step 1 of example 37. MS (ESI, pos. ion) m/z: 644.8 [M+H]+; $^1$H NMR (400 MHz, CDCl$_3$) δ 9.62 (s, 1H), 7.84 (s, 1H), 7.59 (d, J=7.6 Hz, 2H), 7.53-7.42 (m, 3H), 7.30-7.25 (m, 1H), 7.12 (d, J=7.6 Hz, 1H), 6.91 (t, J=6.8 Hz, 1H), 6.19 (s, 1H), 4.33 (d, J=18.0 Hz, 1H), 4.24 (d, J=18.0 Hz, 1H), 4.13-4.06 (m, 1H), 4.00-3.93 (m, 1H), 3.93-3.82 (m, 2H), 3.63-3.54 (m, 4H), 3.21 (t, J=11.3 Hz, 1H), 3.11-3.04 (m, 1H), 2.81 (t, J=9.9 Hz, 2H), 2.43 (t, J=10.1 Hz, 1H), 2.24 (t, J=10.5 Hz, 1H).

Example 45: (R)-methyl 4-(2-chloro-4-fluorophenyl)-6-(((S)-2-(3-(4-methoxyphenyl)prop-2-yn-1-yl)-3-oxohexahydroimidazo[1,5-a]pyrazin-7(1H)-yl) methyl)-2-(thiazol-2-yl)-1,4-dihydropyrimidine-5-carboxylate The title compound as a yellow solid (210 mg, 39%) was prepared by the method according to example 37 by the replacement of (4-iodophenyl)methanol with 4-iodoanisole (235 mg, 1.0 mmol) in step 1 of example 37. MS (ESI, pos. ion) m/z: 649.2 [M+H]+; $^1$H NMR (400 MHz, CDCl3) δ 7.85 (s, 1H), 7.51 (s, 1H), 7.31-7.35 (m, 3H), 7.13-7.15 (m, 1H), 6.96-7.00 (m, 1H), 6.82-6.84 (m, 2H), 6.16 (s, 1H), 4.63 (d, J=15.2 Hz, 1H), 4.40-4.23 (m, 4H), 4.05 (d, J=13.6 Hz, 1H), 3.81 (s, 3H), 3.64-3.68 (m, 1H), 3.61 (s, 3H), 3.51-3.54 (m, 3H), 3.17 (d, J=7.6 Hz, 1H), 2.83-2.87 (m, 2H).

Example 46: (R)-methyl 4-(2-chloro-4-fluorophenyl)-6-(((S)-2-(3-(4-(1-hydroxycyclobutyl) phenyl) prop-2-yn-1-yl)-3-oxohexahydroimidazo[1,5-a] pyrazin-7(1H)-yl)methyl)-2-(thiazol-2-yl)-1,4-dihydropyrimidine-5-carboxylate The title compound as a yellow solid (12 mg, 3.2%) was prepared by the method according to example 37 by the replacement of (4-iodophenyl)methanol with 2-(4-bromophenyl)-cyclobutanol (0.15 g 0.66 mmol) in step 1 of example 37. MS (ESI, pos. ion) m/z: 689.3 [M+H]+; $^1$H NMR (400 MHz, MeOH-d$_4$) δ 7.96 (d, J=3.1 Hz, 1H), 7.75 (d, J=3.1 Hz, 1H), 7.50 (d, J=8.4 Hz, 2H), 7.42 (dd, J=7.0, 5.0 Hz, 3H), 7.24 (dd, J=8.7, 2.6 Hz, 1H), 7.06 (td, J=8.4, 2.6 Hz, 1H), 6.17 (s, 1H), 4.29 (q, J=18.0 Hz, 1H), 4.22 (q, J=17.6 Hz, 1H), 4.12 (m, 1H), 3.92 (m, 3H), 3.65 (t, J=8.8 Hz, 1H), 3.60 (s, 3H), 3.24-3.17 (m, 2H), 2.95-2.89 (m, 2H), 2.51 (m, 2H), 2.41-2.32 (m, 3H), 2.22 (m, 1H), 2.10-1.99 (m, 2H).

Example 47: (R)-methyl 4-(2-chloro-4-fluorophenyl)-6-(((S)-2-(3-(4-(1-hydroxycyclopropyl) phenyl) prop-2-yn-1-yl)-3-oxohexahydroimidazo[1,5-a] pyrazin-7(1H)-yl)methyl)-2-(thiazol-2-yl)-1,4-dihydropyrimidine-5-carboxylate The title compound as a yellow solid (28 mg, 7.5%) was prepared by the method according to example 37 by the replacement of (4-iodophenyl)methanol with 2-(4-iodophenyl)-cyclopropanol (0.18 g 0.66 mmol) in step 1 of example 37. MS (ESI, pos. ion) m/z: 674.8 [M+H]+; $^1$H NMR (400 MHz, MeOH-d$_4$) δ 7.96 (d, J=2.0 Hz, 1H), 7.75 (d, J=1.6 Hz, 1H), 7.46-7.34 (m, 3H), 7.30-7.21 (m, 3H), 7.10-7.02 (m, 1H), 6.17 (s, 1H), 4.24 (m, 2H), 4.11 (m, 1H), 3.99-3.85 (m, 3H), 3.66 (d, J=8.9 Hz, 1H), 3.60 (s, 3H), 3.27-3.17 (m, 2H), 2.92 (t, J=10.2 Hz, 2H), 2.40 (m, 1H), 2.31-2.21 (m, 1H), 1.21 (s, 2H), 1.04 (s, 2H).

Example 48: (R)-methyl 4-(2-chloro-4-fluorophenyl)-6-(((S)-2-(3-(4-cyano-2,6-dimethylphenyl)-2-propynyl)-3-oxohexahydroimidazo[1,5-a]pyrazin-7 (1H)-yl)methyl)-2-me (thiazol-2-yl)-1,4-dihydropyrimidine-5-carboxylate The title compound as a yellow solid (139 mg, 38.8%) was prepared by the method according to example 37 by the replacement of (4-iodophenyl)methanol with 3,5-dimethyl-4-bromoxynil (460 mg, 2.14 mmol) in step 1 of example 37. MS (ESI, pos. ion) m/z: 672.1[M+H]+; 1H NMR (400 MHz, CDCl₃) δ 7.89 (s, 1H), 7.57 (s, 1H), 7.35 (s, 2H), 7.18 (d, J=7.0 Hz, 1H), 7.01 (t, J=8.4 Hz, 1H), 6.18 (s, 1H), 4.47 (d, J=17.6 Hz, 1H), 4.41 (d, J=14.8 Hz, 2H), 4.34 (d, J=17.9 Hz, 1H), 3.74-3.67 (m, 2H), 3.63 (s, 3H), 3.18 (dd, J=8.9, 1.8 Hz, 1H), 2.97-2.84 (m, 6H), 2.44 (s, 6H).

Example 49: (R)-methyl 4-(2-chloro-4-fluorophenyl)-6-(((S)-2-(3-(4-cyano-2-methoxyphenyl) prop-2-yn-1-yl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (75 mg, 32.9%) was prepared by the method according to example 37 by the replacement of (4-iodophenyl)methanol with 4-bromo-3-methoxy-benzonitrile (270 mg, 1.27 mmol) in step 1 of example 37. MS (ESI, pos. ion) m/z: 674.2[M+H]+; ¹H NMR (400 MHz, CDCl₃) δ 9.63 (s, 1H), 7.85 (d, J=3.1 Hz, 1H), 7.49-7.42 (m, 2H), 7.31-7.25 (m, 1H), 7.23-7.19 (m, 1H), 7.14 (dd, J=8.6, 2.4 Hz, 1H), 7.09 (s, 1H), 6.92 (td, J=8.4, 2.4 Hz, 1H), 6.20 (s, 1H), 4.37 (d, J=17.6 Hz, 1H), 4.30 (d, J=18.0 Hz, 1H), 4.10 (d, J=17.2 Hz, 1H), 4.01-3.95 (m, 1H), 3.95-3.89 (m, 4H), 3.89-3.82 (m, 1H), 3.66-3.57 (m, 4H), 3.27-3.16 (m, 1H), 3.14-3.07 (m, 1H), 2.82 (t, J=10.9 Hz, 2H), 2.51-2.38 (m, 1H), 2.25 (t, J=10.8 Hz, 1H).

Example 50: (R)-methyl 4-(2-chloro-4-fluorophenyl)-6-(((S)-2-(3-(4-cyano-2-fluorophenyl)prop-2-yn-1-yl)-3-oxohexahydroimidazo[1,5-a]pyrazin-7(1H)-yl)methyl)-2-(thiazol-2-yl)-1,4-dihydro pyrimidine-5-carboxylate The title compound as a yellow solid (183 mg, 49.2%) was prepared by the method according to example 37 by the replacement of (4-iodophenyl)methanol with 4-bromo-3-fluoro-benzonitrile (340 mg, 1.70 mmol) in step 1 of example 37. MS (ESI, pos. ion) m/z: 662.0[M+H]+; ¹H NMR (400 MHz, CDCl₃) δ 9.62 (s, 1H), 7.86 (d, J=3.1 Hz, 1H), 7.56-7.49 (m, 1H), 7.47 (d, J=3.1 Hz, 1H), 7.44-7.35 (m, 2H), 7.31-7.26 (m, 1H), 7.14 (dd, J=8.6, 2.5 Hz, 1H), 6.93 (td, J=8.3, 2.6 Hz, 1H), 6.21 (s, 1H), 4.37 (d, J=18.0 Hz, 1H), 4.30 (d, J=18.0 Hz, 1H), 4.11 (d, J=17.3 Hz, 1H), 3.98 (dd, J=13.5, 2.3 Hz, 1H), 3.95-3.91 (m, 1H), 3.87 (d, J=17.3 Hz, 1H), 3.64-3.57 (m, 4H), 3.23 (t, J=12.9, 3.2 Hz, 1H), 3.12-3.09 (m, 1H), 2.89-2.77 (m, 2H), 2.45 (td, J=11.5, 3.2 Hz, 1H), 2.25 (t, J=10.9 Hz, 1H).

Example 51: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)-2-fluorobenzoic acid The title compound as a yellow solid (209 mg, 51.7%) was prepared by the method according to example 1 by the replacement of methyl 4-iodobenzenecarboxylate with methyl 4-bromo-3-fluoro-benzoate (200 mg, 0.85826 mmol) in step 2 of example 1. MS (ESI, pos. ion) m/z: 681.0 [M+H]+; ¹H NMR¹H NMR (400 MHz, CDCl₃) δ 7.93 (t, J=7.8 Hz, 1H), 7.85 (d, J=3.1 Hz, 1H), 7.47 (d, J=3.1 Hz, 1H), 7.34-7.29 (m, 1H), 7.24 (d, J=8.0 Hz, 1H), 7.21-7.10 (m, 2H), 6.93 (td, J=8.3, 2.5 Hz, 1H), 6.22 (s, 1H), 4.37 (d, J=18.0 Hz, 1H), 4.26 (d, J=18.0 Hz, 1H), 4.16 (d, J=17.0 Hz, 1H), 4.07-3.85 (m, 3H), 3.72-3.55 (m, 4H), 3.26 (t, J=11.1 Hz, 1H), 3.13-3.10 (m, 1H), 2.87 (s, 2H), 2.50 (t, J=10.2 Hz, 1H), 2.31 (t, J=10.3 Hz, 1H).

Example 52: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)-2-methoxybenzoic acid The title compound as a yellow solid (120 mg, 45.16%) was prepared by the method according to example 1 by the replacement of methyl 4-iodobenzenecarboxylate with methyl 4-bromo-2-methoxy-benzoate (263 mg, 1.07 mmol) in step 2 of example 1. MS (ESI, pos. ion) m/z: 693.1 [M+H]+; ¹H NMR (400 MHz, CDCl₃) δ 9.62 (s, 1H), 8.06 (d, J=7.9 Hz, 1H), 7.85 (d, J=3.0 Hz, 1H), 7.47 (d, J=3.0 Hz, 1H), 7.28 (t, J=7.3 Hz, 1H), 7.18-7.11 (m, 2H), 7.08 (s, 1H), 6.92 (td, J=8.4, 2.4 Hz, 1H), 6.20 (s, 1H), 4.36 (d, J=18.0 Hz, 1H), 4.24 (d, J=17.6 Hz, 1H), 4.11 (d, J=17.2 Hz, 1H), 4.05 (s, 3H), 4.02-3.96 (m, 1H), 3.95-3.89 (m, 1H), 3.86 (d, J=17.2 Hz, 1H), 3.63 (s, 1H), 3.60 (s, 3H), 3.28-3.17 (m, 1H), 3.11-3.08 (m, 1H), 2.83 (t, J=10.4 Hz, 2H), 2.45 (td, J=11.4, 2.8 Hz, 1H), 2.26 (t, J=10.8 Hz, 1H).

Example 53: 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)prop-1-yn-1-yl)-3-methoxybenzoic acid The title compound as a yellow solid (100 mg, 35.5%) was prepared by the method according to example 1 by the replacement of methyl 4-iodobenzenecarboxylate with methyl 4-iodo-3-methoxy-benzoate (314 mg, 1.08 mmol) in step 2 of example 1. MS (ESI, pos. ion) m/z: 693.1 [M+H]+; ¹H NMR (400 MHz, CDCl₃) δ 9.66 (s, 1H), 7.84 (d, J=3.1 Hz, 1H), 7.64 (d, J=7.9 Hz, 1H), 7.58 (s, 1H), 7.47 (d, J=3.1 Hz, 1H), 7.43 (d, J=7.9 Hz, 1H), 7.32-7.27 (m, 1H), 7.14 (dd, J=8.6, 2.5 Hz, 1H), 6.93 (td, J=8.3, 2.6 Hz, 1H), 6.22 (s, 1H), 4.40 (d, J=17.8 Hz, 1H), 4.32 (d, J=17.8 Hz, 1H), 4.17-4.08 (m, 1H), 4.04-3.97 (m, 1H), 3.97-3.93 (m, 1H), 3.91 (s, 3H), 3.90-3.88 (s, 1H), 3.65 (t, J=8.7 Hz, 1H), 3.61 (s, 3H), 3.24 (td, J=13.1, 3.0 Hz 1H), 3.17 5 3.14 (m, 1H), 2.85 (s, 2H), 2.48 (td, J=11.4, 3.0 Hz, 1H), 2.30 (t, J=10.8 Hz, 1H).

Example 54: 4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)but-1-yn-1-yl)benzoic acid The title compound as a yellow solid (120 mg, 47.3%) was prepared by the method according to example 1 by the replacement of 3-bromopropyne with 4-bromo-1-butyne (928 mg, 6.98 mmol) in example 1. MS (ESI, pos. ion) m/z: 677.2 [M+H]+; ¹H NMR (400 MHz, CDCl₃) δ 9.65 (s, 1H), 8.01 (d, J=8.1 Hz, 2H), 7.83 (d, J=3.0 Hz, 1H), 7.48-7.45 (m, 2H), 7.44 (s, 1H), 7.32-7.26 (m, 1H), 7.14 (dd, J=8.5, 2.4 Hz, 1H), 6.92 (td, J=8.4, 2.4 Hz, 1H), 6.21 (s, 1H), 4.09 (d, J=17.0 Hz, 1H), 4.03-3.96 (m, 1H), 3.95-3.88 (m, 1H), 3.85 (d, J=17.2 Hz, 1H), 3.64 (d, J=8.7 Hz, 1H), 3.60 (s, 3H), 3.56-3.50 (m, 2H), 3.26-3.17 (m, 1H), 3.15-3.12 (m, 1H), 2.87-2.74 (m, 2H), 2.69 (t, J=6.5 Hz, 2H), 2.44 (td, J=11.3, 2.8 Hz, 1H), 2.27 (t, J=10.8 Hz, 1H).

Example 55: (R)-methyl 4-(2-chloro-4-fluorophenyl)-6-(((S)-2-(4-(4-cyanophenyl)-2-methylbut-3-yn-2-yl)-3-oxohexahydroimidazo[1,5-a]pyrazin-7(1H)-yl)methyl)-2-(thiazol-2-yl)-1,4-dihydropyrimidine-5-carboxylate Step 1: (R)-tert-butyl 2-(4-(4-cyanophenyl)-2-methylbut-3-yn-2-yl)-3-oxohexahydroimidazo [1,5-a]pyrazine-7(1H)-carboxylate

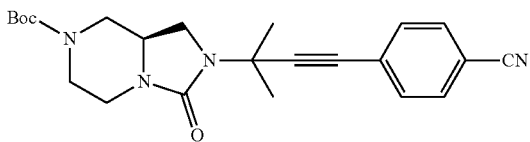 [SMILES: CC(C)(C)OC(=O)N1CCN2C(=O)N(C(C)(C)C#Cc3ccc(C#N)cc3)C[C@@H]2C1]

To a flask were added (R)-tert-butyl 2-(2-methylbut-3-yn-2-yl)-3-oxohexahydroimidazo[1,5-a]pyrazine-7(1H)-carboxylate (100 mg, 0.33 mmol), 4-iodobenzonitrile (107 mg, 0.39 mmol), bis(triphenylphosphine)palladium(II) chloride (11.4 mg, 0.02 mmol), cuprous iodide (6 mg, 0.03 mmol), triethylamine (0.1 mL, 0.7 mmol) and tetrahydrofuran (5 mL) in turn. The mixture was stirred at 65° C. for 8 hours and concentrated in vacuo. The residue was purified by silica gel chromatograph (EA/PE (V/V)=2/1) to get the title compound as colorless oil (120 mg, 90.3%). MS (ESI, pos. ion) m/z: 409.2 [M+H]+.

Step 2: (S)-4-(3-methyl-3-(3-oxohexahydroimidazo [1,5-a]pyrazin-2(3H)-yl)but-1-yn-1-yl) benzonitrile trifluoroacetate

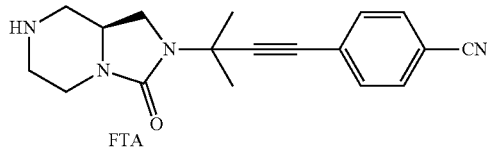

A solution of (R)-tert-butyl 2-(4-(4-cyanophenyl)-2-methylbut-3-yn-2-yl)-3-oxohexahydroimidazo[1,5-a]pyrazine-7(1H)-carboxylate (120 mg, 0.29 mmol) and TFA (3 mL) in DCM (4 mL) was stirred at rt for 4 hours and concentrated in vacuo to get the title compound as a light yellow oil (90 mg, 99.34%), which was used in the next step directly. MS (ESI, pos. ion) m/z: 309.2 [M+H]+.

Step 3: (R)-methyl 4-(2-chloro-4-fluorophenyl)-6-(((S)-2-(4-(4-cyanophenyl)-2-methylbut-3-yn-2-yl)-3-oxohexahydroimidazo[1,5-a]pyrazin-7(1H)-yl)methyl)-2-(thiazol-2-yl)-1,4-dihydro pyrimidine-5-carboxylate

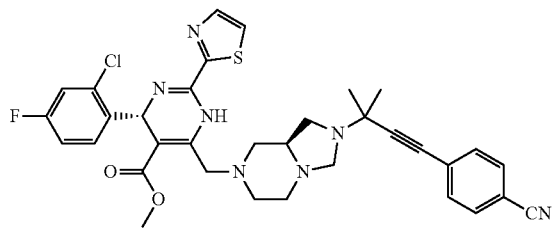 [SMILES: COC(=O)C1=C(CN2CCN3CN(C(C)(C)C#Cc4ccc(C#N)cc4)C[C@@H]3C2)NC(c2nccs2)=N[C@H]1c1ccc(F)cc1Cl]

A mixture of (S)-4-(3-methyl-3-(3-oxohexahydroimidazo [1,5-a]pyrazin-2(3H)-yl) but-1-yn-1-yl)benzonitrile trifluoroacetate (90 mg, 0.29 mmol), potassium carbonate (200 mg, 1.45 mmol), ethanol (3 mL) and (4R)-methyl 6-(bromomethyl)-4-(2-chloro-4-fluorophenyl)-(2-thiazol-2-yl)-1,4-dihydropyrimidine-5-carboxylate (155 mg, 0.35 mmol) was stirred at rt for 12 hours and concentrated in vacuo. The residue was adjusted with hydrochloric acid (1 M) to pH 5-6 and extracted with ethyl acetate (3×20 mL). The combined organic phases were dried over anhydrous sodium sulfate, filtered and the filtrate was concentrated in vacuo. The residue was purified by silica gel chromatograph (PE/EA (V/V)=1/1) to get the title compound as a yellow solid (54 mg, 27.5%). MS (ESI, pos. ion) m/z: 672.1 [M+H]+; 1H NMR (400 MHz, CDCl3) δ 9.61 (s, 1H), 7.84 (s, 1H), 7.65-7.40 (m, 5H), 7.35-7.23 (m, 1H), 7.13 (d, J=6.6 Hz, 1H), 6.95-6.85 (m, 1H), 6.19 (s, 1H), 4.16-4.06 (m, 1H), 3.98-3.76 (m, 3H), 3.67-3.53 (m, 4H), 3.24-3.05 (m, 2H), 2.86-2.68 (m, 2H), 2.50-2.40 (m, 1H), 2.30-2.18 (m, 1H), 1.77 (s, 6H).

Example 56: (R)-methyl 4-(2-chloro-4-fluorophenyl)-6-(((S)-2-(4-(4-(morpholine-4-carbonyl) phenoxy)phenyl)-3-oxohexahydroimidazo[1,5-a] pyrazin-7(1H)-yl)methyl)-2-(thiazol-2-yl)-1,4-dihydropyrimidine-5-carboxylate Step 1: (R)-tert-butyl 2-(4-(4-(morpholine-4-carbonyl)phenoxy)phenyl)-3-oxohexahydroimidazo [1,5-a]pyrazine-7(1H)-carboxylate

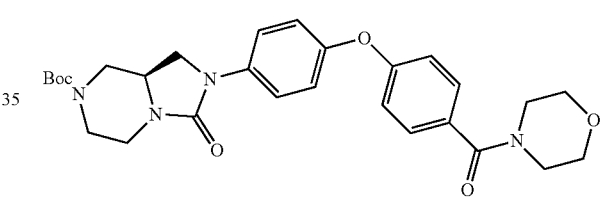

(R)-4-(4-(7-(tert-Butoxycarbonyl)-3-oxohexahydroimidazo[1,5-a]pyrazin-2(3H)-yl) phenoxy)benzoic acid (150 mg, 0.33 mmol) and HATU (159 mg, 0.40 mmol) were dissolved in DMF (6 mL), to the solution was added DIPEA (86 mg, 0.66 mmol) and morpholine (35 mg, 0.40 mmol), the mixture was stirred at rt for 6 hours. The mixture was concentrated in vacuo.

The residue was purified by silica gel column chromatography (PE/EtOAc (V/V)=1/2) to give the title compound as a white solid (120 mg, 70%). MS (ESI, pos. ion) m/z: 466.9 [M+H−56]+.

Step 2: (S)-2-(4-(4-(morpholine-4-carbonyl)phenoxy)phenyl)hexahydroimidazo r[1,5-a]pyrazine-3 (2H)-one trifluoroacetate

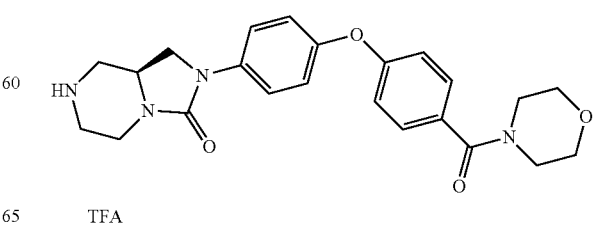

(R)-tert-Butyl 2-(4-(4-(morpholine-4-carbonyl)phenoxy) phenyl)-3-oxohexahydro imidazo[1,5-a]pyrazine-7(1H)-carboxylate (120 mg, 0.23 mmol) was dissolved in DCM (5 mL), to the solution was added trifluoroacetic acid (5 ml). The mixture was stirred at rt for 1 hour and concentrated in vacuo to get the title compound as brown oil (94 mg, 97%). MS (ESI, pos. ion) m/z: 423.1 [M+H]$^+$.

Step 3: (R)-methyl 4-(2-chloro-4-fluorophenyl)-6-(((S)-2-(4-(4-(morpholine-4-carbonyl)phenoxy) phenyl)-3-oxohexahydroimidazo[1,5-a]pyrazin-7(1H)-yl)methyl)-2-(thiazol-2-yl)-1,4-dihydro pyrimidine-5-carboxylate

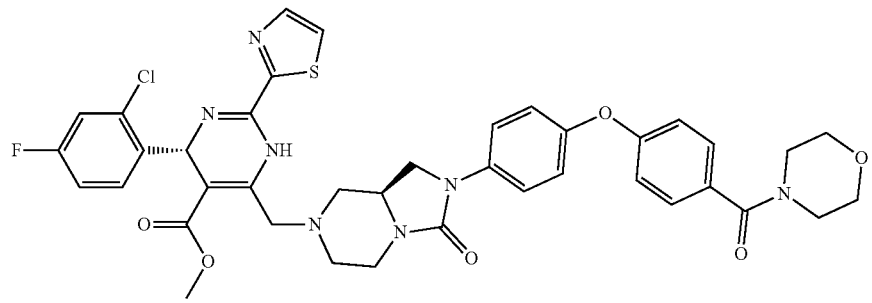 [SMILES: COC(=O)C1=C(CN2CCN3C(=O)N(c4ccc(Oc5ccc(C(=O)N6CCOCC6)cc5)cc4)C[C@@H]3C2)NC(c2nccs2)=N[C@H]1c1ccc(F)cc1Cl]

(S)-2-(4-(4-(Morpholine-4-carbonyl)phenoxy)phenyl) hexahydroimidazo[1,5-a]pyrazin-3(2H)-one trifluoroacetate (100 mg, 0.19 mmol) and DIPEA (72 mg, 0.56 mmol) were dissolved in 1,2-dichloroethane (5 mL), and to the mixture was added (R)-methyl 6-(bromomethyl)-4-(2-chloro-4-fluorophenyl)-2-(thiazol-2-yl)-1,4-dihydropyrimidine-5-carboxy late (100 mg, 0.23 mmol), the resulting mixture was stirred at rt for 8 hours and concentrated in vacuo. The residue was purified by silica gel chromatograph (PE/EA (V/V)=1/1) to get the title compound as a yellow solid (110 mg, 75%). MS (ESI, pos. ion) m/z: 785.8 [M+H]$^+$; $^1$H NMR (400 MHz, CDCl$_3$) δ 9.63 (s, 1H), 7.87 (d, J=3.1 Hz, 1H), 7.55 (d, J=9.0 Hz, 2H), 7.48 (d, J=3.1 Hz, 1H), 7.39 (d, J=8.6 Hz, 2H), 7.33-7.28 (m, 1H), 7.15 (dd, J=8.6, 2.5 Hz, 1H), 7.05 (d, J=9.0 Hz, 2H), 6.98 (d, J=8.6 Hz, 2H), 6.96-6.89 (m, 1H), 6.22 (s, 1H), 4.14 (d, J=17.2 Hz, 1H), 4.10-4.04 (m, 1H), 4.04-3.98 (m, 1H), 3.96-3.86 (m, 2H), 3.79-3.53 (m, 11H), 3.46-3.42 (m, 1H), 3.28 (td, J=13.1, 3.0 Hz, 1H), 2.90 (d, J=10.4 Hz, 2H), 2.52 (td, J=11.4, 2.9 Hz, 1H), 2.29 (t, J=10.8 Hz, 1H).

Example 57: (R)-methyl 4-(2-chloro-4-fluorophenyl)-6-(((S)-2-(4-(4-(2,2-difluoropyrrolidine-1-carbonyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (98 mg, 68%) was prepared by the method according to example 56 by the replacement of morpholine with 2,2-difluoropyrrolidine hydrochloride (57 mg, 0.40 mmol) in step 1 of example 56. MS (ESI, pos. ion) m/z: 806.7 [M+H]$^+$; $^1$H NMR (400 MHz, CDCl$_3$) δ 9.63 (s, 1H), 7.86 (d, J=3.0 Hz, 1H), 7.56 (d, J=8.9 Hz, 2H), 7.52-7.44 (m, 3H), 7.32-7.27 (m, 1H), 7.14 (dd, J=8.5, 2.3 Hz, 1H), 7.05 (d, J=8.9 Hz, 2H), 7.00-6.89 (m, 3H), 6.21 (s, 1H), 4.14 (d, J=17.2 Hz, 1H), 4.10-4.04 (m, 1H), 4.03-3.98 (m, 1H), 3.97-3.69 (m, 6H), 3.60 (s, 3H), 3.45-3.42 (m, 1H), 3.36-3.22 (m, 1H), 2.90 (d, J=9.8 Hz, 2H), 2.56-2.46 (m, 1H), 2.44-2.33 (m, 2H), 2.28 (t, J=10.7 Hz, 1H).

Example 58: (R)-methyl 4-(2-chloro-4-fluorophenyl)-6-(((S)-2-(4-(4-(dipropylcarbamoyl) phenoxy) phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (358 mg, 59.9%) was prepared by the method according to example 56 by the replacement of morpholine with di-n-propylamine (270 mg, 2.67 mmol) in step 1 of example 56. MS (ESI, pos. ion) m/z: 800.3 [M+H]$^+$; $^1$H NMR (400 MHz, CDCl$_3$) δ 7.83 (d, J=2.9 Hz, 1H), 7.51 (d, J=8.8 Hz, 2H), 7.46 (d, J=2.9 Hz, 1H), 7.29 (d, J=8.4 Hz, 3H), 7.10 (dd, J=8.4, 2.2 Hz, 1H), 7.01 (d, J=8.8 Hz, 2H), 6.93 (d, J=8.4 Hz, 3H), 6.17 (s, 1H), 4.28 (d, J=16.7 Hz, 1H), 4.13-4.04 (m, 3H), 3.91 (t, J=8.8 Hz, 1H), 3.58 (s, 3H), 3.45-3.30 (m, 4H), 3.20 (s, 2H), 3.10 (s, 2H), 2.62 (t, J=10.2 Hz, 1H), 2.46 (t, J=10.1 Hz, 1H), 1.60 (m, 4H), 0.88 (m, 6H).

Example 59: (R)-methyl 4-(2-chloro-4-fluorophenyl)-6-(((S)-3-oxo-2-(4-(4-(piperidine-1-carbonyl) phenoxy)phenyl)-hexahydroimidazo[1,5-a]pyrazin-7(1H)-yl)methyl)-2-(thiazol-2-yl)-1,4-dihydropyrimidine-5-carboxylate The title compound as a yellow solid (450 mg, 68.9%) was prepared by the method according to example 56 by the replacement of morpholine with piperidine (290 mg, 3.3 mmol) in step 1 of example 56. MS (ESI, pos. ion) m/z: 784.3 [M+H]$^+$; $^1$H NMR (400 MHz, CDCl$_3$) δ 9.62 (s, 1H), 7.84 (d, J=2.9 Hz, 1H), 7.53 (d, J=8.9 Hz, 2H), 7.45 (d, J=2.8 Hz, 1H), 7.35 (d, J=8.4 Hz, 2H), 7.28 (t, J=7.3 Hz, 1H), 7.12 (dd, J=8.5, 2.0 Hz, 1H), 7.02 (d, J=8.8 Hz, 2H), 6.94 (d, J=8.4 Hz, 2H), 6.90 (d, J=8.2 Hz, 1H), 6.20 (s, 1H), 4.11 (d, J=17.2 Hz, 1H), 4.06-3.98 (m, 2H), 3.92-3.86 (m, 2H), 3.59 (s, 6H), 3.48-3.36 (m, 3H), 3.25 (t, J=11.1 Hz, 1H), 2.88 (d, J=10.0 Hz, 2H), 2.52-2.46 (m, 2H), 2.26 (t, J=10.7 Hz, 1H), 1.66 (s, 4H).

Example 60: (R)-methyl 4-(2-chloro-4-fluorophenyl)-6-(((S)-2-(4-(4-(4-(hydroxymethyl) piperidine-1-carbonyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (538 mg, 70.3%) was prepared by the method according to example 56 by the replacement of morpholine with 4-piperidinemethanol (392 mg, 3.3 mmol) in step 1 of example 56. MS (ESI, pos. ion) m/z: 814.3 [M+H]$^+$; $^1$H NMR (400 MHz, CDCl$_3$) δ 9.62 (s, 1H), 7.84 (d, J=2.7 Hz, 1H), 7.52 (d, J=8.8 Hz, 2H), 7.46 (d, J=2.7 Hz, 1H), 7.34 (d, J=8.3 Hz, 2H), 7.28 (t, J=7.3 Hz, 1H), 7.12 (d, J=8.3 Hz, 1H), 7.02 (d, J=8.7 Hz, 2H), 6.94 (d, J=8.3 Hz, 2H), 6.90 (d, J=8.3 Hz, 1H), 6.20 (s, 1H), 4.11 (d, J=17.2 Hz, 1H), 4.04 (d, J=13.6 Hz, 2H), 3.91 (d, J=7.4 Hz, 2H), 3.87 (d, J=6.2 Hz, 1H), 3.59 (s, 3H), 3.48 (d, J=4.8 Hz, 2H), 3.44-3.40 (m, 1H), 3.25 (t, J=11.2 Hz, 1H), 2.88 (d, J=9.7 Hz, 3H), 2.73 (s, 3H), 2.49 (t, J=10.2 Hz, 1H), 2.27 (t, J=10.6 Hz, 1H), 1.75 (s, 3H), 1.41 (s, 1H). Example 61: (R)-methyl 4-(2-chloro-4-fluorophenyl)-6-(((S)-2-(4-(4-(3-hydroxyazetidine-1-carbonyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (120 mg, 54.1%) was prepared by the method according to example 56 by the replacement of morpholine with 3-hydroxyazetidine hydrochloride (55 mg, 0.50 mmol) in step 1 of example 56. MS (ESI, pos. ion) m/z: 771.8 [M+H]$^+$; $^1$H NMR (400 MHz, MeOH-d$_4$) δ 7.97 (d, J=3.1 Hz, 1H), 7.76 (d, J=3.1 Hz, 1H), 7.69-7.55 (m, 4H), 7.48-7.38 (m, 1H), 7.29-7.18 (m, 1H), 7.11-7.03 (m, 3H), 7.00 (d, J=8.8 Hz, 2H), 6.19 (s, 1H), 4.68-4.49 (m, 2H), 4.48-4.30 (m, 1H), 4.23-4.10 (m, 2H), 4.10-3.88 (m, 5H), 3.61 (s, 3H), 3.57-3.49 (m, 1H), 3.31-3.22 (m, 1H), 2.99 (d, J=10.7 Hz, 2H), 2.52-2.37 (m, 1H), 2.33-2.14 (m, 1H).

Example 62: (R)-methyl 4-(2-chloro-4-fluorophenyl)-6-(((S)-2-(4-(4-((2-chlorobenzyl) carbamoyl) phenoxy)phenyl)-3-oxohexahydroimidazo[1,5-a] pyrazin-7(1H)-yl)methyl)-2-(thiazol-2-yl)-1,4-dihydropyrimidine-5-carboxylate The title compound as a yellow solid (70 mg, 38.3%) was prepared by the method according to example 56 by the replacement of morpholine with (2-chlorophenyl)methylamine (94 mg, 0.66 mmol) in step 1 of example 56. MS (ESI, pos. ion) m/z: 840.2 [M+H]$^+$; $^1$H NMR (400 MHz, MeOH-d$_4$) δ 7.95 (d, J=3.1 Hz, 1H), 7.87 (d, J=8.8 Hz, 2H), 7.74 (d, J=3.1 Hz, 1H), 7.59 (d, J=9.0 Hz, 2H), 7.46-7.36 (m, 4H), 7.31-7.22 (m, 2H), 7.11 (dd, J=8.4, 2.6 Hz 1H), 7.08-7.04 (m, 2H), 7.00 (d, J=8.8 Hz, 2H), 6.17 (s, 1H), 4.66 (s, 2H), 4.15 (d, J=17.0 Hz, 1H), 4.07-3.91 (m, 6H), 3.54 (dd, J=8.9, 4.1 Hz, 1H), 3.26 (d, J=12.0 Hz, 1H), 2.99 (d, J=9.9 Hz, 2H), 2.46 (t, J=10.6 Hz, 1H), 2.25 (s, 1H), 1.13 (t, J=7.1 Hz, 3H).

Example 63: (R)-methyl 6-(((S)-2-(4-(4-(benzyl(2-hydroxyethyl)carbamoyl)phenoxy)phenyl)-3-oxohexahydroimidazo[1,5-a]pyrazin-7(1H)-yl)methyl)-4-(2-chloro-4-fluorophenyl)-2-(thiazol-2-yl)-1,4-dihydropyrimidine-5-carboxylate The title compound as a yellow solid (130 mg, 61.2%) was prepared by the method according to example 56 by the replacement of morpholine with 2-(benzylamino)ethanol (75 mg, 0.50 mmol) in step 1 of example 56. MS (ESI, pos. ion) m/z: 849.7 [M+H]$^+$; $^1$H NMR (400 MHz, acetone-d$_6$) δ 9.79 (s, 1H), 8.00 (d, J=3.1 Hz, 1H), 7.82 (d, J=3.1 Hz, 1H), 7.71 (d, J=9.0 Hz, 2H), 7.56-7.48 (m, 3H), 7.42-7.34 (m, 3H), 7.34-7.23 (m, 3H), 7.10-7.03 (m, 3H), 6.98 (d, J=8.4 Hz, 2H), 6.21 (s, 1H), 4.20-3.95 (m, 7H), 3.72 (s, 2H), 3.58 (s, 3H), 3.48 (s, 1H), 3.24-3.17 (m, 1H), 3.08-3.00 (m, 2H), 2.83 (s, 4H), 2.50-2.42 (m, 1H), 2.30 (t, J=10.6 Hz, 1H).

Example 64: (R)-methyl 6-(((S)-2-(4-(4-(bis(2-hydroxyethyl)carbamoyl)phenoxy)phenyl)-3-oxohexahydroimidazo[1,5-a]pyrazin-7(1H)-yl)methyl)-4-(2-chloro-4-fluorophenyl)-2-(thiazol-2-yl)-1,4-dihydropyrimidine-5-carboxylate The title compound as a yellow solid (83 mg, 52.9%) was prepared by the method according to example 56 by the replacement of morpholine with diethanolamine (450 mg, 4.3 mmol) in step 1 of example 56. MS (ESI, pos. ion) m/z: 804.1[M+H]$^+$; $^1$H NMR (400 MHz, CDCl3) δ 9.62 (s, 1H), 7.85 (s, 1H), 7.51 (d, J=8.6 Hz, 2H), 7.48-7.43 (m, 3H), 7.32-7.26 (m, 1H), 7.13 (d, J=6.9 Hz, 1H), 7.05-6.98 (m, 2H), 6.96-6.87 (m, 3H), 6.19 (s, 1H), 4.17-4.07 (m, 1H), 4.06-3.98 (m, 2H), 3.95-3.82 (m, 4H), 3.77-3.64 (m, 4H), 3.59 (s, 3H), 3.53-3.46 (m, 2H), 3.45-3.37 (m, 1H), 3.25 (t, J=11.4 Hz, 1H), 2.87 (d, J=9.2 Hz, 2H), 2.49 (t, J=10.3 Hz, 1H), 2.26 (t, J=10.4 Hz, 1H).

Example 65: (R)-methyl 4-(2-chloro-4-fluorophenyl)-6-(((S)-2-(4-(4-((2-hydroxyethyl)(methyl)carbamoyl)phenoxy)phen yl)-3-oxohexahydroimidazo [1,5-a]pyrazin-7(1H)-yl)methyl)-2-me (thiazol-2-yl)-1,4-dihydropyrimidine-5-carboxylate The title compound as a yellow solid (123 mg, 75.9%) was prepared by the method according to example 56 by the replacement of morpholine with 2-(methylamino)ethanol (310 mg, 4.1 mmol) in step 1 of example 56. MS (ESI, pos. ion) m/z: 774.3[M+H]$^+$; $^1$H NMR (400 MHz, CDCl$_3$) δ 9.61 (s, 1H), 7.85 (d, J=3.0 Hz, 1H), 7.53 (d, J=8.9 Hz, 2H), 7.46 (d, J=2.9 Hz, 1H), 7.42 (d, J=8.3 Hz, 2H), 7.31-7.26 (m, 1H), 7.13 (dd, J=8.5, 2.3 Hz, 1H), 7.06-7.00 (m, 2H), 6.98-6.88 (m, 3H), 6.20 (s, 1H), 4.16-4.09 (m, 1H), 4.08-3.96 (m, 2H), 3.96-3.81 (m, 4H), 3.77-3.65 (m, 2H), 3.59 (s, 3H), 3.44-3.41 (m, 1H), 3.32-3.21 (m, 1H), 3.09 (s, 3H), 2.92-2.83 (m, 2H), 2.54-2.44 (m, 1H), 2.27 (t, J=10.7 Hz, 1H).

Example 66: (R)-methyl 4-(2-chloro-4-fluorophenyl)-6-(((S)-2-(4-(4-((2-hydroxyethyl)(methyl)carbamoyl)phenoxy)phen yl)-3-oxohexahydroimidazo [1,5-a]pyrazin-7(1H)-yl)methyl)-2-(thiazol-2-yl)-1, 4-dihydropyrimidine-5-carboxylate The title compound as a yellow solid (116 mg, 70.4%) was prepared by the method according to example 56 by the replacement of morpholine with 2-(ethylamino)ethanol (410 mg, 4.6 mmol) in step 1 of example 56. MS (ESI, pos. ion) m/z: 788.4[M+H]$^+$; $^1$H NMR (400 MHz, CDCl3) δ 9.61 (s, 1H), 7.88-7.81 (m, 1H), 7.53 (d, J=8.4 Hz, 2H), 7.46 (s, 1H), 7.37 (d, J=8.1 Hz, 2H), 7.31-7.26 (m, 1H), 7.13 (d, J=7.1 Hz, 1H), 7.03 (d, J=8.4 Hz, 2H), 6.98-6.86 (m, 3H), 6.20 (s, 1H), 4.16-4.08 (m, 1H), 4.07-3.96 (m, 2H), 3.94-3.78 (m, 4H), 3.72-3.62 (m, 2H), 3.59 (s, 3H), 3.47-3.33 (m, 3H), 3.30-3.20 (m, 1H), 2.87 (d, J=9.8 Hz, 2H), 2.49 (t, J=10.2 Hz, 1H), 2.26 (t, J=10.6 Hz, 1H), 1.21-1.12 (m, 3H).

Example 67: (R)-methyl 4-(2-chloro-4-fluorophenyl)-6-(((S)-2-(4-(4-((2-methylbut-3-yn-2-yl) carbamoyl)phenoxy)phenyl)-3-oxohexahydroimidazo [1,5-a]pyrazin-7(1H)-yl)methyl)-2-(thiazol-2-yl)-1, 4-dihydropyrimidine-5-carboxylate The title compound as a yellow solid (101 mg, 69%) was prepared by the method according to example 56 by the replacement of morpholine with 2-methyl-3-butyn-2-amine (33 mg, 0.40 mmol) in step 1 of example 56. MS (ESI, pos.

ion) m/z: 782.3 [M+H]⁺; ¹H NMR (400 MHz, CDCl₃) δ 9.63 (s, 1H), 7.93 (d, J=8.8 Hz, 2H), 7.86 (d, J=3.1 Hz, 1H), 7.56 (d, J=9.0 Hz, 2H), 7.47 (d, J=3.1 Hz, 1H), 7.34-7.27 (m, 1H), 7.14 (dd, J=8.6, 2.5 Hz, 1H), 7.05 (d, J=9.0 Hz, 2H), 6.98 (d, J=8.8 Hz, 2H), 6.93 (td, J=8.4, 2.5 Hz, 1H), 6.22 (s, 1H), 4.73 (d, J=2.8 Hz, 1H), 4.24 (d, J=2.8 Hz, 1H), 4.14 (d, J=17.2 Hz, 1H), 4.07 (d, J=12.6 Hz, 1H), 4.04-3.97 (m, 1H), 3.96-3.86 (m, 2H), 3.61 (s, 3H), 3.46-3.42 (m, 1H), 3.34-3.22 (m, 1H), 2.90 (d, J=10.3 Hz, 2H), 2.51 (td, J=11.4, 2.8 Hz, 1H), 2.28 (t, J=10.8 Hz, 1H), 1.45 (s, 6H).

Example 68: (R)-methyl 4-(2-chloro-4-fluorophenyl)-6-(((S)-2-(4-(4-((1-hydroxy-2-methyl prop-2-yl)carbamoyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (98 mg, 67%) was prepared by the method according to example 56 by the replacement of morpholine with 2-amino-2-methyl-prop-1-ol (35 mg, 0.39 mmol) in step 1 of example 56. MS (ESI, pos. ion) m/z: 788.3 [M+H]⁺; ¹H NMR (400 MHz, CDCl₃) δ 9.63 (s, 1H), 7.86 (s, 1H), 7.78-7.64 (m, 2H), 7.61-7.43 (m, 3H), 7.29 (s, 1H), 7.20-7.10 (m, 1H), 7.07-6.86 (m, 5H), 6.36-6.13 (m, 2H), 4.24-3.98 (m, 3H), 3.96-3.81 (m, 2H), 3.71-3.55 (m, 5H), 3.48-3.39 (m, 1H), 3.27 (s, 1H), 2.99-2.83 (m, 2H), 2.57-2.42 (m, 1H), 2.34-2.21 (m, 1H), 1.41 (s, 6H).

Example 69: (R)-methyl 4-(2-chloro-4-fluorophenyl)-6-(((S)-2-(4-(4-((4-hydroxy-2-methyl but-2-yl)carbamoyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (110 mg, 67%) was prepared by the method according to example 56 by the replacement of morpholine with 3-amino-3-methyl-butan-1-ol (41 mg, 0.39 mmol) in step 1 of example 56. MS (ESI, pos. ion) m/z: 802.3 [M+H]⁺; ¹H NMR (400 MHz, CDCl₃) δ 9.64 (s, 1H), 7.87 (d, J=3.1 Hz, 1H), 7.71 (d, J=8.7 Hz, 2H), 7.56-7.49 (m, 3H), 7.47 (d, J=3.0 Hz, 1H), 7.34-7.28 (m, 1H), 7.15 (dd, J=8.6, 2.5 Hz, 1H), 7.01 (d, J=9.0 Hz, 2H), 6.97-6.87 (m, 3H), 6.22 (s, 1H), 4.13 (d, J=17.2 Hz, 1H), 4.09-3.98 (m, 2H), 3.96-3.87 (m, 4H), 3.61 (s, 3H), 3.45-3.42 (m, 1H), 3.33-3.22 (m, 1H), 2.94-2.85 (m, 2H), 2.51 (td, J=11.2, 2.7 Hz, 1H), 2.28 (t, J=10.8 Hz, 1H), 1.92-1.87 (m, 2H), 1.54 (s, 6H).

Example 70: (R)-methyl 4-(2-chloro-4-fluorophenyl)-6-(((S)-2-(4-(4-((1-methoxy-2-methyl prop-2-yl)carbamoyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (120 mg, 75%) was prepared by the method according to example 56 by the replacement of morpholine with 1-methoxy-2-methyl-propyl-2-amine (41 mg, 0.39 mmol) in step 1 of example 56. MS (ESI, pos. ion) m/z: 802.3 [M+H]⁺; ¹H NMR (400 MHz, CDCl₃) δ 9.63 (s, 1H), 7.86 (d, J=2.9 Hz, 1H), 7.69 (d, J=8.6 Hz, 2H), 7.55 (d, J=8.9 Hz, 2H), 7.47 (d, J=2.9 Hz, 1H), 7.32-7.25 (m, 1H), 7.14 (dd, J=8.5, 2.2 Hz, 1H), 7.03 (d, J=8.9 Hz, 2H), 6.98-6.89 (m, 3H), 6.30 (s, 1H), 6.21 (s, 1H), 4.13 (d, J=17.2 Hz, 1H), 4.09-3.97 (m, 2H), 3.96-3.85 (m, 2H), 3.60 (s, 3H), 3.45 (s, 2H), 3.41 (s, 3H), 3.36 (d, J=10.6 Hz, 1H), 3.32-3.22 (m, 1H), 2.89 (d, J=10.0 Hz, 2H), 2.56-2.47 (m, 1H), 2.28 (t, J=10.7 Hz, 1H), 1.47 (s, 6H).

Example 71: (R)-methyl 4-(2-chloro-4-fluorophenyl)-6-(((S)-2-(4-(4-((4-(dimethylamino)-4-oxobutyl)carbamoyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (136 mg, 26.7%) was prepared by the method according to example 56 by the replacement of morpholine with 4-amino-N,N-dimethyl-butanamide (600 mg, 3.60 mmol) in step 1 of example 56. MS (ESI, pos. ion) m/z: 829.2 [M+H]⁺; ¹H NMR (400 MHz, CDCl₃) δ 9.63 (s, 1H), 7.87 (d, J=2.9 Hz, 1H), 7.81 (d, J=8.5 Hz, 2H), 7.55 (d, J=8.9 Hz, 2H), 7.52-7.45 (m, 2H), 7.33-7.28 (m, 1H), 7.19-7.12 (m, 1H), 7.05 (d, J=8.8 Hz, 2H), 6.97 (d, J=8.6 Hz, 2H), 6.93 (d, J=8.1 Hz, 1H), 6.22 (s, 1H), 4.17-3.99 (m, 3H), 3.95-3.88 (m, 2H), 3.61 (s, 3H), 3.53-3.47 (m, 2H), 3.45-3.43 (m, 1H), 3.28 (t, J=11.0 Hz, 1H), 3.02 (s, 3H), 2.95 (s, 3H), 2.89 (d, J=10.4 Hz, 2H), 2.55-2.48 (m, 3H), 2.29 (t, J=10.8 Hz, 1H), 2.06-1.97 (m, 2H).

Example 72: (4R)-methyl 4-(2-chloro-4-fluorophenyl)-6-(((8aS)-2-(4-(4-((1-hydroxyprop-2-yl) carbamoyl)phenoxy)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (275 mg, 79.4%) was prepared by the method according to example 56 by the replacement of morpholine with 2-amino-prop-1-ol (60 mg, 0.80 mmol) in step 1 of example 56. MS (ESI, pos. ion) m/z: 774.2[M+H]⁺; ¹H NMR (400 MHz, CDCl₃) δ 9.63 (s, 1H), 7.88 (d, J=3.1 Hz, 1H), 7.75 (d, J=8.7 Hz, 2H), 7.56 (d, J=9.0 Hz, 2H), 7.48 (d, J=3.1 Hz, 1H), 7.33-7.29 (m, 1H), 7.16 (dd, J=8.6, 2.5 Hz, 1H), 7.05 (d, J=9.0 Hz, 2H), 6.97 (d, J=8.7 Hz, 2H), 6.93 (dd, J=8.4, 2.5 Hz, 1H), 6.32 (d, J=7.2 Hz, 1H), 6.23 (s, 1H), 4.32-4.26 (m, 1H), 4.15 (d, J=17.2 Hz, 1H), 4.11-4.05 (m, 1H), 4.05-3.99 (m, 1H), 3.97-3.87 (m, 2H), 3.79 (dd, J=10.9, 3.5 Hz, 1H), 3.68-3.64 (m, 1H), 3.62 (s, 3H), 3.47-3.44 (m, 1H), 3.34-3.24 (m, 1H), 2.91 (d, J=10.8 Hz, 2H), 2.57-2.48 (m, 1H), 2.29 (t, J=10.8 Hz, 1H), 1.30 (d, J=6.8 Hz, 3H).

Example 73: 3-((S)-4-(4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)benzoyl)morpholin-3-yl)propanoic acid Step 1: (R)-tert-butyl 2-(4-(4-((S)-3-(3-methoxy-3-oxopropyl)morpholine-4-carbonyl)phenoxy) phenyl)-3-oxohexahydroimidazo[1,5-a]pyrazine-7(1H)-carboxylate

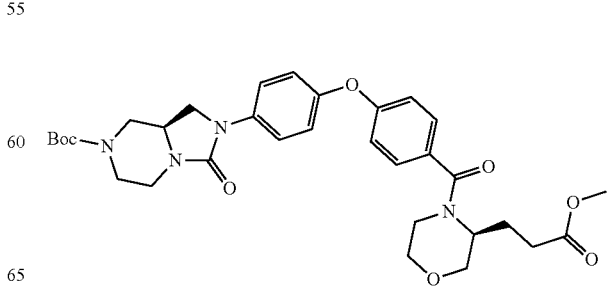

To a dry flask were added (R)-4-(4-(7-(tert-butoxycarbonyl)-3-oxohexahydroimidazo [1,5-a]pyrazin-2(3H)-yl)phenoxy)benzoic acid (202 mg, 0.46 mmol), DMF (20 mL), DIPEA (0.3 mL, 0.2 mmol) and HATU (220 mg, 0.58 mmol) in turn, the mixture was stirred for 10 min, and (S)-methyl 3-morpholine phenylpropionate hydrochloride (112 mg, 0.53 mmol) was added, the mixture was stirred at rt for 12 hours. The mixture was partitioned between water (50 mL) and EtOAc (50 mL), the water phase was extracted with ethyl acetate (50 mL×2), the combined organic layers were washed with saturated aqueous sodium chloride solution. The mixture was dried over anhydrous sodium sulfate and concentrated in vacuo. The residue was purified by silica gel column chromatography (PE/EtOAc (V/V)=1/1) to give the title compound as a white solid (0.19 g 71.2%). MS (ESI, pos. ion) m/z: 609.0 [M+H]⁺.

Step 2: 3-((S)-4-(4-(4-((R)-7-(tert-butyloxycarbonyl)-3-oxohexahydroimidazo[1,5-a]pyrazin-2(3H)-yl)phenoxy)benzoyl)morpholin-3-yl)propanoic acid

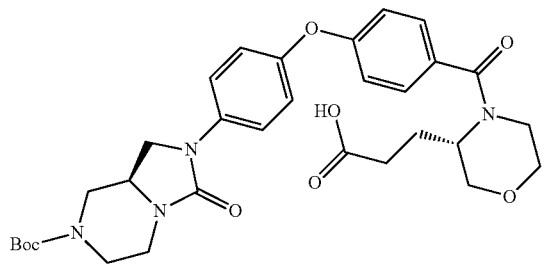 [SMILES: CC(C)(C)OC(=O)N1CCN2C(=O)N(c3ccc(Oc4ccc(C(=O)N5CCOC[C@@H]5CCC(=O)O)cc4)cc3)C[C@@H]2C1]

To a dry flask were added (R)-tert-butyl 2-(4-(4-((S)-3-(3-methoxy-3-oxopropyl) morpholine-4-carbonyl)phenoxy) phenyl)-3-oxohexahydroimidazo[1,5-a]pyrazin-7(1H)-carboxylate (193 mg, 0.32 mmol) and methanol (12 mL), the mixture was dissolved with stirring, and then water (4 mL) and lithium hydroxide monohydrate (67 mg, 1.59 mmol) were added. The resulting mixture was stirred at rt for 12 hours. The mixture was concentrated in vacuo, the residue was diluted with water (30 mL) and ethyl acetate (30 mL), the mixture was partitioned, the organic layer was washed with sodium hydroxide aqueous solution (2 mol/L, 30 mL), and the water phases were combined. The combined water phases were adjusted with hydrochloric acid (1 M) to pH 3 and extracted with ethyl acetate (40 mL×3) 3 times. The combined organic layers were dried over anhydrous sodium sulfate and filtered. The filtrate was concentrated to get the title compound as a white solid (0.12 g 64.2%). MS (ESI, pos. ion) m/z: 595.4 [M+H]⁺.

Step 3: 3-((S)-4-(4-(4-((S)-3-oxohexahydroimidazo [1,5-a]pyrazin-2(3H)-yl)phenoxy)benzoyl) morpholin-3-yl)propanoic acid trifluoroacetate

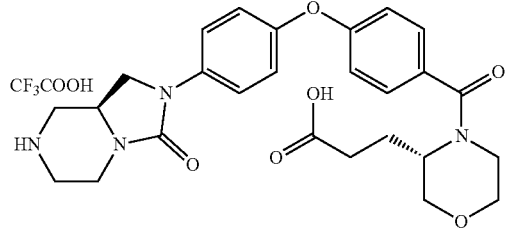 [SMILES: "CF3COOH" ; O=C(O)CC[C@H]1COCCN1C(=O)c1ccc(Oc2ccc(N3C[C@@H]4CNCCN4C3=O)cc2)cc1]

To a dry flask were added 3-((S)-4-(4-(4-((R)-7-(tert-butyloxycarbonyl)-3-oxohexahydroimidazo[1,5-a]pyrazin-2(3H)-yl)phenoxy)benzoyl)morpholin-3-yl))propanoic acid (121 mg, 0.2 mmol), DCM (6 mL) and trifluoroacetic acid (3 ml) in turn, the mixture was stirred for 6 hours. The reaction mixture was diluted with toluene (5 mL) and concentrated by rotary evaporation in vacuo, and the residue was diluted with toluene (5 mL) and concentrated by rotary evaporation in vacuo again, the operation was repeated 3 times to get a yellow oil, which was used in the next step directly. MS(ESI, pos. ion) m/z: 495.0[M+H]⁺.

Step 4: 3-((S)-4-(4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)benzoyl) morpholin-3-yl)propanoic acid

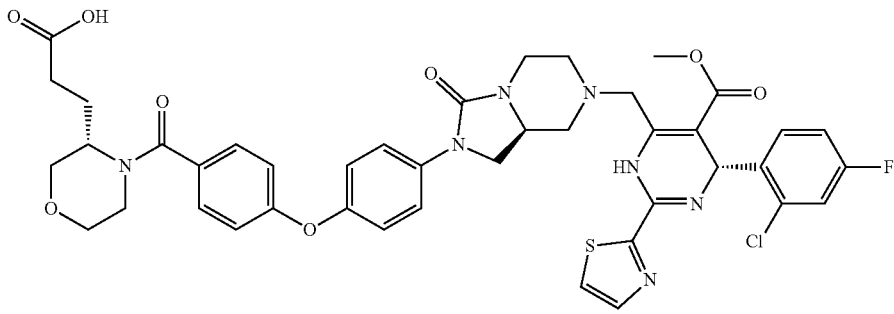 [SMILES: COC(=O)C1=C(CN2CCN3C(=O)N(c4ccc(Oc5ccc(C(=O)N6CCOC[C@@H]6CCC(=O)O)cc5)cc4)C[C@@H]3C2)NC(c2nccs2)=N[C@H]1c1ccc(F)cc1Cl]

To a dry flask were added 3-((S)-4-(4-(4-((S)-3-oxohexahydroimidazo[1,5-a]pyrazin-2(3H)-yl)phenoxy)benzoyl) morpholin-3-yl)propanoic acid trifluoroacetate (124 mg, 0.2 mmol), ethanol (10 mL), potassium carbonate (155 mg, 1.12 mmol) and (4R)-methyl 6-(bromomethyl)-4-(2-chloro-4-fluorophenyl)-2-(thiazol-2-yl)-1,4-dihydropyrimidine-5-carboxy late (100 mg, 0.23 mmol). The mixture was stirred at rt for 12 hours. The reaction mixture was concentrated in vacuo. The residue was purified by silica gel column chromatography (DCM/MeOH (V/V)=25/1) to give the title compound as a yellow solid (116 mg, 66.3%). MS (ESI, pos. ion) m/z: 858.1[M+H]⁺; ¹H NMR (400 MHz, CDCl₃) δ 7.87 (s, 1H), 7.54 (d, J=8.1 Hz, 2H), 7.48 (s, 1H), 7.35 (d, J=7.7 Hz, 2H), 7.31 (d, J=8.0 Hz, 1H), 7.15 (d, J=7.4 Hz, 1H), 7.04 (d, J=8.1 Hz, 2H), 6.96 (d, J=7.5 Hz, 3H), 6.22 (s, 1H), 4.21-3.98 (m, 4H), 3.92 (t, J=7.8 Hz, 2H), 3.88 (s, 1H), 3.82 (d, J=10.6 Hz, 2H), 3.67 (d, J=9.4 Hz, 1H), 3.61 (s, 3H), 3.45

(s, 3H), 3.28 (t, J=11.6 Hz, 1H), 2.90 (d, J=8.8 Hz, 2H), 2.51 (t, J=10.8 Hz, 1H), 2.39 (s, 2H), 2.89 (t, J=10.4 Hz, 2H), 2.01 (s, 1H).

Example 74: 3-((R)-4-(4-(4-(((S)-7-((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)benzoyl)morpholin-2-yl)propanoic acid The title compound as a yellow solid (206 mg, 64.9%) was prepared by the method according to example 73 by the replacement of (S)-methyl 3-(morpholinyl)propanoate hydrochloride with (R)-methyl 2-(morpholinyl)propanoate hydrochloride (112 mg, 0.53 mmol) of example 73. MS (ESI, pos. ion) m/z: 858.1[M+H]+; $^1$H NMR (400 MHz, CDCl$_3$) δ 7.87 (d, J=3.1 Hz, 1H), 7.56 (d, J=9.1 Hz, 2H), 7.49 (d, J=3.1 Hz, 1H), 7.38 (d, J=8.7 Hz, 2H), 7.33-7.29 (m, 1H), 7.16 (d, J=8.6, 2.6 Hz, 1H), 7.06 (d, J=9.0 Hz, 2H), 6.97 (d, J=9.4 Hz, 2H), 6.93 (td, J=8.4, 1.6 Hz, 1H), 6.22 (s, 1H), 4.15 (d, J=17.2 Hz, 1H), 4.09-4.01 (m, 2H), 3.96-3.88 (m, 3H), 3.62 (s, 3H), 3.55 (s, 1H), 3.47-3.43 (m, 2H), 3.36-3.07 (m, 3H), 2.90 (d, J=10.3 Hz, 4H), 2.52 (td, J=11.9, 3.5 Hz, 3H), 2.29 (t, J=10.8 Hz, 1H), 1.79 (s, 2H).

Example 75: 3-(4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)benzamido)-2,2-dimethylpropanoic acid The title compound as a yellow solid (31 mg, 29.02%) was prepared by the method according to example 73 by the replacement of (S)-methyl 3-(morpholinyl)propanoate hydrochloride with ethyl 3-amino-2,2-dimethylpropanoate (77 mg, 0.53 mmol) of example 73. MS (ESI, pos. ion) m/z: 815.7 [M+H]+; $^1$H NMR (400 MHz, MeOH-d$_4$) δ 7.98 (s, 1H), 7.87-7.70 (m, 3H), 7.60 (d, J=7.3 Hz, 2H), 7.44 (s, 1H), 7.24 (d, J=6.1 Hz, 1H), 7.07-6.99 (m, 5H), 6.18 (s, 1H), 4.15 (d, J=15.8 Hz, 1H), 4.05-3.93 (m, 4H), 3.61 (s, 3H), 3.56 (s, 1H), 3.47 (s, 2H), 3.26 (d, J=13.7 Hz, 1H), 2.99 (d, J=8.0 Hz, 2H), 2.47 (s, 1H), 2.27 (s, 1H), 1.19 (s, 6H).

Example 76: 2-(4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)morpholin-2-yl)acetic acid The title compound as a yellow solid (310 mg, 45.9%) was prepared by the method according to example 20 by the replacement of (S)-methyl 3-(morpholinyl)propanoate hydrochloride with methyl 2-(morpholin-2-yl)acetate hydrochloride (119 mg, 0.61 mmol) of example 20. MS (ESI, pos. ion) m/z: 724.4[M+H]+; $^1$H NMR (400 MHz, CDCl$_3$) δ 7.88 (d, J=3.1 Hz, 1H), 7.48 (d, J=3.1 Hz, 1H), 7.45 (d, J=8.9 Hz, 2H), 7.33-7.29 (m, 1H), 7.16 (dd, J=8.6, 2.5 Hz, 1H), 6.99-6.89 (m, 3H), 6.23 (s, 1H), 4.13 (d, J=17.0 Hz, 2H), 4.10-3.96 (m, 3H), 3.92 (s, 1H), 3.90-3.80 (m, 2H), 3.62 (s, 3H), 3.52 (d, J=11.5 Hz, 1H), 3.43-3.40 (m, 1H), 3.36 (d, J=11.7 Hz, 1H), 3.27 (td, J=13.0, 3.0 Hz, 1H), 2.93-2.80 (m, 3H), 2.71-2.65 (m, 1H), 2.63-2.47 (m, 3H), 2.29 (t, J=10.8 Hz, 1H).

Example 77: 4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)morpholine-2-carboxylic acid The title compound as a yellow solid (210 mg, 41.3%) was prepared by the method according to example 20 by the replacement of (S)-methyl 3-(morpholinyl)propanoate hydrochloride with methyl morpholinyl-2-carboxylate hydrochloride (180 mg, 0.99 mmol) of example 20. MS (ESI, pos. ion) m/z: 710.2 [M+H]+; $^1$H NMR (400 MHz, DMSO-d$_6$) δ 9.72 (s, 1H), 8.04 (d, J=2.6 Hz, 1H), 7.95 (d, J=2.9 Hz, 1H), 7.41 (t, J=6.9 Hz, 4H), 7.19 (t, J=8.2 Hz, 1H), 6.89 (d, J=8.8 Hz, 2H), 6.05 (s, 1H), 4.02-3.90 (m, 3H), 3.88-3.77 (m, 3H), 3.68 (d, J=8.8 Hz, 2H), 3.58-3.49 (m, 5H), 3.04 (t, J=12.7 Hz, 1H), 2.91 (d, J=10.2 Hz, 2H), 2.59 (t, J=11.4 Hz, 1H), 2.49-2.44 (m, 2H), 2.29 (t, J=13.1 Hz, 1H), 2.14 (t, J=10.3 Hz, 1H).

Example 78: 6-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenoxy)nicotinic acid The title compound as a yellow solid (210 mg, 41.3%) was prepared by the method according to example 7 by the replacement of methyl 4-hydroxybenzoate and 2,5-dibromopyridine with methyl 6-bromonicotinate (0.50 g 2.3 mmol) and p-bromophenol (0.41 g 2.41 mmol) respectively of example 7. MS (ESI, pos. ion) m/z: 718.2 [M+H]+; $^1$H NMR (400 MHz, MeOH-d$_4$) δ 8.74 (d, J=2.0 Hz, 1H), 8.35 (dd, J=8.7, 2.3 Hz, 1H), 7.99 (d, J=3.1 Hz, 1H), 7.78 (d, J=3.1 Hz, 1H), 7.65 (d, J=9.1 Hz, 2H), 7.47-7.43 (m, 1H), 7.25 (dd, J=8.7, 2.6 Hz, 1H), 7.16 (d, J=9.0 Hz, 2H), 7.07 (td, J=8.4, 2.6 Hz, 1H), 7.01 (d, J=8.7 Hz, 1H), 6.19 (s, 1H), 4.19 (d, J=16.8 Hz, 1H), 4.12-3.94 (m, 5H), 3.62 (s, 3H), 3.62-293.57 (m, 1H), 3.04 (d, J=10.8 Hz, 2H), 2.58-2.47 (m, 1H), 2.39-2.28 (m, 1H).

Example 79: 3-((6-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)oxy)-5-fluorobenzoic acid The title compound as a yellow solid (0.43 g 63%) was prepared by the method according to example 16 by the replacement of methyl 3-hydroxybenzoate with methyl 3-fluoro-5-hydroxybenzoate (0.79 g 4.6 mmol) of example 16. MS (ESI, pos. ion) m/z: 736.4[M+H]+; $^1$H NMR (400 MHz, CDCl$_3$) δ 9.67 (s, 1H), 8.39 (d, J=9.2 Hz, 1H), 8.12 (d, J=2.7 Hz, 1H), 7.87 (d, J=3.1 Hz, 1H), 7.53-7.47 (m, 2H), 7.46-7.41 (m, 2H), 7.33-7.31 (m, 1H), 7.16 (dd, J=8.6, 2.5 Hz, 1H), 6.98-6.87 (m, 2H), 6.24 (s, 1H), 4.21-4.11 (m, 3H), 4.10-4.03 (m, 2H), 3.94 (d, J=17.1 Hz, 1H), 3.73 (dd, J=10.8, 4.7 Hz, 1H), 3.62 (s, 3H), 3.36-3.27 (m, 1H), 2.96 (s, 1H), 2.58-2.49 (m, 1H), 2.31 (t, J=10.7 Hz, 1H).

Example 80: 4-(5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2-oxopyridin-1(2H)-yl)-3-fluorobenzoic acid The title compound as a yellow solid (60 mg, 31%) was prepared by the method according to example 22 by the replacement of 2-bromo-5-hydroxypyridine with 2-hydroxy-5-bromopyridine (2.4 g 14 mmol) of example 22. MS (ESI, pos. ion) m/z: 736.3 [M+H]+; $^1$H NMR (400 MHz, CDCl$_3$) δ 7.90-7.80 (m, 4H), 7.57 (d, J=2.4 Hz, 1H), 7.50-7.44 (m, 2H), 7.33-7.29 (m, 1H), 7.16 (dd, J=8.6, 2.6 Hz, 1H), 6.94 (td, J=8.3, 2.6 Hz, 1H), 6.77 (d, J=10.0 Hz, 1H), 6.22 (s, 1H), 4.16 (d, J=17.0 Hz, 1H), 4.02 (d, J=10.8 Hz, 2H), 3.91 (d, J=17.1 Hz, 1H), 3.85 (t, J=8.8 Hz, 1H), 3.62 (s, 3H), 3.37-3.34 (m, 1H), 3.28 (td, J=13.0, 3.1 Hz, 1H), 2.91 (d, J=10.1 Hz, 2H), 2.51 (td, J=11.4, 2.8 Hz, 1H), 2.30 (t, J=10.7 Hz, 1H).

Example 81: 4-((5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)oxy)-3-fluorobenzoic acid The title compound as a yellow solid (0.36 g 53%) was prepared by the method according to example 22 by the replacement of 2-bromo-5-hydroxypyridine with 5-bromo-3-hydroxypyridine (0.35 g 1.95 mmol) of example 22. MS (ESI, pos. ion) m/z: 736.4[M+H]$^+$; $^1$H NMR (600 MHz, CDCl$_3$) δ 9.60 (s, 1H), 8.36 (s, 1H), 8.16 (d, J=8.0 Hz, 2H), 7.92 (d, J=10.8 Hz, 1H), 7.88 (d, J=8.3 Hz, 1H), 7.85 (d, J=3.0 Hz, 1H), 7.48 (d, J=3.0 Hz, 1H), 7.32-7.29 (m, 1H), 7.14 (dt, J=11.4, 5.7 Hz, 2H), 6.93 (td, J=8.4, 2.4 Hz, 1H), 6.23 (s, 1H), 4.17 (d, J=17.0 Hz, 1H), 4.12-4.02 (m, 2H), 3.99 (t, J=8.9 Hz, 1H), 3.91 (d, J=17.1 Hz, 1H), 3.61 (s, 3H), 3.50 (t, J=6.9 Hz, 1H), 3.28 (t, J=12.5 Hz, 1H), 3.02-2.87 (m, 2H), 2.53-2.49 (m, 1H), 2.29 (t, J=10.6 Hz, 1H).

Example 82: 4-(4-((S)-7-(((R)-6-(2-bromo-4-fluorophenyl)-5-(ethoxycarbonyl)-2-(thiazol-2-yl)-3,6-dihydropyrimidin-4-yl)-3-oxohexahydroimidazo[1,5-a]pyrazin-2(3H)-yl)phenoxy)benzoic acid The title compound as a yellow solid (0.25 g 99%) was prepared by the method according to example 6 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxy late (235 mg, 0.47 mmol) of example 6. MS (ESI, pos. ion) m/z: 775.30 [M+H]$^+$; $^1$H NMR (400 MHz, DMSO-d$_6$) δ 12.73 (br, 1H), 9.68 (s, 1H), 8.04 (d, J=3.1 Hz, 1H), 7.95 (d, J=3.1 Hz, 1H), 7.94-7.90 (m, 2H), 7.64 (d, J=9.1 Hz, 2H), 7.57 (dd, J=8.6, 2.6 Hz, 1H), 7.43-7.40 (m, 1H), 7.27-7.20 (m, 1H), 7.12 (d, J=9.1 Hz, 2H), 6.97 (d, J=8.8 Hz, 2H), 6.04 (s, 1H), 4.02-3.79 (m, 7H), 3.50 (dd, J=9.2, 3.9 Hz, 1H), 3.10-3.04 (m, 1H), 2.95 (d, J=11.1 Hz, 2H), 2.39-2.22 (m, 1H), 2.16 (t, J=10.9 Hz, 1H), 1.05 (t, J=7.1 Hz, 3H).

Example 83: 4-(4-((S)-7-(((R)-6-(2-bromo-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl) phenoxy)benzoic acid The title compound as a yellow solid (0.13 g 40%) was prepared by the method according to example 6 by the replacement of (R)-methyl 6-(bromomethyl)-4-(2-chloro-4-fluorophenyl)-2-(thiazol-2-yl)-1,4-dihydropyrimidine-5-carboxy late with (R)-methyl 4-(2-bromo-4-fluorophenyl)-6-(bromomethyl)-2-(thiazol-2-yl)-1,4-dihydropyrimidine-5-carboxylate (0.2 g 0.4 mmol) of example 6. MS (ESI, pos. ion) m/z: 761.00 [M+H]$^+$; $^1$H NMR (400 MHz, CDCl$_3$) δ 9.61 (s, 1H), 8.04 (d, J=8.8 Hz, 2H), 7.85 (d, J=3.1 Hz, 1H), 7.57 (d, J=9.0 Hz, 2H), 7.46 (d, J=3.1 Hz, 1H), 7.33 (dd, J=8.3, 2.5 Hz, 1H), 7.07 (d, J=9.0 Hz, 2H), 6.97 (d, J=8.8 Hz, 4H), 6.19 (s, 1H), 3.97-3.85 (m, 2H), 3.60 (s, 3H), 3.46-3.42 (m, 1H), 3.27 (t, J=11.0 Hz, 1H), 2.89 (d, J=11.0 Hz, 2H), 2.59-2.47 (m, 2H), 2.28 (t, J=10.7 Hz, 2H).

Example 84: 4-(4-((S)-7-(((R)-6-(2,4-dichlorophenyl)-5-(methoxycarbonyl)-2-(thiazol-2-yl)-3,6-dihydropyrimidin-4-yl)methyl)methyl)-3-oxohexahydroimidazo[1,5-a]pyrazin-2(3H)-yl)phenoxy)benzoic acid The title compound as a yellow solid (0.1 g 23%) was prepared by the method according to example 6 by the replacement of (R)-methyl 6-(bromomethyl)-4-(2,4-chloro-4-fluorophenyl)-2-(thiazol-2-yl)-1,4-dihydropyrimidine-5-carboxylate with (R)-methyl 4-(2,4-dichlorophenyl)-6-(bromomethyl)-2-(thiazol-2-yl)-1,4-dihydropyrimidine-5-carboxylate (0.28 g 0.6 mmol) of example 6. MS (ESI, pos. ion) m/z: 733.30 [M+H]$^+$; $^1$H NMR (400 MHz, CDCl$_3$) δ 9.62 (s, 1H), 8.04 (d, J=8.8 Hz, 2H), 7.86 (d, J=3.1 Hz, 1H), 7.58 (d, J=9.0 Hz, 2H), 7.47 (d, J=3.1 Hz, 1H), 7.41 (d, J=2.0 Hz, 1H), 7.23 (s, 1H), 7.18 (dd, J=8.3, 2.0 Hz, 1H), 7.07 (d, J=9.0 Hz, 2H), 6.97 (d, J=8.8 Hz, 2H), 6.21 (s, 1H), 4.07-3.82 (m, 4H), 3.60 (s, 3H), 3.46-3.42 (m, 1H), 3.32-3.22 (m, 1H), 2.89 (d, J=10.8 Hz, 2H), 2.55-2.45 (m, 1H), 2.28 (t, J=10.8 Hz, 1H).

Example 85: 4-(4-((8aS)-7-((6-(2-chloro-4-fluorophenyl)-5-(methoxycarbonyl)-2-(1-methyl-1H-imidazol-2-yl)-3,6-dihydropyrimidin-4-yl)methyl)-3-oxohexahydroimidazo[1,5-a]pyrazin-2(3H)-yl) phenoxy)benzoic acid Step 1: 4-(4-((8aS)-7-((3-(tert-butyloxycarbonyl)-6-(2-chloro-4-fluorophenyl)-5-(methoxy carbonyl)-2-(1-methyl-1H-imidazol-2-yl)-3,6-dihydropyrimidin-4-yl)methyl)-3-oxohexahydroimidazo[1,5-a]pyrazin-2(3H)-yl)phenoxy)benzoic acid

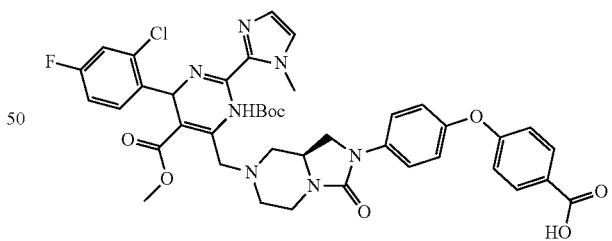

To a flask were added 1-tert-butyl 5-methyl 6-(bromomethyl)-4-(2-chloro-4-fluorophenyl)-2-(1-methyl-1H-imidazol-2-yl)pyrimidine-1,5(4H)-dicarboxylate (0.5 g, 0.92 mmol), (S)-4-(4-(3-oxohexahydroimidazo[1,5-a]pyrazin-2 (3H)-yl)phenoxy)benzoic acid trifluoroacetate (0.43 g 0.92 mmol), potassium carbonate (0.25 g 1.8 mmol) and ethanol (20 mL) in turn, the mixture was stirred at rt for 24 hours, and then filtered and concentrated in vacuo. The residue was purified by silica gel chromatograph (DCM/CH$_3$OH (V/V)= 50/1) to get the title compound as a yellow solid (0.26 g 35%). MS (ESI, pos. ion) m/z: 814.4 [M+H]$^+$.

Step 2: 4-(4-((8aS)-7-((6-(2-chloro-4-fluorophenyl)-5-(methoxycarbonyl)-2-(1-methyl-1H-imidazol-2-yl)-3,6-dihydropyrimidin-4-yl)methyl)-3-oxohexahydroimidazo[1,5-a]pyrazin-2(3H)-yl)phenoxy)benzoic acid

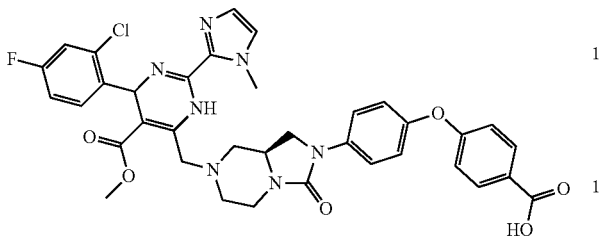

To a dry flask were added 4-(4-((8aS)-7-((3-(butyloxycarbonyl)-6-(2-chloro-4-fluorophenyl)-5-(methoxycarbonyl)-2-(1-methyl-1H-imidazol-2-yl)-3,6-dihydropyrimidin-4-yl) methyl)-3-oxohexahydroimidazo[1,5-a]pyrazin-2 (3H)-yl)phenoxy)benzoic acid (0.26 g 0.32 mmol), DCM (10 mL) and TFA (5 mL), the mixture was stirred at rt for 3 hours and concentrated in vacuo. The residue was diluted with EA (50 mL) and water (50 mL), and adjusted with aqueous sodium hydroxide solution (2 M) to pH 6 to 7. The resulting mixture was stood and layered, the organic layer was washed with saturated aqueous NaCl and dried over anhydrous sodium sulfate. The reaction mixture was filtered and concentrated in vacuo. The residue was purified by silica gel column chromatography (DCM/MeOH (V/V)=50/1) to give the title compound as a yellow solid (82 mg, 36%). MS (ESI, pos. ion) m/z: 714.35 [M+H]$^+$; $^1$H NMR (600 MHz, CDCl$^3$) δ 9.68 (d, J=18.3 Hz, 1H), 8.07-8.01 (m, 2H), 7.60-7.54 (m, 2H), 7.23-7.13 (m, 2H), 7.09-7.05 (m, 2H), 7.03 (dd, J=2.6, 1.0 Hz, 1H), 7.00-6.95 (m, 2H), 6.95-6.88 (m, 2H), 6.19 (d, J=14.7 Hz, 1H), 4.10-3.81 (m, 7H), 3.60 (d, J=1.9 Hz, 3H), 3.42-3.33 (m, 1H), 3.31-3.21 (m, 1H), 2.97-2.75 (m, 2H), 2.51-2.44 (m, 1H), 2.40-2.20 (m, 2H).

Example 86: 4-(3-((S)-7-(((R)-6-(2-chloro-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid The title compound as a yellow solid (0.3 g, 47%) was prepared by the method according to example 13 by the replacement of (R)-methyl 6-(bromomethyl)-4-(2-chloro-4-fluorophenyl)-2-(thiazol-2-yl)-1,4-dihydropyrimidine-5-carboxy late with (R)-ethyl 6-(bromomethyl)-4-(2-chloro-4-fluorophenyl)-2-(thiazol-2-yl)-1,4-dihydropyrimidine-5-carboxylate of example 13. MS (ESI, pos. ion) m/z: 767.3 [M+H]$^+$; $^1$H NMR (400 MHz, CDCl$_3$) δ 9.54 (s, 1H), 7.93-7.82 (m, 3H), 7.46 (d, J=3.1 Hz, 1H), 7.32-7.27 (m, 1H), 7.18-7.07 (m, 4H), 6.95-6.87 (m, 1H), 6.45 (d, J=9.2 Hz, 1H), 6.22 (s, 1H), 4.07-3.95 (m, 4H), 3.92-3.80 (m, 2H), 3.41-3.31 (m, 1H), 3.30-3.18 (m, 1H), 2.89 (d, J=10.8 Hz, 2H), 2.53-2.44 (m, 1H), 2.23 (t, J=10.4 Hz, 1H), 1.12 (t, J=7.1 Hz, 3H).

Example 87: 4-(3-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid The title compound as a yellow solid (90 mg, 40%) was prepared by the method according to example 13 by the replacement of (R)-methyl 6-(bromomethyl)-4-(2-chloro-4-fluorophenyl)-2-(thiazol-2-yl)-1,4-dihydropyrimidine-5-carboxy late with (R)-ethyl 4-(2-bromo-4-fluorophenyl)-6-(bromomethyl)-2-(thiazol-2-yl)-1,4-dihydropyrimidine-5-carboxylate (235 mg, 0.47 mmol) of example 13. MS (ESI, pos. ion) m/z: 811.2 [M+H]$^+$; $^1$H NMR (400 MHz, CDCl$_3$) δ 9.53 (s, 1H), 7.93-7.80 (m, 3H), 7.46 (d, J=3.1 Hz, 1H), 7.35-7.27 (m, 2H), 7.18-7.07 (m, 3H), 6.97 (td, J=8.3, 2.5 Hz, 1H), 6.44 (d, J=9.2 Hz, 1H), 6.19 (s, 1H), 4.15 (d, J=17.1 Hz, 1H), 4.07-3.94 (m, 4H), 3.92-3.81 (m, 2H), 3.41-3.19 (m, 2H), 2.89 (d, J=9.8 Hz, 2H), 2.77 (s, 1H), 1.12 (t, J=7.1 Hz, 3H).

Example 88: 4-(3-((S)-7-(((R)-6-(2,4-dichlorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid The title compound as a yellow solid (77 mg, 46%) was prepared by the method according to example 13 by the replacement of (R)-methyl 6-(bromomethyl)-4-(2-chloro-4-fluorophenyl)-2-(thiazol-2-yl)-1,4-dihydropyrimidine-5-carboxy late with (R)-methyl 4-(2,4-dichlorophenyl)-6-(bromomethyl)-2-(thiazol-2-yl)-1,4-dihydropyrimidine-5-carboxylate (0.1 g 0.22 mmol) of example 13. MS (ESI, pos. ion) m/z: 769.0 [M+H]$^+$; $^1$H NMR (400 MHz, CDCl$_3$) δ 9.58 (s, 1H), 7.96-7.79 (m, 3H), 7.46 (d, J=3.1 Hz, 1H), 7.41 (d, J=2.0 Hz, 1H), 7.23 (d, J=8.4 Hz, 1H), 7.19 (d, J=1.9 Hz, 1H), 7.16 (s, 1H), 7.13 (s, 2H), 7.09 (d, J=8.1 Hz, 1H), 6.45 (d, J=9.2 Hz, 1H), 6.20 (s, 1H), 4.08-3.94 (m, 2H), 3.92-3.81 (m, 2H), 3.59 (s, 3H), 3.38-3.35 (m, 1H), 3.30-3.18 (m, 1H), 2.89 (d, J=10.7 Hz, 2H), 2.53-2.43 (m, 1H), 2.24 (t, J=10.9 Hz, 1H).

Example 89: 4-(3-((8aS)-7-((6-(2-chloro-4-fluorophenyl)-5-(methoxycarbonyl)-2-(1-methyl-1H-imidazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid The title compound as a yellow solid (64 mg, 21%) was prepared by the method according to example 85 by the replacement of (S)-4-(4-(3-oxohexahydroimidazo[1,5-a]pyrazin-2(3H)-yl)phenoxy)benzoic acid trifluoroacetate with (S)-3-fluoro-4-(3-fluoro-5-(3-oxohexahydroimidazo[1,5-a]pyrazin-2(3H)-yl)phenoxy)benzoic acid trifluoroacetate (0.47 g 0.94 mmol) of example 85. MS (ESI, pos. ion) m/z: 750.25 [M+H]$^+$; $^1$H NMR (400 MHz, CDCl$_3$) δ 9.61 (s, 1H), 7.90-7.75 (m, 2H), 7.23-7.05 (m, 5H), 7.01 (d, J=2.0 Hz, 1H), 6.93-6.85 (m, 2H), 6.42 (d, J=9.2 Hz, 1H), 6.19 (s, 1H), 4.09-3.74 (m, 8H), 3.59 (d, J=1.6 Hz, 3H), 3.39-3.13 (m, 2H), 3.02-2.70 (m, 2H), 2.47-2.10 (m, 2H).

Example 90: 4-(3-((S)-7-(((R)-6-(2-chloro-3-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid The title compound as a yellow solid (55 mg, 72%) was prepared by the method according to example 13 by the replacement of (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2-chloro-3-fluorophenyl)-2-(thiazol-2-yl)-1,4-dihydropyrimidine-5-carboxy late of example 13. MS (ESI, pos. ion) m/z: 753.0

[M+H]$^+$; $^1$H NMR (400 MHz, CDCl$_3$) δ 7.94-7.87 (m, 2H), 7.86 (d, J=3.1 Hz, 1H), 7.48 (d, J=3.1 Hz, 1H), 7.23-7.15 (m, 2H), 7.13 (d, J=7.3 Hz, 3H), 7.10-7.04 (m, 1H), 6.46 (d, J=9.2 Hz, 1H), 6.29 (s, 1H), 4.04 (t, J=12.8 Hz, 2H), 3.94 (s, 1H), 3.91-3.85 (m, 2H), 3.68 (s, 1H), 3.61 (s, 3H), 3.41-3.37 (m, 1H), 3.27 (t, J=12.5 Hz, 2H), 2.92 (d, J=9.2 Hz, 2H), 2.70 (t, J=6.6 Hz, 1H), 2.57 (t, J=6.7 Hz, 1H).

Example 91: 4-((4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)thio)benzoic acid The title compound as a yellow solid (120 mg, 53%) was prepared by the method according to example 6 by the replacement of methyl 4-(4-bromophenoxy)benzoate with methyl 4-((4-bromophenyl)thio)benzoate (294 mg, 0.91 mmol) of example 6. MS (ESI, pos. ion) m/z: 733.0 [M+H]$^+$; $^1$H NMR (400 MHz, CDCl$_3$) δ 7.96-7.84 (m, 3H), 7.63 (d, J=8.7 Hz, 2H), 7.57-7.49 (m, 3H), 7.35 (dd, J=8.6, 6.0 Hz, 1H), 7.20-7.13 (m, 3H), 7.00 (td, J=8.6, 2.2 Hz, 1H), 6.19 (s, 1H), 4.73 (d, J=14.6 Hz, 1H), 4.54-4.46 (m, 1H), 4.40 (d, J=14.9 Hz, 1H), 4.19 (d, J=13.7 Hz, 1H), 4.05 (t, J=9.0 Hz, 1H), 3.73-3.66 (m, 2H), 3.64 (s, 3H), 3.55-3.53 (m, 2H), 3.03-2.88 (m, 2H).

Example 92: 4-((5-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)pyridin-2-yl)oxy)benzoic acid The title compound as a yellow solid (160 mg, 37%) was prepared by the method according to example 7 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxy late (250 mg, 0.50 mmol) of example 7. MS (ESI, pos. ion) m/z: 776.3 [M+H]$^+$; $^1$H NMR (400 MHz, DMSO-d$_6$) δ 11.05 (s, 1H), 9.65 (s, 1H), 8.33-8.14 (m, 2H), 8.02 (d, J=3.1 Hz, 1H), 7.94 (dd, J=8.6, 5.9 Hz, 2H), 7.56 (dd, J=8.5, 2.6 Hz, 1H), 7.44-7.35 (m, 1H), 7.27-7.18 (m, 1H), 7.16-7.09 (m, 2H), 6.03 (s, 1H), 4.05-3.80 (m, 7H), 3.13-3.02 (m, 2H), 2.94 (d, J=11.4 Hz, 2H), 2.35-2.25 (m, 1H), 2.17 (t, J=10.8 Hz, 1H), 1.04 (t, J=7.1 Hz, 3H).

Example 93: 4-(3-((S)-7-(((R)-6-(2-chlorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluoro phenoxy)-3-fluorobenzoic acid The title compound as a yellow solid (115 mg, 45%) was prepared by the method according to example 13 by the replacement of (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2-chlorophenyl)-2-(thiazol-2-yl)-1,4-dihydropyrimidine-5-carboxylate (153 mg, 0.36 mmol) of example 13. MS (ESI, pos. ion) m/z: 735.3 [M+H]$^+$; $^1$H NMR (400 MHz, CDCl$_3$) δ 9.55 (s, 1H), 7.98-7.73 (m, 3H), 7.50-7.28 (m, 3H), 7.23-7.03 (m, 5H), 6.43 (d, J=8.0 Hz, 1H), 6.26 (s, 1H), 4.18-3.98 (m, 3H), 3.93-3.81 (m, 2H), 3.58 (s, 3H), 3.36 (s, 1H), 3.29-3.20 (m, 1H), 2.90 (s, 2H), 2.57-2.46 (m, 1H), 2.24 (s, 1H).

Example 94: 3-((6-((S)-7-(((R)-6-(2-bromo-4-fluorophenyl)-5-(ethoxycarbonyl)-2-(thiazol-2-yl)-3,6-dihydropyrimidin-4-yl)-3-oxohexahydroimidazo[1,5-a]pyrazin-2(3H)-yl)pyridin-3-yl)oxy)benzoic acid The title compound as a yellow solid (160 mg, 37%) was prepared by the method according to example 16 by the replacement of (R)-methyl 16-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxy late (300 mg, 0.6 mmol) of example 16. MS (ESI, pos. ion) m/z: 775.7 [M+H]$^+$; $^1$H NMR (400 MHz, DMSO-d$_6$) δ 13.13 (s, 1H), 9.68 (s, 1H), 8.29 (d, J=9.2 Hz, 1H), 8.18 (d, J=2.6 Hz, 1H), 8.04 (d, J=2.9 Hz, 1H), 7.95 (d, J=2.8 Hz, 1H), 7.68 (d, J=7.6 Hz, 1H), 7.63-7.54 (m, 2H), 7.51 (t, J=7.9 Hz, 1H), 7.46-7.40 (m, 1H), 7.38 (s, 1H), 7.32-7.20 (m, 2H), 6.05 (s, 1H), 4.11-4.03 (m, 1H), 4.02-3.91 (m, 4H), 3.88 (d, J=12.0 Hz, 2H), 3.65 (dd, J=10.8, 4.1 Hz, 1H), 3.10 (t, J=11.2 Hz, 1H), 2.98 (t, J=12.6 Hz, 2H), 2.33 (t, J=10.2 Hz, 1H), 2.18 (t, J=10.8 Hz, 1H), 1.06 (t, J=7.0 Hz, 3H).

Example 95: 3-((6-((S)-7-(((R)-6-(2,4-dichlorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)pyridin-3-yl)oxy)benzoic acid The title compound as a yellow solid (138 mg, 48%) was prepared by the method according to example 16 by the replacement of (R)-methyl 6-(bromomethyl)-4-(2-chloro-4-fluorophenyl)-2-(thiazol-2-yl)-1,4-dihydropyrimidine-5-carboxy late with (R)-methyl 6-(bromomethyl)-4-(2,4-dichlorophenyl)-2-(thiazol-2-yl)-1,4-dihydropyrimidine-5-carboxylate (180 mg, 0.38 mmol) of example 16. MS (ESI, pos. ion) m/z: 748.1 [M+H]$^+$; $^1$H NMR (600 MHz, CDCl$_3$) δ 9.64 (s, 1H), 8.36 (d, J=9.1 Hz, 1H), 8.11 (d, J=2.6 Hz, 1H), 7.87 (d, J=3.0 Hz, 1H), 7.84 (d, J=7.5 Hz, 1H), 7.66 (s, 1H), 7.48 (d, J=3.0 Hz, 1H), 7.46-7.39 (m, 3H), 7.30 (s, 1H), 7.26-7.18 (m, 2H), 6.25 (s, 1H), 4.18-4.12 (m, 2H), 4.11-4.01 (m, 4H), 3.95 (d, J=17.1 Hz, 1H), 3.73 (dd, J=10.8, 4.8 Hz, 1H), 3.30 (td, J=13.1, 3.1 Hz, 1H), 2.92 (s, 2H), 2.53 (td, J=11.2, 2.7 Hz, 1H), 2.30 (t, J=10.5 Hz, 1H), 1.15 (t, J=7.1 Hz, 3H).

Example 96: (R)-methyl 4-(2-chloro-4-fluorophenyl)-6-((((S)-2-(3-fluoro-5-(2-fluoro-4-((1-methoxy-2-methylprop-2-yl)carbamoyl)phenoxy)phenyl)-3-oxohexahydroimidazo[1,5-a]pyrazin-7(1H)-yl) methyl)-2-(thiazol-2-yl)-1,4-dihydropyrimidine-5-carboxylate To a flask were added 1-methoxy-2-methylpropane-2-amine hydrochloride (0.1 g 0.69 mmol), 4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-5-fluorophenoxy)-3-fluorobenzoic acid (450 mg, 0.60 mmol) and DCM (8 mL) in turn, the mixture was dissolved with stirring and then DIPEA (0.6 mL, 3 mmol) and HATU (358 mg, 0.89 mmol) were added, the resulting mixture was stirred at rt for 4 hours. The mixture was concentrated by rotary evaporation in vacuo, the mixture was diluted with EtOAc (20 mL) and water (10 mL). The separated organic layer was washed with water twice and saturated brine once, dried over anhydrous sodium sulfate and concentrated in vacuo. The residue was purified by silica gel column chromatography (PE/EtOAc (V/V)=1/1) to give the title compound as a yellow solid (451 mg, 90.1%). MS (ESI, pos. ion) m/z: 838.1 [M+H]⁺; ¹H NMR (400 MHz, DMSO-$d_6$) δ 9.68 (s, 1H), 8.02 (d, J=3.0 Hz, 1H), 7.97-7.91 (m, 1H), 7.85 (d, J=11.7 Hz, 1H), 7.74 (s, 1H), 7.71 (d, J=8.4 Hz, 1H), 7.41 (m, 2H), 7.27 (t, J=8.3 Hz, 1H), 7.23-7.13 (m, 3H), 6.55 (d, J=9.7 Hz, 1H), 6.05 (s, 1H), 4.07-3.92 (m, 2H), 3.91-3.77 (m, 3H), 3.55-3.49 (m, 5H), 3.45 (d, J=5.4 Hz, 1H), 3.27 (s, 3H), 3.04 (t, J=11.2 Hz, 1H), 2.92 (d, J=10.3 Hz, 2H), 2.29 (t, J=10.1 Hz, 1H), 2.13 (t, J=10.5 Hz, 1H), 1.33 (s, 6H).

Example 97: (R)-methyl 4-(2-chloro-4-fluorophenyl)-6-(((S)-2-(4-(4-cyanophenoxy)phenyl)-3-oxohexahydroimidazo[1,5-a]pyrazin-7(1H)-yl)methyl)-2-(thiazol-2-yl)-1,4-dihydropyrimidine-5-carboxylate Step 1: 4-(4-bromophenoxy)benzonitrile

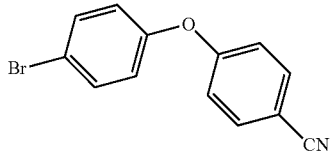 [SMILES: N#Cc1ccc(Oc2ccc(Br)cc2)cc1]

4-Fluorobenzonitrile (1 g 8.26 mmol), 4-bromophenol (1.71 g 9.88 mmol) and potassium carbonate (3.42 g 24.7 mmol) were dissolved in DMF (10 mL), the mixture was stirred at 120° C. for 12 hours. The mixture was diluted with water (50 mL) and the resulting mixture was extracted with (50 mL×3). The organic layer was washed with water (100 mL) and saturated brine (100 mL), dried over anhydrous sodium sulfate and concentrated in vacuo. The residue was purified by silica gel column chromatography (PE/EtOAc (v/v)=50/1) to give the title compound as a white solid (1.8 g 80%).

Step 2: (R)-tert-butyl 2-(4-(4-cyanophenoxy)phenyl)-3-oxohexahydroimidazo[1,5-a]pyrazin-7(1H)-carboxylate

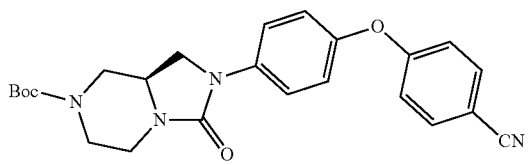 [SMILES: CC(C)(C)OC(=O)N1CCN2C(=O)N(c3ccc(Oc4ccc(C#N)cc4)cc3)C[C@@H]2C1]

4-(4-Bromophenoxy)benzonitrile (200 mg, 0.73 mmol), (R)-tert-butyl 3-oxohexahydroimidazo[1,5-a]pyrazine-7(1H)-carboxylate (193 mg, 0.80 mmol), palladiumacetate (34 mg, 0.15 mmol), 2-di-tert-butylphosphino-2',4',6'-trisopropylbinphenyl (126 mg, 0.29 mmol) and cesium carbonate (475 mg, 1.46 mmol) were dissolved in 1,4-dioxane (5 mL) under $N_2$. The mixture was stirred at 90° C. for 12 hours. The mixture was concentrated in vacuo. The residue was purified by silica gel column chromatography (PE/EtOAc (V/V)=1/1) to give the title compound as a white solid (260 mg, 82%). MS (ESI, pos. ion) m/z: 457.1 [M+Na]⁺.

Step 3: (S)-4-(4-(3-oxohexahydroimidazo[1,5-a]pyrazin-2(3H)-yl)phenoxy)benzonitrile trifluoroacetate

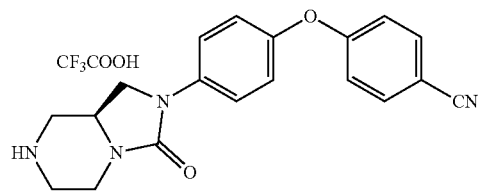 [SMILES: "CF3COOH" ; N#Cc1ccc(Oc2ccc(N3C[C@@H]4CNCCN4C3=O)cc2)cc1]

(R)-tert-Butyl 2-(4-(4-cyanophenoxy)phenyl)-3-oxohexahydroimidazo[1,5-a]pyrazine-7(1H)-carboxylate (100 mg, 0.23 mmol) was dissolved in DCM (5 mL), to the solution was added trifluoroacetic acid (5 mL). The mixture was stirred at rt for 1 hour. And then the mixture was concentrated in vacuo to get the title compound as brown oil (98 mg, 95%) MS (ESI, pos. ion) m/z: 335.1 [M+H]⁺.

Step 4: (R)-methyl 4-(2-chloro-4-fluorophenyl)-6-(((S)-2-(4-(4-cyanophenoxy)phenyl)-3-oxohexahydroimidazo[1,5-a]pyrazin-7(1H)-yl)methyl)-2-(thiazol-2-yl)-1,4-dihydropyrimidine-5-carboxylate

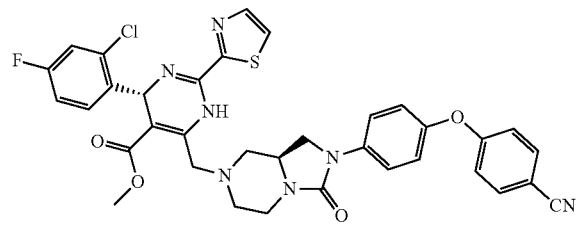 [SMILES: COC(=O)C1=C(CN2CCN3C(=O)N(c4ccc(Oc5ccc(C#N)cc5)cc4)C[C@@H]3C2)NC(c2nccs2)=N[C@H]1c1ccc(F)cc1Cl]

(S)-4-(4-(3-Oxohexahydroimidazo[1,5-a]pyrazin-2(3H)-yl)phenoxy)benzonitrile trifluoroacetate (100 mg, 0.22 mmol) and DIPEA (86 mg, 0.66 mmol) were dissolved in 1,2-dichloroethane, and to the mixture was added (R)-methyl 6-(bromomethyl)-4-(2-chloro-4-fluorophenyl)-2-(thiazol-2-yl)-1,4-dihydropyrimidine-5-carboxy late (119 mg, 0.27 mmol), the resulting mixture was stirred at rt for 6 hours. The mixture was concentrated in vacuo. The residue was purified by silica gel column chromatography (PE/EtOAc (V/V)=1/1) to give the title compound as a yellow solid (118 mg, 76%). MS (ESI, pos. ion) m/z: 698.2 [M+H]⁺. ¹H NMR (400 MHz, CDCl₃) δ 9.63 (s, 1H), 7.87 (d, J=3.1 Hz, 1H), 7.59 (dd, J=8.7, 6.1 Hz, 4H), 7.48 (d, J=3.0 Hz, 1H), 7.33-7.28 (m, 1H), 7.61-7.57 (m, 1H), 7.06 (d, J=9.0 Hz, 2H), 6.98 (d, J=8.7 Hz, 2H), 6.93 (td, J=8.4, 2.5 Hz, 1H), 6.22 (s, 1H), 4.19-4.11 (m, 1H), 4.11-3.99 (m, 2H), 3.97-3.86 (m, 2H), 3.61 (s, 3H), 3.47-3.43 (m, 1H), 3.35-3.23 (m, 1H), 2.91 (d, J=10.0 Hz, 2H), 2.52 (td, J=11.4, 2.8 Hz, 1H), 2.29 (t, J=10.7 Hz, 1H).

Example 98: (R)-methyl 4-(2-chloro-4-fluorophenyl)-6-(((S)-2-(4-((4-cyanophenyl)thio)phenyl)-3-oxohexahydroimidazo[1,5-a]pyrazin-7(1H)-yl) methyl)-2-me (thiazol-2-yl)-1,4-dihydropyrimidine-5-carboxylate The title compound as a yellow solid (120 mg, 52%) was prepared by the method according to example 97 by the replacement of 4-bromophenol with 4-bromophenthiol (375 mg, 1.98 mmol) in example 97. MS (ESI, pos. ion) m/z: 714.1 [M+H]⁺; ¹H NMR (400 MHz, CDCl₃) δ 9.61 (s, 1H), 7.87 (d, J=3.1 Hz, 1H), 7.67 (d, J=8.8 Hz, 2H), 7.54-7.43 (m, 5H), 7.33-7.28 (m, 1H), 7.16 (dd, J=8.6, 2.5 Hz, 1H), 7.11 (d, J=8.4 Hz, 2H), 6.94 (td, J=8.3, 2.5 Hz, 1H), 6.22 (s, 1H), 4.17 (d, J=17.1 Hz, 1H), 4.12-4.01 (m, 2H), 3.99-3.87 (m, 2H), 3.62 (s, 3H), 3.49-3.45 (m, 1H), 3.30 (td, J=13.1, 3.0 Hz, 1H), 2.93 (d, J=10.4 Hz, 2H), 2.53 (td, J=11.5, 3.0 Hz, 1H), 2.28 (t, J=10.7 Hz, 1H).

Example 99: (R)-methyl 4-(2-chloro-4-fluorophenyl)-6-(((S)-2-(4-(4-(hydroxymethyl)phenoxy) phenyl)-3-oxohexahydroimidazo[1,5-a]pyrazin-7(1H)-yl)methyl)-2-(thiazol-2-yl)-1,4-dihydropyrimidine-5-carboxylate Step 1: (R)-tert-butyl 2-(4-(4-(hydroxymethyl)phenoxy)phenyl)-3-oxohexahydroimidazo[1,5-a]pyrazin-7(1H)-carboxylate

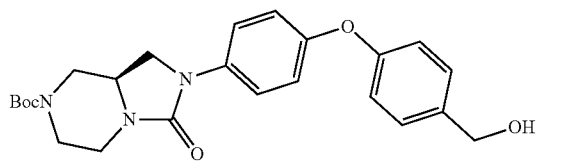 [SMILES: CC(C)(C)OC(=O)N1CCN2C(=O)N(c3ccc(Oc4ccc(CO)cc4)cc3)C[C@@H]2C1]

(R)-4-(4-(7-(tert-butyloxycarbonyl)-3-oxohexahydroimidazo[1,5-a]pyrazin-2(3H)-yl) phenoxy)benzoic acid (500 mg, 1.1 mmol) was dissolved in THF (5 mL), the solution was cooled to 0° C., and BH₃·THF (4 mL, 1 mol/L) solution was added dropwise. After the addition, the mixture was warmed to rt and stirred for 4 hours, and then cooled to 0° C., methanol (15 mL) was added to quench the reaction, the mixture was concentrated by rotary evaporation in vacuo. The residue was partitioned between water (20 mL) and EtOAc (20 mL). The organic layer was washed with aqueous NaOH (1 M, 20 mL) solution and saturated aqueous NaCl once, dried over anhydrous sodium sulfate, and then concentrated in vacuo to give the title compound as a brown solid (459 mg, 94.7%). MS (ESI, pos. ion) m/z: 440.1 [M+H]⁺.

Step 2: (R)-methyl 4-(2-chloro-4-fluorophenyl)-6-(((S)-2-(4-(4-(hydroxymethyl)phenoxy) phenyl)-3-oxohexahydroimidazo[1,5-a]pyrazin-7(1H)-yl)methyl)-2-(thiazol-2-yl)-1,4-dihydropyrimidine-5-carboxylate

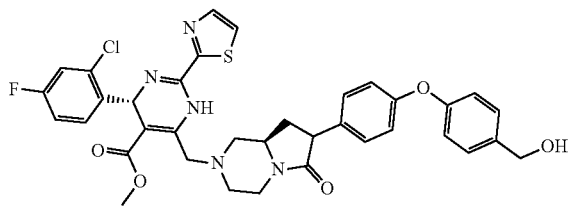

The title compound as a yellow solid (200 mg, 56.1%) was prepared by the method according to example 97 by the replacement of (R)-tert-butyl 2-(4-(4-cyanophenoxy)phenyl)-3-oxohexahydroimidazo[1,5-a]pyrazin-7(1H)-carboxylate with (R)-tert-butyl 2-(4-(4-(hydroxymethyl)phenoxy)phenyl)-3-oxohexahydroimidazo[1,5-a]pyrazin-7(1H)-carboxylate (230 mg, 0.51 mmol) of example 97. MS (ESI, pos. ion) m/z: 703.1 [M+H]⁺; ¹H NMR (400 MHz, CDCl₃) δ 9.64 (s, 1H), 7.87 (d, J=3.0 Hz, 1H), 7.51 (d, J=9.0 Hz, 2H), 7.48 (d, J=3.0 Hz, 1H), 7.32 (d, J=8.4 Hz, 2H), 7.30 (d, J=2.7 Hz, 1H), 7.15 (dd, J=8.5, 2.4 Hz, 1H), 7.01 (d, J=9.0 Hz, 2H), 6.96 (d, J=8.5 Hz, 2H), 6.92 (dd, J=8.4, 2.3 Hz, 1H), 6.22 (s, 1H), 4.66 (s, 2H), 4.13 (d, J=17.3 Hz, 1H), 4.08-3.99 (m, 2H), 3.93-3.88 (m, 2H), 3.75 (t, J=6.3 Hz, 1H), 3.61 (s, 3H), 3.44-3.41 (m, 1H), 3.27 (td, J=12.0, 2.8 Hz, 1H), 2.89 (d, J=10.8 Hz, 2H), 2.51 (td, J=11.4, 2.8 Hz, 1H), 2.28 (t, J=10.8 Hz, 1H).

Example 100: (R)-methyl 4-(2-chloro-4-fluorophenyl)-6-(((S)-2-(4-(4-(2-hydroxyprop-2-yl) phenoxy) phenyl)-3-oxohexahydroimidazo[1,5-a]pyrazin-7(1H)-yl)methyl)-2-(thiazol-2-yl)-1,4-dihydropyrimidine-5-carboxylate Step 1: (S)-methyl 4-(4-(3-oxohexahydroimidazo[1,5-a]pyrazin-2(3H)-yl)phenoxy)phenyl carboxylate trifluoroacetate

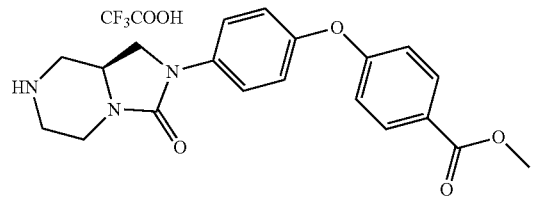 [SMILES: COC(=O)c1ccc(Oc2ccc(N3C[C@@H]4CNCCN4C3=O)cc2)cc1 ; "CF3COOH"]

To a flask were added (R)-tert-butyl 2-(4-(4-(methoxycarbonyl) phenoxy)phenyl)-3-oxohexahydroimidazo[1,5-a]pyrazine-7(1H)-carboxylate (1.00 g, 2.14 mmol), DCM (6 mL) and TFA (1 mL), the mixture was stirred at rt for 1 hour. And then the mixture was concentrated in vacuo to get the title compound as brown oil (1.03 g 100%)

Step 2: (S)-methyl 4-(4-(7-benzyl-3-oxohexahydroimidazo[1,5-a]pyrazin-2(3H)-yl)phenoxy) benzoate

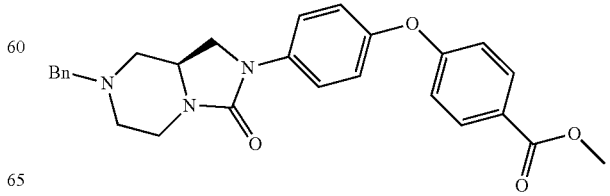

To a flask were added (S)-methyl 4-(4-(3-oxohexahydroimidazo[1,5-a]pyrazin-2(3H)-yl)phenoxy)benzoate trifluoroacetate (1.03 g 2.14 mmol), DCM (10 mL), triethylamine (1.5 mL, 10 mmol) and benzyl bromide (0.6 mL, 6 mmol), the mixture was stirred at rt for 36 h. The mixture was diluted with DCM (30 mL) and water (20 mL). The organic layer was washed with saturated brine once, dried over anhydrous sodium sulfate and concentrated in vacuo. The residue was purified by silica gel column chromatography (PE/EtOAc (V/V)=1/1) to give the title compound as a white solid (685 mg, 69.9%). MS (ESI, pos. ion) m/z: 458.1 [M+H]+.

Step 3: (S)-7-benzyl-2-(4-(4-(2-hydroxyprop-2-yl)phenoxy)phenyl)hexahydroimidazo[1,5-a]pyrazine-3(2H)-one

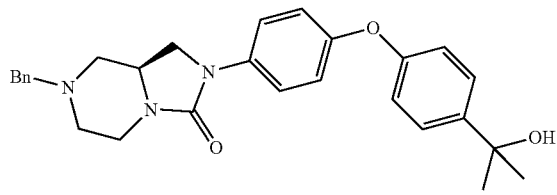 [SMILES: CC(C)(O)c1ccc(Oc2ccc(N3C[C@@H]4CN(Cc5ccccc5)CCN4C3=O)cc2)cc1]

To a flask were added (S)-methyl 4-(4-(7-benzyl-3-oxohexahydroimidazo[1,5-a]pyrazin-2(3H)-yl)phenoxy)benzoate (300 mg, 0.66 mmol) and anhydrous THF (6 mL), the mixture was cooled to −10° C. under N₂. To the mixture was added methylmagnesium bromide in ethyl etherate (2.2 mL, 6.6 mmol, 3 mol/L), the mixture was warmed to 0° C. and stirred for 2 hours. The mixture was quenched by dropwise addition of water (3 mL). The resulting mixture was diluted with ethyl acetate (30 mL) and water (20 mL). The organic phase was washed with saturated brine, dried over anhydrous sodium sulfate, and then concentrated in vacuo to give the title compound as a white solid (287 mg, 95.6%). MS (ESI, pos. ion) m/z: 458.0[M+H]+.

Step 4: (S)-2-(4-(4-(2-hydroxypropan-2-yl)phenoxy)phenyl)hexahydroimidazo[1,5-a]pyrazine-3(2H)-one

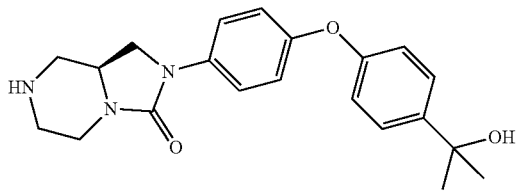 [SMILES: CC(C)(O)c1ccc(Oc2ccc(N3C[C@@H]4CNCCN4C3=O)cc2)cc1]

To a flask were added (S)-7-benzyl-2-(4-(4-(2-hydroxyprop-2-yl)phenoxy)phenyl) hexahydroimidazo[1,5-a]pyrazine-3(2H)-one (285 mg, 0.62 mmol), methanol (4 mL) and 10% Pd/C (40 mg). The mixture was stirred at rt under H₂ for 20 hours, and then filtered by suction. The filtrate was concentrated to get the title compound as a white solid (185 mg, 80.8%). MS (ESI, pos. ion) m/z: 368.3[M+H]+.

Step 5: (R)-methyl 4-(2-chloro-4-fluorophenyl)-6-(((S)-2-(4-(4-(2-hydroxyprop-2-yl)phenoxy) phenyl)-3-oxohexahydroimidazo[1,5-a]pyrazin-7(1H)-yl)methyl)-2-(thiazol-2-yl)-1,4-dihydropyrimidine-5-carboxylate

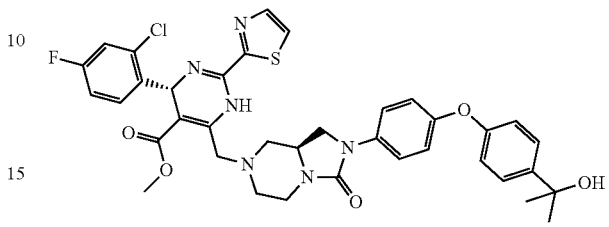

To a flask were added (S)-2-(4-(4-(2-hydroxypropan-2-yl)phenoxy)phenyl) hexahydroimidazo[1,5-a]pyrazine-3(2H)-one (185 mg, 0.50 mmol), (R)-methyl 6-(bromomethyl)-4-(2-chloro-4-fluorophenyl)-2-(thiazol-2-yl)-1,4-dihydropyrimidine-5-carboxylate (200 mg, 0.45 mmol), anhydrous ethanol (6 mL) and potassium carbonate (124 mg, 0.90 mmol). The mixture was stirred at rt for 3 hours. The mixture was diluted with water (15 mL) and EtOAc (30 mL). The organic layer was washed with saturated brine once, dried over anhydrous sodium sulfate and concentrated in vacuo. The residue was purified by silica gel column chromatography (PE/EtOAc (V/V)=1/1) to give the title compound as a yellow solid (256 mg, 77.8%). MS (ESI, pos. ion) m/z: 731.2[M+H]+; ¹H NMR (400 MHz, CDCl₃) δ 9.62 (s, 1H), 7.85 (d, J=3.1 Hz, 1H), 7.49 (d, J=9.0 Hz, 2H), 7.45 (d, J=3.1 Hz, 1H), 7.42 (d, J=8.8 Hz, 2H), 7.30 0 7.26 (m, 1H), 7.13 (dd, J=8.6, 2.5 Hz, 1H), 7.04-6.97 (m, 2H), 6.96-6.88 (m, 3H), 6.20 (s, 1H), 4.15-4.08 (m, 1H), 4.08-4.01 (m, 1H), 4.01-3.95 (m, 1H), 3.93-3.84 (m, 2H), 3.59 (s, 3H), 3.43-3.39 (m, 1H), 3.25 (td, J=13.0, 3.1 Hz, 1H), 2.87 (d, J=10.9 Hz, 2H), 2.49 (td, J=11.6, 3.2 Hz, 1H), 2.25 (t, J=10.79 Hz, 1H), 1.57 (s, 6H).

Example 101: 3-(4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenoxy)-3-fluorophenyl)propanoic acid Step 1: 4-(4-bromo-3-fluorophenoxy)-3-fluorobenzaldehyde

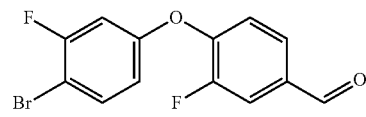 [SMILES: O=Cc1ccc(Oc2ccc(Br)c(F)c2)c(F)c1]

4-Bromo-3-fluoro-phenol (670 mg, 3.51 mmol), 3,4-difluorobenzaldehyde (500 mg, 3.52 mmol) and potassium carbonate (1.46 g 10.6 mmol) were dissolved in DMF (10 mL), the mixture was stirred at 120° C. for 12 hours. The mixture was concentrated in vacuo. The residue was purified by silica gel column chromatography (PE/EtOAc (V/V)=20/1) to give the title compound as a white solid (721 mg, 65%).

Step 2: methyl 3-(4-(4-bromo-3-fluorophenoxy)-3-fluorophenyl)acrylate

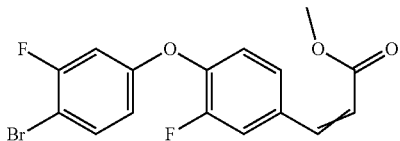 [SMILES: COC(=O)C=Cc1ccc(Oc2ccc(Br)c(F)c2)c(F)c1]

4-(4-Bromo-3-fluorophenoxy)-3-fluorobenzaldehyde (500 mg, 1.59 mmol) and methyl (triphenylphosphoranylidene)acetate (593 mg, 1.76 mmol) were dissolved in DCM (15 mL) under N₂, the mixture was stirred at rt for 12 hours. The mixture was concentrated in vacuo. The residue was purified by silica gel column chromatography (PE/EtOAc (V/V)=10/1) to give the title compound as a white solid (450 mg, 76%). ¹H NMR (400 MHz, CDCl₃) δ 7.64 (d, J=16.0 Hz, 1H), 7.50 (dd, J=8.6, 8.0 Hz, 1H), 7.39 (dd, J=11.2, 1.9 Hz, 1H), 7.31 (d, J=8.5 Hz, 1H), 7.11 (t, J=8.2 Hz, 1H), 6.81 (dd, J=9.4, 2.7 Hz, 1H), 6.72 (dd, J=8.8, 1.8 Hz, 1H), 6.41 (d, J=16.0 Hz, 1H), 3.84 (s, 3H).

Step 3: methyl 3-(4-(4-bromo-3-fluorophenoxy)-3-fluorophenyl)propionate

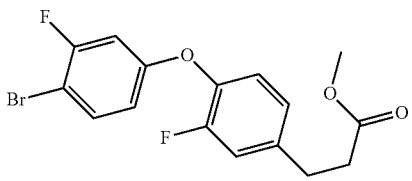 [SMILES: COC(=O)CCc1ccc(Oc2ccc(Br)c(F)c2)c(F)c1]

To a flask were added methyl 3-(4-(4-bromo-3-fluorophenoxy)-3-fluorophenyl)acrylate (300 mg, 0.81 mmol), Pd/C (86 mg, 10 mass %) and EtOAc (10 mL), the mixture was stirred under H₂ at rt for 5 hours. And then the mixture was filtered by suction and the filtrate was concentrated in vacuo to get the title compound as colorless oil (270 mg, 90%)

Step 4: 3-(4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenoxy)-3-fluorophenyl)propanoic acid The title compound as a yellow solid (80 mg, 71%) was prepared by the method according to example 6 by the replacement of methyl 4-(4-bromophenoxy)benzoate with methyl 3-(4-(4-bromo-3-fluorophenoxy)-3-fluorophenyl)propionate (307 mg, 0.83 mmol) in step 1 of example 6. MS (ESI, pos. ion) m/z: 781.4 [M+H]⁺; ¹H NMR (400 MHz, CDCl₃) δ 9.66 (s, 1H), 7.88 (d, J=3.1 Hz, 1H), 7.48 (d, J=3.1 Hz, 1H), 7.39 (t, J=9.0 Hz, 1H), 7.33-7.29 (m, 1H), 7.15 (dd, J=8.6, 2.5 Hz, 1H), 7.09-7.05 (m, 1H), 7.03 (d, J=8.0 Hz, 1H), 7.01-6.97 (m, 1H), 6.94 (td, J=8.3, 2.5 Hz, 1H), 6.77-6.69 (m, 2H), 6.22 (s, 1H), 4.14 (d, J=17.2 Hz, 1H), 4.08-3.98 (m, 2H), 3.93-3.83 (m, 2H), 3.62 (s, 3H), 3.46-3.43 (m, 1H), 3.28 (td, J=13.2, 3.2 Hz, 1H), 2.96 (t, J=7.5 Hz, 2H), 2.91-2.83 (m, 2H), 2.69 (t, J=7.5 Hz, 2H), 2.53 (td, J=11.5, 3.1 Hz, 1H), 2.38 (t, J=10.8 Hz, 1H).

Example 102: (R)-methyl 4-(2-chloro-4-fluorophenyl)-6-(((S)-2-(4-(4-cyanophenoxy)benzyl)-3-oxohexahydroimidazo[1,5-a]pyrazin-7(1H)-yl)methyl)-2-(thiazol-2-yl)-1,4-dihydropyrimidine-5-carboxylate

Step 1: 4-(4-formylphenoxy)benzonitrile

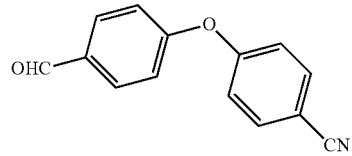

4-Fluorobenzaldehyde (1.21 g 9.91 mmol), 4-fluorobenzonitrile (1 g 8.26 mmol) and potassium carbonate (3.42 g 24.7 mmol) were dissolved in DMF (10 mL), the mixture was stirred at 120° C. for 12 hours. The mixture was diluted with water (50 mL) and the resulting mixture was extracted with (50 mL×3). The organic layer was washed with water (100 mL) and saturated brine (100 mL), dried over anhydrous sodium sulfate and concentrated in vacuo. The residue was purified by silica gel column chromatography (PE/EtOAc (v/v)=5/1) to give the title compound as a white solid (1.6 g 87%).

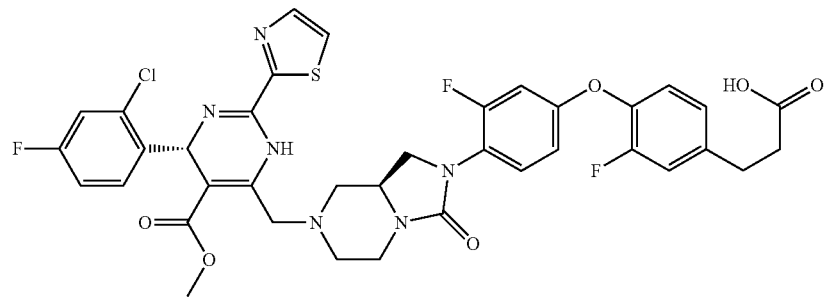 [SMILES: COC(=O)C1=C(CN2CCN3C(=O)N(c4ccc(Oc5ccc(CCC(=O)O)cc5F)cc4F)C[C@@H]3C2)NC(c2nccs2)=N[C@H]1c1ccc(F)cc1Cl]

Step 2: 4-(4-(hydroxymethyl)phenoxy)benzonitrile

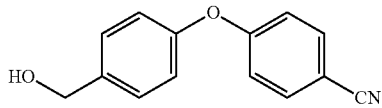 [SMILES: N#Cc1ccc(Oc2ccc(CO)cc2)cc1]

4-(4-Formylphenoxy)benzonitrile (1.5 g 6.7 mmol) was dissolved in methanol (30 mL), and sodium borohydride (0.39 g 10.0 mmol) was added under ice cooling the mixture was stirred at this temperature for 2 hours. The most solvent was stripped off in vacuo. To the reaction mixture was added water (30 mL) to dilute, and the mixture was extracted with EtOAc (30 mL×3). The combined organic layers were washed with saturated aqueous sodium chloride (50 mL), and then concentrated in vacuo to give the title compound as a white solid (1.4 g 93%). MS (ESI, pos. ion) m/z: 226.2 [M+H]$^+$.

Step 3: 4-(4-(bromomethyl)phenoxy)benzonitrile

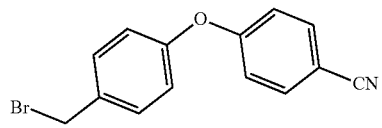 [SMILES: N#Cc1ccc(Oc2ccc(CBr)cc2)cc1]

4-(4-(Hydroxymethyl)phenoxy)benzonitrile (1 g 4.44 mmol) was dissolved in DCM (20 mL) under N$_2$, to the mixture was added phosphorus tribromide (480 mg, 1.77 mmol) on an ice bath, the mixture was continued to stir for 5 hours. The mixture was quenched with water (20 mL), and extracted with DCM (20 mL). The organic layer was washed with saturated brine, dried over anhydrous sodium sulfate and concentrated in vacuo. The residue was purified by silica gel column chromatography (PE/EtOAc (V/V)=20/1) to give the title compound as a white solid (1.1 g, 86%). MS (ESI, pos. ion) m/z: 289.1 [M+H]$^+$.

Step 4: (R)-tert-butyl 2-(4-(4-cyanophenoxy)benzyl)-3-oxohexahydroimidazo[1,5-a]pyrazin-7(1H)-carboxylate

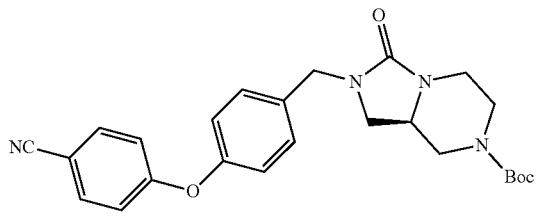 [SMILES: CC(C)(C)OC(=O)N1CCN2C(=O)N(Cc3ccc(Oc4ccc(C#N)cc4)cc3)C[C@@H]2C1]

(R)-tert-Butyl 3-oxohexahydroimidazo[1,5-a]pyrazin-7 (1H)-carboxylate (200 mg, 0.83 mmol) was dissolved in DMF (5 mL) under N$_2$, sodium hydride (99 mg, 2.48 mmol, 60 mass %) was added under ice cooling, the mixture was stirred for 30 min at this temperature, 4-(4-(bromomethyl) phenoxy)benzonitrile (358 mg, 1.2 mmol) was added under ice cooling, the mixture was stirred at rt for 12 h. The mixture was concentrated in vacuo. The residue was purified by silica gel column chromatography (PE/EtOAc (V/V)=2/1) to give the title compound as a white solid (210 mg, 57%). MS (ESI, pos. ion): m/z 471.3 [M+Na]$^+$.

Step 5: (R)-methyl 4-(2-chloro-4-fluorophenyl)-6-(((S)-2-(4-(4-cyanophenoxy)benzyl)-3-oxohexahydroimidazo[1,5-a]pyrazin-7(1H)-yl)methyl)-2-(thiazol-2-yl)-1,4-dihydropyrimidine-5-carboxylate

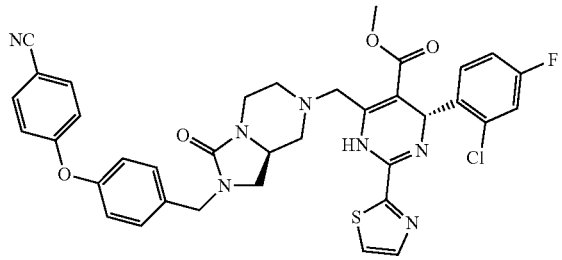 [SMILES: COC(=O)C1=C(CN2CCN3C(=O)N(Cc4ccc(Oc5ccc(C#N)cc5)cc4)C[C@@H]3C2)NC(c2nccs2)=N[C@H]1c1ccc(F)cc1Cl]

The title compound as a yellow solid (128 mg, 83%) was prepared by the method according to example 97 by the replacement of (R)-tert-butyl 2-(4-(4-cyanophenoxy)phenyl)-3-oxohexahydroimidazo[1,5-a]pyrazin-7(1H)-carboxylate with (R)-tert-butyl 2-(4-(4-cyanophenoxy)benzyl)-3-oxohexahydroimidazo[1,5-a]pyrazin-7(1H)-carboxylate (100 mg, 0.22 mmol) of example 97. MS (ESI, pos. ion) m/z: 712.3 [M+H]$^+$; $^1$H NMR (400 MHz, CDCl$_3$) δ 9.62 (s, 1H), 7.84 (d, J=3.1 Hz, 1H), 7.62 (d, J=8.8 Hz, 2H), 7.46 (d, J=3.1 Hz, 1H), 7.35-7.27 (m, 3H), 7.14 (dd, J=8.6, 2.5 Hz, 1H), 7.06-7.01 (m, 4H), 6.93 (td, J=8.4, 2.5 Hz, 1H), 6.20 (s, 1H), 4.47-4.34 (m, 2H), 4.09 (d, J=17.2 Hz, 1H), 4.02 (d, J=11.8 Hz, 1H), 3.92-3.81 (m, 2H), 3.60 (s, 3H), 3.35 (t, J=8.7 Hz, 1H), 3.24 (td, J=13.1, 3.2 Hz, 1H), 2.88-2.79 (m, 2H), 2.72 (d, J=9.5 Hz, 1H), 2.46 (td, J=11.5, 3.1 Hz, 1H), 2.20 (t, J=10.8 Hz, 1H).

Example 103: (R)-methyl 4-(2-chloro-4-fluorophenyl)-6-(((S)-2-(4-(4-methoxyphenoxy)phenyl)-3-oxohexahydroimidazo[1,5-a]pyrazin-7(1H)-yl) methyl)-2-me (thiazol-2-yl)-1,4-dihydropyrimidine-5-carboxylate Step 1: 1-bromo-4-(4-methoxyphenoxy)benzene

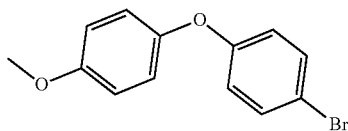 [SMILES: COc1ccc(Oc2ccc(Br)cc2)cc1]

4-(4-Bromophenoxy)phenol (300 mg, 1.13 mmol), iodomethane (320 mg, 2.25 mmol), potassium carbonate (940 mg, 6.8 mmol) were dissolved in acetone (20 mL), the mixture was stirred at 50° C. for 12 h. The mixture was concentrated in vacuo. The residue was purified by silica gel column chromatography (PE) to give the title compound as a white solid (280 mg, 89%).

Step 2: (R)-tert-butyl 2-(4-(4-methoxyphenoxy) phenyl)-3-oxohexahydroimidazo[1,5-a]pyrazin-7(1H)-carboxylate

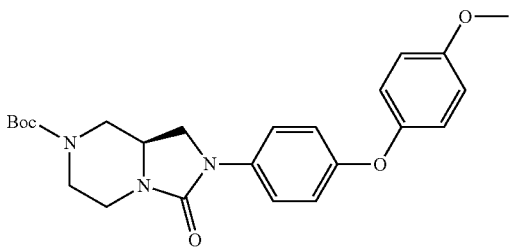 [SMILES: COc1ccc(Oc2ccc(N3C[C@@H]4CN(C(=O)OC(C)(C)C)CCN4C3=O)cc2)cc1]

1-Bromo-4-(4-methoxyphenoxy)benzene (232 mg, 0.83 mmol), (R)-tert-butyl 3-oxohexahydroimidazo[1,5-a]pyrazine-7(1H)-carboxylate (200 mg, 0.83 mmol), palladiumacetate (19 mg, 0.08 mmol), 2-di-tert-butylphosphino-2',4',6'-triisopropylbinphenyl (71 mg, 0.16 mmol) and cesium carbonate (540 mg, 1.66 mmol) were dissolved in 1,4-dioxane (10 mL) under N₂. The mixture was stirred at 90° C. for 12 hours. The mixture was concentrated in vacuo. The residue was purified by silica gel column chromatography (PE/EtOAc (V/V)=2/1) to give the title compound as a white solid (260 mg, 71.7%). MS (ESI, pos. ion): m/z 384.1 [M+H−56]$^+$.

Step 3: (S)-2-(4-(4-methoxyphenoxy)phenyl)hexahydroimidazo[1,5-a]pyrazine-3(2H)-one trifluoroacetate

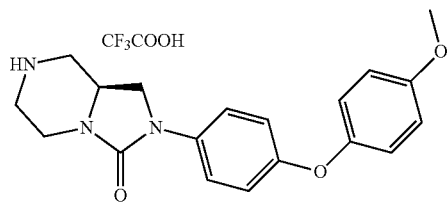 [SMILES: COc1ccc(Oc2ccc(N3C[C@@H]4CNCCN4C3=O)cc2)cc1 ; "CF3COOH"]

(R)-tert-Butyl 2-(4-(4-methoxyphenoxy)phenyl)-3-oxohexahydroimidazo[1,5-a]pyrazine-7(1H)-carboxylate (110 mg, 0.25 mmol) was dissolved in DCM (5 mL), to the solution was added trifluoroacetic acid (5 ml). The mixture was stirred at rt for 1 hour. The reaction mixture was concentrated in vacuo to get the title compound as brown oil (110 mg, 97%).

Step 4: (R)-methyl 4-(2-chloro-4-fluorophenyl)-6-(((S)-2-(4-(4-methoxyphenoxy)phenyl)-3-oxohexahydroimidazo[1,5-a]pyrazin-7(1H)-yl)methyl)-2-(thiazol-2-yl)-1,4-dihydropyrimidine-5-carboxylate

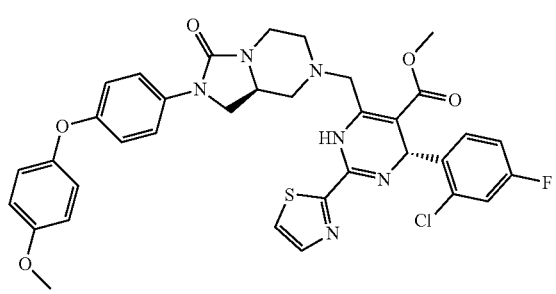 [SMILES: COC(=O)C1=C(CN2CCN3C(=O)N(c4ccc(Oc5ccc(OC)cc5)cc4)C[C@@H]3C2)NC(c2nccs2)=N[C@H]1c1ccc(F)cc1Cl]

To a flask were added (S)-2-(4-(4-Methoxyphenoxy)phenyl)hexahydroimidazo[1,5-a]pyrazine-3(2H)-one trifluoroacetate (70 mg, 0.15 mmol), potassium carbonate (54 mg, 0.39 mmol), ethanol (10 mL), (R)-methyl 6-(bromomethyl)-4-(2-chloro-4-fluorophenyl)-2-(thiazol-2-yl)-1,4-dihydropyrimidine-5-carboxylate (63 mg, 0.14 mmol), the mixture was at rt for 8 hours. The mixture was concentrated in vacuo. The residue was purified by silica gel column chromatography (PE/EtOAc (V/V)=2/1) to give the title compound as a yellow solid (80 mg, 74%). MS (ESI, pos. ion) m/z: 703.2 [M+H]$^+$; $^1$H NMR (400 MHz, CDCl$_3$) δ 9.65 (s, 1H), 7.87 (d, J=3.0 Hz, 1H), 7.50-7.44 (m, 3H), 7.33-7.29 (m, 1H), 7.15 (dd, J=8.5, 2.4 Hz, 1H), 7.00-6.91 (m, 5H), 6.91-6.83 (m, 2H), 6.22 (s, 1H), 4.13 (d, J=17.2 Hz, 1H), 4.10-4.04 (m, 1H), 4.03-3.96 (m, 1H), 3.94-3.86 (m, 2H), 3.81 (s, 3H), 3.61 (s, 3H), 3.44-3.41 (m, 1H), 3.33-3.21 (m, 1H), 2.94-2.82 (m, 2H), 2.52 (td, J=11.4, 2.8 Hz, 1H), 2.29 (t, J=10.7 Hz, 1H).

Example 104: (R)-methyl 4-(2-chloro-4-fluorophenyl)-6-(((S)-3-oxo-2-(4-(4-(2,2,2-trifluoroethoxy) phenoxy)phenyl)hexahydroimidazo[1,5-a]pyrazin-7(1H)-yl)methyl)-2-(thiazol-2-yl)-1,4-dihydropyrimidine-5-carboxylate The title compound as a yellow solid (120 mg, 81%) was prepared by the method according to example 103 by the replacement of iodomethane with 2-iodo-1,1,1-trifluoroethane (480 mg, 2.26 mmol) of example 103. MS (ESI, pos. ion) m/z: 771.2 [M+H]$^+$; $^1$H NMR (400 MHz, CDCl$_3$) δ 7.89 (s, 1H), 7.57 (s, 1H), 7.47 (d, J=9.0 Hz, 2H), 7.39-7.31 (m, 1H), 7.18 (dd, J=8.3, 2.4 Hz, 1H), 7.04-6.91 (m, 7H), 6.18 (s, 1H), 4.75 (d, J=14.4 Hz, 1H), 4.53-4.45 (m, 1H), 4.42 (d, J=14.9 Hz, 1H), 4.35 (q, J=8.2 Hz, 2H), 4.19-4.09 (m, 1H), 4.02 (t, J=8.9 Hz, 1H), 3.77-3.57 (m, 6H), 3.51-3.43 (m, 1H), 3.09-2.86 (m, 2H).

Example 105: (R)-methyl 4-(2-chloro-4-fluorophenyl)-6-(((S)-2-(4-((4-isopropoxyphenyl)thio) phenyl)-3-oxohexahydroimidazo[1,5-a]pyrazin-7(1H)-yl)methyl)-2-(thiazol-2-yl)-1,4-dihydropyrimidine-5-carboxylate Step 1: 1-iodo-4-isopropoxybenzene

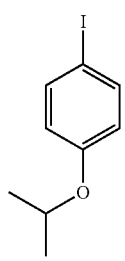

4-Iodophenol (1 g 4.55 mmol), 2-iodopropane (1.55 g 9.12 mmol) and potassium carbonate (940 mg, 6.8 mmol) were dissolved in acetone (20 mL), the mixture was stirred at 60° C. for 12 h. The mixture was filtered and the filtrate was concentrated in vacuo. The residue was purified by silica gel column chromatography (PE) to give the title compound as colorless oil (0.85 g 71%).

Step 2: (4-bromophenyl)(4-isopropoxyphenyl)sulfane

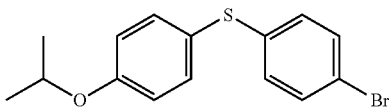 [SMILES: CC(C)Oc1ccc(Sc2ccc(Br)cc2)cc1]

4-Bromine thiophenol (300 mg, 1.59 mmol), 1-iodo-4-isopropoxybenzene (415 mg, 1.58 mmol), tris(dibenzylideneacetone)dipalladium (148 mg, 0.16 mmol), 1,1'-bis(diphenylphosphino)ferrocene (185 mg, 0.32 mmol) and sodium tert-butoxide (314 mg, 3.17 mmol) were dissolved in toluene (5 mL) under $N_2$, the mixture was stirred at 100° C. for 12 h. The mixture was concentrated in vacuo. The residue was purified by silica gel column chromatography (PE) to give the title compound as a light yellow solid (430 mg, 84%).

Step 3: (R)-methyl 4-(2-chloro-4-fluorophenyl)-6-(((S)-2-(4-((4-isopropoxyphenyl)thio)phenyl)-3-oxohexahydroimidazo[1,5-a]pyrazin-7(1H)-yl) methyl)-2-me (thiazol-2-yl)-1,4-dihydropyrimidine-5-carboxylate

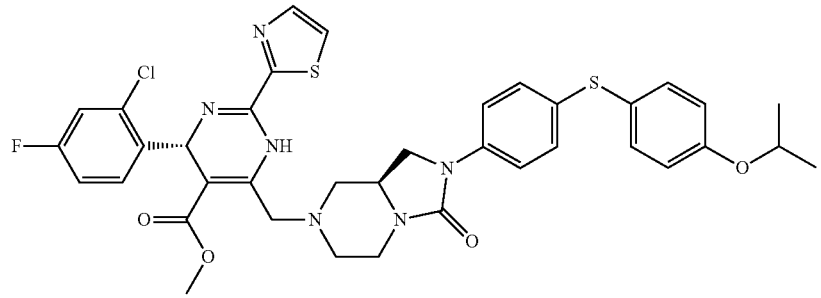 [SMILES: COC(=O)C1=C(CN2CCN3C(=O)N(c4ccc(Sc5ccc(OC(C)C)cc5)cc4)C[C@@H]3C2)NC(c2nccs2)=N[C@H]1c1ccc(F)cc1Cl]

The title compound as a yellow solid (130 mg, 58%) was prepared by the method according to example 103 by the replacement of 1-bromo-4-(4-methoxyphenoxy)benzene with (4-bromophenyl)(4-isopropoxyphenyl)sulfane (235 mg, 0.73 mmol) in step 2 of example 103. MS (ESI, pos. ion) m/z: 747.3 [M+H]$^+$; $^1$H NMR (400 MHz, CDCl$_3$) δ 9.63 (s, 1H), 7.87 (d, J=3.1 Hz, 1H), 7.50-7.46 (m, 3H), 7.33-7.25 (m, 5H), 7.16 (dd, J=8.6, 2.5 Hz, 1H), 6.94 (td, J=8.3, 2.5 Hz, 1H), 6.85 (d, J=8.8 Hz, 2H), 6.22 (s, 1H), 4.59-4.48 (m, 1H), 4.17-4.10 (m, 1H), 4.07 (dd, J=13.3, 2.3 Hz, 1H), 4.03-3.96 (m, 1H), 3.93-3.85 (m, 2H), 3.61 (s, 3H), 3.42-3.39 (m, 1H), 3.27 (td, J=13.1, 3.3 Hz, 1H), 2.96-2.82 (m, 2H), 2.51 (td, J=11.6, 3.2 Hz, 1H), 2.26 (t, J=10.8 Hz, 1H), 1.35 (d, J=6.1 Hz, 6H).

Example 106: (R)-methyl 4-(2-chloro-4-fluorophenyl)-6-(((S)-2-(4-(4-(methylsulfonyl)phenoxy) phenyl)-3-oxohexahydroimidazo[1,5-a]pyrazin-7(1H)-yl)methyl)-2-(thiazol-2-yl)-1,4-dihydropyrimidine-5-carboxylate Step 1: 1-iodo-4-(methylsulfonyl)benzene

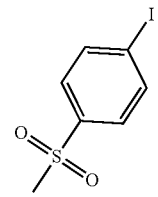

4-Methylsulphonylaniline (1 g 5.84 mmol) was dissolved in concentrated hydrochloric acid (50 mL), the mixture was cooled to 0° C., sodium nitrite (403 mg, 5.84 mmol) was added slowly. The mixture was stirred at this temperature for 30 min, and potassium iodide (1.45 g 8.73 mmol) was added, and then the resulting mixture was stirred for additional 1 hour. The mixture was extracted with DCM (30 mL×3), the combined organic layers were dried over anhydrous sodium sulfate and concentrated in vacuo. The residue was purified by silica gel column chromatography (PE/EtOAc (V/V)=2/1) to give the title compound as a white solid (1.2 g 73%).

Step 2: 1-bromo-4-(4-(methylsulfonyl)phenoxy)benzene

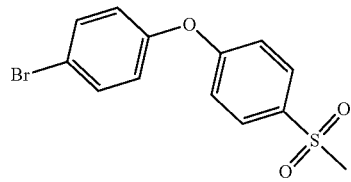 [SMILES: CS(=O)(=O)c1ccc(Oc2ccc(Br)cc2)cc1]

4-Bromophenol (920 mg, 5.32 mmol), 1-iodo-4-(methylsulfonyl)benzene (1 g 3.54 mmol), cuprous iodide (135 mg, 0.71 mmol), pyridinecarboxylic acid (176 mg, 1.42 mmol) and potassium phosphate (1.51 g 7.11 mmol) were dissolved in dimethyl sulfoxide (20 mL) under $N_2$, the mixture was stirred at 100° C. for 24 h. The mixture was diluted with water (50 mL) and the resulting mixture was extracted with EtOAc (50 mL×3). The organic layer was washed with water (100 mL×2) and saturated brine (100 mL), and then concentrated in vacuo. The residue was purified by silica gel column chromatography (PE/EtOAc (v/v)=5/1) to give the title compound as a white solid (500 mg, 43%).

Step 3: (R)-methyl 4-(2-chloro-4-fluorophenyl)-6-(((S)-2-(4-(4-(methylsulfonyl)phenoxy)phenyl)-3-oxohexahydroimidazo[1,5-a]pyrazin-7(1H)-yl)methyl)-2-(thiazol-2-yl)-1,4-dihydro pyrimidine-5-carboxylate

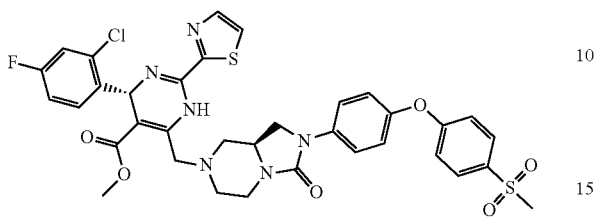

The title compound as a yellow solid (120 mg, 61%) was prepared by the method according to example 103 by the replacement of 1-bromo-4-(4-methoxyphenoxy)benzene with 1-bromo-4-(4-(methylsulfonyl)phenoxy)benzene (300 mg, 0.92 mmol) in step 2 of example 103. MS (ESI, pos. ion) m/z: 751.1 [M+H]$^+$; $^1$H NMR (400 MHz, CDCl$_3$) δ 9.63 (s, 1H), 7.91-7.83 (m, 3H), 7.61 (d, J=9.0 Hz, 2H), 7.49 (d, J=3.1 Hz, 1H), 7.33-7.28 (m, 1H), 7.16 (dd, J=8.6, 2.5 Hz, 1H), 7.10-7.02 (m, 4H), 6.94 (td, J=8.3, 2.5 Hz, 1H), 6.22 (s, 1H), 4.15 (d, J=17.2 Hz, 1H), 4.11-4.00 (m, 2H), 3.98-3.87 (m, 2H), 3.62 (s, 3H), 3.50-3.42 (m, 1H), 3.30 (td, J=13.1, 2.9 Hz, 1H), 3.06 (s, 3H), 2.92 (d, J=10.2 Hz, 2H), 2.53 (td, J=11.6, 3.1 Hz, 1H), 2.29 (t, J=10.7 Hz, 1H).

Example 107: (R)-methyl 4-(2-chloro-4-fluorophenyl)-6-(((S)-2-(4-(2-methyl-1H-imidazol-5-yl) phenyl)-3-oxohexahydroimidazo[1,5-a]pyrazin-7(1H)-yl)methyl)-2-(thiazol-2-yl)-1,4-dihydropyrimidine-5-carboxylate Step 1: 2-bromo-1-(4-bromophenyl)ethanone

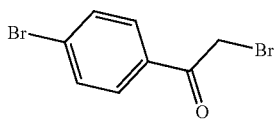 [SMILES: O=C(CBr)c1ccc(Br)cc1]

To a 250 mL two neck flask were added p-bromophenylethanone (10.00 g 50.24 mmol), CH$_3$CN (100 mL), p-toluenesulfonic acid (173 mg, 1.00 mmol) and NBS (13.4 g 75.3 mmol), the mixture was dissolved by stirring. The mixture was stirred at 80° C. for 13 hours under N$_2$.
The mixture was cooled to rt and concentrated in vacuo. The residue was purified by silica gel column chromatography (PE/EtOAc (V/V)=20/1) to give the title compound as a white solid (11.53 g 82.6%). $^1$H NMR (400 MHz, CDCl$_3$) δ 7.88 (d, J=8.6 Hz, 2H), 7.67 (d, J=8.6 Hz, 2H), 4.42 (s, 2H).

Step 2: 5-(4-bromophenyl)-2-methyl-1H-imidazole

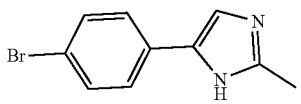

To a 250 mL three neck flask were added acetamidine hydrochloride (3.40 g 36.0 mmol), K$_2$CO$_3$ (7.53 g 53.9 mmol) and MeCN (60 mL), the mixture was dissolved by stirring and 2-bromo-1-(4-bromophenyl)ethanone (5.00 g 18.0 mmol) in MeCN (40 mL) was added by syringe. The mixture was stirred at 30° C. for 10 hours. The mixture was filtered by suction and the filtrate was concentrated in vacuo. The residue was purified by silica gel column chromatography (EA) to give the title compound as a brown yellow solid (1.08 g 25.3%). MS (ESI, pos. ion) m/z: 237.1 [M+H]$^+$.

Step 3: 5-(4-bromophenyl)-2-methyl-1-((2-(trimethylsilyl)ethoxy)methyl)-1H-imidazole

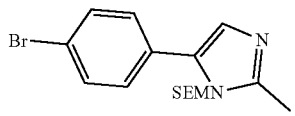 [SMILES: Cc1ncc(-c2ccc(Br)cc2)n1COCC[Si](C)(C)C]

To a 100 mL single neck flask were added 5-(4-bromophenyl)-2-methyl-1H-imidazole (1.08 g 4.56 mmol) and THF (40 mL), the mixture was dissolved by stirring and cooled in an ice bath, and then NaH (454 mg, 11.35 mmol) was added. The mixture was stirred in an ice bath for additional 15 min, and then 2-(chloromethoxy)ethyl-trimethylsilane (2.01 mL, 11.4 mmol) was added. The resulting mixture was warmed to rt and stirred for 3 hours. The mixture was diluted with saturated aqueous NaCl (10 mL) and EtOAc (20 mL) and partitioned, the organic layer was dried over anhydrous sodium sulfate and concentrated in vacuo, the residue was purified by silica gel column chromatography (PE/EtOAc (v/v)=4/1) to give the title compound as a brown yellow solid (792 mg, 47.3%). MS (ESI, pos. ion) m/z: 367.2 [M+H]$^+$.

Step 4: (R)-benzyl 2-(4-(2-methyl-1-((2-(trimethylsilyl)ethoxy)methyl)-1H-imidazol-5-yl)phenyl)-3-oxohexahydroimidazo[1,5-a]pyrazine-7(1H)-carboxylate

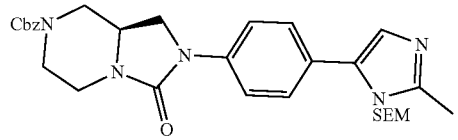 [SMILES: Cc1ncc(-c2ccc(N3C[C@@H]4CN(C(=O)OCc5ccccc5)CCN4C3=O)cc2)n1COCC[Si](C)(C)C]

To a 50 mL single neck flask were added (R)-benzyl 3-oxohexahydroimidazo[1,5-a]pyrazine-7(1H)-carboxylate (487 mg, 1.77 mmol), 5-(4-bromophenyl)-2-methyl-1-((2-(trimethylsilyl)ethoxy)methyl)-1H-imidazole (566 mg, 1.54 mmol), palladium acetate (35 mg, 0.16 mmol), 2-di-tert-butylphosphino-2',4',6'-trisopropylbinphenyl (130 mg, 0.31 mmol), cesium carbonate (1.00 g 3.07 mmol) and 1,4-dioxane (25 mL), the mixture was stirred at 110° C. under N$_2$ for 12 hours. The mixture was cooled to rt and filtered by suction. The filtrate was diluted with EtOAc (20 mL) and washed with saturated aqueous NaCl solution (20 mL×3), and then concentrated in vacuo. The residue was purified by silica gel column chromatography (CH$_2$Cl$_2$/EtOAc (V/V)= 1/1) to give the title compound as a brown yellow solid (474 mg, 54.8%). MS (ESI, pos. ion) m/z: 562.2 [M+H]$^+$;

Step 5: (S)-2-(4-(2-methyl-1-((2-(trimethylsilyl)ethoxy)methyl)-1H-imidazol-5-yl)phenyl) hexahydroimidazo[1,5-a]pyrazine-3(2H)-one

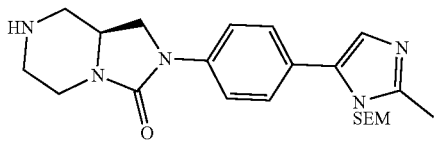 [SMILES: Cc1ncc(-c2ccc(N3C[C@@H]4CNCCN4C3=O)cc2)n1COCC[Si](C)(C)C]

To a 100 mL single neck flask were added (R)-benzyl 2-(4-(2-methyl-1-((2-(trimethylsilyl)ethoxy)methyl)-1H-imidazol-5-yl)phenyl)-3-oxohexahydroimidazo[1,5-a]pyrazine-7(1H)-carboxylate (474 mg, 0.84 mmol), MeOH (30 mL), EtOAc (2 mL) and Pd/C (300 mg). The mixture was stirred at rt under $H_2$ for 4.5 hours. The mixture was filtered by suction and the filter cake was washed with methanol (10 mL), the filtrate was concentrated in vacuo to get the title compound as a white solid (295 mg, 81.8%). MS (ESI, pos. ion) m/z: 428.1 [M+H]$^+$.

Step 6: (R)-methyl 4-(2-chloro-4-fluorophenyl)-6-(((S)-2-(4-(2-methyl-1-((2-(trimethylsilyl)ethoxy)methyl)-1H-imidazol-5-yl)phenyl)-3-oxohexahydroimidazo[1,5-a]pyrazin-7(1H)-yl)methyl)-2-(thiazol-2-yl)-1,4-dihydropyrimidine-5-carboxylate

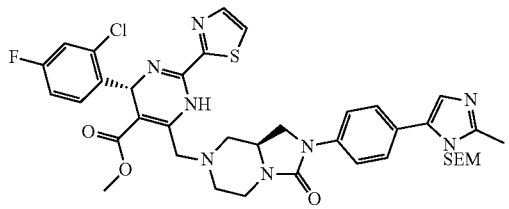 [SMILES: COC(=O)C1=C(CN2CCN3C(=O)N(c4ccc(-c5cnc(C)n5COCC[Si](C)(C)C)cc4)C[C@@H]3C2)NC(c2nccs2)=N[C@H]1c1ccc(F)cc1Cl]

To a 50 mL single neck flask were added (R)-methyl 6-(bromomethyl)-4-(2-chloro-4-fluorophenyl)-2-(thiazol-2-yl)-1,4-dihydropyrimidine-5-carboxy late (291 mg, 0.65 mmol), (S)-2-(4-(2-methyl-1-((2-(trimethylsilyl)ethoxy)methyl)-1H-imidazol-5-yl)phenyl)hexahydroimidazo[1,5-a]pyrazine-3(2H)-one (280 mg, 0.65 mmol), $K_2CO_3$ (183 mg, 1.31 mmol) and EtOH (15 mL), the mixture was stirred at rt for 15 hours. The mixture was filtered by suction and the filter cake was washed with $CH_2Cl_2$ (2 mL), the filtrate was concentrated in vacuo. The residue was purified by silica gel column chromatography (EtOAc) to give the title compound as a yellow solid (408 mg, 78.7%). MS (ESI, pos. ion) m/z: 791.1 [M+H]$^+$.

Step 7): (R)-methyl 4-(2-chloro-4-fluorophenyl)-6-(((S)-2-(4-(2-methyl-1H-imidazol-5-yl)phenyl)-3-oxohexahydroimidazo[1,5-a]pyrazin-7(1H)-yl)methyl)-2-(thiazol-2-yl)-1,4-dihydropyrimidine-5-carboxylate

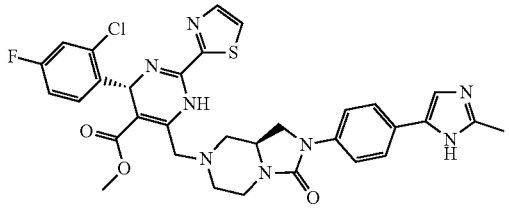 [SMILES: COC(=O)C1=C(CN2CCN3C(=O)N(c4ccc(-c5cnc(C)[nH]5)cc4)C[C@@H]3C2)NC(c2nccs2)=N[C@H]1c1ccc(F)cc1Cl]

To a 50 mL single neck flask were added (R)-methyl 4-(2-chloro-4-fluorophenyl)-6-(((S)-2-(4-(2-methyl-1-((2-(trimethylsilyl)ethoxy)methyl)-1H-imidazol-5-yl)phenyl)-3-oxohexahydroimidazo[1,5-a]pyrazin-7(1H)-yl)methyl)-2-(thiazol-2-yl)-1,4-dihydropyrimidine-5-carboxylate (200 mg, 0.25 mmol), DCM (2 mL) and TFA (2 mL). The mixture was stirred at rt for 6 h. The mixture was concentrated. The residue was diluted with $CH_2Cl_2$ (10 mL) and water (5 mL), the resulting mixture was adjusted with saturated aqueous $K_2CO_3$ to pH 7 to 8, the organic layer was concentrated in vacuo. The residue was purified by silica gel column chromatography (DCM/MeOH (V/V)=15/1) to give the title compound as a yellow solid (149 mg, 89.2%). MS (ESI, pos. ion) m/z: 661.3 [M+H]$^+$; $^1$H NMR (400 MHz, MeOH-d$_4$) δ 7.96 (d, J=3.1 Hz, 1H), 7.74 (d, J=3.1 Hz, 1H), 7.63 (d, J=8.8 Hz, 2H), 7.57 (d, J=8.8 Hz, 2H), 7.45-7.41 (m, 1H), 7.28 (s, 1H), 7.23 (dd, J=8.7, 2.4 Hz, 1H), 7.05 (td, J=8.4, 2.4 Hz, 1H), 6.18 (s, 1H), 4.11 (d, J=17.0 Hz, 1H), 4.05-3.90 (m, 4H), 3.60 (s, 3H), 3.52 (dd, J=9.0, 4.1 Hz, 1H), 3.25 (t, J=11.0 Hz, 1H), 2.96 (d, J=10.7 Hz, 2H), 2.46 (s, 3H), 2.42 (dd, J=11.8, 30.0 Hz, 1H), 2.23 (t, J=10.7 Hz, 1H).

Example 108: (4R)-methyl 4-(2-chloro-4-fluorophenyl)-6-(((8aS)-2-(2-(1-methylpyrrolidin-2-yl)-1H-benzo[d]imidazol-5-yl)-3-oxohexahydroimidazo[1,5-a]pyrazin-7(1H)-yl)methyl)-2-(thiazol-2-yl)-1,4-dihydropyrimidine-5-carboxylate

Step 1: (8aS)-2-(2-(1-methylpyrrolidin-2-yl)-1-((2-(trimethylsilyl)ethoxy)methyl)-1H-benzo[d]imidazol-5-yl)hexahydroimidazo[1,5-a]pyrazine-3(2H)-one

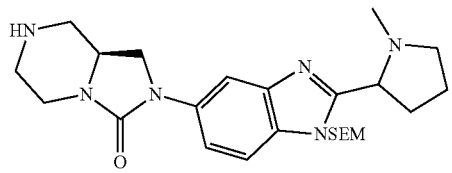 [SMILES: CN1CCCC1c1nc2cc(N3C[C@@H]4CNCCN4C3=O)ccc2n1COCC[Si](C)(C)C]

To a 50 mL single neck flask were added (8aR)-benzyl 2-(2-(1-methylpyrrol-2-yl)-1-((2-(trimethylsilyl)ethoxy)methyl)-1H-benzo[d]imidazol-5-yl)-3-oxohexahydroimidazo[1,5-a]pyrazine-7(1H)-carboxylate (272 mg, 0.45 mmol), MeOH (15 mL) and Pd/C (100 mg, 10 mass %). The mixture was stirred at rt under $H_2$ for 6 hours. The mixture was filtered by suction and the filter cake was washed with methanol (10 mL), the filtrate was concentrated in vacuo to get the title compound as brown yellow oil (188 mg, 89%) MS (ESI, pos. ion) m/z: 471.5 [M+H]+.

Step 2: (4R)-methyl 4-(2-chloro-4-fluorophenyl)-6-(((8aS)-2-(2-(1-methylpyrrolidin-2-yl)-1-((2-(trimethylsilyl)ethoxy)methyl)-1H-benzo[d]imidazol-5-yl)-3-oxohexahydroimidazo[1,5-a]pyrazin-7(1H)-yl)methyl)-2-(thiazol-2-yl)-1,4-dihydropyrimidine-5-carboxylate

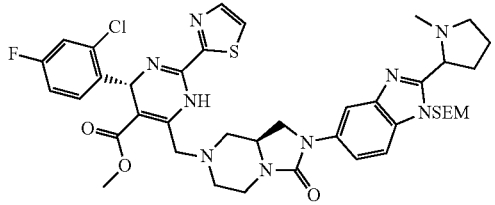 [SMILES: COC(=O)C1=C(CN2CCN3C(=O)N(c4ccc5c(c4)nc(C4CCCN4C)n5COCC[Si](C)(C)C)C[C@@H]3C2)NC(c2nccs2)=N[C@H]1c1ccc(F)cc1Cl]

To a flask were added (8aS)-2-(2-(1-methylpyrrolidin-2-yl)-1-((2-(trimethylsilyl)ethoxy) methyl)-1H-benzo[d]imidazol-5-yl)hexahydroimidazo[1,5-a]pyrazine-3(2H)-one (188 mg, 0.40 mmol), (R)-methyl 6-(bromomethyl)-4-(2-chloro-4-fluorophenyl)-2-(thiazol-2-yl)-1,4-dihydropyrimidine-5-carboxylate (178 mg, 0.40 mmol), potassium carbonate (112 mg, 0.80 mmol) and ethanol (10 mL). The mixture was stirred at rt for 12 hours. The mixture was filtered by suction and the filter cake was washed with EtOAc (10 mL), the filtrate was concentrated in vacuo. The residue was purified by silica gel column chromatography (CH$_2$Cl$_2$/MeOH (V/V)=20/1) to give the title compound as a brown yellow solid (164 mg, 49%). MS (ESI, pos. ion) m/z: 834.5 [M+H]+.

Step 3: (4R)-methyl 4-(2-chloro-4-fluorophenyl)-6-(((8aS)-2-(2-(1-methylpyrrolidin-2-yl)-1H-benzo[d]imidazol-5-yl)-3-oxohexahydroimidazo[1,5-a]pyrazin-7(1H)-yl)methyl)-2-(thiazol-2-yl)-1,4-dihydropyrimidine-5-carboxylate

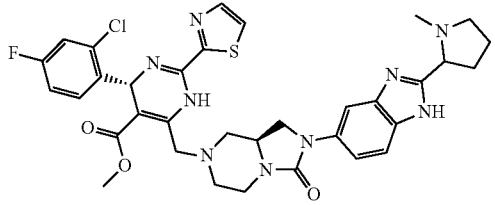 [SMILES: COC(=O)C1=C(CN2CCN3C(=O)N(c4ccc5[nH]c(C6CCCN6C)nc5c4)C[C@@H]3C2)NC(c2nccs2)=N[C@H]1c1ccc(F)cc1Cl]

To a 25 mL single neck flask were added (4R)-methyl 4-(2-chloro-4-fluorophenyl)-6-(((8aS)-2-(2-(1-methylpyrrolidin-2-yl)-1-((2-(trimethylsilyl)ethoxy)methyl)-1H-benzo[d]imidazol-5-yl)-3-oxohexahydroimidazo[1,5-a]pyrazin-7(1H)-yl)methyl)-2-(thiazol-2-yl)-1,4-dihydropyrimidine-5-carboxylate (149 mg, 0.18 mmol), DCM (3 mL) and TFA (3 mL). The mixture was stirred at rt for 21 h. The mixture was concentrated in vacuo, the residue was diluted with CH$_2$Cl$_2$ (20 mL) and water (10 mL), the resulting mixture was adjusted with saturated aqueous K$_2$CO$_3$ to pH 7 to 8, the organic layer was concentrated in vacuo. The residue was purified by silica gel column chromatography (CH$_2$Cl$_2$/MeOH (V/V)=10/1) to give the title compound as a yellow solid (52 mg, 41%). MS (ESI, pos. ion) m/z: 704.4 [M+H]+; $^1$H NMR (400 MHz, MeOH-d$_4$) δ 7.98 (d, J=3.1 Hz, 1H), 7.75 (d, J=3.1 Hz, 1H), 7.72 (s, 1H), 7.52 (d, J=8.6 Hz, 1H), 7.47-7.39 (m, 2H), 7.23 (dd, J=8.7, 2.5 Hz, 1H), 7.06 (td, J=8.3, 2.5 Hz, 1H), 6.19 (s, 1H), 4.14 (d, J=17.0 Hz, 1H), 4.07-3.91 (m, 4H), 3.70-3.64 (m, 1H), 3.61 (s, 3H), 3.59-3.55 (m, 1H), 3.31-3.24 (m, 2H), 2.99 (d, J=10.3 Hz, 2H), 2.53-2.43 (m, 2H), 2.37 (s, 4H), 2.29 (t, J=10.0 Hz, 1H), 2.10-2.01 (m, 2H), 1.99-1.93 (m, 1H).

Example 109: (R)-methyl 4-(2-chloro-4-fluorophenyl)-6-(((S)-2-(4-(4-ethyl-1H-imidazol-2-yl) phenyl)-3-oxohexahydroimidazo[1,5-a]pyrazin-7(1H)-yl)methyl)-2-(thiazol-2-yl)-1,4-dihydropyrimidine-5-carboxylate Step 1: 2-(4-bromophenyl)-5-ethyl-1H-imidazole

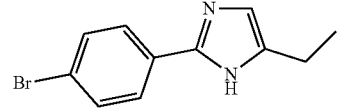

To a 250 mL two neck flask were added 4-bromobenzamidine (2.00 g 10.0 mmol), 1-bromobutane-2-one (2.09 g 11.1 mmol), K$_2$CO$_3$ (2.81 g 20.1 mmol) and EtOH (100 mL). The mixture was stirred at rt for 23 h. The mixture was filtered by suction and the filter cake was washed with EtOH (20 mL), the filtrate was concentrated in vacuo. The residue was purified by silica gel column chromatography (PE/EtOAc (V/V)=3/1) to give the title compound as a white solid (707 mg, 28.0%). MS (ESI, pos. ion) m/z: 251.1 [M+H]+.

Step 2: 2-(4-bromophenyl)-5-ethyl-1-((2-(trimethylsilyl)ethoxy)methyl)-1H-imidazole

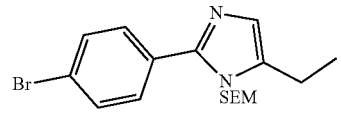 [SMILES: CCc1cnc(-c2ccc(Br)cc2)n1COCC[Si](C)(C)C]

To a 50 mL two neck flask were added NaH (225 mg, 5.63 mmol, 60 mass %) and THF (10 mL), the mixture was cooled in an ice bath for 5 min, 2-(4-bromophenyl)-5-ethyl-1H-imidazole (707 mg, 2.82 mmol) in THF (10 mL) was added slowly to the above reaction system under N$_2$. The mixture was stirred at rt for 1 hour. The reaction mixture was cooled in an ice bath for 5 min, and then 2-(chloromethoxy) ethyl-trimethylsilane (0.75 mL, 4.2 mmol) was added slowly. The reaction mixture was stirred at rt for 16 hours. The mixture was diluted with saturated aqueous NaCl (10 mL) and EtOAc (20 mL), the organic layer was dried over anhydrous sodium sulfate and concentrated in vacuo, the residue was purified by silica gel column chromatography (PE/EtOAc (v/v)=15/1) to give the title compound as yellow oil (472 mg, 44.0%). MS (ESI, pos. ion) m/z: 381.2 [M+H]+.

Step 3: (R)-benzyl 2-(4-(5-ethyl-1-((2-(trimethylsilyl)ethoxy)methyl)-1H-imidazol-2-yl) phenyl)-3-oxohexahydroimidazo[1,5-a]pyrazin-7(1H)-carboxylate

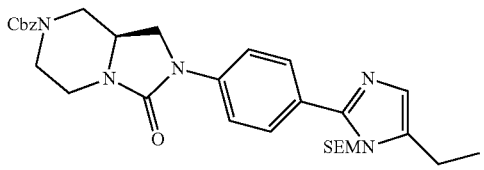 [SMILES: CCc1cnc(-c2ccc(N3C[C@@H]4CN(C(=O)OCc5ccccc5)CCN4C3=O)cc2)n1COCC[Si](C)(C)C]

To a flask were added (R)-benzyl 3-oxohexahydroimidazo[1,5-a]pyrazine-7(1H)-carboxylate (341 mg, 1.24 mmol), 2-(4-bromophenyl)-5-ethyl-1-((2-(trimethylsilyl)ethoxy)methyl)-1H-imidazole (472 mg, 1.24 mmol), palladium acetate (28 mg, 0.12 mmol), 2-di-tert-butylphosphino-2',4',6'-trisopropylbinphenyl (105 mg, 0.25 mmol), cesium carbonate (806 mg, 2.47 mmol) and 1,4-dioxane (20 mL), the mixture was stirred at 90° C. under $N_2$ for 8 hours. The mixture was cooled to rt and filtered by suction, the filter cake was washed with EtOAc (20 mL). The filtrate was washed with saturated aqueous NaCl solution and concentrated in vacuo. The residue was purified by silica gel column chromatography (PE/EtOAc (V/V)=1/1) to give the title compound as a white solid (264 mg, 37%). MS (ESI, pos. ion) m/z: 576.3 [M+H]$^+$.

Step 4: (S)-2-(4-(5-ethyl-1-((2-(trimethylsilyl)ethoxy)methyl)-1H-imidazol-2-yl)phenyl) hexahydroimidazo[1,5-a]pyrazin-3(2H)-one

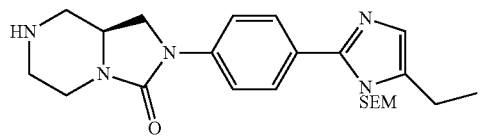 [SMILES: CCc1cnc(-c2ccc(N3C[C@@H]4CNCCN4C3=O)cc2)n1COCC[Si](C)(C)C]

To a 50 mL single neck flask were added (R)-benzyl 2-(4-(5-ethyl-1-((2-(trimethylsilyl)ethoxy)methyl)-1H-imidazol-2-yl)phenyl)-3-oxohexahydroimidazo[1,5-a]pyrazin-7(1H)-carboxylate (264 mg, 0.46 mmol), MeOH (10 mL) and Pd/C (50 mg, 10%). The mixture was stirred at rt under $H_2$ for 14 h. The mixture was filtered by suction and the filter cake was washed with methanol (10 mL), the filtrate was concentrated in vacuo to get the title compound as colorless oil (202 mg, 100%) MS (ESI, pos. ion) m/z: 442.2 [M+H]$^+$.

Step 5: (R)-methyl 4-(2-chloro-4-fluorophenyl)-6-(((S)-2-(4-(5-ethyl-1-((2-(trimethylsilyl) ethoxy)methyl)-1H-imidazol-2-yl)phenyl)-3-oxohexahydroimidazo[1,5-a]pyrazin-7(1H)-yl) methyl)-2-(thiazol-2-yl)-1,4-dihydropyrimidine-5-carboxylate

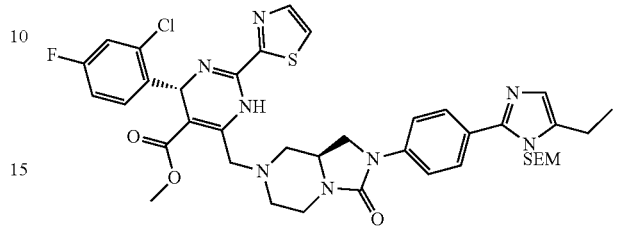

To a flask were added (S)-2-(4-(5-ethyl-1-((2-(trimethylsilyl)ethoxy)methyl)-1H-imidazol-2-yl)phenyl)hexahydroimidazo[1,5-a]pyrazine-3(2H)-one (202 mg, 0.46 mmol), (R)-methyl 6-(bromomethyl)-4-(2-chloro-4-fluorophenyl)-2-(thiazol-2-yl)-1,4-dihydro pyrimidine-5-carboxylate (203 mg, 0.46 mmol), potassium carbonate (128 mg, 0.92 mmol) and ethanol (10 mL). The mixture was stirred at rt for 21 hours. The mixture was filtered by suction and the filter cake was washed with EtOAc (10 mL), the filtrate was concentrated in vacuo. The residue was purified by silica gel column chromatography ($CH_2Cl_2$/MeOH (V/V)=40/1) to give the title compound as a yellow solid (295 mg, 80%). MS (ESI, pos. ion) m/z: 403.2[M/2+H]$^+$.

Step 6: (R)-methyl 4-(2-chloro-4-fluorophenyl)-6-(((S)-2-(4-(4-ethyl-1H-imidazol-2-yl) phenyl)-3-oxohexahydroimidazo[1,5-a]pyrazin-7(1H)-yl) methyl)-2-(thiazol-2-yl)-1,4-dihydropyrimidine-5-carboxylate

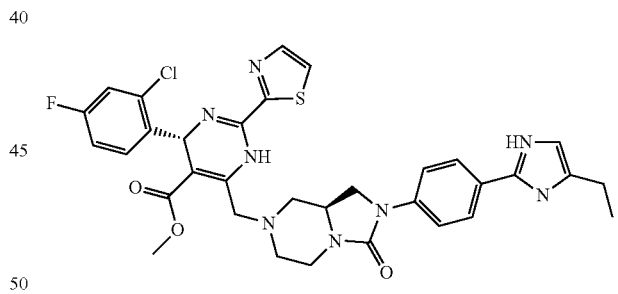

To a 50 mL single neck flask were added (R)-methyl 4-(2-chloro-4-fluorophenyl)-6-(((S)-2-(4-(5-ethyl-1-((2-(trimethylsilyl)ethoxy)methyl)-1H-imidazol-2-yl)phenyl)-3-oxohexahydroimidazo[1,5-a]pyrazin-7(1H)-yl)methyl)-2-(thiazol-2-yl)-1,4-dihydropyrimidine-5-carboxylate (295 mg, 0.37 mmol), DCM (3 mL) and TFA (3 mL). The mixture was stirred at rt for 23 h. The mixture was concentrated in vacuo, the residue was diluted with $CH_2Cl_2$ (20 mL) and water (10 mL), the resulting mixture was adjusted with saturated aqueous $K_2CO_3$ to pH 7 to 8, the organic layer was concentrated in vacuo. The residue was purified by silica gel column chromatography ($CH_2Cl_2$/MeOH (V/V)=20/1) to give the title compound as a yellow solid (76 mg, 31%). MS (ESI, pos. ion) m/z: 675.2 [M+H]$^+$; $^1$H NMR (400 MHz, MeOH-$d_4$) δ 8.02 (d, J=2.9 Hz, 1H), 7.92 (s, 5H), 7.61-7.53 (m, 1H), 7.34 (s, 1H), 7.29 (dd, J=8.6, 2.1 Hz, 1H), 7.19-7.05

(m, 1H), 6.21 (s, 1H), 4.76 (d, J=16.1 Hz, 1H), 4.57 (d, J=16.0 Hz, 1H), 4.47-4.35 (m, 1H), 4.29-4.18 (m, 2H), 3.90-3.75 (m, 3H), 3.65 (s, 3H), 3.58 (d, J=11.6 Hz, 1H), 3.30-3.18 (m, 2H), 2.81 (q, J=7.5 Hz, 2H), 1.38 (t, J=7.6 Hz, 3H).

Example 110: (R)-methyl 4-(2-chloro-4-fluorophenyl)-6-(((S)-2-(4-(5-cyclohexyl-1H-imidazol-2-yl)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (503 mg, 96.4%) was prepared by the method according to example 109 by the replacement of 1-bromobutane-2-one with 2-bromo-1-cyclohexyl-ethanone (1.8 mL, 12 mmol) in step 1 of example 109. MS (ESI, pos. ion) m/z: 729.0[M+H]$^+$; $^1$H NMR (400 MHz, MeOH-d$_4$) δ 8.00 (d, J=3.0 Hz, 1H), 7.95-7.85 (m, 5H), 7.57-7.48 (m, 1H), 7.31 (s, 1H), 7.27 (dd, J=8.6, 2.4 Hz, 1H), 7.11 (td, J=8.4, 2.4 Hz, 1H), 6.20 (s, 1H), 4.59 (d, J=16.3 Hz, 1H), 4.40 (d, J=16.3 Hz, 1H), 4.35-4.26 (m, 1H), 4.22-4.10 (m, 2H), 3.74 (dd, J=9.8, 4.3 Hz, 1H), 3.63 (s, 3H), 3.60-3.46 (m, 2H), 3.13-3.03 (m, 1H), 2.96 (t, J=11.4 Hz, 1H), 2.85-2.73 (m, 1H), 2.11 (d, J=9.0 Hz, 2H), 1.90 (d, J=7.5 Hz, 2H), 1.80 (d, J=13.0 Hz, 1H), 1.59-1.48 (m, 4H), 1.47 (s, 2H).

Example 111: (R)-methyl 4-(2-chloro-4-fluorophenyl)-6-(((S)-2-(4-(4-cyclopropyl-1H-imidazol-2-yl)phenyl)-3-oxohexahydroimidazo[1,5-a]pyrazin-7(1H)-yl)methyl)-2-(thiazol-2-yl)-1,4-dihydropyrimidine-5-carboxylate The title compound as a yellow solid (230 mg, 91.2%) was prepared by the method according to example 109 by the replacement of 1-bromobutane-2-one with 2-bromo-1-cyclopropyl-ethanone (3.6 mL, 37 mmol) in step 1 of example 109. MS (ESI, neg. ion) m/z: 685.0 [M−H]$^−$; $^1$H NMR (400 MHz, MeOH-d$_4$) δ 7.99 (s, 1H), 7.88 (s, 4H), 7.84 (s, 1H), 7.50 (t, J=7.0 Hz, 1H), 7.25 (s, 2H), 7.09 (t, J=6.9 Hz, 1H), 6.19 (s, 1H), 4.47 (d, J=16.2 Hz, 1H), 4.28 (d, J=16.5 Hz, 2H), 4.14 (d, J=10.4 Hz, 2H), 3.70 (d, J=5.3 Hz, 1H), 3.62 (s, 3H), 3.45 (t, J=12.2 Hz, 3H), 2.92 (t, J=11.6 Hz, 1H), 2.78 (t, J=10.8 Hz, 1H), 2.01 (d, J=7.7 Hz, 1H), 1.10 (d, J=6.8 Hz, 2H), 0.88 (s, 2H).

Example 112: 4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3-fluorophenoxy)cyclohexane carboxylic acid The title compound as a yellow solid (252 mg, 27.4%) was prepared by the method according to example 23 by the replacement of 3-bromo-5-fluorophenol with 4-bromo-3-fluoro-phenol (500 mg, 2.62 mmol) in step 1 of example 23. MS (ESI, pos. ion) m/z: 741.4[M+H]$^+$; $^1$H NMR (400 MHz, CDCl$_3$) δ 7.87 (d, J=3.1 Hz, 1H), 7.51 (d, J=3.0 Hz, 1H), 7.34-7.27 (m, 2H), 7.15 (dd, J=8.5, 2.6 Hz, 1H), 7.00-6.92 (m, 1H), 6.72-6.62 (m, 2H), 6.18 (s, 1H), 4.53-4.39 (m, 2H), 4.21-4.02 (m, 3H), 3.84 (d, J=8.7 Hz, 1H), 3.62 (s, 3H), 3.52-3.40 (m, 3H), 3.33 (s, 2H), 2.82-2.70 (m, 2H), 2.48-2.39 (m, 1H), 2.04-1.90 (m, 3H), 1.83-1.73 (m, 2H), 1.70-1.59 (m, 2H).

Example 113: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3'-fluoro-[1,1'-biphenyl]-4-carboxylic acid The title compound as a yellow solid (120 mg, 49%) was prepared by the method according to example 35 by the replacement of 4-bromo-3-fluorophenylboronic acid with 4-bromo-3-fluorophenylboronic acid (275 mg, 1.26 mmol) in step 1 of example 35. MS (ESI, pos. ion) m/z: 719.1 [M+H]$^+$; $^1$H NMR (400 MHz, DMSO-d$_6$) δ 8.12-7.95 (m, 4H), 7.85 (d, J=8.3 Hz, 2H), 7.74-7.58 (m, 3H), 7.54-7.46 (m, 1H), 7.43 (dd, J=8.8, 2.4 Hz, 1H), 7.21 (td, J=8.5, 2.4 Hz, 1H), 6.03 (s, 1H), 4.52-4.38 (m, 1H), 4.38-4.28 (m, 1H), 4.25-4.15 (m, 1H), 4.03-3.88 (m, 3H), 3.63 (s, 2H), 3.56 (s, 3H), 3.47-3.43 (m, 2H), 3.06-2.83 (m, 2H).

Example 114: 5'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2'-fluoro-[1,1'-biphenyl]-4-carboxylic acid The title compound as a yellow solid (180 mg, 56%) was prepared by the method according to example 35 by the replacement of 4-bromo-2-fluorophenylboronic acid with 5-bromo-2-fluorophenylboronic acid (500 mg, 2.28 mmol) in step 1 of example 35. MS (ESI, pos. ion) m/z: 719.0 [M+H]$^+$; $^1$H NMR (400 MHz, DMSO-d$_6$) δ 8.08-7.96 (m, 4H), 7.75-7.62 (m, 4H), 7.55-7.47 (m, 1H), 7.43 (dd, J=8.8, 2.4 Hz, 1H), 7.35 (t, J=9.7 Hz, 1H), 7.21 (td, J=8.5, 2.4 Hz, 1H), 6.03 (s, 1H), 4.53-4.41 (m, 1H), 4.40-4.30 (m, 1H), 4.29-4.18 (m, 1H), 4.06 (t, J=9.0 Hz, 1H), 3.95 (d, J=12.3 Hz, 2H), 3.69 (d, J=7.1 Hz, 1H), 3.55 (s, 3H), 3.51-3.39 (m, 2H), 3.01 (s, 2H).

Example 115: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2-fluoro-[1,1'-biphenyl]-4-carboxylic acid The title compound as a yellow solid (263 mg, 26.5%) was prepared by the method according to example 12 by the replacement of methyl 4-iodobenzoate with methyl 3-fluoro-4-iodobenzoate (500 mg, 1.79 mmol) in step 1 of example 12. MS (ESI, pos. ion) m/z: 719.0 [M+H]$^+$; $^1$H NMR (400 MHz, acetone-d$_6$) δ 7.97 (d, J=3.1 Hz, 1H), 7.94 (dd, J=8.0, 1.6 Hz, 1H), 7.87-7.75 (m, 4H), 7.70 (t, J=8.0 Hz, 1H), 7.66-7.64 (m, 3H), 7.28 (dd, J=8.8, 2.6 Hz, 1H), 7.11 (td, J=8.5, 2.6 Hz, 1H), 6.23 (s, 1H), 4.67-4.40 (m, 3H), 4.40-4.23 (m, 2H), 4.14 (t, 1H), 4.08 (dd, J=13.6, 3.2 Hz, 1H), 3.73 (dd, J=9.5, 3.6 Hz, 1H), 3.61 (s, 3H), 3.43 (s, 1H), 3.32 (s, 1H), 2.17 (t, 1H).

Example 116: 4'-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-6-fluoro-[1,1'-biphenyl]-3-carboxylic acid The title compound as a yellow solid (263 mg, 26.5%) was prepared by the method according to example 12 by the replacement of methyl 4-iodobenzoate with methyl 4-fluoro-3-iodobenzoate (300 mg, 1.1 mmol) in step 1 of example 12. MS (ESI, pos. ion) m/z: 719.3 [M+H]$^+$; $^1$H NMR (400 MHz, DMSO-d₆) δ 8.09 (s, 2H), 8.05 (dd, J=7.7, 1.8 Hz, 1H), 8.00-7.92 (m, 1H), 7.73 (d, J=8.7 Hz, 2H), 7.60 (d, J=8.0 Hz, 2H), 7.56-7.50 (m, 1H), 7.47-7.41 (m, 2H), 7.24 (td, J=8.5, 2.3 Hz, 1H), 6.04 (s, 1H), 4.59 (d, J=16.0 Hz, 1H), 4.51 (d, J=15.5 Hz, 1H), 4.27 (s, 1H), 4.13-3.99 (m, 2H), 3.78-3.62 (m, 2H), 3.58 (s, 4H), 3.53-3.39 (m, 1H), 3.18 (s, 2H).

Example 117: 3'-((S)-7-(((R)-6-(2-chloro-4-fluorophenyl)-5-(methoxycarbonyl)-2-(thiazol-2-yl)-3,6-dihydroprimidin-4-yl)methyl)-3-oxohexahydroimidazo[1,5-a]pyrazin-2(3H)-yl)-5'-fluoro-[1,1'-biphenyl]-4-carboxylic acid The title compound as a yellow solid (120 mg, 53%) was prepared by the method according to example 35 by the replacement of 4-bromo-5-fluorophenylboronic acid with 3-bromo-2-fluorophenylboronic acid (500 mg, 2.29 mmol) in step 1 of example 35. MS (ESI, pos. ion) m/z: 719.0 [M+H]⁺; ¹H NMR (400 MHz, DMSO-d₆) δ 9.72 (s, 1H), 8.09-7.98 (m, 3H), 7.96-7.92 (m, 1H), 7.80 (d, J=8.1 Hz, 2H), 7.68-7.57 (m, 2H), 7.46-7.36 (m, 2H), 7.24-7.12 (m, 2H), 6.06 (s, 1H), 4.07-3.95 (m, 3H), 3.93-3.84 (m, 2H), 3.64-3.60 (m, 1H), 3.52 (s, 3H), 3.13-3.06 (m, 1H), 2.95 (d, J=10.5 Hz, 2H), 2.33 (t, J=10.1 Hz, 1H), 2.19 (t, J=10.8 Hz, 1H).

Example 118: 3'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2,5'-difluoro-[1,1'-biphenyl]-4-carboxylic acid The title compound as a yellow solid (200 mg, 68%) was prepared by the method according to example 33 by the replacement of 4-bromo-2-fluorophenylboronic acid with 3-bromo-5-fluorophenylboronic acid (375 mg, 1.71 mmol) in step 1 of example 33. MS (ESI, pos. ion) m/z: 737.3 [M+H]⁺; ¹H NMR (400 MHz, DMSO-d₆) δ 10.39 (s, 1H), 8.06 (t, J=3.2 Hz, 2H), 7.87 (dd, J=7.78 (d, J=11.8 Hz, 1H), 7.74-7.63 (m, 2H), 7.53 (dd, J=15.0, 7.0 Hz, 2H), 7.44 (dd, J=8.8, 2.3 Hz, 1H), 7.21 (td, J=8.5, 2.4 Hz, 1H), 7.12 (d, J=9.2 Hz, 1H), 6.03 (s, 1H), 4.57-4.18 (m, 4H), 4.07 (t, J=9.2 Hz, 1H), 4.01-3.93 (m, 1H), 3.70 (d, J=7.0 Hz, 1H), 3.56 (s, 3H), 3.53-3.38 (m, 2H), 3.16-2.76 (m, 2H).

Example 119: 3'-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-3,5'-difluoro-[1,1'-biphenyl]-4-carboxylic acid The title compound as a yellow solid (130 mg, 55%) was prepared by the method according to example 34 by the replacement of 4-bromo-2-fluorophenylboronic acid with 3-bromo-5-fluorophenylboronic acid (343 mg, 1.57 mmol) in step 1 of example 34. MS (ESI, pos. ion) m/z: 737.0 [M+H]⁺; ¹H NMR (400 MHz, DMSO-d₆) δ 8.11-8.01 (m, 2H), 7.95 (t, J=8.0 Hz, 1H), 7.78-7.61 (m, 3H), 7.57 (s, 1H), 7.51-7.47 (m, 1H), 7.44 (dd, J=8.8, 2.3 Hz, 1H), 7.31 (d, J=9.4 Hz, 1H), 7.22 (td, J=8.4, 2.3 Hz, 1H), 6.04 (s, 1H), 4.49-4.29 (m, 2H), 4.24-4.02 (m, 3H), 4.01-3.94 (m, 1H), 3.75 (d, J=6.7 Hz, 2H), 3.56 (s, 3H), 3.45-3.35 (m, 2H), 2.94 (s, 2H).

Example 120: 4'-((S)-7-(((R)-6-(2-chloro-4-fluorophenyl)-5-(methoxycarbonyl)-2-(thiazol-2-yl)-3,6-dihydropyrimidin-4-yl)-3-oxohexahydroimidazo[1,5-a]pyrazin-2(3H)-yl)-2,3'-difluoro-[1,1'-biphenyl]-4-carboxylic acid The title compound as a yellow solid (70 mg, 16.5%) was prepared by the method according to example 33 by the replacement of 4-bromo-2-fluorophenylboronic acid with 4-fluoro-3-fluorophenylboronic acid (0.50 g, 2.28 mmol) in step 1 of example 33. MS (ESI, pos. ion) m/z: 737.3 [M+H]⁺; ¹H NMR (400 MHz, MeOH-d₄) δ 7.99 (d, J=3.1 Hz, 1H), 7.93 (d, J=7.8 Hz, 1H), 7.82 (d, J=11.3 Hz, 1H), 7.77 (d, J=3.1 Hz, 1H), 7.67-7.61 (m, 2H), 7.53-7.42 (m, 3H), 7.25 (dd, J=8.7, 2.5 Hz, 1H), 7.07 (td, J=8.4, 2.5 Hz, 1H), 6.19 (s, 1H), 4.19 (d, J=16.9 Hz, 1H), 4.14-4.08 (m, 1H), 4.03-3.97 (m, 3H), 3.66 (d, J=2.3 Hz, 1H), 3.65-3.60 (m, 4H), 3.03 (d, J=10.7 Hz, 2H), 2.52 (td, J=12.1, 3.3 Hz, 1H), 2.41 (t, J=10.9 Hz, 1H).

Example 121: 4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-3,3'-difluoro-[1,1'-biphenyl]-4-carboxylic acid The title compound as a yellow solid (101 mg, 29%) was prepared by the method according to example 34 by the replacement of 4-bromo-2-fluorophenylboronic acid with 4-fluoro-3-fluorophenylboronic acid (0.50 g 2.28 mmol) in step 1 of example 34. MS (ESI, pos. ion) m/z: 737.3 [M+H]⁺; ¹H NMR (400 MHz, DMSO-d₆) δ 13.26 (s, 1H), 9.72 (s, 1H), 8.05 (d, J=3.1 Hz, 1H), 7.94 (m, 2H), 7.79-7.65 (m, 5H), 7.45-7.40 (m, 2H), 7.19 (td, J=8.5, 2.5 Hz, 1H), 6.06 (s, 1H), 4.08-4.03 (m, 1H), 3.97-3.82 (m, 4H), 3.57-3.52 (m, 1H), 3.53 (s, 3H), 3.16-3.04 (m, 1H), 3.00-2.91 (m, 2H), 2.33 (td, J=11.5, 2.7 Hz, 1H), 2.24 (t, J=10.7 Hz, 1H).

Example 122: 4-(5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-2-yl)benzoic acid Step 1: methyl 4-(5-bromopyridin-2-yl)benzoate

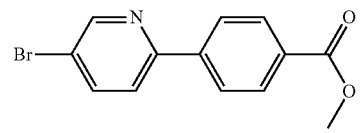

To a 50 mL two neck flask were added 2,5-dibromopyridine (500 mg, 2.11 mmol), (4-methoxycarbonylphenyl)boronic acid (380 mg, 2.11 mmol), Pd[P(Ph₃)]₄ (123 mg, 0.11 mmol), cesium carbonate (1.03 g 3.16 mmol) and dioxane (15 mL), the mixture was stirred at 90° C. for 6 h. The mixture was cooled to rt and filtered by suction, the filter cake was washed with EtOAc (20 mL). The filtrate was washed with saturated aqueous NaCl solution (15 mL×2) and concentrated in vacuo. The residue was purified by silica gel column chromatography (PE/EtOAc (V/V)=20/1) to give the title compound as a white solid (241 mg, 39.1%). MS (ESI, pos. ion) m/z: 292.0 [M+H]⁺.

Step 2: (R)-tert-butyl 2-(6-(4-(methoxycarbonyl)phenyl)pyridin-3-yl)-3-oxohexahydroimidazo [1,5-a]pyrazin-7(1H)-carboxylate

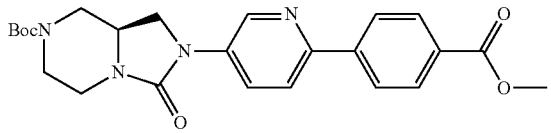 [SMILES: COC(=O)c1ccc(-c2ccc(N3C[C@@H]4CN(C(=O)OC(C)(C)C)CCN4C3=O)cn2)cc1]

To a two-neck flask were added methyl 4-(5-bromopyridin-2-yl)benzoate (207 mg, 0.71 mmol), (R)-tert-butyl 3-oxohexahydroimidazo[1,5-a]pyrazine-7(1H)-carboxylate (171 mg, 0.71 mmol), tris(dibenzylideneacetone)dipalladium (39 mg, 0.04 mmol), Xantphos (41 mg, 0.07 mmol), cesium carbonate (462 mg, 1.42 mmol) and dioxane (15 mL). The mixture was stirred at 90° C. under $N_2$ for 2 hours. The mixture was cooled to rt and filtered by suction. The filter cake was washed with EtOAc (15 mL). The filtrate was washed with saturated aqueous NaCl solution (15 mL×3) and concentrated in vacuo. The residue was purified by silica gel column chromatography (PE/EtOAc (V/V)=1/1) to give the title compound as a yellow solid (209 mg, 65.2%). MS (ESI, pos. ion) m/z: 453.3 [M+H]$^+$.

NaCl and dried over anhydrous sodium sulfate. The mixture was filtered and the filtrate was concentrated in vacuo to give the title compound as a yellow solid (192 mg, 96.2%). MS (ESI, pos. ion) m/z: 438.1 [M+H]$^+$.

Step 4: (S)-4-(5-(3-oxohexahydroimidazo[1,5-a]pyrazin-2(3H)-yl)pyridin-2-yl)benzoic acid trifluoroacetate

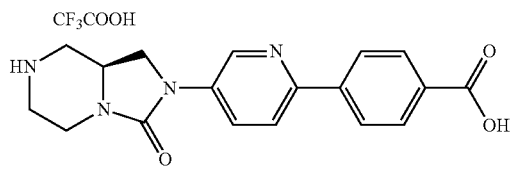 [SMILES: "CF3COOH" ; O=C(O)c1ccc(-c2ccc(N3C[C@@H]4CNCCN4C3=O)cn2)cc1]

To a 50 mL single neck flask were added (R)-4-(5-(7-(tert-butoxycarbonyl)-3-oxohexahydroimidazo[1,5-a]pyrazin-2(3H)-yl)pyridin-2-yl)benzoic acid (192 mg, 0.44 mmol), DCM (3 mL) and TFA (3 mL), the mixture was stirred at rt for 1 hours. The reaction mixture was concentrated in vacuo to get the title compound as yellow oil (198 mg, 99.9%). MS (ESI, pos. ion) m/z: 339.0[M+H]$^+$.

Step 5: 4-(5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-2-yl) benzoic acid

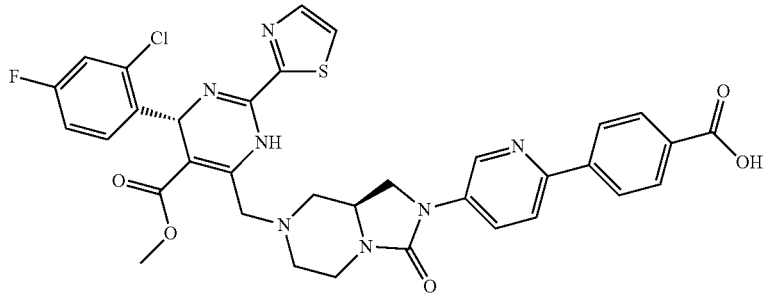 [SMILES: COC(=O)C1=C(CN2CCN3C(=O)N(c4ccc(-c5ccc(C(=O)O)cc5)nc4)C[C@@H]3C2)NC(c2nccs2)=N[C@H]1c1ccc(F)cc1Cl]

Step 3: (R)-4-(5-(7-(tert-butoxycarbonyl)-3-oxohexahydroimidazo[1,5-a]pyrazin-2(3H)-yl) pyridin-2-yl)benzoic acid

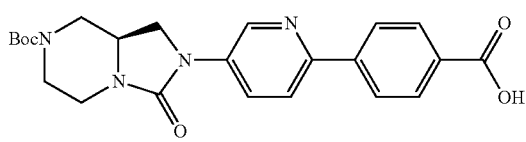

To a 50 mL single neck flask were added (R)-tert-butyl 2-(6-(4-(methoxycarbonyl)phenyl)pyridin-3-yl)-3-oxohexahydroimidazo[1,5-a]pyrazin-7(1H)-carboxylate (206 mg, 0.46 mmol), THF (5 mL), methanol (2 mL), water (3 mL) and lithium hydroxide monohydrate (96 mg, 2.29 mmol). The mixture was stirred at rt for 11 hours. The mixture was adjusted with hydrochloric acid (6 M) to pH 6 to 7, the most MeOH and THF were removed. The residue was diluted with water (10 mL) and EtOAc (20 mL), the resulting mixture was adjusted with hydrochloric acid (6 M) to pH 3 to 4, the organic layer was washed with saturated aqueous To a 50 mL single neck flask were added (S)-4-(5-(3-oxohexahydroimidazo[1,5-a]pyrazin-2(3H)-yl)pyridin-2-yl) benzoic acid trifluoroacetate (198 mg, 0.59 mmol), (R)-methyl 6-(bromomethyl)-4-(2-chloro-4-fluorophenyl)-2-(thiazol-2-yl)-1,4-dihydropyrimidine-5-carboxylate (247 mg, 0.56 mmol), potassium carbonate (155 mg, 1.11 mmol) and ethanol (15 mL). The mixture was stirred at rt for 16 hours. The mixture was filtered by suction. The filter cake was washed with EtOH (5 mL), the filtrate was concentrated in vacuo. The residue was diluted with water (10 mL) and EtOAc (15 mL), and then adjusted with hydrochloric acid (6 M) to pH 2 to 3, the organic layer was washed with saturated aqueous NaCl and dried over anhydrous sodium sulfate, and then filtered and the filtrate was concentrated in vacuo. The residue was purified by silica gel column chromatography ($CH_2Cl_2$/MeOH (V/V)=15/1) to give the title compound as a yellow solid (198 mg, 48.2%). MS (ESI, pos. ion) m/z: 702.4 [M+H]$^+$; $^1$H NMR (400 MHz, DMSO-$d_6$) δ 9.72 (s, 1H), 8.89 (s, 1H), 8.25-7.92 (m, 9H), 7.43 (d, J=7.2 Hz, 2H), 7.19 (s, 1H), 6.06 (s, 1H), 4.05-3.87 (m, 5H), 3.60 (s, 1H), 3.52 (s, 3H), 3.12 (t, J=12.0 Hz, 1H), 2.97 (s, 2H), 2.35 (s, 1H), 2.21 (t, J=10.5 Hz, 1H).

Example 123: 4-(4-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-2-yl)benzoic acid The title compound as a yellow solid (178 mg, 64.8%) was prepared by the method according to example 122 by the replacement of 2,5-dibromopyridine with 2,4-dibromopyridine (735 mg, 3.10 mmol) in step 1 of example 122. MS (ESI, pos. ion) m/z: 702.3 [M+H]$^+$; $^1$H NMR (400 MHz, DMSO-d$_6$) δ 9.71 (s, 1H), 8.52 (d, J=5.2 Hz, 1H), 8.16 (d, J=7.8 Hz, 2H), 8.11-8.02 (m, 5H), 7.96 (s, 1H), 7.64 (d, J=4.3 Hz, 1H), 7.43 (d, J=7.7 Hz, 2H), 7.20 (t, J=7.2 Hz, 1H), 6.06 (s, 1H), 4.08-3.97 (m, 3H), 3.95-3.87 (m, 2H), 3.66-3.61 (m, 1H), 3.52 (s, 3H), 3.12 (t, J=12.0 Hz, 1H), 2.98 (s, 2H), 2.36 (t, J=10.0 Hz, 1H), 2.21 (t, J=10.5 Hz, 1H).

Example 124: 4-(5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-2-yl)-3-fluorobenzoic acid The title compound as a yellow solid (101 mg, 44.8%) was prepared by the method according to example 122 by the replacement of (4-methoxycarbonylphenyl)boronic acid with (2-fluoro-4-(methoxycarbonyl)phenyl)boronic acid (185 mg, 0.93 mmol) in step 1 of example 122. MS (ESI, pos. ion) m/z: 720.1 [M+H]$^+$; $^1$H NMR (400 MHz, DMSO-d$_6$) δ 9.71 (s, 1H), 8.96 (s, 1H), 8.15-8.06 (m, 2H), 8.04 (s, 1H), 7.96 (s, 1H), 7.91-7.81 (m, 2H), 7.76 (d, J=11.6 Hz, 1H), 7.50-7.33 (m, 2H), 7.26-7.11 (m, 1H), 6.06 (s, 1H), 4.05-3.87 (m, 6H), 3.52 (s, 3H), 3.16-3.04 (m, 2H), 3.03-2.92 (m, 2H), 2.40-2.28 (m, 1H), 2.21 (t, J=10.2 Hz, 1H).

Example 125: 2-(4-(5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)pyridin-2-yl)phenyl)-2-methylpropanoic acid The title compound as a yellow solid (95 mg, 60%) was prepared by the method according to example 18 by the replacement of p-bromoiodobenzene with 2,5-dibromopyridine (500 mg, 2.11 mmol) in step 1 of example 18. MS (ESI, pos. ion) m/z: 744.2 [M+H]$^+$; $^1$H NMR (400 MHz, CDCl$_3$) δ 9.58 (s, 1H), 8.53 (d, J=5.9 Hz, 1H), 7.97-7.90 (m, 1H), 7.87 (d, J=3.1 Hz, 1H), 7.81 (d, J=8.3 Hz, 2H), 7.54-7.46 (m, 3H), 7.42 (d, J=4.7 Hz, 1H), 7.33-7.28 (m, 1H), 7.16 (dd, J=8.5, 2.5 Hz, 1H), 6.94 (td, J=8.3, 2.5 Hz, 1H), 6.22 (s, 1H), 4.19-4.01 (m, 3H), 3.99-3.87 (m, 2H), 3.61 (s, 3H), 3.48-3.43 (m, 1H), 3.29 (td, J=13.3, 2.6 Hz, 1H), 2.94 (d, J=9.9 Hz, 2H), 2.52 (td, J=11.2, 2.7 Hz, 1H), 2.26 (t, J=10.7 Hz, 1H), 1.64 (s, 6H).

Example 126: 3-(4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-[1,1'-biphenyl]-4-yl)propanoic acid Step 1: (R)-tert-butyl 2-(4'-(3-ethoxy-3-oxopropyl)-[1,1'-biphenyl]-4-yl)-3-oxohexahydro imidazo[1,5-a]pyrazin-7(1H)-carboxylate

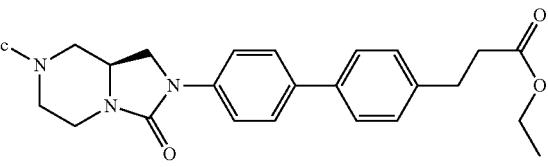

To a dry flask were added (R)-tert-butyl 2-(4-bromophenyl)-3-oxohexahydroimidazo [1,5-a]pyrazin-7(1H)-carboxylate (724 mg, 1.83 mmol), (4-(3-ethoxy-3-oxopropyl)phenyl) boronic acid (486 mg, 2.19 mmol), potassium carbonate (505 mg, 3.65 mmol), (dppf)$_2$PdCl$_2$ (135 mg, 0.18 mmol) and toluene (25 mL), the mixture was stirred at 100° C. under N$_2$ for 16 h. The stirrer was stopped, the mixture was cooled to rt and filtered by suction and the filtrate was concentrated in vacuo. The residue was purified by silica gel column chromatography (PE/EtOAc (V/V)=3/1) to give the title compound as a brown solid (329 mg, 36.5%). MS (ESI, pos. ion) m/z: 438.4[M+H−56]$^+$.

Step 2: (R)-3-(4'-(7-(tert-butoxycarbonyl)-3-oxohexahydroimidazo[1,5-a]pyrazin-2(3H)-yl)-[1,1'-biphenyl]-4-yl)propanoic acid

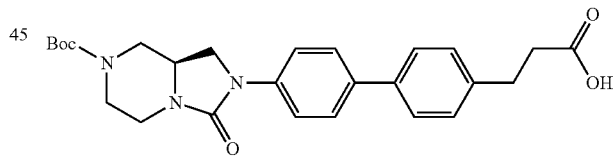

To a dry flask were added (R)-tert-butyl 2-(4'-(3-ethoxy-3-oxopropyl)-[1,1'-biphenyl]-4-yl)-3-oxohexahydroimidazo [1,5-a]pyrazine-7(1H)-carboxylate (444 mg, 0.90 mmol), methanol (12 mL), tetrahydrofuran (24 mL), lithium hydroxide monohydrate (190 mg, 4.50 mmol) and water (4 mL) in turn, the mixture was stirred for 12 hours till the reaction complete and concentrated in vacuo, the residue was diluted with water (20 mL) and EtOAc (30 mL), and adjusted with hydrochloric acid (1 M) to pH 4, the mixture was partitioned, the water phase was extracted with EtOAc (20 mL) once, the organic layers were combined. The combined organic layers were washed with saturated aqueous NaCl and dried over anhydrous Na$_2$SO$_4$, and then filtered, the filtrate was concentrated in vacuo to get the title compound as an off-white solid (395 mg, 94.3%). MS (ESI, pos. ion) m/z: 410.3 [M+H−56]$^+$.

Step 3: (S)-3-(4'-(3-oxohexahydroimidazo[1,5-a]pyrazin-2(3H)-yl)-[1,1'-biphenyl]-4-yl) propanoic acid trifluoroacetate

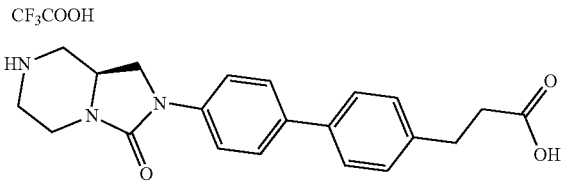 [SMILES: "CF3COOH" ; O=C(O)CCc1ccc(-c2ccc(N3C[C@@H]4CNCCN4C3=O)cc2)cc1]

To a dry flask were added (R)-3-(4'-(7-(tert-butoxycarbonyl)-3-oxohexahydroimidazo [1,5-a]pyrazin-2(3H)-yl)-[1,1'-biphenyl]-4-yl)propanoic acid (395 mg, 0.85 mmol), DCM (15 mL) and trifluoroacetic acid (20 ml) in turn, the mixture was stirred at rt for 6 hours and concentrated in vacuo to get the title compound as dark brown oil (406 mg, 99.8%).

Step 4: 3-(4'-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-[1,1'-biphenyl]-4-yl)propanoic acid

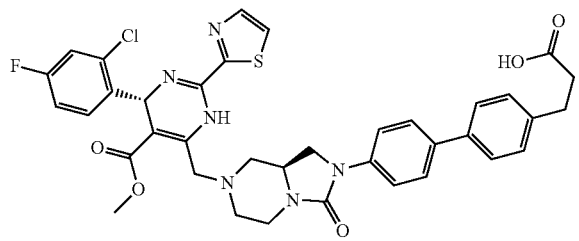 [SMILES: COC(=O)C1=C(CN2CCN3C(=O)N(c4ccc(-c5ccc(CCC(=O)O)cc5)cc4)C[C@@H]3C2)NC(c2nccs2)=N[C@H]1c1ccc(F)cc1Cl]

To a dry flask were added (S)-3-(4'-(3-oxohexahydroimidazo[1,5-a]pyrazin-2(3H)-yl)-[1,1'-diphenyl]-4-yl)propanoic acid trifluoroacetate (406 mg, 0.85 mmol), 1,2-dichloroethane (15 mL), N,N-diisopropylethylamine (330 mg, 2.55 mmol) and (R)-methyl 6-(bromomethyl)-4-(2-chloro-4-fluorophenyl)-(2-thiazol-2-yl)-1,4-dihydropyrimidine-5-carboxy late (414 mg, 0.93 mmol), the reaction mixture was stirred at rt for 12 hours. The stirrer was stopped, the mixture was concentrated by rotary evaporation. The residue was purified by silica gel column chromatography (DCM/MeOH (V/V)=18/1) to give the title compound as a yellow solid (103 mg, 16.9%). MS (ESI, pos. ion) m/z: 729.1 [M+H]$^+$; $^1$H NMR (400 MHz, CDCl$_3$) δ 7.88 (d, J=3.1 Hz, 1H), 7.61 (d, J=8.8 Hz, 2H), 7.57 (d, J=8.8 Hz, 2H), 7.52 (d, J=8.0 Hz, 2H), 7.48 (d, J=3.1 Hz, 1H), 7.37-7.25 (m, 3H), 7.16 (dd, J=8.5, 2.5 Hz, 1H), 6.95 (td, J=8.4, 2.5 Hz, 1H), 6.24 (s, 1H), 4.12 (t, J=17.3 Hz, 2H), 4.06-3.98 (m, 1H), 3.98-3.87 (m, 2H), 3.62 (s, 3H), 3.48-3.45 (m, 1H), 3.28 (t, J=11.1 Hz, 1H), 3.01 (t, J=7.6 Hz, 2H), 2.91 (d, J=9.6 Hz, 2H), 2.73 (t, J=7.7 Hz, 2H), 2.53 (td, J=11.9, 3.1 Hz, 1H), 2.29 (t, J=10.6 Hz, 1H).

Example 127: 2-(4'-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)-[1,1'-biphenyl]-4-yl)-2-methylpropanoic acid The title compound as a yellow solid (210 mg, 64%) was prepared by the method according to example 18 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxy late (224 mg, 0.45 mmol) of example 18. MS (ESI, pos. ion) m/z: 801.1 [M+H]$^+$; $^1$H NMR (400 MHz, CDCl$_3$) δ 9.62 (s, 1H), 7.88 (d, J=3.1 Hz, 1H), 7.63-7.54 (m, 6H), 7.50-7.44 (m, 3H), 7.37-7.29 (m, 2H), 7.00 (td, J=8.3, 2.5 Hz, 1H), 6.23 (s, 1H), 4.16 (d, J=17.2 Hz, 1H), 4.12-3.98 (m, 4H), 3.98-3.88 (m, 2H), 3.49-3.45 (m, 1H), 3.33-3.22 (m, 1H), 2.91 (d, J=9.6 Hz, 2H), 2.58-2.46 (m, 1H), 2.29 (t, J=10.5 Hz, 1H), 1.65 (s, 6H), 1.15 (t, J=7.1 Hz, 3H).

Example 128: 2-(4'-((S)-7-(((R)-6-(2,4-dichlorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-[1,1'-biphenyl]-4-yl)-2-methylpropanoic acid The title compound as a yellow solid (105 mg, 34%) was prepared by the method according to example 18 by the replacement of (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2,4-dichlorophenyl)-2-(thiazol-2-yl)-1,4-dihydropyrimidine-5-carboxylate (204 mg, 0.45 mmol) of example 18. MS (ESI, pos. ion) m/z: 759.3 [M+H]$^+$; $^1$H NMR (400 MHz, CDCl$_3$) δ 9.66 (s, 1H), 7.88 (d, J=3.0 Hz, 1H), 7.63-7.53 (m, 6H), 7.51-7.45 (m, 3H), 7.43 (d, J=1.9 Hz, 1H), 7.27 (d, J=9.6 Hz, 2H), 7.20 (dd, J=8.3, 1.9 Hz, 1H), 6.23 (s, 1H), 4.12 (t, J=15.6 Hz, 2H), 4.05-3.98 (m, 1H), 3.97-3.87 (m, 2H), 3.62 (s, 3H), 3.48-3.45 (m, 1H), 3.33-3.23 (m, 1H), 2.90 (d, J=10.0 Hz, 2H), 2.57-2.46 (m, 1H), 2.29 (t, J=10.7 Hz, 1H), 1.65 (s, 6H).

Example 129: 4'-((S)-7-(((R)-6-(2-bromo-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)-2,2'-difluoro-[1,1'-biphenyl]-4-carboxylic acid The title compound as a yellow solid (48 mg, 21.4%) was prepared by the method according to example 33 by the replacement of (R)-methyl 6-(bromomethyl)-4-(2-chloro-4-fluorophenyl)-2-(thiazol-2-yl)-1,4-dihydropyrimidine-5-carboxylate with (R)-methyl 4-(2-bromo-4-fluorophenyl)-6-(bromomethyl)-2-(thiazol-2-yl)-1,4-dihydro pyrimidine-5-carboxylate (156 mg, 0.29 mmol) of example 33. MS (ESI, pos. ion) m/z: 781.1 [M+H]$^+$; $^1$H NMR (400 MHz, CDCl$_3$) δ 9.65 (s, 1H), 7.95 (s, 1H), 7.87 (s, 2H), 7.59 (d, J=12.2 Hz, 1H), 7.49 (s, 2H), 7.42-7.30 (m, 4H), 6.99 (s, 1H), 6.22 (s, 1H), 4.26-4.02 (m, 3H), 3.94 (d, J=15.9 Hz, 2H), 3.63 (s, 3H), 3.47 (s, 1H), 3.31 (t, J=12.1 Hz, 1H), 3.00-2.88 (m, 2H), 2.55 (t, J=9.8 Hz, 1H), 2.37-2.21 (m, 1H).

Example 130: 4'-((S)-7-(((R)-6-(2,4-dichlorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)-2,2'-difluoro-[1,1'-biphenyl]-4-carboxylic acid The title compound as a yellow solid (54 mg, 16.4%) was prepared by the method according to example 33 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 6-(bromomethyl)-4-(2,4-dichlorophenyl)-2-(thiazol-2-yl)-1,4-dihydropyrimidine-5-carboxylate (204 mg, 0.43 mmol) of example 33. MS (ESI, pos. ion) m/z: 767.1 [M+H]$^+$; $^1$H NMR (400 MHz, CDCl$_3$) δ 9.62 (s, 1H), 7.96 (d, J=7.4 Hz, 1H), 7.89 (d, J=8.8 Hz, 2H), 7.59 (d, J=12.4 Hz, 1H), 7.55-7.47 (m, 2H), 7.43 (s, 1H), 7.38 (s, 2H), 7.31 (s, 1H), 7.21 (d, J=7.9 Hz, 1H), 6.26 (s, 1H), 4.18 (d, J=16.8 Hz, 1H), 4.14-4.03 (m, 4H), 4.00-3.91 (m, 2H), 3.48 (s, 1H), 3.31 (t, J=11.3 Hz, 1H), 3.01-2.91 (m, 2H), 2.56 (t, J=9.5 Hz, 1H), 2.30 (t, J=10.0 Hz, 1H), 1.16 (t, J=6.6 Hz, 3H).

Example 131: 3-((R)-4-(3-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)5-fluorophenyl)morpholin-2-yl)propanoic acid The title compound as a yellow solid (93 mg, 35.2%) was prepared by the method according to example 20 by the replacement of p-bromoiodobenzene with 1-bromo-3-fluoro-5-iodobenzene (2 g, 6.65 mmol) in step 1 of example 20. MS (ESI, pos. ion) m/z: 378.6 [M/2+H]+; $^1$H NMR (400 MHz, CDCl$_3$) δ 7.87 (d, J=3.0 Hz, 1H), 7.48 (d, J=3.0 Hz, 1H), 7.35-7.29 (m, 1H), 7.24 (s, 1H), 7.16 (dd, J=8.5, 2.4 Hz, 1H), 6.94 (td, J=8.3, 2.4 Hz, 1H), 6.57 (d, J=10.8 Hz, 1H), 6.31 (d, J=11.7 Hz, 1H), 6.23 (s, 1H), 4.14 (d, J=17.2 Hz, 1H), 4.06 (d, J=14.7 Hz, 1H), 4.01 (d, J=9.4 Hz, 2H), 3.94-3.81 (m, 2H), 3.74 (td, J=11.3, 1.8 Hz, 1H), 3.62 (s, 4H), 3.49 (d, J=11.4 Hz, 1H), 3.45-3.37 (m, 2H), 3.27 (td, J=12.8, 3.2 Hz, 1H), 2.94-2.80 (m, 3H), 2.65-2.42 (m, 4H), 2.26 (t, J=10.6 Hz, 1H), 1.99-1.72 (m, 2H).

Example 132: 1-(4-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)phenyl) piperidine-4-carboxylic acid The title compound as a yellow solid (168 mg, 67%) was prepared by the method according to example 21 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxylate (181 mg, 0.36 mmol) of example 21. MS (ESI, pos. ion) m/z: 766.1 [M+H]$^+$; $^1$H NMR (400 MHz, CDCl$_3$) δ 9.62 (s, 1H), 7.87 (d, J=3.1 Hz, 1H), 7.47 (d, J=3.1 Hz, 1H), 7.42 (d, J=9.0 Hz, 2H), 7.36-7.29 (m, 2H), 7.02-6.93 (m, 3H), 6.22 (s, 1H), 4.18-4.10 (m, 1H), 4.09-4.01 (m, 3H), 4.00-3.94 (m, 1H), 3.92 (d, J=8.0 Hz, 1H), 3.88 (d, J=8.6 Hz, 1H), 3.58 (d, J=12.2 Hz, 2H), 3.43-3.39 (m, 1H), 3.30-3.22 (m, 1H), 2.87 (t, J=7.3 Hz, 2H), 2.82-2.72 (m, 4H), 2.57-2.42 (m, 2H), 2.28 (t, J=10.8 Hz, 1H), 2.11-2.02 (m, 2H), 1.99-1.85 (m, 2H), 1.15 (t, J=7.1 Hz, 3H).

Example 133: 1-(3-chloro-5-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl)piperidine-4-carboxylic acid The title compound as a yellow solid (150 mg, 40%) was prepared by the method according to example 32 by the replacement of 1-bromo-3-fluoro-5-iodobenzene with 1-bromo-3-chloro-5-iodobenzene (2.9 g, 9.1 mmol) in step 1 of example 32. MS (ESI, pos. ion) m/z: 742.1 [M+H]$^+$; $^1$H NMR (400 MHz, CDCl$_3$) δ 9.63 (s, 1H), 7.87 (d, J=2.7 Hz, 1H), 7.50-7.40 (m, 2H), 7.31 (d, J=8.5 Hz, 1H), 7.15 (dd, J=8.3, 1.7 Hz, 1H), 6.96-6.92 (m, 1H), 6.73 (s, 1H), 6.61 (s, 1H), 6.22 (s, 1H), 4.17-3.98 (m, 3H), 3.95-3.86 (m, 2H), 3.67 (d, J=11.8 Hz, 2H), 3.61 (s, 3H), 3.42-3.39 (m, 1H), 3.27 (t, J=11.2 Hz, 1H), 2.93-2.82 (m, 4H), 2.51 (t, J=10.4 Hz, 2H), 2.26 (t, J=10.3 Hz, 1H), 2.04 (m, 2H), 1.86 (m, 2H).

Example 134: 2-(4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl) acetic acid The title compound as a yellow solid (0.2 g, 60%) was prepared by the method according to example 15 by the replacement of (4-methoxycarbonylphenyl)boronic acid with (4-(2-methoxy-2-oxoethyl)phenyl)boronic acid in step 1 of example 15. MS (ESI, pos. ion) m/z: 722.3 [M+H]$^+$; $^1$H NMR (400 MHz, CDCl$_3$) δ 7.88 (d, J=2.5 Hz, 1H), 7.82 (d, J=7.6 Hz, 2H), 7.49 (d, J=2.5 Hz, 1H), 7.32 (d, J=7.3 Hz, 3H), 7.16 (d, J=6.8 Hz, 1H), 7.08 (s, 1H), 6.94 (t, J=7.1 Hz, 1H), 6.23 (s, 1H), 4.29 (t, J=9.8 Hz, 1H), 4.12 (t, J=17.9 Hz, 3H), 3.92 (d, J=17.2 Hz, 1H), 3.85-3.81 (m, 1H), 3.68 (s, 2H), 3.62 (s, 3H), 3.33 (t, J=11.1 Hz, 1H), 2.95 (s, 2H), 2.52 (t, J=10.2 Hz, 1H), 2.30 (t, J=10.8 Hz, 1H).

Example 135: 3-(4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl) propanoic acid The title compound as a yellow solid (280 mg, 37%) was prepared by the method according to example 15 by the replacement of (4-methoxycarbonylphenyl)boronic acid with (4-(3-ethoxy-3-oxopropyl)phenyl)boronic acid (0.22 g 0.99 mmol) in step 1 of example 15. MS (ESI, pos. ion) m/z: 736.0 [M+H]$^+$; $^1$H NMR (400 MHz, CDCl$_3$) δ 7.88 (d, J=3.1 Hz, 1H), 7.77 (d, J=8.1 Hz, 2H), 7.55 (d, J=3.1 Hz, 1H), 7.36-7.32 (m, 1H), 7.28 (s, 1H), 7.24 (s, 1H), 7.16 (dd, J=8.3, 2.5 Hz, 1H), 7.05 (s, 1H), 6.99 (td, J=8.4, 2.5 Hz, 1H), 6.18 (s, 1H), 4.67 (m, 1H), 4.36 (d, J=12.0 Hz, 1H), 4.24 (m, 1H), 4.20-4.08 (m, 2H), 3.85 (dd, J=10.7, 2.9 Hz, 1H), 3.62 (m, 4H), 3.59-3.49 (m, 2H), 2.98 (t, J=7.3 Hz, 2H), 2.94-2.88 (m, 1H), 2.83 (m, 1H), 2.68 (t, J=7.3 Hz, 2H).

Example 136: 4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)-3-fluorobenzoic acid The title compound as a yellow solid (200 mg, 42%) was prepared by the method according to example 15 by the replacement of (4-methoxycarbonylphenyl)boronic acid with (2-fluoro-4-(methoxycarbonyl)phenyl)boronic acid (0.38 g 1.92 mmol) in step 1 of example 15. MS (ESI, pos. ion) m/z: 726.0 [M+H]$^+$; $^1$H NMR (400 MHz, MeOH-d$_4$) δ 7.99-7.92 (m, 2H), 7.80-7.71 (m, 3H), 7.59 (s, 1H), 7.46-7.43 (m, 1H), 7.24 (dd, J=8.7, 2.6 Hz, 1H), 7.07 (td, J=8.4, 2.6 Hz, 1H), 6.19 (s, 1H), 4.35-4.28 (m, 1H), 4.22-4.13 (m, 2H), 4.00 (m, 2H), 3.90-3.86 (m, 1H), 3.61 (s, 3H), 3.34 (s, 1H), 3.08 (m, 2H), 2.52 (td, J=11.8, 3.4 Hz, 1H), 2.32 (t, J=10.9 Hz, 1H).

Example 137: 4-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)-2-fluorobenzoic acid The title compound as a yellow solid (130 mg, 27%) was prepared by the method according to example 15 by the replacement of (4-methoxycarbonylphenyl)boronic acid with (3-fluoro-4-(methoxycarbonyl)phenyl)boronic acid (0.30 g, 1.52 mmol) in step 1 of example 15. MS (ESI, pos. ion) m/z: 726.1 [M+H]$^+$; $^1$H NMR (400 MHz, MeOH-d$_4$) δ 7.99-7.92 (m, 2H), 7.80-7.71 (m, 3H), 7.59 (s, 1H), 7.46-7.43 (m, 1H), 7.24 (dd, J=8.7, 2.6 Hz, 1H), 7.07 (td, J=8.4, 2.6 Hz, 1H), 6.19 (s, 1H), 4.35-4.28 (m, 1H), 4.22-4.13 (m, 2H), 4.00 (m, 2H), 3.90-3.86 (m, 1H), 3.61 (s, 3H), 3.34 (s, 1H), 3.08 (m, 2H), 2.52 (td, J=11.8, 3.4 Hz, 1H), 2.32 (t, J=10.9 Hz, 1H).

Example 138: 3-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)-5-fluorobenzoic acid The title compound as a yellow solid (0.52 g, 71%) was prepared by the method according to example 15 by the replacement of (4-methoxycarbonylphenyl)boronic acid with (3-fluoro-5-(methoxycarbonyl)phenyl)boronic acid (0.30 g, 1.52 mmol) in step 1 of example 15. M (ESI, pos. ion) m/z: 726.3 [M+H]$^+$; $^1$H NMR (400 MHz, MeOH-d$_4$) δ 8.34 (s, 1H), 8.01 (d, J=3.1 Hz, 1H), 7.87 (d, J=3.1 Hz, 1H), 7.87-7.80 (m, 1H), 7.62-7.58 (m, 1H), 7.55-7.46 (m, 2H), 7.28 (dd, J=8.6, 2.5 Hz, 1H), 7.10 (td, J=8.4, 2.5 Hz, 1H), 6.17 (s, 1H), 4.57 (d, J=16.4 Hz, 1H), 4.45-4.28 (m, 3H), 4.22-4.15 (m, 1H), 4.03-3.96 (m, 1H), 3.70-3.64 (m, 1H), 3.63 (s, 3H), 3.59-3.46 (m, 2H), 3.16-2.96 (m, 2H).

Example 139: 3-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)benzoic acid The title compound as a yellow solid (0.28 g 67%) was prepared by the method according to example 15 by the replacement of (4-methoxycarbonylphenyl)boronic acid with (3-(methoxycarbonyl)phenyl)boronic acid (0.30 g 1.52 mmol) in step 1 of example 15. MS (ESI, pos. ion) m/z: 708.3 [M+H]$^+$; $^1$H NMR (400 MHz, CDCl$_3$) δ 9.60 (s, 1H), 8.59 (s, 1H), 8.11 (d, J=7.8 Hz, 1H), 8.05 (d, J=7.8 Hz, 1H), 7.87 (d, J=3.1 Hz, 1H), 7.54-7.49 (m, 2H), 7.35-7.29 (m, 1H), 7.21 (s, 1H), 7.16 (dd, J=8.6, 2.5 Hz, 1H), 6.95 (td, J=8.3, 2.5 Hz, 1H), 6.24 (s, 1H), 4.34 (t, J=9.7 Hz, 1H), 4.20-4.07 (m, 3H), 3.95 (d, J=17.2 Hz, 1H), 3.88 (dd, J=10.7, 4.8 Hz, 1H), 3.62 (s, 3H), 3.40-3.32 (m, 1H), 3.04-2.89 (m, 2H), 2.57-2.50 (m, 2H), 2.33 (t, J=10.8 Hz, 1H).

Example 140 3-(3-(2-((S)-7-(((R)-6-(2-chloro-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl)propanoic acid The title compound as a yellow solid (465 mg, 58.3%) was prepared by the method according to example 15 by the replacement of (4-methoxycarbonylphenyl)boronic acid with (3-(3-methoxy-3-oxopropyl)phenyl)boronic acid (0.42 g 2 mmol) in step 1 of example 15. MS (ESI, pos. ion) m/z: 736.0 [M+H]$^+$; $^1$H NMR (400 MHz, DMSO-d$_6$) δ 12.14 (s, 1H), 9.75 (s, 1H), 8.05 (d, J=2.9 Hz, 1H), 7.98 (s, 1H), 7.77 (s, 1H), 7.71 (d, J=7.8 Hz, 1H), 7.55 (s, 1H), 7.44 (dd, J=8.7, 2.6 Hz, 2H), 7.31 (t, J=7.6 Hz, 1H), 7.24-7.12 (m, 2H), 6.05 (s, 1H), 4.25 (t, J=9.6 Hz, 1H), 4.14-3.96 (m, 2H), 3.94-3.85 (m, 1H), 3.84-3.76 (m, 1H), 3.53 (s, 3H), 3.45-3.30 (m, 2H), 3.26-3.03 (m, 2H), 2.86 (t, J=7.5 Hz, 2H), 2.57 (t, J=7.6 Hz, 2H), 2.52-2.50 (n, 2H).

Example 141: 4-(2-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)benzoic acid The title compound as a yellow solid (97 mg, 27.7%) was prepared by the method according to example 15 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxylate (230 mg, 0.46 mmol) of example 15. MS (ESI, pos. ion) m/z: 766.4 [M+H]$^+$; $^1$H NMR (400 MHz, CDCl$_3$) δ 9.54 (s, 1H), 8.10 (d, J=8.1 Hz, 2H), 7.92 (d, J=8.2 Hz, 2H), 7.85 (d, J=3.0 Hz, 1H), 7.46 (d, J=3.0 Hz, 1H), 7.36-7.25 (m, 2H), 7.23 (s, 1H), 6.97 (td, J=8.3, 2.2 Hz, 1H), 6.21 (s, 1H), 4.27 (t, J=9.7 Hz, 1H), 4.19-3.99 (m, 5H), 3.95 (d, J=17.1 Hz, 1H), 3.82 (dd, J=10.5, 4.7 Hz, 1H), 3.33 (t, J=11.0 Hz, 1H), 3.02-2.88 (m, 2H), 2.51 (t, J=10.1 Hz, 1H), 2.30 (t, J=10.3 Hz, 1H), 1.12 (t, J=7.1 Hz, 3H).

Example 142: 4-(2-((S)-7-(((R)-6-(2,4-dichlorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)benzoic acid The title compound as a yellow solid (212 mg, 37.5%) was prepared by the method according to example 15 by the replacement of (R)-methyl 6-(bromomethyl)-4-(2-chloro-4-fluorophenyl)-2-(thiazol-2-yl)-1,4-dihydropyrimidine-5-carboxylate with (R)-methyl 6-(bromomethyl)-4-(2,4-dichlorophenyl)-2-(thiazol-2-yl)-1,4-dihydropyrimidine-5-carboxylate (360 mg, 0.78 mmol) of example 15. MS (ESI, pos. ion) m/z: 724.1 [M+H]$^+$; $^1$H NMR (400 MHz, CDCl$_3$) δ 9.58 (s, 1H), 8.11 (d, J=8.2 Hz, 2H), 7.93 (d, J=8.3 Hz, 2H), 7.86 (d, J=3.1 Hz, 1H), 7.47 (d, J=3.1 Hz, 1H), 7.41 (d, J=2.0 Hz, 1H), 7.25-7.21 (m, 2H), 7.18 (dd, J=8.3, 2.0 Hz, 1H), 6.21 (s, 1H), 4.28 (t, J=9.8 Hz, 1H), 4.17-4.02 (m, 3H), 3.93 (d, J=17.2 Hz, 1H), 3.82 (dd, J=10.6, 4.9 Hz, 1H), 3.59 (s, 3H), 3.38-3.26 (m, 1H), 3.01-2.87 (m, 2H), 2.57-2.46 (m, 1H), 2.30 (t, J=10.8 Hz, 1H).

Example 143: 2-(4-(2-((S)-7-(((R)-6-(2-chloro-4-fluorophenyl)-5-(ethoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl)-2-methylpropanoic acid The title compound as a yellow solid (65 mg, 21.7%) was prepared by the method according to example 17 by the replacement of (R)-methyl 6-(bromomethyl)-4-(2-chloro-4-fluorophenyl)-2-(thiazol-2-yl)-1,4-dihydropyrimidine-5-carboxy late with (R)-ethyl 6-(bromomethyl)-4-(2-chloro-4-fluorophenyl)-2-(thiazol-2-yl)-1,4-dihydropyrimidine-5- carboxylate (180 mg, 0.39 mmol) of example 17. MS (ESI, pos. ion) m/z: 764.1 [M+H]+; 1H NMR (400 MHz, CDCl3) δ 9.53 (s, 1H), 7.86 (d, J=2.3 Hz, 1H), 7.79 (d, J=8.0 Hz, 2H), 7.46 (d, J=2.4 Hz, 1H), 7.42 (d, J=8.0 Hz, 2H), 7.35-7.26 (m, 1H), 7.13 (d, J=6.6 Hz, 1H), 7.04 (s, 1H), 6.92 (t, J=7.4 Hz, 1H), 6.23 (s, 1H), 4.25 (t, J=9.5 Hz, 1H), 4.17-3.98 (m, 5H), 3.91 (d, J=17.1 Hz, 1H), 3.80 (d, J=6.3 Hz, 1H), 3.30 (t, J=11.3 Hz, 1H), 2.97-2.85 (m, 2H), 2.49 (t, J=9.8 Hz, 1H), 2.26 (t, J=10.7 Hz, 1H), 1.61 (s, 6H), 1.12 (t, J=7.0 Hz, 3H).

Example 144: 2-(4-(2-((S)-7-(((R)-6-(2,4-dichlorophenyl)-5-(ethoxycarbonyl)-2-(thiazol-2-yl)-3,6-dihydropyrimidin-4-yl)-3-oxohexahydroimidazo[1,5-a]pyrazin-2(3H)-yl)thiazol-4-yl)phenyl)-2-methylpropanoic acid The title compound as a yellow solid (125 mg, 31.8%) was prepared by the method according to example 17 by the replacement of (R)-methyl 6-(bromomethyl)-4-(2-chloro-4-fluorophenyl)-2-(thiazol-2-yl)-1,4-dihydropyrimidine5-carboxylate with (R)-ethyl 6-(bromomethyl)-4-(2,4-dichlorophenyl)-2-(thiazol-2-yl)-1,4-dihydropyrimidine-5-carboxylate (239 mg, 0.50 mmol) of example 17. MS (ESI, pos. ion) m/z: 780.1 [M+H]+; 1H NMR (400 MHz, CDCl3) δ 9.55 (s, 1H), 7.85 (s, 1H), 7.79 (d, J=7.9 Hz, 2H), 7.46 (d, J=2.4 Hz, 1H), 7.41 (d, J=7.8 Hz, 3H), 7.29-7.24 (m, 1H), 7.18 (d, J=7.6 Hz, 1H), 7.04 (s, 1H), 6.23 (s, 1H), 4.25 (t, J=9.4 Hz, 1H), 4.18-3.95 (m, 5H), 3.90 (d, J=17.1 Hz, 1H), 3.83-3.74 (m, 1H), 3.29 (t, J=11.4 Hz, 1H), 2.97-2.81 (m, 2H), 2.48 (t, J=9.9 Hz, 1H), 2.25 (t, J=10.5 Hz, 1H), 1.60 (s, 6H), 1.13 (t, J=7.0 Hz, 3H).

Example 145: 3-(4-(2-((S)-7-(((R)-6-(2-bromo-4-fluorophenyl)-5-(ethoxycarbonyl)-2-(thiazol-2-yl)-3,6-dihydropyrimidin-4-yl)methyl)-3-oxohexahydro-imidazo[1,5-a]pyrazin-2(3H)-yl)thiazol-4-yl)phenyl)-2,2-dimethylpropanoic acid The title compound as a yellow solid (189 mg, 50%) was prepared by the method according to example 36 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5-carboxy late (230 mg, 0.46 mmol) of example 36. MS (ESI, pos. ion) m/z: 822.1 [M+H]+; 1H NMR (600 MHz, CDCl3) δ 9.54 (s, 1H), 7.84 (d, J=3.0 Hz, 1H), 7.75 (d, J=8.1 Hz, 2H), 7.45 (d, J=3.0 Hz, 1H), 7.33 (dd, J=8.2, 2.4 Hz, 1H), 7.31-7.26 (m, 1H), 7.19 (d, J=8.1 Hz, 2H), 7.01 (s, 1H), 7.00-6.92 (m, 1H), 6.21 (s, 1H), 4.24 (t, J=9.7 Hz, 1H), 4.11 (d, J=17.1 Hz, 1H), 4.07-3.98 (m, 4H), 3.92 (d, J=17.2 Hz, 1H), 3.78 (dd, J=10.6, 4.9 Hz, 1H), 3.30 (t, J=11.0 Hz, 1H), 2.90 (s, 4H), 2.54-2.45 (m, 1H), 2.24 (t, J=10.9 Hz, 1H), 1.21 (d, J=3.6 Hz, 6H), 1.12 (t, J=7.1 Hz, 3H).

Example 146: 3-(4-(2-((S)-7-(((R)-6-(2,4-dichlorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)thiazol-4-yl)phenyl)-2,2-dimethylpropanoic acid The title compound as a yellow solid (170 mg, 42%) was prepared by the method according to example 36 by the replacement of (R)-methyl 6-(bromomethyl)-4-(2-chloro-4-fluorophenyl)-2-(thiazol-2-yl)-1,4-dihydropyrimidine5-carboxylate with (R)-methyl 6-(bromomethyl)-4-(2,4-dichlorophenyl)-2-(thiazol-2-yl)-1,4-dihydropyrimidine-5-carboxylate (239 mg, 0.52 mmol) of example 36. MS (ESI, pos. ion) m/z: 780.2 [M+H]+; 1H NMR (400 MHz, CDCl3) δ 9.61 (s, 1H), 7.87 (d, J=3.1 Hz, 1H), 7.77 (d, J=8.0 Hz, 2H), 7.49 (d, J=3.1 Hz, 1H), 7.43 (d, J=1.8 Hz, 1H), 7.32-7.27 (m, 1H), 7.24-7.20 (m, 2H), 7.03 (s, 1H), 6.24 (s, 1H), 4.26 (t, J=9.8 Hz, 1H), 4.17-4.01 (m, 3H), 3.92 (d, J=17.2 Hz, 1H), 3.80 (dd, J=10.6, 4.8 Hz, 1H), 3.62 (s, 3H), 3.31 (t, J=11.0 Hz, 1H), 2.98-2.85 (m, 4H), 2.56-2.46 (m, 1H), 2.26 (t, J=10.8 Hz, 1H), 1.23 (d, J=2.8 Hz, 6H).

Example 147: 1-(4-((S)-7-(((R)-6-(2-bromo-4-fluorophenyl)-5-(methoxycarbonyl)-2-(thiazol-2-yl)-3,6-dihydropyrimidin-4-yl)methyl)-3-oxohexahydroimidazo[1,5-a]pyrazin-2(3H)-yl)phenyl) cyclopentane carboxylic acid The title compound as a yellow solid (250 mg, 33%) was prepared by the method according to example 29 by the replacement of (R)-methyl 6-(bromomethyl)-4-(2-chloro-4-fluorophenyl)-2-(thiazol-2-yl)-1,4-dihydropyrimidine-5-carboxy late with (R)-methyl 4-(2-bromo-4-fluorophenyl)-6-(bromomethyl)-2-(thiazol-2-yl)-1,4-dihydropyrimidine-5-carboxylate (0.51 g, 1.0 mmol) of example 29. MS (ESI, pos. ion) m/z: 737.3 [M+H]+; 1H NMR (400 MHz, CDCl3) δ 9.64 (s, 1H), 7.86 (d, J=3.0 Hz, 1H), 7.49 (d, J=8.1 Hz, 3H), 7.39-7.32 (m, 3H), 7.28 (s, 1H), 6.98 (td, J=8.4, 2.4 Hz, 1H), 6.20 (s, 1H), 4.10 (d, J=4.0 Hz, 1H), 4.05 (d, J=12.9 Hz, 1H), 3.98 (s, 1H), 3.93-3.85 (m, 2H), 3.61 (s, 3H), 3.42-3.39 (m, 1H), 3.24 (t, J=11.3 Hz, 1H), 2.89-2.82 (m, 2H), 2.68-2.60 (m, 2H), 2.49 (m, 1H), 2.24 (t, J=10.6 Hz, 1H), 1.95-1.86 (m, 2H), 1.74 (m, 4H).

Example 148: 1-(4-((S)-7-(((R)-6-(2,4-dichlorophenyl)-5-(ethoxycarbonyl)-2-(thiazol-2-yl)-3,6-dihydropyrimidin-4-yl)methyl)methyl)-3-oxohexahydroimidazo[1,5-a]pyrazin-2(3H)-yl)phenyl) cyclopentane carboxylic acid The title compound as a yellow solid (250 mg, 34%) was prepared by the method according to example 29 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2,4-dichlorophenyl)-6-(bromomethyl)-2-(thiazol-2-yl)-1,4-dihydropyrimidine-5-carboxylate (0.48 g 1.0 mmol) of example 29. MS (ESI, pos. ion) m/z: 723.1 [M+H]+; 1H NMR (400 MHz, CDCl3) δ 9.62 (s, 1H), 7.87 (d, J=3.1 Hz, 1H), 7.52-7.48 (m, 3H), 7.43-7.37 (m, 3H), 7.29 (s, 1H), 7.27 (s, 1H), 7.20 (dd, J=8.4, 2.0 Hz, 1H), 6.24 (s, 1H), 4.12-4.04 (m, 3H), 4.04-3.96 (m, 2H), 3.95-3.87 (m, 2H), 3.44-3.41 (m, 1H), 3.25 (d, J=9.9 Hz, 1H), 2.88 (d, J=10.6 Hz, 2H), 2.65 (d, J=11.9 Hz, 2H), 2.54-2.53-2.47 (m, 1H), 2.24 (t, J=10.8 Hz, 1H), 1.95-1.93 (m, 2H), 1.80-1.70 (m, 4H), 1.15 (t, J=7.1 Hz, 3H).

Example 149: (R)-ethyl 4-(2-bromo-4-fluorophenyl)-6-(((S)-2-(4-(1-cyanocyclopropyl) phenyl)-3-oxohexahydroimidazo[1,5-a]pyrazin-7(1H)-yl) methyl)-2-(thiazol-2-yl)-1,4-dihydropyrimidine-5-carboxylate The title compound as a yellow solid (165 mg, 60.10%) was prepared by the method according to example 26 by the replacement of (R)-methyl 6-(bromomethyl)-4-(2-chloro-4-fluorophenyl)-2-(thiazol-2-yl)-1,4-dihydropyrimidine-5-carboxylate with (R)-ethyl 4-(2-bromo-4-fluorophenyl)-6-(bromomethyl)-2-(thiazol-2-yl)-1,4-dihydropyrimidine-5- carboxylate (205 mg, 0.41 mmol) of example 26. MS (ESI, pos. ion) m/z: 704.3 [M+H]$^+$; 1H NMR (600 MHz, CDCl$_3$) δ 9.56 (s, 1H), 7.84 (d, J=3.1 Hz, 1H), 7.53 (d, J=8.8 Hz, 2H), 7.45 (d, J=3.1 Hz, 1H), 7.32 (dd, J=8.3, 2.5 Hz, 1H), 7.30-7.27 (m, 1H), 7.27 (s, 1H), 7.25 (s, 1H), 7.00-6.93 (m, 1H), 4.13 (d, J=17.3 Hz, 1H), 4.04-3.97 (m, 3H), 3.93-3.85 (m, 2H), 3.42-3.40 (m, 1H), 3.29-3.19 (m, 1H), 2.91-2.84 (m, 2H), 2.54-2.45 (m, 1H), 2.24 (t, J=10.9 Hz, 1H), 1.69-1.67 (m, 3H), 1.36-1.34 (m, 2H), 1.12 (t, J=7.1 Hz, 3H).

Example 150: (R)-methyl 6-(((S)-2-(4-(1-cyanocyclopropyl)phenyl)-3-oxohexahydroimidazo[1,5-a]pyrazin-7(1H)-yl)methyl)-4-(2,4-dichlorophenyl)-2-(thiazol-2-yl)-1,4-dihydropyrimidine-5-carboxylate The title compound as a yellow solid (463 mg, 70%) was prepared by the method according to example 26 by the replacement of (R)-methyl 6-(bromomethyl)-4-(2-chloro-4-fluorophenyl)-2-(thiazol-2-yl)-1,4-dihydropyrimidine5-carboxylate with (R)-methyl 6-(bromomethyl)-4-(2,4-dichlorophenyl)-2-(thiazol-2-yl)-1,4-dihydropyrimidine-5-carboxylate (461 mg, 1 mmol) of example 26. MS (ESI, pos. ion) m/z: 662.1 [M+H]$^+$; $^1$H NMR (400 MHz, CDCl$_3$) δ 9.61 (s, 1H), 7.84 (d, J=3.0 Hz, 1H), 7.53 (d, J=8.7 Hz, 2H), 7.45 (d, J=2.9 Hz, 1H), 7.40 (d, J=1.6 Hz, 1H), 7.26 (s, 1H), 7.25-7.21 (m, 2H), 7.20-7.13 (m, 1H), 6.20 (s, 1H), 4.11 (d, J=17.3 Hz, 1H), 4.08-3.95 (m, 2H), 3.92-3.84 (m, 2H), 3.59 (s, 3H), 3.42-3.39 (m, 1H), 3.25 (t, J=11.0 Hz, 1H), 2.87 (d, J=9.2 Hz, 2H), 2.56-2.43 (m, 1H), 2.24 (t, J=10.8 Hz, 1H), 1.69-1.66 (m, 2H), 1.36-1.33 (m, 2H).

Biological Test

Test 1: Test Method of Calculating Anti HBV EC$_{50}$

HBV Cell Line and Culture Conditions

HepG2.2.15 (SELLS, PNAS, 1987 and SELLS, JV, 1988) chromosomes have an integrated complete HBV genome, and stably express viral RNA and viral protein. HepG2.2.15 cells can secrete mature HBV particles, HBsAg and HBeAg, to medium. HepG2.2.15 cells were cultured in DMEM containing 10% fetal bovine serum, 100 U/mL penicillin, 100 U/mL streptomycin, 1% non essential amino acid, 1 mM sodium pyruvate and 300 μg/mL G418.

Viral particles DNA secreted from HepG2.2.15 cells can be quantified by qPCR, and the effect of the compound on viral replication can be detected.

Test of Anti HBV Activity In Vitro

8000 HepG 2.2.15 cells per well were seeded into a 96-well plate, the plate was cultured at 37° C. and 5% CO$_2$ for 3 days till the cells grew to full wells. Old liquid medium can be removed and replaced with new medium (200 μL) on day 0.

Formulating the compound and treating the cells in the experiment of anti virus: the compound was dissolved in DMSO to a concentration of 30 mM, and then the compound solution was diluted with DMSO to a concentration of 800 μM, and then eight dilutions at 4 fold were performed, the highest concentration is 800 μM. The serial diluted compound was added to the above plate at 1 μL per well, the highest final concentration in the experiment is 4 μM (200 fold dilution). TDF (tenofovir dipiroxil fumarate, Selleck, Cat S1400) has a highest concentration of 4 μM as a positive control. 1 μL of DMSO was added in to the positive control well at a final concentration of 0.5%, TDF was added in to the positive control well at a final concentration of 1 μM.

Detection of Viral Genomic DNA by aPCR

Primer: HBV-For-202, CAGGCGGGGTTTTTCTTGTTGA; HBV-Rev-315, GTGATTGGAGGTTGGGGACTGC. Copies of virus can be calculated using a standard curve plotted by using plasmid containing HBV genome and using SYBR Premix Ex Taq II—Takara DRR081S kit and 1 μL cell culture supernatant as a template. EC50 values of the compound on viral replication were calculated by a four parametric nonlinear regression model using Graphpad Prism 5 software to manage concentration—viral copy number. The results were shown as table 3.

TABLE 3

| EC50 values of the compound of the invention on viral replication | |
|---|---|
| Example | EC$_{50}$ (nM) |
| Example 1 | 8.45 |
| Example 2 | 10.37 |
| Example 4 | 19.81 |
| Example 6 | 13.97 |
| Example 7 | 8.78 |
| Example 10 | 19.95 |
| Example 11 | 32.45 |
| Example 12 | 12.97 |
| Example 13 | 22.09 |
| Example 14 | 22.71 |
| Example 15 | 10.80 |
| Example 16 | 12 |
| Example 17 | 6 |
| Example 18 | 13 |
| Example 19 | 14 |
| Example 20 | 4 |
| Example 21 | 5 |
| Example 22 | 18 |
| Example 23 | 7 |
| Example 26 | 1 |
| Example 27 | 10 |
| Example 28 | 4 |
| Example 29 | 6 |
| Example 30 | 9 |
| Example 31 | 16 |
| Example 32 | 6 |
| Example 33 | 7 |
| Example 34 | 7 |
| Example 35 | 7 |
| Example 36 | 22 |
| Example 37 | 12.1 |
| Example 38 | 7.1 |
| Example 39 | 6.6 |
| Example 40 | 8.2 |
| Example 41 | 5.1 |
| Example 42 | 8.0 |
| Example 43 | 7.2 |
| Example 44 | 3.6 |
| Example 45 | 14.4 |
| Example 48 | 6.3 |
| Example 52 | 41.8 |
| Example 53 | 34.1 |
| Example 54 | 61.3 |
| Example 56 | 12.4 |
| Example 57 | 28.1 |
| Example 60 | 32.3 |
| Example 61 | 15 |
| Example 63 | 27.6 |
| Example 64 | 24.9 |
| Example 68 | 11.1 |
| Example 70 | 15.9 |
| Example 71 | 16.6 |
| Example 72 | 21.2 |
| Example 74 | 30.7 |
| Example 76 | 5.4 |
| Example 77 | 9.7 |
| Example 78 | 38.7 |
| Example 79 | 29 |
| Example 80 | 15.8 |
| Example 90 | 12.5 |
| Example 91 | 37.7 |
| Example 93 | 21.5 |
| Example 97 | 36.8 |

TABLE 3-continued

EC50 values of the compound of the invention on viral replication

| Example | $EC_{50}$ (nM) |
|---|---|
| Example 98 | 11.9 |
| Example 99 | 12.6 |
| Example 100 | 16.8 |
| Example 101 | 14.8 |
| Example 102 | 4.2 |
| Example 103 | 19.4 |
| Example 105 | 29 |
| Example 106 | 6.2 |
| Example 107 | 6.5 |
| Example 108 | 6.8 |
| Example 109 | 12.4 |
| Example 110 | 30.5 |
| Example 111 | 7.5 |
| Example 112 | 15.4 |
| Example 113 | 23.9 |
| Example 114 | 27.7 |
| Example 115 | 17.2 |
| Example 116 | 19.9 |
| Example 117 | 18.8 |
| Example 118 | 8.9 |
| Example 119 | 15.6 |
| Example 120 | 25.5 |
| Example 121 | 36.4 |
| Example 122 | 45.6 |
| Example 123 | 37.9 |
| Example 124 | 47.4 |
| Example 125 | 21 |
| Example 126 | 6.7 |
| Example 131 | 8.6 |
| Example 134 | 4.0 |
| Example 135 | 6.5 |
| Example 136 | 20.1 |
| Example 137 | 10 |
| Example 138 | 34 |
| Example 139 | 10.7 |
| Example 140 | 18.3 |

Conclusion: the data of the experiment indicate that the compounds of the invention have better inhibitory activity, and which give a prospect in development and application in the aspect of anti HBV.

Test 2: Cytotoxicity and Selectivity Index

Methods of Testing Cytotoxicity and Selectivity Index

The serial diluted compound was added to a 384 wells plate at 50 μL HepG2.2.15 cell per well (3000 cells per well), the highest final concentration in the experiment is 150 μM (200 fold dilution). The plate was cultured at 37° C. in an incubator with $CO_2$ for 4 days, and cytotoxicity of the compound was detected using CellTiter Glo agent.

The cytotoxicity of the compound was calculated using the following formulate, cytotoxicity (%)=100−(detection value/mean of DMSO control wells values×100) $CC_{50}$ values were calculated by a four parametric nonlinear regression model using Graphpad Prism 5 software to manage concentration-cytotoxicity (%). The results were shown as table 4.

TABLE 4

$CC_{50}$ values of the compounds of the invention

| Example | $CC_{50}$ (μM) |
|---|---|
| Example 17 | >150 |
| Example 19 | >150 |
| Example 20 | >150 |
| Example 22 | >150 |
| Example 23 | >150 |
| Example 26 | >150 |
| Example 31 | >150 |
| Example 32 | >150 |
| Example 33 | >150 |
| Example 34 | >150 |
| Example 35 | >150 |
| Example 36 | >150 |
| Example 37 | >150 |
| Example 38 | >150 |
| Example 41 | >150 |
| Example 42 | >150 |
| Example 43 | >150 |
| Example 44 | >150 |
| Example 48 | >150 |
| Example 54 | >150 |
| Example 56 | >150 |
| Example 57 | >150 |
| Example 60 | >150 |
| Example 61 | >150 |
| Example 62 | >150 |
| Example 63 | >150 |
| Example 64 | >150 |
| Example 68 | >150 |
| Example 70 | >150 |
| Example 71 | >150 |
| Example 72 | >150 |
| Example 73 | >150 |
| Example 74 | >150 |
| Example 75 | >150 |
| Example 77 | >150 |
| Example 79 | >150 |
| Example 80 | >150 |
| Example 81 | >150 |
| Example 90 | >150 |
| Example 91 | >150 |
| Example 93 | >150 |
| Example 97 | >150 |
| Example 98 | >150 |
| Example 99 | >150 |
| Example 100 | >150 |
| Example 102 | >150 |
| Example 103 | >150 |
| Example 104 | >150 |
| Example 105 | >150 |
| Example 106 | >150 |
| Example 111 | >150 |
| Example 112 | >150 |
| Example 114 | >150 |
| Example 116 | >150 |
| Example 117 | >150 |
| Example 118 | >150 |
| Example 119 | >150 |
| Example 122 | >150 |
| Example 123 | >150 |
| Example 125 | >150 |
| Example 126 | >150 |
| Example 135 | >150 |
| Example 136 | >150 |
| Example 137 | >150 |
| Example 138 | >150 |
| Example 139 | >150 |

Conclusion: the cytotoxicity and selectivity index experimental data indicate that the compounds of the invention have low cytotoxicity.

Test 3: Pharmacokinetic Activities the Compounds of the Invention on Beagle Dogs, Mice, Rats (1) PK Test on Beagle Dogs the PK test method of the compound in vivo of beagle dogs (weight: 10-12 kg, male, ages of 10-12 months, 3 per oral group, 3 per intravenous injection group):

The beagle dogs were administered intragastrically with the test compound at doses of 2.5 mg/kg or 5 mg/kg or administered intravenously with the test compound at doses of 1 mg/kg or 2 mg/kg.

Blood samples were taken at 0.083, 0.25, 0.5, 1, 2, 4, 6, 8 and 24 hours from vein after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reactions monitoring (MRM). Pharmacokinetic parameters were calculated using a noncompartmental method by WinNonLin 6.3 software.

Conclusion: the data of the PK experiment indicates that the compounds of the invention have better pharmacokinetics properties in vivo of beagle dogs, and which give a prospect in development and application in the aspect of anti HBV.

(2) PK Test on Mice the PK test method of the compound in vivo of mice (weight: 20-25 g, male, ages of 45-60 days, 3 per oral group, 3 per intravenous injection group):

The ICR mice were administered intragastrically with the test compound at doses of 10 mg/kg or administered intravenously in the tail veins with the test compound at doses of 2 mg/kg or 10 mg/kg. Blood samples were taken at 0.083, 0.25, 0.5, 1, 2, 4, 6, 8 and 24 hours from orbital vein after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reactions monitoring (MRM). Pharmacokinetic parameters were calculated using a noncompartmental method by WinNonLin 6.1 software.

Conclusion: the data of the PK experiment indicates that the compounds of the invention have better pharmacokinetics properties in vivo of mice, and which give a prospect in development and application in the aspect of anti HBV.

(3) PK Test on Rats the PK test method of the compound in vivo of SD rats (weight: 200-250 kg, male, ages of 2-3 months, 3 per oral group, 3 per intravenous injection group):

The Rats were administered intragastrically with the test compound at doses of 2.5 mg/kg or 5 mg/kg or administered intravenously with the test compound at doses of 1 mg/kg.

Blood samples were taken at 0.083, 0.25, 0.5, 1, 2, 5, 7 and 24 hours from vein after the administration, and collected in anticoagulation tube with EDTA-$K_2$. The test compounds were extracted from plasma samples by liquid-liquid extraction. Then quantitative analysis was performed on a triple-quadrupole tandem mass spectrometer using multiple reactions monitoring (MRM). Pharmacokinetic parameters were calculated using a noncompartmental method by WinNonLin 6.3 software.

Conclusion: the data of the PK experiment indicates that the compounds of the invention have better pharmacokinetics properties in vivo of SD rats, and which give a prospect in development and application in the aspect of anti HBV.

Test 4: Stability Test of the Compound of the Invention in Liver Microsome of Different Species Stability Test Method of the Compound in Liver Microsome of Different Species:

To a 96 wells plate were added 30 μL of blank solution and 30 μL of liver microsomal mixed solution, and to each well was added 15 μL of buffer solution containing the test compound, the sample was prepared in duplicate. The plates were preincubated at 37° C. for 10 min, and 15 μL of NADPH solution (8 mM) was added at points in time, the final concentration of the test compound is 1 μM, the concentration of liver microsome is 0.5 mg/mL, the final concentration of NADPH is 2 mM. The plates were incubated for 0, 15, 30, 60 mM respectively, after incubation was complete, 150 μL of acetonitrile containing interior label was added to the mixed system. The samples diluted with acetonitrile were centrifuged at 4000 rpm for 5 min, 150 μL of the supernatant was sampled to be analyzed by LC-MS/MS.

Conclusion: the compounds of the invention in liver microsome of different species have better stability.

Test 5: Solubility Test Method

Solubility Test Method of the Compound

Unless otherwise indicated, the test sample ground to a fine powder was weighed or the liquid sample was measured and added into a certain amount of solvent at 25° C.±2° C., the mixture was shook vigorously for 30 sec every other 5 mM, the solubility was observed in 30 min, which was dissolved completely if there was no visible solute particle or liquid drop.

Very soluble is that 1 g (mL) of solute can be dissolved completely in a <1 mL of solvent Freely solu is that 1 g (mL) of solute can be dissolved completely in a 1 to <10 mL of solvent Soluble is that 1 g (mL) of solute can be dissolved completely in a 10 to <30 mL of solvent Sparingly soluble is that 1 g (mL) of solute can be dissolved completely in a 30 to <100 mL of solvent Less soluble is that 1 g (mL) of solute can be dissolved completely in a 100 to <1000 mL of solvent Very slightly soluble is that 1 g (mL) of solute can be dissolved completely in a 1000 to <10000 mL of solvent Little or no solubility is that 1 g (mL) of solute can not be dissolved completely in a 10000 000 mL of solvent Conclusion: the results of the stability test indicate that the compounds of the invention have better solubility.

Test 6: hERG Test Method

Test Method of the Compound to the Heart

To a 384 wells plate were added a compound, a positive control, a negative control, membrane-bound fragments containing hERG channel, a tracer with a high affinity to the hERG channel in turn, the plate was incubated at 25° C. and 250 rpm for 4 hours. Fluorescence polarization value of each well can be measured by a multimode reader, the relative inhibition rate and 50% inhibitory concentration ($IC_{50}$) on hERG channel were calculated.

Conclusion: the hERG test experiment data indicate that the compounds of the invention have a low toxicity on heart.

Test 7: Liver Drug Enzyme Induction Effect Test

Incubation of Cells

All of the incubations are carried out at 37° C. in an incubator with 5% $CO_2$ and 95% humidity.

After resuscitation of cryopreserved human hepatocytes (Baltimore, Md., USA), cell number and cell viability were measured on a cell counter by a trypan blue staining. After counting, the hepatocytes were diluted with preheated plate culture medium to 700 thousand living cells per ml. The diluted hepatocytes suspension were seeded into the 48 wells plate with pre-laying collagen at 0.2 mL per well, which was incubated in an incubator for at least 4 hours, the seed culture fluid was replaced with incubation medium containing 2% base matrigel while the cells is adherent.

The administration liquid was freshly prepared every day using incubation medium, including the sample (the concentration is not less than 0.1 μM), positive inducers (omeprazole, phenobarbital, rifampicin) of CYP1A2, CYP2B6 and CYP3A4 obtained through diluting with DMSO stock solution to 1000 fold. The administration liquid was listed as following table.

| Positive inducer | Final concentration of positive inducer | Final concentration of organic phase |
| --- | --- | --- |
| Omeprazole | 50 μM | 0.1% DMSO |
| Rifampicin | 10 μM | (v/v) |
| Phenobarbital | 1000 μM | |

After the incubation system was established, the upper culture medium of sandwich culture medium was abandoned, 200 μL, of preheated to 37° C. and freshly prepared administration liquid (including sample, positive control, negative control and base control) was added to each cell incubation well, the cell incubation plate was placed in the incubator and further incubated for 24 hours. After 24 hours incubation, the administration liquid was replaced with the freshly prepared administration liquid and further incubated for 24 hours. The whole incubation time is 48 hours. Each compound concentration and control concentration have triplicates.

After 48 hours incubation of the cells and administration liquid, the remainder drug solution of the plate was abandoned, and the cell wells were washed with 0.5 mL of preheated to 37° C. HBSS solution twice, and then to each well was added 100 μL, of preheated to 37° C. enzyme labelled substrate liquid, the plate was incubated for 30 min. After 30 min incubation, 75 μL, of the supernatant sample was sampled from each well and added to a 96 deep well plate containing 150 μL, of stop buffer. The plate was shaken for 10 min and centrifuged at 4° C. and 3220 g for 20 min, the supernatant solution was taken and diluted with 0.1% aqueous formic acid solution in the proportion of 1:4. The diluted sample plate was shaken for 10 min, and the amount of the metabolite production was measured by liquid chromatography-tandem mass spectrometry (LC/MS/MS).

After the detection of the enzyme activity, the remainder of the supernatant solution was abandoned, and the cells were washed with 0.5 mL of preheated HBSS. To each well was added 280 μL of 1% RLT lysis solution of β-mercaptoethanol, the plate was sealed and shaken for 10 min, and then the plate was moved to a refrigerator (−80° C.).

Cytotoxicity Test

The potential toxicity of the sample was evaluated through releases of lactate dehydrogenase (LDH) from hepatocytes. The 100 μL, administration liquid incubated with cells for 24 hours and 48 hours was sampled respectively and the concentrating of the lactate dehydrogenase therein was detected using a commercial LDH kit. The cell lysis solution was as the positive control, and the incubation medium was as the blank control.

RNA Analysis Test

The frozen sample plate was at room temperature, all of the samples were removed into a new 48 well cell incubation plate. RNA was extracted by an automatic nucleic acid extraction workstation. The samples more than 10% of total samples were taken out randomly from different position of the sample plate, the OD values at 260 nM and 280 nM were measured by using an ND2000 micro spectrophotometer, the total RNA purify was determined by calculating the ratio of the two. Reverse transcription can get cDNA. The selective gene was real time quantitatively analyzed by a CFX Connect™ realtime qPCR. The reaction conditions were set as follows: 50° C. two minutes; 95° C. ten minutes; the following two steps were repeated in 40 cycles: 95° C. fifteen seconds, 60° C. one minute. Endogenous control 18S rRNA was as the interior label.

Sample Analysis Test

The concentration of metabolites (Acetaminophen, Hydroxybupropion and 1'-Hydroxymidazolam) is detected by liquid chromatography-tandem mass spectrometry (LC/MS/MS), the metabolites are of three CYP enzyme substrates in hepatocytes precipitated by protein. The analysis methods would be described in detail in the appendix.

Calculation Gene Expression Data

The differences of gene expression between different treatment groups were compared by using $\Delta Ct$ relative quantify in this project, 18S rRNA is used as the internal reference gene to correct the gene expression of each sample. The Ct value of the target gene minus the Ct value of the reference gene equal to $\Delta Ct$, i.e. $Ct_{target\ gene} - Ct_{18S} = \Delta Ct$ The $\Delta Ct$ value of the treatment group minus the $\Delta Ct$ value of the blank control equal to $\Delta\Delta Ct$, i.e. $\Delta Ct_{treatment\ group} - \Delta Ct_{blank\ control} = \Delta\Delta Ct$ The changes of multiple between the treatment group and the blank control were compared by the statistical analysis by the 2 method.

Calculation of Enzyme Activity Data

The amount of enzyme metabolite production of CYP1A2, CYP2B6 and CYP3A4 were shown as the data of the experiment. The changes of the enzyme activity were represented by comparison of induction multiples of the corresponding cytochrome enzyme in the presence or absence of a test compound. The calculation method of induction multiple and the calculation method of induction ratio to the control compound were shown as follows:

induction multiple=enzyme activity of the sample treated with the test compound/nzyme activity of the sample treated with control group induction ratio to the control compound=(induction multiple of the sample treated with the test compound−1)/(induction multiple of the sample treated with the control compound−1)×

Conclusion: the experiment data of the liver drug enzyme induction effect test indicate that the compounds of the invention have no induction effect to liver drug enzyme.

Test 8: Effect of Human Serum on Anti HBV Efficacy of Compounds

Experiment Principle

HepG2.2.15 chromosomes have an integrated complete HBV genome, and stably express viral RNA and viral protein. HepG2.2.15 cells can secrete mature HBV particles, HBsAg and HBeAg, to medium. Viral DNA secreted from HepG2.2.15 cells can be quantified by qPCR, human serum with different concentrations were added during the treatment process with the test compound, and the effect of human serum on anti HBV efficacy of compounds was detected.

Test Method

Treatment of HepG2.2.15 with Compounds

Step 1: 15000 per well HepG2.2.15 cells were paved in a 96 wells cell incubation plate, 200 μL cell culture medium per well.

Step 2: the plate was incubated at 37° C. in a cell incubator with 5% $CO_2$ for 3 days till the cells grew to full wells.

Step 3: Old liquid medium can be removed and replaced with new medium (200 μL) containing 2% FBS and human serum (HS) with different concentrations (0% HS, 5% HS, 10% HS, 20% HS, 40% HS and 50% HS) on day 0.

Step 4: Formulating the compound and treating the cells in the experiment of anti virus: the compound was dissolved in DMSO to a concentration of 30 mM, and then the compound solution was diluted with DMSO to a concentration of 800 μM, and then eight dilutions at 4 fold were performed, the highest concentration is 800 μM. The serial diluted compound was added to the plate from step 3 at 1 μL per well, the highest final concentration in the experiment is 4 μM (200 fold dilution).

Step 5: the experiment was carried out under the condition of 2% FBS, TDF (tenofovir dipiroxil fumarate, Selleck, Cat S1400) has a highest concentration of 4 μM as a positive control. To the negative control well was added 1 μL of DMSO to an experiment final concentration of 0.5%.

Step 6: the 96 wells cell incubation plate was incubated at 37° C. in an incubator with $CO_2$ for 11 days, the liquid was replaced every other day (at 2, 4, 6, 8, 10 days), and 1 μL of freshly formulated test compound was added, the method was shown in steps 3 to 5.

Step 7: 150 μL of supernatant was sampled from each well at 11 days for detection of viral DNA.

Step 8: formulation of the compound and treatment of the cells in the cytotoxicity experiment: the serial dilute compound was formulated with Bravo liquid handling system, 11 dilutions at 3 fold were performed, the highest concentration is 30 mM. 0.25 μL of the serial dilute compound was removed into each well of a 384 wells cytotoxicity plate (Greiner 781098) by using Echo550. HepG2.2.15 cells were prepared and resuspended in culture medium with different concentrations of human serum (50%, 40%, 20%, 10%, 5% and 0%). 50 μL of the HepG2.2.15 cells (4000 cells) prepared above per well were added into the 384 wells cytotoxicity plate, the highest final concentration in the experiment is 150 μM (200 fold dilution). After 4 days incubation at 37° C. in an incubator with $CO_2$, the cytotoxicity test was carried out.

Detection of Viral Genomic DNA by qPCR

Step 1: the supernatant was diluted with DPBS 2 folds under the experiment condition of 20% HS, the supernatant was diluted with DPBS 4 folds under the experiment condition of 40% HS, the supernatant was diluted with DPBS 5 folds under the experiment condition of 50% HS. After uniformly mixing, 1 μL of which was sampled, and detected by qPCR.

Step 2: 1 μL of the supernatant was sampled directly to be detected by qPCR under the experiment conditions of 0% HS, 5% HS and 10% HS.

Step 3: the qPCR reaction system was formulated as following components.

| SYBR Premix Ex Taq ™ II (2×) | 10 μL |
|---|---|
| HBV-For-202 (10 μM) | 0.8 μL |
| HBV-Rev-315 (10 μM) | 0.8 μL |
| ROX Reference Dye (50×) | 0.4 μL |
| viral supernatant | 1 μL |
| the final volume after adding water | 20 μL |

Step 4: the parameters of ABI ViiA7 qPCR instrument were set as follows
Stage 1:
  Reps: 95° C., 30 s, 1 cycle
Stage 2:
  Reps: 95° C., 5 s and 60° C., 34 s, 40 cycles
Adding the curve of dissolution Detection of Cytotoxic Effects of Compounds Step 1: PromegaCelltiter-Glo reagent was balanced to room temperature.

Step 2: culture medium in the cytotoxicity experimental plate was discarded, and 50 μL of DPBS was added into each well.

Step 3: 10 μL of CellTiter-Glo reagent was added into each well.

Step 4: the plate was shaken on a vibrator for 2 min.

Step 5: the plate was balanced at rt away from light for 10 min.

Step 6: the data was read on the Envision reading board (0.1 sec/well)

Analysis of Results

The standard curve was plotted based on the plasmids containing the HBV genome (Virus copy number: 2×10E6, 2×10E5, 2×10E4, 2×10E3), and the virus copy number was calculated by the standard curve. EC50 values were calculated by a four parametric nonlinear regression model using Graphpad Prism 5 software to process the data and plot the concentration–viral copy number curve. cytotoxicity %=100-(detection value/mean of DMSO control wells values×100) CC50 values were calculated by a four parametric nonlinear regression model using Graphpad Prism 5 software to process the cytotoxicity % data and plot the curve.

Conclusion: the experiment data indicate that the effects of human serum on the antiviral efficacy of the compound is small, and the compounds of the invention play good antiviral effects in the human body.

Though the invention is described in detail in the above with reference to general description and detailed embodiments, modifications and variants are possible obvious to a person of ordinary skills in the art may be made based on the invention. Therefore, the modifications and variants all belong to the scopes of the invention without departing from the spirits of the invention.

What is claimed is:

1. A compound having Formula (I) or Formula (Ia), a stereoisomer, a tautomer, an N-oxide, a solvate, a metabolite, a pharmaceutically acceptable salt or a prodrug thereof,

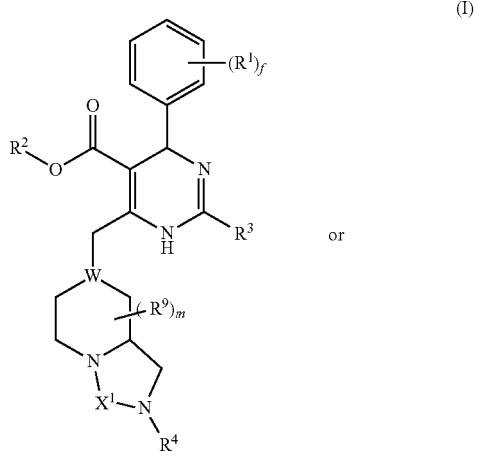

-continued

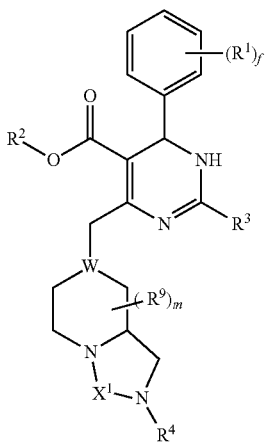

(Ia)

wherein each $R^1$ is independently H, deuterium, F, Cl, Br or I;
each $R^2$ is independently $C_{1-6}$ alkyl or $C_{1-6}$ haloalkyl;
each $R^3$ is independently 5 membered heteroaryl unsubstituted or substituted with methyl;
each W is N;
each $X^1$ is C(=O)— or —CH$_2$—;
each $R^4$ is independently —(CR$^7$R$^8$)$_j$—R$^5$-L-R$^6$;
$R^5$ is 3-12 membered heterocyclyl, $C_{3-7}$ cycloalkyl, $C_{2-12}$ alkynyl, 5-12 membered heteroaryl or $C_{6-10}$ aryl, wherein each of the 3-12 membered heterocyclyl, $C_{3-7}$ cycloalkyl, $C_{2-12}$ alkynyl, 5-12 membered heteroaryl and $C_{6-10}$ aryl is independently unsubstituted or substituted with one, two, three, four or five substituents independently selected from deuterium, F, Cl, Br, OH, CN, $C_{1-6}$ alkoxy, $C_{1-6}$ alkyl, HOOC-(CR$^7$R$^8$)$_h$— and $C_{1-6}$ alkoxy-C(=O)—;
$R^6$ is 3-12 membered heterocyclyl, $C_{3-7}$ cycloalkyl, $C_{2-12}$ alkynyl, 5-12 membered heteroaryl or $C_{6-10}$ aryl, wherein each of the 3-12 membered heterocyclyl, $C_{3-7}$ cycloalkyl, $C_{2-12}$ alkynyl, 5-12 membered heteroaryl and $C_{6-10}$ aryl is independently unsubstituted or substituted with one, two, three, four or five R$^w$;
L is a single bond, —O—, —S(=O)$_t$—, —C(=O)—, —NH—, —(CR$^7$R$^8$)$_j$— or —O—(CR$^7$R$^8$)$_n$—;
each $R^w$ is independently deuterium, F, Cl, Br, OH, CN, HOOC—(CR$^7$R$^8$)$_h$—, R$^{11}$C(=O)—, R$^c$R$^d$P(=O)—, R$^{10}$—S(=O)$_t$—, R$^3$O—, R$^{12}$—(CR$^7$R$^8$)$_j$—, amino, $C_{1-12}$ alkoxy, $C_{3-7}$ cycloalkyl, $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-10 membered heterocyclyl or 5-10 membered heteroaryl, wherein each of the amino, $C_{1-12}$ alkoxy, $C_{3-7}$ cycloalkyl, $C_{1-8}$ alkoxy of $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-10 membered heterocyclyl and 5-10 membered heteroaryl is independently unsubstituted or substituted with one, two, three, four or five R$^x$;
each $R^{10}$ and $R^{11}$ is independently R$^a$R$^b$N—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five R$^y$;
each $R^{12}$ is independently OH, HOOC—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five R$^z$;
each $R^3$ is independently $C_{1-8}$ alkyl, $C_{3-7}$ cycloalkyl, 5-10 membered heteroaryl, $C_{6-10}$ aryl or 5-10 membered heterocyclyl, wherein each of the $C_{1-8}$ alkyl, $C_{3-7}$ cycloalkyl, 5-10 membered heteroaryl, $C_{6-10}$ aryl and 5-10 membered heterocyclyl is independently unsubstituted or substituted with one, two, three, four or five R$^g$;
each $R^x$, $R^y$, $R^z$ and $R^g$ is independently deuterium, F, Cl, Br, OH, CN, HOOC—(CR$^7$R$^8$)$_h$—, R$^{14}$C(=O)—, R$^c$R$^d$P(=O)—, R$^1$—S(=O)$_t$—, R$^{16}$O—, R$^{17}$-(CR$^7$R$^8$)$_j$—, amino, $C_{1-12}$ alkoxy, $C_{3-7}$ cycloalkyl, $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-12 membered heterocyclyl or 5-10 membered heteroaryl, wherein each of the amino, $C_{1-12}$ alkoxy, $C_{3-7}$ cycloalkyl, $C_{1-8}$ alkoxy of $C_{1-8}$ alkoxy-(CR$^7$R$^8$)$_n$—O—, $C_{1-8}$ alkyl, hydroxy-$C_{1-8}$ alkyl, $C_{2-12}$ alkynyl, $C_{6-10}$ aryl, 3-12 membered heterocyclyl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, hydroxy-$C_{1-8}$ alkyl, HOOC—(CR$^7$R$^8$)$_h$— and $C_{1-8}$ alkoxy-(CR$^7$R$^8$)$_n$—;
each $R^{14}$ and $R^{15}$ is independently R$^a$R$^b$N—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, HOOC—(CR$^7$R$^8$)$_h$— and $C_{1-8}$ alkoxy-(CR$^7$R$^8$)$_n$—;
each $R^7$ is independently OH, HOOC—, $C_{1-8}$ alkyl, $C_{1-8}$ alkoxy, $C_{3-7}$ cycloalkyl, 3-12 membered heterocyclyl, $C_{6-10}$ aryl or 5-10 membered heteroaryl, wherein each of the $C_{1-8}$ alkyl, $C_{1-8}$ alkoxy, $C_{3-7}$ cycloalkyl, 3-12 membered heterocyclyl, $C_{6-10}$ aryl and 5-10 membered heteroaryl is independently unsubstituted or substituted with one, two, three, four or five substituents independently selected from deuterium, F, Cl, Br, OH, $C_{1-8}$ alkoxy, $C_{1-8}$ alkyl, HOOC—(CR$^7$R$^8$)$_h$— and $C_{1-8}$ alkoxy-(CR$^7$R$^8$)$_n$O—;
each $R^{16}$ is independently $C_{1-8}$ alkyl, $C_{3-7}$ cycloalkyl, 5-10 membered heteroaryl, $C_{6-10}$ aryl or 5-10 membered heterocyclyl, wherein each of the $C_{1-8}$ alkyl, $C_{3-7}$ cycloalkyl, 5-10 membered heteroaryl, $C_{6-10}$ aryl and 5-10 membered heterocyclyl is independently unsubstituted or substituted with one, two, three, four or five substituents independently selected from deuterium, F, Cl, Br, OH, $C_{1-8}$ alkoxy, $C_{1-8}$ alkyl, HOOC—(CR$^7$R$^8$)$_h$— and $C_{1-8}$ alkoxy-(CR$^7$R$^8$)$_n$—O—;
each $R^a$, $R^b$, $R^c$ and $R^d$ is independently H, deuterium, $C_{1-8}$ alkyl, $C_{2-8}$ alkynyl, $C_{1-8}$ alkoxy, $C_{3-7}$ cycloalkyl, HOOC—(CR$^7$R$^8$)$_h$—, $C_{6-10}$ aryl-$C_{1-4}$ alkylene or 3-12 membered heterocyclyl, wherein each of the $C_{1-8}$ alkyl, $C_{2-8}$ alkynyl, $C_{1-8}$ alkoxy, $C_{3-7}$ cycloalkyl, $C_{6-10}$ aryl of $C_{6-10}$ aryl-$C_{1-4}$ alkylene and 3-12 membered heterocyclyl is independently unsubstituted or substituted with one, two, three, four or five substituents independently selected from deuterium, F, Cl, Br, OH, $C_{1-8}$ alkyl, ($C_{1-6}$ alkyl)$_2$NC(=O)—, $C_{1-8}$ alkoxy, HOOC—(CR$^7$R$^8$)$_h$— and $C_{1-8}$ alkoxy-(CR$^7$R$^8$)—O—;

each $R^7$ and $R^8$ is independently H, deuterium, F, Cl, Br, $C_{1-6}$ alkyl, $NH_2C(=O)—$, $C_{1-6}$ alkyl-$OC(=O)—$, carboxy, carboxy-$C_{1-6}$ alkylene, hydroxy-$C_{1-6}$ alkyl or $C_{1-6}$ haloalkyl, or $R^7$ and $R^8$, together with the carbon atom to which they are attached, form $C_{3-6}$ cycloalkyl or carbonyl;

each $R^9$ is independently H, deuterium or $C_{1-6}$alkyl;
each f, m and h is independently 0, 1, 2, 3, or 4;
each n is independently 1, 2, 3 or 4;
each t is independently 0, 1 or 2;
each j is independently 0, 1, 2 or 3.

2. The compound of claim 1 having Formula (II) or Formula (IIa),

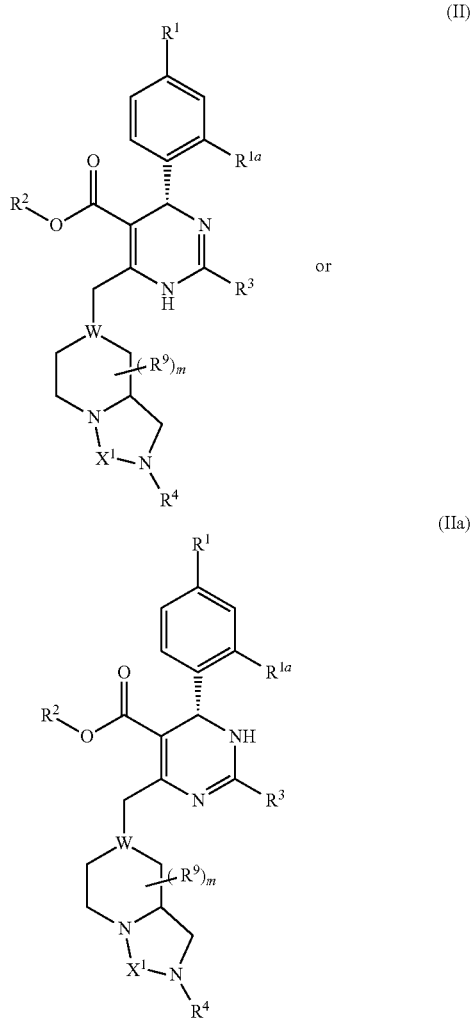

wherein each $R^1$ and $R^{1a}$ is independently H, deuterium, F, Cl, Br or I.

3. The compound of claim 1, wherein each $R^2$ is independently methyl, ethyl, n-propyl, i-propyl or $C_{1-4}$ haloalkyl;

$R^3$ is furyl, pyrrolyl, pyrazolyl, imidazolyl, triazolyl, tetrazolyl, oxazolyl, oxadiazolyl, thiazolyl or thienyl, wherein each of the furyl, pyrrolyl, pyrazolyl, imidazolyl, triazolyl, tetrazolyl, oxazolyl, oxadiazolyl, thiazolyl, and thienyl is independently unsubstituted or substituted with methyl;

each $R^7$ and $R^8$ is independently H, deuterium, F, Cl, Br, methyl, ethyl, n-propyl, i-propyl, $NH_2C(=O)—$, $C_{1-4}$ alkyl-$OC(=O)—$, carboxy, carboxy-$C_{1-3}$ alkylene, hydroxy-$C_{1-4}$ alkyl or $C_{1-4}$ haloalkyl, or $R^7$ and $R^8$, together with the carbon atom to which they are attached, form cyclopropyl, cyclobutyl, cyclopentyl, cyclohexyl or carbonyl; and each $R^6$ independently H, deuterium, methyl, ethyl, n-propyl or i-propyl.

4. The compound of claim 1, wherein $R^5$ is 5-10 membered heterocyclyl, $C_{3-6}$ cycloalkyl, $C_{2-8}$ alkynyl, 5-10 membered heteroaryl, phenyl or naphthyl, wherein each of the 5-10 membered heterocyclyl, $C_{3-6}$ cycloalkyl, $C_{2-8}$ alkynyl, 5-10 membered heteroaryl, phenyl and naphthyl is independently unsubstituted or substituted with one, two, three, four or five substituents independently selected from deuterium, F, Cl, Br, OH, CN, $C_{1-4}$ alkoxy, $C_{1-4}$ alkyl, HOOC—$(CR^7R^8)_h—$ and $C_{1-4}$ alkoxy-$C(=O)—$;

$R^6$ is 5-10 membered heterocyclyl, $C_{3-6}$ cycloalkyl, $C_{2-8}$ alkynyl, 5-10 membered heteroaryl, phenyl or naphthyl, wherein each of the 5-10 membered heterocyclyl, $C_{3-6}$ cycloalkyl, $C_{2-8}$ alkynyl, 5-10 membered heteroaryl, phenyl and naphthyl is independently unsubstituted or substituted with one, two, three, four or five $R^w$.

5. The compound of claim 1, wherein $R^5$ is 5-6 membered heterocyclyl, $C_{3-6}$ cycloalkyl, $C_{2-6}$ alkynyl, 5-6 membered heteroaryl, 9-10 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, 9-10 membered heteroaryl, phenyl and naphthyl is independently unsubstituted or substituted with one, two, three, four or five substituents independently selected from deuterium, F, Cl, Br, OH, CN, $C_{1-3}$ alkoxy, $C_{1-3}$ alkyl, HOOC—$(CR^7R^8)_h—$ and $C_{1-3}$ alkoxy-$C(=O)—$;

$R^6$ is 5-6 membered heterocyclyl, $C_{3-6}$ cycloalkyl, $C_{2-6}$ alkynyl, 5-6 membered heteroaryl, phenyl or naphthyl, wherein each of the 5-6 membered heterocyclyl, $C_{3-6}$ cycloalkyl, $C_{2-6}$ alkynyl, 5-6 membered heteroaryl, phenyl and naphthyl is independently unsubstituted or substituted with one, two, three, four or five $R^w$.

6. The compound of claim 1, wherein $R^5$ is pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzimidazolyl, benzofuranyl, benzothienyl, indolyl, purinyl, quinolyl, isoquinolyl, phenyl or naphthyl, wherein each of the pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, benzothiazolyl, benzimidazolyl, benzofuranyl, benzothienyl, indolyl, purinyl, quinolyl, isoquinolyl, phenyl and naphthyl is independently unsubstituted or substituted with one, two, three, four or five substituents independently selected from deuterium, F, Cl, Br, CN, OH, $C_{1-3}$ alkoxy, $C_{1-3}$ alkyl, HOOC—$(CR^7R^8)_h—$ and $C_{1-3}$ alkoxy-$C(=O)—$;

R⁶ is pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, phenyl or naphthyl, wherein each of the pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, cyclopropyl, cyclobutyl, cyclopentyl, cyclohexyl, ethynyl, propargyl, propynyl, butynyl, pentynyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, phenyl and naphthyl is independently unsubstituted or substituted with one, two, three, four or five $R^w$.

7. The compound of claim 1, wherein each $R^w$ is independently deuterium, F, Cl, Br, OH, CN, HOOC—(CR⁷R⁸)ₕ—, R¹¹C(=O)—, RᶜRᵈP(=O)—, R¹⁰—S(=O)ₜ—, R¹³O—, R¹²—(CR⁷R⁸)ⱼ—, amino, $C_{1-6}$ alkoxy, $C_{3-6}$ cycloalkyl, $C_{1-6}$ alkoxy-(CR⁷R⁸)ₙ—O—, $C_{1-6}$ alkyl, hydroxy-$C_{1-6}$ alkyl, $C_{2-6}$ alkynyl, phenyl, naphthyl, 5-6 membered heterocyclyl or 5-6 membered heteroaryl, and wherein each of the amino, $C_{1-6}$ alkoxy, $C_{3-6}$ cycloalkyl, $C_{1-6}$ alkoxy of $C_{1-6}$ alkoxy-(CR⁷R⁸)ₙ—O—, $C_{1-6}$ alkyl, hydroxy-$C_{1-6}$ alkyl, $C_{2-6}$ alkynyl, phenyl, naphthyl, 5-6 membered heterocyclyl and 5-6 membered heteroaryl is independently unsubstituted or substituted with one, two, three, four or five $R^x$.

8. The compound of claim 1, wherein each $R^w$ is independently deuterium, F, Cl, Br, OH, CN, HOOC—(CR⁷R⁸)ₕ—, R¹¹C(=O)—, RᶜRᵈP(=O)—, R¹⁰—S(=O)ₜ—, R¹³O—, R¹²—(CR⁷R⁸)ⱼ—, amino, $C_{1-4}$ alkoxy, $C_{3-6}$ cycloalkyl, $C_{1-4}$ alkoxy-(CR⁷R⁸)ₙ—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl or piperazinyl, and wherein each of the amino, $C_{1-4}$ alkoxy, $C_{3-6}$ cycloalkyl, $C_{1-4}$ alkoxy-(CR⁷R⁸)ₙ—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl and piperazinyl is independently unsubstituted or substituted with one, two, three, four or five $R^x$.

9. The compound of claim 1, wherein each $R^{10}$ and $R^{11}$ is independently $R^aR^bN$—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, and wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five $R^1$;

each $R^{12}$ is independently OH, HOOC—, $C_{1-6}$ alkyl, $C_{1-6}$ alkoxy, $C_{3-6}$ cycloalkyl, 4 membered heterocyclyl, 5-6 membered heterocyclyl, phenyl, naphthyl or 5-6 membered heteroaryl, and wherein each of the $C_{1-6}$ alkyl, $C_{1-6}$ alkoxy, $C_{3-6}$ cycloalkyl, 4 membered heterocyclyl, 5-6 membered heterocyclyl, phenyl, naphthyl and 5-6 membered heteroaryl is independently unsubstituted or substituted with one, two, three, four or five $R^z$;

each $R^3$ is independently $C_{1-6}$ alkyl, $C_{3-6}$ cycloalkyl, 5-6 membered heteroaryl, phenyl, naphthyl or 5-6 membered heterocyclyl, and wherein each of the $C_{1-6}$ alkyl, $C_{3-6}$ cycloalkyl, 5-6 membered heteroaryl, phenyl, naphthyl and 5-6 membered heterocyclyl is independently unsubstituted or substituted with one, two, three, four or five $R^1$.

10. The compound of claim 1, wherein each $R^{10}$ and $R^{11}$ is independently $R^aR^bN$—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^y$;

each $R^{12}$ is independently OH, HOOC—, $C_{1-4}$ alkyl, $C_{1-4}$ alkoxy, cyclopropyl, cyclobutyl, cyclopentyl, cyclohexyl, azetidinyl, oxetanyl, thietanyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, azetidinyl, oxetanyl, thietanyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^z$;

each $R^{13}$ is independently $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five $R^g$.

11. The compound of claim 1, wherein each $R^x$, $R^y$, $R^z$ and $R^g$ is independently deuterium, F, Cl, Br, OH, CN, HOOC—$(CR^7R^8)_h$—, $R^{14}C(=O)$—, $R^cR^dP(=O)$—, $R^{15}$—S$(=O)_t$—, $R^{16}O$—, $R^{17}$—$(CR^7R^8)_j$—, amino, $C_{1-6}$ alkoxy, $C_{3-6}$ cycloalkyl, $C_{1-6}$ alkoxy-$(CR^7R^8)_n$—O—, $C_{1-6}$ alkyl, hydroxy-$C_{1-6}$ alkyl, $C_{2-6}$ alkynyl, phenyl, naphthyl, 5-6 membered heterocyclyl or 5-6 membered heteroaryl, wherein each of the amino, $C_{1-6}$ alkoxy, $C_{3-6}$ cycloalkyl, $C_{1-6}$ alkoxy of $C_{1-6}$ alkoxy-$(CR^7R^8)_n$—O—, $C_{1-6}$ alkyl, hydroxy-$C_{1-6}$ alkyl, $C_{2-6}$ alkynyl, phenyl, naphthyl, 5-6 membered heterocyclyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, hydroxy-$C_{1-6}$ alkyl, HOOC—$(CR^7R^8)_h$— and $C_{1-6}$ alkoxy-$(CR^7R^8)_n$—.

12. The compound of claim 1, wherein each $R^x$, $R^y$, $R^z$ and $R^g$ is independently deuterium, F, Cl, Br, OH, CN, HOOC—$(CR^7R^8)_h$—, $R^{14}C(=O)$—, $R^cR^dP(=O)$—, $R^{15}$—S$(=O)_t$—, $R^{16}O$—, $R^{17}$—$(CR^7R^8)_j$—, amino, $C_{1-4}$ alkoxy, $C_{3-6}$ cycloalkyl, $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl or piperazinyl, and wherein each of the amino, $C_{1-4}$ alkoxy, $C_{3-6}$ cycloalkyl, $C_{1-4}$ alkoxy-$(CR^7R^8)_n$—O—, $C_{1-4}$ alkyl, hydroxy-$C_{1-4}$ alkyl, $C_{2-4}$ alkynyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl, thienyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl and piperazinyl is independently unsubstituted or substituted with one, two, three, four or five substituents independently selected from deuterium, F, Cl, Br, OH, $C_{1-4}$ alkoxy, $C_{1-4}$ alkyl, hydroxy-$C_{1-4}$ alkyl, HOOC—$(CR^7R^8)_h$— and $C_{1-4}$ alkoxy-$(CR^7R^8)_n$—.

13. The compound of claim 1, wherein each $R^{14}$ and $R^{15}$ is independently $R^aR^bN$—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—;

each $R^7$ is independently OH, HOOC—, $C_{1-6}$ alkyl, $C_{1-6}$ alkoxy, $C_{3-6}$ cycloalkyl, 5-6 membered heterocyclyl, phenyl, naphthyl or 5-6 membered heteroaryl, wherein each of the $C_{1-6}$ alkyl, $C_{1-6}$ alkoxy, $C_{3-6}$ cycloalkyl, 5-6 membered heterocyclyl, phenyl, naphthyl and 5-6 membered heteroaryl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—;

each $R^{16}$ is independently $C_{1-6}$ alkyl, $C_{3-6}$ cycloalkyl, 5-6 membered heteroaryl, phenyl, naphthyl or 5-6 membered heterocyclyl, wherein each of the $C_{1-6}$ alkyl, $C_{3-6}$ cycloalkyl, 5-6 membered heteroaryl, phenyl, naphthyl and 5-6 membered heterocyclyl is independently unsubstituted or substituted with one, two, three, four or five substituents independently selected from deuterium, F, Cl, Br, OH, $C_{1-6}$ alkoxy, $C_{1-6}$ alkyl, HOOC—$(CR^7R^8)_h$— and $C_{1-6}$ alkoxy-$(CR^7R^8)_n$—O—.

14. The compound of claim 1, wherein each $R^{14}$ and $R^{15}$ is independently $R^aR^bN$—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-4}$ alkoxy, $C_{1-4}$ alkyl, HOOC—$(CR^7R^8)_h$— and $C_{1-4}$ alkoxy-$(CR^7R^8)$—O—;

each $R^{17}$ is independently OH, HOOC—, $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, $C_{1-4}$ alkoxy, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, $C_{1-4}$ alkoxy, $C_{1-4}$ alkyl, HOOC—$(CR^7R^8)_h$— and $C_{1-4}$ alkoxy-$(CR^7R^8)_n$—O—;

each $R^{16}$ is independently $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl or thienyl, and wherein each of the $C_{1-4}$ alkyl, cyclopropyl, cyclobutyl, cyclopentyl, cyclohexyl, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl, piperazinyl, phenyl, pyridyl, 1,3,5-triazinyl, pyrazinyl, pyridazinyl, pyrimidinyl, furyl, pyrrolyl, pyrazolyl, imidazolyl, triazolyl, tetrazolyl, oxazolyl, isoxazolyl, oxadiazolyl, thiazolyl and thienyl is independently unsubstituted or substituted with one, two, three, four or five substituents independently selected from deuterium, F, Cl, Br, OH, C$_{1-4}$ alkoxy, C$_{1-4}$ alkyl, HOOC—(CR$^7$R$^8$)$_h$— and C$_{1-4}$ alkoxy-(CR$^7$R$^8$)$_n$—O—.

15. The compound of claim 1, wherein each R$^a$, R$^b$, R$^c$ and R$^d$ is independently H, deuterium, C$_{1-6}$ alkyl, C$_{2-6}$ alkynyl, C$_{1-6}$ alkoxy, C$_{3-6}$ cycloalkyl, HOOC—(CR$^7$R$^8$)$_h$—, phenyl-C$_{1-3}$ alkylene or 5-6 membered heterocyclyl, wherein each of the C$_{1-6}$ alkyl, C$_{2-6}$ alkynyl, C$_{1-6}$ alkoxy, C$_{3-6}$ cycloalkyl, phenyl-C$_{1-3}$ alkylene and 5-6 membered heterocyclyl is independently unsubstituted or substituted with one, two, three, four or five substituents independently selected from deuterium, F, Cl, Br, OH, C$_{1-6}$ alkyl, (C$_{1-4}$ alkyl)$_2$NC(=O)—, C$_{1-6}$ alkoxy, HOOC—(CR$^7$R$^8$)$_h$— and C$_{1-6}$ alkoxy-(CR$^7$R$^8$)$_n$—O—.

16. The compound of claim 1, wherein each R$^a$, R$^b$, R$^c$ and R$^d$ is independently H, deuterium, C$_{1-4}$ alkyl, C$_{2-4}$ alkynyl, C$_{1-4}$ alkoxy, cyclopropyl, cyclobutyl, cyclopentyl, cyclohexyl, HOOC—(CR$^7$R$^8$)$_h$—, phenyl-methylene, pyrrolidyl, pyrazolidyl, imidazolidinyl, tetrahydrofuryl, tetrahydrothienyl, tetrahydropyranyl, tetraphydrothiopyranyl, piperidyl, morpholinyl, thiomorpholinyl or piperazinyl, and wherein each of the C$_{1-4}$ alkyl, C$_{2-4}$ alkynyl, C$_{1-4}$ alkoxy, cyclopropyl, cyclobutyl, cyclopentyl, cyclohexyl, phenyl-methylene, pyrrolidyl, pyrazolidyl, imidazolidinyl, tetrahydrofuryl, tetrahydrothienyl, tetrahydropyranyl, tetrahydrothiopyranyl, piperidyl, morpholinyl, thiomorpholinyl and piperazinyl is independently unsubstituted or substituted with one, two, three, four or five substituents independently selected from deuterium, F, Cl, Br, OH, C$_{1-4}$ alkyl, (CH$_3$)$_2$NC(=O)—, (CH$_2$CH$_3$)$_2$NC(=O)—, CH$_3$CH$_2$N(CH$_3$)C(=O)—, C$_{1-4}$ alkoxy, HOOC—(CR$^7$R$^8$)$_h$— and C$_{1-4}$ alkoxy-(CR$^7$R$^8$)$_n$—O—.

17. The compound of claim 1 having one of the following structures:

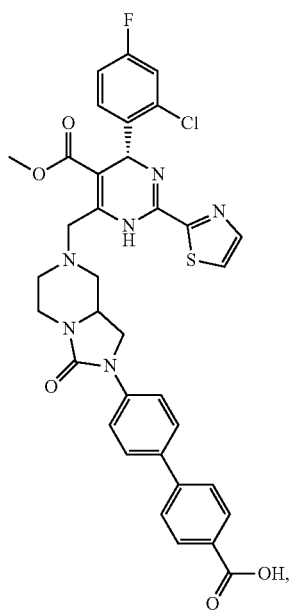

(1)

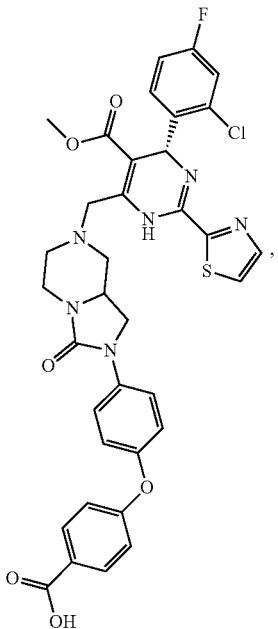

(2)

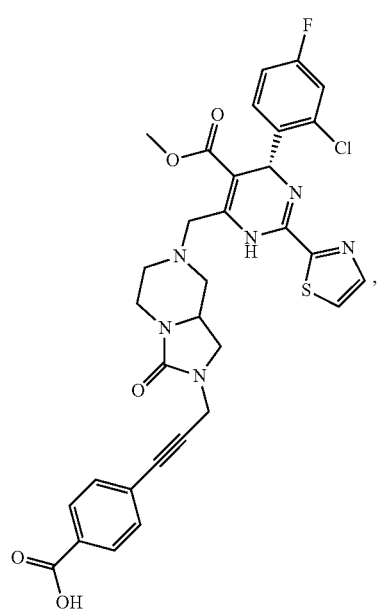

(3)

415
-continued
(4)
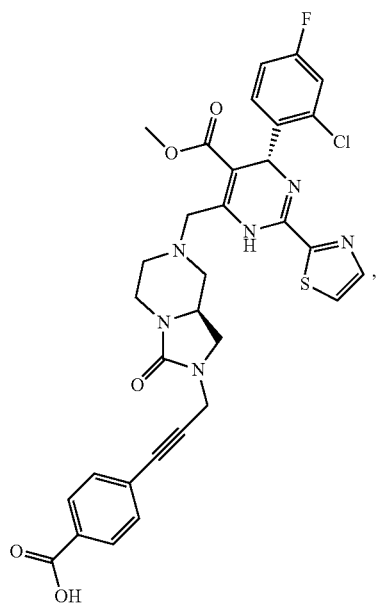
416
-continued
(6)
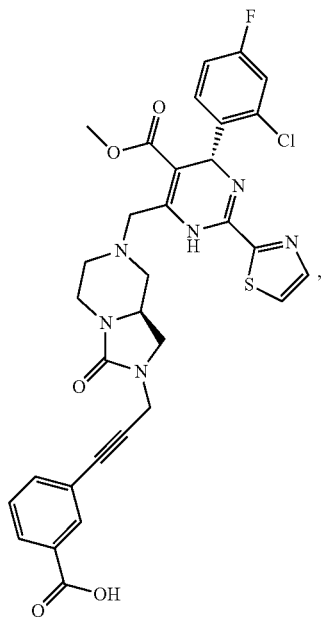
(5)
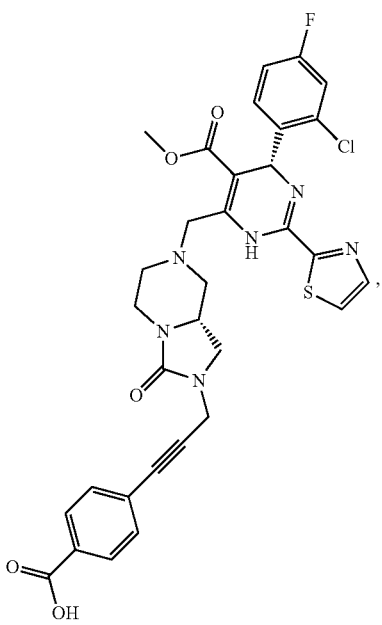
(7)

(8)
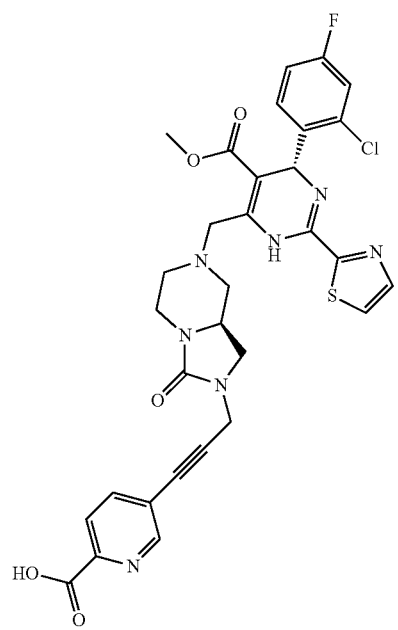
(10)
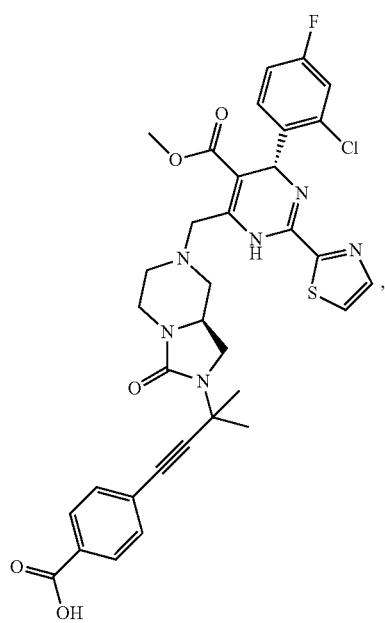
(9)
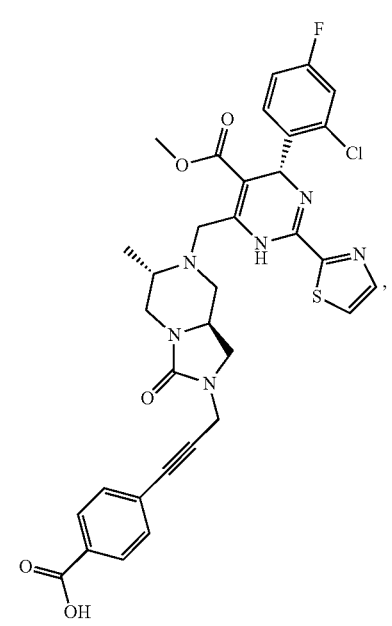
(11)
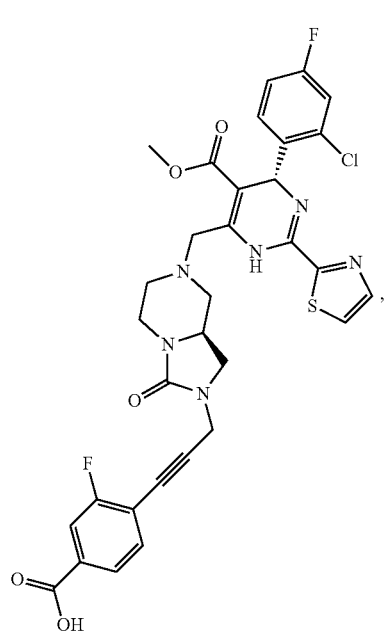

-continued
(12)
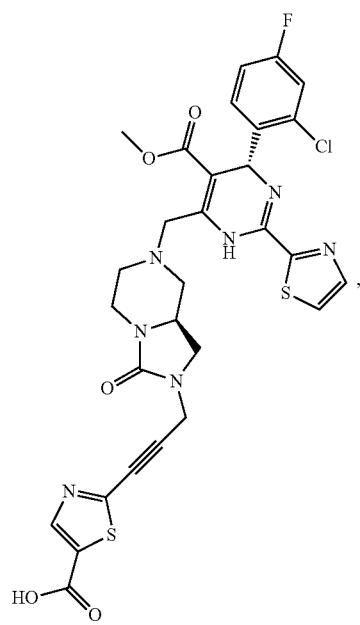
(13)
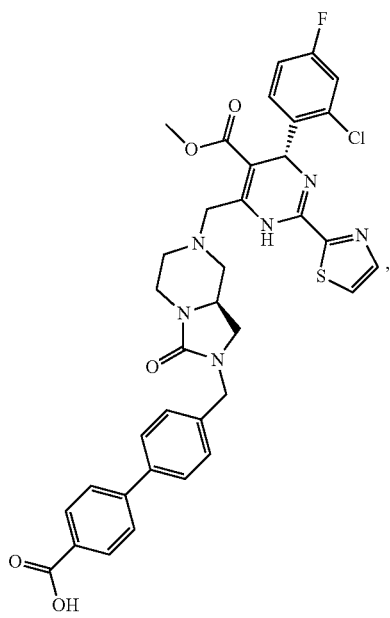
(14)
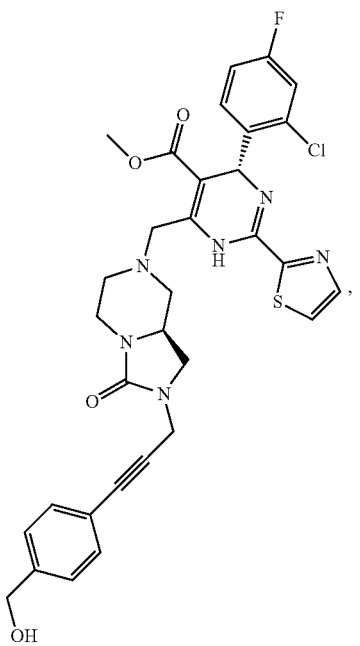
(15)
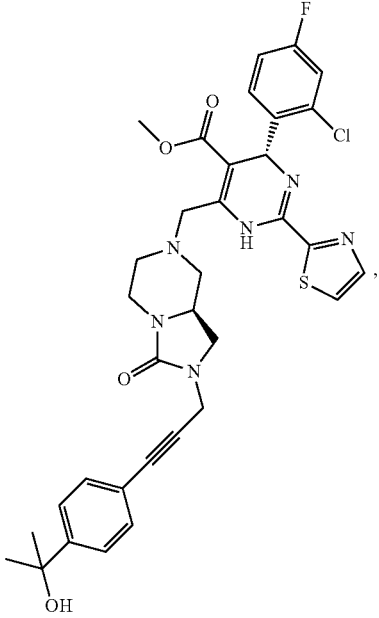

-continued
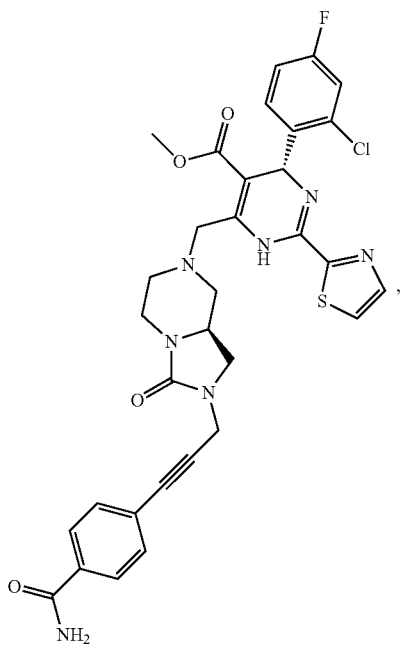
(16)
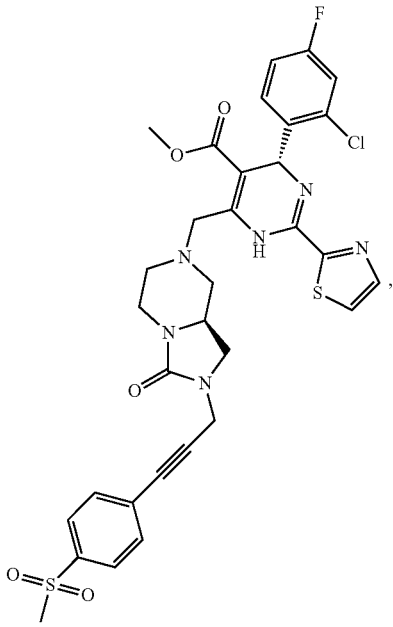
(18)
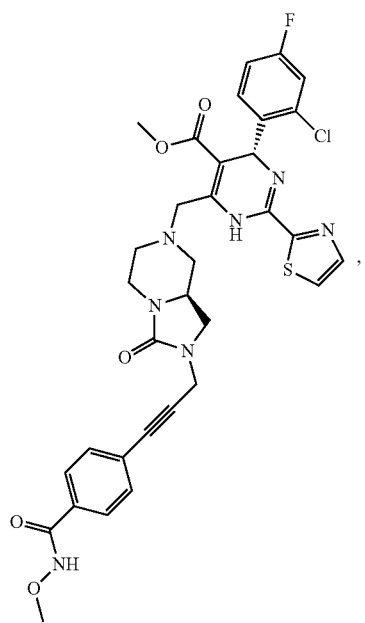
(17)
(19)

423
-continued
(20)
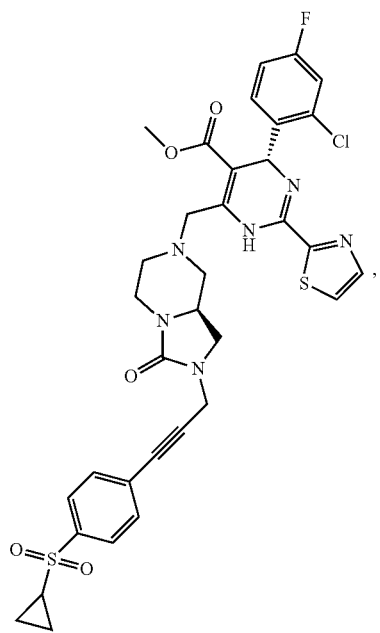
(22)
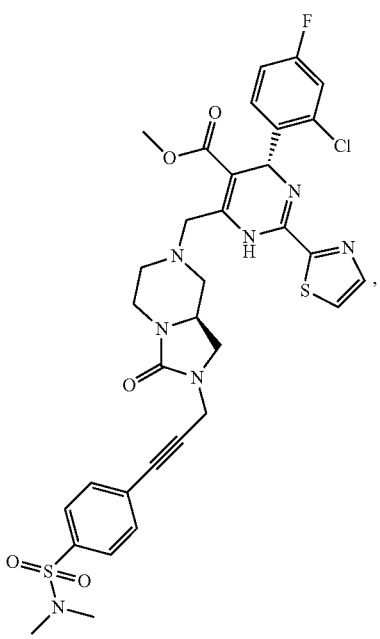
(21)
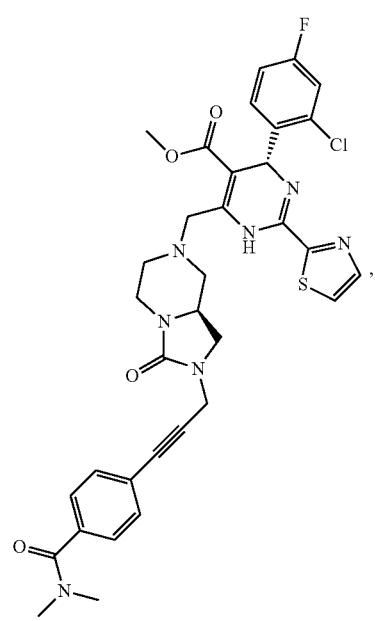
(23)
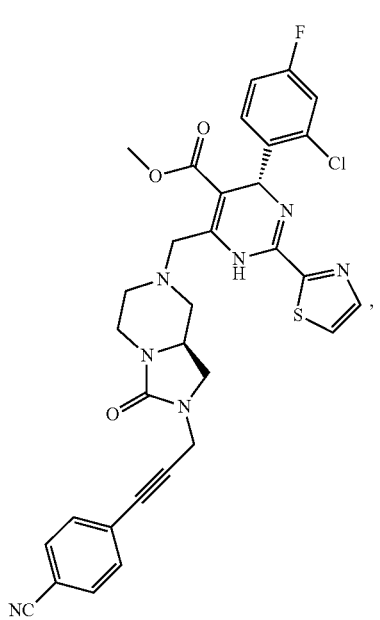

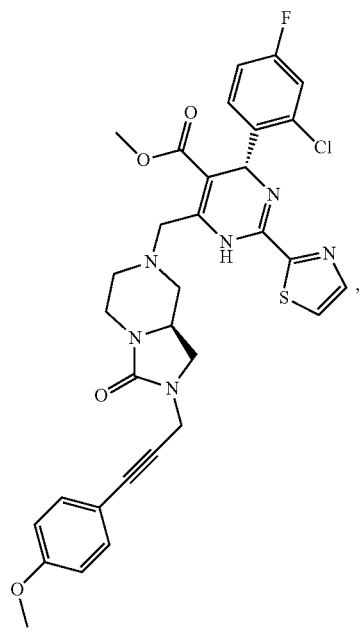
(24)
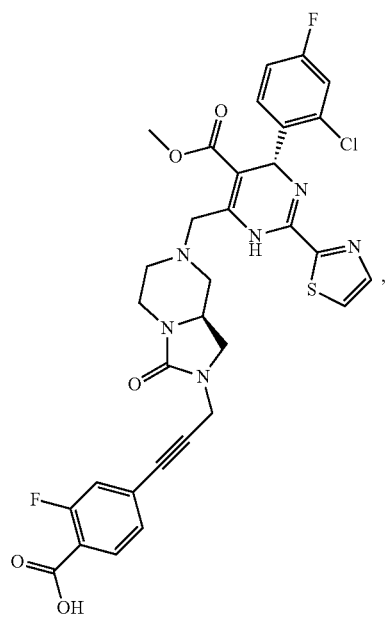
(25)
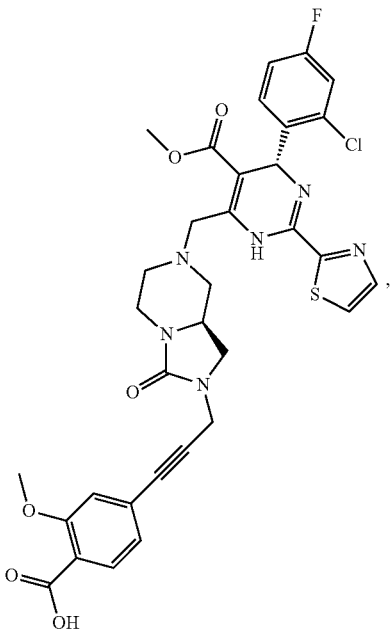
(26)
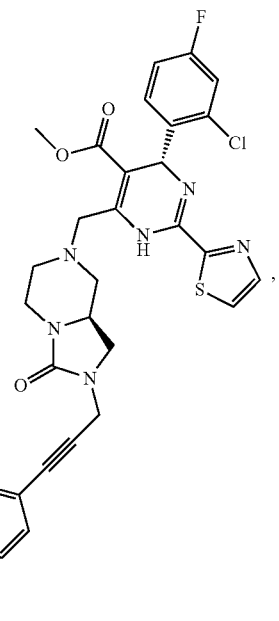
(27)

-continued
(28)
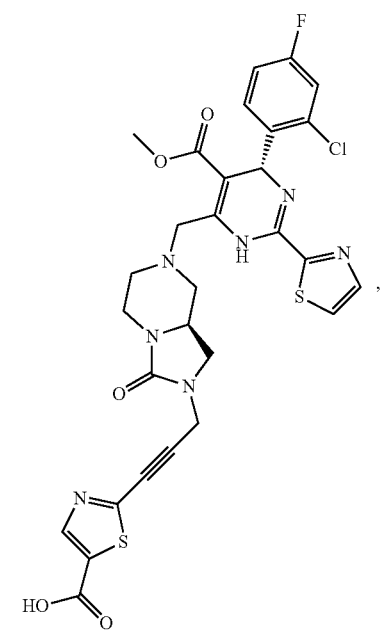
(29)
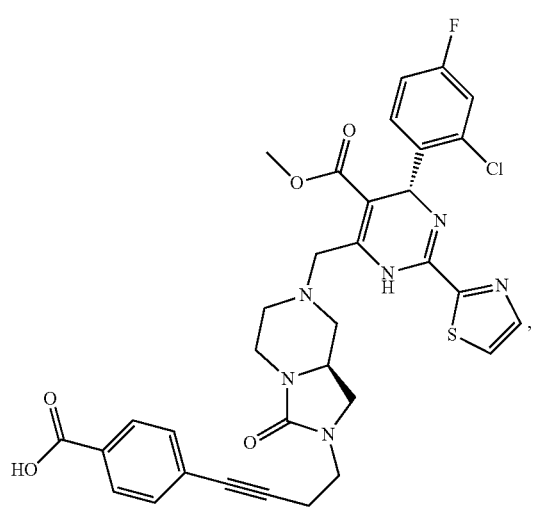
-continued
(30)
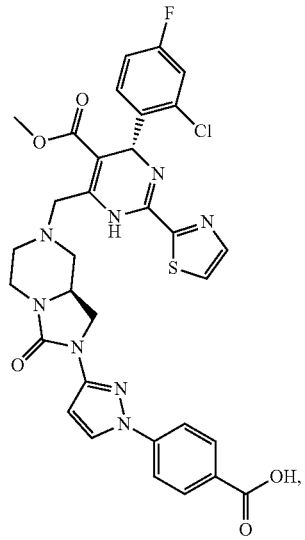
(31)
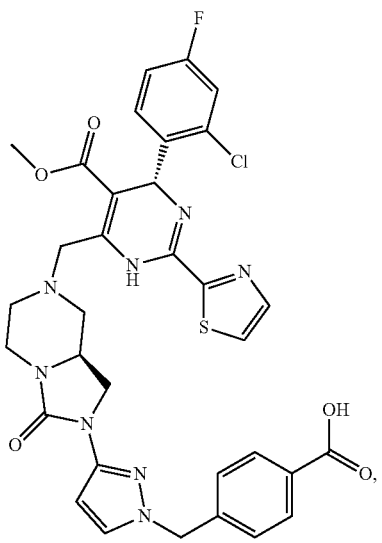
(32)
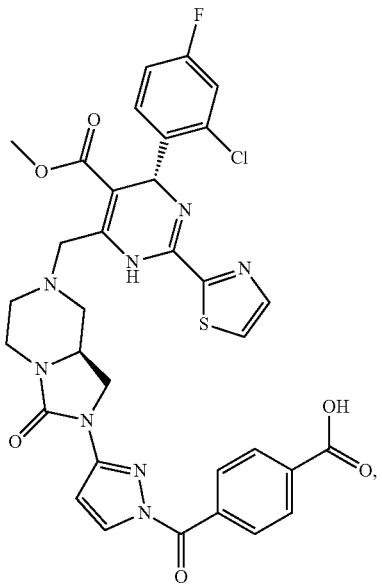

429
-continued
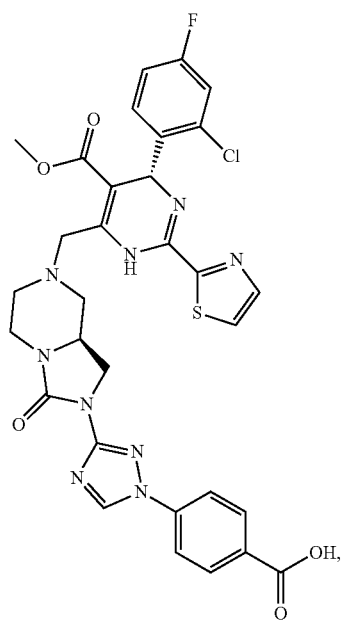
(33)
430
-continued
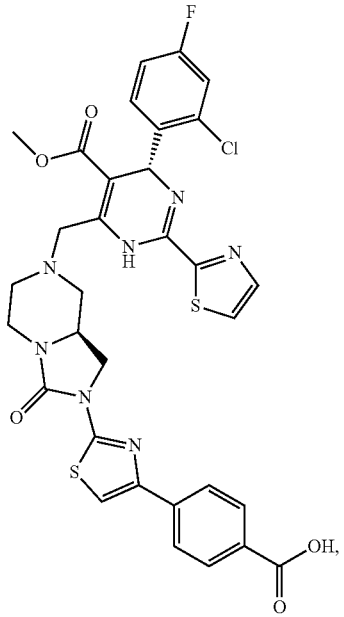
(35)
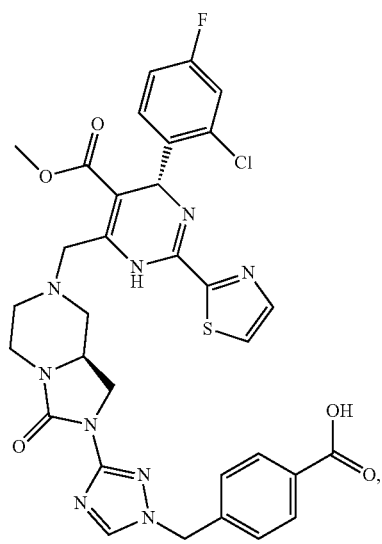
(34)
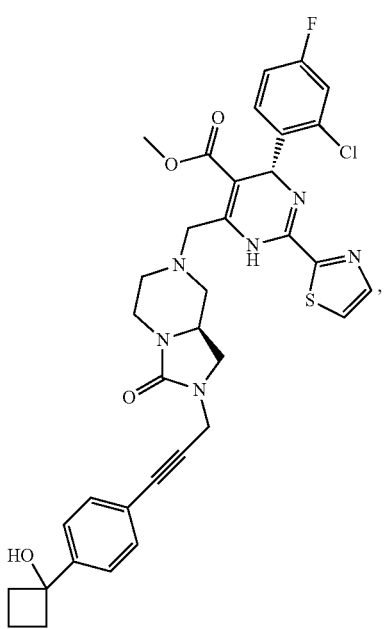
(36)

-continued
(37)
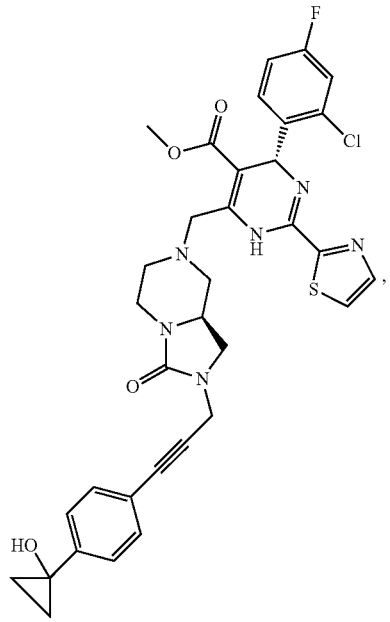
(39)
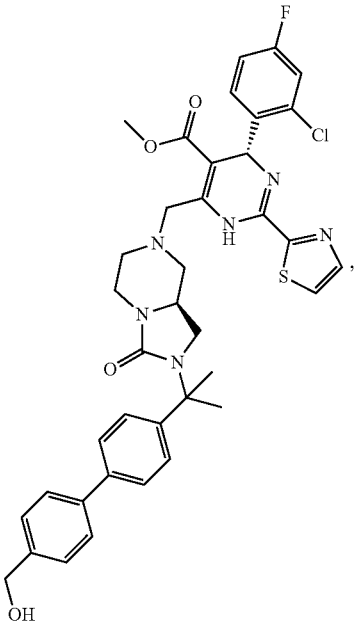
(38)
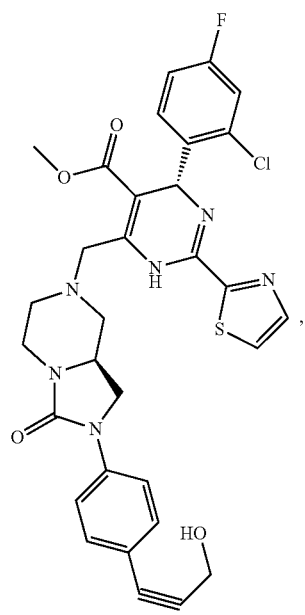
(40)
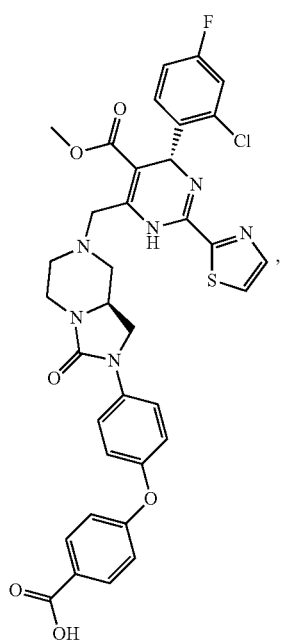

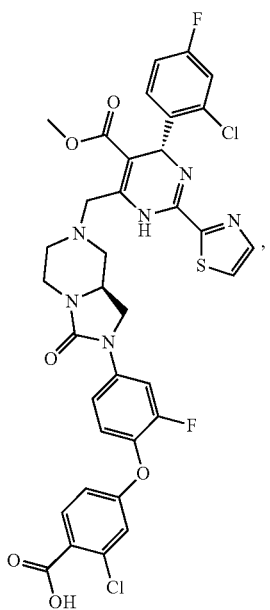
(41)
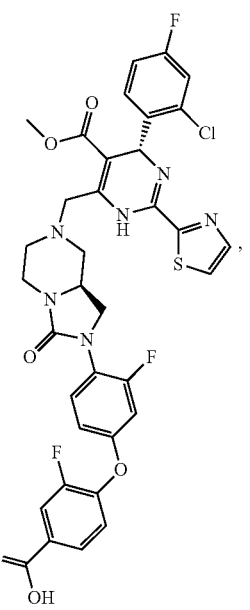
(43)
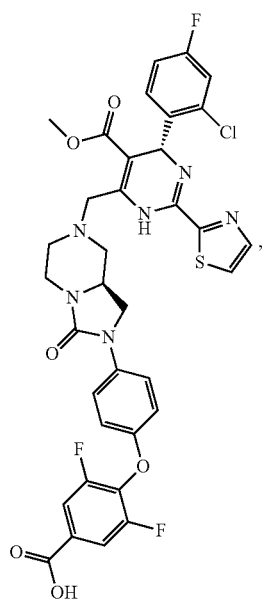
(42)
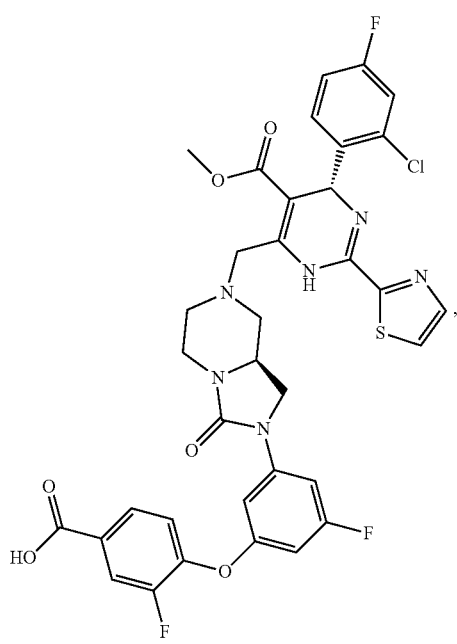
(44)

435
-continued
(45)
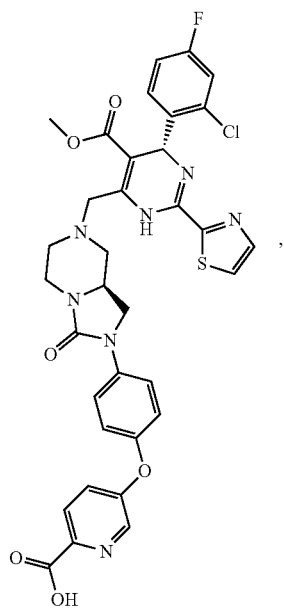
(46)
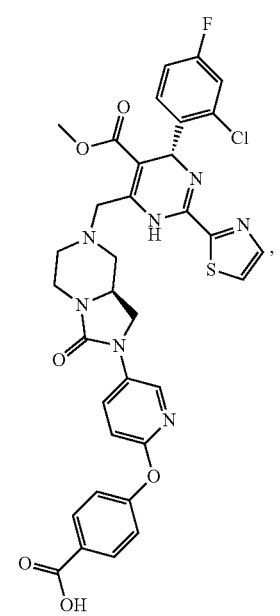
436
-continued
(47)
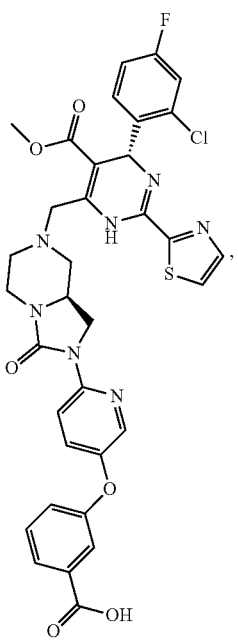
(48)
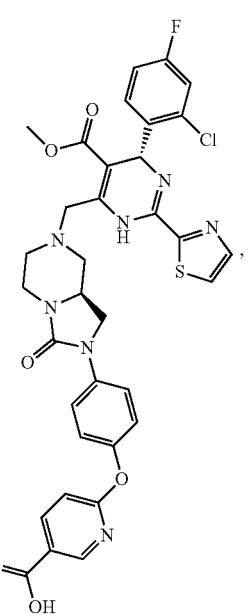

437
-continued
(49)
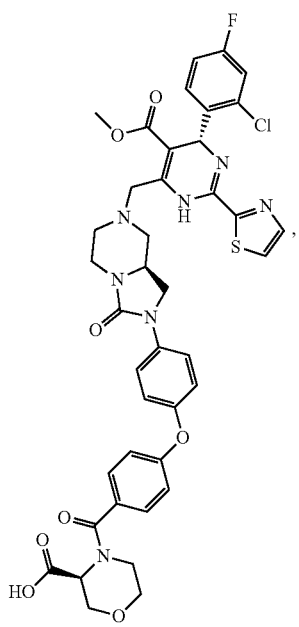
438
-continued
(51)
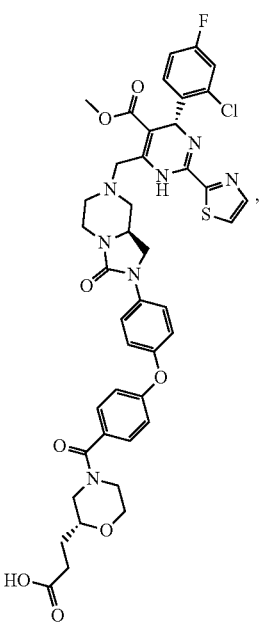
(50)
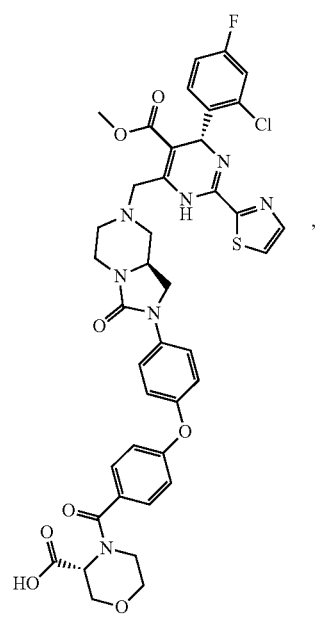
(52)
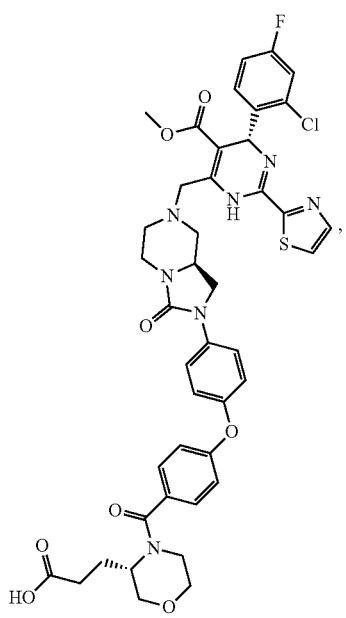

(53)
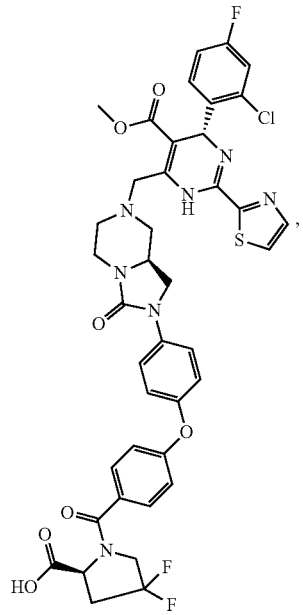
(55)
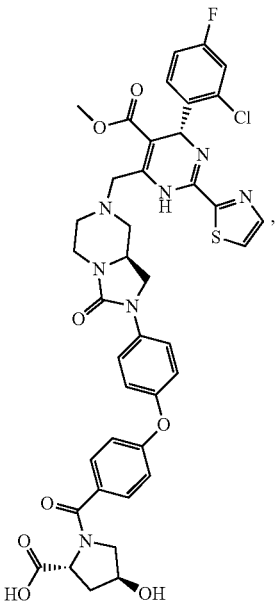
(54)
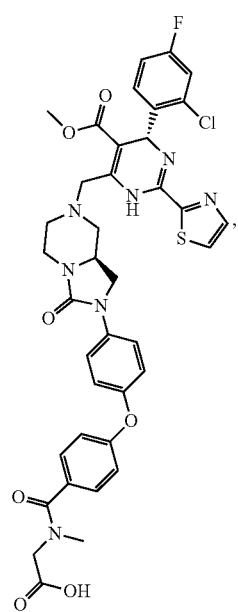
(56)
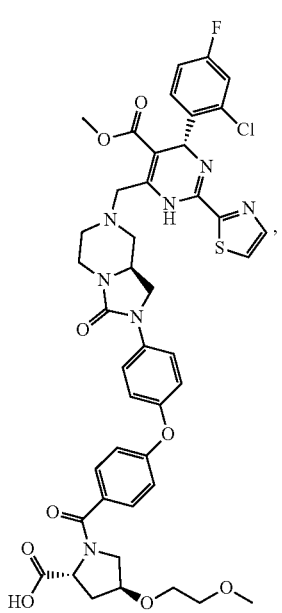

-continued
(57)
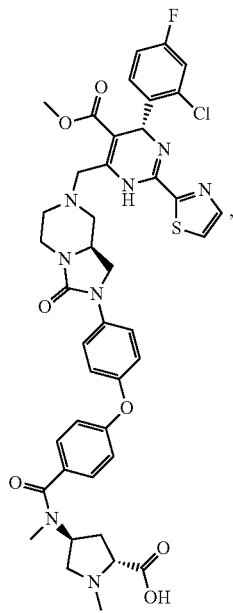
(58)
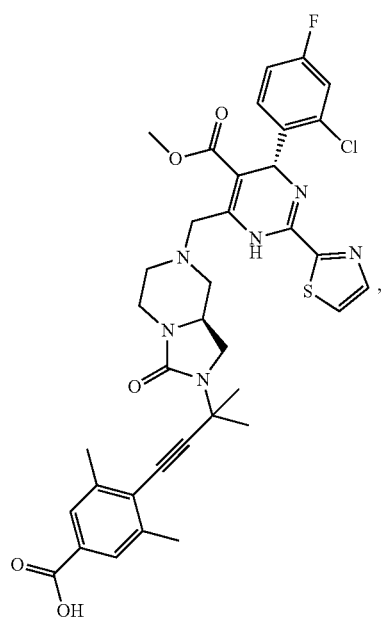
(59)
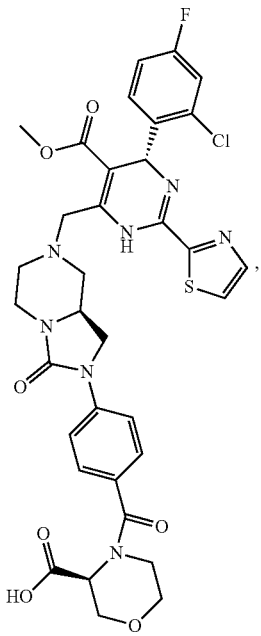
(60)
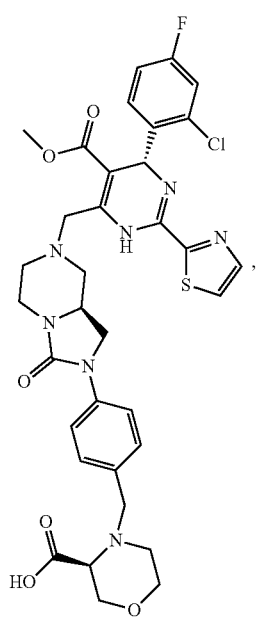

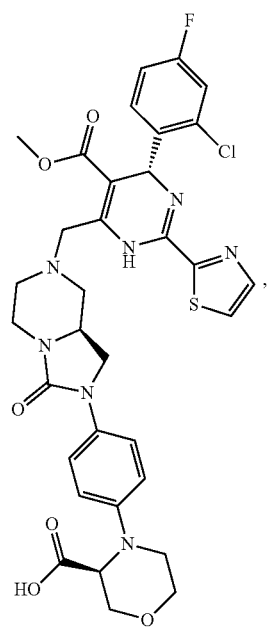
(61)
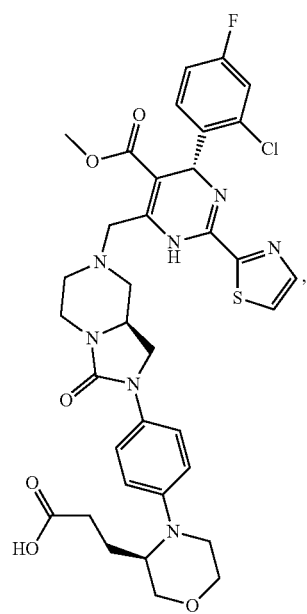
(62)
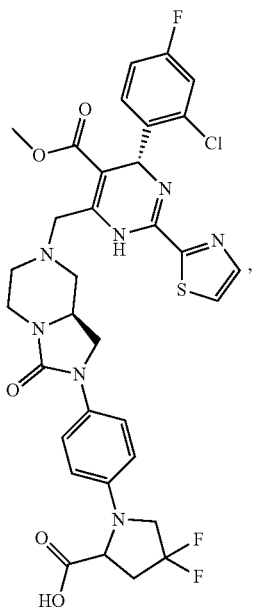
(63)
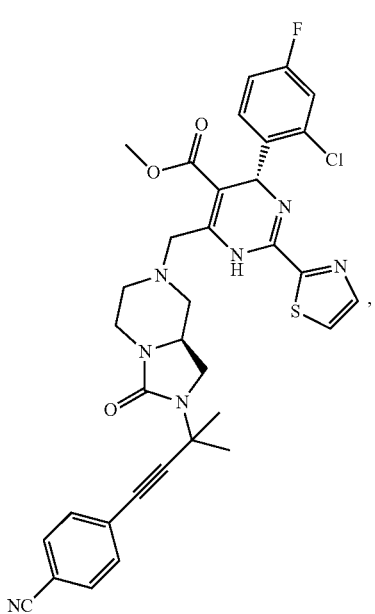
(64)

-continued
(65)
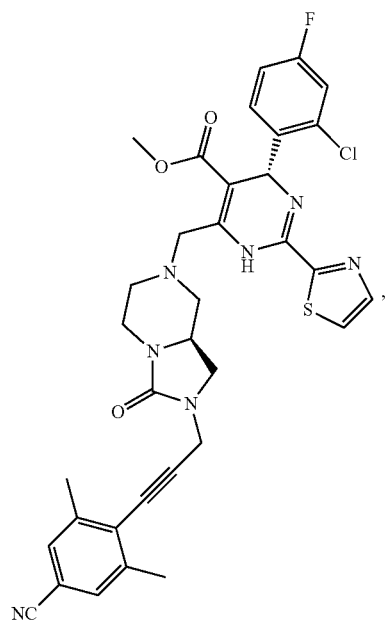
(66)
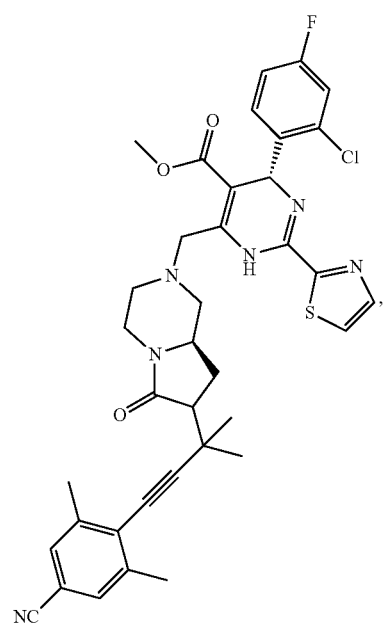
-continued
(67)
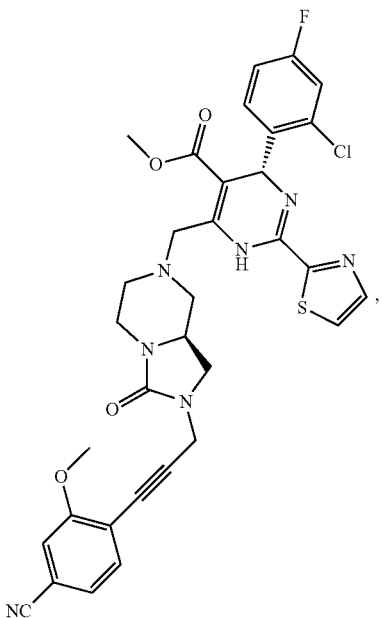
(68)
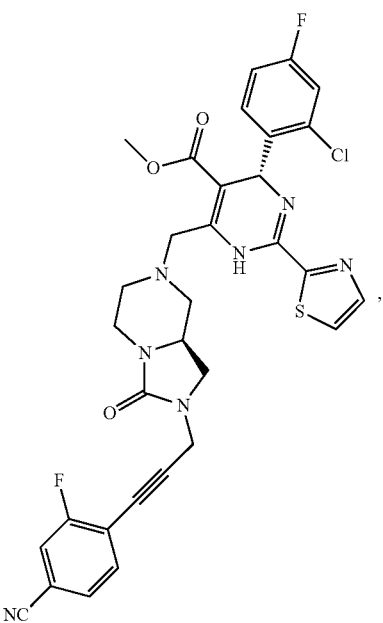

447
-continued
(69)
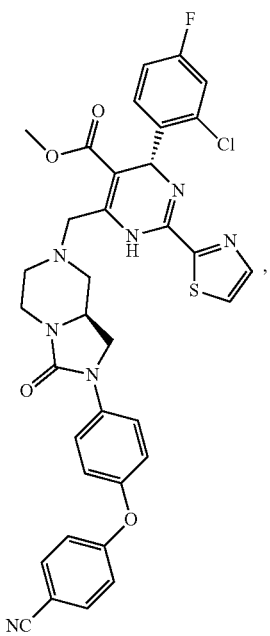
448
-continued
(71)
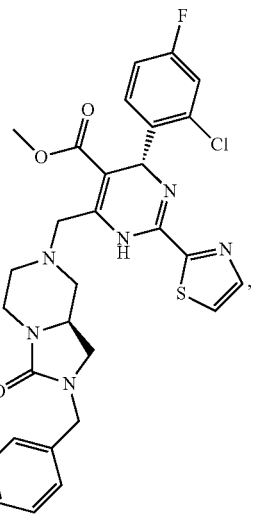
(70)
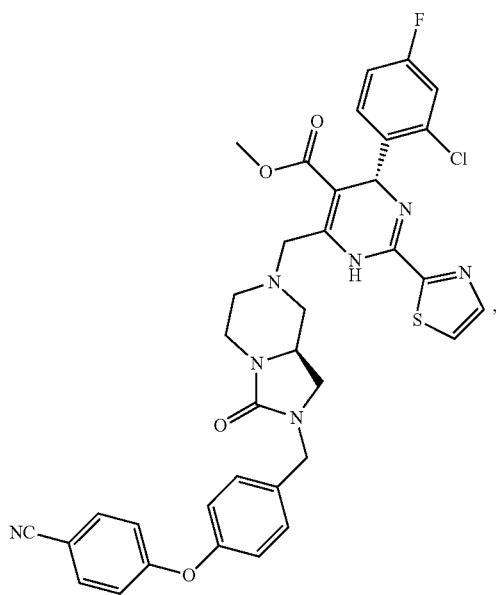
(72)

449
-continued
(73)
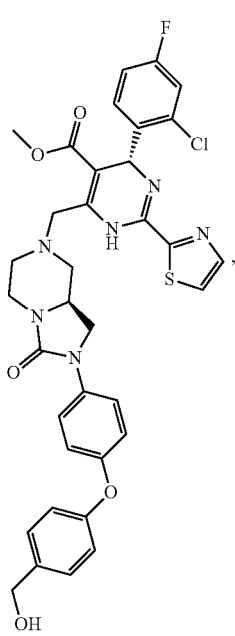
(74)
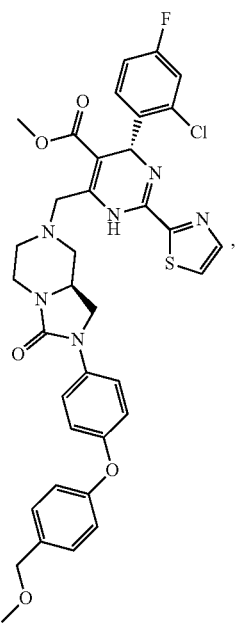
450
-continued
(75)
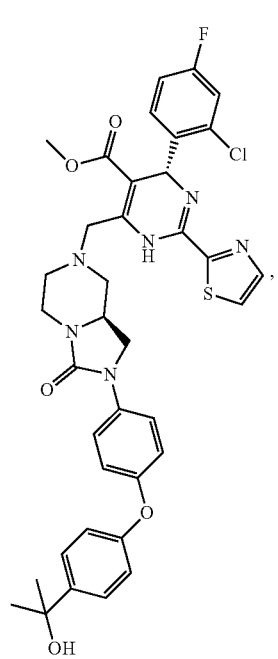
(76)
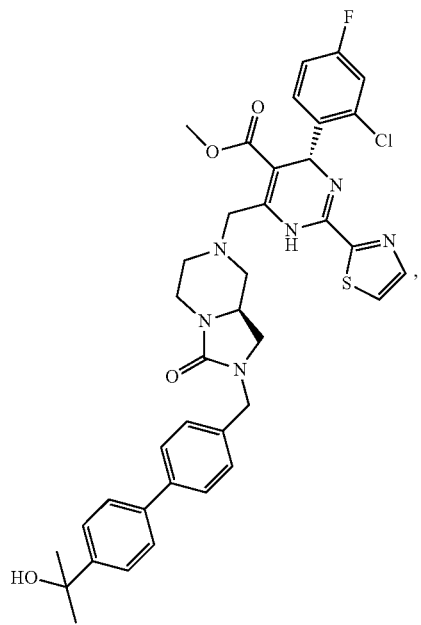

451
-continued
(77)
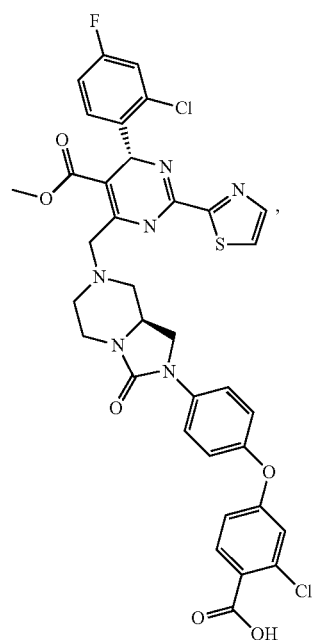
(78)
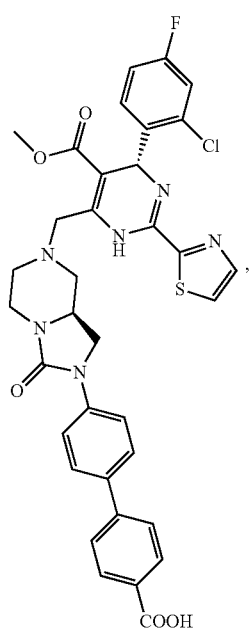
452
-continued
(79)
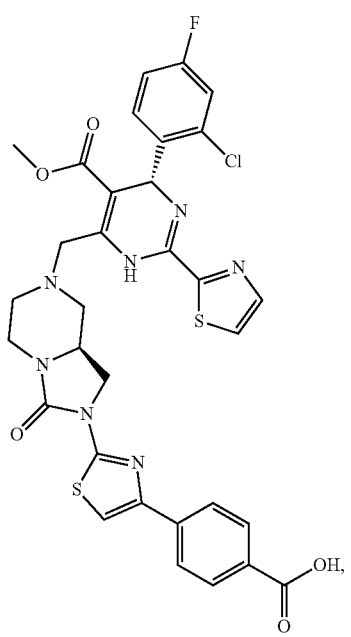
(80)
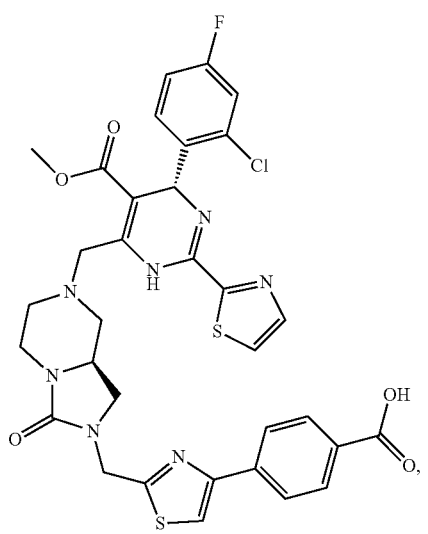

453
-continued
(81)
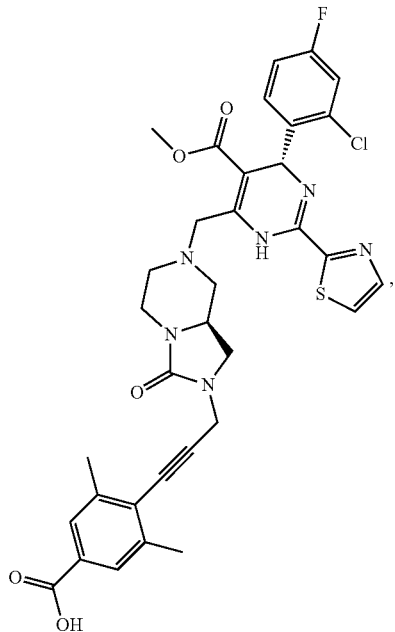
(82)
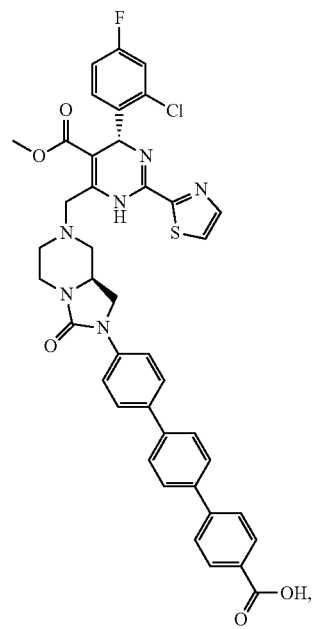
454
-continued
(83)
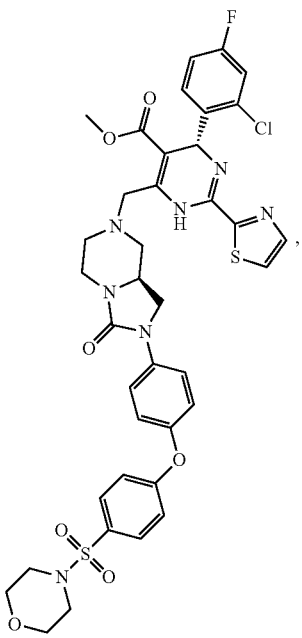
(84)
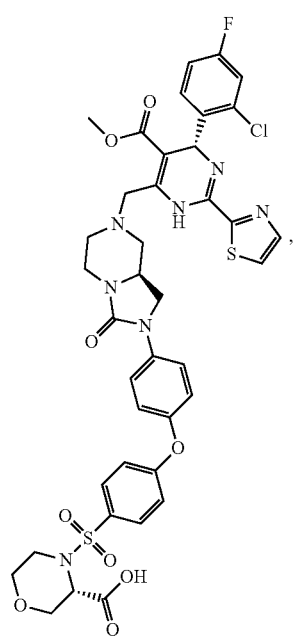

(85)
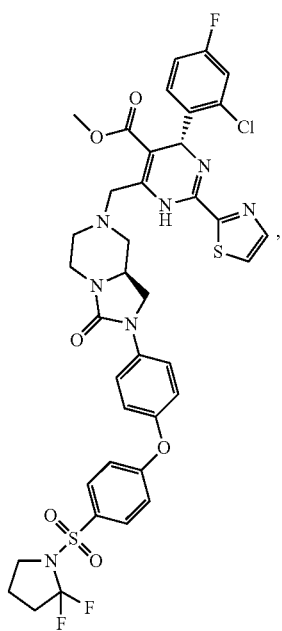
(86)
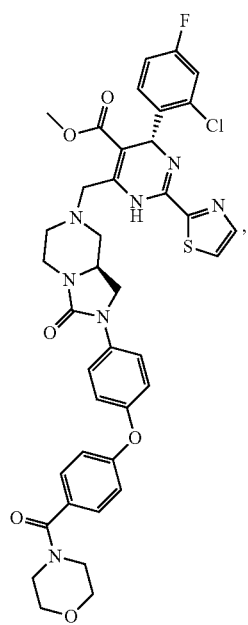
(87)
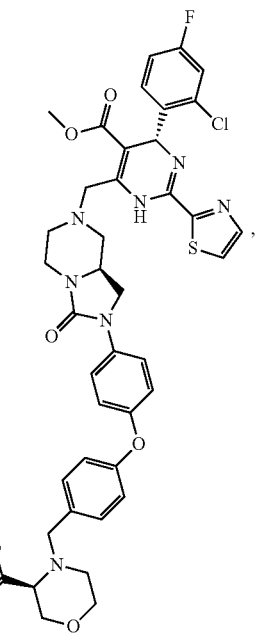
(88)
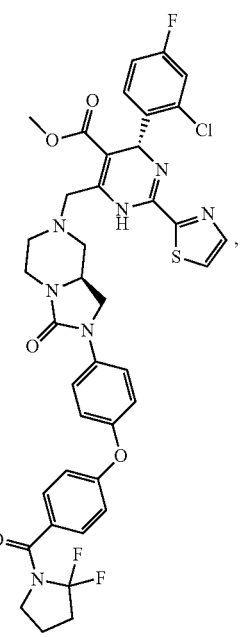

457
-continued
(89)
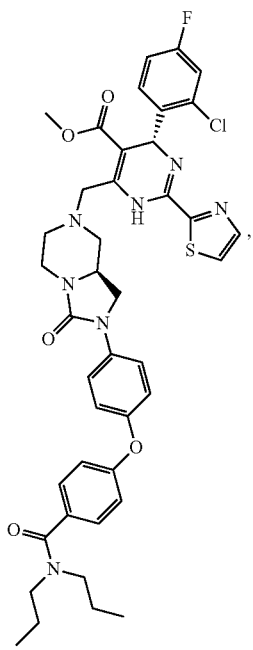
458
-continued
(91)
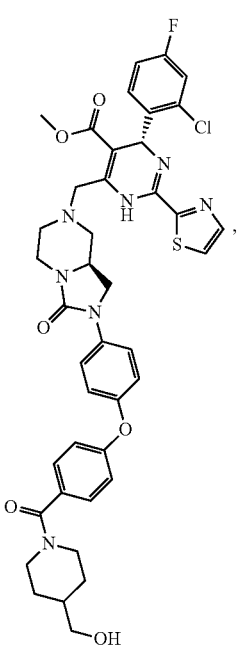
(90)
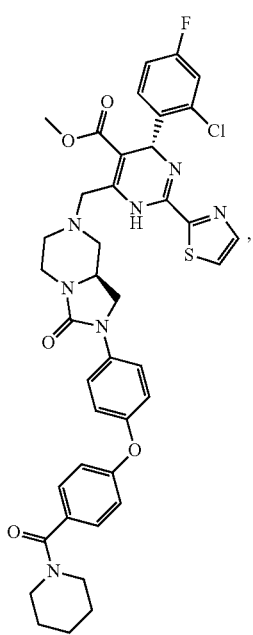
(92)
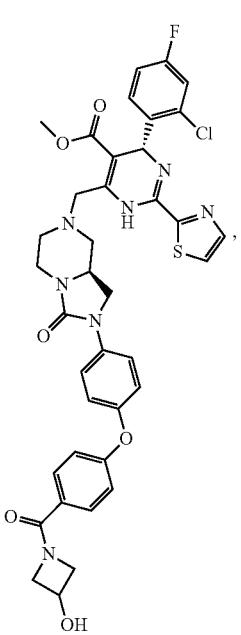

459
-continued
(93)
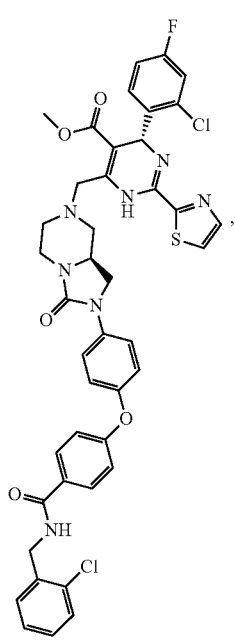
460
-continued
(95)
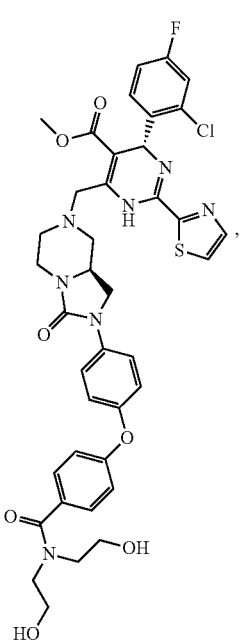
(94)
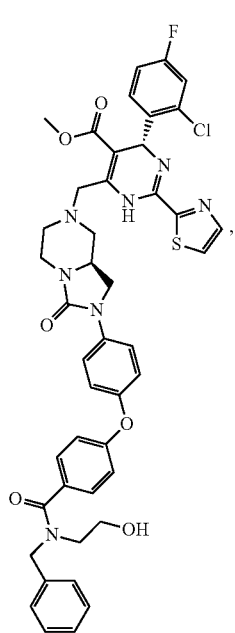
(96)
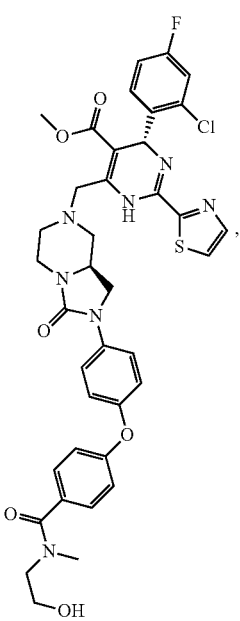

461
-continued
(97)
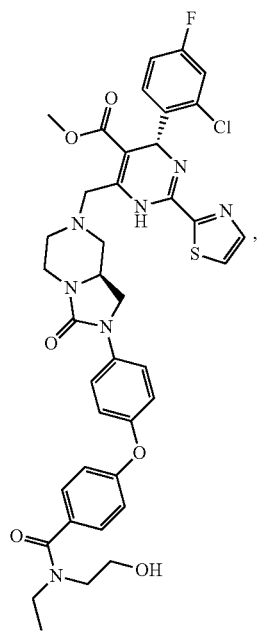
462
-continued
(99)
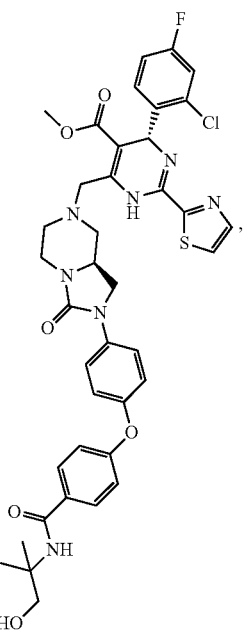
(98)
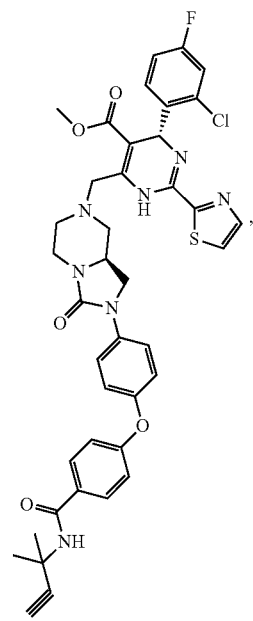
(100)
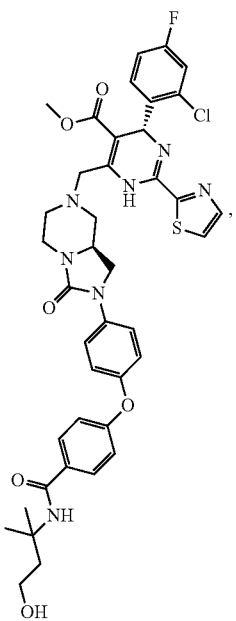

463
-continued
(101)
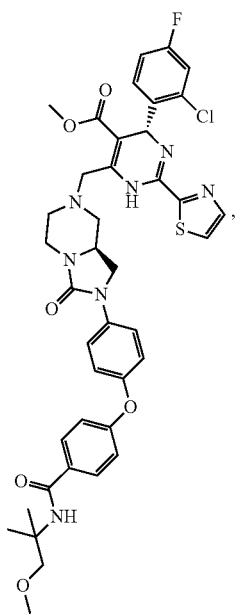
464
-continued
(103)
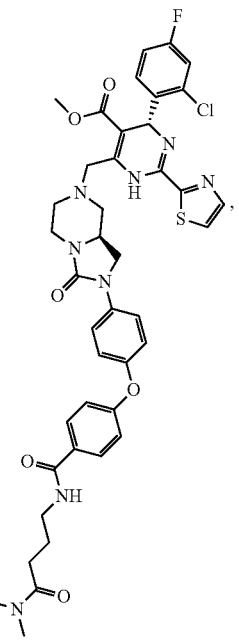
(102)
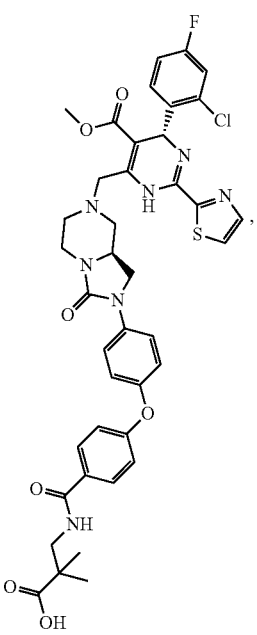
(104)
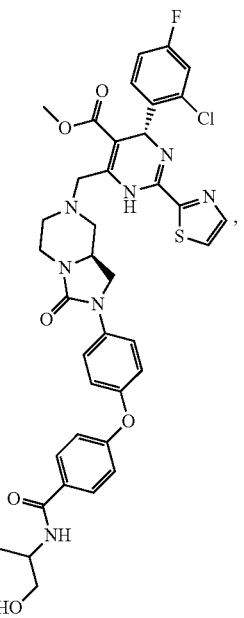

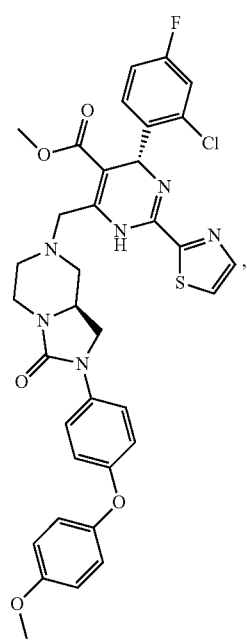
(105)
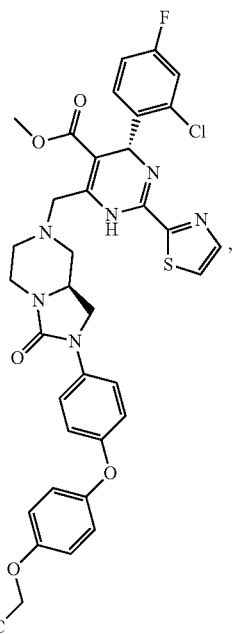
(107)
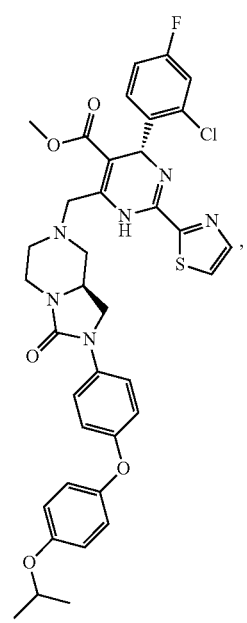
(106)
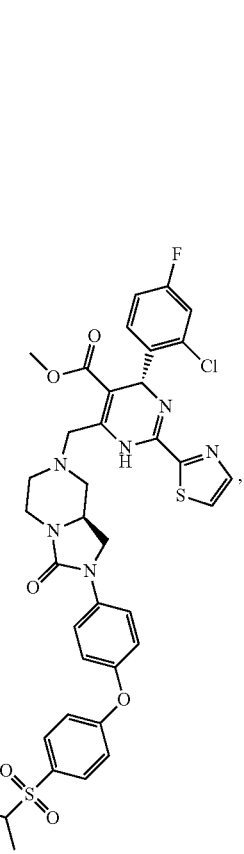
(108)

467
-continued
(109)
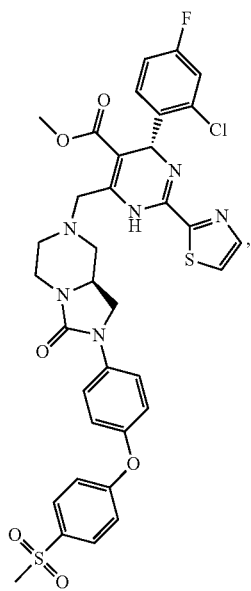
(111)
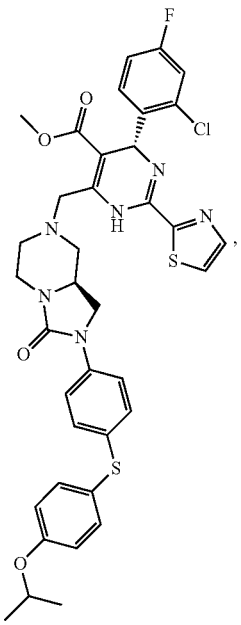
(110)
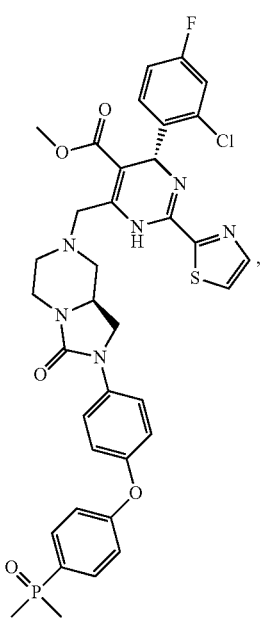
(112)
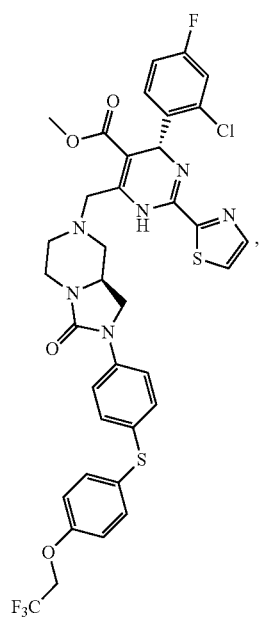

-continued
(113)
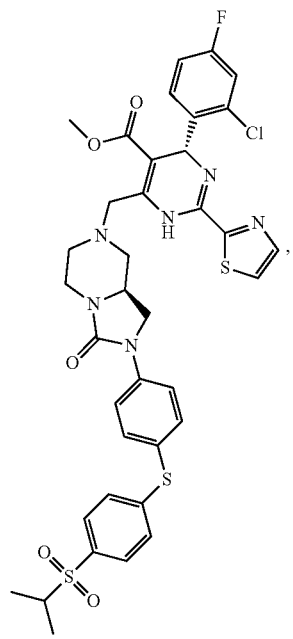
(114)
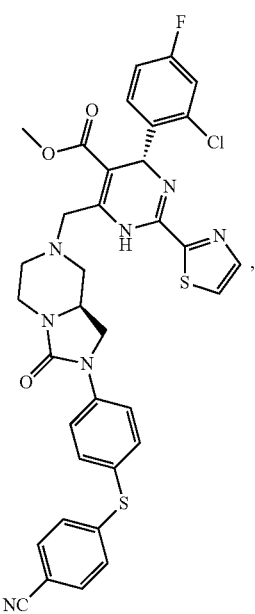
(115)
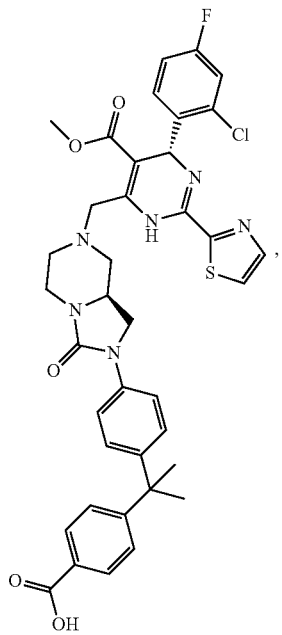
(116)
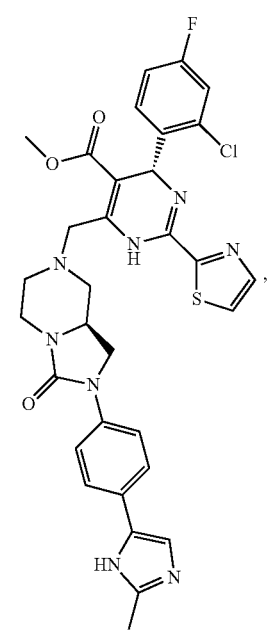

(117)
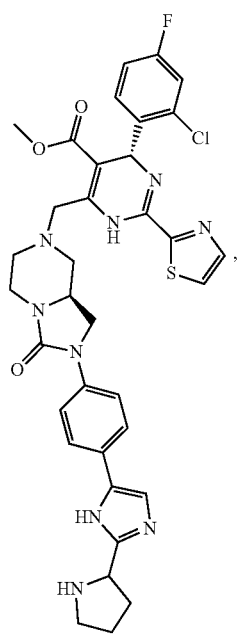
(118)
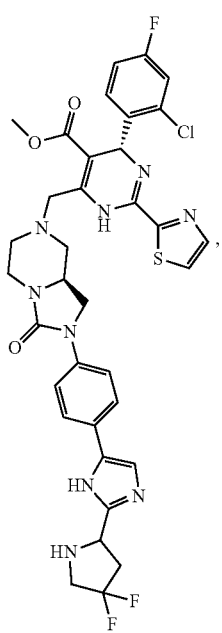
(119)
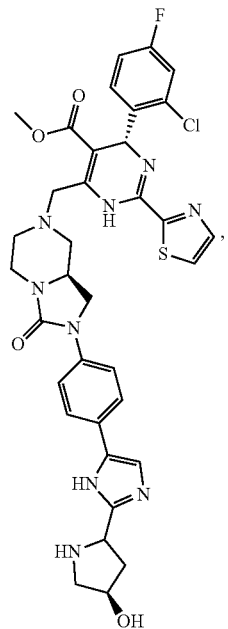
(120)
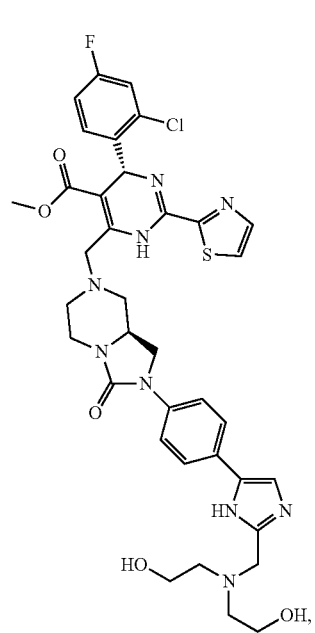

473
-continued
(121)
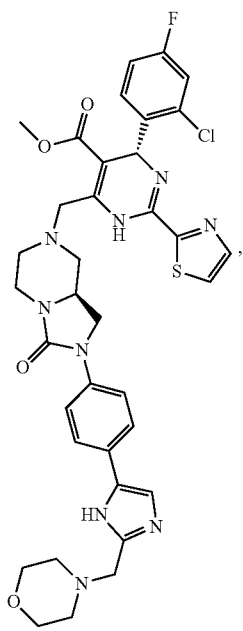
474
-continued
(123)
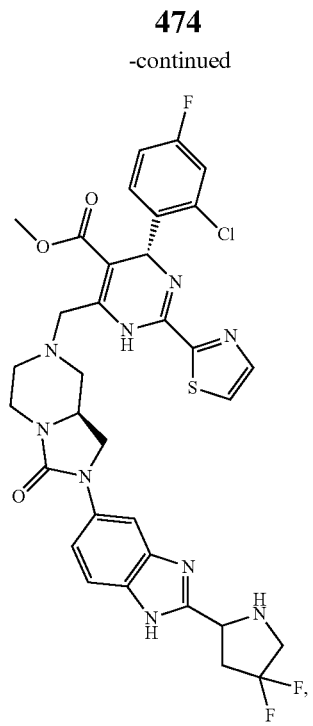
(122)
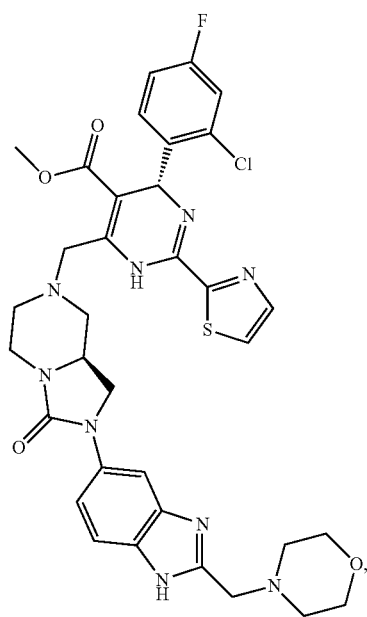
(124)
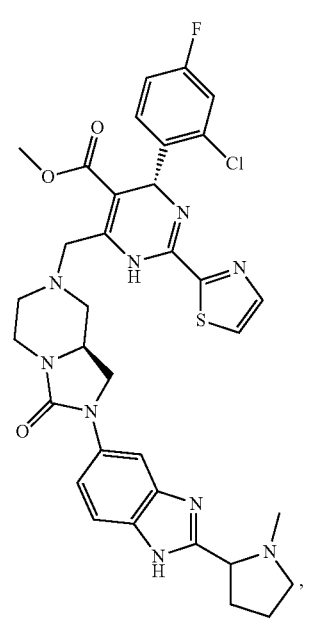

475
-continued
(125)
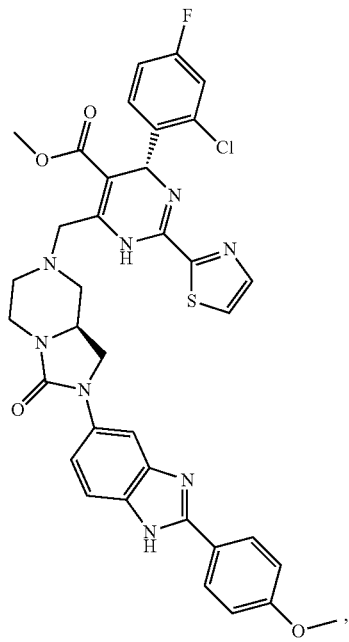
476
-continued
(127)
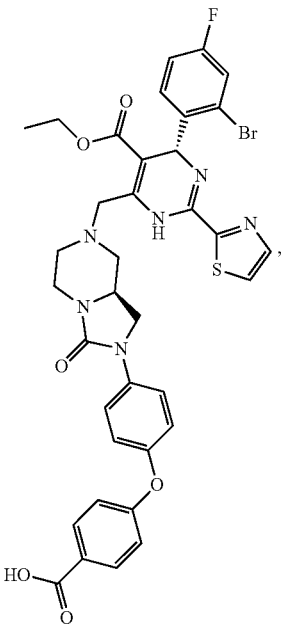
(126)
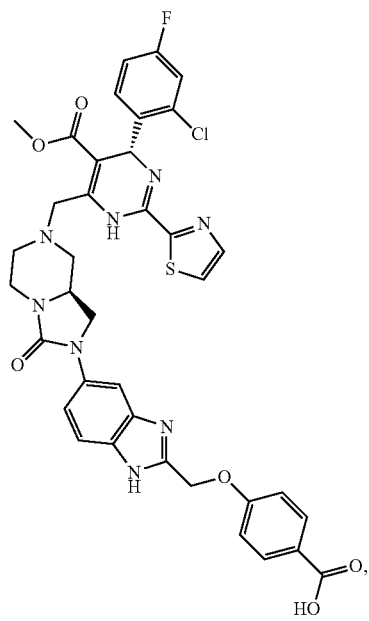
(128)

477
-continued
(129)
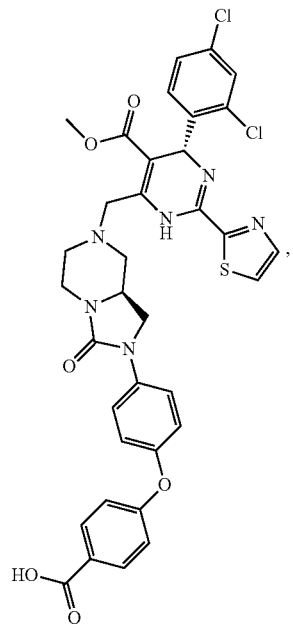
478
-continued
(131)
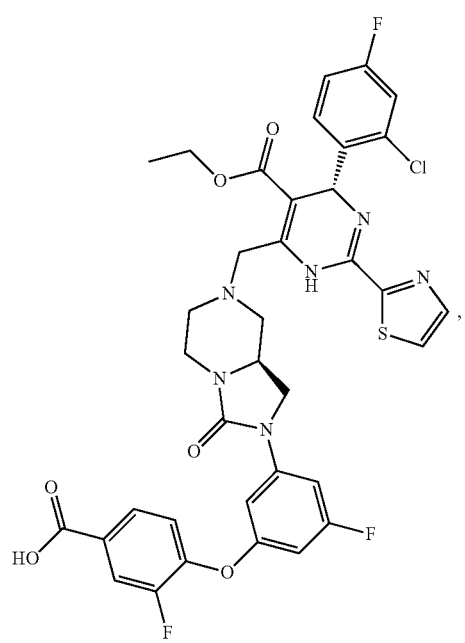
(130)
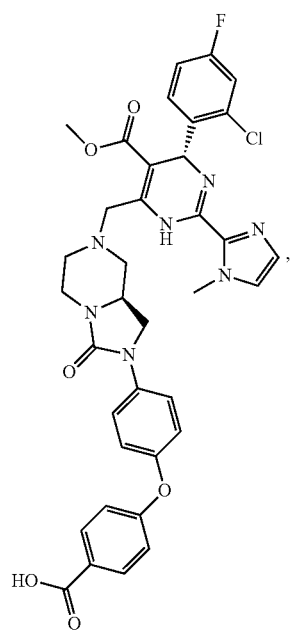
(132)
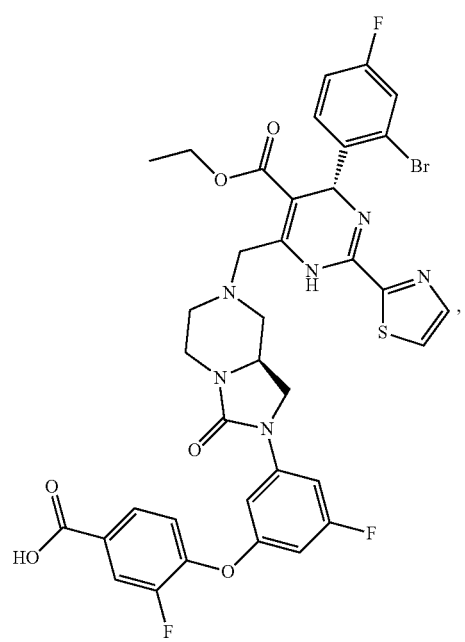

(133)
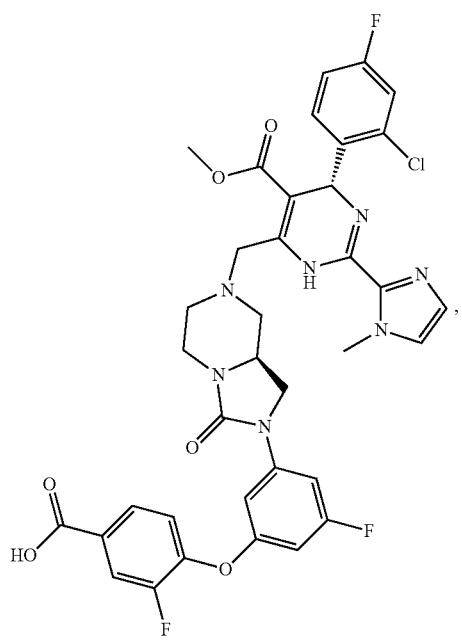
(134)
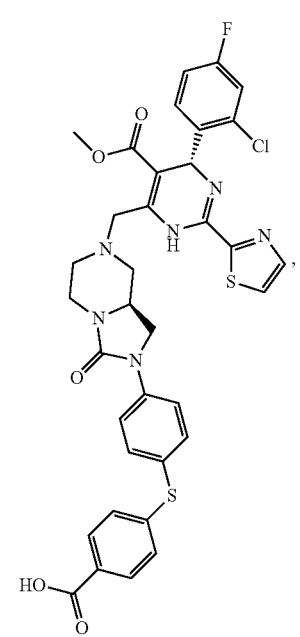
(135)
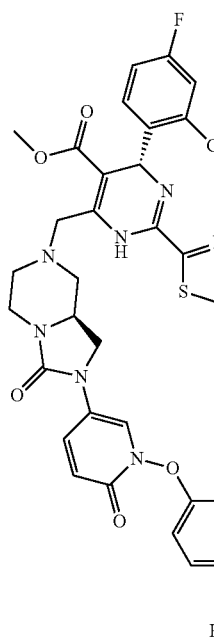
(136)
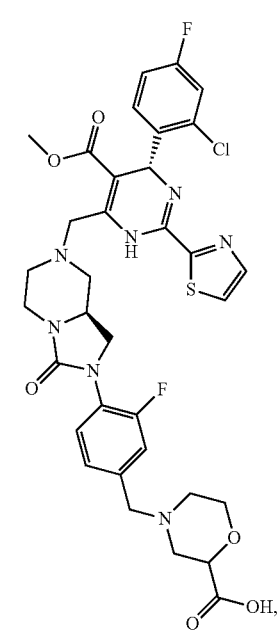

481
-continued
(137)
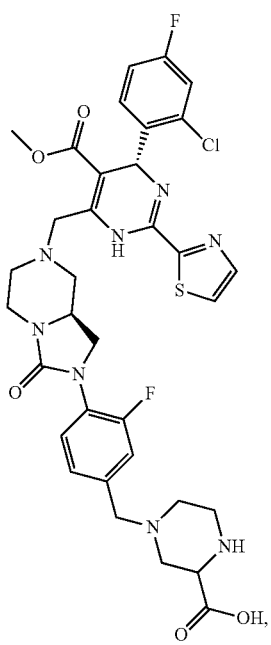
(138)
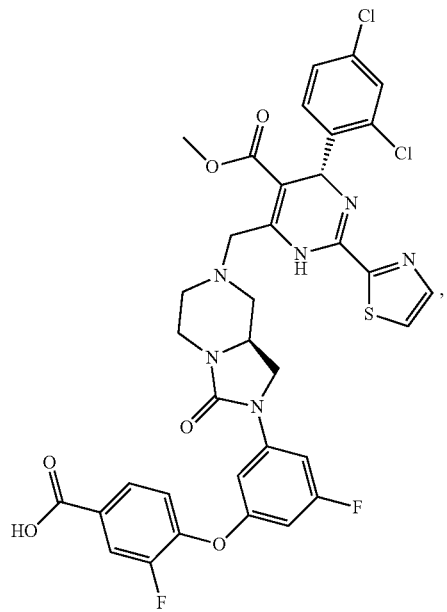
482
-continued
(139)
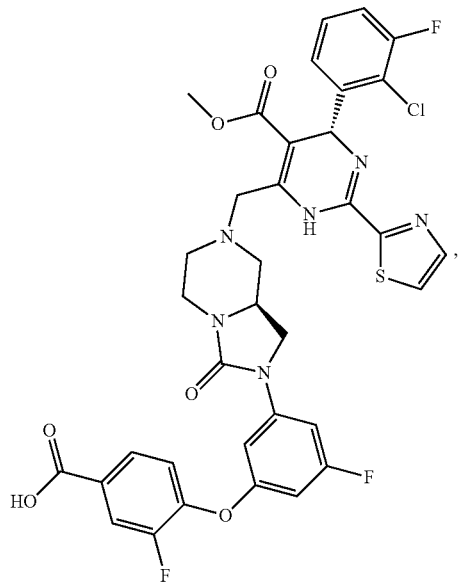
(140)
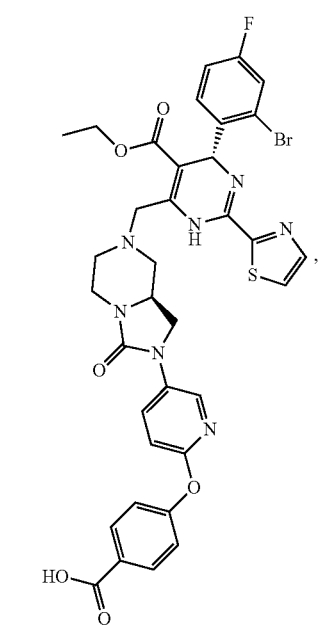

483
-continued
(141)
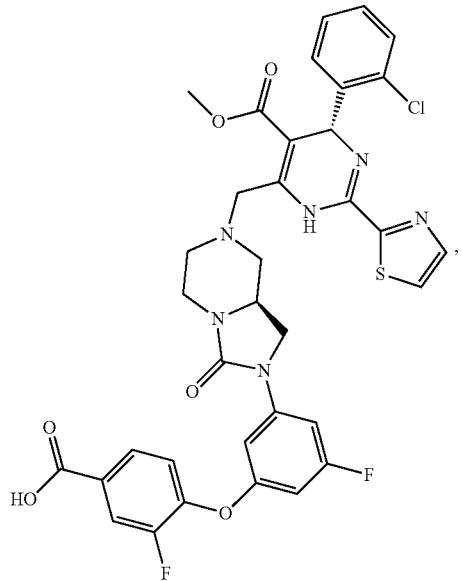
(142)
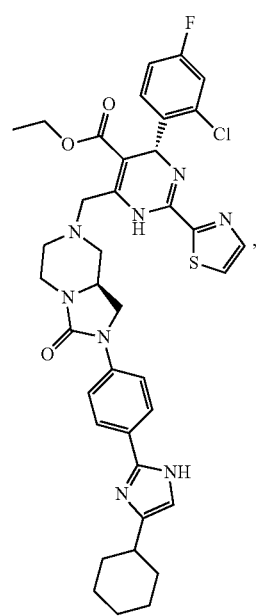
484
-continued
(143)
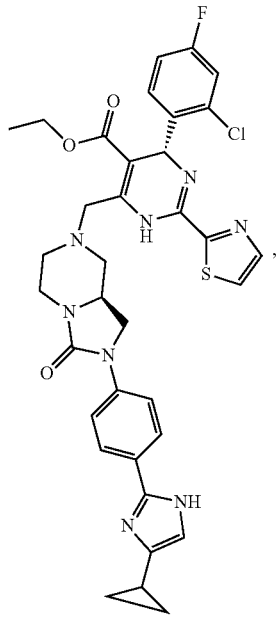
(144)
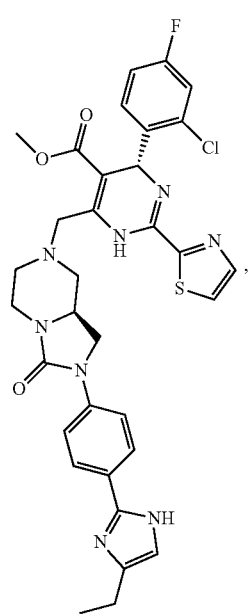

(145)
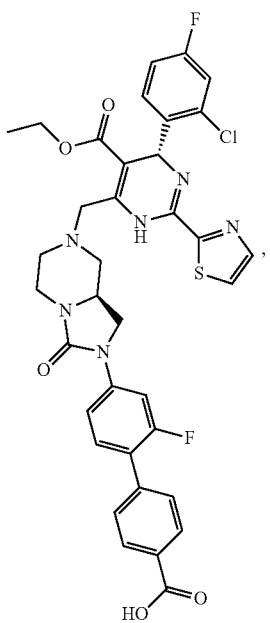
(146)
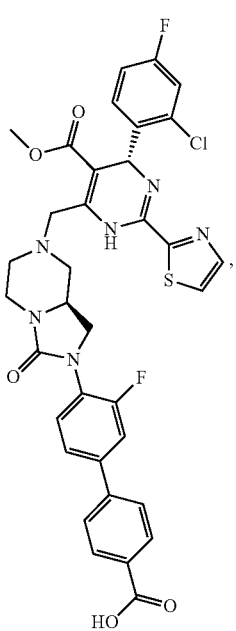
(147)
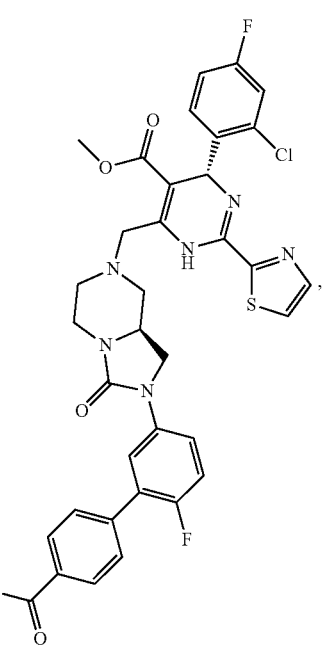
(148)
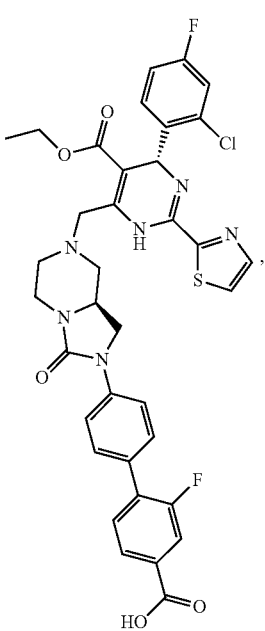

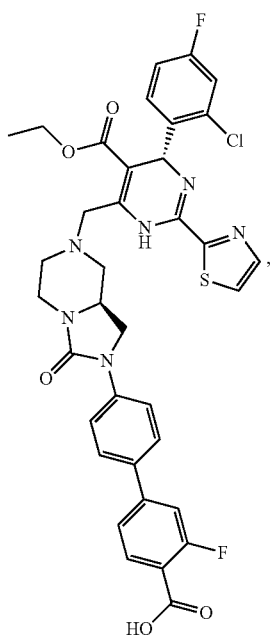
(149)
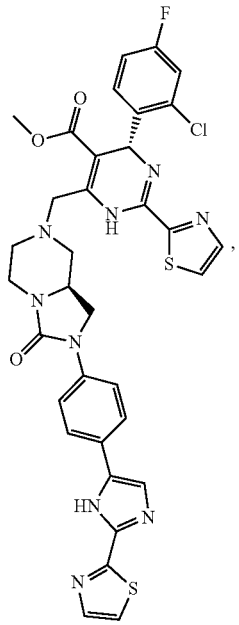
(151)
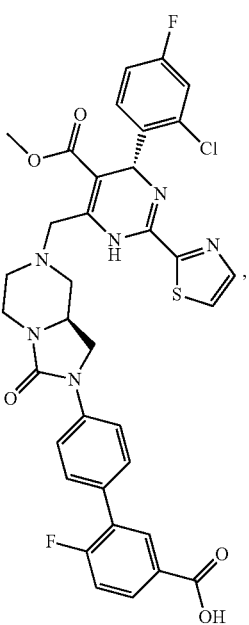
(150)
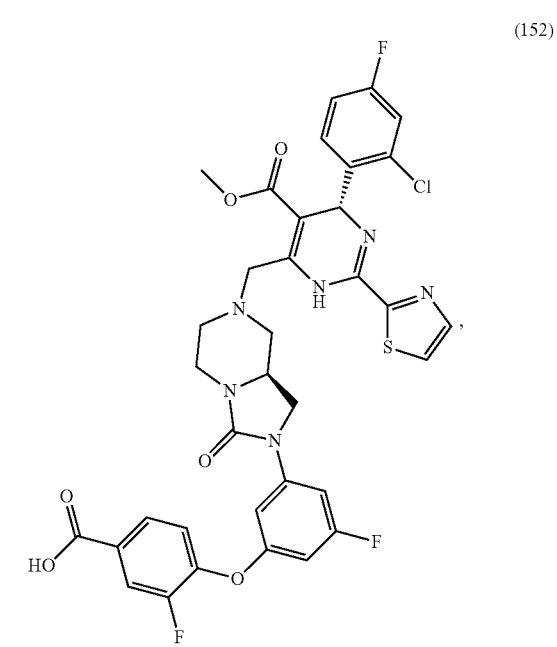
(152)

489
-continued
(153)
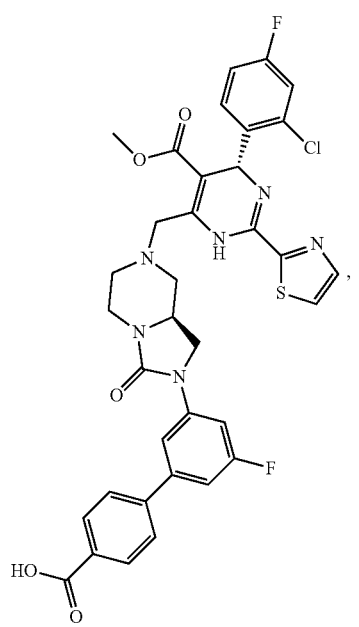
490
-continued
(155)
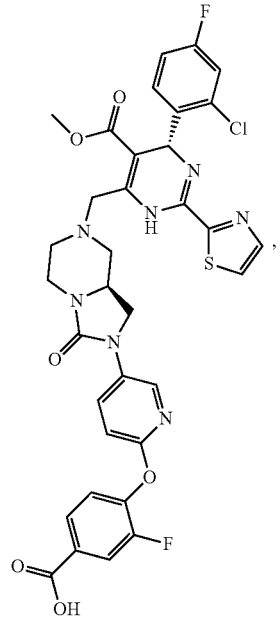
(154)
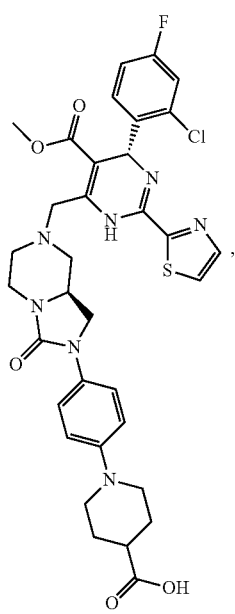
(156)
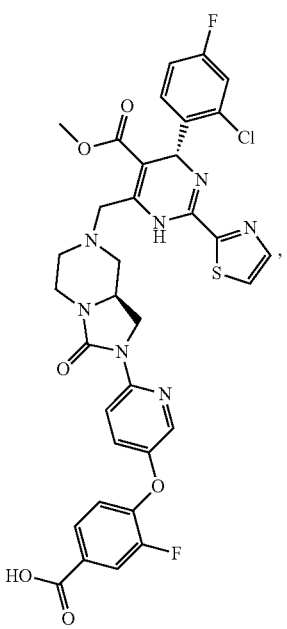

491
-continued
(157)
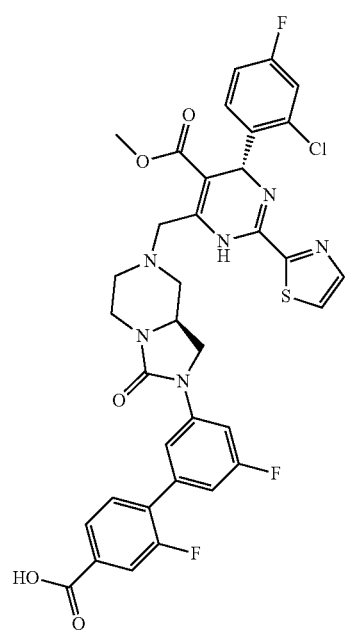
(158)
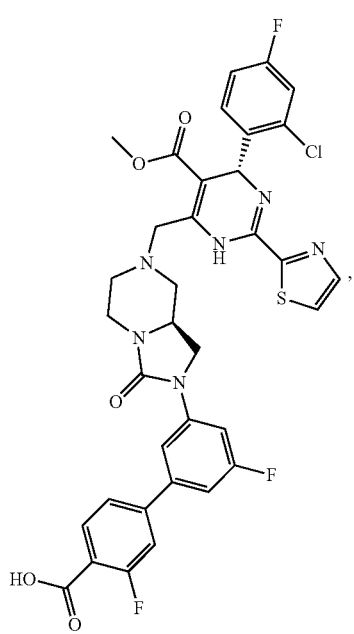
492
-continued
(159)
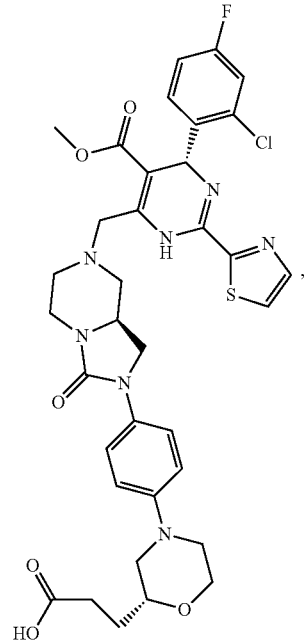
(160)
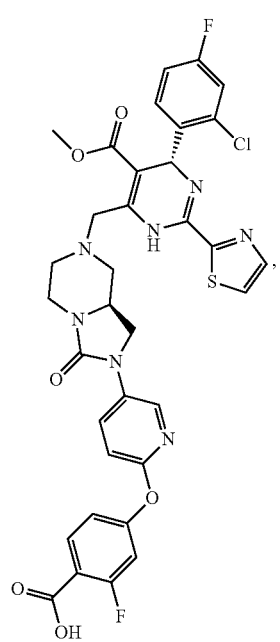

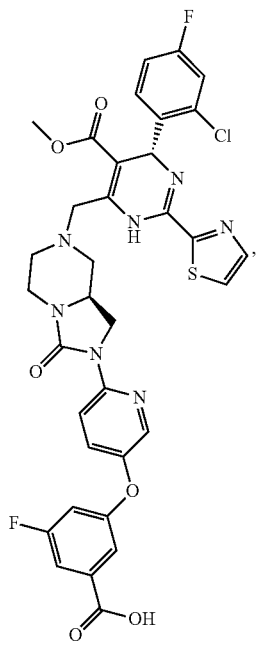
(161)
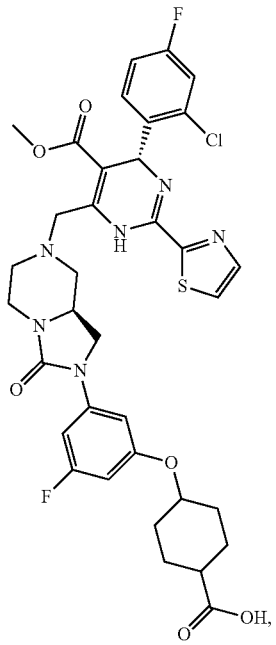
(163)
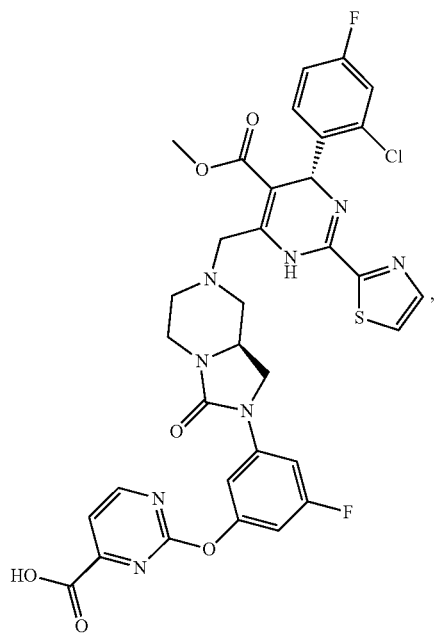
(162)
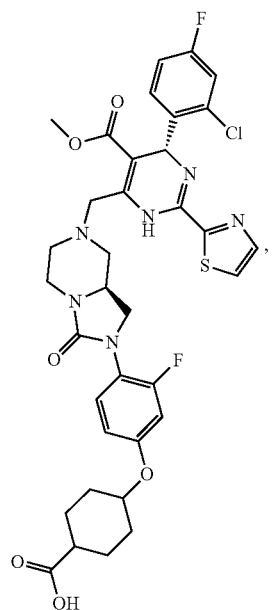
(164)

495
-continued
(165)
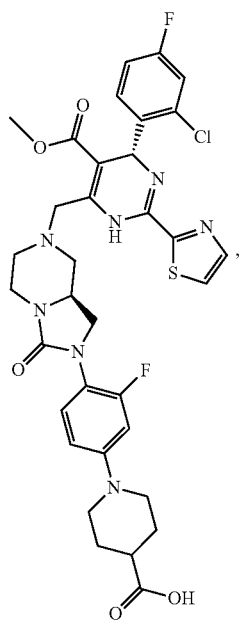
(166)
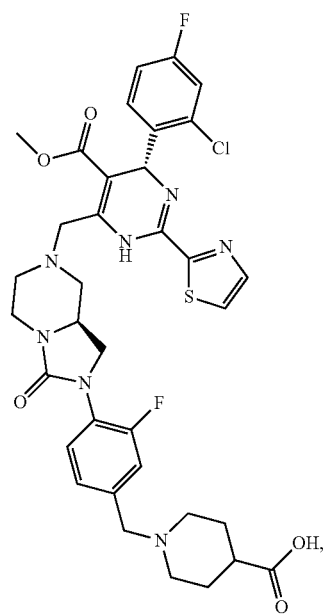
496
-continued
(167)
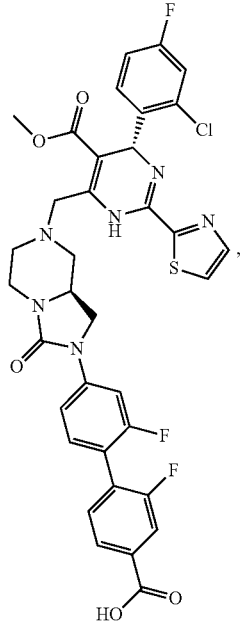
(168)
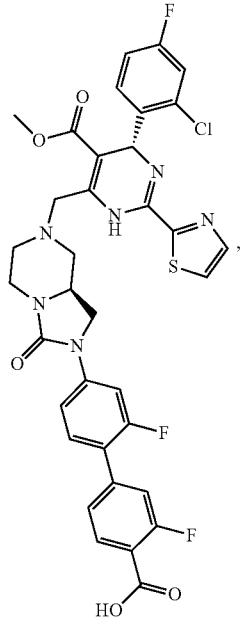

497
-continued
(169)
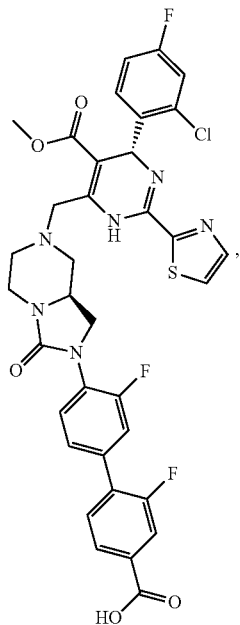
(170)
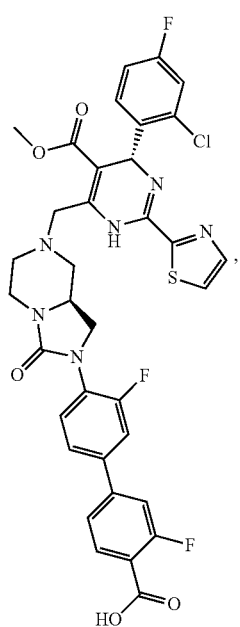
498
-continued
(171)
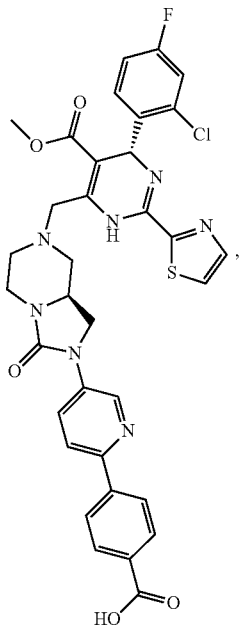
(172)
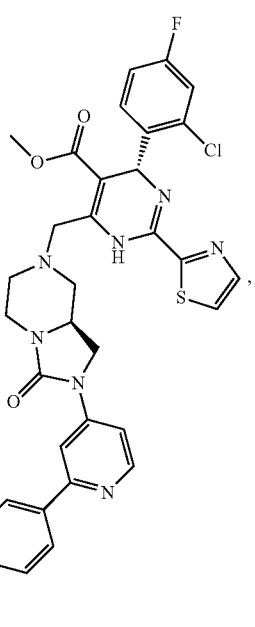

499
-continued
(173)
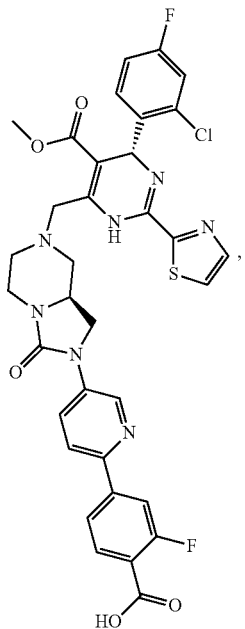
500
-continued
(175)
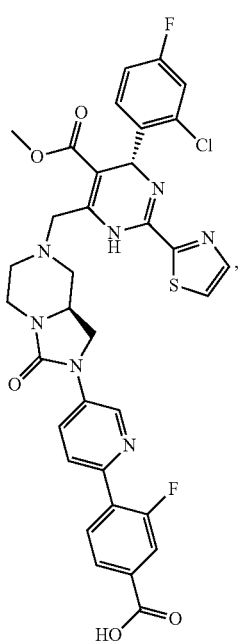
(174)
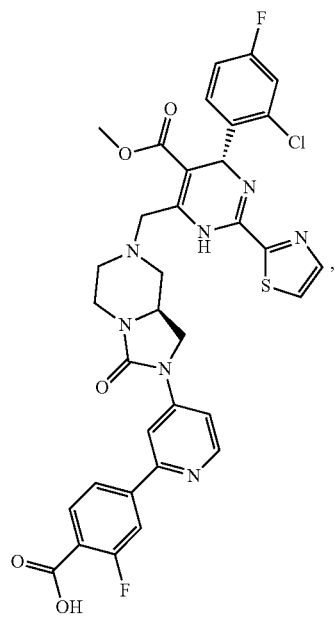
(176)

501
-continued
(177)
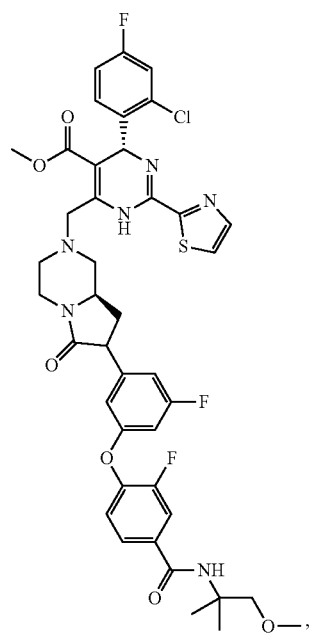
502
-continued
(179)
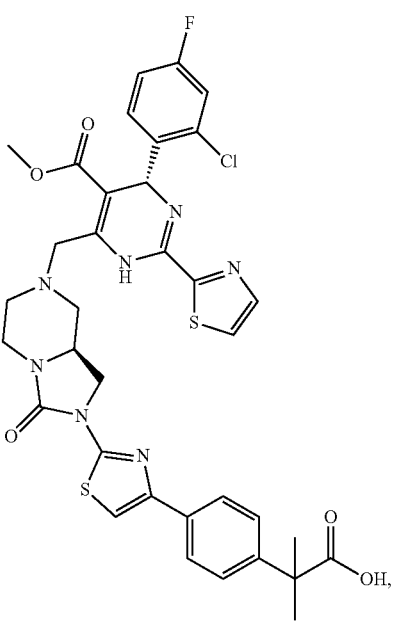
(178)
(180)
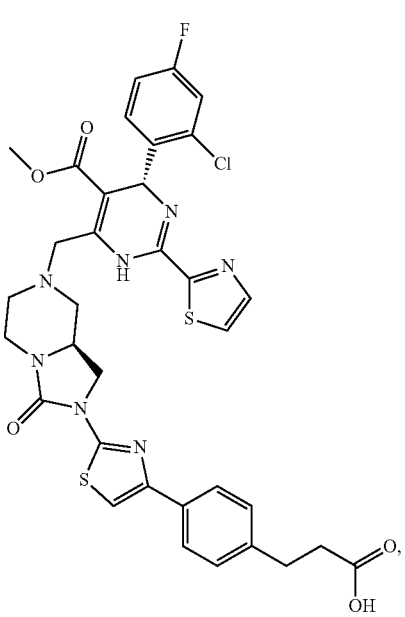

503
-continued
(181)
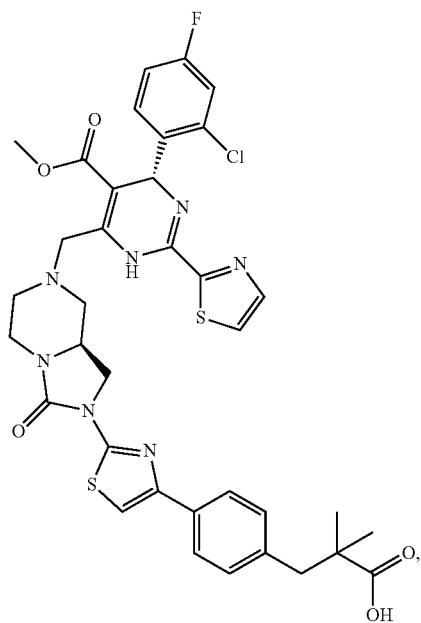
(182)
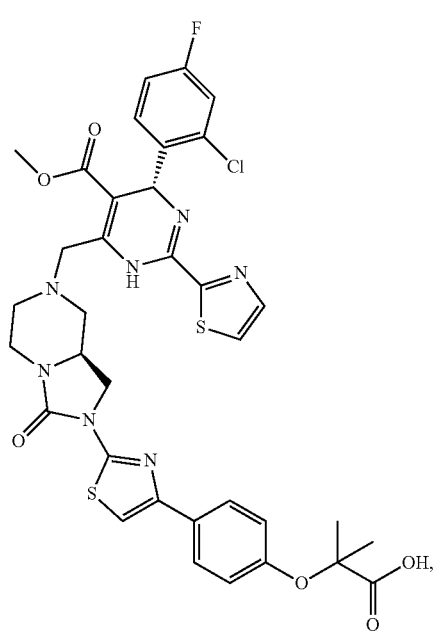
504
-continued
(183)
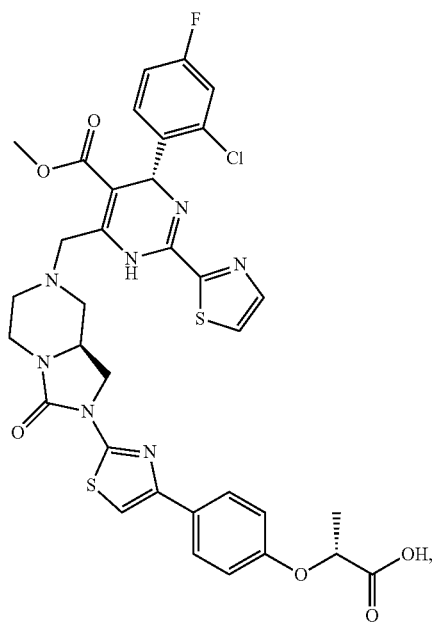
(184)
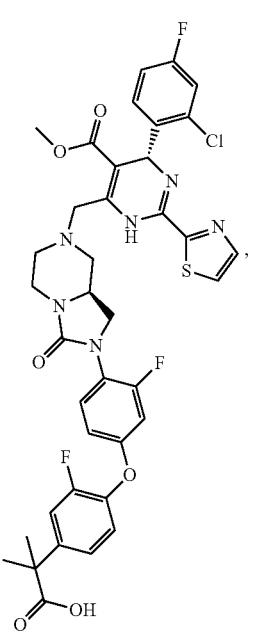

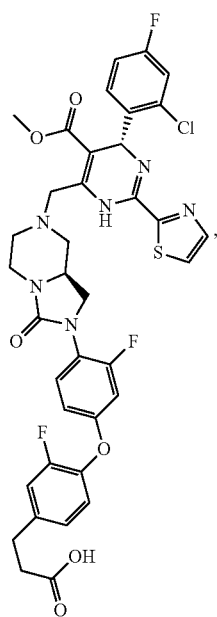
(185)
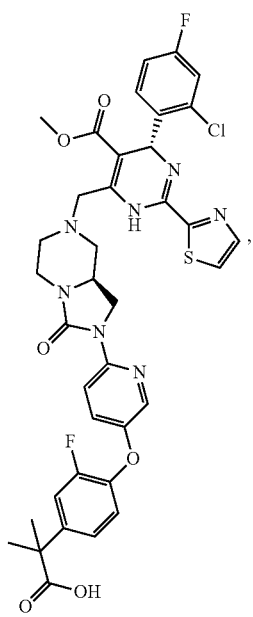
(187)
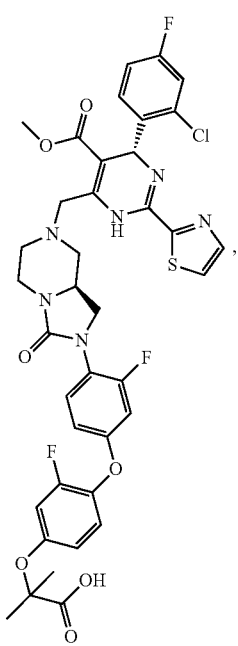
(186)
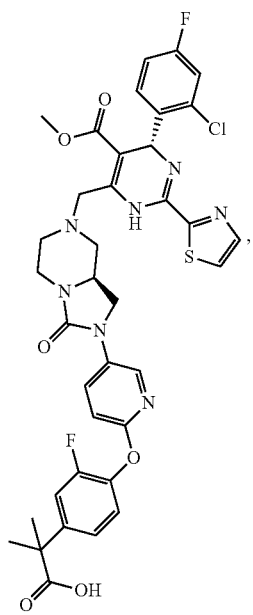
(188)

507
-continued
(189)
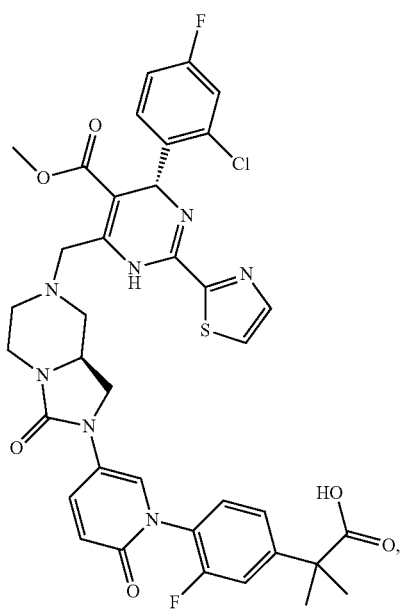
(190)
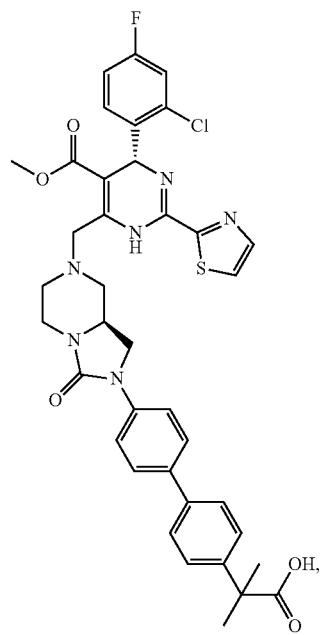
508
-continued
(191)
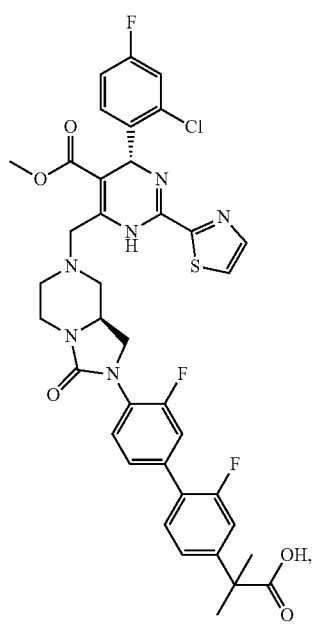
(192)
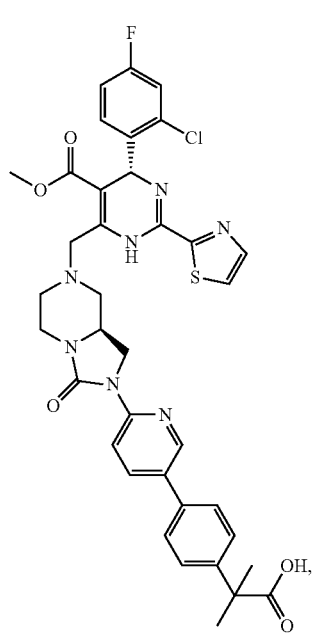

509
-continued
(193)
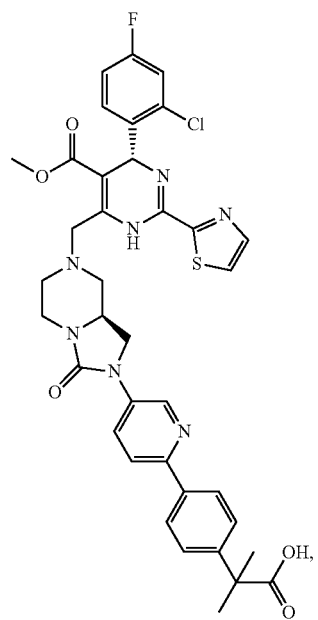
510
-continued
(195)
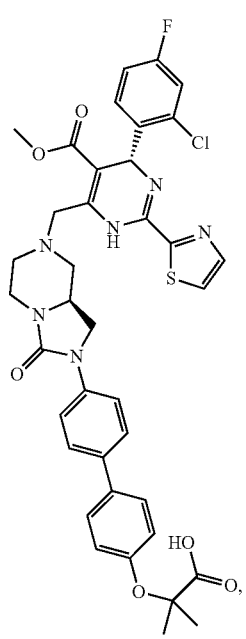
(194)
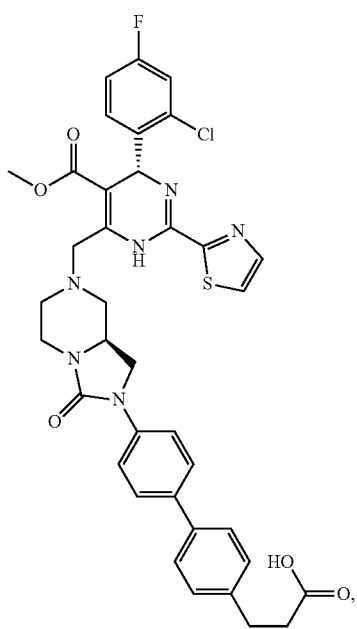
(196)
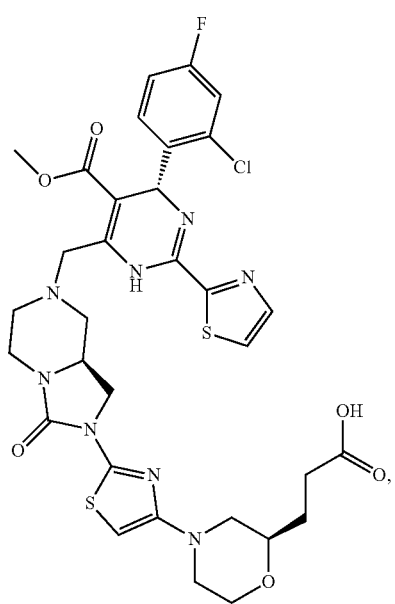

511
-continued
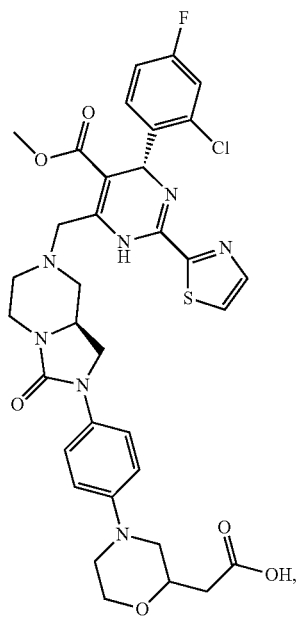
(197)
512
-continued
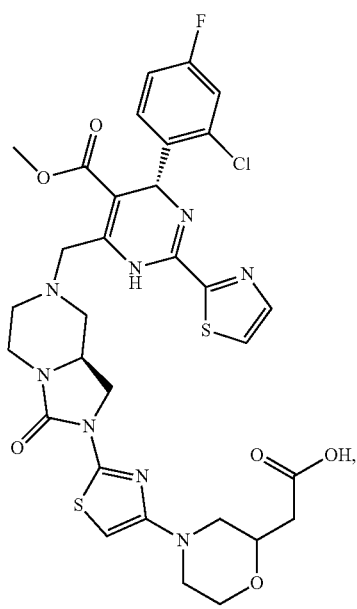
(199)
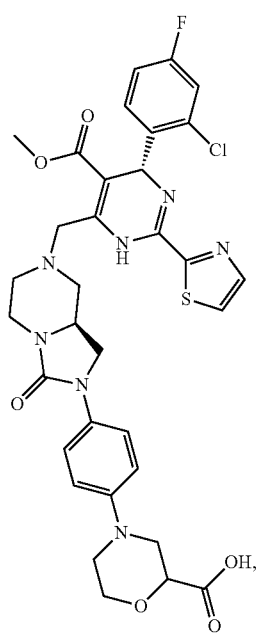
(198)
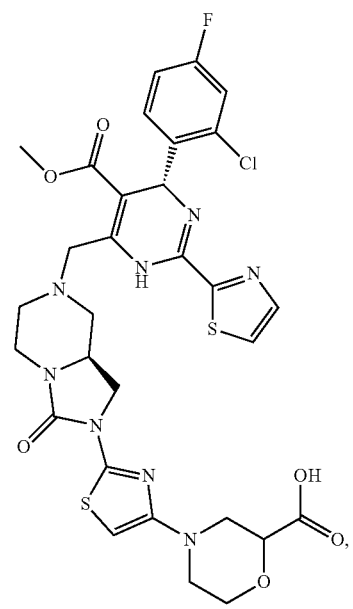
(200)

(201)
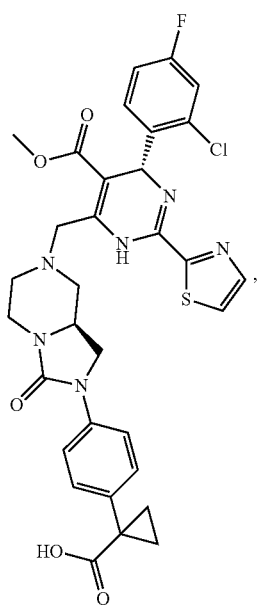
(203)
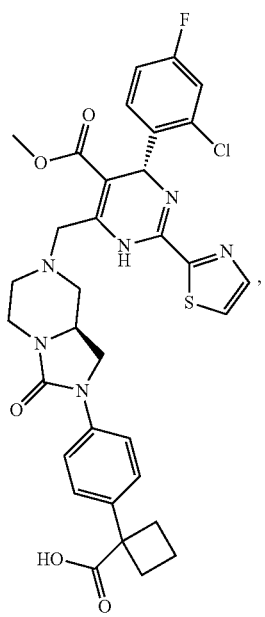
(202)
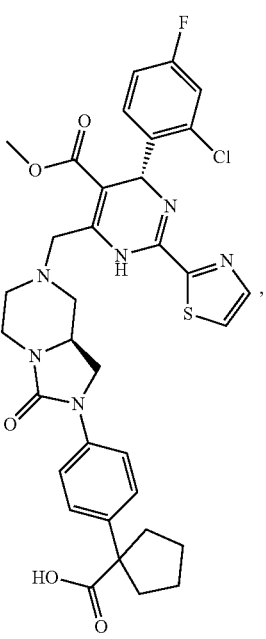
(204)
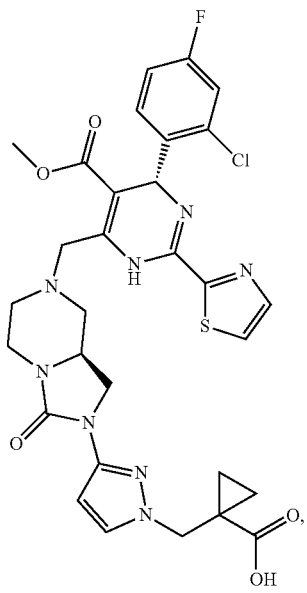

-continued
(205)
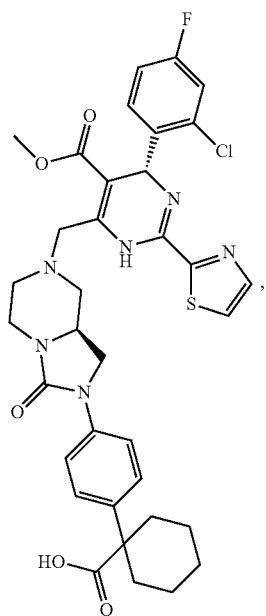
(206)
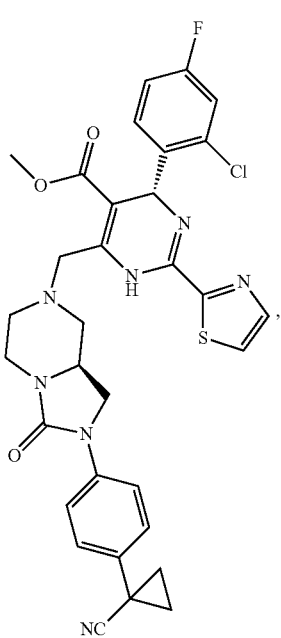
-continued
(207)
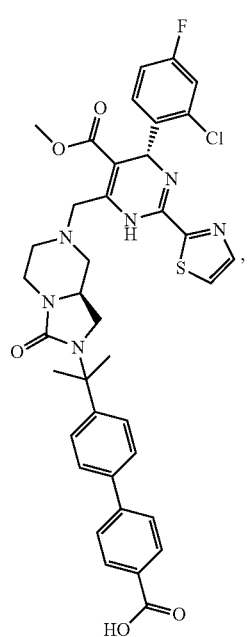
(208)
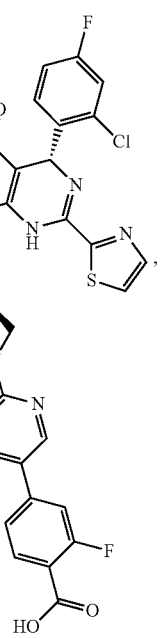

517
-continued
(209)
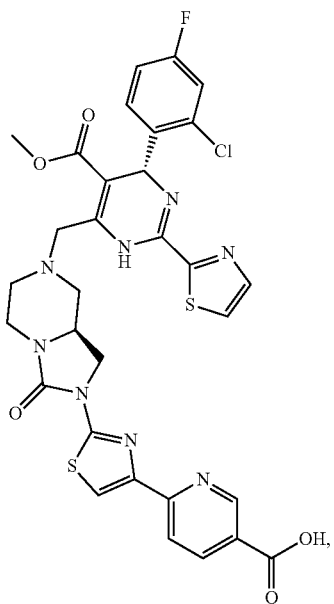
(210)
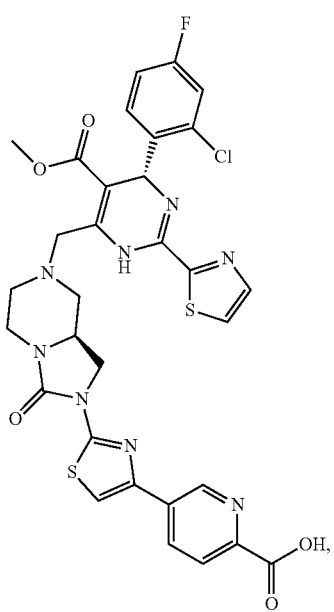
518
-continued
(211)
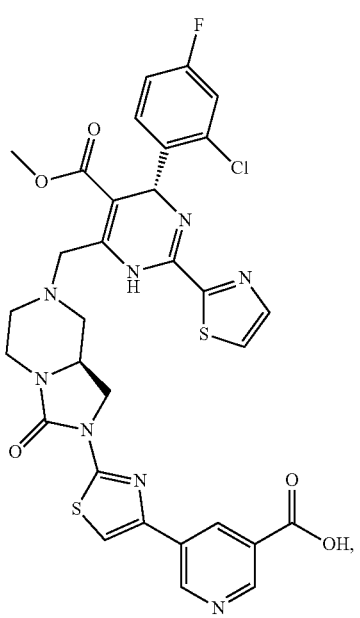
(212)
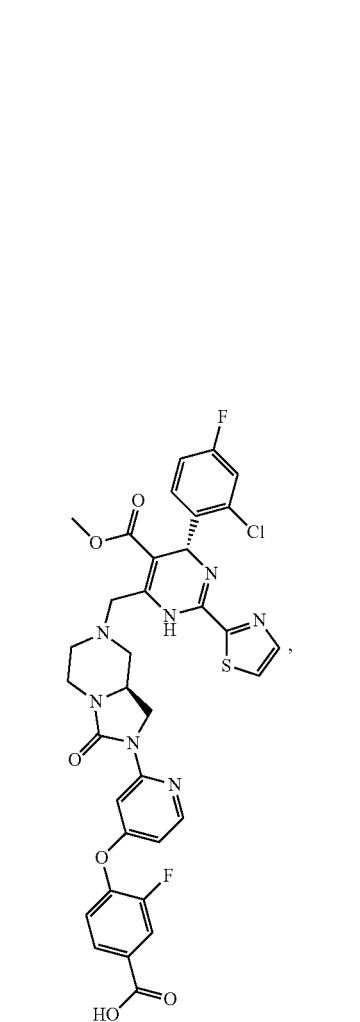

519
-continued
(213)
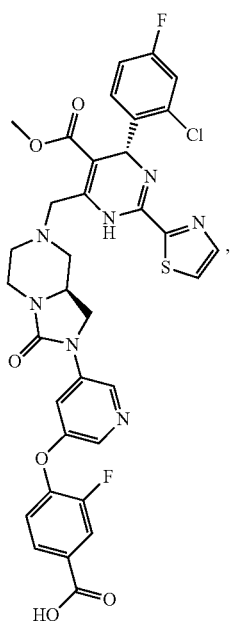
(214)
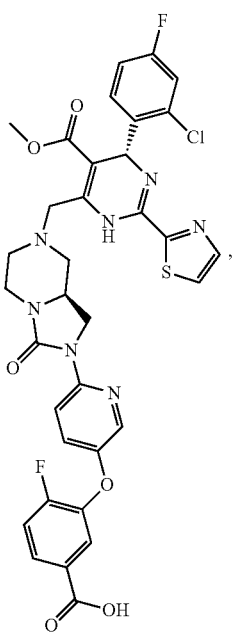
520
-continued
(215)
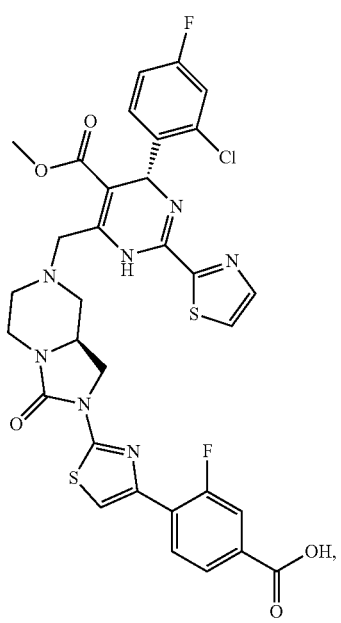
(216)
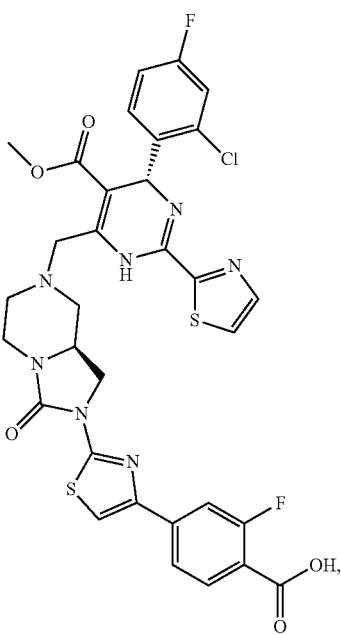

521
-continued
(217)
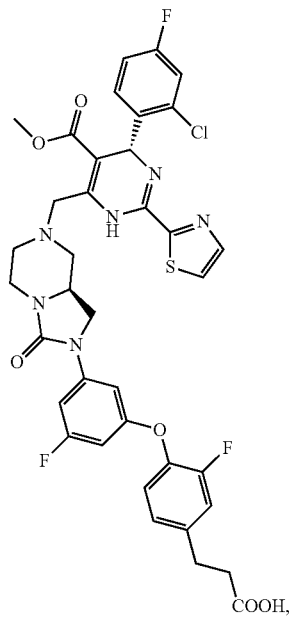
522
-continued
(219)
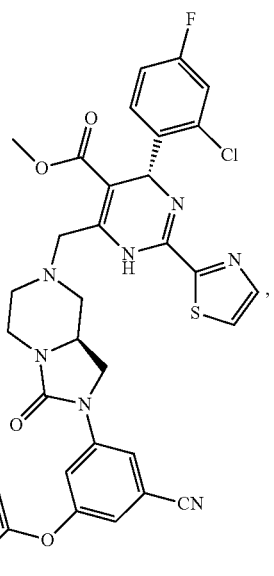
(218)
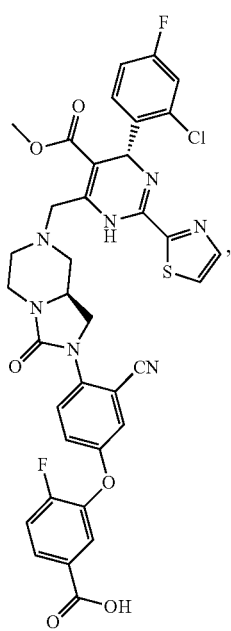
(220)
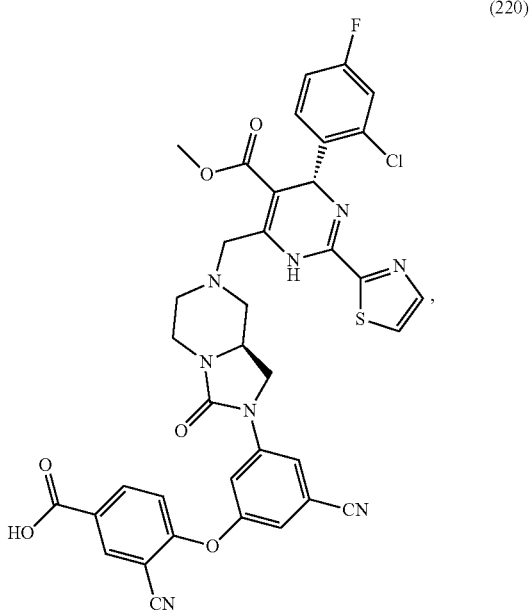

523
-continued
524
-continued
(221)
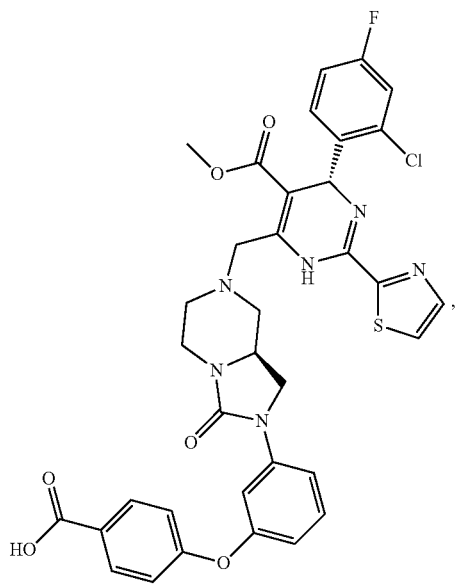
(223)
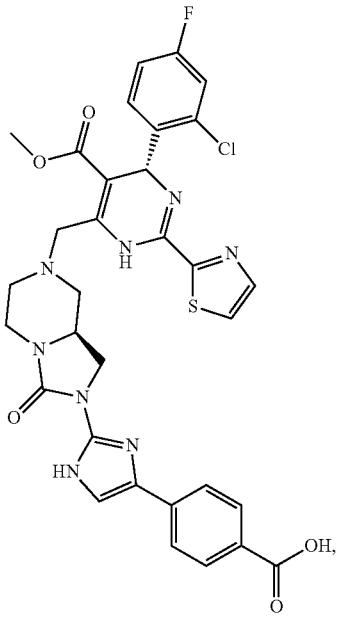
(222)
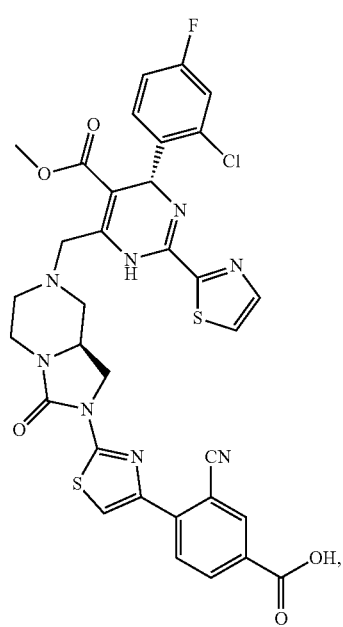
(224)
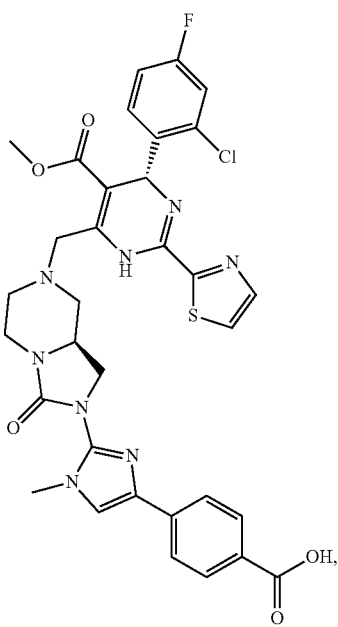

-continued
(225)
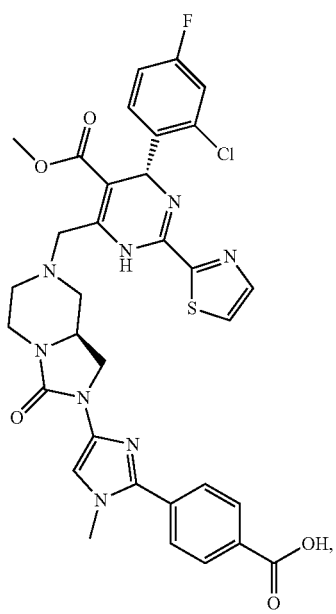
(226)
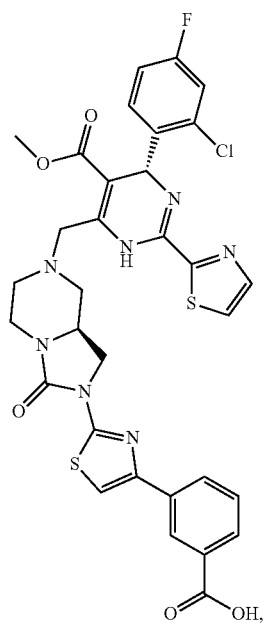
-continued
(227)
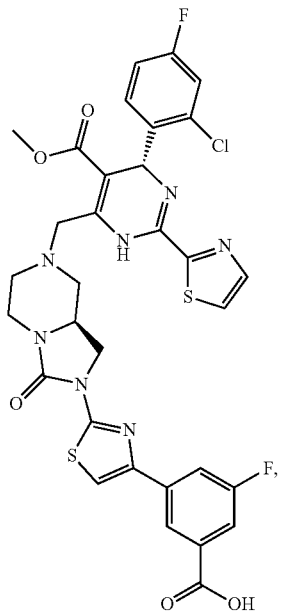
(228)
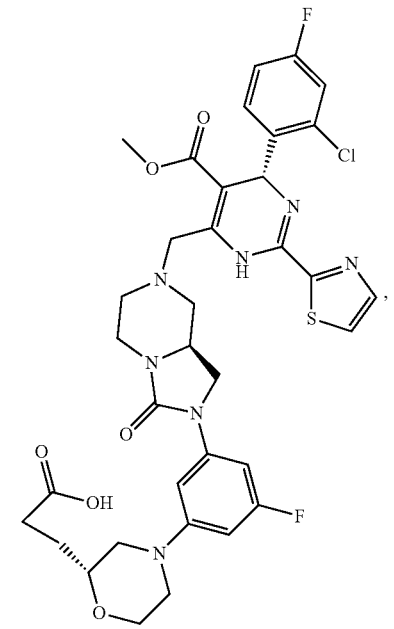

527
-continued
(229)
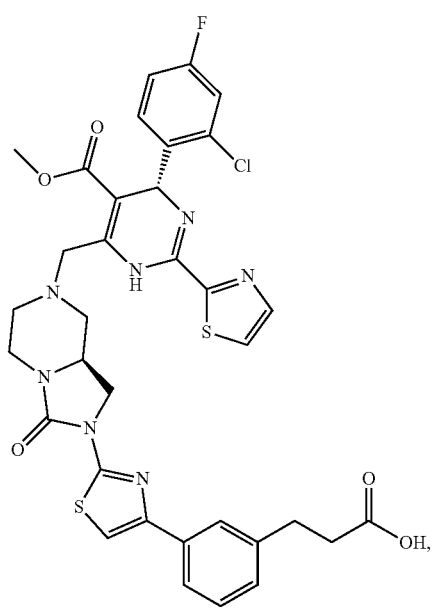
(230)
(231)
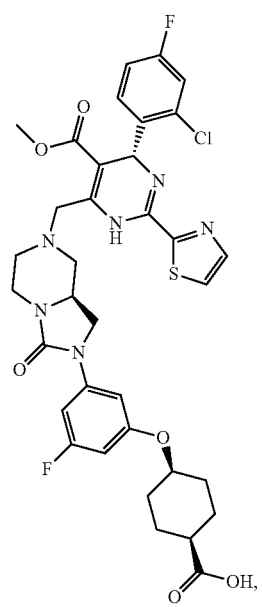
(232)

529
-continued
(233)
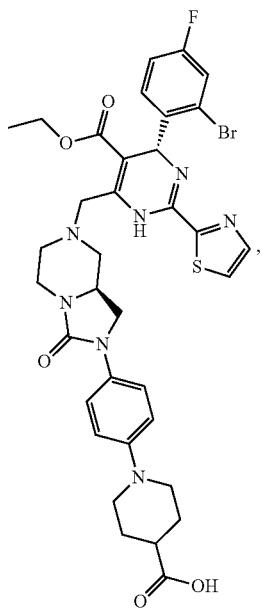
(234)
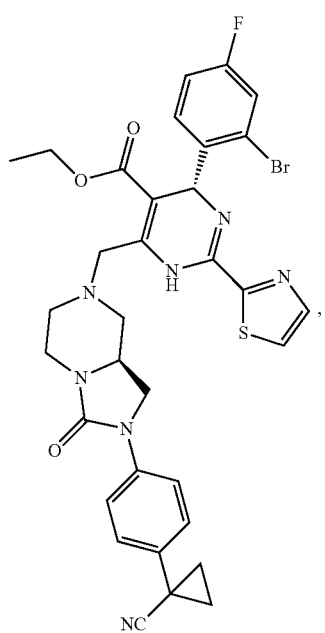
530
-continued
(235)
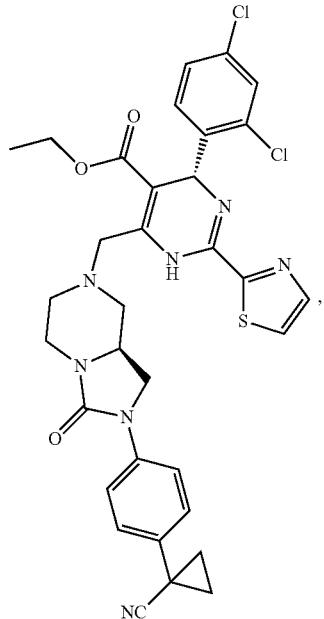
(236)
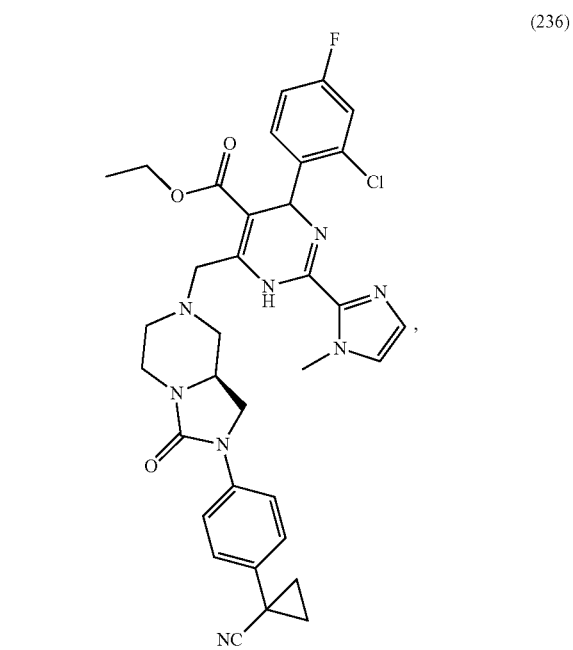

531
-continued
(237)
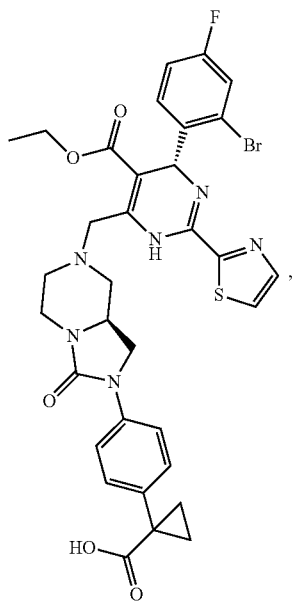
(238)
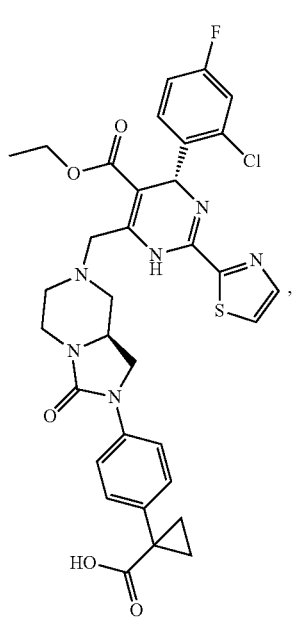
532
-continued
(239)
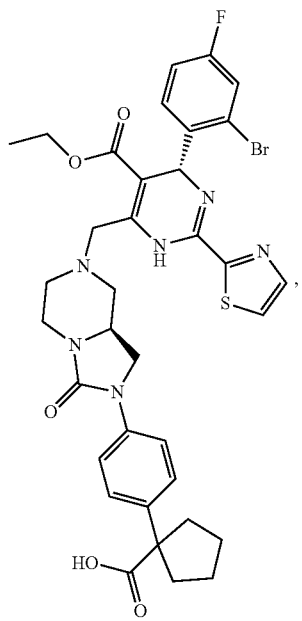
(240)
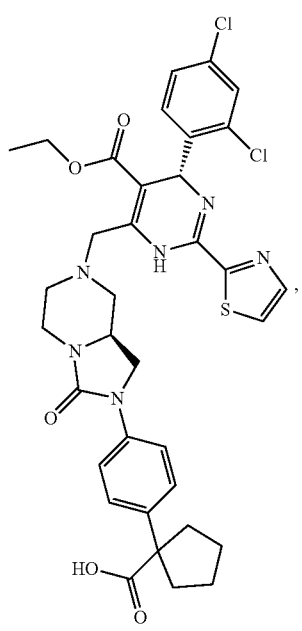

533
-continued
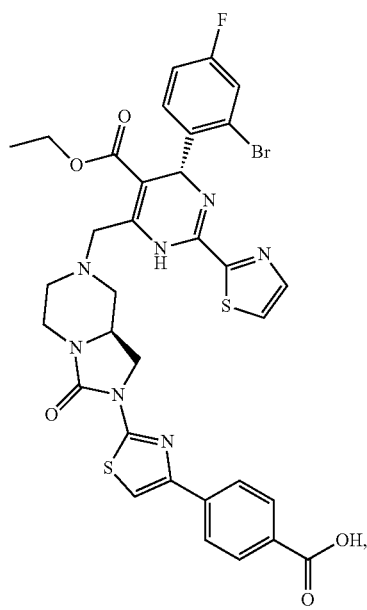
(241)
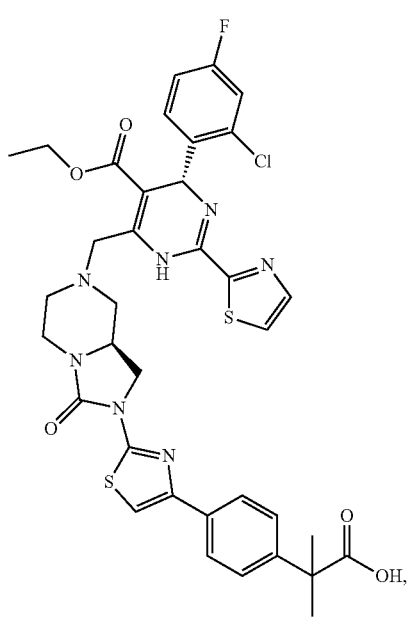
(243)
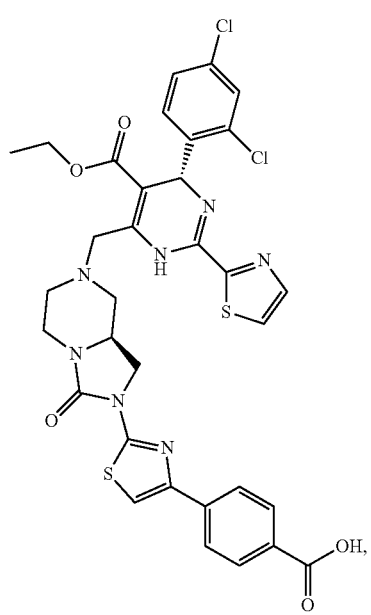
(242)
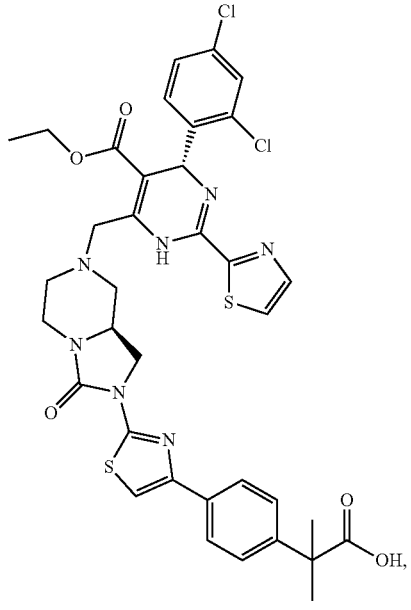
(244)

535
-continued
(245)
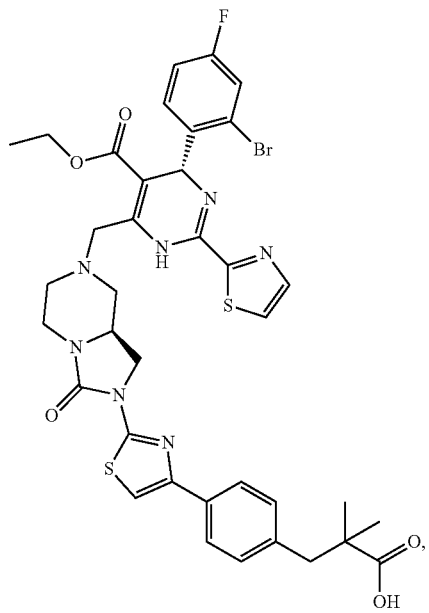
536
-continued
(247)
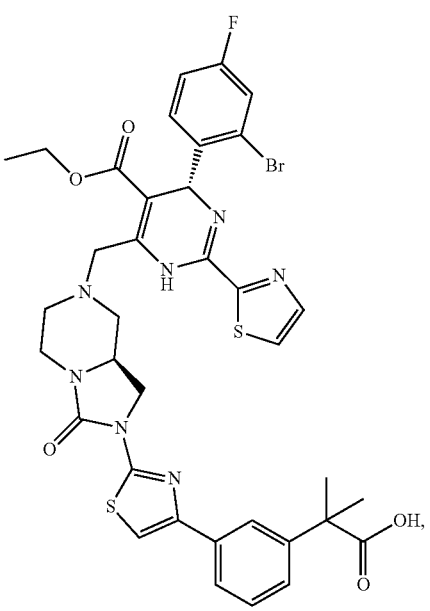
(246)
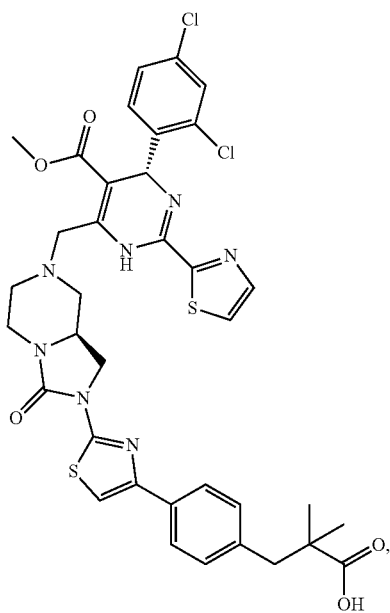
(248)

537
-continued
(249)
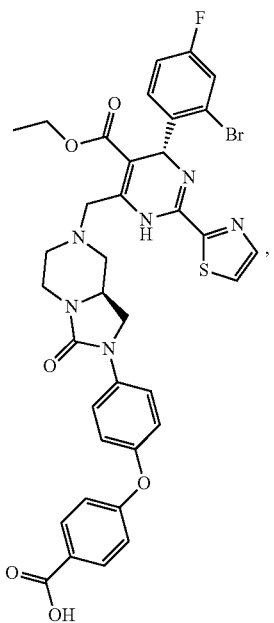
538
-continued
(251)
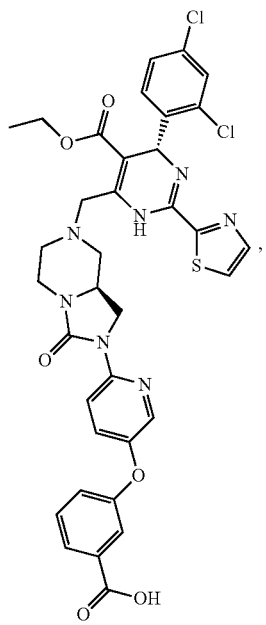
(250)
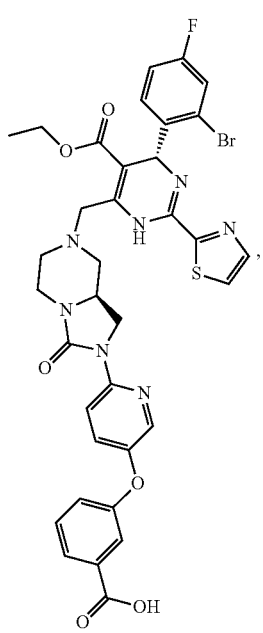
(252)
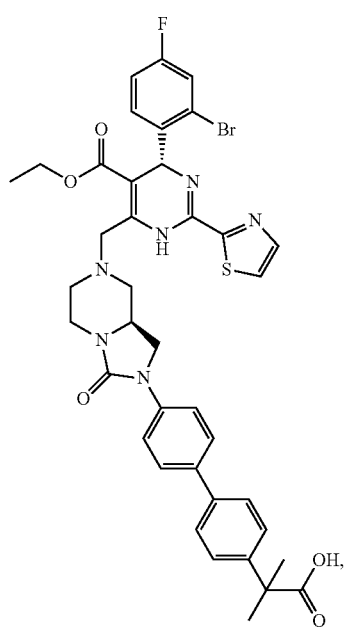

(253)
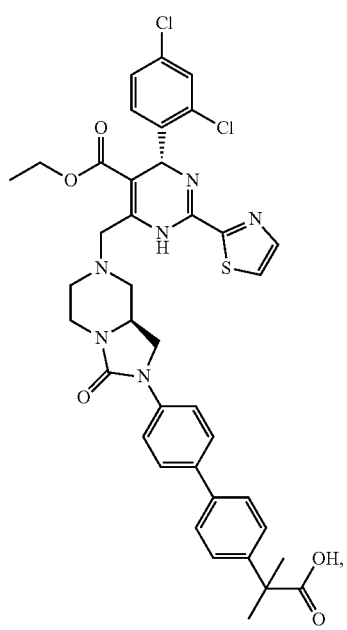
(254)
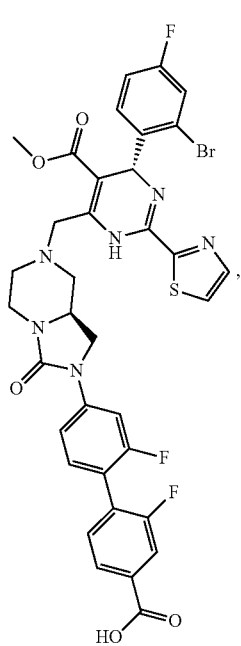
(255)
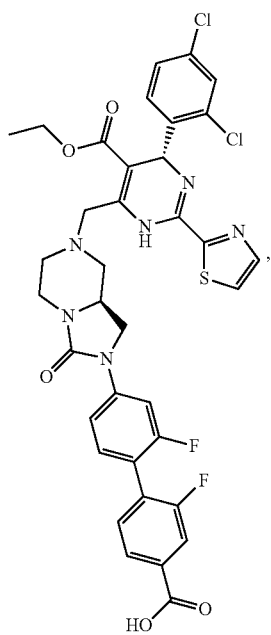
(256)
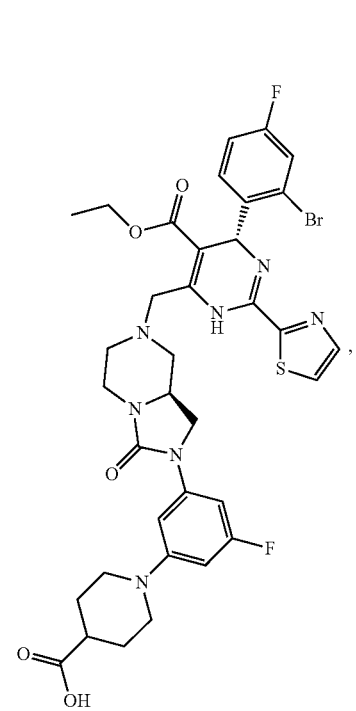

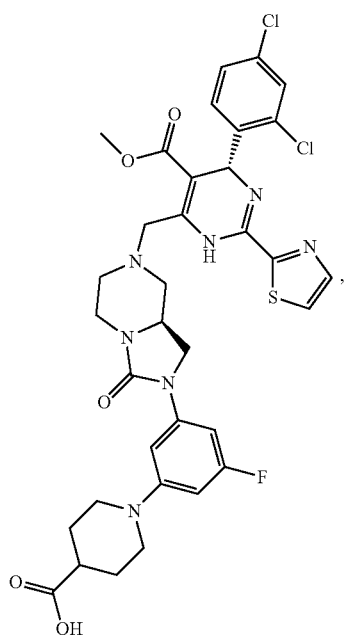 (257)
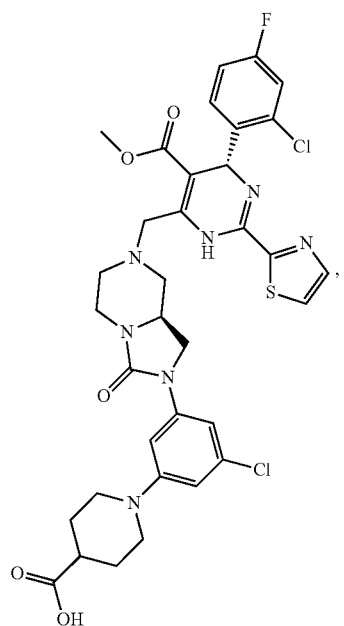 (259)
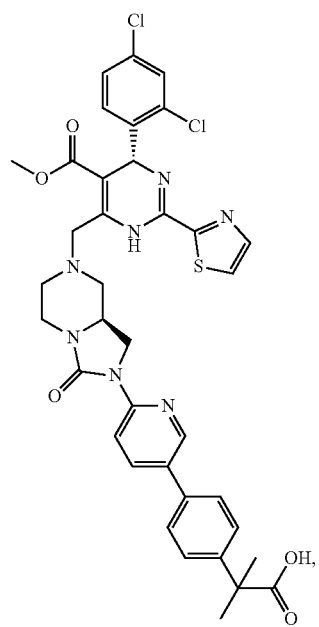 (258)
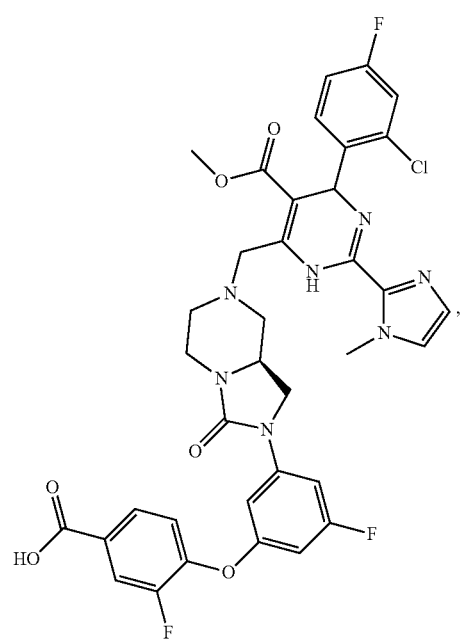 (260)

-continued (261)

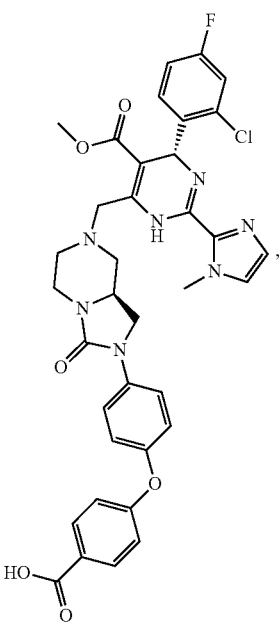

a stereoisomer, a tautomer, an N-oxide, a solvate, a metabolite, a pharmaceutically acceptable salt or a prodrug thereof.

18. A pharmaceutical composition comprising the compound of claim 1 and one or more pharmaceutically acceptable adjuvants.

19. The pharmaceutical composition of claim 18, further comprising one or more other anti-HBV drugs selected from the group consisting of lamivudine, telbivudine, tenofovir, entecavir, adefovir dipivoxil, alfaferone, alloferon, celmoleukin, clevudine, emtricitabine, famciclovir, feron, hepatect CP, intefen, interferon α-1b, interferon α, interferon α-2a, interferon β-1a, interferon α-2, interleukin-2, mivotilate, nitazoxanide, peginterferon alfa-2a, ribavirin, roferon-A, sizofiran, Euforavac, rintatolimod, Phosphazid, Heplisav, interferon α-2b, levamisole, and propagermanium.

20. A method of managing, treating or lessening a virus disease comprising administering the compound of claim 1 to a patient in need thereof, wherein
the virus disease is hepatitis B infection or a disease caused by hepatitis B infection, and
the disease caused by hepatitis B infection is hepatic cirrhosis or hepatocellular carcinogenesis.

21. A method of managing, treating or lessening a virus disease comprising administering the pharmaceutical composition of claim 18 to a patient in need thereof, wherein
the virus disease is hepatitis B infection or a disease caused by hepatitis B infection, and
the disease caused by hepatitis B infection is hepatic cirrhosis or hepatocellular carcinogenesis.

* * * * *